US008623873B2

(12) United States Patent
Gilbert et al.

(10) Patent No.: US 8,623,873 B2
(45) Date of Patent: *Jan. 7, 2014

(54) SUBSTITUTED PIPERAZINES AS CB1 ANTAGONISTS

(75) Inventors: Eric J. Gilbert, Scotch Plains, NJ (US); Michael W. Miller, Scotch Plains, NJ (US); Jack D. Scott, Scotch Plains, NJ (US); Duane Eugene DeMong, Somerset, NJ (US); Andrew Stamford, Chatham Township, NJ (US); William J. Greenlee, Teaneck, NJ (US); Chander Shekher Celly, Colonia, NJ (US)

(73) Assignee: Intervet Inc., Summit, NJ (US)

( * ) Notice: Subject to any disclaimer, the term of this patent is extended or adjusted under 35 U.S.C. 154(b) by 831 days.

This patent is subject to a terminal disclaimer.

(21) Appl. No.: 12/146,039

(22) Filed: Jun. 25, 2008

(65) Prior Publication Data

US 2009/0105208 A1   Apr. 23, 2009

Related U.S. Application Data

(60) Provisional application No. 60/946,873, filed on Jun. 28, 2007.

(51) Int. Cl.
A61K 31/497 (2006.01)
C07D 401/00 (2006.01)

(52) U.S. Cl.
USPC .................................... 514/253.01; 544/360

(58) Field of Classification Search
USPC .................................... 514/253.01; 544/360
See application file for complete search history.

(56) References Cited

U.S. PATENT DOCUMENTS

| | | | |
|---|---|---|---|
| 3,663,548 A | 5/1972 | Nitta et al. |
| 4,229,207 A | 10/1980 | Laanio et al. |
| 4,839,360 A | 6/1989 | Sato et al. |
| 4,917,896 A | 4/1990 | Peck et al. |
| 4,983,597 A | 1/1991 | Yang et al. |
| 5,073,544 A | 12/1991 | Peck et al. |
| 5,185,349 A | 2/1993 | Augelli-Szafran |
| 5,234,895 A | 8/1993 | Felix |
| 5,306,817 A | 4/1994 | Thiruvengadam et al. |
| 5,332,817 A | 7/1994 | Desai et al. |
| 5,464,788 A | 11/1995 | Bock et al. |
| 5,508,424 A | 4/1996 | Carmosin et al. |
| 5,561,227 A | 10/1996 | Thiruvengadam et al. |
| 5,580,883 A | 12/1996 | Goto et al. |
| 5,624,920 A | 4/1997 | McKittrick et al. |
| 5,624,941 A | 4/1997 | Barth et al. |
| 5,631,365 A | 5/1997 | Rosenblum et al. |
| 5,633,246 A | 5/1997 | McKittrick et al. |
| 5,656,624 A | 8/1997 | Vaccaro et al. |
| 5,688,785 A | 11/1997 | Vaccaro |
| 5,688,787 A | 11/1997 | Burnett et al. |
| 5,688,990 A | 11/1997 | Shankar |
| 5,698,548 A | 12/1997 | Dugar et al. |
| 5,756,470 A | 5/1998 | Yumibe et al. |
| 5,756,504 A | 5/1998 | Bock et al. |
| 5,763,444 A | 6/1998 | Smith et al. |
| 5,767,115 A | 6/1998 | Rosenblum et al. |
| 5,780,480 A | 7/1998 | Wai et al. |
| 5,846,966 A | 12/1998 | Rosenblum et al. |
| 6,093,812 A | 7/2000 | Thiruvengadam et al. |
| 6,121,319 A | 9/2000 | Somers |
| 6,147,090 A | 11/2000 | DeNinno et al. |
| 6,147,250 A | 11/2000 | Somers |
| 6,207,822 B1 | 3/2001 | Thiruvengadam et al. |
| 6,369,077 B1 | 4/2002 | Marquis et al. |
| RE37,721 E | 5/2002 | Rosenblum et al. |
| 6,391,865 B1 | 5/2002 | Baroudy et al. |
| 6,432,984 B1 | 8/2002 | Barth et al. |
| 6,441,001 B1 | 8/2002 | Watson et al. |
| 6,498,156 B2 | 12/2002 | Glombik et al. |
| 6,528,529 B1 | 3/2003 | Brann et al. |
| 6,627,757 B2 | 9/2003 | Fu et al. |
| 6,642,258 B1 | 11/2003 | Bourrie et al. |
| 6,703,386 B2 | 3/2004 | Glombik et al. |
| 6,720,328 B2 | 4/2004 | Aslanian et al. |

(Continued)

FOREIGN PATENT DOCUMENTS

EP   0230402   4/1993
EP   0612745   8/1994

(Continued)

OTHER PUBLICATIONS

Bensaid et al., "The Cannabinoid CB1 Receptor Antagonist SR141716 Increases Acrp30 mRNA Expression in Adipose Tissue of Obese fa/fa Rats and in Cultured Adipocyte Cells", Molecular Pharmacology, vol. 63, No. 4, pp. 908-914 (2003).

Wikström et al., "Synthesis and Pharmacological Testing of 1,2,3,4,10,14b-Hexahydro-6-methoxy-2-methyldibenzo[c,f]pyrazino[1,2-a]azepin and its Enantiomers in Comparison with the Two Antidepressants Mianserin and Mirtazapine", J. Med. Chem., vol. 45, pp. 3280-3285 (2002).

International Search Report for PCT/US 2008/007868, mailed Jan. 28, 2009 for CV06641 (6 pages).

(Continued)

Primary Examiner — Erich A Leeser

(57) ABSTRACT

Compounds of Formula (I):

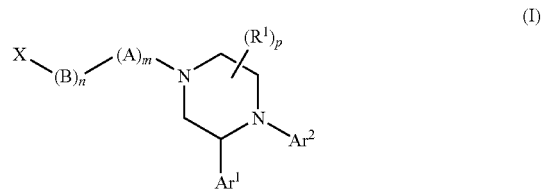

or pharmaceutically acceptable salts, solvates, or esters thereof, are useful in treating diseases or conditions mediated by $CB_1$ receptors, such as metabolic syndrome and obesity, neuroinflammatory disorders, cognitive disorders and psychosis, addiction (e.g., smoking cessation), gastrointestinal disorders, and cardiovascular conditions.

94 Claims, No Drawings

(56) References Cited

U.S. PATENT DOCUMENTS

| | | |
|---|---|---|
| 6,902,902 B2 | 6/2005 | Unett et al. |
| 6,982,267 B2 | 1/2006 | Stamford et al. |
| 7,105,505 B2 | 9/2006 | Zeng et al. |
| 7,700,597 B2 | 4/2010 | Gilbert et al. |
| 2001/0006972 A1 | 7/2001 | Williams |
| 2002/0039774 A1 | 4/2002 | Kramer et al. |
| 2002/0128252 A1 | 9/2002 | Glombik et al. |
| 2002/0128253 A1 | 9/2002 | Glombik et al. |
| 2002/0128476 A1 | 9/2002 | Marquis, Jr. et al. |
| 2002/0137689 A1 | 9/2002 | Glombik et al. |
| 2003/0087933 A1 | 5/2003 | Blanchard et al. |
| 2003/0105028 A1 | 6/2003 | Ghosal et al. |
| 2003/0109673 A1 | 6/2003 | Yonghong |
| 2003/0139343 A1 | 7/2003 | Ramakrishnan |
| 2003/0171588 A1 | 9/2003 | Kahl et al. |
| 2003/0186960 A1 | 10/2003 | Lauffer et al. |
| 2004/0058820 A1 | 3/2004 | Hagmann et al. |
| 2004/0063929 A1 | 4/2004 | Tomiyama et al. |
| 2004/0106800 A1 | 6/2004 | Lange et al. |
| 2004/0142377 A1 | 7/2004 | Unett et al. |
| 2004/0142922 A1 | 7/2004 | Alanine et al. |
| 2004/0147572 A1 | 7/2004 | Guba et al. |
| 2004/0167129 A1 | 8/2004 | Mayweg et al. |
| 2004/0167185 A1 | 8/2004 | Shankar et al. |
| 2004/0180927 A1 | 9/2004 | Marquis, Jr. et al. |
| 2004/0235854 A1 | 11/2004 | Kruse et al. |
| 2004/0254224 A1 | 12/2004 | Foord et al. |
| 2005/0004178 A1 | 1/2005 | Unett et al. |
| 2005/0154029 A1 | 7/2005 | Unett et al. |
| 2005/0187263 A1 | 8/2005 | Minnich et al. |
| 2005/0187280 A1 | 8/2005 | Minnich et al. |
| 2007/0197628 A1 | 8/2007 | Chackalamannil et al. |
| 2007/0203183 A1 | 8/2007 | Gilbert et al. |
| 2009/0105208 A1 | 4/2009 | Gilbert et al. |
| 2010/0029607 A1* | 2/2010 | Gilbert et al. ............ 514/210.02 |
| 2010/0197564 A1 | 8/2010 | Scott et al. |
| 2010/0249144 A1 | 9/2010 | Demong et al. |
| 2010/0286160 A1 | 11/2010 | Gilbert et al. |

FOREIGN PATENT DOCUMENTS

| | | |
|---|---|---|
| EP | 0268222 | 3/1996 |
| JP | 3-200758 | 9/1991 |
| JP | 4-266830 | 9/1992 |
| JP | 4-364175 | 12/1992 |
| NL | 6603256 | 9/1967 |
| WO | WO 88/01131 | 2/1988 |
| WO | WO 93/02048 | 2/1993 |
| WO | WO 94/17038 | 8/1994 |
| WO | WO 95/08532 | 3/1995 |
| WO | WO 95/25443 | 9/1995 |
| WO | WO 96/01656 | 1/1996 |
| WO | WO 97/22597 | 6/1997 |
| WO | WO 98/56820 | 12/1998 |
| WO | WO 99/38498 | 8/1999 |
| WO | WO 00/38721 | 7/2000 |
| WO | WO 00/38727 | 7/2000 |
| WO | WO 00/66558 | 11/2000 |
| WO | WO 01/02372 | 1/2001 |
| WO | WO 01/58869 | 8/2001 |
| WO | WO 01/77320 | 10/2001 |
| WO | WO 01/94385 | 12/2001 |
| WO | WO 02/066464 | 8/2002 |
| WO | WO 02/098853 | 12/2002 |
| WO | WO 03/008559 | 1/2003 |
| WO | WO 03/027637 | 4/2003 |
| WO | WO 03/042174 | 5/2003 |
| WO | WO 03/051850 | 6/2003 |
| WO | WO 03/062392 | 7/2003 |
| WO | WO 03/082190 | 10/2003 |
| WO | WO 03/084942 | 10/2003 |
| WO | WO 2004/000803 | 12/2003 |
| WO | WO 2004/000804 | 12/2003 |
| WO | WO 2004/000805 | 12/2003 |
| WO | WO 2004/005247 | 1/2004 |
| WO | WO 2004/033431 | 4/2004 |
| WO | WO 2004/058255 | 7/2004 |
| WO | WO 2004/071378 | 8/2004 |
| WO | WO 2004/071394 | 8/2004 |
| WO | WO 2004/083388 | 9/2004 |
| WO | WO 2004/085408 | 10/2004 |
| WO | WO 2004/099157 | 11/2004 |
| WO | WO 2005/000775 | 1/2005 |
| WO | WO 2005/011677 | 2/2005 |
| WO | WO 2005/016867 | 2/2005 |
| WO | WO 2005/016870 | 2/2005 |
| WO | WO 2005/020988 | 3/2005 |
| WO | WO 2005/020992 | 3/2005 |
| WO | WO 2005/051937 | 6/2005 |
| WO | WO 2005/077950 | 8/2005 |
| WO | WO 2005/080386 | 9/2005 |
| WO | WO 2006/060461 * | 6/2006 |
| WO | WO 2007/018459 | 2/2007 |
| WO | WO 2007/018460 | 2/2007 |
| WO | WO 2007/020502 | 2/2007 |
| WO | WO 2007/029773 | 3/2007 |
| WO | WO 2007/057687 | 5/2007 |
| WO | WO 2007/084319 | 7/2007 |
| WO | WO 2007/084450 | 7/2007 |
| WO | WO 2008/130616 | 10/2008 |
| WO | WO 2009/005645 | 1/2009 |
| WO | WO 2009/005671 | 1/2009 |

OTHER PUBLICATIONS

PCT Written Opinion for PCT/US2008/007868 for CV06641 (9 pages).

Adam, et al., "Recent Advances in the Cannabinoids", Expert Opin. Ther. Patents; (2002), pp. 1475-1489, vol. 12, Issue 10.

Anderson, et al., "The Preparation of β-Substituted Amines from Mixtures of Epoxide Opening Products via a Common Aziridinium Ion Intermediate", Tetrahedron: *Asymmetry*, (1999), pp. 2655-2663, vol. 10.

Bingham, et al., "Over One Hundred Solvates of Sulfathiazole†", Chem. Commun., (2001), pp. 603-604.

Borisy et al, "Systematic Discovery of Multicomponent Therapeutics", PNAS, vol. 100, No. 13, pp. 7977-7982 (2003).

Brettle, Roger, et al., "The Selective Reduction of αβ-Olefinic Amides", Tetrahedron Letters, 1980, pp. 2915-2916, vol. 21. (XP-002441723).

Caira, et al., "Preparation and Crystal Characterization of a Polymorph, a Monohydrate, and an Ethyl Acetate Solvate of the Antifungal Fluconazole", Journal of Pharmaceutical Sciences, (2004) pp. 601-611, vol. 93, No. 3.

Chemical Abstracts Service, Columbus, Ohio, US; Banciu, Mircea D. et al., (XP002441898); Database accession No. 1996:738817; abstract.

Chemical Abstracts Service, Columbus, Ohio, US; Dhaon, Madhup K. et al., (XP002441901); Database accession No. 1977:106004; abstract.

Chemical Abstracts Service, Columbus, Ohio, US; Dodds, E.C., et al., (XP002441902); Database accession No. 1955:42823; abstract.

Chemical Abstracts Service, Columbus, Ohio, US; Eto, Masashi et al., (XP002441899); Database accession No. 1993:427963; abstract.

Chemical Abstracts Service, Columbus, Ohio, US; Langer, F., et al., (XP002441904);Database accession No. 1956:24005; abstract.

Chemical Abstracts Service, Columbus, Ohio, US; Melles, J.L., (XP002441903);Database accession No. 1953:44564; abstract.

Chemical Abstracts Service, Columbus, Ohio, US; Tokita, Sumio, et al., (XP002441900); Database accession No. 1991:228432; abstract.

Chemical Abstracts Service, Columbus, Ohio, US; Zhang J.-H., at al., (XP002441897); Database accession No. 2004:785021; abstract.

Chong et al., "Current, New and Future Treatments in Dyslipidaemia and Atherosclerosis"—Drugs, (2000), pp. 55-93, vol. 60, Issue 1.

Fancher et al, "4-Alkyl+(or Aralkyl) 1-Aryl-2-piperazinones", Chemical Therapeutics Research Laboratory, Miles Labs, Inc., Indiana, (1963) vol. 7 pp. 154-158.

(56) References Cited

OTHER PUBLICATIONS

Gerson, Fabian, et al., "The Radical Anions of 1,2-Diphenylcyclohexene and Structurally Related Compounds. Conformational ESR and ENDOR Studies", Helvetica Chimica Acta, 1987, pp. 1558-1568, vol. 70, No. 6. (XP-002441721).

Gschwend, Heinz W., et al., "Intramolecular [x4-x2]-cycloadditions: Preparative and Kinetic Aspects", Angew. Chem. Internat. Edit 1972, pp. 294-295, vol. 11, No. 4.(XP-009086254).

Gschwend, Heinz W., et al., "Rates of Intramolecular Diels-Alder Reactions of Pentadienylacrylamides", J. Org. Chem., 1973, pp. 2169-2175, vol. 38, No. 12.(XP-002441724).

Gylling et al., "Serum Sterols During Stanol Ester Feeding in a Mildly Hypercholesterolemic Population"—Journal of Lipid Research, (1999), pp. 593-600, vol. 40.

Huettinger et al., "Hypolipidemic activity of HOE-402 is Mediated by Stimulation of the LDL Receptor Pathway"—Arterioscler. Thromb., (1993), pp. 1005-1012, vol. 13.

Japanese Patent No. 03200758, dated Sep. 2, 1991 (English Abstract).

Japanese Patent No. 04026683, dated Jan. 29, 1992 (English Abstract).

Japanese Patent No. 04364175, dated Dec. 16, 1992 (English Abstract).

Josephsohn, Nathan S. et al., "Efficient and Practical Ag-Catalyzed Cycloadditions between Arylimines and the Danishefsky Diene", J. Am. Chem. Society, 2003, pp. 4018-4019, vol. 125, No. 14.

Kirkham, "Endogenous cannabinoids: a new target in the treatment of obesity", Am. J. Physiol. Regul. Integr. Comp. Physiol., (2002), pp. R343-R344, vol. 284.

Kvaerno et al., "An in Vitro Assay for Evaluation of Small-Molecule Inhibitors of Cholesterol Absorption", Angew. Chem. Int. Ed., (2004), pp. 4653-4656, vol. 43.

Lange et al., "Synthesis, Biological Properties, and Molecular Modeling Investigations of Novel 3,4-Diarylpyrazolines as Potent and Selective CB1 Cannabinoid Receptor Antagonists", J. Med. Chem., (2004), pp. 627-643, vol. 47.

Lange, Jos H.M., et al, "Novel 3,4-diarylpyrazolines as potent cannabinoid CB1 receptor antagonists with lower lipophilicity", Bioorganic & Medicinal Chemistry Letters, 2005, pp. 4794-4798, vol. 15, No. 21.

PCT International Search Report mailed Jul. 30, 2007 for counterpart PCT Application No. PCT/US2007/000705.

PCT Written Opinion of the International Searching Authority for PCT/US2007/001024—8 pages for CV06385.

International Search Report (PCT/US2007/001024), mail date Aug. 21, 2007—8 pages for CV06385.

International Search Report for PCT/US2005/043281 dated May 19, 2006 for CV06241US01—5 Pages.

Petite et al, The therapeutic applications of annabinoid agonists and antagonists, Ashley Publications, Emerging Drugs (1998) 3:39-53.

Porter et al., "The Endocannabinoid Nervous System: Unique Opportunities for Therapeutic Intervention", Pharmacology and Therapeutics vol. 90, pp. 45-60, 2001.

Ram et al., "Potential Hypolipidemic Agents: Part V†-Synthesis and Biological Activity of New Ethyl 4-(2-oxoazetidin-4-yl) phenoxyalkanoates‡", Indian J. Chem. Sect. B. 29B, pp. 1134-1137, vol. 12.

Sanofl-Avent is Publication, "A New Approach to Cardiovascular Risk Management"—Bear Stearns Conference, New York (Sep. 2004), pp. 19-24.

Shea, K.J., et al., Kinetic Investigation of the Type 2 Intramolecular Diels-Alder Cycloaddition, American Chemical Society, 1988, pp. 860-864, vol. 110, No. 3.(XP-002441722).

Trillou, C.R. et al., "Anti-obesity effect of SR141716, a CB1 receptor antagonist, in diet-induced obese mice"—Am. J. Physiol. Regul. Integr. Comp., Physiol., (2003), pp. R345-R353, vol. 284.

Van Tonder, et al., "Preparation and Physicochemical Characterization of 5 Niclosamide Solvates and 1 Hemisolvate", *AAPS PharmSciTech*, (2004), pp. 1-10, vol. 5, Issue 1.

Weis, Robert et al., "Synthesis of 2-substituted bamipine derivatives", Tetrahedron, (2003), vol. 9 pp. 1395-1402.

Weis, Robert et al., "Synthesis of new 1,2,7 analogs of diphenylpyraline", Tetrahedron, (2003) vol. 9 pp. 1403-1411.

Vippagunta et al, "Crystalline Solids", Advanced Drug Delivery Reviews 48 (2001) 3-26.

\* cited by examiner

SUBSTITUTED PIPERAZINES AS CB1 ANTAGONISTS

PRIOR APPLICATIONS

This application claims the benefit of priority to Application Ser. No. 60/946,873, filed Jun. 28, 2007, which is incorporated in its entirety by reference.

BACKGROUND OF THE INVENTION

The $CB_1$ receptor is one of the most abundant neuromodulatory receptors in the brain, and is expressed at high levels in the hippocampus, cortex, cerebellum, and basal ganglia (e.g., Wilson et al., *Science*, 2002, vol. 296, 678-682). Selective $CB_1$ receptor antagonists, for example pyrazole derivatives such as rimonabant (e.g., U.S. Pat. No. 6,432,984), can be used to treat various conditions, such as obesity and metabolic syndrome (e.g., Bensaid et al., *Molecular Pharmacology*, 2003 vol. 63, no. 4, pp. 908-914; Trillou et al., *Am. J. Physiol. Regul. Integr. Comp. Physiol.* 2002 vol. 284, R345-R353; Kirkham, *Am. J. Physiol. Regul. Integr. Comp. Physiol.* 2002 vol. 284, R343-R344), neuroinflammatory disorders (e.g., Adam, et al., *Expert Opin. Ther. Patents,* 2002, vol. 12, no. 10, 1475-1489; U.S. Pat. No. 6,642,258), cognitive disorders and psychosis (e.g., Adam et al., *Expert Opin. Ther. Pat,* 2002, vol. 12, pp. 1475-1489), addiction (e.g., smoking cessation; U.S. Patent Publ. 2003/0087933), gastrointestinal disorders (e.g., Lange et al., *J. Med. Chem.* 2004, vol. 47, 627-643) and cardiovascular conditions (e.g., Porter et al., *Pharmacology and Therapeutics,* 2001 vol. 90, 45-60; Sanofi-Aventis Publication, Bear Stearns Conference, New York, Sep. 14, 2004, pages 19-24).

There now exists extensive pre-clinical and clinical data supporting the use of CB1 receptor antagonists/inverse agonists for the treatment of obesity.

Preparations of marijuana (*Cannabis sativa*) have been used for over 5000 years for both medicinal and recreational purposes. The major psychoactive ingredient of marijuana has been identified as delta-9-tetrahydrocannabinol (delta-9-THC), one of a member of over 60 related cannabinoid compounds isolated from this plant. It has been demonstrated that delta-9-THC exerts its effects via agonist interaction with cannabinoid (CB) receptors. So far, two cannabinoid receptor subtypes have been characterised ($CB_1$ and $CB_2$). The $CB_1$ receptor subtype is found predominantly in the central nervous system, and to a lesser extent in the peripheral nervous system and various peripheral organs. The $CB_2$ receptor subtype is found predominantly in lymphoid tissues and cells. To date, three endogenous agonists (endocannabinoids) have been identified which interact with both $CB_1$ and $CB_2$ receptors (anandamide, 2-arachidonyl glycerol and noladin ether).

Genetically obese rats and mice exhibit markedly elevated endocannabinoid levels in brain regions associated with ingestive behaviour (Di Marzo et al. 2001 Nature 410: 822-825). Furthermore, increased levels of endocannabinoids are observed upon the fasting of normal, lean animals (Kirkham et al., British Journal of Pharmacology 2002, 136(4) 550-557).

Exogenous application of endocannabinoids leads to the same physiological effects observed with delta-9-THC treatment, including appetite stimulation (Jamshida et al., British Journal of Pharmacology 2001, 134: 1151-1 154), analgesia, hypolocomotion, hypothermia, and catalepsy.

$CB_1$ ($CB_1-/-$) and $CB_2$ ($CB_2-/-$) receptor knockout mice have been used to elucidate the specific role of the two cannabinoid receptor subtypes. Furthermore, for ligands such as delta-9-THC which act as agonists at both receptors, these mice have allowed identification of which receptor subtype is mediating specific physiological effects. $CB_1-/-$, but not $CB_2-/-$, mice are resistant to the behavioural effects of agonists such as delta-9-THC. $CB_1-/-$ animals have also been shown to be resistant to both the body weight gain associated with chronic high fat diet exposure, and the appetite-stimulating effects of acute food deprivation.

These findings suggest a clear role for both endogenous and exogenous cannabinoid receptor agonists in increasing food intake and body weight via selective activation of the $CB_1$ receptor subtype.

The therapeutic potential for cannabinoid receptor ligands has been extensively reviewed (Exp. Opin. Ther. Pat. 1998, 8, 3010-313; Exp. Opin. Ther. Pat. 2000, 10, 1529-1538; Trends in Pharm. Sci. 2000, 2 1, 218-224; Exp. Opin. Ther. Pat. 2002, 12(10), 1475-1489).

At least one compound (SR-14171 6A; Rimonabant) characterised as a $CB_1$ receptor antagonist/inverse agonist is known to be in clinical trials for the treatment of obesity.

Clinical trials with the $CB_1$ receptor antagonist rimonabant have also observed an antidiabetic action that exceeds that accounted for by weight loss alone (Scheen A. J., et al., Lancet, 2006 in press). $CB_1$ receptor mRNA is located on α- and β-cells in the Islets of Langerhans and it has been reported that $CB_1$ receptor agonists reduce insulin release from pancreatic beta cells in vitro in response to a glucose load (Juan-Pico et al, Cell Calcium, 39, (2006), 155-162). Consistent with this, Bermudez-Siva et al., (Eur J Pharmacol., 531 (2006), 282-284) have reported that $CB_1$ receptor agonists increase glucose intolerance following ip injection of a glucose load to rats. This effect was reversed by a $CB_1$ receptor antagonist that increased glucose tolerance in the test when given alone. Thus, the action of rimonabant may be due to a direct action on the pancreas. It is also possible that $CB_1$ receptor antagonists affect insulin sensitivity indirectly via an action on adiponectin (Chandran et al., Diabetes care, 26, (2003), 2442-2450) which is elevated by $CB_1$ receptor antagonists (Cota et al., J Clin Invest., 112 (2003), 423-431; Bensaid et al., Mol Pharmacol., 63 (2003, 908-914). Indeed, it has been reported that endocannabinoid levels are enhanced in the pancreas and adipose tissue of obese and diabetic mice and in the plasma and adipose tissue of obese or type 2 diabetic patients (Matias et al., J Clin Endocrinol and Metab., 9 1 (2006), 3171-3180) suggesting a possible causal role of elevated cannabinoid tone in the onset of type 2 diabetes.

However, there is still a need for improved cannabinoid agents, particularly selective CB receptor antagonists, with fewer side-effects and improved efficacy.

WO 95125443, U.S. Pat. No. 5,464,788, and U.S. Pat. No. 5,756,504 describe N-aryl piperazine compounds useful for treating preterm labor, stopping labor, and dysmenorrhea. However, none of the N-aryl piperazines exemplified therein have an aryl and/or heteroaryl substituent at both the 1- and 2-positions of the piperazine ring.

WO 01/02372 and U.S. Published Application No. 200310186960 describe cyclized amino acid derivatives for treating or preventing neuronal damage associated with neurological diseases. However, none of the 3-aryl piperazine 2-ones exemplified therein have an aryl and/or heteroaryl substituent at both the 1- and 2-positions of the piperazine ring.

WO 96/01656 describes radiolabelled substituted piperazines useful in pharmacological screening procedures, including labeled N-aryl piperazines. However, none of the N-aryl piperazines exemplified therein have an aryl and/or heteroaryl substituent at both the 1- and 2-positions of the piperazine ring.

U.S. Pat. No. 5,780,480 describes N-aryl piperazines useful as fibrinogen receptor antagonists for inhibiting the binding of fibrinogen to blood platelets, and for inhibiting the aggregation of blood platelets. However, none of the N-aryl piperazines exemplified therein have an aryl and/or heteroaryl substituent at both the 1- and 2-positions of the piperazine ring.

WO 03/008559 describes choline analogs useful for treating conditions or disorders. However, the only substituted piperazine derivative exemplified is N-(2-hydroxyethyl)-N'-(2-pyridylmethyl)-piperazine.

JP 3-200758, JP 4-26683, and JP 4-364175 describe N,N'-diarylpiperazines (i.e., 1,4-diarylpiperazines) prepared by reacting bis(2-hydroxyethyl)arylamines with an amine such as aniline. However, no 1,2-disubstituted piperazines are exemplified.

WO 97122597 describes various 1,2,4-trisubstituted piperazine derivatives as tachykinin antagonists for treating tachykinin-mediated diseases such as asthma, bronchitis, rhinitis, cough, expectoration, etc. However, none of the 1,2,4-trisubstituted piperazine derivatives exemplified therein have an aryl and/or heteroaryl substituent at both the 1- and 2-positions of the piperazine ring.

EP 0268222, WO 88/01131, U.S. Pat. No. 4,917,896, and U.S. Pat. No. 5,073,544 describe compositions for enhancing the penetration of active agents through the skin, comprising azacyclohexanes, including N-acyl and N,N'-diacylpiperazines. However, none of the N-acyl or N,N'-diacylpiperazines exemplified therein have an aryl and/or heteroaryl substituent at both the 1- and 2-positions of the piperazine ring.

U.S. Pat. No. 6,528,529 describes compounds, including N,N'-disubstituted piperazines, which are selective for muscarinic acetylcholine receptors and are useful for treating diseases such as Alzheimer's disease. However, none of the N,N'-disubstituted piperazines exemplified therein have an aryl and/or heteroaryl substituent at both the 1- and 2-positions of the piperazine ring.

NL 6603256 describes various biologically active piperazine derivatives. However, none of the piperazine derivatives exemplified therein have a substituted aryl and/or heteroaryl substituent at both the 1- and 2-positions of the piperazine ring.

Wikström et al., J. Med. Chem. 2002, 45, 3280-3285, describe the synthesis of 1,2,3,4,10,14b-hexahydro-6-methoxy-2-methyldibnzo[c,f]pyrazine[1,2-a]azepin. However, none of the piperazine intermediates described therein have a substituted aryl and/or heteroaryl substituent at both the 1- and 2-positions of the piperazine ring.

WO 2007/018460 and WO 2007/018459 describe tricyclic piperidines and piperazine containing compounds, compositions, and methods for their use in treating obesity, psychiatric and neurological disorders. However, none of the compounds disclosed have a substituted aryl and/or heteroaryl substituent at both the 1- and 2-positions of a piperazine ring.

WO 2007/020502 describes pyrrolidone compounds as cannabinoid receptor ligands, in particular CB1 receptor ligands, and their use in treating diseases, conditions, and/or disorders modulated by cannabinoid receptor antagonists. However, none of the compounds disclosed have a substituted aryl and/or heteroaryl substituent at both the 1- and 2-positions of a piperazine ring.

WO 2007/057687 and W02006/060461 describe piperazine derivatives and their use as CB1 antagonists and in treating various diseases, conditions, and/or disorders modulated by cannabinoid receptor antagonists. However, there remains a need in the art for selective CB1 antagonists having a different functional group substitution pattern around the piperazine ring.

BRIEF SUMMARY OF THE INVENTION

In its many embodiments, the present invention provides novel substituted piperazine compounds as selective $CB_1$ receptor antagonists for treating various conditions including, but not limited to metabolic syndrome (e.g., obesity, waist circumference, abdominal girth, lipid profile, and insulin sensitivity), neuroinflammatory disorders, cognitive disorders, psychosis, addictive behavior, gastrointestinal disorders, and cardiovascular conditions.

The selective CB1 receptor antagonists of the present invention are piperazine derivatives having the structure of Formula (I):

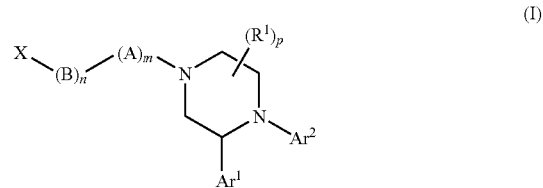

or a pharmaceutically acceptable salt, solvate, ester, or isomer thereof, wherein:

$Ar^1$ and $Ar^2$ are independently aryl or heteroaryl,
  wherein $Ar^1$ is substituted with one or more groups independently selected from $Y^1$ or $Y^3$, and
  $Ar^2$ is substituted with one or more groups independently selected from $Y^1$ or $Y^3$,
  with the proviso that when $Ar^2$ is pyridine or pyrimidine, a nitrogen of said pyridine or pyrimidine is not in the para position relative to the point of attachment to the piperazine ring;
  with the proviso that at least one of $Ar^1$ or $Ar^2$ is substituted with at least one group independently selected from $Y^3$;
n and m are independently 0 or 1;
A is selected from the group consisting of —C(O)—, —S(O)$_2$—, —C(=N—OR$^2$)—, and —(C(R$^2$)$_2$)$_q$- wherein q is 1, 2, or 3;
B is selected from the group consisting of —N(R$^2$)—, —C(O)—, and —(C(R$^3$)$_2$)$_r$— wherein r is 1, 2 or 3, with the proviso that when B is —C(O)—, then A is —C(O)— or —(C(R$^2$)$_2$)$_q$-;
X is selected from the group consisting of H, alkyl, —S-alkyl, —S(O)$_2$-alkyl, —S(O)$_2$-cycloalkyl —S(O)$_2$-aryl, —S(O)$_2$-heteroaryl, cycloalkyl, benzo-fused cycloalkyl-, benzo-fused heterocycloalkyl-, benzo-fused heterocycloalkenyl-, heterocycloalkyl, —C(R$^2$)=C(R$^2$)-aryl, —C(R$^2$)=C(R$^2$)-heteroaryl, —OR$^2$, —O-alkylene-O-alkyl, —S-aryl, —N(R$^4$)$_2$, —NR$^4$R$^6$, —N(R$^6$)$_2$, —(C(R$^2$)$_2$)$_s$-heteroaryl —C(O)—O-alkyl, —O-aryl, —O-heteroaryl, —C(O)aryl, —C(O)-heteroaryl, —N=O, —C(S-alkyl)=N—S(O)$_2$-aryl, —C(N(R$^2$)$_2$)=N—S(O)$_2$-aryl, and —(C(R$^2$)$_2$)$_s$-aryl, wherein s is 0, 1, or 2,
  wherein each aryl portion of said —O-aryl, each heteroaryl portion of said —(C(R$^2$)$_2$)$_s$-heteroaryl, each heteroaryl portion of said —O-heteroaryl, each aryl portion of said —C(R$^2$)=C(R$^2$)-aryl, each heteroaryl portion of said —C(R$^2$)=C(R$^2$)-heteroaryl, each aryl portion of said —S-aryl, each aryl portion of said —S(O)$_2$-aryl, each heteroaryl portion of said —S(O)$_2$-heteroaryl, each aryl portion of said —C(O)-aryl, each heteroaryl portion of said —C(O)-heteroaryl, each aryl portion of said —(C(R$^2$)$_2$)$_s$-aryl, each aryl portion of said —C(S-alkyl)=N—S(O)$_2$-aryl, each aryl portion of said —C(N(R$^2$)$_2$)=N—S(O)$_2$-aryl, each benzo portion of said benzo-fused cycloalkyl, each benzo portion of said benzo-fused heterocycloalkyl, and each benzo portion of said benzo-fused heterocycloalkenyl of X is unsubstituted or optionally substituted with one or more groups independently selected from, —C(=NH)—O-alkyl, —C(=N-alkyl)-O-alkyl, —C(O)OH, -alkylene-O-heterocycloalkyl, Y$^1$ and Y$^3$, and each said cycloalkyl, each cycloalkyl portion of said —S(O)$_2$-cycloalkyl, each said heterocycloalkyl, each cycloalkyl portion of said benzo-fused cycloalkyl, each heterocycloalkyl portion of said benzo-fused heterocycloalkyl, and each heterocycloalkenyl portion of said benzo-fused heterocycloalkenyl of X are unsubstituted optionally substituted with one or more groups independently selected from Y$^2$;

each R$^1$ is independently selected from the group consisting of alkyl, haloalkyl, -alkylene-N(R$^5$)$_2$, -alkylene-OR$^2$, alkylene-N$_3$, -alkylene-CN, and alkylene-O—S(O)$_2$-alkyl; or two R$^1$ groups attached to the same ring carbon atom form a carbonyl group;

p is 0, 1, 2, 3, or 4;

each R$^2$ is independently H, alkyl, aryl, heteroaryl, cycloalkyl, or heterocycloalkyl, wherein each said aryl, heteroaryl, cycloalkyl, or heterocycloalkyl of R$^2$ is independently unsubstituted or optionally substituted with one or more groups independently selected from Y$^1$ and Y$^3$;

each R$^3$ is independently selected from the group consisting of H, alkyl, —OR$^2$, -alkylene-O-alkyl, -alkylene-OH, unsubstituted aryl, and aryl substituted with one or more groups independently selected from Y$^1$ and Y$^3$;

each R$^4$ is independently selected from the group consisting of H, alkyl, aryl, —C(O)—O-alkyl, —C(O)-alkyl, —C(O)-aryl, —C(O)-heteroaryl, —C(O)-heterocycloalkyl, —S(O)$_2$alkyl, —S(O)$_2$aryl, —S(O)$_2$heteroaryl, and —S(O)$_2$heterocycloalkyl;

wherein each said aryl, each aryl portion of said —C(O)-aryl, each aryl portion of said —S(O)$_2$aryl, and each heteroaryl portion of said —C(O)-heteroaryl and said —S(O)$_2$heteroaryl of R$^4$ is unsubstituted or optionally substituted with one or more groups independently selected from Y$^1$ and Y$^3$;

each R$^5$ is independently selected from the group consisting of H, alkyl, aryl, —S(O)$_2$-alkyl, —S(O)$_2$-cycloalkyl, —S(O)$_2$-aryl, —C(O)—N(R$^2$)$_2$, —C(O)-alkyl, and alkylene-OH, wherein each said aryl and each aryl portion of said —S(O)2-aryl of R$^5$ are unsubstituted or optionally substituted with one or more groups independently selected from Z;

each Y$^1$ is independently selected from the group consisting of alkyl, cycloalkyl, heterocycloalkyl, heterocycloalkenyl, halo, haloalkyl, aryl, -alkylene-aryl, heteroaryl, —O-alkyl, —O-aryl, —O-heteroaryl, —O-cycloalkyl, —O-heterocycloalkyl, —S-alkyl, —S-aryl, —S-heteroaryl, —S-cycoalkyl, —S-heterocycloalkyl, —S(O)$_2$-alkyl, —S(O)$_2$-aryl, —S(O)$_2$-heteroaryl, —S(O)$_2$-cycloalkyl, —S(O)$_2$-heterocycloalkyl, -alkylene-CN, —CN, —C(O)-alkyl, —C(O)-aryl, —C(O)-haloalkyl, —C(O)-heteroaryl, —C(O)— cycloalkyl, —C(O)-heterocycloalkyl, —C(O)O-alkyl, —C(O)O-aryl, —C(O)O-haloalkyl —C(O)O-heteroaryl, —C(O)O— cycloalkyl, —C(O)O-heterocycloalkyl, —N(R$^2$)C(O)-alkyl, —N(R$^2$)C(O)—N(R$^2$)$_2$, —OH, —O-alkyl, —O-haloalkyl, —O-alkylene-C(O)OH, —S-alkyl, —S-haloalkyl, -alkylene-OH, -alkylene-C(O)—O-alkyl, —O-alkylene-aryl, and —N(R$^5$)$_2$, wherein each each aryl, each heteroaryl, each aryl portion of said —O-aryl, each aryl portion of said —S-aryl, each aryl portion of said —S(O)$_2$-aryl, each aryl portion of said —C(O)-aryl, each aryl portion of said —C(O)O-aryl, each aryl portion of said benzyl, and each aryl portion of said —O-alkylene-aryl of Y$^1$ and each heteroaryl portion of said —O-heteroaryl, each heteroaryl portion of said —S-heteroaryl, each heteroaryl portion of said —S(O)$_2$-heteroaryl, each heteroaryl portion of said —C(O)- heteroaryl, each heteroaryl portion of said —C(O)O-heteroaryl, each heteroaryl portion of said —O-alkylene-heteroaryl of Y$^1$are unsubstituted or optionally substituted with one or more groups independently selected from Z; or two groups Y$^1$ form a —O—CH$_2$—O— group;

each Y$^2$ is independently selected from the group consisting of alkyl, haloalkyl, aryl, -alkylene-aryl, —CN, —OH, —C(O)-alkyl, —S(O)$_2$-cycloalkyl, -alkylene-N(R$^4$)$_2$, —C(O)-alkylene-N(R$^4$)$_2$, —C(O)-O-alkyl, —C(O)-aryl, and —C(O)-haloalkyl, wherein each said aryl and each aryl portion of said —C(O)-aryl of Y$^2$ are unsubstituted or optionally substituted with one or more groups independently selected from Z; or two groups Y$^2$ form a —O—CH$_2$CH$_2$—O— group; or two of said Y$^2$ substituents attached to the same ring carbon atom of a cycloalkyl, benzo-fused cycloalkyl, benzo-fused heterocycloalkyl, benzo-fused heterocycloalkenyl, or heterocycloalkyl, ring, together with the ring carbon atom to which they are both attached, form a carbonyl group;

each Y$^3$ is independently selected from —C(O)N(R$^6$)$_2$, —S(O)$_2$N(R$^6$)$_2$, —O-Q-L$_{1\ \text{-}R}$$^7$, —O-Q-L$_2$-R$^8$, —O-Q-CN, —O-Q —C(O)N(R$^6$)$_2$, 'O-Q-S(O)$_2$N(R$^6$)$_2$, —O-Q-OC(O)N(R$^6$)$_2$, and —O-Q-N(R$^6$)C(O)N(R$^6$)$_2$;

with the proviso that when A is —C(O)—, or when m=n=0 and X is —C(O)-aryl or —C(O)-heteroaryl, then Ar$^2$ is substituted with at least one Y$^1$ or Y$^3$ group independently selected from cycloalkyl, benzyl, aryl, —O-haloalkyl, —O-aryl, —O-cycloalkyl —S-aryl, —S-haloalkyl, —S-cycloalkyl —S(O)$_2$-alkyl, —S(O)$_2$-cycloalkyl, —S(O)$_2$-aryl, -alkylene-CN, —C(O)-aryl, —C(O)-haloalkyl, —C(O)— cycloalkyl, —C(O)O-aryl, —C(O)O-haloalkyl, —C(O)O-heteroaryl, —C(O)O— cycloalkyl, —C(O)O-heterocycloalkyl, -alkylene-C(O)—O-alkyl, and —O-alkylene-aryl, wherein each benzyl and each aryl portion of said Y$^1$ or Y$^3$ group and each aryl portion and each heteroaryl portion of said —O-aryl, said —S-aryl, said —S(O)$_2$-aryl, said —C(O)-aryl, said —C(O)O-aryl, —C(O)O-heteroaryl, —C(O)O-heterocycloalkyl, and —O-alkylene-aryl of said Y$^1$ or Y$^3$ group is unsubstituted or substituted with one or more groups independently selected from Z;

each -Q- is a divalent radical independently selected from -alkylene-, -alkenylene-, -alkynylene-, -cycloalkylene-, -heterocycloalkylene-, -alkylene-cycloalkylene-, -cycloalkylene-alkylene-, -cycloalkylene-alkylene-cycloalkylenewherein the alkylene, alkenylene, alkynylene, cycloalkylene, and heterocycloalkylene portion of said Q is optionally substituted with one to three groups independently selected from

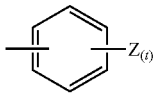

and Z, wherein t is 0, 1, 2, or 3;
each $L_1$ is independently selected from the group consisting of —O—, —S—, —S(O)—, —S(O)$_2$—, —OS(O)$_2$—, —C(O)—, and —OC(O)—,
each $L_2$ is —C(O)O—;
each $R^6$ is independently selected from the group consisting of H, alkyl, halo alkyl, alkoxy, cycloalkyl, heterocycloalkyl, unsubstituted aryl, aryl substituted with one or more groups independently selected from $Y^1$, unsubstituted heteroaryl, heteroaryl substituted with one or more groups independently selected from $Y^1$, cycloalkyl, heterocycloalkyl, -alkylene-OH, -alkylene-O-alkyl, -alkylene-O-aryl, -alkylene-OC(O)-alkyl, -alkylene-OC(O)-aryl, -alkylene-OC(O)-heteroaryl, and alkylene-N(R$_4$)$_2$, or
two $R^6$ groups, together with the nitrogen to which they are aached, form a heteroaryl, heterocycloalkyl, heterocycloalkenyl, or a benzo-fused heterocycloalkyl group;
each $R^7$ is independently selected from the group consisting of H, —N(R$^6$)$_2$, alkyl, cycloalkyl, heterocycloalkyl, aryl, substituted aryl, heteroaryl, and substituted heteroaryl, wherein said substituents are independently selected from Z and —C(O)N(R$^6$)$_2$;
each $R^8$ is independently selected from the group consisting of alkyl, 'N(R$^6$)$_2$, cycloalkyl, heterocycloalkyl, aryl, substituted aryl, heteroaryl, and substituted heteroaryl, wherein said substituents are independently selected from Z and —C(O)N(R$^6$)$_2$; and
each Z is independently selected from the group consisting of alkyl, halo, haloalkyl, —OH, —O-alkyl, and —CN.

In another embodiment, the present invention also provides for compositions comprising at least one selective $CB_1$ receptor antagonist compound of Formula (I), above, or its various embodiments as described herein, or a pharmaceutically acceptable salt, solvate, or ester thereof, and a pharmaceutically acceptable carrier.

In another embodiment, the present invention also provides for compositions comprising at least on selective $CB_1$ receptor antagonist compound of Formula (I), or its various embodiments as described herein, or a pharmaceutically acceptable salt, solvate, or ester thereof, in combination with at least one cholesterol lowering compound or other pharmaceutically active agent, as described herein.

In yet another embodiment, the present invention also provides for a method of treating, reducing, or ameliorating metabolic syndrome, obesity, waist circumference, abdominal girth, lipid profile, insulin sensitivity, neuroinflammatory disorders, cognitive disorders, psychosis, addictive behavior, gastrointestinal disorders, and cardiovascular conditions by administering an effective amount of at least one compound of Formula (I) or its various embodiments as described herein, or a pharmaceutically acceptable salt, solvate, or ester thereof, to a patient in need thereof.

In yet another embodiment, the present invention also provides for a method of treating vascular conditions, hyperlipidaemia, atherosclerosis, hypercholesterolemia, sitosterolemia, vascular inflammation, metabolic syndrome, stroke, diabetes, obesity and/or reducing the level of sterol(s) in a host in need thereof by administering an effective amount of a composition comprising a combination of at least one compound of Formula (I) or its various embodiments as described herein, or a pharmaceutically acceptable salt, solvate, or ester thereof, and at least one cholesterol lowering compound.

DETAILED DESCRIPTION OF THE INVENTION

The selective $CB_1$ receptor antagonist compounds of the present invention are selective $CB_1$ receptor antagonists of mammalian $CB_1$ receptors, preferably human $CB_1$ receptors, and variants thereof. Mammalian $CB_1$ receptors also include $CB_1$ receptors found in rodents, primates, and other mammalian species.

In one embodiment, the selective $CB_1$ receptor antagonist compounds of the present invention are selective $CB_1$ receptor antagonists that bind to a $CB_1$ receptor with a binding affinity ($K_{i(CB1)}$, measured as described herein) of about 2 µM or less, or about 1 µM or less, or about 400 nM or less, or about 200 nM or less, or about 100 nM or less, or about 10 nM or less. These ranges are inclusive of all values and subranges therebetween.

In one embodiment, the selective $CB_1$ receptor antagonist compounds of the present invention are selective $CB_1$ receptor antagonists that have a ratio of $CB_1$ receptor affinity to $CB_2$ receptor affinity ($K_{i(CB1)}$:$K_{i(CB2)}$, measured as described herein) of about 1:2 or better, or about 1:10 or better, or about 1:25 or better, or about 1:50 or better, or about 1:75 or better, or about 1:90 or better. These ranges are inclusive of all values and subranges therebetween.

Thus, in one embodiment, a selective $CB_1$ receptor antagonist of the present invention has an affinity for the $CB_1$ receptor, measured as described herein, of at least 400 nM or less, and a ratio of $CB_1$ to $CB_2$ receptor affinity (i.e., $K_{i(CB1)}$:$K_{i(CB2)}$ of at least 1:2 or better. In another embodiment the $CB_1$ receptor affinity is about 200 nM or less, and the $K_{i(CB1)}$:$K_{i(CB2)}$ is about 1:10 or better. In another embodiment the $CB_1$ affinity is about 100 nM or less, and the $K_{i(CB1)}$:$K_{i(CB2)}$ is about 1:25 or better. In another embodiment the $CB_1$ affinity is about 10 nM or less, and the $K_{i(CB1)}$:$K_{i(CB2)}$ is about 1:75 or better. In another embodiment the $CB_1$ affinity is about 10 nM or less, and the $K_{i(CB1)}$:$K_{i(CB2)}$ is about 1:90 or better. These ranges are inclusive of all values and subranges therebetween.

In one embodiment, the present invention provides for a selective $CB_1$ receptor antagonist compound of Formula (I), or a pharmaceutically acceptable salt, solvate, isomer, or ester thereof, wherein the various substituent groups (i.e., X, $Ar^1$, $Ar^2$, etc.) are as defined hereinabove.

In another embodiment, the present invention relates to a compound of Formula (I), or a pharmaceutically acceptable salt, solvate, isomer, or ester thereof, wherein:
$Ar^1$ and $Ar^2$ are independently ($C_6$-$C_{10}$)aryl or ($C_2$-$C_{10}$)heteroaryl, wherein
  $Ar^1$ is substituted with one or more groups independently selected from $Y^1$ or $Y^3$, and
  $A^2$ is substituted with one or more groups independently selected from $Y^1$ or $Y^3$,
  with the proviso that when $Ar^2$ is pyridine or pyrimidine, a nitrogen of said pyridine or pyrimidine is not in the para position relative to the point of attachment to the piperazine ring;
  with the proviso that at least one of $Ar^1$ or $Ar^2$ is substituted with at least one group independently selected from $Y^3$.
n and m are independently 0 or 1,
A is selected from the group consisting of —C(O)—, —S(O)$_2$—, —C(=N—OR$^2$)—, and —(C(R$^2$)$_2$)$_q$— wherein q is 1, 2, or 3;
B is selected from the group consisting of —N(R$^2$)—, —C(O)—, and —(C(R$^3$)$_2$)$_r$— wherein r is 1 2 or 3, with the proviso that when B is —C(O)—, then A is —C(O)— or —(C(R²)₂)_q—;

X is selected from the group consisting of H, (C₁-C₆)alkyl, —S—(C₁-C₆)alkyl, —S(O)₂—(C₁-C₆)alkyl, —S(O)₂—(C₃-C₁₀)cycloalkyl, —S(O)₂—(C₆-C₁₀)aryl, —S(O)₂—(C₂-C₁₀)heteroaryl, —(C₃-C₁₀)cycloalkyl, benzo-fused (C₃-C₁₀)cycloalkyl-, benzo-fused (C₂-C₁₀)heterocycloalkyl-, benzo-fused (C₂-C₁₀)heterocycloalkenyl-, —(C₂-C₁₀)heterocycloalkyl, —C(R²)C(R²)—(C₆-C₁₀)aryl, —C(R²)═C(R²)—(C₂-C₁₀)heteroaryl, —OR², —O—(C₁-C₆)alkylene-O—(C₁-C₆)alkyl, —S—(C₆-C₁₀)aryl, —N(R⁴)₂, —NR⁴R⁶, —N(R⁶)₂, —(C(R²)₂)_s—(C₂-C₁₀)heteroaryl, —C(O)—O—(C₁-C₆)alkyl, —C(O)—(C₆-C₁₀)aryl, —C(O)—(C₂-C₁₀)heteroaryl, —O—(C₆-C₁₀)aryl, —O—(C₂-C₁₀)heteroaryl, —N═O, —C(S—(C₁-C₆)alkyl)═N—S(O)₂-(C₆-C₁₀)aryl, —C(N(R²)₂)═N—S(O)₂-(C₆-C₁₀)aryl, and —(C(R²)₂)_s—(C₆-C₁₀)aryl, wherein s is 0, 1, or 2, wherein each aryl portion of said —O—(C₆-C₁₀)aryl, (C₂-C₁₀)heteroaryl portion of said —(C(R²)₂)_s—(C₂-C₁₀)heteroaryl, each heteroaryl portion of said —O—(C₂-C₁₀)heteroaryl, each (C₆-C₁₀)aryl portion of said —C(R²)═C(R²)—(C₆-C₁₀)aryl each (C₂-C₁₀)heteroaryl portion of said —C(R²)═C(R²)—(C₂-C₁₀)heteroaryl, each (C₆-C₁₀)aryl portion of said —S—(C₆-C₁₀)aryl, each (C₆-C₁₀)aryl portion of said —S(O)₂—(C₆-C₁₀)aryl, each (C₂-C₁₀)heteroaryl portion of said —S(O)₂—(C₂-C₁₀)heteroaryl, each (C₆-C₁₀)aryl portion of said —C(O)—(C₆-C₁₀)aryl, each (C₂-C₁₀)heteroaryl portion of said —C(O)—(C₂-C₁₀)heteroaryl, each (C₆-C₁₀)aryl portion of said —(C(R₃)₂)_s—(C₆-C₁₀)aryl, each (C₆-C₁₀)aryl portion of said —C(S—(C₁-C₆)alkyl)═N—S(O)₂—(C₆-C₁₀)aryl, each (C₆-C₁₀)aryl portion of said —C(N(R²)₂)═N—S(O)₂—(C₆-C₁₀)aryl, each benzo portion of said benzo-fused (C₃-C₁₀)cycloalkyl, each benzo portion of said benzo-fused (C₂-C₁₀)heterocycloalkyl, and each benzo portion of said benzo-fused (C₂-C₁₀)heterocycloalkenyl of X is unsubstituted or optionally substituted with one or more groups independently selected from —C(═NH)—O—(C₁-C₆), —C(═N—(C₁-C₁₆)alkyl)-O—(C₂-C₆)alkyl, —C(O)OH), —(C₁-C₆)alkylene-O—(C₂-C₁₀)heterocycloalkyl, Y¹ and Y³, each said (C₃-C₁₀)cycloalkyl, each (C₃-C₁₀)cycloalkyl portion of said —S(O)₂—(C₃-C₁₀)cycloalkyl, each (C₂-C₁₀)heterocycloalkyl, each (C₃-C₁₀)cycloalkyl portion of said benzo-fused (C₃-C₁₀)cycloalkyl, each (C₂-C₁₀)heterocycloalkyl portion of said benzo-fused (C₂-C₁₀)heterocycloalkyl, and each (C₂-C₁₀)heterocycloalkenyl portion of said benzo-fused (C₂-C₁₀)heterocycloalkenyl of X is unsubstituted or optionally substituted with one or more groups independently selected from Y²;

each R¹ is independently selected from the group consisting of (C₁-C₆)alkyl, (C₁-C₆)haloalkyl, —(C₁-C₆)alkylene-N(R⁵)₂, —(C₁-C₆)alkylene-OR², —(C₁-C₆)alkylene-N₃, —(C₁-C₆)alkylene-CN, and (C₁-C₆)alkylene-O—S(O)₂—(C₁-C₆)alkyl; or two R¹ groups attached to the same ring carbon atom form a carbonyl group;

p is 0, 1,2,3 or 4;

each R² is independently H, (C₁-C₆)alkyl, (C₆-C₁₀)aryl, (C₂-C₁₀)heteroaryl, (C₃-C₁₀)cycloalkyl, or (C₂-C₁₀)heterocycloalkyl, wherein each said (C₆-C₁₀)aryl (C₂-C₁₀)heteroaryl, (C₃-C₁₀)cycloalkyl, or (C₂-C₁₀)heterocycloalkyl of R² is optionally unsubstituted or substituted with one or more groups independently selected from Y¹ and Y³;

each R³ is independently selected from the group consisting of H, (C₁-C₆)alkyl, —OR², —(C₁-C₆)alkylene-O—(C₁-C₆)alkyl, —(C₁-C₆)alkylene-OH, unsubstituted (C₆-C₁₀)aryl, and (C₆-C₁₀)aryl substituted with one or more groups independently selected from Y¹ and Y³;

each R⁴ is independently selected from the group consisting of H, (C₁-C₆)alkyl, (C₆-C₁₀)aryl, —C(O)—O—(C₁-C₆)alkyl, —C(O)—(C₁-C₆)alkyl, —C(O)—(C₆-C₁₀)aryl, —C(O)—(C₂-C₁₀)heteroaryl, —C(O)—(C₃-C₁₀)heterocycloalkyl) —S(O)₂(C₁-C₆)alkyl, —S(O)₂(C₆-C₁₀)aryl, —S(O)₂(C₂-C₁₀)heteroaryl) and —S(O)₂ (C₃-C₁₀)heterocycloalkyl;

wherein each said (C₆-C₁₀)aryl, each aryl portion of said —C(O)—(C₆-C₁₀)aryl, each aryl portion of said —S(O)₂(C₆-C₁₀)aryl, and each heteroaryl portion of said —C(O)—(C₂-C₁₀)heteroaryl and said —S(O)₂(C₂-C₁₀)heteroaryl of R⁴ is unsubstituted or optionally substituted with one or more groups independently selected from Y¹ and Y³;

each R⁵ is independently selected from the group consisting of H, (C₁-C₆)alkyl, (C₆-C₁₀)aryl, —S(O)₂—(C₁-C₆)alkyl, —S(O)₂—(C₃-C₁₀)cycloalkyl, —S(O)₂-aryl, —C(O)—N(R²)₂, —C(O)—(C₁-C₆)alkyl, and —(C₁-C₆)alkylene-OH, wherein each said (C₆-C₁₀)aryl and each (C₆-C₁₀)aryl portion of said —S(O)₂—(C₆-C₁₀)aryl of R⁵ are unsubstituted or optionally substituted with one or more groups independently selected from Z;

each Y¹ is independently selected from the group consisting of (C₁-C₆)alkyl, (C₃-C₁₀)cycloalkyl, (C₂-C₁₀)heterocycloalkyl, (C₂-C₁₀)heterocycloalkenyl, halo, (C₁-C₆)haloalkyl, benzyl, (C₆-C₁₀)aryl, (C₂-C₁₀)heteroaryl, —O—(C₆-C₁₀)alkyl, —O—(C₆-C₁₀)aryl, —O—(C₂-C₁₀)heteroaryl, —O—(C₃-C₁₀)cycloalkyl, —O—(C₂-C₁₀)heterocycloalkyl, —S—(C₁-C₆)alkyl, —S—(C₁-C₆)aryl, —S—(C₂-C₁₀)heteroaryl, —S—(C₃-C₁₀)cycloalkyl, —S—(C₂-C₁₀)heterocycloalkyl, —S(O)₂—(C₁-C₆)alkyl, ≥S(O)₂—(C₆-C₁₀)aryl, —S(O)₂—(C₂-C₁₀)heteroaryl, —S(O)₂—(C₃-C₁₀)cycloalkyl, —S(O)₂—(C₂-C₁₀)heterocycloalkyl, -alkylene-ON, —CN, —C(O)—(C₁-C₆)alkyl, —C(O)—(C₆-C₁₀)aryl, —C(O)—(C₁-C₆)haloalkyl, —C(O)—(C₂-C₁₀)heteroaryl, —C(O)—(C₃-C₁₀)cycloalkyl, —C(O)—(C₂-C₁₀)heterocycloalkyl, —C(O)O-alkyl, —C(O)O—(C₆-C₁₀)aryl, —C(O)O—(C₁-C₆)haloalkyl, —C(O)O—(C₂-C₁₀)heteroaryl, —C(O)O—(C₃-C₁₀)cycloalkyl, —C(O)O—(C₂-C₁₀)heterocycloalkyl —N(R²)C(O)-alkyl, —N(R²)C(O)—N(R²)₂, —OH, —O—(C₁-C₆)alkyl, —O—(C₁-C₆)haloalkyl, —O—(C₁-C₆)alkylene-C(O)OH, —S—(C₁-C₆)alkyl, —S—(C₁-C₆)haloalkyl, —(C₁-C₆)alkylene-OH, —(C₁-C₆)alkylene-C(O)—O—(C₁-C₆)alkyl, —O—(C₁-C₆)alkylene-(C₆-C₁₀)aryl, and —N(R⁵)₂, wherein each each (C₆-C₁₀)aryl, each (C₆-C₁₀)heteroaryl, each aryl portion of said —O—(C₆-C₁₀)aryl, each aryl portion of said —S—(C₆-C₁₀)aryl, each aryl portion of said —S(O)₂—(C₆-C₁₀ )aryl, each aryl portion of said —C(O)—(C₆-C₁₀)aryl each aryl portion of said —C(O)O—(C₆-C₁₀)aryl, each aryl portion of said benzyl, and each aryl portion of said —O—(C₁-C₆)alkylene-aryl of Y¹, and each heteroaryl portion of said —O—(C₂-C₁₀)heteroaryl, each heteroaryl portion of said —S—(C₂-C₁₀)heteroaryl, each heteroaryl portion of said —S(O)₂—(C₂-C₁₀)heteroaryl, each heteroaryl portion of said —C(O)—(C₂-C₁₀)heteroaryl, each heteroaryl portion of said —C(O)O—(C₂-C₁₀)heteroaryl, each heteroaryl portion of said —O—(C₁-C₆)alkylene-(C₂-C₁₀)heteroaryl of Y¹ are unsubstituted or optionally substituted with one or more groups independently selected from Z; or two groups $Y^1$ form a —O—CH$_2$—O— group;

each $Y^2$ is independently selected from the group consisting of (C$_1$-C$_6$)alkyl, (C$_1$-C$_6$)haloalkyl, (C$_6$-C$_{10}$)aryl, —(C$_1$-C$_6$)alkylene-(C$_6$-C$_{10}$)aryl, —CN, —OH, —C(O)—(C$_1$-C$_6$)alkyl, —S(O)$_2$—(C$_3$-C$_{10}$)cycloalkyl, —(C$_1$-C$_6$)alkylene-N(R$^4$)$_2$, —C(O)—(C$_1$-C$_6$)alkylene-N(R$^4$)$_2$, —C(O)—O—(C$_1$-C$_6$)alkyl, —C(O)—(C$_6$-C$_{10}$)aryl, and —C(O)—(C$_1$-C$_6$)haloalkyl, wherein each said (C$_6$-C$_{10}$)aryl and each (C$_6$-C$_{10}$)aryl portion of said —C(O)—(C$_6$-C$_{10}$)aryl of $Y^2$ are unsubstituted or optionally substituted with one or more groups independently selected from Z; or two groups $Y^2$ form a —O—CH$_2$CH$_2$—O— group; or two of said $Y^2$ substituents attached to the same ring carbon atom of a (C$_3$-C$_{10}$)cycloalkyl, benzo-fused (C$_3$-C$_{10}$)cycloalkyl, benzo-fused (C$_2$-C$_{10}$)heterocycloalkyl, benzo-fused (C$_2$-C$_{10}$)heterocycloalkenyl, or (C$_2$-C$_{10}$)heterocycloalkyl ring, together with the ring carbon atom to which they are both attached, form a carbonyl group;

each $Y^3$ is independently selected from —C(O)N(R$^6$)$_2$, —S(O)$_2$N(R$_6$)$_2$, —O-Q-L$_1$-R$^7$, —O-Q-L$_2$-R$^8$, —O-Q-CN, —O-Q—C(O)N(R$^6$)$_2$, —O-Q-S(O)$_2$N(R$^6$)$_2$, —O-Q-OC(O)N(R$^6$)$_2$, and —O-Q-N(R$^6$)C(O)N(R$^6$)$_2$;

with the proviso that when A is —C(O)—, or when m=n=0 and X is —C(O)—(C$_6$-C$_{10}$)aryl or —C(O)—(C$_2$-C$_{10}$)heteroaryl, then Ar$^2$ is substituted with at least one $Y^1$ or $Y^3$ group independently selected from (C$_3$-C$_{10}$)cycloalkyl, benzyl, (C$_6$-C$_{10}$)aryl, —O—(C$_1$-C$_6$)haloalkyl, —O—(C$_6$-C$_{10}$)aryl, —O—(C$_3$-C$_{10}$)cycloalkyl, —S—(C$_6$-C$_{10}$)aryl, —S—C(C$_1$-C$_6$)haloalkyl, —S—(C$_3$-C$_{10}$)cycloalkyl, —S(O)$_2$-(C$_1$-C$_6$)alkyl, —S(O)$_2$—(C$_3$-C$_{10}$)cycloalkyl, —S(O)$_2$—(C$_6$-C$_{10}$)aryl, —(C$_1$-C$_6$)alkylene-CN, —C(O)—(C$_6$-C$_{10}$)aryl —C(O)—(C$_1$-C$_6$)haloalkyl, —C(O)—(C$_3$-C$_{10}$)cycloalkyl, —C(O)O—(C$_6$-C$_{10}$)aryl, —C(O)O—(C$_1$-C$_6$)haloalkyl, —C(O)O—(C$_2$-C$_{10}$)heteroaryl, —C(O)O—(C$_3$-C$_{10}$)cycloalkyl, —C(O)O—(C$_2$-C$_{10}$)heterocycloalkyl, —(C$_1$-C$_{10}$)alkylene-C(O)—O—(C$_1$-C$_6$)alkyl, and —O—(C$_1$-C$_6$)alkylene-(C$_6$-C$_{10}$)aryl, wherein each benzyl and each (C$_6$-C$_{10}$)aryl portion of said $Y^1$ or $Y^3$ group and each aryl portion and each heteroaryl portion of said —O—(C$_6$-C$_{10}$)aryl, said —S—(C$_6$-C$_{10}$)aryl, said —S(O)$_2$—(C$_6$-C$_{10}$)aryl, said —C(O)—(C$_6$-C$_{10}$)aryl, said —C(O)O—(C$_6$-C$_{10}$)aryl, —C(O)O—(C$_2$-C$_{10}$)heteroaryl, —C(O)O—(C2-C$_{10}$)heterocycloalkyl, and —O—(C$_1$-C$_6$)alkylene-(C$_6$-C$_{10}$)aryl of said $Y^1$ or $Y^3$ group is unsubstituted or substituted with one or more groups independently selected from Z;

each -Q- is a divalent radical independently selected from —(C$_1$-C$_6$)alkylene-—(C$_1$-C$_6$)alkenylene-, —(C$_1$-C$_{10}$)alkynylene-, —(C$_3$-C$_{10}$)cycloalkylene-, —(C$_2$-C$_{10}$)heterocycloalkylene-, —(C$_1$-C$_6$)alkylene-(C$_3$-C$_{10}$)cycloalkylene-, —(C3-C$_{10}$)cycloalkylene-(C$_1$-C$_6$)alkylene-, —(C$_3$-C$_{10}$)cycloalkylene-(C$_1$-C$_6$)alkylene-(C$_3$-C$_{10}$)cycloalkylene-wherein the alkylene, alkenylene, alkynylene, cycloalkylene, and heterocycloalkylene portion of said Q is optionally substituted with one to three groups independently selected from

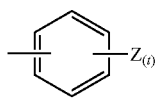

and Z, wherein t is 0, 1, 2, or 3;

each $L_1$ is independently selected from the group consisting of —O—, —S—, —S(O)—, —S(O)$_2$—, —OS(O)$_2$—, —C(O)—, and —OC(O)—;

each $L_2$ is —C(O)O—;

each $R^6$ is independently selected from the group consisting of H, (C$_1$-C$_6$)alkyl, (C$_1$-C$_6$)halo alkyl, (C$_1$-C$_6$)alkoxy, (C$_3$-C$_{10}$)cycloalkyl, (C$_3$-C$_{10}$)heterocycloalkyl, unsubstituted (C$_6$-C$_{10}$)aryl, (C$_6$-C$_{10}$)aryl substituted with on or more groups independently selected from $Y^1$ unsubstituted (C$_2$-C$_{10}$)heteroaryl, (C$_2$-C$_{10}$)heteroaryl substituted with one or more groups independently selected from $Y^1$, (C$_3$-C$_{10}$)cycloalkyl, (C$_2$-C$_{10}$)heterocycloalkyl, —(C$_1$-C$_6$)alkylene-OH, —(C$_1$-C$_6$)alkylene-O—(C$_1$-C$_6$)alkyl, —(C$_1$-C$_6$)alkylene-O—(C$_6$-C$_{10}$)aryl, —(C$_1$-C$_6$)alkylene-OC(O)—(C$_1$-C$_6$)alkyl, —(C$_1$-C$_6$)alkylene-OC(O)—(C$_6$-C$_{10}$)aryl, —(C$_1$-C$_6$)alkylene-OC(O)—(C$_2$-C$_{10}$)heteroaryl, and (C$_1$-C$_6$)alkylene-N(R$_4$)$_2$, or two $R^6$ groups, together with the nitrogen to which they are attached, form a (C$_2$-C$_{10}$)heteroaryl, (C$_2$-C$_{10}$)heterocycloalkyl, (C$_2$-C$_{10}$)heterocycloalkenyl, or a benzo-fused (C$_2$-C$_{10}$)heterocycloalkyl group;

each $R^7$ is independently selected from the group consisting of H, (C$_1$-C$_6$)alkyl, —N(R$^6$)$_2$, (C$_3$-C$_{10}$)cycloalkyl, (C$_2$-C$_{10}$)heterocycloalkyl, (C$_6$-C$_{10}$)aryl, substituted (C$_6$-C$_{10}$)aryl, (C$_2$-C$_{10}$)heteroaryl, and substituted (C$_2$-C$_{10}$)heteroaryl, wherein said substituents are independently selected from Z and —C(O)N(R$^6$)$_2$;

each $R^8$ is independently selected from the group consisting of (C$_1$-C$_6$)alkyl, —N(R$^6$)$_2$, (C$_3$-C$_{10}$)cycloalkyl, (C$_2$-C$_{10}$)heterocycloalkyl, (C$_6$-C$_{10}$)aryl, substituted (C$_6$-C$_{10}$)aryl, (C$_2$-C$_{10}$)heteroaryl, and substituted (C$_2$-C$_{10}$)heteroaryl, wherein said substituents are independently selected from Z and —C(O)N(R$^6$)$_2$; and each Z is independently selected from the group consisting of (C$_1$-C$_6$)alkyl, halo, (C$_1$-C$_6$)haloalkyl, —OH, —O—(C$_1$-C$_6$)alkyl, and —CN.

In another embodiment, in Formula (I), at least one group $Y^3$ is —C(O)N(R$^6$)$_2$.

In another embodiment, in Formula (I), at least one group $Y^3$ is —C(O)N(R$^6$)$_2$, wherein each $R^6$ is independently selected from H, alkyl, and -alkylene-OH.

In another embodiment, in Formula (I), at least one group $Y^3$ is —O-Q-L$_1$-R$^7$.

In another embodiment, in Formula (I), at least one group $Y^3$ is —O-Q-L$_1$-R$^7$, wherein -Q- is unsubstituted -alkylene-.

In another embodiment, in Formula (I), at least one group $Y^3$ is —O-Q-L$_1$-R$^7$, wherein -Q- is -alkylene- substituted with from one to three groups independently selected from

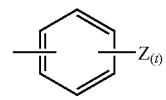

and Z, wherein t is 0, 1, 2, or 3.

In another embodiment, in Formula (I), at least one group $Y^3$ is —O-Q-L$_1$-R$^7$, wherein -Q- is -alkylene- substituted with methyl and

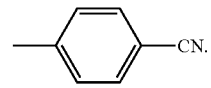

In another embodiment, in Formula (I), at least one group $Y^3$ is —O-Q-$L_1$-$R^7$, wherein -Q- is -alkylene- substituted with one to three groups Z, wherein each Z is independently selected from -alkyl.

In another embodiment, in Formula (I), at least one group $Y^3$ is —O-Q-$L_1$-$R^7$, wherein $L_1$ is —O—.

In another embodiment, in Formula (I), at least one group $Y^3$ is —O-Q-$L_1$-$R^7$, wherein $L_1$ is —OC(O)—.

In another embodiment, in Formula (I), at least one group $Y^3$ is —O-Q-$L_1$-$R^7$, wherein $R^7$ is selected from H, alkyl, —N($R^6$)$_2$, cycloalkyl, and heterocycloalkyl. In one such embodiment, $R^7$ is NH$_2$. In another such embodiment, $R^7$ is tetrahydropyran a In another embodiment, in Formula (I), at least one group $Y^3$ is

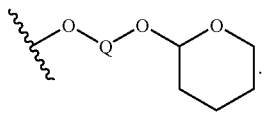

In another embodiment, in Formula (I), at least one group $Y^3$ is

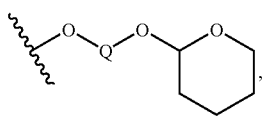

wherein Q is unsubstituted -alkylene-. In another such embodiment, Q is -alkylene- substituted with from one to three groups independently selected from

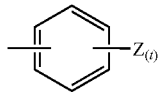

and Z, wherein t is 0, 1, 2, or 3.

In another embodiment, in Formula (I), at least one group $Y^3$ is —O-Q-$L_2$-$R^8$. In one such embodiment, $R^8$ is selected from H, alkyl, —N($R^6$)$_2$, cycloalkyl, and heterocycloalkyl. In one such embodiment, $R^8$ is NH$_2$. In another such embodiment, $R^8$ is cyclopropyl.

In another embodiment, in Formula (I), at least one group $Y^3$ is —O-Q-CN.

In another embodiment, in Formula (I), $Ar^1$ and $Ar^2$ are aryl.

In another embodiment, in Formula (I), $Ar^1$ is phenyl.

In another embodiment, in Formula (I), $Ar^2$ is phenyl.

In another embodiment, in Formula (I), both $Ar^1$ and $Ar^2$ are phenyl.

In another embodiment, in Formula (I), $Ar^2$ is phenyl substituted with one $Y^3$ group and one $Y^1$ group.

In another embodiment, in Formula (I), $Ar^2$ is phenyl substituted with one $Y^3$ group in the 4-position of the ring (relative to the ring's point of attachment to the piperazine nitrogen) and one $Y^1$ group in the 2-position (relative to the ring's point of attachment to the piperazine nitrogen).

In another embodiment, in Formula (I), $Ar^1$ is phenyl substituted with one or more groups independently selected from $Y^1$ and $Y^3$.

In another embodiment, in Formula (I), $Ar^1$ is phenyl substituted with one $Y^1$ group at the 4-position.

In another embodiment, in Formula (I), $Ar^1$ is aryl and $Ar^2$ is heteroaryl.

In another embodiment, in Formula (I), $Ar^1$ is phenyl and $A^2$ is pyridyl.

In another embodiment, in Formula (I), $Ar^1$ is heteroaryl and $Ar^2$ is aryl.

In another embodiment, in Formula (I) $Ar^1$ is pyridyl and $Ar^2$ is phenyl,

In another embodiment, in Formula (I), $Ar^1$ and $Ar^2$ are heteroaryl.

In another embodiment, in Formula (I), $Ar^1$ is pyridyl.

In another embodiment, in Formula (I), $Ar^2$ is pyridyl,

In another embodiment, in Formula (I), both $Ar^1$ and $Ar^2$ are pyridyl.

In another embodiment, in Formula (I), $Ar^2$ is pyridyl substituted with one $Y^3$ group and one $Y^1$ group.

In another embodiment, in Formula (I), $Ar^2$ is pyridyl substituted with one $Y^3$ group in the 2-position and one $Y^1$ group in the 4-position, relative to the point of attachment to the piperazine ring.

In another embodiment, in Formula (I), $Ar^1$ is pyridyl substituted with one or more groups independently selected from $Y^1$ and $Y^3$.

In another embodiment, in Formula (I), $Ar^1$ is pyridyl substituted with one $Y^1$ group at the 4-position, relative to the point of attachment to the piperazine ring.

In another embodiment, in Formula (I), $Ar^2$ is:

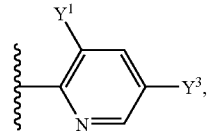

wherein $Y^1$ and $Y^3$ are as defined herein.

In another embodiment, in Formula (I), $Ar^1$ or $Ar^2$ is substituted with one $Y^3$ group.

In another embodiment, in Formula (I), $Ar^1$ or $Ar^2$ is substituted with two $Y^3$ groups.

In another embodiment, in Formula (I), $Ar^1$ or $Ar^2$ is substituted with three $Y^3$ groups.

In another embodiment, in Formula (I), $Ar^1$ or $Ar^2$ is substituted with four $Y^3$ groups.

In another embodiment, in Formula (I), $Ar^1$ or $Ar^2$ is substituted with five $Y^3$ groups.

In another embodiment, in Formula (I), $Ar^1$ and/or $Ar^2$ is substituted with two $Y^1$ groups.

In another embodiment, in Formula (I), $Ar^1$ and/or $Ar^2$ is substituted with three $Y^1$ groups.

In another embodiment, in Formula (I), $Ar^1$ and/or $Ar^2$ is substituted with four $Y^1$ groups.

In another embodiment, in Formula (I), each $Y^1$ is independently selected from halo, CN, and alkyl, including ($C_1$-$C_6$) alkyl. In one such embodiment, each $Y^1$ is independently selected from Cl, F, CN, and methyl.

In another embodiment, in Formula (I), m=0 and n=0.

In another embodiment, in Formula (I), m=0, n=1, and B is —(C($R^3$)$_2$)$_r$—. In one such embodiment, r=1. In another such embodiment each $R^3$ is independently selected from H and -alkylene-OH. In another such embodiment, each $R^3$ is independently selected from H and —(CH$_2$)—OH. In another such embodiment, each $R^3$ is independently selected from H and —(CH$_2$)$_2$—OH. In another such embodiment, each R$^3$ is independently selected from H and —(CH$_2$)$_3$—OH.

In another embodiment, in Formula (I), m=0, n=1, and B is —(C(R$^3$)$_2$)$_r$—, wherein r=1, and each R$^3$ is independently selected from H and -alkyl. In another such embodiment, each R$^3$ is independently selected from H and methyl. In another such embodiment, each R$^3$ is independently selected from H and ethyl.

In another embodiment, in Formula (I), m=1, n=0, and A is —(C(R$^2$)$_2$)$_q$—. In one such embodiment, each R$^2$ is independently H or alkyl. In another such embodiment, q is 1 and each R$^2$ is H. In another such embodiment, q is 2 and each R$^2$ is independently selected from H and alkyl.

In another embodiment, in Formula (I), m=1, n=0, and A is —C(O)—.

In another embodiment, in Formula (I), m=1 n=0, and A is —S(O)$_2$—.

In another embodiment, in Formula (I), m=1, n=1, and A is —(C(R$^2$)$_2$)$_q$— and B is —(C(R$^3$)$_2$)$_r$—. In one such embodiment, each R$^2$ is H. In one such embodiment, r=1. In another such embodiment, q=1. In another such embodiment, each R$^3$ is independently selected from alkyl and —OR$^2$, wherein each R$^2$ is independently H or alkyl. In another such embodiment, m=1, n=1, and A is —CH$_2$—, and B is —C(CH$_3$)(OH)—. In another such embodiment, m=1, n=1, and A is —CH$_2$—, and B is —CH(OH)—.

In another embodiment, in Formula (I), m=1, n=1, A is —C(=N—OR$^2$)—. In one such embodiment, R$^2$ is H.

In another embodiment, in Formula (I), m=1, n=1, A is —(C(R$^2$)$_2$)$_q$— and B is —C(O)—. In one such embodiment, q is 1. In another such embodiment, q is 1 and R$^2$ is H.

In another embodiment, in Formula (I), m=1, n=1, A is —C(O)—, and B is —(C(R$^3$)$_2$)$_r$—. In one such embodiment, each R$^3$ is independently selected from H, —OH and -alkyl. In one such embodiment, r is 1. in another such embodiment, r is 1 and each R$^3$ is independently selected from H and alkyl. In another such embodiment, r=1 and B is selected from —C(OH)(CH$_3$)—, —C(OH)(CH$_2$CH$_3$)—, —C(OH)H—. In another such embodiment, r=1 and B is —CH$_2$—.

In another embodiment, in Formula (I), m=1, n=1, A is —C(O)—, and B is —N(R$^6$)—. In one such embodiment, R$^6$ is H.

In another embodiment, in Formula (I), X is H.
In another embodiment, in Formula (I), X is alkyl.
In another embodiment, in Formula (I), X is cycloalkyl.
In another embodiment, in Formula (I), X is cyclopropyl.
In another embodiment, in Formula (I), X is —(C(R$^2$)$_2$)$_s$-aryl, wherein the aryl portion of X is unsubstituted.

In another embodiment, in Formula (I), X is —(C(R$^2$)$_2$)$_s$-aryl, wherein the aryl portion of X is substituted with one or more groups independently selected from —C(=NH)—O-alkyl, —C(=N-alkyl)-O-alkyl, —C(O)OH, -alkylene-O-heterocycloalkyl, Y$^1$ and Y$^3$.

In another embodiment, in Formula (I), X is —(C(R$^2$)$_2$)$_s$-heteroaryl, wherein the heteroaryl portion of X is unsubstituted.

In another embodiment, in Formula (I), X is —(C(R$^2$)$_2$)$_s$-heteroaryl, wherein the heteroaryl portion of X is substituted with one or more groups independently selected from —C(=NH)-O-alkyl, —C(=N-alkyl)-O-alkyl, —C(O)OH, -alkylene-O-heterocycloalkyl, Y$^1$ and Y$^3$.

In another embodiment, in Formula (I), p=0.
In another embodiment, in Formula (I), p=1, and R$^1$ is alkyl.
In another embodiment, in Formula (I), p=1, and R$^1$ is methyl In another embodiment, in Formula (I), p=2. In one such embodiment, two groups R$^1$ are taken together to form a carbonyl group.

In another embodiment, in Formula (I), the present invention relates to compounds, pharmaceutically acceptable salts, solvates, esters, or isomers of the following Formula (IA):

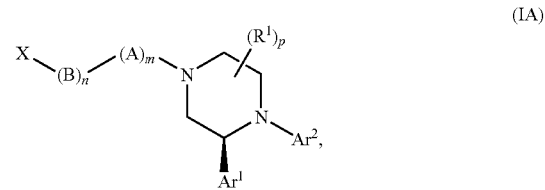

wherein the variables of the formula (e.g., X, B, A, R$^1$, Ar$^1$, Ar$^2$, n, m, and p) are as defined in Formula (I) above.

In another embodiment of Formula (I), the present invention relates to compounds, pharmaceutically acceptable salts, solvates, esters, or isomers of the following Formula (IB):

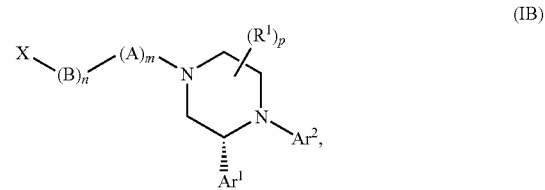

wherein the variables of the formula (e.g., X, B, A, R$^1$, Ar$^1$, Ar$^2$, n, m, and p) are as defined in Formula (I) above.

In another embodiment of Formula (I), the present invention relates to compounds, pharmaceutically acceptable salts, solvates, esters, or isomers of the following Formula (IC):

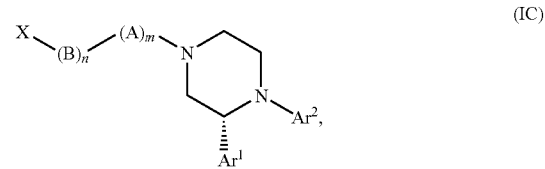

wherein the variables of the formula (e.g., X, B, A, R$^1$, Ar$^1$, Ar$^2$, n, m, and p) are as defined in Formula (I) above.

In embodiments where n=1 and m=1, then X is attached to B, B is attached to A, and A is attached to the nitrogen of the piperazine ring as shown in the following formula.

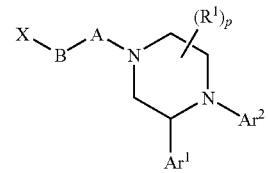

In embodiments where n=0 and m=1, then X is attached directly to A and A is attached to the nitrogen of the piperazine ring as shown in the following formula:

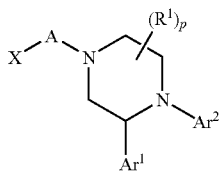

In embodiments where n=1 and m=0, then X is attached to B and B is attached directly to the nitrogen of the piperazine ring as shown in the following formula:

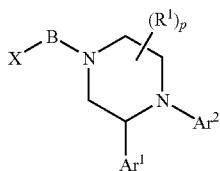

In embodiments where both n and m=0, then X is attached directly to the nitrogen of the piperazine ring as shown in the following formula:

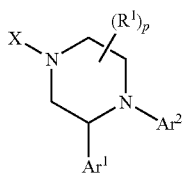

In another embodiment of the compounds of the present invention, or pharmaceutically acceptable salts, solvates, esters, or isomers thereof, is a compound of the formula:

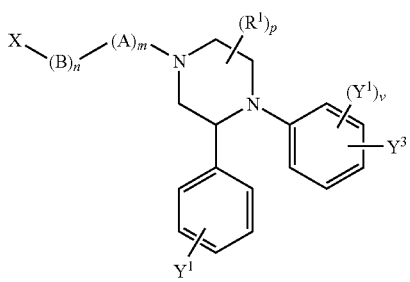

wherein:

each $R^1$ is independently selected from alkyl and —C(O)—;

p is 0, 1,or2;

$Y^3$ is selected from —C(O)N($R^6$)$_2$, —S(O)$_2$N($R^6$)$_2$, —O-Q-$L_1$-$R^7$, —O-Q-$L_2$-$R^8$, and —O-Q-CN, with the proviso that when A is —C(O)—, then $Y^3$ is not —C(O)N(H)$_2$, —C(O)NH($C_1$-$C_6$)alkyl, —C(O)N(($C_1$-$C_6$)alkyl)$_2$, —S(O)$_2$N(H)$_2$, —S(O)$_2$NH($C_1$-$C_6$)alkyl, or —S(O)$_2$N(($C_1$-$C_6$)alkyl)$_2$;

Q is unsubstituted -alkylene- or -alkylene- substituted with from one to three groups independently selected from

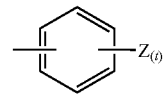

and Z, wherein t is 0, 1, 2, or3;

each $Y^1$ is independently selected from halo, —CN, and alkyl;

v is 0 or 1;

X is selected from H, alkyl, cycloalkyl, —C(($R^2$)$_2$)$_s$-aryl, —C((R2)$_2$)$_s$-heteroaryl, —OR$_2$, —O-aryl, and —O-heteroaryl, wherein said aryl and said heteroaryl portions of X are unsubstituted or substituted with from one to three groups independently selected from —C(=NH)—O-alkyl, —C(=N-alkyl)-O-alkyl, —C(O)OH, -alkylene-0-heterocycloalkyl, $Y^1$ and $Y^3$;

and A, B, $R^2$, $R^6$, $R^7$, $R^8$, $L_1$, $L_2$, Z, n, m and s are as defined above.

In another embodiment of the compounds of the present invention, or pharmaceutically acceptable salts, solvates, esters, or isomers thereof, is a compound of the formula:

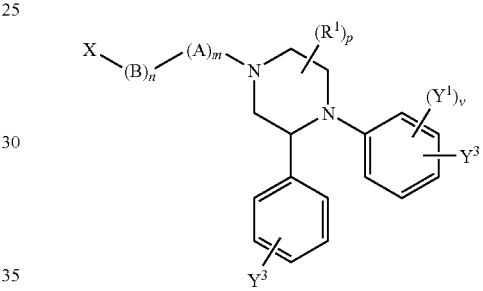

wherein:

each $R^1$ is independently selected from alkyl and —C(O)—;

p is 0, 1,or 2;

$Y^3$ is selected from —C(O)N($R^6$)$^2$, —S(O)$_2$N($R^6$)$_2$, —O-Q-$L_1$-$R^7$, —O-Q-$L_2$-$R^8$, and 13 O-Q-CN, with the proviso that when A is —C(O)—, then $Y^3$ is not —C(O)N(H)$_2$, —C(O)NH($C_1$-$C_6$)alkyl, —C(O)N(($C_1$-$C_6$)alkyl)$_2$, —S(O)$_2$N(H)$_2$, —S(O)$_2$NH($C_1$-$C_6$)alkyl, or —S(O)$_2$N(($C_1$-$C_6$)alkyl)$_2$;

Q is unsubstituted -alkylene- or -alkylene- substituted with from one to three groups independently selected from

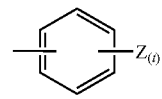

and Z, wherein t is 0, 1, 2, or 3;

each $Y^1$ is independently selected from halo, —CN, and alkyl;

v is 0 or 1;

X is selected from H, alkyl, cycloalkyl, —C(($R^2$)$_2$)$_s$-aryl, —C(($R^2$)$_2$)$_s$-heteroaryl, —OR$_2$, —O-aryl, and —O-heteroaryl, wherein said aryl and said heteroaryl portions of X are unsubstituted or substituted with from one to three groups independently selected from —C(=NH)—O-alkyl, —C(=N-alkyl)-O-alkyl, —C(O)OH, -alkylene-O-heterocycloalkyl, $Y^1$ and $Y^3$;

and A, B, $R^2$, $R^6$, $R^7$, $R^8$, $L_1$, $L_2$, Z, n, m and s are as defined above.

In another embodiment of the compounds of the present invention, or pharmaceutically acceptable salts, solvates, esters, or isomers thereof, is a compound of the formula:

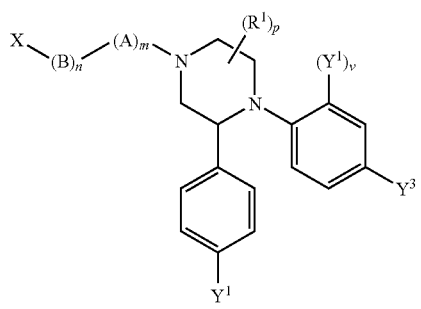

wherein:
each $R^1$ is independently selected from alkyl and —C(O)—;
p is 0, 1, or 2;
$Y^3$ is —C(O)N($R^6$)$_2$,
with the proviso that when A is —C(O)—, then $Y^3$ is not —C(O)N(H)$_2$, —C(O)NH($C_1$-$C_6$)alkyl, or —C(O)N(($C_1$-$C_6$)alkyl)$_2$;
each $R^6$ is independently selected from H, alkyl, and -alkylene-OH;
each $Y^1$ is independently selected from halo, —CN, and alkyl;
v is 0 or 1;
X is selected from H, alkyl, cycloalkyl, —C(($R^2$)$_2$)$_s$-aryl, —C(($R^2$)$_2$)$_s$-heteroaryl, —O$R_2$, —O-aryl, and —O-heteroaryl, wherein said aryl and said heteroaryl portions of X are unsubstituted or substituted with from one to three groups independently selected from —C(═NH)—O-alkyl, —C(═N-alkyl)-O-alkyl, —C(O)OH, -alkylene-O-heterocycloalkyl, $Y^1$ and $Y^3$;
and $R^2$, A, B, n, m, and s are as defined above.

In another embodiment of the compounds of the present invention, or pharmaceutically acceptable salts, solvates, esters, or isomers thereof, is a compound of the formula:

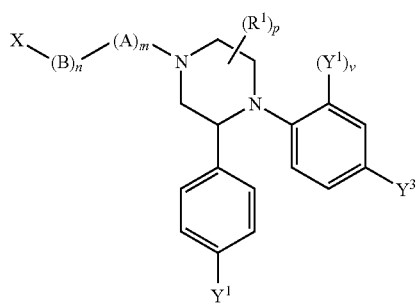

wherein:
each $R^1$ is independently selected from alkyl and —C(O)—;
p is 0, 1, or 2;
$Y^3$ selected from —O-$L_1$-$R^7$, —O-Q-$L_2R^8$, or —O-Q-CN;
Q is unsubstituted -alkylene- or -alkylene- substituted with from one to three groups independently selected from

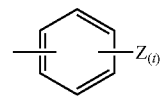

and Z, wherein t is 0, 1, 2, or 3;
each Z is independently selected from alkyl, halo, haloalkyl, —OH, —O-alkyl, and —CN;
$L_1$ is —O— or —OC(O)—;
$L_2$ is —C(O)O—;
$R^7$ is selected from H, alkyl, —NH$_2$, cycloalkyl, and heterocycloalkyl;
$R^8$ is selected from alkyl, —NH$_2$, cycloalkyl, and heterocycloalkyl;
each $Y^1$ is independently selected from halo, —CN, and alkyl;
v is 0 or 1;
X is selected from H, alkyl, cycloalkyl, —C(($R^2$)$_2$)$_s$-aryl, —C(($R^2$)$_2$)$_s$-heteroaryl, —O$R_2$, —O-aryl, and —O-heteroaryl, wherein said aryl and said heteroaryl portions of X are, independently, unsubstituted or substituted with one or more groups independently selected from —C(═NH)—O-alkyl, —C(═N-alkyl)-O-alkyl, —C(O)OH, -alkylene-O-heterocycloalkyl, $Y^1$ and $Y^3$;
and $R^2$, A, B, n, m, and s are as defined above, In another embodiment of the compounds of the present invention, or pharmaceutically acceptable salts, solvates, esters, or isomers thereof, is a compound of the formula:

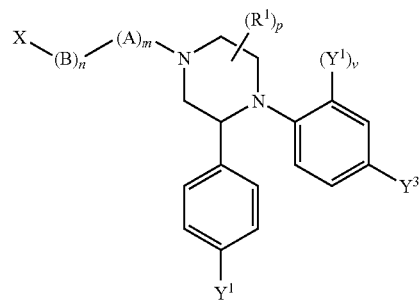

wherein:
each $R^1$ is independently selected from alkyl and —C(O)—;
p is 0, 1, or 2;
$Y^3$ is selected from —O-Q-$L_1$-$R^7$, —O-Q-$L_2$-$R^8$, or —O-Q-CN;
Q is unsubstituted —($C_1$ to $C_3$)alkylene- or —($C_1$ to $C_3$)alkylene- substituted with

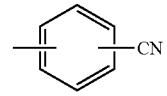

or one to three groups independently selected from alkyl;
$L_1$ is —O— or —OC(O)—;
$L_2$ is —C(O)O—;
$R^7$ is selected from H, alkyl, —N($R^6$)$_2$, cyclopropyl, and tetrahydropyran;
$R^8$ is selected from alkyl, —N($R^6$)$_2$, cyclopropyl, and tetrahydropyran;

each $Y^1$ is independently selected from halo, —CN, and alkyl;

v is 0 or 1;

X is selected from H, alkyl, cycloalkyl, —C(($R^2$)$_2$)$_s$-aryl, —C(($R^2$)$_2$)$_s$-heteroaryl, —$OR_2$, —O-aryl, and —O-heteroaryl, wherein said aryl and said heteroaryl portions of X are, independently, unsubstituted or substituted with one or more groups independently selected from —C(=NH)—O-alkyl, —C(=N-alkyl)-O-alkyl, —C(O)OH,-alkylene-O-heterocycloalkyl, $Y^1$ and $Y^3$;

and $R^2$, A, B, n, m, and s are as defined above.

In another embodiment of the compounds of the present invention, or pharmaceutically acceptable salts, solvates, esters, or isomers thereof, is a compound of the formula:

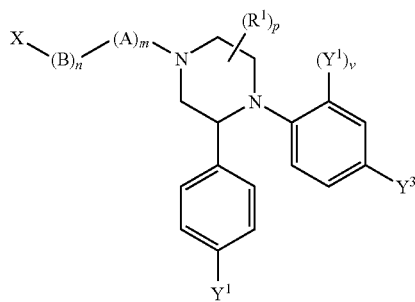

wherein each $R^1$ is independently selected from alkyl and —C(O)—;

p is 0, 1,or 2;

$Y^3$ is —C(O)N($R^3$)$_2$, with the proviso that when A is —C(O)—, then $Y^3$ is not —C(O)N(H)$_2$, —C(O)NH($C_1$-$C_6$)alkyl, or —C(O)N(($C_1$-$C_6$)alkyl)$_2$;

each $R^6$ is independently selected from H, alkyl, and -alkylene-OH;

each Y1 is independently selected from halo, —CN, and alkyl;

v is 0 or 1;

X is selected from H, alkyl, cycloalkyl, aryl, —C(($R^2$)$_2$)$_s$-aryl, heteroaryl, —C(($R^2$)$_2$)$_s$-heteroaryl, —$OR_2$, —O-aryl, and —O-heteroaryl, wherein said aryl and said heteroaryl portions of X are unsubstituted or substituted with from one to three groups independently selected from —C(=NH)—O-alkyl, —C(=N-alkyl)-O-alkyl, —C(O)OH, -alkylene-O-heterocycloalkyl, $Y^1$ and $Y^3$;

m=1;

n=1;

A is —C(O)— or —(C($R^2$)$_2$)$_q$—;

B is —C(O)— or —(C($R^3$)$_2$)$_r$—;

$R^2$ is H;

each $R^3$ is independently selected from H, alkyl, —OH, -alkylene-OH, and -alkylene-O-alkyl;

q=1 or 2;

r=1 or 2; and s=1 or 2.

In another embodiment of the compounds of the present invention, or pharmaceutically acceptable salts, solvates, esters, or isomers thereof, is a compound of the formula:

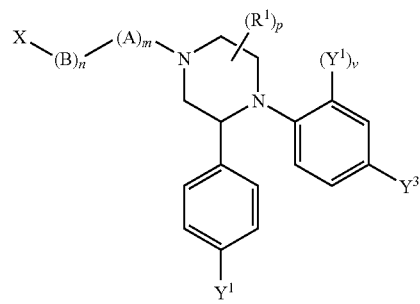

wherein:

each $R^1$ is independently selected from alkyl and —C(O)—;

p is 0, 1,or 2;

$Y^3$ is selected from —O-Q-$L_1$-$R^7$, —O-Q-$L_2$-$R^8$, or —O-Q-CN;

Q is unsubstituted -alkylene- or alkylene- substituted with from one to three groups independently selected from

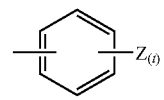

and Z, wherein t is 0, 1, 2, or3;

each Z is independently selected from alkyl, halo, haloalkyl, —OH, —O-alkyl, and —CN;

$L_1$ is —O— or —OC(O)—;

$L_2$ is —C(O)O—;

$R^7$ is selected from H, alkyl, —N($R^6$)$_2$, cycloalkyl, and heterocycloalkyl;

$R^8$ is selected from alkyl, —N($R^3$)$_2$, cycloalkyl, and heterocycloalkyl;

each $Y^1$ is independently selected from halo, —CN, and alkyl;

v is 0 or 1;

X is selected from H, alkyl, cycloalkyl, aryl, —C(($R^2$)$_2$)$_s$-aryl, heteroaryl, —C(($R^2$)$_2$)$_s$-heteroaryl, —$OR_2$, —O-aryl, and —O -heteroaryl, wherein said aryl and said heteroaryl portions of X are, independently, unsubstituted or substituted with one or more groups independently selected from —C(=NH)—O-alkyl, —C(=N-alkyl)-O-alkyl, —C(O)OH, -alkylene-O-heterocycloalkyl, $Y^1$ and $Y^3$;

m=1;

n=1;

A is —C(O)— or —(C($R^2$)$_2$)$_q$—;

B is —C(O)— or —(C($R^3$)$_2$)$_r$—;

$R^2$ is H;

each $R^3$ is independently selected from H, alkyl, —OH, -alkylene-OH, and -alkylene-O-alkyl;

q=1 or 2;

r=1 or 2; and s=1 or 2.

In another embodiment of the compounds of the present invention, or pharmaceutically acceptable salts, solvates, esters, or isomers thereof, is a compound of the formula.

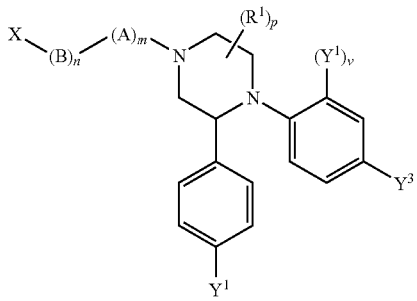

wherein:

each $R^1$ is independently selected from alkyl and —C(O)—;

p is 0, 1, or 2;

$Y^3$ is selected from —O-Q-$L_1$-$R^7$, —O-Q-$L_2$-$R^8$, or —O-Q-CN;

Q is unsubstituted —($C_1$ to $C_3$)alkylene- or —($C_1$ to $C_3$)alkylene- substituted with

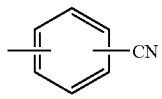

one to three groups independently selected from alkyl;

$L_1$ is —O— or —OC(O)—;

$L_2$ is —C(O)O—;

$R^7$ is selected from H, alkyl, —N($R^6$)$_2$, cyclopropyl, and tetrahydropyran;

$R^8$ is selected from alkyl, —N($R^6$)$_2$, cyclopropyl, and tetrahydropyran;

each $Y^1$ is independently selected from halo, —CN, and alkyl;

v is 0 or 1;

X is selected from H, alkyl, cycloalkyl, aryl, —C(($R^2$)$_2$)$_s$-aryl, heteroaryl, —C(($R^2$)$_2$)$_s$-heteroaryl, —O$R_2$, —O-aryl, and —O-heteroaryl, wherein said aryl and said heteroaryl portions of X are, independently, unsubstituted or substituted with one or more groups independently selected from —C(=NH)—O-alkyl, —C(=N-alkyl)-O-alkyl, —C(O)OH, -alkylene-O-heterocycloalkyl, $Y^1$ and $Y^3$;

m=1;

n=1;

A is —C(O)— or —(C($R^2$)$_2$)$_q$—;

B is —C(O)— or —(C($R^3$)$_2$)$_r$—;

$R^2$ is H;

each $R^3$ is independently selected from H, alkyl, —OH, -alkylene-OH, and -alkylene-O-alkyl;

q=1 or 2;

r=1 or 2; and s=1 or 2.

In another embodiment of the compounds of the present invention, or pharmaceutically acceptable salts, solvates, esters, or isomers thereof, is a compound of the formula:

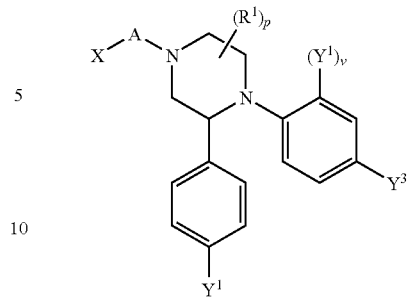

wherein:

each $R^1$ is independently selected from alkyl and —C(O)—;

p is 0, 1, or 2;

$Y^3$ is —C(O)N($R^6$)$_2$, with the proviso that when A is —C(O)—, then $Y^3$ is not
—C(O)N(H)$_2$,
—C(O)NH($C_1$-$C_6$)alkyl, or —C(O)N(($C_1$-$C_6$)alkyl)$_2$;

each $R^6$ is independently selected from H, alkyl, and -alkylene-OH;

each $Y^1$ is independently selected from halo, —CN, and alkyl;

v is 0 or 1;

X is selected from H, alkyl, cycloalkyl, aryl, —C(($R^2$)$_2$)$_s$-aryl, heteroaryl, —C(($R^2$)$_2$)$_s$-heteroaryl, —O$R_2$, —O-aryl, and —O-heteroaryl, wherein said aryl and said heteroaryl portions of X are unsubstituted or substituted with from one to three groups independently selected from —C(=NH)—O-alkyl, —C(=N-alkyl)-O-alkyl, —C(O)OH, -alkylene-O-heterocycloalkyl, $Y^1$ and $Y^3$;

m=1;

n=0;

A is —C(O)—, —S(O)$_2$—, —(C($R^2$)$_2$)$_q$-, or —C(=N—O$R^2$)—;

each $R^2$ is independently selected from H and alkyl;

q=1 or 2;

and s=1 or 2.

In another embodiment of the compounds of the present invention, or pharmaceutically acceptable salts, solvates, esters, or isomers thereof, is a compound of the formula:

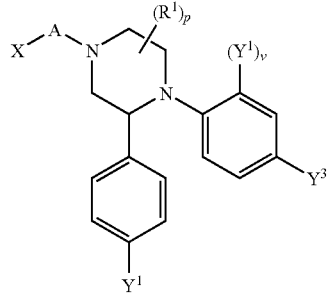

wherein, each $R^1$ is independently selected from alkyl and —C(O)—;

p is 0, 1, or 2;

$Y^3$ is selected from —O-Q-$L_1$-$R^7$—O-Q-$L_2$-$R^8$, or —O-Q-CN;

Q is unsubstituted -alkylene- or -alkylene- substituted with from one to three groups independently selected from

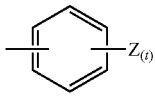

and Z, wherein t is 0, 1 2, or 3;

each Z is independently selected from alkyl, halo, haloalkyl, —OH, —O-alkyl, and —CN;

$L_1$ is —O— or —OC(O)—;

$L_2$ is —C(O)O—;

$R^7$ is selected from H, alkyl, —N($R^6$)$_2$, cycloalkyl, and heterocycloalkyl;

$R^8$ is selected from alkyl, —N($R^6$)$_2$, cycloalkyl, and heterocycloalkyl;

each $Y^1$ is independently selected from halo, —CN, and alkyl;

v is 0 or 1;

X is selected from H, alkyl, cycloalkyl, aryl, —C(($R^2$)$_2$)$_s$-aryl, heteroaryl, —C(($R^2$)$_2$)$_s$-heteroaryl, —OR$_2$, —O-aryl, and -0-heteroaryl, wherein said aryl and said heteroaryl portions of X are, independently, unsubstituted or substituted with one or more groups independently selected from —C(=NH)—O-alkyl, —C(=N-alkyl)-O-alkyl, —C(O) OH, -alkylene-O-heterocycloalkyl, $Y^1$ and $Y^3$;

m=1;

n=0;

A is —C(O)—, —S(O)$_2$—, —(C($R^2$)$_2$)$_q$-, or —C(=N—O$R^2$)—;

each $R^2$ is independently selected from H and alkyl;

q=1 or 2;

and s=1 or 2.

In another embodiment of the compounds of the present invention, or pharmaceutically acceptable salts, solvates, esters, or isomers thereof, is a compound of the formula:

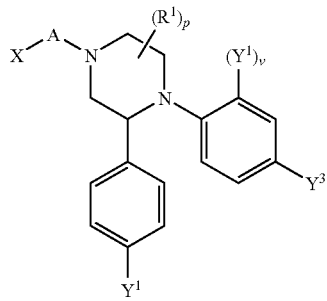

wherein:

each $R^1$ is independently selected from alkyl and —C(O)—;

p is 0, 1 or 2;

$Y^3$ is selected from —O-Q-$L_1$-$R^7$, —O-Q-$L_2$-$R^8$ or —O-Q-CN;

Q is unsubstituted —(C$_1$ to C$_3$)alkylene- or -(C$_1$ to C$_3$)alkylene- substituted with

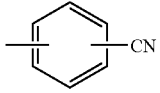

or one to three groups independently selected from alkyl;

$L_1$ is —O— or —OC(O)—;

$L_2$ is —C(O)O—;

$R^7$ is selected from H, alkyl, —N($R^6$)$_2$, cyclopropyl, and tetrahydropyran;

$R^8$ is selected from alkyl, —N($R^6$)$_2$, cyclopropyl, and tetrahydropyran;

each $Y^1$ is independently selected from halo, —CN, and alkyl;

v is 0 or 1;

X is selected from H, alkyl, cycloalkyl, aryl, —C(($R^2$)$^2$)$_s$-aryl, heteroaryl, —C(($R^2$)$_2$)$_s$-heteroaryl, —OR$_2$, —O-aryl, and —O-heteroaryl, wherein said aryl and said heteroaryl portions of X are, independently, unsubstituted or substituted with one or more groups independently selected from —C(=NH)—O-alkyl, —C(=N-alkyl)-O-alkyl, —C(O) OH, -alkylene-O-heterocycloalkyl, $Y^1$ and $Y^3$;

m=1;

n=0;

A is —C(O)—, —S(O)$_2$—, —(C($R^2$)$_2$)$_q$-, or —C(=N—O$R^2$)—;

each $R^2$ s independently selected from H and alkyl;

q=1 or 2;

and s=1 or 2.

In another embodiment of the compounds of the present invention, or pharmaceutically acceptable salts, solvates, esters, or isomers thereof, is a compound of the formula.

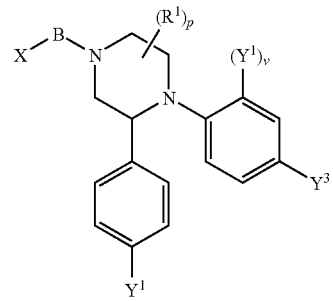

wherein:

each $R^1$ is independently selected from alkyl and —C(O)—;

p is0, 1, or2;

$Y^3$ is —C(O)N($R^6$)$_2$;

each $R^6$ is independently selected from H, alkyl, and -alkylene-OH;

each $Y^1$ is independently selected from halo, —CN, and alkyl;

v is 0 or 1;

X is selected from H, alkyl, cycloalkyl, aryl, —C(($R^2$)$_2$)$_s$-aryl, heteroaryl, —C(($R^2$)$_2$)$_s$-heteroaryl, —OR$_2$, —O-aryl, and —O-heteroaryl, wherein said aryl and said heteroaryl portions of X are unsubstituted or substituted with from one to three groups independently selected from —C(=NH)—O-alkyl, —C(=N-alkyl)-O-alkyl, —C(O)OH, -alkylene-O-heterocycloalkyl, $Y^1$ and $Y^3$;

m=0;

n=1;

B is —(C($R^3$)$_2$)$_r$-, each $R^2$ is independently selected from H and alkyl, each $R^3$ is independently selected from H, alkyl, —OR$^2$, -alkylene-OH, and -alkylene-O-alkyl;

r=1 or 2;

and s=1 or 2.

In another embodiment of the compounds of the present invention, or pharmaceutically acceptable salts, solvates, esters, or isomers thereof, is a compound of the formula:

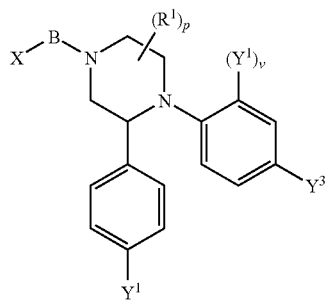

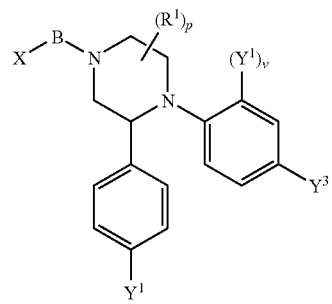

wherein:

each $R^1$ is independently selected from alkyl and —C(O)—;

p is 0, 1, or 2;

$Y^3$ is selected from —O-Q-$L_1$-$R^7$, —O-Q-$L_2$-$R^8$, or —O-Q-CN;

Q is unsubstituted -alkylene- or -alkylene- substituted with from one to three groups independently selected from

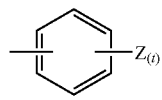

and Z, wherein t is 0, 1, 2, or 3, each Z is independently selected from alkyl, halo, haloalkyl, —OH, —O-alkyl, and —CN;

$L_1$ is —O— or —OC(O)—;

$L_2$ is —C(O)O—;

$R^7$ is selected from H, alkyl, —N($R^6$)$_2$, cycloalkyl, and heterocycloalkyl;

$R^8$ is selected from alkyl, —N($R^6$)$_2$, cycloalkyl, and heterocycloalkyl;

each $Y^1$ is independently selected from halo, —CN, and alkyl;

v is 0 or 1;

X is selected from H, alkyl, cycloalkyl, aryl, —C(($R^2$)$_2$)$_s$-aryl, heteroaryl, —C(($R^2$)$_2$)$_s$-heteroaryl, —O$R_2$, —O-aryl, and —O-heteroaryl, wherein said aryl and said heteroaryl portions of X are independently, unsubstituted or substituted with one or more groups independently selected from —C(=NH)—O-alkyl, —C(=N-alkyl)-O-alkyl, —C(O)OH, -alkylene-O-heterocycloalkyl, $Y^1$ and $Y^3$;

m=0;

n=1;

B is —(C($R^3$)$_2$)$_r$-, each $R^2$ is independently selected from H and alkyl;

each $R^3$ is independently selected from H, alkyl, —O$R^2$, -alkylene-OH, and -alkylene-O-alkyl;

r=1 or 2;

and s=1 or 2.

In another embodiment of the compounds of the present invention, or pharmaceutically acceptable salts, solvates, esters, or isomers thereof, is a compound of the formula:

wherein:

each $R^1$ is independently selected from alkyl and —C(O)—;

p is 0, 1, or 2;

$Y^3$ is selected from —O-Q-L-$R^7$, —O-Q-$L_2$-$R^8$, or —O-Q-CN;

Q is unsubstituted —($C_1$ to $C_3$)alkylene- or —($C_1$ to $C_3$)alkylene- substituted with

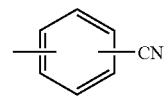

or one to three groups independently selected from alkyl;

$L_1$ is —O— or —OC(O)—;

$L_2$ is —C(O)O—:

$R^7$ is selected from H, alkyl, —N($R^6$)$_2$, cyclopropyl, and tetrahydropyran;

$R^8$ is selected from alkyl, —N($R^6$)$_2$, cyclopropyl, and tetrahydropyran:

each $Y^1$ is independently selected from halo, —CN, and alkyl;

v is 0 or 1;

X is selected from H, alkyl, cycloalkyl, aryl, —C(($R^2$)$_2$)$_s$-aryl, heteroaryl, —C(($R^2$)$_2$)$_s$-heteroaryl, —O$R_2$, —O-aryl, and —O-heteroaryl, wherein said aryl and said heteroaryl portions of X are, independently, unsubstituted or substituted with one or more groups independently selected from —C(=NH)—O-alkyl, —C(=N-alkyl)-O-alkyl, —C(O)OH, -alkylene-O-heterocycloalkyl, $Y^1$ and $Y^3$;

m=0;

n=1;

B is —(C($R^3$)$_2$)$_r$-, each $R^2$ is independently selected from H and alkyl;

each $R^3$ is independently selected from H, alkyl, —O$R^2$, -alkylene-OH, and -alkylene-O-alkyl, r=1 or 2;

and s=1 or 2.

In another embodiment of the compounds of the present invention, or pharmaceutically acceptable salts, solvates, esters, or isomers thereof, is a compound of the formula:

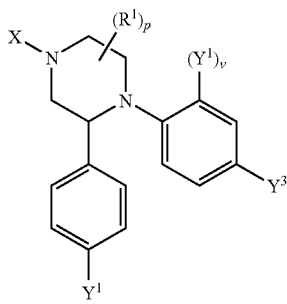

wherein:
each $R^1$ is independently selected from alkyl and —C(O)—;
p is 0, 1, or 2;
$Y^3$ is —C(O)N($R^6$)$_2$;
each $R^6$ is independently selected from H, alkyl, and -alkylene-OH;
each $Y^1$ is independently selected from halo, —CN, and alkyl;
v is 0 or 1;
X is selected from H, alkyl, cycloalkyl, aryl, —O($R^2$)$_2$)$_s$-aryl, heteroaryl, —C(($R^2$)$_2$)$_s$-heteroaryl, —OR$_2$, —O-aryl, and —O-heteroaryl, wherein said aryl and said heteroaryl portions of X are unsubstituted or substituted with from one to three groups independently selected from —C(=NH)—O-alkyl, —C(=N-alkyl)-O-alkyl, —C(O)OH, -alkylene-O-heterocycloalkyl, $Y^1$ and $Y^3$;
each $R^2$ is independently selected from H and alkyl;
and s=1 or 2.

In another embodiment of the compounds of the present invention, or pharmaceutically acceptable salts, solvates, esters, or isomers thereof, is a compound of the formula:

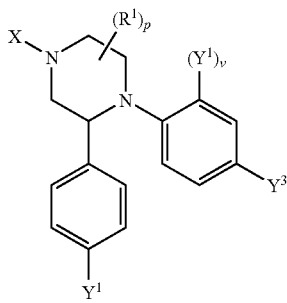

wherein:
each $R^1$ is independently selected from alkyl and —C(O)—;
p is 0, 1, or 2;
$Y^3$ is selected from —O-Q-L$_1$-R$^7$, —O-Q-L$_2$-R$^8$, or —O-Q-CN;
Q is unsubstituted -alkylene- or -alkylene- substituted with from one to three groups independently selected from

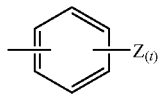

and Z, wherein t is 0, 1, 2, or 3;
each Z is independently selected from alkyl, halo, haloalkyl, —OH, —O-alkyl, and —CN;

L$_1$ is —O— or —OC(O)—;
L$_2$ is —C(O)O—;
$R^7$ is selected from H, alkyl, —N($R^6$)$_2$, cycloalkyl, and heterocycloalkyl;
$R^8$ is selected from alkyl, —N($R^6$)$_2$, cycloalkyl, and heterocycloalkyl;
each $Y^1$ is independently selected from halo, —CN, and alkyl;
v is 0 or 1;
X is selected from H, alkyl, cycloalkyl, aryl, —C(($R^2$)$_2$)$_s$-aryl, heteroaryl, —C(($R^2$)$_2$)$_s$-heteroaryl, —OR$_2$, —O-aryl, and —O-heteroaryl, wherein said aryl and said heteroaryl portions of X are, independently, unsubstituted or substituted with one or more groups independently selected from —C(=NH)—O-alkyl, —C(=N-alkyl)-O-alkyl, —C(O)OH, -alkylene-O-heterocycloalkyl, $Y^1$ and $Y^3$;
each $R^2$ is independently selected from H and alkyl;
and s=1 or 2.

In another embodiment of the compounds of the present invention, or pharmaceutically acceptable salts, solvates, esters, or isomers thereof, is a compound of the formula:

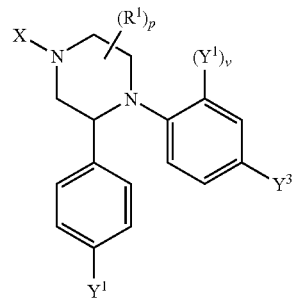

wherein:
each $R^1$ is independently selected from alkyl and —C(O)—;
p is 0, 1, or 2;
$Y^3$ is selected from —O-Q-L$_1$-R$^7$, —O-Q-L$_2$-R$^8$, or —O-Q-CN;
Q is unsubstituted —(C$_1$ to C$_3$)alkylene- or —(C$_1$ to C$_3$)alkylene- substituted with

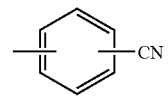

or one to three groups independently selected from alkyl;
L$_1$ is —O— or —OC(O)—;
L$_2$ is —C(O)O—;
$R^7$ is selected from H, alkyl, —N($R^6$)$_2$, cyclopropyl, and tetrahydropyran;
$R^8$ is selected from alkyl, —N($R^6$))$_2$, cyclopropyl, and tetrahydropyran;
each $Y^1$ is independently selected from halo, —CN, and alkyl;
v is 0 or 1;
X is selected from H, alkyl, cycloalkyl, aryl, —C(($R^2$)$_2$)$_s$-aryl, heteroaryl, —C(($R^2$)$_2$)$_s$-heteroaryl, —OR$_2$, —O-aryl, and —O-heteroaryl, wherein said aryl and said heteroaryl portions of X are, independently, unsubstituted or substituted with one or more groups independently selected from —C(=NH)—O-alkyl, —C(=N-alkyl)-O-alkyl, —C(O)OH, -alkylene-O-heterocycloalkyl, $Y^1$ and $Y^3$;

each $R^2$ is independently selected from H and alkyl;

and s=1 or 2.

In one embodiment, $Ar^1$ and $Ar^3$ are independently aryl or heteroaryl, wherein said at least one of $Ar^1$ and $Ar^2$ is substituted with one or more groups independently selected from $Y^3$, and wherein $Ar^1$ and $Ar^2$ are optionally additionally substituted with one or more groups independently selected from $Y^1$. Non-limiting examples of said aryl and heteroaryl of $Ar^1$ and/or $Ar^2$ include, for example, phenyl, naphthyl, pyridyl (e.g., 2-, 3-, and 4-pyridyl), pyrimidinyl, quinolyl, thienyl, imidazolyl, furanyl, etc. substituted with one or more (e.g., 1, 2, 3, or 4) groups independently selected from $Y^1$ as defined herein.

In one embodiment, A is selected from —C(O)—, —S(O)$_2$—, —C(=N—OR$^2$)—, and —(C(R$^2$)$_2$)$_q$- wherein q is 1, 2, or 3. Non-limiting examples of A when A is —(C(R$^2$)$_2$)$_q$- include, for example, —CH$_2$—, —CH$_2$CH$_2$—, —CH(CH$_3$)—, —C(CH$_3$)$_2$—, —CH$_2$CH$_2$CH$_2$—, —CH(CH$_3$)CH$_2$—, —CH$_2$CH(CH$_3$)—, —CH(CH$_3$)—(CH$_2$)$_2$—, —(CH$_2$)$_2$—CH(CH$_3$)—, —CH(phenyl)-CH$_2$—, —CH$_2$—CH(phenyl)-, —CH(phenyl)-, etc. Non-limiting examples of A when A is —C(=N—OR$^2$)- include —C(=N—OH)—, —C(=N—OCH$_3$)—, —C(=N—OCH$_2$CH$_3$)—, —C(=N—OCH(CH$_3$)$_2$)—, —C(=N—OC(CH$_3$)$_3$)—, —C(=N—O-phenyl), etc.

In one embodiment, B is selected from —N(R$^2$)—, —C(O)—, and —(C(R$^3$)$_2$)$_r$—, wherein r is 1, 2, or 3. Non-limiting examples of B when B is —(C(R$_2$)$_r$— include, for example, —CH$_2$—, —CH$_2$CH$_2$—, —CH(CH$_3$)—, —C(CH$_3$)$_2$—, —CH(CH(CH$_3$)$_2$)—, —CH(CH$_2$CH(CH$_3$)$_2$)—, —CH$_2$CH$_2$CH$_2$—, —CH(CH$_3$)CH$_2$—, —CH$_2$CH(CH$_3$)—, —CH(CH$_3$)—(CH$_2$)$_2$—, —(CH$_2$)$_2$—CH(CH$_3$)—, —CH(phenyl)-CH$_2$—CH (phenyl)-, —CH(phenyl)-, —CH(OH)—, —C(CH$_3$)(OH)—, —CH(OH)CH$_2$—, —CH$_2$CH(OH)—, —CH(OH)CH$_2$CH(CH$_3$)—, —CH(CH(OH)(CH$_3$))—, —CH(CH$_3$)CH$_2$CH(OH)—, —CH(CH$_2$OH)—, —CH(OCH$_3$)—, —CH(OCH$_3$)CH$_2$—, —CH$_2$CH(OCH$_3$)—, —CH(OCH$_3$)CH$_2$CH(CH$_3$)—, —CH(CH$_3$)CH$_2$CH(OCH$_3$)—, —CH(CH$_2$OCH$_3$)—, —CH(OCH$_3$)—, —CH(OCH$_2$CH$_3$)CH$_2$—, —CH$_2$CH(OCH$_2$CH$_3$)—, —CH(OCH$_2$CH$_3$)CH$_2$CH(CH$_3$)—, —CH(CH$_3$)CH$_2$CH(OCH$_2$CH$_3$)—, —CH(CH$_2$OCH$_2$CH$_3$)—, etc. Non-limiting examples of B when B is —N(R$^2$)— include —NH—, —N(alkyl)-, —N(aryl)-, wherein the terms "alkyl" and "aryl" are as defined herein.

In one embodiment, X is selected from H, alkyl, —S-alkyl, —S(O)$_2$-alkyl, —S(O)$_2$-cycloalkyl, —S(O)$_2$-aryl, —S(O)$_2$-heteroaryl, cycloalkyl, benzo-fused cycloalkyl-, benzo-fused heterocycloalkyl-, benzo-fused heterocycloalkenyl-, heterocycloalkyl, —C(RR$^2$)=C(R$^2$)-aryl, —C(R$^2$)=C(R$^2$)-heteroaryl, —OR$^2$, —O-alkylene-C-alkyl, —S-aryl, —N(R$^4$)$_2$, —NR$^4$R$^6$, —N(R$^6$)$_2$, —(C(R$^2$)$_2$ )-heteroaryl, —O-aryl, —O-heteroaryl, —(C(R$^2$)$_2$)$_s$-heteroaryl, —C(O)—O-alkyl, —C(O)-aryl, —C(O)-heteroaryl —N=O, —C(S-alkyl)=N—S(O)$_2$-aryl, —C(N(R$^2$)$_2$)=N—S(O)$_2$-aryl, and —(C(R$^2$)$_2$)-aryl wherein s is 0, 1, or 2. Non-limiting examples of X when X is alkyl include methyl, ethyl, n-propyl, iso-propyl, n-butyl, iso-butyl, sec-butyl, tert-butyl, n-pentyl, iso-pentyl, neo-pentyl, n-hexyl, iso-hexyl, etc. Non-limiting examples of X when X is-S-alkyl include —S-methyl, —S-ethyl, —S-(n-propyl), —S-(iso-propyl), —S-(n-butyl), —S-(iso-butyl), —S-(sec-butyl), —S-(tert-butyl), —S-(n-pentyl), —S-(iso-pentyl), —S-(neo-pentyl), —S-(n-hexyl), —S-(iso-hexyl), etc. Non-limiting examples of X when X is —S(O)$_2$-alkyl include —S(O)$_2$-methyl, —S(O)$_2$-ethyl, —S(O)$_2$-(n-propyl), —S(O)$_2$-(so-propyl), —S(O)$_2$-(n-butyl) —S(O)$_2$-(iso-butyl), —S(O)$_2$-(sec-butyl), S(O)$_2$-(tert-butyl), —S(O)$_2$-(n-pentyl), —S(O)$_2$-(iso-pentyl) —S(O)$_2$-(neo-pentyl), —S(O)$_2$-(n-hexyl), —S(O)$_2$-(iso-hexyl), etc. Non-limiting examples of X when X is —S(O)$_2$-cycloalkyl include —S(O)$_2$-cyclopropyl, —S(O)$_2$-cyclobutyl, —S(O)$_2$-cyclopentyl, —S(O)$_2$-cyclohexyl, —S(O)$_2$-cycloheptyl, —S(O)$_2$-adamantyl, —S(O)$_2$-(bicyclo[2.1.1]hexanyl) —S(O)$_2$-(bicyclo[2.2.1]heptenyl), —S(O)$_2$-(bicyclo[3.1.1]heptenyl) —S(O)$_2$-(bicyclo[2.2.2]octenyl), —S(O)$_2$-(bicyclo[3.2.1]octenyl), etc. Non-limiting examples of X when X is —S(O)$_2$-aryl includes —S(O)$_2$-phenyl, —S(O)$_2$-naphthyl, etc. Non-limiting examples of X when X is —O- aryl include —O-phenyl, —O-naphthyl, etc. Non-limiting examples of X when X is —O-heteroaryl include —O-pyridyl, —O-azaindolyl, —O-benzimidazolyl, —O-benzofuranyl, —O-furanyl, —O-indolyl, etc. Non-limiting examples of X when X is —S(O)$_2$-heteroaryl include —S(O)$_2$-pyridyl, —S(O)$_2$-azaindolyl, —S(O)$_2$-benzimidazolyl, —S(O)$_2$-benzofuranyl, —S(O)$_2$-furanyl, —S(O)$_2$-indolyl, etc. Non-limiting examples of X when X is cycloalkyl include cyclopropyl, cyclobutyl, cyclopentyl, cyclohexyl, cycloheptyl, adamantyl, bicyclo[2.1.1]hexanyl, bicyclo[2.2.1]heptenyl, bicyclo[3.1.1]heptenyl, bicyclo[2.2.2]octenyl, bicyclo[3.2.1]octenyl, etc. Non-limiting examples of X when X is —(C(R$^2$)$_2$)$_s$-heteroaryl include —(C(R$^2$)$_2$)$_s$-pyridyl, —(C(R$_2$)$_2$)$_s$-azaindolyl, —(C(R$^2$)$_2$)$_s$-benzimidazolyl, —(C(R$^2$)$_2$)$_s$-benzofuranyl, —(C(R$^2$)$_2$)$_s$-furanyl, —(C(R$^2$)$_2$)$_s$-indolyl, etc. Non-limiting examples of X when X is benzo-fused cycloalkyl include 1,2,3,4-tetrahydronaphthyl, indanyl, bicyclo[4.2.0]octa-1,3,5-trienyl, etc. Non-limiting examples of X when X is benzo-fused heterocycloalkyl includes 3,4-dihydro-2H-benzo[1,4]oxazinyl, chromanyl, 2,3-dihydro-1H-indolyl, 2,3-dihydro-1H-isoindolyl, 2,3-dihydro-benzofuranyl, 1,3-dihydro-isobenzofuranyl, 2,3-dihydro-benzo[b]thiophenyl, 1,3-dihydro-benzo[c]thiophenyl, etc. Non-limiting examples of X when X is benzo-fused heterocycloalkenyl include 2H-benzo [1,4]oxazinyl, 4H-chromenyl, 4H-chromenyl, 3H-indolyl, 1H-isoindolyl, 4H-benzo [1,4]oxazinyl, etc. Non-limiting examples of X when X is heterocycloalkyl include morpholinyl, piperazinyl, piperidinyl, pyrrolidinyl, tetrahydrofuranyl, tetrahydrothiophenyl, tetrahydropyranyl, azetidinyl, etc. When X is —C(R$^2$)=C(R$^2$)-aryl, non-limiting examples of X include —CH=CH-aryl, —C(CH$_3$)=CH-aryl, —CH=C(CH$_3$)-aryl, —C(CH$_3$)=C(CH$_3$)-aryl, —C(phenyl)=CH-aryl, —C(phenyl)=C(CH$_3$)-aryl, where "aryl" includes, for example, the aryl groups listed above. When X is —C(R$^2$)=(R$^2$)-heteroaryl, non-limiting examples of X include —CH=CH-heteroaryl, —C(CH$_3$)=CH-heteroaryl, —CH=C(CH$_3$)— heteroaryl, —C(CH$_3$)=C(CH$_3$)— heteroaryl, —C(phenyl)=CH-heteroaryl, —C(phenyl)=C(CH$_3$)—heteroaryl, where "heteroaryl" includes, for example, the heteroaryl groups listed above. When X is —OR$^2$, R$^2$ is defined as described herein. Thus, X includes —OH, —O-alkyl (where the term "alkyl" is defined as described above), and —O-aryl (where the term "aryl" is defined as described above). When X is —O-alkylene-O-alkyl, non-limiting examples of X include —O—CH$_2$—O—CH$_3$, —O—CH(CH$_3$)—O—CH$_3$, —O—CH$_2$CH$_2$—O—CH$_3$, —O—CH$_2$CH$_2$—O—CH$_2$CH$_3$, —O—CH(OCH$_3$)CH$_2$CH(CH$_3$)$_2$, —O—CH(CH$_3$)CH$_2$—O—CH$_3$, —O—CH$_2$CH$_2$—O—CH$_2$CH$_3$, etc. Non-limiting examples of X when X is —S-aryl includes —S-phenyl, —S-naphthyl, etc. Non-limiting examples of X when X is —N(R$^4$)$_2$ include —NH$_2$, —NH(alkyl), —N(alkyl)$_2$, —NH(aryl), —N(alkyl)(aryl), —N(aryl)$_2$, —NH—C(O)—O-alkyl, —N(alkyl)-C(O)—O-alkyl, —N(aryl)-C(O—O-alkyl, —NH—C(O)alkyl, —N(alkyl)-C(O)alkyl, and —N(aryl)-C(O)alkyl where the terms "alkyl" and "aryl" are defined as described above. Non-limiting examples of X when X is —(C(R$^2$)$_2$)$_s$-heteroaryl, include heteroaryl, —C(R$^2$)$_2$-heteroaryl, —C(R$^2$)$_2$)$_2$-heteroaryl, where R$^2$ and the term "heteroaryl" are as defined herein, and "—(C(R$^2$)$_2$)$_s$—" includes —CH$_2$—, —CH$_2$CH$_2$—, —CH(CH$_3$)—, —C(CH$_3$)$_2$—, —CH(CH(CH$_3$)$_2$)—, —CH(CH$_2$CH(CH$_3$)$_2$)—, —CH$_2$CH$_2$CH$_2$—, —CH(CH$_3$)CH$_2$—, —CH$_2$CH(CH$_3$)—, —CH(CH$_3$)—(CH$_2$)$_2$—, —(CH$_2$)$_2$—CH(CH$_3$)—, —CH(phenyl)-CH$_2$—, —CH$_2$—CH(phenyl)-, —CH(phenyl)-, etc. Non-limiting examples of X when X is —C(O)—O-alkyl include —C(O)—O-(methyl), —C(O)—O-(ethyl), —C(O)—O-(n-propyl), —C(O)—O-(iso-propyl), —C(O)—O-(n-butyl), —C(O)—O-(iso-butyl), —C(O)—O-(sec-butyl), —C(O)—O-(tert-butyl), —C(O)—O-(n-pentyl), —C(O)—O-(iso-pentyl), —C(O)—O-(neo-pentyl), etc. Non-limiting examples of X when X is —C(O)-aryl include —C(O)-phenyl, —C(O)-naphthyl, etc. Non-limiting examples of X when X is —C(O)-heteroaryl include —C(O)-pyridyl, —C(O)-azaindolyl —C(O)-benzimidazolyl, —C(O)-benzothiophenyl, —C(O)-furanyl, —C(O)-furazanyl, —C(O)-indolyl, —C(O)-isoquinol, etc. When X is —C(S-alkyl)N—S(O)-aryl, the "alkyl" and "aryl" portions thereof can independently include any of the alkyl and aryl groups described herein. Likewise, when X is —C(N(R$^2$)$_2$)=N—S(O)$_2$-aryl said R$^2$ groups and the "aryl" portion are as defined herein. Non-limiting examples of X when X is —(C(R$^2$)$_2$)-aryl, include aryl, —C(R$^2$)$_2$-aryl, —(C(R$^2$)$_2$)$_2$-aryl, where R$^2$ and the term "aryl" are as defined herein, and "—(C(R$^2$)$_2$)$_s$-" is as defined above. Said heteroaryl, the heteroaryl portion of said —(C(R$^2$)$_2$)$_s$-heteroaryl, the aryl portion of said —C(R$_2$)=C(R$^2$)-aryl, the heteroaryl portion of said —C(R$_2$)C(R$_2$)-heteroaryl, the aryl portion of said —-S-aryl, the aryl portion of said —S(O)$_2$-aryl, the heteroaryl portion of said —S(O)$_2$-heteroaryl, the aryl portion of said —C(O)-aryl, the heteroaryl portion of said —C(O)-heteroaryl, the aryl portion of said —(C(R$^2$)$_2$)$_s$-aryl, the benzo portion of said benzo-fused cycloalkyl, the benzo portion of said benzo-fused heterocycloalkyl, and the benzo portion of said benzo-fused heterocycloalkenyl of X are unsubstituted or substituted with one or more groups independently selected from Y$^1$ and Y$^3$, where Y$^1$ and Y$^3$ are defined as described herein, and said cycloalkyl, the cycloalkyl portion of said —S(O)$_2$-cycloalkyl, said heterocycloalkyl, the cycloalkyl portion of said benzo-fused cycloalkyl, the heterocycloalkyl portion of said benzo-fused heterocycloalkyl, and the heterocycloalkenyl portion of said benzo-fused heterocycloalkenyl of X is unsubstituted or substituted with one or more groups independently selected from Y$^2$ where Y$^2$ is defined as described herein.

In one embodiment, each R$^1$ is independently selected from alkyl, haloalkyl, -alkylene-N(R$^5$)$_2$, -alkylene-OR$^2$, alkylene-N$_3$, and alkylene-O—S(O)$_2$-alkyl. Non-limiting examples of R$^1$ when R$^1$ is alkyl include methyl, ethyl, n-propyl, iso-propyl, n-butyl, iso-butyl, sec-butyl, tert-butyl, n-pentyl, iso-pentyl, neo-pentyl, n-hexyl, iso-hexyl, etc. Non-limiting examples of R$^1$ when R$^1$ is haloalkyl include —CF$_3$, —CHF$_2$, —CH$_2$F, —CH$_2$CF$_3$, —CF$_2$CF$_3$, —CH$_2$Br, —CH$_2$Cl, —CCl$_3$, etc. When HR is alkylene-N$_3$ or alkylene-O—S(O)$_2$-alkyl, the alkylene portion thereof can include any of the alkylene groups described herein (e.g., —CH$_2$—, —CH$_2$CH$_2$—, —CH(CH$_3$)—, —OH$_2$CH$_2$CH$_2$—, —CH(CH$_3$)CH$_2$CH$_2$—, etc. Similarly, the "alkyl" portion of alkylene-O—S(O)$_2$-alkyl can include any alkyl group described herein (e.g., methyl, ethyl, propyl, butyl, pentyl, etc) Non-limiting examples of R$^1$ when R$^1$ is -alkylene-N(R$^5$)$_2$ include —CH$_2$—N(R$^5$)$_2$, —CH(CH$_3$)—N(R$^5$)$_2$, —CH$_2$CH$_2$—N(R$^5$)$_2$, —CH$_2$CH$_2$CH$_2$—N(R$^5$)$_2$, —CH(CH$_3$)CH$_2$CH$_2$—N(R$^5$)$_2$,etc., wherein each R$^5$ is independently defined as described herein. For example, the "—N(R$^5$)$_2$" portion of -alkylene-N(R$^5$)$_2$ of R$^1$ can be —NH$_2$, —N(CH$_3$)$_2$, —NH(CH$_3$), —NH(phenyl), —N(phenyl)$_2$, —NH—S(O)$_2$—CH$_3$, —NH—S(O)$_2$-cyclopropyl, —NH—C(O)—NH$_2$, —NH—C(O)—N(CH$_3$)$_2$, —NH—C(O)—CH$_3$, —NH—CH$_2$CH$_2$—OH, etc. Non-limiting examples of R$^1$ when R$^1$ is -alkylene-OR$^2$ include —CH$_2$—OR$^2$, —CH(CH$_3$)—OR$^2$, —CH$_2$CH$_2$—OR$^2$, —CH(OR$^2$)CH$_2$CH(CH$_3$)$_2$, —CH(CH$_3$)CH$_2$CH$_2$—OR$^2$, wherein R$^2$ is defined as described herein. For example, the "—OR$^2$" portion of said -alkylene-OR$^2$ of R$^1$ can be —OH, —OCH$_3$, —OCH$_2$CH$_3$, —OCH(CH$_3$)$_2$, —O-phenyl. Alternatively, two R$^1$ groups attached to the same ring carbon atom can form a carbonyl group, for example as shown below:

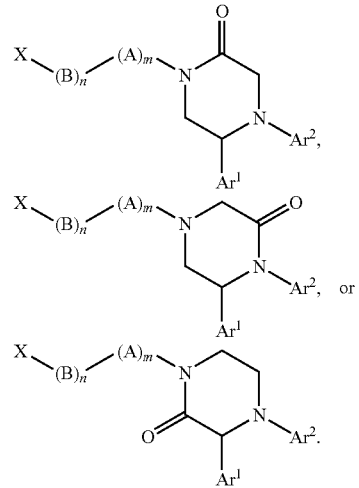

In one embodiment, each R$^2$ is independently selected from H, alkyl, aryl, heteroaryl, cycloalkyl, and heterocycloalkyl. Non-limiting examples of R$^2$ when R$^2$ is alkyl include methyl, ethyl, n-propyl, iso-propyl, n-butyl, iso-butyl, sec-butyl, tert-butyl, n-pentyl, iso-pentyl, neo-pentyl, n-hexyl, iso-hexyl, etc. Non-limiting examples of R$^2$ when R$^2$ is aryl include phenyl, naphthyl, etc. Non-limiting examples of R$^2$ when R$^2$ is heteroaryl include heteroaryl include azaindolyl, benzimidazolyl, benzofuranyl, furanyl, 2-pyridinyl, 3-pyridinyl, 4-pyridinyl, furazanyl, indolyl, quinolyl, isoquinolyl, phthalazinyl, pyrazinyl, pyridazinyl, pyrimidyl, pyrrolyl, quinoxalinyl, thiophenyl, isoxazolyl, triazolyl, thiazolyl, indazolyl, thiadiazolyl, imidazolyl, benzo[b]thiophenyl, tetrazolyl, pyrazolyl, etc. Non-limiting examples of R$^2$ when R$^2$ is cycloalkyl include cycloalkyl include cyclopropyl, cyclobutyl, cyclopentyl, cyclohexyl, adamantyl, norbornyl, etc. Non-limiting examples of R$^2$ when R$^2$ is heterocycloalkyl include heterocycloalkyl include morpholinyl, piperazinyl, piperidinyl, pyrrolidinyl, tetrahydrofuranyl, tetrahydrothiophenyl, tetrahydropyranyl, azetidinyl, etc., wherein each said aryl, heteroaryl, cycloalkyl, and heterocycloalkyl may be unsubstituted or substituted with one or more groups independently selected from Y$^1$ and Y$^3$, as defined herein.

In one embodiment, each R$^3$ is independently selected from H, alkyl, unsubstituted aryl, (or aryl substituted with one or more groups independently selected from Y$^1$), OR$^2$, -alkylene-O-alkyl, and -alkylene-OH. Non-limiting examples of R$^3$ when R$^3$ is alkyl include methyl, ethyl, n-propyl, iso-propyl, n-butyl, iso-butyl, sec-butyl, tert-butyl, n-pentyl, iso-pentyl, neo-pentyl, n-hexyl, iso-hexyl, etc. Non-limiting examples of $R^3$ when $R^3$ is aryl include phenyl, naphthyl, etc., wherein said aryl may be unsubstituted or substituted with one or more groups independently selected from $Y^1$ and $Y^3$ as defined herein. Non-limiting examples of $R^3$ when $R^3$ is —$OR^2$ include —OH, —$OCH_3$, —$OCH_2CH_3$, —$OCH(CH_3)_2$, —O-phenyl, etc. Non-limiting examples of $R^3$ when $R^3$ is -alkylene-O-alkyl include —O—$CH_2$—O—$CH_3$, —O—$CH_2CH_2$—O—$C(CH_3)_3$, —O—$CH(CH_3)$—O—$CH_3$, —O—$CH_2CH_2$—O—$CH_3$, —O—$CH_2CH_2$—O—$CH_2CH_3$, —O—$CH(OCH_3)CH_2CH(CH_3)_2$, —O—$CH(CH_3)CH_2CH_2$—O—$CH_3$, —O—$CH_2CH_2$—O—$CH_2CH_3$, etc. Non-limiting examples of $R^3$ when $R^3$ is -alkylene-OH include —$CH_2$—OH, —$CH_2CH_2$—OH, —$CH_2CH_2CH_2$—OH, —$CH(OH)CH_3$, —$CH_2CH(OH)CH_3$, etc.

In one embodiment, each $R^4$ is independently selected from H alkyl, aryl, —C(O)—O-alkyl, —C(O)-alkyl, —C(O)-aryl, —C(O)— heteroaryl, —C(O)-heterocycloalkyl, —S(O)$_2$alkyl, —S(O)$_2$aryl, —S(O)$_2$heteroaryl, and —S(O)$_2$heterocycloalkyl. Non-limiting examples of $R^4$ when $R^4$ is alkyl include methyl, ethyl, n-propyl, iso-propyl, n-butyl, iso-butyl, sec-butyl, tert-butyl, n-pentyl, iso-pentyl, neo-pentyl, n-hexyl, iso-hexyl, etc. Non-limiting examples of $R^4$ when $R^4$ is aryl include phenyl, naphthyl, etc., wherein said aryl may be unsubstituted or substituted with one or more groups independently selected from $Y^1$ or $Y^3$ as defined herein. Non-limiting examples of $R^4$ when $R^4$ is —C(O)—O-alkyl include —C(O)—O—$CH_3$, —C(O)—O—$CH_2CH_3$, —C(O)—O—$CH_2CH_2CH_3$, —C(O)—O—$CH(CH_3)_2$, —C(O)—O—$CH_2CH_2CH_2CH_3$, —C(O)—O—$CH_2CH(CH_{13})_2$, —C(O)—O—$CH(CH_3)CH_2CH_3$, —C(O)—O—$C(CH_3)_3$, —C(O)—C—$CH_2CH_2CH_2CH_2CH_3$, —C(O)—O—$CH_2CH(CH_3)CH_2CH_3$, —C(O)—O—$CH_2CH_2CH(CH_3)_2$, —C(O)—O—$CH_2CH_2CH_2CH_2CH_2CH_3$, —C(O)—O—$CH(CH_3)CH_2CH_2CH_2CH_3$, —C(O)—O—$CH_2CH(CH_3)CH_2CH_2CH_3$, —C(O)—O—$CH_2CH_2CH(CH_3)CH_2CH_3$, —C(O)—O—$CH_2CH_2CH_2CH(CH_3)_2$, etc. Non-limiting examples of $R^4$ when $R^4$ is —C(O)-alkyl include —C(O)—$CH_3$, —C(O)—$CH_2CH_3$, —C(O)—$CH_2CH_2CH_3$, —C(O)—$CH(CH_3)_2$, —C(O)—$CH_2CH_2CH_2CH_3$, —C(O)—$CH_2CH(CH_3)_2$, —C(O)—$CH(CH_3)CH_2CH_3$, —C(O)—$C(CH_3)_3$, —C(O)—$CH_2CH_2CH_2CH_2CH_3$, —C(O)—$CH_2CH(CH_3)CH_2CH_3$, —C(O)—$CH_2CH_2CH(CH_3)_2$, —C(O)—$CH_2CH_2CH_2CH_2CH_2CH_3$, —C(O)—$CH(CH_3)CH_2CH_2CH_2CH_3$, —C(O)—$CH_2CH_2CH(CH_3)CH_2CH_3$, —C(O)—$CH_2CH_2CH_2CH(CH_3)_2$, etc. Non-limiting examples of $R^4$ when $R^4$ is —C(O)-aryl include —C(O)-phenyl, —C(O)-naphthyl, etc., optionally substituted with one or more groups independently selected from $Y^1$ and $Y^3$. Non-limiting examples of $R^4$ when $R^4$ is —S(O)$_2$aryl include —S(O)$_2$-phenyl, —S(O)$_2$-naphthyl, etc., optionally substituted with one or more groups independently selected from $Y^1$ and $Y^3$.

In one embodiment, each $R^5$ is independently selected from H, alkyl, aryl, —S(O)$_2$-alkyl, —S(O)$_2$-cycloalkyl, —S(O)$_2$-aryl, —C(O)—N($R^2$)$_2$, —C(O)-alkyl, and -alkylene-OH. Non-limiting examples of $R^5$ when $R^5$ is alkyl include methyl, ethyl, n-propyl, iso-propyl, n-butyl, iso-butyl, sec-butyl, tert-butyl, n-pentyl, iso-pentyl, neo-pentyl, n-hexyl, iso-hexyl, etc. Non-limiting examples of $R^5$ when $R^5$ is aryl include phenyl, naphthyl, etc., wherein said aryl may be unsubstituted or substituted with one or more groups independently selected from Z as defined herein. Non-limiting examples of $R^5$ when $R^5$ is —S(O)$_2$-alkyl include —S(O)$_2$—$CH_3$, —S(O)$_2$—$CH_2CH_3$, —S(O)$_2$—$CH_2CH_2CH_3$, —S(O)$_2$—$CH(CH_3)_2$, —S(O)$_2$—$CH_2CH_2CH_2CH_3$, —S(O)$_2$—$CH_2CH(CH_3)_2$, —S(O)$_2$—$CH(CH_3)CH_2CH_3$, —S(O)$_2$—$C(CH_3)_3$, —S(O)$_2$—$CH_2CH_2CH_2CH_2CH_3$, —S(O)$_2$—$CH_2CH(CH_3)CH_2CH_3$, —S(O)$_2$—$CH_2CH_2CH(CH_3)_2$, —S(O)$_2$—$CH_2CH_2CH_2CH_2CH_3$—S(O)$_2$—$CH(CH_3)$ $CH_2CH_2CH_3$, —S(O)$_2$—$CH_2CH(CH_3)CH_2CH_3$, —S(O)$_2$—$CH_2CH_2CH(CH_3)CH_2CH_3$, —S(O)$_2$—$CH_2CH_2CH_2CH(CH_3)_2$, etc. Non-limiting examples of $R^5$ when $R^5$ is —S(O)$_2$-cycloalkyl include —S(O)$_2$-cyclopropyl, —S(O)$_2$-cyclobutyl, —S(O)$_2$-cyclopentyl, —S(O)$_2$-cyclohexyl, —S(O)$_2$-adamantyl, —S(O)$_2$-norbornyl, —S(O)$_2$-decalyl, etc. Non-limiting examples of $R^5$ when $R^5$ is —C(O)—N($R^2$)$_2$ include —C(O)—$NH_2$, —C(O)—NH(alkyl), —C(O)—N(alkyl)$_2$, —C(O)—NH(aryl), —C(O)—N(alkyl)(aryl), —C(O)—N(aryl)$_2$, wherein the terms "aryl" and "alkyl" are as defined above, and said "aryl" may be unsubstituted or substituted with one or more groups independently selected from $Y^1$ as defined herein. Non-limiting examples of $R^5$ when $R^5$ is —C(O)-alkyl include —C(O)—$CH_3$, —C(O)—$CH_2CH_3$, —C(O)—$CH_2CH_2CH_3$, —C(O)—$CH(CH_3)_2$, —C(O)—$CH_2CH_2CH_2CH_3$, —C(O)—$CH_2CH(CH_3)_2$, —C(O)—$CH(CH_3)CH_2CH_3$, —C(O)—$C(CH_3)_3$, —C(O)—$CH_2CH_2CH_2CH_2CH_3$, —C(O)—$CH_2CH(CH_3)CH_2CH_3$, —C(O)—$CH_2CH_2CH(CH_3)_2$, —C(O)—$CH_2CH_2CH_2CH_2CH_3$, —C(O)—$CH(CH_3)CH_2CH_2CH_2CH_3$, —C(O)—$CH_2CH_2CH(CH_3)CH_2CH_3$, —C(O)—$CH_2CH_2CH_2CH(CH_3)_2$, etc. Non-limiting examples of $R^5$ when $R^5$ is -alkylene-OH include —$CH_2$—OH, —$CH_2CH_2$—OH, —$CH_2CH_2CH_2$—OH, —$CH(OH)CH_3$, —$CH_2CH(OH)CH_3$, etc. Non-limiting examples of $R^5$ when $R^5$ is —S(O)$_2$aryl include —S(O)$_2$-phenyl, -S(O)$_2$-naphthyl, etc., optionally substituted with one or more groups independently selected from $Y^1$.

In one embodiment, each $Y^1$ is independently selected from alkyl, cycloalkyl, heterocycloalkyl, heterocycloalkenyl, halo, haloalkyl, aryl, -alkylene-aryl, heteroaryl, —O-alkyl, —O-aryl, —O-heteroaryl, —O-cycloalkyl, —O-heterocycloalkyl, —S-alkyl, —S-aryl, —S-heteroaryl, —S—cycloalkyl, —S-heterocycloalkyl, —S(O)$_2$-alkyl, —S(O)$_2$-aryl, —S(O)$_2$-heteroaryl, —S(O)$_2$-cycloalkyl, —S(O)$_2$-heterocycloalkyl, -alkylene-CN, —CN, —C(O)-alkyl, —C(O)-aryl, —C(O)-haloalkyl, —C(O)-heteroaryl, —C(O)—cycloalkyl, —C(O)-heterocycloalkyl, —C(O)O-alkyl, —C(O)O-aryl, —C(O)O-haloalkyl, —C(O)O-heteroaryl, —C(O)O—cycloalkyl, —C(O)O-heterocycloalkyl, —N($R^2$)C(O)-alkyl, —N($R^2$)C(O)—N($R^2$)$_2$, —OH, —O-alkyl, —O-haloalkyl, —O-alkylene-C(O)OH, —S-alkyl, —S-haloalkyl, -alkylene-OH, -alkylene-C(O)—O-alkyl, —O-alkylene-aryl, and —N($R^5$)$_2$. Non-limiting examples of $Y^1$ when $Y^1$ is alkyl include methyl, ethyl, n-propyl, iso-propyl, n-butyl, iso-butyl, sec-butyl, tert-butyl, n-pentyl, iso-pentyl, neo-pentyl, n-hexyl, iso-hexyl, etc. Non-limiting examples of $Y^1$ when $Y^1$ is cycloalkyl include cyclopropyl, cyclobutyl, cyclopentyl, cyclohexyl, adamantyl, norbornyl, etc. Non-limiting examples of $Y^1$ when $Y^1$ is heterocycloalkyl include morpholinyl, piperazinyl, piperidinyl, pyrrolidinyl, tetrahydrofuranyl, tetrahydrothiophenyl, tetrahydropyranyl, azetidinyl, etc. Non-limiting examples of $Y^1$ when $Y^1$ is heterocycloalkenyl include 2H-benzo[1,4]oxazinyl, 4H-chromenyl, 4H-chromenyl, 3H-indolyl, 1H-isoindolyl, 4H-benzo[1,4]oxazinyl, etc. Non-limiting examples of $Y^1$ when $Y^1$ is halo include chloro, bromo, and iodo. Non-limiting examples of $Y^1$ when $Y^1$ is haloalkyl include —$CF_3$, —$CHF_2$, —$CH_2F$, —$CH_2CF_3$, —$CF_2CF_3$, —$CH_2Br$, —$CH_2Cl$, —$CCl_3$, etc. Non-limiting examples of $Y^1$ when $Y^1$ is -alkylene-aryl include benzyl, -ethylene-phenyl, -propylene-phenyl, -methylene-naphthyl, and -ethylene-naphthyl, etc. Non-limiting examples of $Y^1$ when $Y^1$ is aryl include phenyl, naphthyl, etc. Non-limiting examples of $Y^1$ when $Y^1$ is heteroaryl include azaindolyl, benzimidazolyl, benzofuranyl, furanyl, 2-pyridinyl, 3-pyridinyl, 4-pyridinyl, furazanyl, indolyl, quinolyl, isoquinolyl, phthalazinyl, pyrazinyl, pyridazinyl, pyrimidyl, pyrrolyl, quinoxalinyl, thiophenyl, isoxazolyl, triazolyl thiazolyl, indazolyl, thiadiazolyl, imidazolyl, benzo[b]thiophenyl, tetrazolyl, pyrazolyl, etc. Non-limiting examples of $Y^1$ when $Y^1$ is —O-aryl include —O-phenyl, —O-naphthyl, etc. Non-limiting examples of $Y^1$ when $Y^1$ is -S-aryl include —S-phenyl, —S-naphthyl, etc. Non-limiting examples of $Y^1$ when $Y^1$ is —S(O)$_2$-alkyl include —S(O)$_2$—CH$_3$, —S(O)$_2$—CH$_2$CH$_3$, —S(O)$_2$—CH$_2$CH$_2$CH$_3$, —S(O)$_2$—CH(CH$_3$)$_2$, —S(O)$_2$—CH$_2$CH$_2$CH$_2$CH$_3$, —S(O)$_2$—CH$_2$CH(CH$_3$)$_2$, —S(O)$_2$—CH(CH$_3$)CH$_2$CH$_3$, —S(O)$_2$—C(CH$_3$)$_3$, —S(O)$_2$—CH$_2$CH$_2$CH$_2$CH$_2$CH$_3$, —S(O)$_2$—CH$_2$CH(CH$_3$)CH$_2$CH$_3$, —S(O)$_2$—CH$_2$CH$_2$CH$_2$CH$_2$CH$_2$CH$_3$, —S(O)$_2$—CH(CH$_3$)CH$_2$CH$_2$CH$_3$, —S(O)$_2$—CH$_2$CH(CH$_3$)CH$_2$CH$_2$CH$_3$, —S(O)$_2$—CH$_2$CH$_2$CH(CH$_3$)CH$_2$CH$_3$, —S(O)$_2$—CH$_2$CH$_2$CH$_2$CH(CH$_3$)$_2$, etc. Non-limiting examples of $Y^1$ when $Y^1$ is —S(O)$_2$-cycloalkyl include —S(O)$_2$-cyclopropyl, —S(O)$_2$-cyclobutyl, —S(O)$_2$-cyclopentyl, —S(O)$_2$-cyclohexyl, —S(O)$_2$-adamantyl, —S(O)$_2$-norbornyl, etc, Non-limiting examples of $Y^1$ when $Y^1$ is —S(O)$_2$-aryl include —S(O)$_2$-phenyl, —S(O)$_2$-naphthyl, etc, Non-limiting examples of $Y^1$ when $Y^1$ is -alkylene-CN include —O—CH$_2$—CN, —O—CH$_2$CH$_2$—CN, —CH$_2$CH$_2$CH$_2$CN, —O—CH(CH$_3$)—CN, —O—CH(CN)CH$_2$CH(CH$_3$)$_2$, —O—CH(CH$_3$)CH$_2$CH$_2$—CN, etc. Non-limiting examples of $Y^1$ when $Y^1$ is —C(O)-alkyl include —C(O)—CH$_3$, —C(O)—CH$_2$CH$_3$, —C(O)—CH$_2$CH$_2$CH$_3$, —C(O)—CH(CH$_3$)$_2$, —C(O)—CH$_2$CH$_2$CH$_2$CH$_3$, —C(O)—CH$_2$CH(CH$_3$)$_2$, —C(O)—CH(CH$_3$)CH$_2$CH$_3$, —C(O)—C(CH$_3$)$_3$, —C(O)—CH$_2$CH$_2$CH$_2$CH$_2$CH$_3$, —C(O)—CH$_2$CH(CH$_3$)CH$_2$CH$_3$, —C(O)—CH$_2$CH$_2$CH(CH$_3$)$_2$, —C(O)—CH$_2$CH$_2$CH$_2$CH$_2$CH$_2$CH$_3$, —C(O)—CH(CH$_3$)CH$_2$CH$_2$CH$_3$, —C(O)—CH$_2$CH(CH$_3$)CH$_2$CH$_2$CH$_3$, —C(O)—CH$_2$CH$_2$CH(CH$_3$)CH$_2$CH$_3$, —C(O)—CH$_2$CH$_2$CH$_2$CH(CH$_3$)$_2$, etc. Non-limiting examples of $Y^1$ when $Y^1$ is -alkylene-OH include —CH$_2$—OH, —CH$_2$CH$_2$—OH, —CH$_2$CH$_2$CH$_2$—OH, —CH(OH)CH$_3$, —CH$_2$CH(OH)CH$_3$, etc. Non-limiting examples of $Y^1$ when $Y^1$ is —C(O)-aryl include —C(O)-phenyl, —C(O)-naphthyl, etc. Non-limiting examples of $Y^1$ when $Y^1$ is —C(O)-haloalkyl include —C(O)—CF$_3$, —C(O)—CHF$_2$, —C(O)—CH$_2$F, —C(O)—CH$_2$CF$_3$, —C(O)—CF$_2$CF$_3$, —C(O)—CH$_2$Br, —C(O)—CH$_2$Cl, —C(O)—CCl$_3$, etc. Non-limiting examples of $Y^1$ when $Y^1$ is —C(O)O-alkyl include —C(O)—O—CH$_3$, —C(O)—O—CH$_2$OH$_3$, —C(O)—O—CH$_2$CH$_3$, —C(O)—O—CH(CH$_3$)$_2$, —C(O)—O—CH$_2$CH$_2$CH$_3$, —C(O)—O—CH$_2$CH(CH$_3$)$_2$, —C(O)—O—CH(CH$_3$)CH$_2$CH$_3$, —C(O)—O—C(CH$_3$)$_3$, —C(O)—O—CH$_2$CH$_2$CH$_2$CH$_3$, —C(O)—O—CH$_2$CH(CH$_3$)CH$_2$CH$_3$, —C(O)—O—CH$_2$CH$_2$CH(CH$_3$)$_2$, —C(O)—O—CH$_2$CH$_2$CH$_2$CH$_2$CH$_3$, —C(O)—O—CH(CH$_3$)CH$_2$CH$_2$CH$_3$, —C(O)—O—CH$_2$CH(CH$_3$)CH$_2$CH$_3$, —C(O)—O—CH$_2$CH$_2$CH$_2$CH(CH$_3$)$_2$, etc. Non-limiting examples of $Y^1$ when $Y^1$ is —N(R$^2$)C(O)-alkyl include —NH—C(O)-alkyl, —N(alkyl)-C(O)-alkyl, and —N(aryl)-C(O)-alkyl wherein the terms "alkyl" and "aryl" are as defined above. Non-limiting examples of $Y^1$ when $Y^1$ is —N(R$^2$)C(O)—N(R$^2$)$_2$ include —NHC(O)—NH$_2$, —NHC(O)-N(alkyl)$_2$, —NHC(O)—NH(aryl)$_2$, —NHC(O)—NH-alkyl, —NHC(O)—NH-aryl, —N(alkyl)C(O)—NH-alkyl, —N(alkyl)C(O)—NH-aryl, —N(aryl)C(O)—NH-aryl, —N(aryl)C(O)—NH-aryl, etc. Non-limiting examples of $Y^1$ when $Y^1$ is —O-alkyl include —O—CH$_3$, —O—CH$_2$CH$_3$, —O—CH$_2$CH$_2$CH$_3$, —O—CH(CH$_3$)$_2$, —O—CH$_2$CH$_2$CH$_3$, —O—CH$_2$CH(CH$_3$)$_2$, —O—CH(CH$_3$)CH$_2$CH$_3$, —O—C(CH$_3$)$_3$, —O—CH$_2$CH$_2$CH$_2$CH$_2$CH$_3$, —O—CH$_2$CH(CH$_3$)CH$_2$CH$_3$, —O—CH$_2$CH$_2$CH(CH$_3$)$_2$, —O—CH$_2$CH$_2$CH$_2$CH$_2$CH$_2$CH$_3$, —O—CH(CH$_3$)CH$_2$CH$_2$CH$_3$, —O—CH$_2$CH(CH$_3$)CH$_2$CH$_2$CH$_3$, —O—CH$_2$CH$_2$CH(CH$_3$)CH$_2$CH$_3$, —O—CH$_2$CH$_2$CH$_2$CH(CH$_3$)$_2$, etc. Non-limiting examples of $Y^1$ when $Y^1$ is —O-haloalkyl include —O—CF$_3$, —O—CHF$_2$, —O—CH$_2$F, —O—CH$_2$CF$_3$, —O—CF$_2$CF$_3$, —O—CH$_2$Br, —O—CH$_2$Cl, —O—CCl$_3$, etc. Non-limiting examples of $Y^1$ when $Y^1$ is —O-alkylene-C(O)OH include —O—CH$_2$—C(O)OH, —O—CH$_2$CH$_2$—C(O)OH, —CH$_2$CH$_2$CH$_2$C(O)OH, —O—CH(CH$_3$)—C(O)OH, —O—CH(C(O)OH)CH$_2$CH(CH$_3$)$_2$, —O—CH(CH$_3$)CH$_2$—C(O)OH, etc. Non-limiting examples of $Y^1$ when $Y^1$ is —S-alkyl include —S—CH$_3$, —S—CH$_2$CH$_3$, —S—CH$_2$CH$_2$CH$_3$, —S—CH(CH$_3$)$_2$, —S—CH$_2$CH$_2$CH$_2$CH$_3$, —S—CH$_2$CH(CH$_3$)$_2$, —S—CH(CH$_3$)CH$_2$CH$_3$, —S—C(CH$_3$)$_3$, —S—CH$_2$CH$_2$CH$_2$CH$_2$CH$_3$, —S—CH$_2$CH(CH$_3$)CH$_2$CH$_3$, —S—CH$_2$CH$_2$CH(CH$_3$)$_2$, —S—CH$_2$CH$_2$CH$_2$CH$_2$CH$_2$CH$_3$, —S—CH(CH$_3$)CH$_2$CH$_2$CH$_3$, —S—CH$_2$CH(CH$_3$)CH$_2$CH$_2$CH$_3$, —S—CH$_2$CH$_2$CH(CH$_3$)CH$_2$CH$_3$, —S—CH$_2$CH$_2$CH$_2$CH(CH$_3$)$_2$, etc. Non-limiting examples of $Y^1$ when $Y^1$ is —S-haloalkyl include —S—CF$_3$, —S—CHF$_2$, —S—CH$_2$F, —S—CH$_2$CF$_3$, —S—CF$_2$CF$_3$, —S—CH$_2$Br, —S—CH$_2$Cl, —S—CCl$_3$, etc. Non-limiting examples of $Y^1$ when $Y^1$ is -alkylene-OH include —CH$_2$—OH, —CH$_2$CH$_2$—OH, —CH$_2$CH$_2$CH$_2$—OH, —CH(OH)CH$_3$, —CH$_2$CH(OH)CH$_3$, etc. Non-limiting examples of $Y^1$ when $Y^1$ is -alkylene-C(O)—O-alkyl include —O—CH$_2$—C(O)O—CHR, —O—CH$_2$—C(O)O—CH$_2$CH$_3$, —O—CH$_2$CH$_2$—C(O)O—CH$_2$CH$_3$, —O—CH$_2$CH$_2$CH$_2$—C(O)O—CH$_3$, —O—CH$_2$CH$_2$—C(O)O—C(CH$_3$)$_3$, —O—CHCH$_3$)—C(O)O—CH$_3$, —O—CH$_2$CH$_2$—C(O)O—CH$_3$, —O—CH(C(O)OCH$_3$)CH$_2$CH(CH$_3$)$_2$, —O—CH(CH$_3$)CH$_2$CH$_2$—C(O)O—CH$_3$, etc. Non-limiting examples of $Y^1$ when $Y^1$ is —O-alkylene-aryl include —O—CH$_2$-phenyl, —O—CH$_2$CH$_2$-phenyl, —O—CH(CH$_3$)-phenyl, —O—CH$_2$CH(CH$_3$)-phenyl, —OC(CH$_3$)$_2$-phenyl, —O—CH(CH$_2$CH$_3$)-phenyl, etc. Non-limiting examples of $Y^1$ when $Y^1$ is —N(R$^6$)$_2$ include —NH$_2$, —N(CH$_3$)$_2$, —NH(CH$_3$), —NH(phenyl), —N(phenyl)$_2$, —NH—S(O)$_2$—CH$_3$—NH—S(O)$_2$-cyclopropyl, —NH—C(O)—NH$_2$, —NH—C(O)—N(CH$_3$)$_2$, —NH—C(O)—CH$_3$, —NH—CH$_2$CH$_2$—OH, etc. The aryl or heteroaryl portions of any of the groups of $Y^1$ may be unsubstituted or substituted with one or more groups independently selected from Z as defined herein.

In one embodiment, each $Y^2$ is independently selected from alkyl, haloalkyl, aryl, -alkylene-aryl, —CN —OH, —C(O)-alkyl, —S(O)$_2$-cycloalkyl, -alkylene-N(R$^2$)$_2$, —C(O)-alkylene-N(R$^4$)$_2$, —C(O)—O-alkyl, —C(O)-aryl, and —C(O)-haloalkyl. Non-limiting examples of $Y^2$ when $Y^2$ is alkyl include —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)CH$_2$CH$_3$, —(CH$_3$)$_3$, —CH$_2$CH$_2$CH$_2$CH$_2$CH$_3$, —CH$_2$CH(CH$_3$)CH$_2$CH$_3$, —CH$_2$CH$_2$CH(CH$_3$)$_2$, —CH$_2$CH$_2$CH$_2$CH$_2$CH$_2$CH$_3$, —CH(CH$_3$)CH$_2$CH$_2$CH$_3$, —CH$_2$CH(CH$_3$)CH$_2$CH$_2$CH$_3$, —CH$_2$CH$_2$CH(CH$_3$)CH$_2$CH$_3$, —CH$_2$CH$_2$CH(CH$_3$)CH$_2$CH$_3$, —CH$_2$CH$_2$CH$_2$CH(CH$_3$)$_2$, etc. Non-limiting examples of $Y^2$ when $Y^2$ is aryl include phenyl, naphthyl, etc. Non-limiting examples of $Y^2$ when $Y^2$ is -alkylene-aryl include —$CH_2$-phenyl, —$CH_2CH_2$-phenyl, —$CH(CH_3)$-phenyl, —$CH_2CH(CH_3)$-phenyl, —$C(CH_3)_2$-phenyl, —$CH(CH_2CH_3)$-phenyl, etc. Non-limiting examples of $Y^2$ when $Y^2$ is —C(O)-alkyl include —C(O)—$CH_3$, —C(O)—$CH_2CH_3$, —C(O)—$CH_2CH_2CH_3$, —C(O)—CH$(CH_3)_2$, —C(O)—$CH_2CH_2CH_2CH_3$, —C(O)—$CH_2CH(CH_3)_2$, —C(O)—$CH(CH_3)CH_2CH_3$, —C(O)—$C(CH_3)_3$, —C(O)—$CH_2CH_2CH_2CH_2CH_3$, —C(O)—$CH_2CH(CH_3)CH_2CH_3$, —C(O)—$CH_2CH_2CH(CH_3)_2$, —C(O)—$CH(CH_3)CH_2CH_2CH_3$, —C(O)—$CH_2CH_2CH_2CH_2CH_2CH_3$, —C(O)—$CH(CH_3)CH_2CH_2CH_3$, —C(O)—$CH_2CH(CH_3)CH_2CH_2CH_3$, —C(O)—$CH_2CH_2CH(CH_3)CH_2CH_3$, —C(O)—$CH_2CH_2CH_2CH(CH_3)_2$, etc. Non-limiting examples of $Y^2$ when $Y^2$ is —$S(O)_2$-cycloalkyl include —$S(O)_2$-cyclopropyl, —$S(O)_2$-cyclobutyl, —$S(O)_2$-cyclopentyl, —$S(O)_2$-cyclohexyl, —$S(O)_2$-norbornyl, —$S(O)_2$-adamantyl, etc. Non-limiting examples of $Y^2$ when $Y^2$ is -alkylene-$N(R^2)_2$ include -alkylene-$N(R^2)_2$ include —$CH_2$—$N(R^2)_2$, —$CH(CH_3)$—$N(R^2)_2$, —$CH_2CH_2$—$N(R^2)_2$, —$CH_2CH_2CH_2$—$N(R^2)_2$, —$CH(CH_3)CH_2CH_2$—$N(R^2)_2$, etc., wherein each $R^2$ is independently defined as described herein. For example, the "—$N(R^2)_2$" portion of -alkylene-$N(R^2)_2$ of $Y^2$ can be —$NH_2$, —$N(CH_3)_2$, —$NH(CH_3)$, —NH(phenyl), —N(phenyl)$_2$, —$N(CH_2CH_3)_2$, —$NH(CH_2CH3)$, etc. Non-limiting examples of $Y^2$ when $Y^2$ is —C(O)-alkylene-$N(R^4)_2$ include —C(O)—$CH_2$—$N(R^4)_2$, —C(O)—$CH(CH_3)$—$N(R^4)_2$, —C(O)—$CH_2CH_2$—$N(R^4)_2$, —C(O)—$CH_2CH_2CH_2$—$N(R^4)_2$, —C(O)—$CH(CH_3)CH_2CH_2$—$N(R^4)_2$, etc., wherein each $R^4$ is independently defined as described herein. For example the "—$N(R^4)_2$" portion of —C(O)-alkylene-$N(R^4)_2$ of $Y^2$ can be —$NH_2$, —$N(CH_3)_2$, —$NH(CH_3)$, —NH(phenyl), —N(phenyl)$_2$, —$N(CH_2CH_3)_2$, —$NH(CH_2CH_3)$, —NH—C(O)—O—$CH_3$, —NH—C(O)—O—$CH_2CH_3$, —$N(CH_3)$—C(O)—O—$CH_3$, —$N(CH_3)$—C(O)—O—$CH_2CH_3$, —NH—C(O)—$CH_3$, —NH—C(O)—$CH_2CH_3$, —$N(CH_3)$—C(O)—$CH_3$, —$N(CH_3)$—C(O)—$CH_2CH_3$, etc. Non-limiting examples of $Y^2$ when $Y^2$ is —C(O)—O-alkyl include —C(O)—O—$CH_3$, —C(O)—O—$CH_2CH_3$, —C(O)—O—$CH_2CH_2CH_3$, —C(O)—O—$CH(CH_3)_2$, —C(O)O—$CH_2CH_2CH_2CH_3$, —C(O)—O—$CH_2CH(CH_3)_2$, —C(O)—O—$CH(CH_3)CH_2CH_3$, —C(O)—O—C$(CH_3)_3$, —C(O)—O—$CH_2CH_2CH_2CH_2CH_3$, —C(O)—O—$CH_2CH(CH_3)CH_2CH_3$, —C(O)—O—$CH_2CH_2CH(CH_3)_2$, —C(O)—O—$CH_2CH_2CH_2CH_2CH_2CH_3$, —C(O)—O—$CH(CH_3)CH_2CH_2CH_3$, —C(O)—O—$CH_2CH(CH_3)CH_2CH_2CH_3$, —C(O)—O—$CH_2CH_2CH(CH_3)CH_2CH_3$, —C(O)—O—$CH_2CH_2CH_2CH(CH_3)_2$, etc. Non-limiting examples of $Y^2$ when $Y^2$ is —C(O)-aryl include —C(O)-phenyl, —C(O)-naphthyl, etc., optionally substituted with one or more groups independently selected from Z. Non-limiting examples of $Y^2$ when $Y^2$ is —C(O)-haloalkyl include —C(O)—$CF_3$, —C(O)—$CHF_2$, —C(O)—$CH_2F$, —C(O)—$CH_2CF_3$, —C(O)—$CF_2CF_3$, —C(O)—$CH_2Br$, —C(O)—$CH_2Cl$, —C(O)—$CCl_3$, etc.

In one embodiment, each $Y^3$ is independently selected from —C(O)N$(R^6)_2$, —S(O)$_2$N$(R^6)_2$, —O-Q-$L_1$-$R^7$, —O-Q-$L_2$-$R^8$, —O-Q-CN, —O-Q-C(O)N$(R^6)_2$, —O-Q-S(O)$_2$N$(R^6)_2$, —O-Q-OC(O)N$(R^6)_2$, and —O-Q-N$(R^6)$C(O)N$(R^6)_2$. In one embodiment, each $R^6$ is independently selected from H, alkyl, halo alkyl, alkoxy, unsubstituted aryl, (or aryl substituted with one or more (e.g., 1, 2, 3, or 4 or more) groups independently selected from $Y^1$), -alkylene-OH, -alkylene-O-alkyl, -alkylene-O-aryl, -alkylene-OC(O)-alkyl, -alkylene-OC(O)-aryl, -alkylene-OC(O)-heteroaryl, and -alkylene-N$(R_4)_2$.

Non-limiting examples of $R^6$ when $R^6$ is alkyl include any of the examples for alkyl described herein, including methyl, ethyl, n-propyl, iso-propyl, n-butyl, iso-butyl, sec-butyl, tert-butyl, n-pentyl, iso-pentyl, neo-pentyl, n-hexyl, iso-hexyl, etc.

Non-limiting examples of $R^6$ when $R^3$ is halo alkyl include any of the examples for alkyl described herein, including —$CF_3$, —$CHF_2$, —$CH_2F$, —$CH_2CF_3$, —$CF_2CF_3$, —$CH_2Br$, —$CH_2Cl$, —$CCl_3$, etc.

The "alkyl" portion of $R^6$ when $R^6$ is alkoxy includes any alkyl group described herein. Non-limiting examples include methyl, ethyl, n-propyl, iso-propyl, n-butyl, iso-butyl, sec-butyl, tert-butyl, n-pentyl, iso-pentyl, neo-pentyl, n-hexyl, iso-hexyl, etc.

Non-limiting examples of $R^6$ when $R^6$ is cycloalkyl or heterocycloalkyl include any of the examples for cycloalkyl or heterocycloalkyl described herein.

Non-limiting examples of $R^6$ when $R^6$ is aryl include any of the examples for aryl described herein, including phenyl, naphthyl, etc. When $R^6$ is aryl substituted with one or more (e.g., 1, 2, 3, or 4 or more) $Y^1$ groups, each $Y^1$ may be independently selected from any of the non-limiting examples for $Y^1$ described above.

When $R^6$ is -alkylene-OH, -alkylene-O-alkyl, -alkylene-O-aryl, -alkylene-OC(O)-alkyl, -alkylene-OC(O)-aryl, -alkylene-OC(O)-heteroaryl, and -alkylene-N$(R_4)_2$, non-limiting examples of alkylene and heteroaryl groups include any of those such groups described above.

When two $R^6$ groups, together with the nitrogen to which they are attached, form a heteroaryl, heterocycloalkyl, heterocycloalkenyl, or a benzo-fused heterocycloalkyl group, non-limiting examples of such heteroaryl, heterocycloalkyl, heterocycloalkenyl, and benzo-fused heterocycloalkyl groups include any of those such groups described above.

In one embodiment, each -Q- is a divalent radical independently selected from -alkylene-, -alkenylene-, -alkynylene-, -cycloalkylene-, -heterocycloalkylene-, -alkylene-cycloalkylene-, -cycloalkylene-alkylene-, -cycloalkylene-alkylene-cycloalkylene-, or -alkylene-cycloalkylene-alkylene, wherein the alkylene, alkenylene, alkynylene, cycloalkylene, and heterocycloalkylene portion of said Q is optionally substituted with one to three groups independently selected from

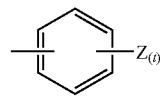

and Z, wherein t is 0, 1, 2, or 3. Non-limiting examples of such -alkylene-, -alkenylene-, -alkynylene-, -cycloalkylene-, -heterocycloalkylene-, include any of those such groups described above When Q is -alkylene-cycloalkylene-, -cycloalkylene-alkylene-, -cycloalkylene-alkylene-cycloalkylene-, or -alkylene-cycloalkylene-alkylene, a divalent cycloalkyl group is introduced at one or more locations along the alkylene chain, as described below. Cycloalkyl groups are obtained by the removal of two hydrogens from the same carbon atom of the alkylene chain, or a hydrogen from each of two adjacent or non-adjacent carbon atoms of the alkylene chain. Such cyclized groups may be introduced to alkenylene and alkynylene chains in Q in the compounds of the present invention. Z is as S described herein.

In one embodiment, each $L_1$ is independently selected from the group consisting of —O—, —S—, —S(O)—, —S(O)$_2$—, —OS(O)$_2$—, —C(O)—, and —OC(O)—. In one embodiment, each $L_2$ is —C(O)O—.

In one embodiment, each $R^7$ is independently selected from the group consisting of H, alkyl, —N$(R^6)_2$, cycloalkyl, heterocycloalkyl, aryl, substituted aryl, heteroaryl, and substituted heteroaryl, wherein said substituents are independently selected from Z and —C(O)N(R$^6$)$_2$. Non-limiting examples of alkyl, cycloalkyl, heterocycloalkyl, aryl, substituted aryl, heteroaryl, and substituted heteroaryl groups of R$^7$ include any of those described herein.

In one embodiment, each R$^8$ is independently selected from the group consisting of alkyl, —N(R$^6$)$_2$, cycloalkyl, heterocycloalkyl, aryl, substituted aryl, heteroaryl, and substituted heteroaryl, wherein said substituents are independently selected from Z and —C(O)N(R$^6$)$_2$, wherein each of Z and —C(O)N(R$^6$)$_2$ are as described herein. Non-limiting examples of alkyl, cycloalkyl, heterocycloalkyl, aryl, substituted aryl, heteroaryl, and substituted heteroaryl groups of R$^8$ include any of those described herein.

In one embodiment, each Z is independently selected from the group consisting of alkyl, halo, haloalkyl, —OH, —O-alkyl, and —CN. The terms "alkyl", "halo", aloalkyl", and "—O-alkyl" are as defined herein.

Also included within the scope of the invention are metabolites of compounds of Formula (I) or its various embodiments described herein, that is, compounds formed in vivo upon administration. Some examples of metablites include:

(i) where a compound of the invention contains a methyl group, an hydroxymethyl derivative thereof (e.g., —CH$_3$→—OH or —C(R)$_2$H→—C(R)$_2$OH, wherein each R is, independently, any corresponding substituent in Formula (I));

(ii) where a compound of the invention contains an alkoxy group, an hydroxyl derivative thereof (—OR→—OH, wherein R is any corresponding substituent in Formula (I));

(iii) where a compound of the invention contains a tertiary amino a group, a secondary amino derivative thereof (—N(R)$_2$→—NHR, wherein each R is, independently, any corresponding secondary or tertiary amino substituent in Formula (I));

(iv) where a compound of the invention contains a secondary amino group, a primary derivative thereof (—NHR→—NH$_2$, wherein R is any corresponding secondary amino or pimary amino substituent of Formula (I);

(v) where a compound of the invention contains a phenyl moiety, a phenol derivative thereof (—Ph→—PhOH);

(vi) where a compound of the invention contains an amide group, a carboxylic acid derivative thereof (—CONH$_2$→—COOH).

As used throughout the specification, the following terms, unless otherwise indicated, shall be understood to have the following meanings:

The term "Patient" includes humans and/or other animals. Animals include mammals and non-mammalian animals Mammals include humans and other mammalian animals. In some embodiments, the patient is a human. In other embodiments, the patient is non-human. In some embodiments, non-human animals include companion animals. Examples of companion animals include house cats (feline), dogs (canine), rabbits, horses (equine), guinea pigs, rodents (e.g., rats, mice, gerbils, or hamsters), primates (e.g., monkeys), and avians (e.g., pigeons, doves, parrots, parakeets, macaws, or canaries). In some embodiments, the animals are felines (e.g., house cats). In some embodiments, the animals are canines. Canines include, for example, wild and zoo canines such as wolves, coyotes, and foxes. Canines also include dogs, particularly domestic dogs, such as, for example, pure-bred and/or mongrel companion dogs, show dogs, working dogs, herding dogs, hunting dogs, guard dogs, police dogs, racing dogs, and/or laboratory dogs. In some embodiments, non-human animals include wild animals, livestock animals (e.g., animals raised for food and/or other products, such as, for example, meat, poultry, fish, milk, butter, eggs, fur, leather, feathers, and/or wool); beasts of burden; research animals; companion animals; and animals raised for/in zoos, wild habitats, and/or circuses. In other embodiments, non-human animals include primates, such as monkeys and great apes. In other embodiments, animals include bovine (e.g., cattle or dairy cows), porcine (e.g., hogs or pigs), ovine (e.g., goats or sheep), equine (e.g., horses), canine (e.g., dogs), feline (e.g, house cats), camels, deer, antelope, rabbits, guinea pigs, rodents (e.g, squirrels, rats, mice, gerbils, or hamsters), cetaceans (e.g., whales, dolphins, or porpoises), pinnipeds (e.g., seals or walruses). In other embodiments, animals include avians. Avians include birds associated with either commercial or noncommercial aviculture. These include, for example, Anatidae, such as swans, geese, and ducks; Columbidae, such as doves and pigeons (e.g., such as domestic pigeons); Phasianidae, such as partridges, grouse and turkeys; Thesienidae, such as domestic chickens; *Psittacines*, such as parakeets, macaws, and parrots (e.g., parakeets, macaws, and parrots raised for pets or collector markets; game birds; and ratites, such as ostriches. In other embodiments, animals include fish. Fish include, for example, the *Teleosti* grouping of fish (i.e., teleosts), such as, for example, the Salmoniformes order (which includes the Salmonidae family) and the Perciformes order (which includes the Centrarchidae family). Examples of fish include the Salmonidae family, the Serranidae family, the Sparidae family, the Cichlidae family, the Centrarchidae family, the three-Line Grunt (*Paraprstipoma trilineatum*), and the Blue-Eyed Plecostomus (*Plecostomus* spp). Additional examples of fish include, for example, catfish, sea bass, tuna, halibut, arctic charr, sturgeon, turbot, flounder, sole, carp, tilapia, striped bass, eel, sea bream, yellowtail, amberjack, grouper, and milkfish. In other embodiments, animals include marsupials (e.g., kangaroos), reptiles (e.g., farmed turtles), amphibians (e.g., farmed frogs), crustaceans (e.g., lobsters, crabs, shrimp, or prawns), mollusks (e.g., octopus and shellfish), and other economically-important animals.

"Body Condition Score" refers to an assessment of an animal's weight for age and weight for height ratios, and its relative proporions of muscle and fat. The assessment is made by eye, on the basis of amount of tissue cover between the points of the hip, over the transverse processes of the lumbar vertebrae, the cover over the ribs and the pin bones below the tail. Each animal is graded by comparison with animals pictured on a chart. The grading may be expressed as a score ranging from 1 to 8. As used herein, Body Condition Scores of 1 to 8 are described as follows:

| Score | Description |
|---|---|
| 1 | Emaciated. Ribs, lumbar vertebrae, pelvic bones and all bony prominences evident from a distance. No discernable body fat. Obvious loss of muscle mass. |
| 2 | Very thin. Ribs, lumbar vertebrae and pelvic bond easily visible. No palpable fat. Some evidence of other bony prominence. Minimal loss of muscle mass. |
| 3 | Thin. Ribs easily palpated and may be visible with no palpable fat. Tops of lumbar vertebrae visible. Pelvic bones becoming prominent. Obvious waist and lack of abdominal tuck. |

| Score | Description |
|---|---|
| 4 | Underweight. Ribs easily palpable with minimal fat covering. Waist easily noted from above. Abdominal tuck evident. |
| 5 | Ideal. Ribs palpable without excess fat covering. Waist observed behind ribs when viewed from above. Abdomen tucked when viewed from the side. |
| 6 | Overweight. Ribs palpable with slight excess fat covering. Waist is discernable viewed from above, but is not prominent. Abdominal tuck apparent. |
| 7 | Heavy. Ribs palpable with difficulty, heavy fat cover. Noticeable fat deposits over lumbar area and base of tail. Waist absent or barely visible. Abdominal tuck may be present. |
| 8 | Obese. Ribs not palpable under very heavy fat cover, or palpable only with significant pressure. Heavy fat deposits over lumbar area and base of tail. Waist absent. NO abdominal tuck. Obvious abdominal distension may be present. |

"Alkyl" means an aliphatic hydrocarbon group which may be straight or branched and comprising about 1 to about 20 carbon atoms in the chain. In one embodiment alkyl groups contain about 1 to about 12 carbon atoms in the chain. In another embodiment alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. Non-limiting examples of suitable alkyl groups include methyl, ethyl, n-propyl, isopropyl, n-butyl, t-butyl, n-pentyl, heptyl, nonyl, or decyl.

"Alkylene" means a divalent group obtained by removal of a hydrogen atom from an alkyl group that is defined above. Non-limiting examples of alkylene include methylene, ethylene and propylene. In one embodiment, alkylene groups have about 1-18 carbon atoms in the chain, which may be straight or branched. In another embodiment, alkylene groups have about 1-12 carbon atoms in the chain, which may be straight or branched. In another embodiment, alkylene groups may be lower alkylenes. "Lower alkylene" means an alkylene having about 1 to 6 carbon atoms in the chain, which may be straight or branched.

"Alkenyl" means an aliphatic hydrocarbon group containing at least one carbon-carbon double bond and which may be straight or branched and comprising about 2 to about 15 carbon atoms in the chain. In one embodiment alkenyl groups have about 2 to about 12 carbon atoms in the chain. In another embodiment alkenyl groups have about 2 to about 6 carbon atoms in the chain. Branched means that one or more tower alkyl groups such as methyl, ethyl or propyl, are attached to a linear alkenyl chain. "Lower alkenyl" means about 2 to about 6 carbon atoms in the chain which may be straight or branched. The term "substituted alkenyl" means that the alkenyl group may be substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkenylene" means a divalent group obtained by removal of a hydrogen atom from an alkenyl group that is defined above.

"Alkynyl" means an aliphatic hydrocarbon group containing at least one carbon-carbon triple bond and which may be straight or branched and comprising about 2 to about 15 carbon atoms in the chain. In one embodiment alkynyl groups have about 2 to about 12 carbon atoms in the chain. In another embodiment alkynyl groups have about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl, 3-methylbutynyl, n-pentynyl, and decynyl. The term "substituted alkynyl" means that the alkynyl group may be substituted by one or more substituents which may be the same or different, each substituent being independently selected from the group consisting of alkyl, aryl and cycloalkyl.

"Aryl" (sometimes abbreviated "ar" or "Ar") means an aromatic monocyclic or multicyclic ring system comprising about 6 to about 14 carbon atoms, or about 6 to about 10 carbon atoms. The aryl group can be optionally substituted with one or more "ring system substituents" which may be the same or different, and are as defined herein. Non-limiting examples of suitable aryl groups include phenyl, naphthyl, and biphenyl.

"Aryloxy" means a —O-aryl group, wherein aryl is defined as above, the aryloxy group is attached to the parent moiety through the ether oxygen.

"Arylene" means a divalent aryl group obtained by the removal of a hydrogen atom from an aryl group as defined above. Non-limiting examples of arylenes include, for example, 1,2-phenylene, 1,3-phenylene, or 1,4-phenylene.

"Heteroaryl" means an aromatic monocyclic or multicyclic ring system comprising about 5 to about 14 ring atoms, or about 5 to about 10 ring atoms, in which one or more of the ring atoms is an element other than carbon, for example nitrogen, oxygen or sulfur, alone or in combination. In one embodiment heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Cycloalkyl" means a non-aromatic mono- or multicyclic ring system comprising about 3 to about 13 carbon atoms, or about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalin, norbornyl, adamantyl and the like.

"Cycloalkylene" means a divalent cycloalkyl group obtained by the removal of a hydrogen atom from a cycloalkyl group as defined above. Non-limiting examples of cycloalkylenes include:

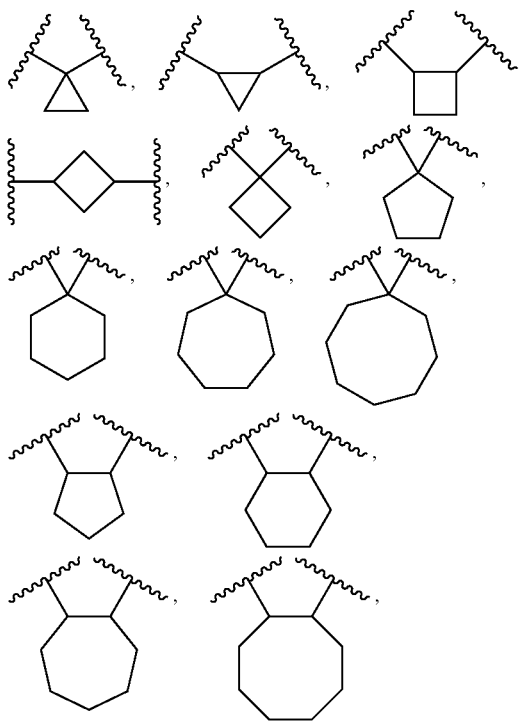

etc.

"Alkylene containing one or more cycloalkylene groups" means an alkylene group is bound to one or both of the open valancies of a cycloalkylene group. Similarly, "alkenylene (or alkynylene) containing one or more cycloalkylene groups" means an alkenylene (or alkynylene) group bound to one or both of the open valancies of a cycloalkylene group.

"Heterocycloalkyl" means a non-aromatic saturated monocyclic or multicyclic ring system comprising about 3 to about 10 ring atoms, or about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. In one embodiment heterocycloalkyls contain about 5 to about 6 ring atoms. The prefix aza, oxa or thia before the heterocycloalkyl root name means that at least a nitrogen, oxygen or sulfur atom respectively is present as a ring atom. The heterocycloalkyl can be optionally substituted by one or more "ring system substituents" which may be the same or different, and are as defined herein. The nitrogen or sulfur atom of the heterocycloalkyl can be optionally oxidized to the corresponding N-oxide, S-oxide or S,S-dioxide. Non-limiting examples of suitable monocyclic heterocycloalkyl rings include piperidyl, pyrrolidinyl, piperazinyl, morpholinyl, thiomorpholinyl, thiazolidinyl, 1,3-dioxolanyl, 1,4-dioxanyl, tetrahydropyranyl, tetrahydrofuranyl, tetrahydrothiophenyl, tetrahydrothiophenyl, and the like.

"Heterocycloalkenyl" means a non-aromatic unsaturated monocyclic or multicyclic ring system comprising about 3 to about 10 ring atoms, or about 5 to about 10 ring atoms, in which one or more of the atoms in the ring system is an element other than carbon, for example nitrogen, oxygen or sulfur, alone or in S combination. There are no adjacent oxygen and/or sulfur atoms present in the ring system. Heterocycloalkenyls have at least one double bond, wherein said double bond may be between two ring carbon atoms, between a ring carbon atom and a ring heteroatom (e.g., between a ring carbon atom and a ring nitrogen atom), or between two ring heteroatoms (e.g., between two ring nitrogen atoms). If more than one double bond is present in the ring, each double bond is independently defined as described herein. In another embodiment heterocycloalkenyls contain about 5 to about 6 ring atoms. The prefix aza, oxa or thia before the heterocycloalkenyl root name means that at least a nitrogen, oxygen or sulfur atom respectively is present as a ring atom. The heterocycloalkenyl can be optionally substituted by one or more "ring system substituents" which may be the same or different, and are as defined herein. The nitrogen or sulfur atom of the heterocycloalkenyl can be optionally oxidized to the corresponding N-oxide, S-oxide or SS-dioxide. Non-limiting examples of suitable monocyclic heterocycloalkenyl rings include thiazolinyl, 2,3-dihydro-1H-pyrrolyl, 2,5-dihydro-1H-pyrrolyl, 3,4-dihydro-2H-pyrrolyl, 2,3-dihydro-furan, 2,5-dihydro-furan, etc.

"Benzo-fused heterocycloalkenyl" means a heterocycloalkenyl, as defined above, to which one or more phenyl rings has been fused, so that each phenyl ring shares two ring carbon atoms with the cycloalkyl ring. In one embodiment, the benzo-fused heterocycloalkenyl group is attached to the rest of the molecule through the heterocycloalkenyl group. In another embodiment, the benzo-fused heterocycloalkenyl group is attached to the rest of the molecule through the benzyl group. Non-limiting examples of benzo-fused cycloalkyls are 4H-chromene, chromene-4-one, 1H-isochromene, etc.

"Benzo-fused cycloalkyl" means a cycloalkyl, as defined above, to which one or more phenyl rings has been fused, so that each phenyl ring shares two ring carbon atoms with the cycloalkyl ring. In one embodiment, the benzo-fused cycloalkyl group is attached to the rest of the molecule through the cycloalkenyl group. In another embodiment, the benzo-fused cycloalkenyl group is attached to the rest of the molecule through the benzyl group. Non-limiting examples of benzo-fused cycloalkyls are indanyl and tetradehydronaphthyl:

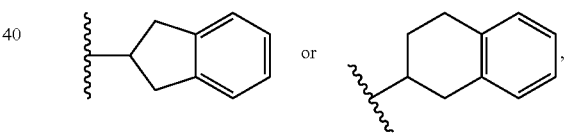

and non-limiting examples of a dibenzo-fused cycloalkyls are fluorenyl:

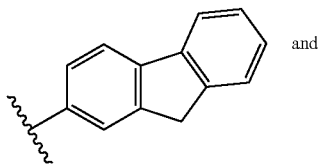 [SMILES: *c1ccc2c(c1)Cc1ccccc1-2]

and acenaphthenyl:

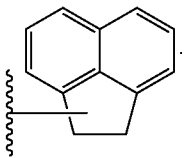

"Benzo-fused heterocycloalkyl" means a heterocycloalkyl, as defined above, to which one or more phenyl rings has been fused, so that each phenyl ring shares two ring carbon atoms with the heterocycloalkyl ring. In one embodiment, the benzo-fused heterocycloalkyl group is attached to the rest of the molecule through the heterocycloalkenyl group. In another embodiment, the benzo-fused heterocycloalkyl group is attached to the rest of the molecule through the benzyl group. A non-limiting example of a benzo-fused heterocycloalkyls is 2,3-dihydro-benzo[1,4]dioxinyl.

"Cycloalkenyl" means a non-aromatic mono or multicyclic ring system comprising about 3 to about 10 carbon atoms, or about 5 to about 10 carbon atoms, which contains at least one carbon-carbon double bond. In one embodiment cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexonyl, cycloheptenyl, and the like. Non-limiting example of a suitable multicyclic cycloalkenyl is norbornylenyl.

"Halo" (or "halogeno" or "halogen") means fluoro, chloro, bromo, or iodo groups. Preferred are fluoro, chloro or bromo, and more preferred are fluoro and chloro.

"Haloalkyl" means an alkyl as defined above wherein one or more hydrogen atoms on the alkyl are replaced by a halo group as defined above.

"Ring system substituent" means a substituent attached to an aromatic or non-aromatic ring system which, for example, replaces an available hydrogen on the ring system. Ring system substituents may be the same or different, and are defined as described herein.

"Alkoxy" means an —O-alkyl group in which the alkyl group is as previously described. Non-limiting examples of suitable alkoxy groups include methoxy, ethoxy, n-propoxy, isopropoxy, n-butoxy and heptoxy. The bond to the parent moiety is through the ether oxygen.

With reference to the number of moieties (e.g., substituents, groups or rings) in a compound, unless otherwise defined, the phrases "one or more" and "at least one" mean that there can be as many moieties as chemically permitted, and the determination of the maximum number of such moieties is well within the knowledge of those skilled in the art.

When used herein, the term "independently", in reference to the substitution of a parent moiety with one or more substituents, means that the parent moiety may be substituted with any of the listed substituents, either individually or in combination, and any number of chemically possible substituents may be used. As a non-limiting example, a phenyl independently substituted with one or more alkyl or halo substituents can include, chlorophenyl, dichlorophenyl, trichlorophenyl, tolyl, xylyl, 2-chloro-3-methylphenyl, 2,3-dichloro-4-methylphenyl, etc.

As used herein, the term "composition" is intended to encompass a product comprising the specified ingredients in the specified amounts, as well as any product which results, directly or indirectly, from combination of the specified ingredients in the specified amounts.

The wavy line ⁓ as a bond generally indicates a mixture of, or either of, the possible isomers, e.g., containing (R)— and (S)— stereochemistry. For example,

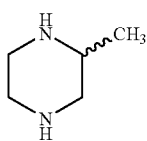

means containing both

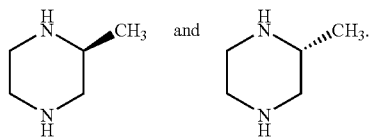

Moreover, when the stereochemistry of a chiral center (or stereogenic center) is not expressly indicated, a mixture of, or any of the individual possible isomers are contemplated. Thus, for example,

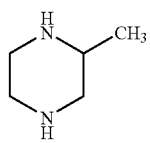

means containing

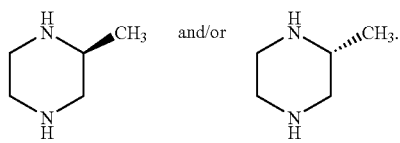

Lines drawn into the ring systems, such as, for example:

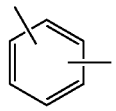

indicate that the indicated line (bond) may be attached to any of the substitutable ring carbon atoms. Hetero-atom containing ring systems, when present in a compound according to the invention, can be optionally substituted with a ring system substituent at an available ring carbon atom, an available ring heteroatom, or both, where allowed by appropriate valency rules.

As well known in the art, a bond drawn from a particular atom wherein no moiety is depicted at the terminal end of the bond indicates a methyl group bound through that bond to the atom, unless stated otherwise. For example:

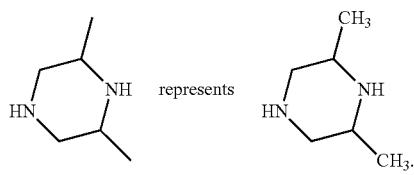

It should also be noted that any carbon or heteroatom with unsatisfied valences in the text, schemes, examples, structural formulae, and any Tables herein is assumed to have the hydrogen atom or atoms to satisfy the valences.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "isolated" or "in isolated form" for a compound refers to the physical state of said compound after being isolated from a synthetic process or natural source or combination thereof. The term "purified" or "in purified form" for a compound refers to the physical state of said compound after being obtained from a purification process or processes described herein or well known to the skilled artisan, in sufficient purity to be characterizable by standard analytical techniques described herein or well known to the skilled artisan.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, N.Y.

When any variable (e.g., aryl, heterocycle, $R^2$, etc.) occurs more than one time in any constituent or in any Formula (e.g., Formula I), its definition on each occurrence is independent of its definition at every other occurrence.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of formula I or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the present invention may also exist as, or optionally be converted to a solvate. The preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I.R. spectroscopy, show the presence of the solvent (or water) in the crystals as a solvate (or hydrate).

The compounds of Formula (I) form salts that are also within the scope of this invention. Reference to a compound of Formula (I) herein is understood to include reference to salts thereof, unless otherwise indicated. The term "salt(s)" as employed herein, denotes acidic salts formed with inorganic and/or organic acids, as well as basic salts formed with inorganic and/or organic bases. In addition, when a compound of Formula (I) contains both a basic moiety, such as, but not limited to a piperazine, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula (I) may be formed, for example, by reacting a compound of Formula (I) with an amount of acid or base, such as an equivalent amount, in a medium such as one in which the salt precipitates or in an aqueous medium followed by lyophilization. Acids (and bases) which are generally considered suitable for the formation of pharmaceutically useful salts from basic (or acidic) pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; in *The Orange Book* (Food & Drug Administration, Washington, D.C. on their website); and P. Heinrich Stahl, Camille G. Wermuth (Eds.), *Handbook of Pharmaceutical Salts: Properties, Selection, and Use*, (2002) Int'l. Union of Pure and Applied Chemistry, pp. 330-331. These disclosures are incorporated herein by reference thereto.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like.

Exemplary basic salts include ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis (dehydroabietyl)ethylenediamine), N-methyl-D-glucamines, N-methyl-D-glucamides, t-butyl amines, piperazine, phenylcyclohexylamine, choline, tromethamine, and salts with amino acids such as arginine, lysine and the like. Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

The compounds of the present invention may contain asymmetric or chiral centers, and, therefore, exist in different stereoisomeric forms. It is intended that all stereoisomeric forms of the compounds of the invention as well as mixtures thereof, including racemic mixtures, form part of the present invention. In addition, the present invention embraces all geometric and positional isomers. For example, if a compound of the invention incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, those of ordinary skill In the art will recognize any compounds of the present invention that may be atropisomers (e.g., substituted biaryls). Such atropisomers are considered as part of this invention. Enantiomers can also be separated by use of chiral HPLC column.

Compounds of Formula (I), and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively.

Certain isotopically-labelled compounds of Formula I (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labelled compounds of Formula (I can generally be prepared by following procedures analogous to those disclosed in the Schemes and/or in the Examples hereinbelow, by substituting an appropriate isotopically labelled reagent for a non-isotopically labelled reagent.

Polymorphic forms of the compounds of Formula (I), and of the salts, solvates and prodrugs of the compounds of Formula (I), are intended to be included in the present invention.

In still another embodiment, the present invention provides a composition comprising at least one compound of Formula (I), or a pharmaceutically acceptable salt, solvate, or ester thereof, and a pharmaceutically acceptable carrier.

The term "pharmaceutical composition" is also intended to encompass both the bulk composition and individual dosage units comprised of more than one (e.g., two, three, four, or more) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

Unit dosage forms, without limitation, can include tablets, pills, capsules, sustained release pills, sustained release tablets, sustained release capsules, powders, granules, or in the form of solutions or mixtures (i.e., elixirs, tinctures, syrups, emulsions, suspensions). For example, one or more compounds of Formula (I), or salts or solvates thereof, may be combined, without limitation, with one or more pharmaceutically acceptable liquid carriers such as ethanol, glycerol, or water, and/or one or more solid binders such as, for example, starch, gelatin, natural sugars (e.g., glucose or β-lactose), and/or natural or synthetic gums (e.g., acacia, tragacanth, or sodium alginate), carboxymethylcellulose, polyethylene glycol, waxes and the like, and/or disintegrants, buffers, preservatives, anti-oxidants, lubricants, flavorings, thickeners, coloring agents, emulsifiers and the like. In addition, the unit dosage forms can include, without limitation, pharmaceutically acceptable lubricants (e.g., sodium oleate, sodium stearate, magnesium stearate, sodium benzoate, sodium acetate, and sodium chloride) and disintegrators (e.g., starch, methyl cellulose, agar, bentonite, and xanthan gum). The amount of excipient or additive can range from about 0.1 to about 90% by weight of the total weight of the treatment composition. One skilled in the art understands that the amount of carrier(s), excipients, and additives (if present) can vary.

In another embodiment, the present invention provides a method of treating, reducing, or ameliorating a disease or condition selected from psychic disorders, anxiety, schizophrenia, depression, abuse of psychotropes, abuse and/or dependence of a substance, alcohol dependency, nicotine dependency, neuropathies, migraine, stress, epilepsy, dyskinesias, Parkinson's disease. amnesia, senile dementia, Alzheimer's disease, eating disorders, diabetes type II or non insulin dependent diabetes (NIDD), gastrointestinal diseases, vomiting, diarrhea, urinary disorders, infertility disorders, inflammations, infections, cancer, neuroinflammation, in particular in atherosclerosis, or the Guillain-Barr syndrome, viral encephalitis, cerebral vascular incidents and cranial trauma.

In yet another embodiment, the present invention provides a method of treating, reducing, or ameliorating obesity, in a patient in need thereof, comprising administering to said patient an effective amount of at least one compound of Formula (I), or a pharmaceutically acceptable salt, solvate, or ester thereof.

In another embodiment, the present invention provides a method of treating, reducing, or ameliorating metabolic syndrome, obesity, waist circumference, abdominal girth, lipid profile, insulin sensitivity, neuroinflammatory disorders, cognitive disorders, psychosis, addictive behavior, gastrointestinal disorders, and cardiovascular conditions, in a patient in need thereof, comprising administering to said patient an effective amount of a composition comprising at least one compound of Formula (I), or a pharmaceutically acceptable salt, solvate, or ester thereof and a pharmaceutically acceptable carrier.

In another embodiment, the present invention provides a method of treating, reducing, or ameliorating hepatic lipidosis and/or fatty liver disease (including but not limited to non-alcoholic fatty liver disease) in a patient in need thereof, comprising administering to said patient an effective amount of a composition comprising at least one compound of Formula (I), or a pharmaceutically acceptable salt, solvate, or ester thereof and a pharmaceutically acceptable carrier.

In another embodiment, the present invention provides a method of reducing body condition score (BCS) in a patient in need thereof, comprising administering to said patient an effective amount of a composition comprising at least one compound of Formula (I), or a pharmaceutically acceptable salt, solvate, or ester thereof (optionally together with at least one additional active agent) and one or more pharmaceutically acceptable carriers. In one embodiment, BCS is reduced from obese to ideal. In another embodiment, BCS is reduced from obese to heavy, overweight, or ideal. In another embodiment, BCS is reduced from obese to heavy. In another embodiment, BCS is reduced from obese to overweight. In another embodiment, BCS is reduced from heavy to overweight or ideal. In another embodiment, BCS is reduced from heavy to ideal. In another embodiment, BCS is reduced from overweight to ideal.

In other embodiments, the present invention provides a method of reducing the abdominal girth in a patient in need thereof. The method comprises administering an effective amount of a composition comprising at least one compound of Formula (I), or a pharmaceutically acceptable salt, solvate, or ester thereof (optionally together with at least one additional active agent) and one or more pharmaceutically acceptable carriers. In some embodiments, the patient is a non-human animal. In some such embodiments, for example, the patient may be a companion mammal, such as a dog, cat, or horse. Girth measurements are taken at the widest point behind the last rib and in front of the pelvis.

In other embodiments, the present invention provides a method of repartitioning, wherein energy of an animal is partitioned away from fat deposition toward protein accretion. The method comprising administering to said patient an effective amount of a composition comprising at least one compound of Formula (I), or a pharmaceutically acceptable salt, solvate, or ester thereof (optionally together with at least one additional active agent) and one or more pharmaceutically acceptable carriers In some embodiments, the patient is a non-human animal. In some such embodiments, for example, the patient may be a food animal, such as a bovine animal, swine animal, sheep, goat, or poultry animal (chicken, turkey, etc.) In other embodiments, the animal is an equine animal.

In other embodiments, the present invention provides a method of treating, reducing, or ameliorating a disease or condition selected from the group consisting of metabolic syndrome, obesity, waist circumference, abdominal girth, lipid profile, insulin sensitivity, neuroinflammatory disorders, cognitive disorders, psychosis, addictive behavior, gastrointestinal disorders, and cardiovascular conditions, in a patient in need thereof, comprising administering to said patient an effective amount of at least one compound of Formula (I), or a pharmaceutically acceptable salt, solvate, isomer, or ester thereof.

In yet another embodiment, the present invention provides a method of treating, reducing, or ameliorating obesity, in a patient in need thereof, comprising administering to said patient an effective amount of a composition comprising at least one compound of Formula (I), or a pharmaceutically acceptable salt, solvate, or ester thereof and a pharmaceutically acceptable carrier.

The compounds of Formula (I) can be useful as $CB_1$ receptor antagonists for treating, reducing, or ameliorating metabolic syndrome, obesity, waist circumference, abdominal girth, lipid profile, insulin sensitivity, neuroinflammatory disorders, cognitive disorders, psychosis, addictive behavior (e.g., smoking cessation), gastrointestinal disorders, and cardiovascular conditions (e g., elevated cholesterol and triglyceride levels). It is contemplated that the compounds of Formula (I) of the present invention, or pharmaceutically acceptable salts, solvates, or esters thereof, can be useful in treating one or more the conditions or diseases listed above. In particular, the compounds of Formula (I) of the present invention are useful in treating obesity.

"Effective amount" or "therapeutically effective amount" is meant to describe an amount of compound or a composition of the present invention effective in antagonizing a $CB_1$ receptor and thus producing the desired therapeutic effect in a suitable patient.

The selective $CB_1$ receptor antagonist compound of Formula (I), or a pharmaceutically acceptable salt, solvate, isomer or ester thereof, can be administered in a therapeutically effective amount and manner to treat the specified condition. The daily dose of the selective $CB_1$ receptor antagonist of Formula (I) (or pharmaceutically acceptable salts, solvates, or esters thereof) administered to a mammalian patient or subject can range from about 1 mg/kg to about 50 mg/kg (where the units mg/kg refer to the amount of selective $CB_1$ receptor antagonist compound of Formula (I) per kg body weight of the patient), or about 1 mg/kg to about 25 mg/kg, or about 1 mg/kg to about 10 mg/kg.

Alternatively, the daily dose can range from about 1 mg to about 50 mg, or about 1 mg to about 25 mg, or about 5 mg to about 20 mg. In one embodiment, the daily dose can range from about 0.01 mg/kg to about 1 mg/kg. In another embodiment, the daily dose can range from about 1 mg/kg to about 10 mg/kg. In another embodiment, the daily dose can range from about 1 mg/kg to about 25 mg/kg. Although a single administration of the selective $CB_1$ receptor antagonist compound of Formula (I), or salts, solvates, or esters thereof, can be efficacious, multiple dosages can also be administered. The exact dose, however, can readily be determined by the attending clinician and will depend on such factors as the potency of the compound administered, the age, weight, condition and response of the patient.

The treatment compositions of the present invention can be administered in any conventional dosage form, preferably an oral dosage form such as a capsule, tablet, powder, cachet, suspension or solution. The formulations and pharmaceutical compositions can be prepared using conventional pharmaceutically acceptable and conventional techniques.

In the veterinary context, in particular, the compounds of this invention can be administered to an animal patient in one or more of a variety of routes. For example, the compounds may be administered orally via, for example, a capsule, bolus, tablet (e.g., a chewable treat), powder, drench, elixir, cachet, solution, paste, suspension, or drink (e.g., in the drinking water or as a buccal or sublingual formulation). The compounds may alternatively (or additionally) be administered via a medicated feed (e.g., when administered to a non-human animal) by, for example, being dispersed in the feed or used as a top dressing or in the form of pellets or liquid which is added to the finished feed or fed separately. The compounds also may be administered (alternatively or additionally) parenterally via, for example, an implant or an intraruminal, intramuscular, intravascular, intratracheal, or subcutaneous injection. It is contemplated that other administration routes (e.g., topical, intranasal, rectal, etc.) may be used as well. Formulations for any such administration routes can be prepared using, for example, various conventional techniques known in the art. In some embodiments, from about 5 to about 70% by weight of the veterinary formulation (e.g., a powder or tablet) comprises active ingredient.

Suitable solid carriers are known in the art, and include, for example, magnesium carbonate, magnesium stearate, talc, sugar, and lactose. Tablets, powders, cachets, and capsules can be used as solid dosage forms suitable for oral administration To prepare suppositories, the active ingredient may be dispersed homogeneously into a melted wax that melts at low temperatures (e.g., a mixture of fatty acid glycerides or cocoa butter). Such dispersion may be achieved by, for example, stirring. The molten homogeneous mixture may be poured into convenient-sized molds, allowed to cool, and, thereby, solidify.

Liquid form preparations include solutions, suspensions, and emulsions. In some embodiments, for example, water or water-propylene glycol solutions are used for parenteral injection. Liquid form preparations also may include solutions for intranasal administration.

Aerosol preparations suitable for inhalation may include solutions and solids in powder form, which may be combined with a pharmaceutically acceptable carrier, such as an inert compressed gas.

Solid form preparations also include, for example, preparations that are intended to be converted, shortly before use, to liquid form preparations for either oral or parenteral administration. Such liquid forms include solutions, suspensions, and emulsions.

In some embodiments, the compounds of this invention are formulated for transdermal delivery. Transdermal compositions may be, for example, creams, lotions, aerosols, and/or emulsions, and can be included in a transdermal patch of the matrix or reservoir type as are conventional in the art for this purpose.

It is contemplated that the active can be incorporated into animal feed. A suitable amount of compound of the present invention can be placed into a commercially available feed product to achieve desired dosing levels. The amount of compound of the present invention incorporated into the feed will depend on the rate at which the animals are fed. Compounds or compositions of the present invention can be incorporated into feed mixtures before pelleting.

Alternatively, the medicated feed is formed by coating feed pellets with a compound(s) or compositions of the present invention.

In some embodiments, the present invention provides a method of treating fish for an indication described herein. Such methods include administering an effective amount of an inventive compound (or compounds) of the invention (optionally together with one or more additional active agents as described herein) to a fish or a fish population. Administration generally is achieved by either feeding the fish an effective amount of the inventive compound or by immersing the fish in a solution that contains an effective amount of the inventive compound. It is to be further understood that the inventive compound can be administered by application of the inventive compound(s) to a pool or other water-holding area containing the animal, and allowing the fish to absorb the compound through its gills, or otherwise allowing the dosage of the inventive compound to be taken in. For individual treatment of specific animals, such as a particular fish (e.g., in a veterinary or aquarium setting), direct injection or injection of osmotic release devices comprising the inventive compound, alone or in combination with other agents, is an optional method of administering the inventive compound. Suitable routes of administration include, for example, intravenous, subcutaneous, intramuscular, spraying, dipping, or adding the compound directly into the water in a holding volume.

In other embodiments, the present invention provides a composition comprising: (a) at least one compound of Formula (I), or a pharmaceutically acceptable salt, solvate, isomer or ester thereof, and (b) at least one additional active ingredient. Thus, it is contemplated that any of the indications suitable for treatment by at least one compound of Formula (I) may be treated using at least one compound of Formula (I) together with at least one additional active ingredient. Such additional active ingredient(s) may be combined with one or more compounds of the invention to form a single composition for use or the active ingredients may be formulated for separate (simultaneous or sequential) administration. Such additional active ingredients are described herein or are know to those of ordinary skill in the art. Non-limiting examples include centrally acting agents and peripherally acting agents. Non-limiting examples of centrally acting agents include histamine-3 receptor antagonists such as those disclosed in U.S. Pat. No. 6,720,328 (incorporated herein by reference). Non-limiting examples of such histamine H-3 receptor antagonists include the compound having a structure (as well as salts, solvates, isomers, esters, prodrugs, etc. thereof):

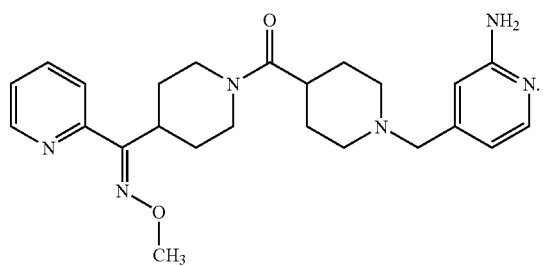 [SMILES: CO/N=C(/c1ccccn1)C1CCN(C(=O)C2CCN(Cc3ccnc(N)c3)CC2)CC1]

Other non-limiting examples of histamine-3 receptor antagonists include those disclosed in U.S. Pat. No. 7,105,505 (incorporated herein by reference). Non-limiting examples of such histamine H-3 receptor antagonists include the compound having a structure (as well as salts, solvates, isomers, esters, prodrugs, etc. thereof):

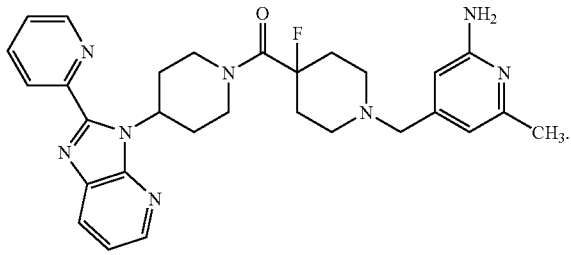 [SMILES: Cc1cc(CN2CCC(F)(C(=O)N3CCC(n4c(-c5ccccn5)nc5cccnc54)CC3)CC2)cc(N)n1]

Additional non-limiting examples of centrally acting agents include neuropeptide Y5 (NPY5) antagonists such as those disclosed in U.S. Pat. No. 6,982,267 (incorporated herein by reference). Non-limiting examples of such histamine NPY5 receptor antagonists include the compound having a structure (and salts, solvates, isomers, esters, prodrugs, etc. thereof):

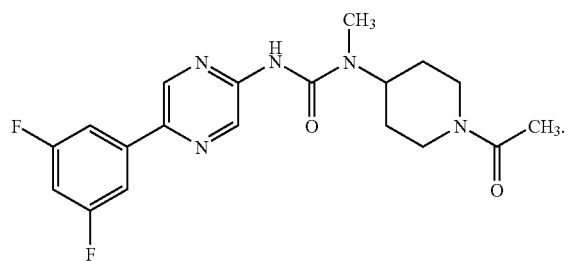 [SMILES: CC(=O)N1CCC(N(C)C(=O)Nc2cnc(-c3cc(F)cc(F)c3)cn2)CC1]

Non-limiting examples of peripherally acting agents include microsomal triglyceride transfer protein (MTP) inhibitors. Non-limiting examples of MTP inhibitors include dirlotapide (Slentrol™, Pfizer). Additional non-limiting examples of additional active ingredients are described herein.

In another embodiment, the present invention provides a composition comprising: (a) at least one compound of Formula (I), or a pharmaceutically acceptable salt, solvate, isomer or ester thereof, and (b) at least one cholesterol lowering compound.

Therapeutic combinations also are provided comprising: (a) a first amount of at least one selective $CB_1$ receptor antagonist, or a pharmaceutically acceptable salt, solvate, isomer or ester thereof; and (b) a second amount of at least one cholesterol lowering compound, wherein the first amount and the second amount together comprise a therapeutically effective amount for the treatment or prevention of a vascular condition, diabetes, obesity, hyperlipidemia, metabolic syndrome, or lowering a concentration of a sterol in the plasma of a subject.

Pharmaceutical compositions for the treatment or prevention of a vascular condition, diabetes, obesity, hyperlipidemia, metabolic syndrome, or lowering a concentration of a sterol in the plasma of a subject comprising a therapeutically effective amount of the above compositions or therapeutic combinations and a pharmaceutically acceptable carrier also are provided.

In still yet another embodiment, the compositions and combinations of the present invention comprise at least one compound of Formula (I), or a pharmaceutically acceptable salt, solvate, isomer, or ester thereof, and one or more antidiabetic drugs. Non-limiting examples of anti-diabetic drugs include sulffonyl ureas, meglitinides, biguanides, thiazolidinediones, alpha glucosidase inhibitors, incretin mietics, DPP-IV (dipeptidyl peptidase-4 or DPP-4) inhibitors, amylin analogues, insulin (including insulin by mouth), and herbal extracts.

Non-limiting examples of sulfonylureas include tolbutamide (Orinase®), acetohexamide (Dymelor®), tolazamide (Tolinase®), chlorpropamide (Diabinese®), glipizide (Glucotrol(RO), glyburide (Diabeta®, Micronase®, and Glynase®), glimepiride (Amaryl®), and gliclazide (Diamicron®).

Non-limiting examples of meglitinides include repaglinide (Prandin®), and mateglinide (Starlix®).

Non-limiting examples of biguanides include metformin (Glucophage®).

Non-limiting examples of thaizolidinediones, also known as glitazines, include rosiglitazone (Avandia®), pioglitazone (Actos®), and troglitazine (Rezulin®).

Non-limiting examples of gludosidase inhibitors include miglitol (Glyset®) and acarbose (Precose/Glucobay®).

Non-limiting examples of incretin mimetics include GLP agonists such as exenatide and exendin-4, marketed as Byetta® (Amylin Pharmaceuticals, Inc. and Eli Lilly and Company.)

Non-limiting examples of Amylin analogues include pramlintide acetate (Symlin® Amylin Pharmaceuticals, Inc.).

Non-limiting examples of DPP4 inhibitors and other antidiabetic drugs include the following: sitagliptin (marketed as Januvia®, available from Merck, pyrazine-based DPP-IV derivatives such as those disclosed in WO-2004085661, bicyclictetrahydropyrazine DPP IV inhibitors such as those disclosed in WO-03004498, PHX1149 (available from Phenomix, Inc.), ABT-279 and ABT-341 (available from Abbott, see WO-2005023762 and WO-2004026822), ALS-2-0426 (available Alantos and Servier), ARI 2243 (available from Arisaph Pharmaceuticals Inc., U.S. Ser. No. 06/803,357 and U.S. Ser. No. 06/890,898), boronic acid DPP-IV inhibitors such as those described in U.S. patent application Ser. No. 06/303,661, BI-A and BI-B (available from Boehringer Ingelheim), xanthine-based DPP-IV inhibitors such as those described in WO-2004046148, WO-2004041820, WO-2004018469, WO-2004018468 and WO-2004018467, saxagliptin (Bristol-Meyers Squibb and Astra Zenica), Biovitrim (developed by Santhera Pharmaceuticals (formerly Graffinity)), MP-513 (Mitsubishi Pharma), NVP-DPP-728 (qv) and structurally related 1-((S)-gamma-substituted prolyl)-(S)-2-cyanopyrrolidine compounds and analogs of NVP-DPP-728 (qv), DP-893 (Pfizer), vildagliptin (Novartis Institutes for BioMedical Research Inc), tetrahydroisoquinoline 3-carboxamide derivatives such as those disclosed in U.S. patent application Ser. No. 06/172,081, N-substituted 2-cyanopyrrolidines, including LAF-237, such as those disclosed in PCT Publication Nos. WO-00034241, WO-00152825, WO-02072146 and WO-03080070, WO-09920614, WO-00152825 and WO-02072146, SYR-322 (Takeda), denagliptin, SNT-189546, Ro-0730699, BMS-2, Aurigene, ABT-341, Dong-A, GSK-2, HanAll, LC-15-0044, SYR-619, Bexel, alogliptin benzoate, and ALS-2-0426 Non-limiting examples of other anti-diabetic drugs include metformin, thiazolidinediones (TZD), and sodium glucose cotransporter-2 inhibitors such as dapagliflozin (Bristol Meyers Squibb) and sergliflozin (GlaxoSmithKline), and FBPase (fructose 1,6-bisphosphatase) inhibitors.

In still yet another embodiment, the compositions and combinations of the present invention comprise at least one compound of Formula (I), or a pharmaceutically acceptable salt, solvate, isomer or ester thereof, and at least one sterol absorption inhibitor or at least one 5α-stanol absorption inhibitor.

In still yet another embodiment of the present invention, there is provided a therapeutic combination comprising: (a) a first amount of at least one compound of Formula (I), or a pharmaceutically acceptable salt, solvate, isomer or ester thereof; and (b) a second amount of at least one cholesterol lowering compound; wherein the first amount and the second amount together comprise a therapeutically effective amount for the treatment or prevention of one or more of a vascular condition, diabetes, obesity, metabolic syndrome, or lowering a concentration of a sterol in the plasma of a subject.

In still yet another embodiment, the present invention provides for a pharmaceutical composition for the treatment or prevention of one or more of a vascular condition, diabetes, obesity, metabolic syndrome, or lowering a concentration of a sterol in the plasma of a subject, comprising a therapeutically effective amount of a composition or therapeutic combination comprising: (a) at least one compound of Formula (I), or a pharmaceutically acceptable salt, solvate, or isomer ester thereof; (b) a cholesterol lowering compound; and (c) a pharmaceutically acceptable carrier.

As used herein, "therapeutic combination" or "combination therapy" means the administration of two or more therapeutic agents, such as a compound according to Formula (I) of the present invention, and a cholesterol lowering compound such as one or more substituted azetidinone or one or more substituted P-lactam, to prevent or treat a condition, for example a vascular condition, such as hyperlipidaemia (for example atherosclerosis, hypercholesterolemia or sitosterolemia), vascular inflammation, metabolic syndrome, stroke, diabetes, obesity and/or reduce the level of sterol(s) (such as cholesterol) in the plasma or tissue. As used herein, "vascular" comprises cardiovascular, cerebrovascular and combinations thereof. The compositions, combinations and treatments of the present invention can be administered by any suitable means which produce contact of these compounds with the site of action in the body, for example in the plasma, liver, small intestine, or brain (e.g., hippocampus, cortex, cerebellum, and basal ganglia) of a subject (mammal or human or other animal). Such administration includes co-administration of these therapeutic agents in a substantially simultaneous manner, such as in a single tablet or capsule having a fixed ratio of active ingredients or in multiple, separate capsules for each therapeutic agent. Also, such administration includes the administration of each type of therapeutic agent in a sequential manner. In either case, the treatment using the combination therapy will provide beneficial effects in treating the condition. A potential advantage of the combination therapy disclosed herein may be a reduction in the required amount of an individual therapeutic compound or the overall total amount of therapeutic compounds that are effective in treating the condition. By using a combination of therapeutic agents, the side effects of the individual compounds can be reduced as compared to a monotherapy, which can improve patient compliance. Also, therapeutic agents can be selected to provide a broader range of complimentary effects or complimentary modes of action.

As discussed above, the compositions, pharmaceutical compositions and therapeutic combinations of the present invention comprise: (a) one or more compounds according to Formula (I) of the present invention, or pharmaceutically acceptable salts, solvates, isomers or esters thereof; and (b) one or more cholesterol lowering agents. A non-limiting list of cholesterol lowering agents useful in the present invention include HMG CoA reductase inhibitor compounds such as lovastatin (for example MEVACOR® which is available from Merck & Co.), simvastatin (for example ZOCOR® which is available from Merck & Co.), pravastatin (for example PRAVACHOL® which is available from Bristol Meyers Squibb), atorvastatin, fluvastatin (for example LESCOL®), cerivastatin, CI-981, rivastatin (sodium 7-(4-fluorophenyl)-2,6-diisopropyl-5-methoxymethylpyridin-3-yl)-3,5-dihydroxy-6-heptanoate), rosuvastatin calcium (CRESTOR® from AstraZeneca Pharmaceuticals), Pravastatin (marketed as LIVALO®), cerivastatin, itavastatin (or pitavastatin, NK-104 of Negma Kowa of Japan); HMG CoA synthetase inhibitors, for example L-659,699 ((E,E)-11-[3'R-(hydroxy-methyl)-4'-oxo-2'R-oxetanyl]-3,5,7R-trimethyl-2,4-undecadienoic acid); squalene synthesis inhibitors, for example squalestatin 1; squalene epoxidase inhibitors, for example, NB-598 ((E)-N-ethyl-N-(6,6-dimethyl-2-hepten-4-ynyl)-3-[(3,3'-bithiophen-5-yl)methoxy]benzene-methanamine hydrochloride); sterol (e.g., cholesterol) biosynthesis inhibitors such as DMP-565; nicotinic acid derivatives (e.g., compounds comprising a pyridine-3-carboxylate structure or a pyrazine-2-carboxylate structure, including acid forms, salts, esters, zwitterions and tautomers) such as niceritrol, nicofuranose and acipimox (5-methyl pyrazine-2-carboxylic acid 4-oxide), and niacin extended-release tablets such as NIASPAN®; clofibrate; gemfibrazol; bile acid sequestrants such as cholestyramine (a styrene-divinylbenzene copolymer containing quaternary ammonium cationic groups capable of binding bile acids, such as QUESTRAN® or QUESTRAN LIGHT® cholestyramine which are available from Bristol-Myers Squibb), colestipol (a copolymer of diethylenetriamine and 1-chloro-2,3-epoxypropane, such as COLESTID® tablets which are available from Pharmacia), colesevelam hydrochloride (such as WelChol® Tablets (poly (allylamine hydrochloride) cross-linked with epichlorohydrin and alkylated with 1-bromodecane and (6-bromohexyl)-trimethylammonium bromide) which are available from Sankyo), water soluble derivatives such as 3,3-ioene, N-(cycloalkyl) alkylamines and poliglusam, insoluble quaternized polystyrenes, saponins and mixtures thereof; inorganic cholesterol sequestrants such as bismuth salicylate plus montmorillonite clay, aluminum hydroxide and calcium carbonate antacids; ileal bile acid transport ("BAT") inhibitors (or apical sodium co-dependent bile acid transport ("ASBT") inhibitors) such as benzothiepines, for example the therapeutic compounds comprising a 2,3,4,5-tetrahydro-1-benzothiepine 1,1-dioxide structure such as are disclosed in PCT Patent Application WO 00/38727 which is incorporated herein by reference; AcylCoA:Cholesterol O-acyltransferase ("ACAT") Inhibitors such as avasimibe ([[2,4,6-tris(1-methylethyl)phenyl]acetyl]sulfamic acid, 2,6-bis(1-methylethyl) phenyl ester, formerly known as CI-1011), HL-004, lecimibide (DuP-128) and CL-277082 (N-(2,4-difluorophenyl)-N-[[4-(2,2-dimethydpropyl)phenyl]methyl]-N-heptylurea), and the compounds described in P. Chang et al., "Current, New and Future Treatments in Dyslipidaemia and Atherosclerosis", Drugs 2000 Jul;60(1); 55-93, which is incorporated by reference herein; Cholesteryl Ester Transfer Protein ("CETP") Inhibitors such as those disclosed in PCT Patent Application No. WO 00/38721 and U.S. Pat. No. 6,147,090, which are incorporated herein by reference; probucol or derivatives thereof, such as AGI-1067 and other derivatives disclosed in U.S. Pat. Nos. 6,121,319 and 6,147,250, herein incorporated by reference; low-density lipoprotein (LDL) receptor activators such as HOE-402, an imidazolidinyl-pyrimidine derivative that directly stimulates LDL receptor activity, described in M. Huettinger et al., "Hypolipidemic activity of HOE-402 is Mediated by Stimulation of the LDL Receptor Pathway", Arterioscier. Thromb. 1993; 13:1005-12, herein incorporated by reference; fish oils containing Omega 3 fatty acids (3-PUFA); natural water soluble fibers, such as psyllium, guar, oat and pectin; plant stanols and/or fatty acid esters of plant stanols, such as sitostanol ester used in BENECOL® margarine; nicotinic acid receptor agonists (e.g., agonists of the HM74 and HM74A receptor which receptor is described in US 2004/0142377, US 2005/0004178, US 2005/0154029, U.S. Pat. No. 6,902,902, WO 2004/071378, WO 2004/071394, WO 01/77320, US 2003/0139343, WO 01/94385, WO 2004/083388, US 2004/254224, US 2004/0254224, US 2003/0109673 and WO 98/56820) for example those described in WO 2004/033431, WO 2005/011677, WO 2005/051937, US 2005/0187280, US 2005/0187263, WO 2005/077950, WO 2005/016867, WO 2005/016870, W02005061495, W02006005195, W02007059203, US2007105961, CA2574987, and AU2007200621; and the substituted azetidinone or substituted β-lactam sterol absorption inhibitors discussed in detail below.

As used herein, "sterol absorption inhibitor" means a compound capable of inhibiting the absorption of one or more sterols, including but not limited to cholesterol, phytosterols (such as sitosterol, campesterol, stigmasterol and avenosterol), 5α-stanols (such as cholestanol, 5α-campestanol, 5α-sitostanol), and/or mixtures thereof, when administered in a therapeutically effective (sterol and/or 5α-stanol absorption inhibiting) amount to a patient (e.g., mammal or human). Non-limiting examples of stanol absorption inhibitors include those compounds that inhibit cholesterol absorption in the small intestine. Such compounds are well known in the art and are described, for example, in US RE 37,721; U.S. Pat. No. 5,631,356; U.S. Pat. No. 5,767,115; U.S. Pat. No. 5,846,966, U.S. Pat. No. 5,698,548; U.S. Pat. No. 5,633,246; U.S. Pat. No. 5,656,624; U.S. Pat. No. 5,624,920; U.S. Pat. No. 5,688,787; U.S. Pat. No. 5,756,470; US Publication No. 2002/0137689; WO 02/066464; WO 95/08522 and WO96/19450. Non-limiting examples of cholesterol absorption inhibitors also include non-small molecule agents, microorganisms such as *Bifidobacterium animalis* subsp. animalis YIT 10394, *Bifidobacterium animalis* subsp. lactis JCM 1253, *Bifidobacterium animalis* subsp. lactis JCM 7117 and *Bifidobacterium pseudolongum* subsp. Globosum, which are described, e.g., in WO2007029773. Each of the aforementioned publications is incorporated by reference.

Substituted Azetidinones of Formula (II)

In one embodiment, substituted azetidinones useful in the compositions, therapeutic combinations and methods of the present invention are represented by Formula (II) below:

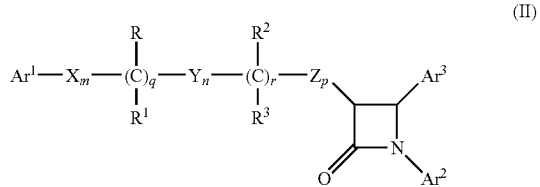

(II)

or pharmaceutically acceptable salts, solvates, or esters of the compounds of Formula (II), wherein, in Formula (II) above.

$Ar^1$ and $Ar^2$ are independently selected from the group consisting of aryl and $R^4$-substituted aryl;

$Ar^3$ is aryl or $R^5$-substituted aryl;

X, Y and Z are independently selected from the group consisting of —$CH_2$—, —CH(lower alkyl)- and —C(lower alkyl)$_2$-;

R and $R^2$ are independently selected from the group consisting of —$OR^6$, —OC(O)$R^6$, —OC(O)O$R^9$ and —OC(O)N$R^6R^7$;

$R^1$ and $R^3$ are independently selected from the group consisting of hydrogen, lower alkyl and aryl;

q is 0 or 1; r is 0 or 1; m, n and p are independently selected from 0, 1, 2, 3 or 4; provided that at least one of q and r is 1, and the sum of m, n, p, q and r is 1, 2, 3, 4, 5 or 6; and provided that when p is 0 and r is 1; the sum of m, q and n is 1,2,3,4or5;

$R^4$ is 1-5 substituents independently selected from the group consisting of lower alkyl, —$OR^6$, —OC(O)$R^6$, —OC(O)O$R^9$, —O(CH$_2$)$_{1-5}$O$R^6$, —OC(O)N$R^6R^7$, —N$R^6R^7$, —N$R^6$C(O)$R^7$, —N$R^6$C(O)O$R^9$, —N$R^6$C(O)N$R^7R^8$, —N$R^6$SO$_2R^9$, —C(O)O$R^6$, —C(O)N$R^6B^7$, —C(O)$R^6$, —S(O)$_2$N$R^6R^7$, S(O )$_{0-2}R^9$, —O(CH$_2$)$_{1-10}$—C(O)O$R^6$, —O(CH$_2$)$_{1-10}$CON$R^6R^7$, -(lower alkylene)COO$R^6$, —CH=CH—C(O)O$R^6$, —CF$_3$, —CN, —NO$_2$ and halogen;

$R^5$ is 1-5 substituents independently selected from the group consisting of —$OR^6$, —OC(O)$R^6$, —OC(O)O$R^9$, —O(CH$_2$)$_{1-5}$O$R^6$, —OC(O)N$R^6R^7$, —N$R^6R^7$, —N$R^6$C(O)$R^7$, —N$R^6$C(O)O$R^9$, —N$R^6$C(O)N$R^7R^8$, —N$R^6$S(O)$_2R^7$, —N$R^6$C(O)N$R^7R^8$, —N$R^6$S(O)$_2R^9$, —C(O)O$R^6$, —C(O)N$R^6R^7$, —C(O)$R^6$, —SO$_2$N$R^6R^7$, S(O)$_{0-2}R^9$, —O(CH$_{21-10}$—C(O)O$R^6$, —O(CH$_2$)$_{1-10}$C(O)NP$^6R^7$, -(lower alkylene)C(O)O$R^6$ and —CH=CH—C(O)O$R^6$;

$R^6$, $R^7$ and $R^8$ are independently selected from the group consisting of hydrogen, lower alkyl, aryl and aryl-substituted lower alkyl; and $R^9$ is lower alkyl, aryl or aryl-substituted lower alkyl.

Preferably, $R^4$ is 1-3 independently selected substituents, and $R^5$ is preferably 1-3 independently selected substituents Certain compounds useful in the therapeutic compositions or combinations of the invention may have at least one asymmetrical carbon atom and therefore all isomers, including enantiomers, diastereomers, stereoisomers, rotamers, tautomers and racemates of the compounds of Formula II-XIII (where they exist) are contemplated as being part of this invention The invention includes d and l isomers in both pure form and in admixture, including racemic mixtures. Isomers can be prepared using conventional techniques, either by reacting optically pure or optically enriched starting materials or by separating isomers of a compound of the Formulae II-XIII. Isomers may also include geometric isomers, e.g., when a double bond is present.

Those skilled in the art wilt appreciate that for some of the compounds of the Formulae II-XIII, one isomer may show greater pharmacological activity than other isomers.

Preferred compounds of Formula (II) are those in which $Ar^1$ is phenyl or $R^4$-substituted phenyl, more preferably (4-$R^4$)-substituted phenyl. $Ar^2$ is preferably phenyl or $R^4$-substituted phenyl, more preferably (4-$R^4$)-substituted phenyl. $Ar^3$ is preferably $R^5$-substituted phenyl, more preferably (4-$R^5$)-substituted phenyl. When $Ar^1$ is (4-$R^4$)-substituted phenyl, $R^4$ is preferably a halogen. When $Ar^2$ and $Ar^3$ are $R^4$- and $R^5$-substituted phenyl, respectively, $R^4$ is preferably halogen or —$OR^6$ and $R^5$ is preferably —$OR^6$, wherein $R^6$ is lower alkyl or hydrogen Especially preferred are compounds wherein each of $Ar^1$ and $A^2$ is 4-fluorophenyl and $Ar^3$ is 4-hydroxyphenyl or 4-methoxyphenyl.

X, Y and Z are each preferably —$CH_2$—. $R^1$ and $R^3$ are each preferably hydrogen. R and $R^2$ are preferably —$OR^6$ wherein $R^6$ is hydrogen, or a group readily metabolizable to a hydroxyl (such as —OC(O)$R^6$, —OC(O)$R^9$ and —OC(O)N$R^6R^7$, defined above).

The sum of m, n, p, q and r is preferably 2, 3 or 4, more preferably 3. Preferred are compounds OF Formula (II) wherein m, n and r are each zero, q is 1 and p is 2.

Also preferred are compounds of Formula (II) in which p, q and n are each zero, r is 1 and m is 2 or 3. More preferred are compounds wherein m, n and r are each zero, q is 1, p is 2, Z is —$CH_2$— and R is —$OR^6$, especially when $R^6$ is hydrogen.

Also more preferred are compounds of Formula (II) wherein p, q and n are each zero, r is 1, m is 2, X is —$CH_2$— and $R^2$ is —$OR^6$, especially when $R^6$ is hydrogen.

Another group of preferred compounds of Formula (II) is that in which $Ar^1$ is phenyl or $R^4$-substituted phenyl, $Ar^2$ is phenyl or $R^4$-substituted phenyl and $Ar^3$ is $R^5$-substituted phenyl. Also preferred are compounds in which $Ar^1$ is phenyl or $R^4$-substituted phenyl, $Ar^2$ is phenyl or $R^4$-substituted phenyl, $Ar^3$ is $R^5$-substituted phenyl, and the sum of m, n, p, q and r is 2, 3 or 4, more preferably 3. More preferred are compounds wherein $Ar^1$ is phenyl or $R^4$-substituted phenyl, $Ar^2$ is phenyl or $R^4$-substituted phenyl, $Ar^3$ is $R^5$-substituted phenyl, and wherein m, n and r are each zero, q is 1 and p is 2, or wherein p, q and n are each zero, r is 1 and m is 2 or 3.

Substituted Azetidinones of Formula (III)

In a preferred embodiment, a substituted azetidinone of Formula (II) useful in the compositions, therapeutic combinations and methods of the present invention is represented by Formula (III) (ezetimibe) below:

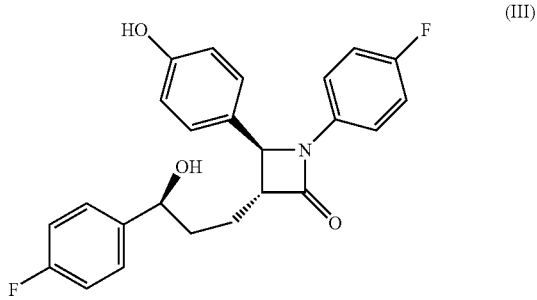 [SMILES: O=C1[C@H](CC[C@H](O)c2ccc(F)cc2)[C@@H](c2ccc(O)cc2)N1c1ccc(F)cc1]

(III)

or pharmaceutically acceptable salts, solvates, or esters of the compound of Formula (III). The compound of Formula (III) can be in anhydrous or hydrated form. A product containing ezetimibe compound is commercially available as ZETI® ezetimibe formulation from MSP Pharmaceuticals Compounds of Formula (II) can be prepared by a variety of methods well known to those skilled in the art, for example such as are disclosed in U.S. Pat. Nos. 5,631,365, 5,767,115, 5,846,966, 6,207,822, 6,627,757, 6,093,812, 5,306,817, 5,561,227, 5,688,785, and 5,688,787, each of which is incorporated herein by reference.

Substituted Azetidinones of Formula (IV)

Alternative substituted azetidinones useful in the compositions, therapeutic combinations and methods of the present invention are represented by Formula (IV) below:

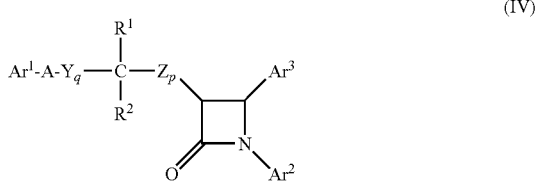

(IV)

or a pharmaceutically acceptable salt thereof or a solvate thereof, or an ester thereof, wherein, in Formula (IV) above.

$Ar^1$ is $R^3$-substituted aryl;

$Ar^2$ is $R^4$-substituted aryl;

$Ar^3$ is $R^5$-substituted aryl;

Y and Z are independently selected from the group consisting of —$CH_2$—, —CH(lower alkyl)- and —C(lower alkyl)$_2$-;

A is selected from —O—, —S—, —S(O)— or —S(O)$_2$—;

$R^1$ is selected from the group consisting of —$OR^6$, —OC(O)$R^6$, —OC(O)$OR^9$ and —OC(O)$NR^6R^7$;

$R^2$ is selected from the group consisting of hydrogen, lower alkyl and aryl; or $R^1$ and $R^2$ together are =O;

q is 1, 2 or 3;

p is 0, 1, 2, 3 or 4;

$R^5$ is 1-3 substituents independently selected from the group consisting of —$OR^6$, —OC(O)$R^6$, —OC(O)$OR^9$, —O($CH_2$)$_{1-5}$$OR^9$, —OC(O)$NR^6R^7$, —$NR^6R^7$, —$NR^6$C(O)$R^7$, —$NR^6$C(O)$OR^9$, —$NR^6$C(O)$NR^7R^8$, —$NR^6$S(O)$_2$-lower alkyl, —$NR^6$S(O)$_2$-aryl, —C(O)$NR^6R^7$, —$COR^6$, —$SO_2NR^6R^7$, S(O)$_{0-2}$-alkyl, S(O)$_{0-2}$-aryl, —O($CH_2$)$_{1-10}$—C(O)$OR^6$, —O($CH_2$)$_{1-10}$C(O)$NR^6R^7$, o-halogeno, m-halogeno, o-lower alkyl, m-lower alkyl, -(lower alkylene)-C(O)$OR^6$, and —CH=CH—C(O)$OR^6$;

$R^3$ and $R^4$ are independently 1-3 substituents independently selected from the group consisting of $R^5$, hydrogen, p-lower alkyl, aryl, —$NO^2$, —$CF_3$ and p-halogeno;

$R^6$, $R^7$ and $R^8$ are independently selected from the group consisting of hydrogen, lower alkyl, aryl and aryl-substituted lower alkyl; and $R^9$ is lower alkyl, aryl or aryl-substituted lower alkyl.

Methods for making compounds of Formula (IV) are well known to those skilled in the art. Non-limiting examples of suitable methods are disclosed in U.S. Pat. No. 5,688,990, which is incorporated herein by reference.

Substituted Azetidinones of Formula (V)

In another embodiment, substituted azetidinones useful in the compositions, therapeutic combinations and methods of the present invention are represented by Formula (V):

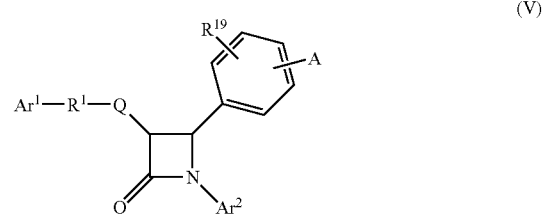

(V)

or a pharmaceutically acceptable salt thereof or a solvate thereof, or an ester thereof, wherein, in Formula (V) above:

A is selected from the group consisting of $R^2$-substituted heterocycloalkyl, $R^2$-substituted heteroaryl, $R^2$-substituted benzo-fused heterocycloalkyl, and $R^2$-substituted benzo-fused heteroaryl;

$Ar^1$ is aryl or $R^3$-substituted aryl;

$Ar^2$ is aryl or $R^4$-substituted aryl;

Q is a bond or, with the 3-position ring carbon of the azetidinone, forms the spiro group

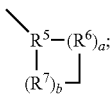

and $R^1$ is selected from the group consisting of:

—$(CH_2)_q$—, wherein q is 2-6, provided that when Q forms a spiro ring, q can also be zero or 1;

—$(CH_2)_e$-G-$(CH_2)_r$—, wherein G is —O—, —C(O)—, phenylene, —$NR^8$— or —$S(O)_{0-2}$—, e is 0-5 and r is 0-5, provided that the sum of e and r is 1-6;

—$(C_2$-$C_6$ alkenylene)-; and

—$(CH_2)_f$—V—$(CH_2)_g$—, wherein V is $C_3$-$C_6$ cycloalkylene, f is 1-5 and g is 0-5, provided that the sum of f and g is 1-6;

$R^5$ is selected from:

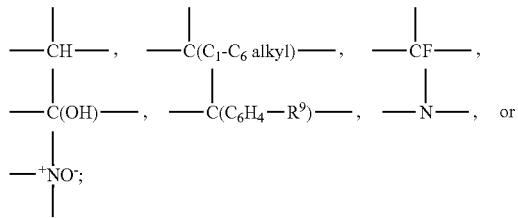

$R^6$ and $R^7$ are independently selected from the group consisting of —$CH_2$—, —$CH(C_0$-$C_6$ alkyl)-, —$C(di$-$(C_1$-$C_6)$ alkyl), —CH=CH— and —$C(C_1$-$C_6$ alkyl)=CH—; or $R^5$ together with an adjacent $R^6$, or $R^5$ together with an adjacent $R^7$, form a —CH=CH— or a —OH=$C(C_1$-$C_6$ alkyl)- group;

a and b are independently 0, 1, 2 or 3, provided both are not zero; provided that when $R^6$ is —CH=CH— or —$C(C_1$-$C_6$ alkyl)=CH—, a is 1; provided that when $R^7$ is —CH=CH— or —$C(C_1$-$C_6$ alkyl)=CH—, b is 1; provided that when a is 2 or 3, the $R^6$'s can be the same or different; and provided that when b is 2 or 3, the $R^7$'s can be the same or different:

and when Q is a bond, $R^1$ also can be selected from:

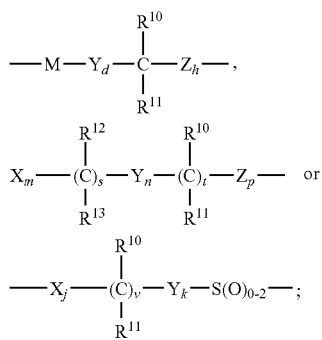

where M is —O—, —S—, —S(O)— or —$S(O)_2$—;

X, Y and Z are independently selected from the group consisting of —$CH_2$—, —$CH(C_1$-$C_6$ alkyl)- and —$C(di$-$(C_1$-$C_6)$ alkyl);

$R^{10}$ and $R^{12}$ are independently selected from the group consisting of —$OR^{14}$, —$OC(O)R^{14}$, —$OC(O)OR^{16}$ and —$OC(O)NR^{14}R^{15}$;

$R^{11}$ and $R^{13}$ are independently selected from the group consisting of hydrogen, $(C_1$-$C_6)$alkyl and aryl; or $R^{10}$ and $R^{11}$ together are =O, or $R^{12}$ and $R^{13}$ together are =O;

d is 1, 2 or 3;

h is 0, 1, 2, 3 or 4;

s is 0 or 1; t is 0 or 1; m, n and p are independently 0-4; provided that at least one of s and t is 1, and the sum of m, n, p, s and t is 1-6; provided that when p is 0 and t is 1, the sum of m, s and n is 1-5; and provided that when p is 0 and s is 1 the sum of m, t and n is 1-5;

v is 0 or 1;

j and k are independently 1-5, provided that the sum of j, k and v is 1-5;

$R^2$ is 1-3 substituents on the ring carbon atoms selected from the group consisting of hydrogen, $(C_1$-$C_{10})$alkyl, $(C_2$-$C_{10})$alkenyl, $(C_2$-$C_{10})$alkynyl, $(C_3$-$C_6)$cycloalkyl, $(C_3$-$C_6,)$cycloalkenyl, $R^{17}$-substituted aryl, $R^{17}$-substituted benzyl, $R^{17}$-substituted benzyloxy, $R^{17}$-substituted aryloxy, halogeno, -$NR^{14}R^{15}$, $NR^{14}R^{15}(C_1$-$C_6$ alkylene)-, $NR^{14}R^{15}C(O)$ $(C_1$-$C_6$ alkylene)-, —$NHC(O)R^{16}$, OH, $C_1$-$C_6$ alkoxy, —$OC(O)R^{16}$, —$C(O)R^{14}$, hydroxy$(C_1$-$C_6)$alkyl, $(C_1$-$C_6)$alkoxy $(C_1$-$C_6)$alkyl, $NO_2$, —$S(O)_{0-2}R^{16}$, —$S(O)_2NR^{14}R^{15}$ and —$(C_1$-$C_6$ alkylene)$C(O)OR^{14}$; when $R^2$ is a substituent on a heterocycloalkyl ring, $R^2$ is as defined, or $R^2$ is =O or

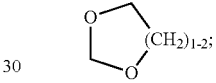

and, where $R^2$ is a substituent on a substitutable ring nitrogen, $R^2$ is hydrogen, $(C_1$-$C_6)$alkyl, aryl, $(C_1$-$C_6)$alkoxy, aryloxy, $(C_1$-$C_6)$alkylcarbonyl, arylcarbonyl, hydroxy, —$(CH_2)_{1-6}CONR^8R^{18}$,

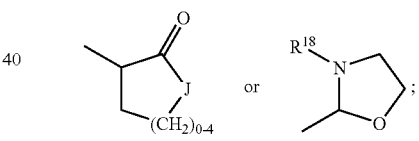

wherein J is —O—, —NH—, —$NR^{18}$— or —$CH_2$—;

$R^3$ and $R^4$ are independently selected from the group consisting of 1-3 substituents independently selected from the group consisting of $(C_1$-$C_6)$alkyl, —$OR^{14}$, —$OC(O)R^{14}$, —$OC(O)OR^{16}$, —$O(CH_2)_{1-5}OR^{14}$, —$OC(O)NR^{14}R^{15}$, —$NR^{14}R^{15}$, —$NR^{14}C(O)R^{15}$, —$NR^{14}C(O)OR^{16}$, —$NR^{14}C(O)NR^{15}R^{19}$, —$NR^{14}S(O)_2R^{16}$, —$C(O)OR^{14}$, —$C(O)NR^{14}R^{15}$, —$C(O)R^{14}$, —$S(O)_2NR^{14}R^{15}$, $S(O)_{1-2}R^{16}$, —$O(CH_2)_{1-10}$—$C(O)OR^{14}$, —$O(CH_2)_{1-10}C(O)NR^{14}R^{15}$, —$(C_1$-$C_6$alkylene)—$C(O)OR^{14}$, —CH=CH—$C(O)OR^{14}$, —$CF_3$, —CN, —$NO_2$ and halogen;

$R^8$ is hydrogen, $(C_1$-$C_6)$alkyl, aryl $(C_1$-$C_6)$alkyl, —$C(O)R^{14}$ or —$C(O)OR^{14}$;

$R^9$ and $R^{17}$ are independently 1-3 groups independently selected from the group consisting of hydrogen, $(C_1$-$C_6)$ alkyl, $(C_1$-$C_6)$alkoxy, —C(O)OH, $NO_2$, —$NR^{14}R^{15}$, OH and halogeno;

$R^{14}$ and $R^{15}$ are independently selected from the group consisting of hydrogen, $(C_1$-$C_6)$alkyl, aryl and aryl-substituted $(C_1$-$C_6)$alkyl;

$R^{16}$ is $(C_1$-$C_6)$alkyl, aryl or $R^{17}$-substituted aryl;

$R^{18}$ is hydrogen or $(C_1$-$C_6)$alkyl; and $R^{19}$ is hydrogen, hydroxy or $(C_1$-$C_6)$alkoxy.

Methods for making compounds of Formula (V) are well known to those skilled in the art. Non-limiting examples of suitable methods are disclosed in U.S. Pat. No. 5,656,624, which is incorporated herein by reference. Substituted Azetidinones of Formula (VI)

In another embodiment, substituted azetidinones useful in the compositions, therapeutic combinations and methods of the present invention are represented by Formula (VI):

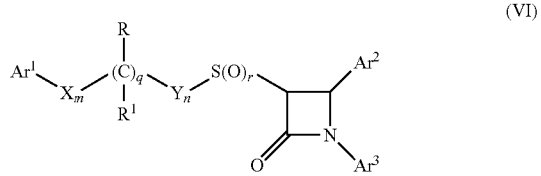

(VI)

or a pharmaceutically acceptable salt thereof or a solvate thereof, or an ester thereof, wherein, in Formula (VI) above:

$Ar^1$ is aryl, $R^{10}$-substituted aryl or heteroaryl;
$Ar^2$ is aryl or $R^4$-substituted aryl;
$Ar^3$ is aryl or $R^5$-substituted aryl;
X and Y are independently selected from the group consisting of —$CH_2$—, —CH(lower alkyl)- and -C(lower alkyl)$_2$-;
R is —$OR^6$, —$OC(O)R^6$, —$OC(O)R^9$ or —$OC(O)NR^6R^7$;
$R^1$ is hydrogen, lower alkyl or aryl; or R and $R^1$ together are =O;
q is 0 or 1;
r is 0, 1 or 2;
m and n are independently 0, 1, 2, 3, 4 or 5; provided that the sum of m, n and q is 1, 2, 3, 4 or 5;
$R^4$ is 1-5 substituents independently selected from the group consisting of lower alkyl, —$OR^6$, —$OC(O)R^6$, —$OC(O)OR^9$, —$O(CH_2)_{1-5}$—$OR^6$, —$OC(O)NR^6R^7$, —$NR^6R^7$, —$NR^6C(O)R^7$, —$NR^6C(O)OR^9$, —$NR^6C(O)NR^7R^8$, —$NR^6S(O)_2R^9$, —$C(O)OR^6$, —$C(O)NR^6R^7$, —$C(O)R^6$, —$S(O)_2NR^6R^7$, $S(O)_{0-2}R^9$, —$O(CH_2)_{1-10}$—$C(O)OR^6$, —$O(CH_2)_{1-10}C(O)NR^6R^7$, -(lower alkylene)$C(O)OR^6$ and —CH=CH—$C(O)OR^6$;
$R^5$ is 1-5 substituents independently selected from the group consisting of —$OR^6$, —$OC(O)R^6$, —$OC(O)OR^9$, —$O(CH_2)_{1-5}OR^6$, —$OC(O)NR^6R^7$, —$NR^6R^7$, —$NR^6C(O)R^7$, —$NR^6C(O)OR^9$, —$NR^6(O)NR^7R^8$, —$NR^6S(O)_2R^9$, —$C(O)OR^6$, —$C(O)NR^6R^7$, —$C(O)R^6$, —$S(O)_2NR^6R^7$, $S(O)_{0-2}R^9$, —$O(CH_2)_{1-10}$—$C(O)OR^6$, —$O(CH_2)_{1-10}C(O)$ $NR^6R^7$, —$CF_3$, —CN, —$NO_2$, halogen, -(lower alkylene)$C(O)OR^6$ and —CH=CH—$C(O)OR^6$;
$R^6$, $R^7$ and $R^8$ are independently selected from the group consisting of hydrogen, lower alkyl, aryl and aryl-substituted lower alkyl;
$R^9$ is lower alkyl, aryl or aryl-substituted lower alkyl; and
$R^{10}$ is 1-5 substituents independently selected from the group consisting of lower alkyl, —$OR^6$, —$OC(O)R^6$, —$OC(O)OR^9$, —$O(CH_2)_{1-5}OR^6$, —$OC(O)NR^6R^7$, —$NR^6R^7$, —$NR^6C(O)R^7$, —$NR^6C(O)OR^9$, —$NR^6C(O)NR^7R^8$, —$NR^6S(O)_2R^9$, —$C(O)OR^6$, —$C(O)NR^6R^7$, —$C(O)R^6$, —$S(O)_2NR^6R^7$, —$S(O)_{0-2}R^9$, —$O(CH_2)_{1-10}$—$C(O)OR^6$, —$O(CH_2)_{1-10}C(O)NR^6R^7$, —$CF_3$, —CN, —$NO_2$ and halogen.

Methods for making compounds of Formula (VI) are well known to those skilled in the art. Non-limiting examples of suitable methods are disclosed in U.S. Pat. No. 5,624,920, which is incorporated herein by reference. Substituted Azetidinones of Formula (VII)

In another embodiment, substituted azetidinones useful in the compositions, therapeutic combinations and methods of the present invention are represented by Formula (VII):

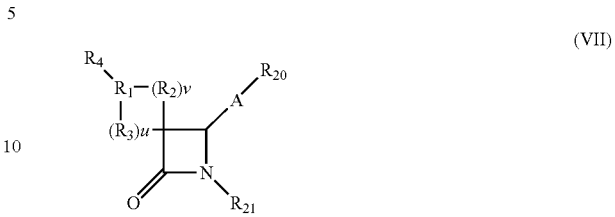

(VII)

or a pharmaceutically acceptable salt thereof or a solvate thereof, or an ester thereof, wherein.
$R^1$ is:

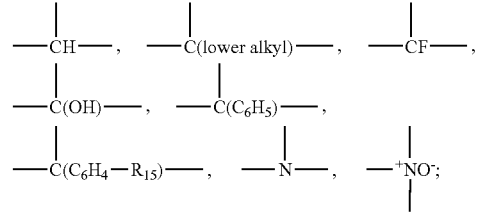

$R^2$ and $R^3$ are independently selected from the group consisting of: —$CH_2$—, —CH(lower alkyl)-, —C(lower alkyl)$_2$-, —CH=CH— and —C(lower alkyl)=CH—; or $R^1$ together with an adjacent $R^2$, or $R^1$ together with an adjacent $R^3$, form a —CH=CH— or a —CH=C(lower alkyl)- group;
u and v are independently 0, 1, 2 or 3, provided both are not zero; provided that when $R^2$ is —CH=CH— or —C(lower alkyl)=CH—, v is 1; provided that when $R^3$ is —CH=CH— or —C(lower alkyl)-CH—, u is 1; provided that when v is 2 or 3, each $R^2$ can be the same or different; and provided that when u is 2 or 3, each $R^3$ can be the same or different;
$R^4$ is selected from B—$(CH_2)_mC(O)$—, wherein m is 0, 1, 2, 3, 4 or 5; B—$(CH_2)_q$-, wherein q is 0, 1, 2, 3, 4, 5 or 6; B—$(CH_2)_e$-Z-$(CH_2)_r$-, wherein Z is —O—, —C(O)—, phenylene, —$N(R^8)$— or —$S(O)_{0-2}$-, e is 0, 1, 2, 3, 4 or 5 and r is 0, 1, 2, 3, 4 or 5, provided that the sum of e and r is 0, 1, 2, 3, 4, 5 or 6; B—($C_2$-$C_6$ alkenylene)-; B—($C_4$-$C_6$ alkadienylene)-; B—$(CH_2)_t$-Z-($C_2$-$C_6$ alkenylene)-, wherein Z is as defined above, and wherein t is 0, 1, 2 or 3, provided that the sum of t and the number of carbon atoms in the alkenylene chain is 2, 3, 4, 5 or 6; B—$(CH_2)_f$—V—$(CH_2)_g$—, wherein V is $C_3$-$C_6$ cycloalkylene, f is 1, 2, 3, 4 or 5 and g is 0, 1, 2, 3, 4 or 5, provided that the sum of f and g is 1, 2, 3, 4, 5 or 6; B—$(CH_2)_t$—V—($C_2$-$C_6$ alkenylene)- or B—($C_2$-$C_6$ alkenylene)-V—$(CH_2)_t$—, wherein V and t are as defined above, provided that the sum of t and the number of carbon atoms in the alkenylene chain is 2, 3, 4, 5 or 6; B—$(CH_2)_a$-Z-$(CH_2)_b$—V—$(CH_2)_d$—, wherein Z and V are as defined above and a, b and d are independently 0, 1, 2, 3, 4, 5 or 6, provided that the sum of a, b and d is 0, 1, 2, 3, 4, 5 or 6; or T-$(CH_2)_s$—, wherein T is a $C_3$-$C_6$ cycloalkyl and s is 0, 1, 2, 3, 4, 5 or 6; or
$R^1$ and $R^4$ together form the group B—CH=C—;
B is selected from indanyl, indenyl, naphthyl, tetrahydronaphthyl, heteroaryl or W-substituted heteroaryl, wherein heteroaryl is selected from the group consisting of pyrrolyl, pyridinyl, pyrimidinyl, pyrazinyl, triazinyl, imidazolyl, thiazolyl, pyrazolyl, thienyl, oxazolyl and furanyl, and for nitrogen-containing heteroaryls, the N-oxides thereof, or

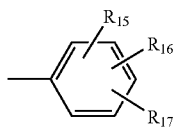

W is 1 to 3 substituents independently selected from the group consisting of lower alkyl, hydroxy lower alkyl, lower alkoxy, alkoxyalkyl, alkoxyalkoxy, alkoxycarbonylalkoxy, (lower alkoxyimino)-lower alkyl, lower alkanedioyl, lower alkyl lower alkanedioyl, allyloxy, —$CF_3$, —$OCF_3$, benzyl, $R^7$-benzyl, benzyloxy, $R^7$-benzyloxy, phenoxy, $R^7$-phenoxy, dioxolanyl, $NO_2$, —$N(R^8)(R^9)$, $N(R^8)(R^9)$-lower alkylene-, $N(R^8)(R^9)$-lower alkylenyloxy-, OH, halogeno, —CN, —$N_3$, —NHC(O)$OR^{10}$, —NHC(O)$R^{10}$, $R^{11}(O)_2$SNH—, ($R^{11}(O)_2$S)$_2$N—, —$S(O)_2NH_2$, —$S(O)_{0-2}R^8$, tert-butyldimethyl-silyloxymethyl, —C(O)$R^{12}$, —C(O)$OR^{19}$, —C(O)N($R^8$)($R^9$), —CH=CHC(O)$R^{12}$, -lower alkylene-C(O)$R^{12}$, $R^{10}$C(O)(lower alkylenyloxy)-, $N(R^8)(R^9)$C(O)(lower alkylenyloxy)- and

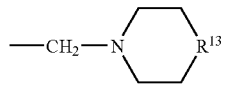

for substitution on ring carbon atoms, and the substituents on the substituted heteroaryl ring nitrogen atoms, when present, are selected from the group consisting of lower alkyl, lower alkoxy, —C(O)$OR^{10}$, —C(O)$R^{10}$, OH, $N(R^8)(R^9)$-lower alkylene-, $N(R^8)(R^9)$-lower alkylenyloxy-, —$S(O)_2NH_2$ and 2-(trimethylsilyl)-ethoxymethyl;

$R^7$ is 1-3 groups independently selected from the group consisting of lower alkyl, lower alkoxy, —C(O)OH, $NO_2$, —$N(R^8)(R^9)$, OH, and halogeno;

$R^8$ and $R^9$ are independently selected from H or lower alkyl;

$R^{10}$ is selected from lower alkyl, phenyl, $R^7$-phenyl, benzyl or $R^7$-benzyl;

$R^{11}$ is selected from OH, lower alkyl, phenyl, benzyl, $R^7$-phenyl or $R^7$-benzyl;

$R^{12}$ is selected from H, OH, alkoxy, phenoxy, benzyloxy,

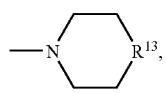

—$N(R^8)(R^9)$, lower alkyl, phenyl or $R^7$-phenyl;

$R^{13}$ is selected from —O—, —$CH_2$—, —NH—, —N(lower alkyl)- or —NC(O)$R^{19}$-;

$R^{15}$, $R^{16}$ and $R^{17}$ are independently selected from the group consisting of H and the groups defined for W; or $R^{15}$ is hydrogen and $R^{16}$ and $R^{17}$, together with adjacent carbon atoms to which they are attached, form a dioxolanyl ring;

$R^{19}$ s H, lower alkyl, phenyl or phenyl lower alkyl; and $R^{20}$ and $R^{21}$ are independently selected from the group consisting of phenyl, W-substituted phenyl, naphthyl, W-substituted naphthyl, indanyl, indenyl, tetrahydronaphthyl, benzodioxolyl, heteroaryl, W-substituted heteroaryl, benzo-fused heteroaryl, W-substituted benzo-fused heteroaryl and cyclopropyl, wherein heteroaryl is as defined above.

Methods for making compounds of Formula (VII) are well known to those skilled in the art. Non-limiting examples of suitable methods are disclosed in U.S. Pat. No. 5,698,548, which is incorporated herein by reference. Substituted Azetidinones of Formula (VIII)

In another embodiment, substituted azetidinones useful in the compositions, therapeutic combinations and methods of the present invention are represented by Formulas (VIIIA) and (VIIIB):

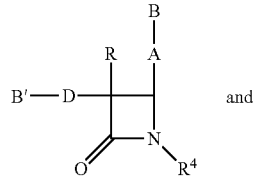

(VIIIA)

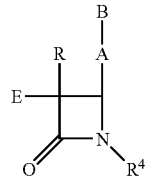

(VIIIB)

or a pharmaceutically acceptable salt, solvate, or ester thereof, wherein:

A is —CH=CH—, —C≡C— or —$(CH_2)_p$— wherein p is 0, 1 or 2;

B is

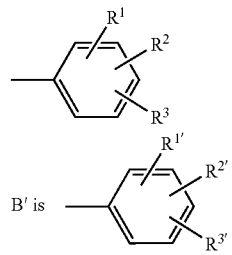

B' is

D is —$(CH_2)_mC(O)$— or —$(CH_2)_q$— wherein m is 1, 2, 3 or 4 and q is 2, 3 or 4;

E is $C_{10}$ to $C_{20}$ alkyl or —C(O)—($C_9$ to $C_{19}$)-alkyl, wherein the alkyl is straight or branched, saturated or containing one or more double bonds;

R is hydrogen, $C_1$-$C_{15}$ alkyl, straight or branched, saturated or containing one or more double bonds, or B—$(CH_2)_r$—, wherein r is 0, 1, 2, or 3;

$R^1$, $R^2$, $R^3$, $R^{1'}$, $R^{2'}$, and $R^{3'}$ are independently selected from the group consisting of hydrogen, lower alkyl, lower alkoxy, carboxy, $NO_2$, $NH_2$, OH, halogeno, lower alkylamino, dilower alkylamino, —NHC(O)$OR^5$, $R^6(O)_2$SNH— and —$S(O)_2NH_2$;

$R^4$ is

wherein n is 0, 1, 2 or 3;

$R^5$ is lower alkyl; and $R^6$ is OH, lower alkyl, phenyl, benzyl or substituted phenyl wherein the substituents are 1-3 groups independently selected from the group consisting of lower alkyl, lower alkoxy, carboxy, $NO_2$, $NH_2$, OH, halogeno, lower alkylamino and dilower alkylamino; or a pharmaceutically acceptable salt, solvate, or ester thereof.

Sterol Absorption Inhibitors of Formula (IX)

In another embodiment, sterol absorption inhibitors useful in the compositions and methods of the present invention are represented by Formula (IX):

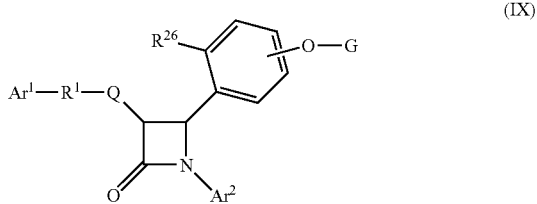

(IX)

or a pharmaceutically acceptable salt, solvate, or ester thereof, wherein, in Formula (IX) above, $R^{26}$ is H or $OG^1$;

G and $G^1$ are independently selected from the group consisting of

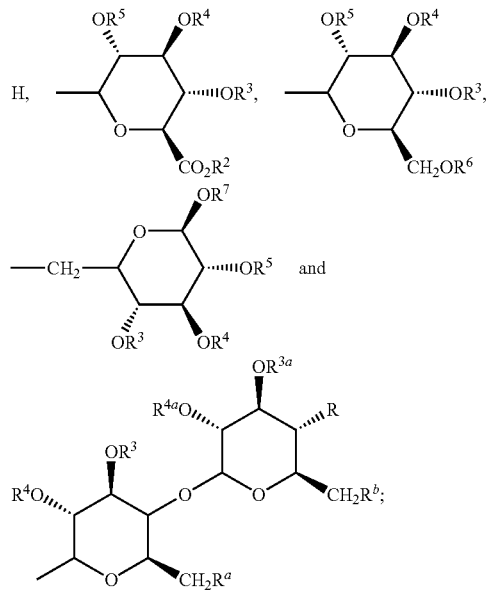

provided that when $R^{26}$ is H or OH, G is not H;

R, $R^a$ and $R^b$ are independently selected from the group consisting of H, —OH, halogeno, —$NH_2$, azido, ($C_1$-$C_6$) alkoxy($C_1$-$C_6$)-alkoxy or —W—$R^{30}$;

W is independently selected from the group consisting of —NH—C(O)—, —O—C(O)—, —O—C(O)—($R^{31}$)—, —NH—C(O)—N($R^{31}$)— and —O—C(S)—N($R^{31}$)—;

$R^2$ and $R^6$ are independently selected from the group consisting of H, ($C_1$-$C_6$)alkyl, aryl and aryl($C_1$-$C_6$)alkyl;

$R^3$, $R^4$, $R^5$, $R^7$, $R^{3a}$ and $R^{4a}$ are independently selected from the group consisting of H, ($C_1$-$C_6$)alkyl, aryl($C_1$-$C_6$)alkyl, —C(O)($C_1$-$C_6$)alkyl and —C(O)aryl;

$R^{30}$ is selected from the group consisting of $R^{32}$-substituted T, $R^{32}$-substituted-T-($C_1$-$C_6$)alkyl, $R^{32}$-substituted-($C_2$-$C_4$) alkenyl, $R^{32}$-substituted-($C_1$-$C_6$)alkyl, $R^{32}$-substituted-($C_3$-$C_7$)cycloalkyl and $R^{32}$-substituted-($C_3$-$C_7$)cycloalkyl($C_1$-$C_6$)alkyl;

$R^{31}$ is selected from the group consisting of H and ($C_1$-$C_4$) alkyl;

T is selected from the group consisting of phenyl, furyl, thienyl, pyrrolyl, oxazolyl, isoxazolyl, thiazolyl, iosthiazolyl, benzothiazolyl, thiadiazolyl, pyrazolyl, imidazolyl and pyridyl;

$R^{32}$ is independently selected from 1-3 substituents independently selected from the group consisting of halogeno, ($C_1$-$C_4$)alkyl, —OH, phenoxy, —$CF_3$, —$NO_2$, ($C_1$-$C_4$) alkoxy, methylenedioxy, oxo, ($C_1$-$C_4$)alkylsulfanyl, ($C_1$-$C_4$) alkylsulfinyl, ($C_1$-$C_4$)alkylsulfonyl, —N($CH_3$)$_2$, —C(O)—NH($C_1$-$C_4$)alkyl, —C(O)—N(($C_1$-$C_4$)alkyl)$_2$, —C(O)—($C_1$-$C_4$)alkyl, —C(O)—($C_1$-$C_4$)alkoxy and pyrrolidinylcarbonyl; or $R^{32}$ is a covalent bond and $R^{31}$, the nitrogen to which it is attached and $R^{32}$ form a pyrrolidinyl, piperidinyl, N-methylpiperazinyl, indolinyl or morpholinyl group, or a ($C_1$-$C_4$) alkoxycarbonyl-substituted pyrrolidinyl, piperidinyl, N-methylpiperazinyl, indolinyl or morpholinyl group;

$Ar^1$ is aryl or $R^{10}$-substituted aryl;

$Ar^2$ is aryl or $R^{11}$-substituted aryl;

Q is a bond or, with the 3-position ring carbon of the azetidinone, forms the spiro group

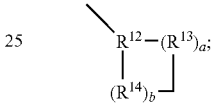

and $R^1$ is selected from the group consisting of —($CH_2$)$_q$—, wherein q is 2-6, provided that when Q forms a spiro ring, q can also be zero or 1;

—($CH_2$)$_e$-E-($CH_2$)$_r$—, wherein E is —O—, —C(O)—, phenylene, —$NR^{22}$— or —S(O)$_{0-2}$—, e is 0-5 and r is 0-5, provided that the sum of e and r is 1-6;

—($C_2$-$C_6$)alkenylene-; and

—($CH_2$)$_f$—V—($CH_2$)$_g$—, wherein V is $C_3$-$C_6$ cycloalkylene, f is 1-5 and g is 0-5, provided that the sum of f and g is 1-6;

$R^{12}$ is:

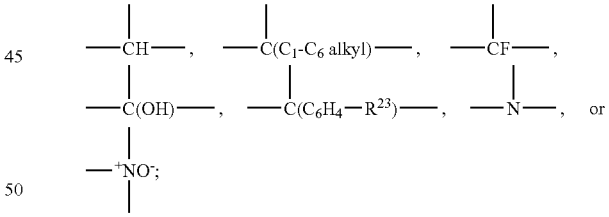

$R^{13}$ and $R^{14}$ are independently selected from the group consisting of

—$CH_2$—, —CH(($C_1$-$C_6$)alkyl)-, —C(($C_1$-$C_6$) alkyl)$_2$, —CH=CH— and —C(($C_1$-$C_6$) alkyl)=CH—; or $R^{12}$ together with an adjacent $R^{13}$, or $R^{12}$ together with an adjacent $R^{14}$ form a —CH=CH— or a —CH—C($C_1$-$C_6$ alkyl)- group;

a and b are independently 0, 1, 2 or 3, provided both are not zero;

provided that when $R^{13}$ is —CH=CH— or —C($C_1$-$C_6$ alkyl)=CH—, a is 1;

provided that when $R^{14}$ is —CH=CH— or —C($C_1$-$C_6$ alkyl)=CH—, b is 1;

provided that when a is 2 or 3, each $R^{13}$ can be the same or different; and provided that when b is 2 or 3, each $R^{14}$ can be the same or different;

and when Q is a bond, $R^1$ also can be:

$$-M-Y_d-\overset{\overset{R^{15}}{|}}{\underset{\underset{R^{16}}{|}}{C}}-Z_h-,$$

$$-X_m-\overset{\overset{R^{17}}{|}}{\underset{\underset{R^{18}}{|}}{(C)_s}}-Y_n-\overset{\overset{R^{15}}{|}}{\underset{\underset{R^{16}}{|}}{(C)_t}}-Z_p- \quad \text{or}$$

$$-X_j-\overset{\overset{R^{15}}{|}}{\underset{\underset{R^{16}}{|}}{(C)_v}}-Y_k-S(O)_{0\text{-}2}-;$$

M is —O—, —S—, —S(O)— or —S(O)$_2$—;

X, Y and Z are independently selected from the group consisting of —CH$_2$—, —CH(C$_1$-C$_6$)alkyl- and —C((C$_1$-C$_6$)alkyl)$_2$;

$R^{10}$ and $R^{11}$ are independently selected from the group consisting of 1-3 substituents independently selected from the group consisting of (C$_1$-C$_6$)alkyl, —OR$^{19}$, —OC(O)R$^{19}$, —OC(O)OR$^{21}$, —O(CH$_2$)$_{1\text{-}5}$OR$^{19}$, —OC(O)NR$^{19}$R$^{20}$, —NR$^{19}$R$^{20}$, —NR$_{19}$C(O)R$^{20}$, —NR$^{19}$C(O)OR$^{21}$, —NR$^{19}$C(O)NR$^{20}$R$^{25}$, —NR$^{19}$S(O)$_2$R$^{21}$, —C(O)OR$^{19}$, —C(O)NR$^{19}$R$^{20}$, —C(O)R$^{19}$, —S(O)$_2$NR$^{19}$R$^{20}$, S(O)$_{0\text{-}2}$R$^{21}$, —O(CH)$_2$)$_{1\text{-}10}$—C(O)OR$^{19}$, —O(CH$_2$)$_{1\text{-}10}$C(O)NR$^{19}$R$^{20}$, —(C$_1$-C$_6$ alkylene)-C(O)OR$^{19}$, —CH═CH—C(O)OR$^{19}$, —CF$_3$, —CN, —NO$_2$ and halogen;

$R^{15}$ and $R^{17}$ are independently selected from the group consisting of —OR$^{19}$, —OC(O)R$^{19}$, —OC(O)OR$^{21}$ and —OC(O)NR$^{19}$R$^{20}$;

$R^{16}$ and $R^{18}$ are independently selected from the group consisting of H, (C$_1$-C$_6$)alkyl and aryl; or $R^{15}$ and $R^{16}$ together are ═O, or $R^{17}$ and $R^{18}$ together are ═O;

d is 1, 2 or 3;

h is 0, 1, 2, 3 or 4;

s is 0 or 1; t is 0 or 1; m, n and p are independently 0-4;

provided that at least one of s and t is 1, and the sum of m, n, p, s and t is 1-6;

provided that when p is 0 and t is 1, the sum of m, s and n is 1-5; and provided that when p is 0 and s is 1, the sum of m, t and n is 1-5;

v is 0 or 1;

j and k are independently 1-5, provided that the sum of j, k and v is 1-5;

and when Q is a bond and $R^1$ is $$-X_j-\overset{\overset{R^{15}}{|}}{\underset{\underset{R^{16}}{|}}{(C)_v}}-Y_k-S(O)_{0\text{-}2}-,$$

Ar$^1$ can also be pyridyl, isoxazolyl, furanyl, pyrrolyl, thienyl, imidazolyl, pyrazolyl, thiazolyl, pyrazinyl, pyrimidinyl or pyridazinyl;

$R^{19}$ and $R^{20}$ are independently selected from the group consisting of H, (C$_1$-C$_6$)alkyl, aryl and aryl-substituted (C$_1$-C$_6$)alkyl;

$R^{21}$ is (C$_1$-C$_6$)alkyl, aryl or $R^{24}$-substituted aryl;

$R^{22}$ is H, (C$_1$-C$_6$)alkyl, aryl (C$_1$-C$_6$)alkyl, —C(O)R$^{19}$ or —C(O)OR$^{19}$;

$R^{23}$ and $R^{24}$ are independently 1-3 groups independently selected from the group consisting of H, (C$_1$-C$_6$)alkyl, (C$_1$-C$_6$)alkoxy, —C(O)OH, NO$_2$, —NR$^{19}$R$^{20}$, —OH and halogeno; and $R^{25}$ is H, —OH or (C$_1$-C$_6$)alkoxy.

Methods for making compounds of Formula (IX) are well known to those skilled in the art. Non-limiting examples of suitable methods are disclosed in U.S. Pat. No. 5,756,470, which is incorporated herein by reference.

Substituted Azetidinones of Formula (X)

In another embodiment, substituted azetidinones useful in the compositions and methods of the present invention are represented by Formula (X) below:

$$\text{(X)}$$

or a pharmaceutically acceptable salt, solvate, or ester thereof, wherein in Formula (X):

$R^1$ is selected from the group consisting of H, G, G$^1$, G$^3$, —SO$_3$H and —PO$_3$H;

G is selected from the group consisting of: H, (sugar derivatives)

wherein R, R$^a$ and R$^b$ are each independently selected from the group consisting of H, —OH, halo, —NH$_2$, azido, (C$_1$-C$_6$)alkoxy(C$_1$-C$_6$)alkoxy or —W—R$^{30}$;

W is independently selected from the group consisting of —NH—C(O)—, —O—C(O)—, —O—C(O)—N($R^{31}$)—, —NH—C(O)—N($R^{31}$)— and —O—C(S)—N($R^{31}$)—;

$R^2$ and $R^6$ are each independently selected from the group consisting of H, $(C_1-C_6)$alkyl, acetyl, aryl and aryl$(C_1-C_6)$ alkyl;

$R^3$, $R^4$, $R^5$ $R^7$, $R^{3a}$ and $R^{4a}$ are each independently selected from the group consisting of H, $(C_1-C_6)$alkyl, acetyl, aryl$(C_1-C_6)$alkyl, —C(O)$(C_1-C_6)$alkyl and —C(O)aryl;

$R^{30}$ is independently selected from the group consisting of $R^{32}$-substituted T, $R^{32}$-substituted-T-$(C_1-C_6)$alkyl, $R^{32}$-substituted-$(C_2-C_4)$alkenyl, $R^{32}$-substituted-$(C_1-C_6)$alkyl, $R^{32}$-substituted-$(C_3-C_7)$cycloalkyl and $R^{32}$-substituted-$(C_3-C_7)$cycloalkyl$(C_1-C_6)$alkyl;

$R^{31}$ is independently selected from the group consisting of H and $(C_1-C_4)$alkyl;

T is independently selected from the group consisting of phenyl, furyl, thienyl, pyrrolyl, oxazolyl, isoxazolyl, thiazolyl, isothiazolyl, benzothiazolyl, thiadiazolyl, pyrazolyl, imidazolyl and pyridyl;

$R^{32}$ is independently selected from 1-3 substituents which are each independently selected from the group consisting of H, halo, $(C_1-C_4)$alkyl, —OH, phenoxy, —$CF_3$, —$NO_2$, $(C_1-C_4)$alkoxy, methylenedioxy, oxo, $(C_1-C_4)$alkylsulfanyl, $(C_1-C_4)$alkylsulfinyl, $(C_1-C_4)$alkylsulfonyl, —N$(CH_3)_2$, —C(O)—NH$(C_1-C_4)$alkyl, —C(O)—N$(C_1-C_4$alkyl$)_2$, —C(O)—$(C_1-C_4)$alkyl, —C(O)—$(C_1-C_4)$alkoxy and pyrrolidinylcarbonyl; or $R^{32}$ is a covalent bond and $R^{31}$, the nitrogen to which it is attached and $R^{32}$ form a pyrrolidinyl, piperidinyl, N-methylpiperazinyl, indolinyl or morpholinyl group, or a $(C_1-C_4)$ alkoxycarbonyl-substituted pyrrolidinyl, piperidinyl, N-methylpiperazinyl, indolinyl or morpholinyl group;

$G^1$ is represented by the structure:

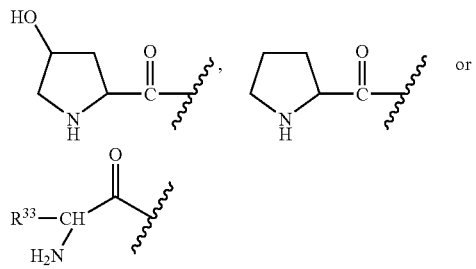

wherein $R^{32}$ is independently selected from the group consisting of unsubstituted alkyl, $R^{34}$-substituted alkyl, $(R^{35})$ $(R^{36})$alkyl-,

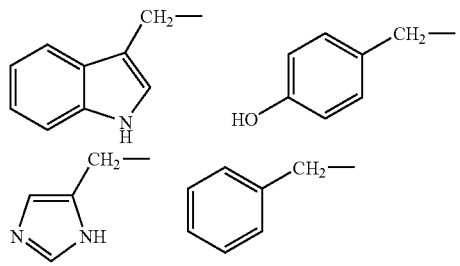

$R^{34}$ is one to three substituents, each $R^{34}$ being independently selected from the group consisting of HO(O)C—, —O—, HS—, $(CH_3)S$—, $H_2N$—, $(NH_2)(NH)C(NH)$—, $(NH_2)C(O)$— and HO(O)CCH$(NH_3^+)$CH$_2$SS—;

$R^{35}$ is independently selected from the group consisting of H and $NH_2$—;

$R^{36}$ is independently selected from the group consisting of H, unsubstituted alkyl, $R^{34}$-substituted alkyl, unsubstituted cycloalkyl and $R^{34}$-substituted cycloalkyl;

$G^2$ is represented by the structure.

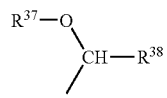

wherein $R^{37}$ and $R^{38}$ are each independently selected from the group consisting of $(C_1-C_6)$alkyl and aryl;

$R^{26}$ is one to five substituents, each $R^{26}$ being independently selected from the group consisting of:
a) H;
b) —OH;
c) —$OCH_3$;
d) fluorine;
e) chlorine;
f) —O-G ;
g) —O-$G^1$;
h) —O-$G^2$;
i) —$SO_3H$; and
j) —$PO_3H$;

provided that when $R^1$ is H, $R^{26}$ is not H, —OH, —$OCH_3$ or —O-G;

$Ar^1$ is aryl, $R^{10}$-substituted aryl, heteroaryl or $R^{10}$-substituted heteroaryl;

$Ar^2$ is aryl, $R^{11}$-substituted aryl, heteroaryl or $R^{11}$-substituted heteroaryl;

L is selected from the group consisting of:
a) a covalent bond;
b) —$(CH_2)_q$—, wherein q is 1-6;
c) —$(CH_2)_e$-E-$(CH_2)_r$—, wherein E is —O—, —C(O)—, phenylene, —$NR^{22}$— or —$S(O)_{0-2}$—, e is 0-5 and r is 0-5, provided that the sum of e and r is 1-6;
d) —$(C_2-C_6)$alkenylene-;
e) —$(CH_2)_f$—V—$(CH_2)_g$—, wherein V is $C_3-C_6$cycloalkylene, f is 1-5 and g is 0-5, provided that the sum of f and g is 1-6; and
f)

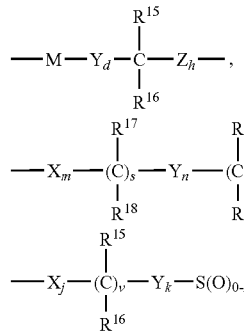

wherein M is —O—, —S—, —S(O)— or —$S(O)_2$—;

X, Y and Z are each independently selected from the group consisting of —$CH_2$—, —CH$(C_1-C_6)$alkyl- and C($(C_1C_6)$alkyl$)_2$-;

$R^8$ is selected from the group consisting of H and alkyl;

$R^{10}$ and $R^{11}$ are each independently selected from the group consisting of 1-3 substituents which are each independently selected from the group consisting of $(C_1-C_6)$alkyl, —$OR^{19}$, —$OC(O)R^{19}$, —$OC(O)OR^{21}$, —$O(CH_2)_{1-5}OR^{19}$, —$OC(O)NR^{19}R^{20}$, —$NR^{19}R^{20}$, —$NR^{19}C(O)R^{20}$, —$NR^{19}C(O)OR^{21}$, —$NR^{19}C(O)NR^{20}R^{25}$, —$NR^{19}S(O)_2R^{21}$, —$C(O)OR^{19}$, —$C(O)NR^{19}R^{20}$, —$C(O)R^{19}$, —$S(O)_2NR^{19}R^{20}$, $S(O)_{0-2}R^{21}$, —$O(CH_2)_{1-10}$—$C(O)OR^{19}$, —$O(CH_2)_{1-10}C(O)NR^{19}R^{20}$, —$(C_1-C_6$ alkylene)-$C(O)OR^{19}$, —CH=CH—$C(O)OR^{19}$, —$CF_3$, —CN, —$NO_2$ and halo;

$R^{15}$ and $R^{17}$ are each independently selected from the group consisting of —$OR^{19}$, —$OC(O)R^{19}$, —$OC(O)R^{21}$, —$OC(O)NR^{19}R^{20}$;

$R^{16}$ and $R^{18}$ are each independently selected from the group consisting of H, $(C_1-C_6)$alkyl and aryl; or $R^{15}$ and $R^{16}$ together are =O, or $R^{17}$ and $R^{18}$ together are =O;

d is 1, 2 or 3;

h is 0, 1, 2, 3 or 4;

s is 0 or 1;

t is 0 or 1;

m, n and p are each independently selected from 0-4;

provided that at least one of s and t is 1, and the sum of m, n, p, s and t is 1-6; provided that when p is 0 and t is 1, the sum of m, n and p is 1-5; and provided that when p is 0 and s is 1, the sum of m, t and n is 1-5;

v is 0 or 1;

j and k are each independently 1-5, provided that the sum of j, k and v is 1-5;

Q is a bond, —$(CH_2)_q$—, wherein q is 1-6, or, with the 3-position ring carbon of the azetidinone, forms the spiro group

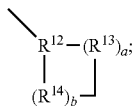

wherein $R^{12}$ is

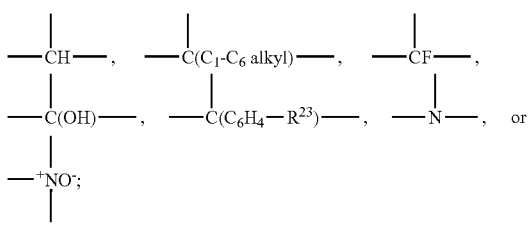

$R^{13}$ and $R^{14}$ are each independently selected from the group consisting of —$CH_2$—, —CH$(C_1-C_6$ alkyl)-, —C(($C_1$-$C_6$) alkyl)$_2$, —CH=CH— and —C($C_1$-$C_6$ alkyl)-CH—; or $R^{12}$ together with an adjacent $R^{13}$, or $R^{12}$ together with an adjacent $R^{14}$, form a —CH=CH— or a —CH=C($C_1$-$C_6$ alkyl)- group;

a and b are each independently 0, 1, 2 or 3, provided both are not zero; provided that when $R^{13}$ is —CH=CH— or —C($C_1$-$C_6$ alkyl)=CH—, a is 1, provided that when $R^{14}$ —CH=CH— or —C($C_1$-$C_6$ alkyl)-CH—, b is 1; provided that when a is 2 or 3, each $R^{13}$ can be the same or different; and provided that when b is 2 or 3, each $R^{14}$ can be the same or different;

and when Q is a bond and L is

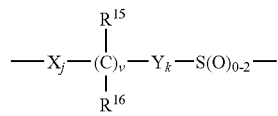

then $Ar^1$ can also be pyridyl, isoxazolyl, furanyl, pyrrolyl, thienyl, imidazolyl, pyrazolyl, thiazolyl, pyrazinyl, pyrimidinyl or pyridazinyl;

$R^{19}$ and $R^{20}$ are each independently selected from the group consisting of H, $(C_1-C_6)$alkyl, aryl and aryl-substituted $(C_1-C_6)$alkyl;

$R^{21}$ is $(C_1-C_6)$alkyl, aryl or $R^{24}$-substituted aryl;

$R^{22}$ is H, $(C_1-C_6)$alkyl, aryl $(C_1-C_6)$alkyl, —$C(O)R^{19}$ or —$C(O)OR^{19}$;

$R^{23}$ and $R^{24}$ are each independently selected from the group consisting of 1-3 substituents which are each independently selected from the group consisting of H, $(C_1-C_6)$alkyl, $(C_1-C_6)$alkoxy, —C(O)OH, $NO_2$, —$NR^{19}R^{20}$, —OH and halo; and $R^{25}$ is H, —OH or $(C_1-C_6)$alkoxy.

Examples of compounds of Formula (X) which are useful in the methods and combinations of the present invention and methods for making such compounds are disclosed in U.S. patent application Ser. No. 10/166,942, filed Jun. 11, 2002, incorporated herein by reference.

Substituted Azetidinones of Formulae (XI)-(XIII)

An example of a useful substituted azetidinone is one represented by the Formula (XI):

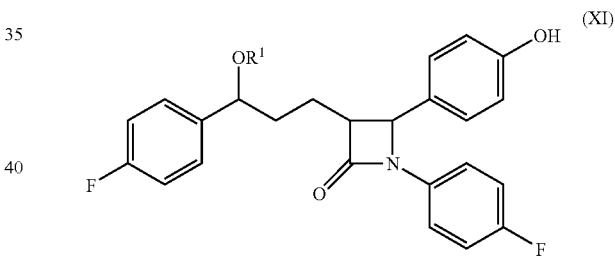

wherein $R^1$ is defined as above.

A more preferred compound is one represented by Formula (XII):

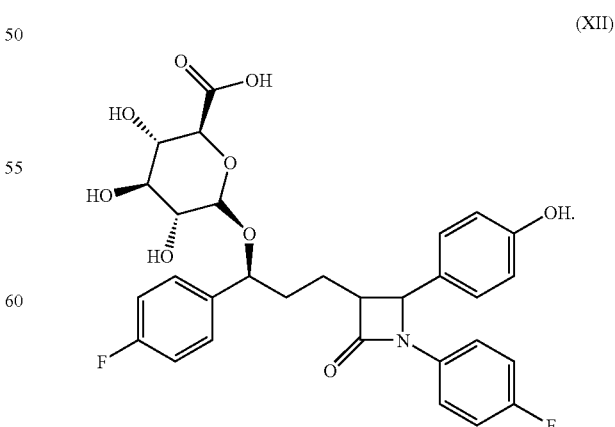

Another useful compound is represented by Formula (XIII).

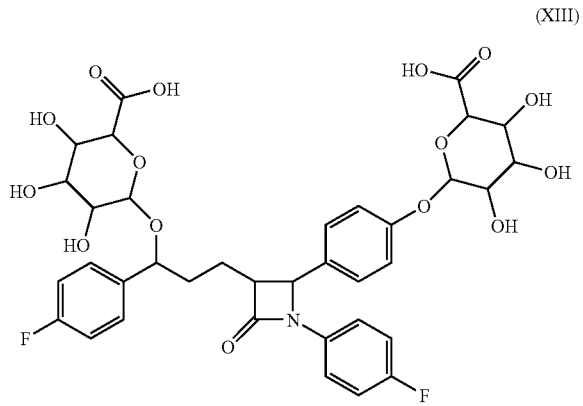 [SMILES: O=C(O)C1OC(Oc2ccc(C3C(CCC(OC4OC(C(=O)O)C(O)C(O)C4O)c4ccc(F)cc4)C(=O)N3c3ccc(F)cc3)cc2)C(O)C(O)C1O]

(XIII)

Other useful substituted azetidinone compounds include N-sulfonyl-2-azetidinones such as are disclosed in U.S. Pat. No. 4,983,597, ethyl 4-(2-oxoazetidin-4-yl)phenoxy-alkanoates such as are disclosed in Ram et al., Indian J. Chem. Sect. B. 29B, 12 (1990), p. 1134-7, diphenyl azetidinones and derivatives disclosed in U.S. Patent Publication Nos. 2002/0039774, 2002/0128252, 2002/0128253 and 2002/0137689, 2004/063929, WO 2002/066464. U.S. Pat. Nos. 6,498,156 and 6,703,386, each of which is incorporated by reference herein.

Other sterol absorption inhibitors useful in the compositions, therapeutic combinations and methods of the present invention are described in WO 2004/0052477 WO 2004/000803, WO 2004/000804, WO 2004/000805, WO 0250027, U.S. published application 2002/0137689, and the compounds described in L. Kværnø et al., Angew. Chem., Int. Ed., 2004, vol. 43, pp. 4653-4656, all of which are incorporated herein by reference. An illustrative compound of Kværnø et al. is:

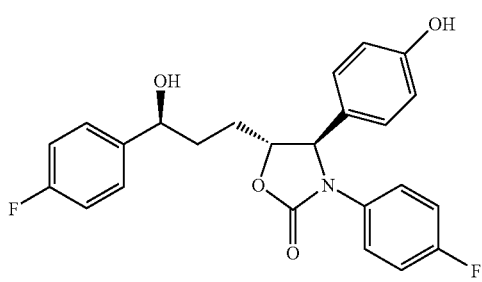 [SMILES: O=C1O[C@H](CC[C@H](O)c2ccc(F)cc2)[C@@H](c2ccc(O)cc2)N1c1ccc(F)cc1]

The compounds of Formulae II-XIII can be prepared by known methods, including the methods discussed above and, for example, in WO 93/02048, U.S. Pat. No. 5,306,817 and 5,561,227, herein incorporated by reference, which describe the preparation of compounds wherein —$R^1$-Q- is alkylene, alkenylene or alkylene interrupted by a hetero atom, phenylene or cycloalkylene; WO 94/17038 and U.S. Pat. No. 5,698,548, herein incorporated by reference, describe the preparation of compounds wherein Q is a spirocyclic group; WO 95/08532, U.S. Pat. No. 5,631,365, U.S. Pat. No. 5,767,115, U.S. Pat. No. 5,846,966, and U.S. R.E. 37,721, herein incorporated by reference, describe the preparation of compounds wherein —$R^1$-Q- is a hydroxy-substituted alkylene group; PCT/US95/03196, herein incorporated by reference, describes compounds wherein —$R^1$-Q- is a hydroxy-substituted alkylene attached to the $Ar^1$ moiety through an —O— or $S(O)_{0-2}$— group, and U.S. Ser. No. 08/463,619, filed Jun. 5, 1995, herein incorporated by reference, describes the preparation of compounds wherein —$R^1$-Q- is a hydroxy-substituted alkylene group attached to the azetidinone ring by a —$S(O)_{0-2}$- group. Each of the above patents or publications are herein incorporated by reference in their entirety.

The daily dose of the sterol absorption inhibitor(s) administered to the subject can range from about 0.1 to about 1000 mg per day preferably about 0.25 to about 50 mg/day, and more preferably about 10 mg per day, given in a single dose or 2-4 divided doses. The exact dose, however, is determined by the attending clinician and is dependent on the potency of the compound administered, the age, weight, condition and response of the patient.

For administration of pharmaceutically acceptable salts of the above compounds, the weights indicated above refer to the weight of the acid equivalent or the base equivalent of the therapeutic compound derived from the salt.

In another embodiment of the present invention, the compositions or therapeutic combinations described above comprise one or more selective $CB_1$ receptor antagonist compounds of Formula (I) in combination with one or more cholesterol biosynthesis inhibitors and/or lipid-lowering compounds discussed below.

Generally, a total daily dosage of cholesterol biosynthesis inhibitor(s) can range from about 0.1 to about 160 mg per day, and preferably about 0.2 to about 80 mg/day in single or 2-3 divided doses.

In another alternative embodiment, the compositions, therapeutic combinations or methods of the present invention can comprise at least one compound of Formula (I), or pharmaceutically acceptable salts, solvates, or esters thereof, and one or more bile acid sequestrants (insoluble anion exchange resins), co-administered with or in combination with the compound of Formula (I), or a pharmaceutically acceptable salt, solvate, or ester thereof, and a substituted azetidinone or a substituted β-lactam discussed above.

Bile acid sequestrants bind bile acids in the intestine, interrupting the enterohepatic circulation of bile acids and causing an increase in the faecal excretion of steroids. Use of bile acid sequestrants is desirable because of their non-systemic mode of action. Bile acid sequestrants can lower intrahepatic cholesterol and promote the synthesis of apo B/E (LDL) receptors that bind LDL from plasma to further reduce cholesterol levels in the blood.

Generally, a total daily dosage of bile acid sequestrant(s) can range from about 1 to about 50 grams per day, and preferably about 2 to about 16 grams per day in single or 2-4 divided doses.

In an alternative embodiment, the compositions or treatments of the present invention can comprise at least one compound of Formula (I), or pharmaceutically acceptable salts, solvates, or esters thereof, and one or more IBAT inhibitors. The IBAT inhibitors can inhibit bile acid transport to reduce LDL cholesterol levels. Generally, a total daily dosage of IBAT inhibitor(s) can range from about 0.01 to about 1000 mg/day, and preferably about 0.1 to about 50 mg/day in single or 2-4 divided doses.

In another alternative embodiment, the compositions or treatments of the present invention can comprise at least one compound of Formula (I), or pharmaceutically acceptable salts, solvates, or esters thereof, and nicotinic acid (niacin) and/or derivatives thereof. Nicotinic acid and its derivatives inhibit hepatic production of VLDL and its metabolite LDL and increases HDL and apo A-1 levels. An example of a suitable nicotinic acid product is NIASPAN® (niacin extended-release tablets), which are available from Kos.

Generally, a total daily dosage of nicotinic acid or a derivative thereof can range from about 500 to about 10,000 mg/day, preferably about 1000 to about 8000 mg/day, and more preferably about 3000 to about 6000 mg/day in single or divided doses.

In another alternative embodiment, the compositions or treatments of the present invention can comprise at least one compound of Formula (I), or pharmaceutically acceptable salts, solvates, or estes thereof, and one or more AcylCoA: Cholesterol O-acyltransferase ("ACAT") Inhibitors, which can reduce LDL and VLDL levels. ACAT is an enzyme responsible for esterifying excess intracellular cholesterol and may reduce the synthesis of VLDL, which is a product of cholesterol esterification, and overproduction of apo B-100-containing lipoproteins. Generally, a total daily dosage of ACAT inhibitor(s) can range from about 0.1 to about 1000 mg/day in single or 2-4 divided doses.

In another alternative embodiment, the compositions or treatments of the present invention can comprise at least one compound of Formula (I), or pharmaceutically acceptable salts, solvates, or esters thereof, and one or more Cholesteryl Ester Transfer Protein ("CETP") Inhibitors, such as torcetrapib. CETP is responsible for the exchange or transfer of cholesteryl ester carrying HDL and triglycerides in VLDL. Pancreatic cholesteryl ester hydrolase (pCEH) inhibitors such as WAY-121898 also can be co-administered with or in combination.

Generally, a total daily dosage of CETP inhibitor(s) can range from about 0.01 to about 1000 mg/day, and preferably about 0.5 to about 20 mg/kg body weight/day in single or divided doses.

In another alternative embodiment, the compositions or treatments of the present invention can comprise at least one compound of Formula (I), or pharmaceutically acceptable salts, solvates, or esters thereof, and probucol or derivatives thereof, which can reduce LDL levels.

Generally, a total daily dosage of probucol or derivatives thereof can range from about 10 to about 2000 mg/day, and preferably about 500 to about 1500 mg/day in single or 2-4 divided doses.

In another alternative embodiment, the compositions or treatments of the present invention can comprise at least one compound of Formula (I), or pharmaceutically acceptable salts, solvates, or esters thereof, and low-density lipoprotein (LDL) receptor activators.

Generally, a total daily dosage of LDL receptor activator(s) can range from about 1 to about 1000 mg/day in single or 2-4 divided doses.

In another alternative embodiment, the compositions or treatments of the present invention can comprise at least one compound of Formula (I), or pharmaceutically acceptable salts, solvates, or esters thereof, and fish oil. Generally, a total daily dosage of fish oil or Omega 3 fatty acids can range from about 1 to about 30 grams per day in single or 2-4 divided doses.

In another alternative embodiment, the compositions or treatments of the present invention can further comprise at least one compound of Formula (I), or pharmaceutically acceptable salts, solvates, or esters thereof, and natural water soluble fibers, such as psyllium, guar, oat and pectin, which can reduce cholesterol levels. Generally, a total daily dosage of natural water soluble fibers can range from about 0.1 to about 10 grams per day in single or 2-4 divided doses.

In another alternative embodiment, the compositions or treatments of the present invention can comprise at least one compound of Formula (I1), or pharmaceutically acceptable salts, solvates, or esters thereof, and plant sterols, plant stanods and/or fatty acid esters of plant stanols, such as sitostanol ester used in BENECOL® margarine, which can reduce cholesterol levels. Generally, a total daily dosage of plant sterols, plant stanols and/or fatty acid esters of plant stanols can range from about 0.5 to about 20 grams per day in single or 2-4 divided doses.

In another alternative embodiment, the compositions or treatments of the present invention can comprise at least one compound of Formula (I), or pharmaceutically acceptable salts, solvates, or esters thereof, and antioxidants, such as probucol, tocopherol, ascorbic acid, β-carotene and selenium, or vitamins such as vitamin $B_6$ or vitamin $B_{12}$. Generally, a total daily dosage of antioxidants or vitamins can range from about 0.05 to about 10 grams per day in single or 2-4 divided doses.

In another alternative embodiment, the compositions or treatments of the present invention can comprise at least one compound of Formula (I), or pharmaceutically acceptable salts, solvates, or esters thereof, and monocyte and macrophage inhibitors such as polyunsaturated fatty acids (PUFA), thyroid hormones including throxine analogues such as CGS-26214 (a thyroxine compound with a fluorinated ring), gene therapy and use of recombinant proteins such as recombinant apo E. Generally, a total daily dosage of these agents can range from about 0.01 to about 1000 mg/day in single or 2-4 divided doses.

Also useful with the present invention are compositions or therapeutic combinations that further comprise hormone replacement agents and compositions. Useful hormone agents and compositions for hormone replacement therapy of the present invention include androgens, estrogens, progestins, their pharmaceutically acceptable salts and derivatives thereof. Combinations of these agents and compositions are also useful, The dosage of androgen and estrogen combinations vary, desirably from about 1 mg to about 4 mg androgen and from about 1 mg to about 3 mg estrogen. Examples include, but are not limited to, androgen and estrogen combinations such as the combination of esterified estrogens (sodium estrone sulfate and sodium equilin sulfate) and methyltestosterone (17-hydroxy-17-methyl-, (17B)- androst-4-en-3-one) available from Solvay Pharmaceuticals, Inc., Marietta, Ga., under the tradename Estratest.

Estrogens and estrogen combinations may vary in dosage from about 0.01 mg up to 8 mg, desirably from about 0.3 mg to about 3.0 mg. Examples of useful estrogens and estrogen combinations include:

(a) the blend of nine (9) synthetic estrogenic substances including sodium estrone sulfate, sodium equilin sulfate, sodium 17 α-dihydroequilin sulfate, sodium 17 α-estradiol sulfate, sodium 17 β-dihydroequilin sulfate, sodium 17 α-dihydroequilenin sulfate, sodium 17 β-dihydroequilenin sulfate, sodium equilenin sulfate and sodium 17 β-estradiol sulfate; available from Duramed Pharmaceuticals, Inc., Cincinnati, Ohio, under the tradename Cenestin;

(b) ethinyl estradiol (19-nor-17 α-pregna-1,3,5(10)-trien-20-yne-3, 17-diol; available by Schering Plough Corporation, Kenilworth, N.J., under the tradename Estinyl;

(c) esterified estrogen combinations such as sodium estrone sulfate and sodium equilin sulfate; available from Solvay under the tradename Estratab and from Monarch Pharmaceuticals, Bristol, Tenn., under the tradename Menest;

(d) estropipate (piperazine estra-1,3,5(10)-trien-17-one, 3-(sulfooxy)-estrone sulfate); available from Pharmacia &

Upjohn, Peapack, N.J., under the tradename Ogen and from Women First Health Care, Inc., San Diego, Calif., under the tradename Ortho-Est; and (e) conjugated estrogens (17 α-dihydroequilin, 17 α-estradiol, and 17 β-dihydroequilin); available from Wyeth-Ayerst Pharmaceuticals, Philadelphia, Pa., under the tradename Premarin.

Progestins and estrogens may also be administered with a variety of dosages generally from about 0.05 to about 2.0 mg progestin and about 0.001 mg to about 2 mg estrogen, desirably from about 0.1 mg to about 1 my progestin and about 0.01 mg to about 0.5 mg estrogen. Examples of progestin and estrogen combinations that may vary in dosage and regimen include:

(a) the combination of estradiol (estra-1,3,5 (10)-triene-3, 17 β-diol hemihydrate) and norethindrone (17 β-acetoxy-19-nor-17 α-pregn-4-en-20-yn-3-one); which is available from Pharmacia & Upjohn, Peapack, N.J., under the tradename Activella;

(b) the combination of levonorgestrel (d(−)-13 β-ethyl-17 α-ethinyl-17 β-hydroxygon-4-en-3-one) and ethinyl estradiol; available from Wyeth-Ayerst under the tradename Alesse, from Watson Laboratories, Inc., Corona, Calif., under the tradenames Levora and Trivora, Monarch Pharmaceuticals, under the tradename Nordette, and from Wyeth-Ayerst under the tradename Triphasil;

(c) the combination of ethynodiol diacetate (19-nor-17 α-pregn-4-en-20-yne-3 β, 17-diol diacetate) and ethinyl estradiol; available from G. D. Searle & Co., Chicago, Ill., under the tradename Demulen and from Watson under the tradename Zovia;

(d) the combination of desogestrel (13-ethyl-11- methylene-18,19-dinor-17 α-pregn-4-en-20-yn-17-ol) and ethinyl estradiol; available from Organon under the tradenames Desogen and Mircette, and from Ortho-McNeil Pharmaceutical, Raritan, N.J., under the tradename Ortho-Cept;

(e) the combination of norethindrone and ethinyl estradiol; available from Parke-Davis, Morris Plains, N.J., under the tradenames Estrostep and FemHRT, from Watson under the tradenames Microgestin, Necon, and Tri-Norinyl, from Ortho-McNeil under the tradenames Modicon and Ortho-Novum, and from Warner Chilcott Laboratories, Rockaway, N.J., under the tradename Ovcon;

(f) the combination of norgestrel ( (±)-13-ethyl-17-hydroxy-18, 19-dinor-17 α-preg-4-en-20-yn-3-one) and ethinyl estradiol; available from Wyeth-Ayerst under the tradenames Ovral and Lo/Ovral, and from Watson under the tradenames Ogestrel and Low-Ogestrel;

(g) the combination of norethindrone, ethinyl estradiol, and mestranol (3-methoxy-19-nor-17 α-pregna-1,3,5(10)-trien-20-yn-17-ol); available from Watson under the tradenames Brevicon and Norinyl;

(h) the combination of 17 β-estradiol (estra-1,3,5(10)-triene-3,17 β-diol) and micronized norgestimate (17 α-17-(Acetyloxyl)-13-ethyl-1 8,1 9-dinorpregn-4-en-20-yn-3-one3-oxime); available from Ortho-McNeil under the tradename Ortho-Prefest;

(i) the combination of norgestimate (18,19-dinor-17-pregn-4-en-20-yn-3-one, 17-(acetyloxy)-13-ethyl-,oxime, (17(α)-(+)-) and ethinyl estradiol; available from Ortho-McNeil under the tradenames Ortho Cyclen and Ortho Tri-Cyclen; and (j) the combination of conjugated estrogens (sodium estrone sulfate and sodium equilin sulfate) and medroxyprogesterone acetate (20-dione, 17-(acetyloxy)-6-methyl-, (6(α))-pregn-4-ene-3); available from Wyeth-Ayerst under the tradenames Premphase and Prempro.

In general, a dosage of progestins may vary from about 0.05 mg to about 10 mg or up to about 200 mg if microsized progesterone is administered. Examples of progestins include norethindrone; available from ESI Lederle, Inc., Philadelphia, Pa., under the tradename Aygestin, from Ortho-McNeil under the tradename Micronor, and from Watson under the tradename Nor-QD; norgestrel; available from Wyeth-Ayerst under the tradename Ovrette; micronized progesterone (pregn-4-ene-3, 20-dione); available from Solvay under the tradename Prometrium; and medroxyprogesterone acetate; available from Pharmacia & Upjohn under the tradename Provera.

In another alternative embodiment, the compositions, therapeutic combinations or methods of the present invention can comprise at least one compound of Formula (I), or pharmaceutically acceptable salts, solvates, isomers or esters thereof, and one or more obesity control medications. Useful obesity control medications include, but are not limited to, drugs that reduce energy intake or suppress appetite, drugs that increase energy expenditure and nutrient-partitioning agents. Suitable obesity control medications include, but are not limited to, noradrenergic agents (such as diethylpropion, mazindol, phenylpropanolamine, phentermine, phendimetrazine, phendamine tartrate, methamphetamine, phendimetrazine and tartrate); serotonergic agents (such as sibutramine, fenfluramine, dexfenfluramine, fluoxetine, fluvoxamine and paroxtine); thermogenic agents (such as ephedrine, caffeine, theophylline, and selective β3-adrenergic agonists); alpha-blocking agents; kainite or AMPA receptor antagonists; leptin-lipolysis stimulated receptors; phosphodiesterase enzyme inhibitors (such as milrinoone, theophylline, vinpocetine, EHNA (erythro-9-(2-hydroxy-3-monyl)adenine), sildenafil citrate, marketed as VIAGRA®, and tadalafil, marketed as Cialis®); compounds having nucleotide sequences of the mahogany gene; fibroblast growth factor-10 polypeptides; monoamine oxidase inhibitors (such as befloxatone, mociobemide, brofaromine, phenoxathine, esuprone, befol, toloxatone, pirlindol, amiflamine, sercloremine, bazinaprine, lazabemide, milacemide and caroxazone); compounds for increasing lipid metabolism (such as evodiamine compounds); and lipase inhibitors (such as orlistat). Generally, a total dosage of the above-described obesity control medications can range from 1 to 3,000 mg/day, desirably from about 1 to 1,000 mg/day and more desirably from about 1 to 200 mg/day in single or 2-4 divided doses.

The compositions, therapeutic combinations or methods of the present invention can comprise at least one compound of Formula (I), or pharmaceutically acceptable salts, solvates, isomers or esters thereof, and one or more blood modifiers which are chemically different from the substituted azetidinone and substituted β-lactam compounds (such as compounds II-XIII above) and the lipid modulating agents discussed above, for example, they contain one or more different atoms, have a different arrangement of atoms or a different number of one or more atoms than the sterol absorption inhibitor(s) or lipid modulating agents discussed above. Useful blood modifiers include but are not limited to anti-coagulants (argatroban, bivalirudin, dalteparin sodium, desirudin, dicumarol, lyapolate sodium, nafamostat mesylate, phenprocoumon, tinzaparin sodium, warfarin sodium); antithrombotic (Abcoximab, aspirin, anagrelide hydrochloride, Beraprost, bivalirudin, cilostazol, Carbasalate calcium, Cloricromen, Clopidogrel, dalteparin sodium, danaparoid sodium, dazoxiben hydrochloride, Ditazole, Ditazole, Dipyridamole, Eptifibatide, efegatran sulfate, enoxaparin sodium, fluretofen, ifetroban, ifetroban sodium, Indobufen, Iloprost, lamifiban, lotrafiban hydrochloride, napsagatran, orbofiban acetate, Picotamide, Prasugrel, Prostacyclin, Treprostinil, Ticlopidine, Treprostinil, Triflusal, roxifiban acetate, sibrafiban, tinzaparin sodium, trifenagrel, abciximab, vitamin K antagonists, zolimomab aritox, enzymes such as Alteplase, Ancrod, Anistreplase, Brinase, Drotrecogin alfa, Fibrinolysin, Protein C, Reteplase, Saruplase, Steptokinase, Tenecteplase, and Urokinase), other antithrobotic agents such as Aragatroban, Bivalirudin, Dabigatran, Desirudin, Jirduin, Lepirudin, Melagatran, and Ximelagatran); fibrinogen receptor antagonists (roxifiban acetate, fradafiban, orbofiban, lotrafiban hydrochloride, tirofiban, xemilofiban, monoclonal antibody 7E3, sibrafiban); platelet inhibitors (cilostazol, clopidogrel bisulfate (marketed as Plavix®), epoprostenol, epoprostenol sodium, ticlopidine hydrochloride, aspirin, ibuprofen, naproxen, sulindac, idomethacin, mefenamate, droxicam, diclofenac, sulfinpyrazone, piroxicam, dipyridamole); platelet aggregation inhibitors (acadesine, beraprost, beraprost sodium, ciprostene calcium, itazigrel, lifarizine, lotrafiban hydrochloride, orbofiban acetate, oxagrelate, fradafiban, orbofiban, tirofiban, xemilofiban); hemorrheologic agents (pentoxifylline); lipoprotein associated coagulation inhibitors; Factor Vila inhibitors (4H-31-benzoxazin-4-ones, 4H-3, 1-benzoxazin-4-thiones, quinazolin-4-ones, quinazolin-4-thiones, benzothiazin-4-ones, imidazolyl-boronic acid-derived peptide analogues TFPI-derived peptides, naphthalene-2-sulfonic acid {1-[3-(aminoiminomethyl)-benzyl]-2-oxo-pyrrolidin-3-(S)-yl}amide trifluoroacetate, dibenzofuran-2-sulfonic acid {1-[3-(aminomethyl)-benzyl]-5-oxo-pyrrolidin-3-yl}-amide, tolulene-4-sulfonic acid {1-[3-(aminoiminomethyl)-benzyl]-2-oxo-pyrrolidin-3-(S)-yl}-amide trifluoroacetate, 3,4-dihydro-1H-isoquinoline-2-sulfonic acid {1-[3-(aminoiminomethyl)-benzyl]-2-oxo-pyrrolin-3-(S)-yl}-amide trifluoroacetate); Factor Xa inhibitors (disubstituted pyrazolines, disubstituted triazolines, substituted n-[(aminoiminomethyl)phenyl] propylamides, substituted n-[(aminomethyl)phenyl] propylamides, tissue factor pathway inhibitor (TFPI), low molecular weight heparins (such as dalteparin sodium, marketed as FRAGMIN®), heparinoids, benzimidazolines, benzoxazolinones, benzopiperazinones, indanones, dibasic (amidinoaryl) propanoic acid derivatives, amidinophenyl-pyrrolidines, amidinophenyl-pyrrolines, amidinophenyl-isoxazolidines, amidinoindoles, amidinoazoles, bis-arylsulfonylaminobenzamide derivatives, peptidic Factor Xa inhibitors).

The compositions, therapeutic combinations or methods of the present invention can comprise at least one compound of Formula (I), or pharmaceutically acceptable salts, solvates, isomers or esters thereof, and one or more cardiovascular agents which are chemically different from the substituted azetidinone and substituted β-lactam compounds (such as compounds II-XIII above) and the lipid modulating agents discussed above, for example, they contain one or more different atoms, have a different arrangement of atoms or a different number of one or more atoms than the sterol absorption inhibitor(s) or PPAR receptor activators discussed above. Useful cardiovascular agents include but are not limited to calcium channel blockers (clentiazem maleate, amlodipine besylate (marketed as NORVASC® and LOTREL®), isradipine, nimodipine, felodipine (marketed as PLENDIL®), nilvadipine, nifedipine, teludipine hydrochloride, diltiazem hydrochloride (marketed as CARDIZEM®), belfosdil, verapamil hydrochloride (marketed as CALAN®), fostedil), nifedipine (marketed as ADALAT®), nicardipine (marketed as CARDENE®), nisoldipine (marketed as SULAR®), bepridil (marketed as VASCOR®); adrenergic blockers (fenspiride hydrochloride, labetalol hydrochloride, proroxan, alfuzosin hydrochloride, acebutolol, acebutolol hydrochloride, alprenolol hydrochloride, atenolol, bunolol hydrochloride, carteolol hydrochloride, celiprolol hydrochloride, cetamolol hydrochloride, cicloprolol hydrochloride, dexpropranolol hydrochloride, diacetolol hydrochloride, dilevalol hydrochloride, esmolol hydrochloride, exaprolol hydrochloride, flestolol sulfate, labetalol hydrochloride, levobetaxolol hydrochloride, levobunolol hydrochloride, metalol hydrochloride, metoprolol, metoprolol tartrate, nadolol, pamatolol sulfate, penbutolol sulfate, practolol, propranolol hydrochloride, sotalol hydrochloride, timolol, timolol maleate. tiprenolol hydrochloride, tolamolol, bisoprolol, bisoprolol fumarate, nebivolol); adrenergic stimulants; angiotensin converting enzyme (ACE) inhibitors (benazepril hydrochloride (marketed as LOTENSIN®), benazeprilat, captopril (marketed as CAPTOEN®, delapril hydrochloride, fosinopril sodium, libenzapril, moexipril hydrochloride (marketed as UNIVASC®), pentopril, perindopril, quinapril hydrochloride (marketed as ACCUPRIL®), quinaprilat, ramipril (marketed as RAMACE® and ALTACE®) (or ACE/NEP inhibitors such as ramipril, marketed as DELIX®/TRITACE®), spirapril hydrochloride, peridopril, (marketed as ACEON®), spiraprilat, trandolapil (marketed as MAVIK®), teprotide, enalapril maleate (marketed as VASOTEC®), lisinopril (marketed as ZESTRIL®), zofenopril calcium, perindopril erbumine); antihypertensive agents (althiazide, benzthiazide, captopril, carvedilol, chlorothiazide sodium, clonidine hydrochloride, cyclothiazide, delapril hydrochloride, dilevalol hydrochloride, doxazosin mesylate, fosinopril sodium (marketed as MONOPRIL®), guanfacine hydrochloride, lomerizine, methyldopa, metoprolol succinate, moexipril hydrochloride, monatepil maleate, pelanserin hydrochloride, phenoxybenzamine hydrochloride, prazosin hydrochloride, primidolol, quinapril hydrochloride, quinaprilat, ramipril, terazosin hydrochloride, candesartan, candesartan cilexetil, telmisartan, amlodipine besylate, amiodipine maleate, bevantolol hydrochloride); angiotensin II receptor antagonists (candesartan, irbesartan, losartan potassium, candesartan cilexetil, telmisartan); anti-anginal agents (amiodipine besylate, amlodipine maleate, betaxolol hydrochloride, bevantolol hydrochloride, butoprozine hydrochloride, carvedilol, cinepazet maleate, metoprolol succinate, molsidomine, monatepil maleate, primidolol, ranolazine hydrochoride, tosifen, verapamil hydrochloride); coronary vasodilators (fostedil, azaclorzine hydrochloride, chromonar hydrochloride, clonitrate, diltiazem hydrochloride, dipyridamole, droprenilamine, erythrityl tetranitrate, isosorbide dinitrate, isosorbide mononitrate, lidoflazine, mioflazine hydrochioride, mixidine, molsidomine, nicorandil, nifedipine, nisoldipine, nitroglycerine, oxprenolol hydrochloride, pentrinitrol, perhexiline maleate, prenylamine, propatyl nitrate, terodiline hydrochloride, tolamolol, verapamil); diuretics (the combination product of hydrochlorothiazide and spironolactone and the combination product of hydrochlorothiazide and triamterene).

The compositions, therapeutic combinations or methods of the present invention can comprise at least one compound of Formula (I), or pharmaceutically acceptable salts, solvates, isomers or esters thereof, and one or more antidiabetic medications for reducing blood glucose levels in a patient. Useful antidiabetic medications include, but are not limited to, drugs that reduce energy intake or suppress appetite, drugs that increase energy expenditure and nutrient-partitioning agents. Suitable antidiabetic medications include, but are not limited to, sulfonylurea (such as acetohexamide, chlorpropamide, gliamilide, gliclazide, glimepiride, glipizide, glyburide, glibenclamide, tolazamide, and tolbutamide), meglitinide (such as repaglinide and nateglinide), biguanide (such as metformin and buformin), alpha-glucosidase inhibitor (such as acarbose, miglitol, camiglibose, and voglibose), certain peptides (such as amlintide, pramlintide, exendin, and GLP-1 agonistic peptides), and orally administrable insulin or insulin composition for intestinal delivery thereof. Generally, a total dosage of the above-described antidiabetic medications can range from 0.1 to 1,000 mg/day in single or 2-4 divided doses.

Mixtures of two, three, four or more of any of the pharmacological or therapeutic agents described above can be used in the compositions and therapeutic combinations of the present invention.

Since the present invention relates to treating conditions as discussed above, by treatment with a combination of active ingredients wherein the active ingredients may be administered separately, the invention also relates to combining separate pharmaceutical compositions in kit form. That is, a kit is contemplated wherein two separate units are combined: a pharmaceutical composition comprising at least one selective $CB_1$ receptor antagonist of Formula (I), or a pharmaceutically acceptable salt, solvate, or ester thereof, and a separate pharmaceutical composition comprising at least one cholesterol lowering compound as described above. The kit will preferably include directions for the administration of the separate components. The kit form is particularly advantageous when the separate components must be administered in different dosage forms (e.g., oral and parenteral) or are administered at different dosage intervals.

In yet another embodiment, the present invention provides a method of treating, reducing, or ameliorating a disease or condition selected from the group consisting of metabolic syndrome, obesity, waist circumference, abdominal girth, lipid profile, insulin sensitivity, neuroinflammatory disorders, cognitive disorders, psychosis, addictive behavior, gastrointestinal disorders, vascular conditions, hyperlipidaemia, atherosclerosis, hypercholesterolemia, sitosterolemia, vascular inflammation, stroke, diabetes, and cardiovascular conditions, and/or reduce the level of sterol(s) in a patient in need thereof, comprising administering to said patient an effective amount of at least one compound of Formula (I), or a pharmaceutically acceptable salt, solvate, or ester thereof, and one or more cholesterol lowering compound.

The treatment compositions and therapeutic combinations comprising at least one compound of Formula (I) and at least one cholesterol lowering agent can inhibit the intestinal absorption of cholesterol in mammals can be useful in the treatment and/or prevention of conditions, for example vascular conditions, such as atherosclerosis, hypercholesterolemia and sitosterolemia, stroke, obesity and lowering of plasma levels of cholesterol in mammals, in particular in mammals.

In another embodiment of the present invention, the compositions and therapeutic combinations of the present invention can inhibit sterol or 5α-stanol absorption or reduce plasma concentration of at least one sterol selected from the group consisting of phytosterols (such as sitosterol, campesterol, stigmasterol and avenosterol) and/or 5α-stanol (such as cholestanol, 5α-campestanol, 5α-sitostanol), cholesterol and mixtures thereof. The plasma concentration can be reduced by administering to a mammal in need of such treatment an effective amount of at least one treatment composition or therapeutic combination comprising at least one selective $CB_1$ receptor antagonist and at least one cholesterol lowering compound, for example a sterol absorption inhibitor described above. The reduction in plasma concentration of sterols or 5α-stanols can range from about 1 to about 70 percent, and preferably about 10 to about 50 percent. Methods of measuring serum total blood cholesterol and total LDL cholesterol are well known to those skilled in the art and for example include those disclosed in PCT WO 99/38498 at page 11, incorporated by reference herein. Methods of determining levels of other sterols in serum are disclosed in H. Gylling et al., "Serum Sterols During Stanol Ester Feeding in a Mildly Hypercholesterolemic Population", J. Lipid Res. 40: 593-600 (1999), incorporated by reference herein.

The treatments of the present invention can also reduce the size or presence of plaque deposits in vascular vessels. The plaque volume can be measured using (IVUS), in which a tiny ultrasound probe is inserted into an artery to directly image and measure the size of atherosclerotic plaques, in a manner well known to those skilled in the art.

Synthesis

The following solvents and reagents may be referred to herein by the abbreviations indicated: tetrahydrofuran (THF), ethanol (EtOH), methanol (MeOH), acetic acid (HOAc or AcOH), ethyl acetate (EtOAc), N,N-dimethylformamide (DMF), trifluoroacetic acid (TFA), hex is hexanes, 1-hydroxybenzotriazole (HOBT), triethyl amine (TEA), 1-chloroethyl chloroformate (ACECI), m-chlorobenzoic acid (MCPBA), diethyl ether ($Et_2O$), dimethylsulfoxide (DMSO), N-(3-dimethylaminopropyl)-N'-ethylcarbodiimide hydrochloride (EDCI), RT is room temperature, and TLC is thin-layer chromatography, Me is methyl, Et is ethyl, Pr is propyl, Bu is butyl, Ph is phenyl, THP is tetrahydropyran, DHP is 3,4-dihydro-2H-pyran, DCM is dichloromethane, DOCE is dichloroethane, PTSA is p-toluenesulfonic acid, TsOH is p-toluenesulfonic acid, MsCl is methanesulfonyl chloride, TBDMS is tert-butyldimethyl silyl, TBS is tert-butyldimethyl silyl, IPA is isopropanol. Alloc is allyloxy carbonyl. Boc is tert-butoxy carbonyl.

Piperazines g are prepared according the steps outlined in Scheme A, A benzyl protected ethanol amine a can be heated with an epoxide b to furnish a mixture of the amino-alcohols c and d; The alcohols c and d can be converted into the diamine e via sequential treatment with MsCl followed by $Ar^2 NH_2$. The diamine e can be converted into the piperazine f via deprotection of the THP group in e followed by activation of the alcohol. The benzyl group in f can be removed via treatment with ACECI followed by basic hydrolysis which provides piperazines g.

Scheme A

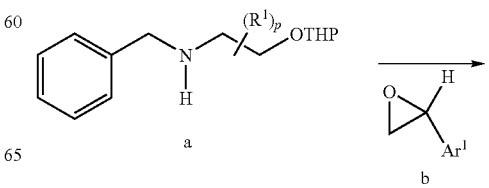

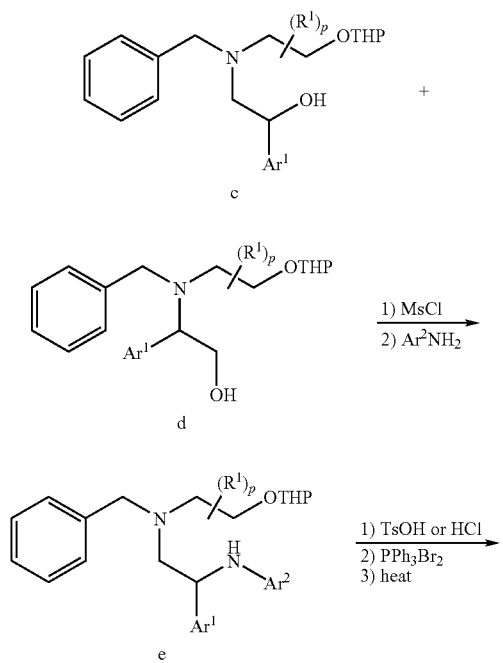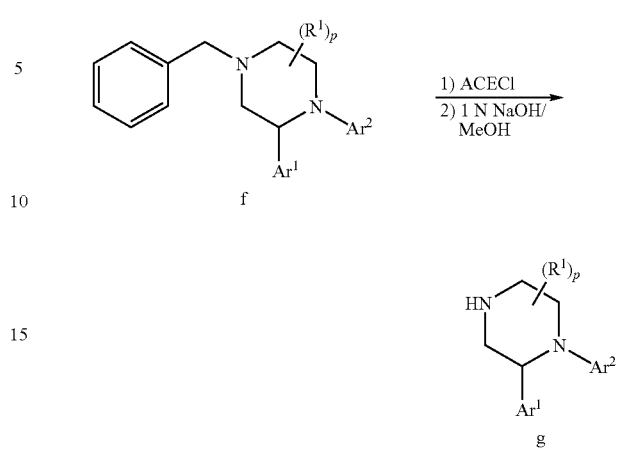

Also, chiral epoxides, such as h and i, can be utilized as that described in Scheme A to provide enantiopure piperazines j and k (Scheme B). The chiral epoxides can be prepared either via asymmetric di-hydroxylation of a styrene (e.g. Sharpless AD mix α or β) or chiral reduction of a bromo-ketone (e.g. CBS reduction). These methods allow the preparation of either enantiomer of the epoxide, h or i.

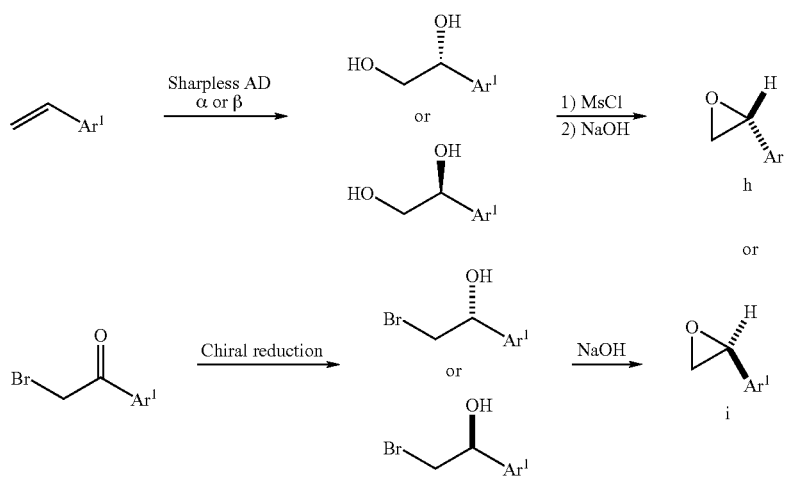

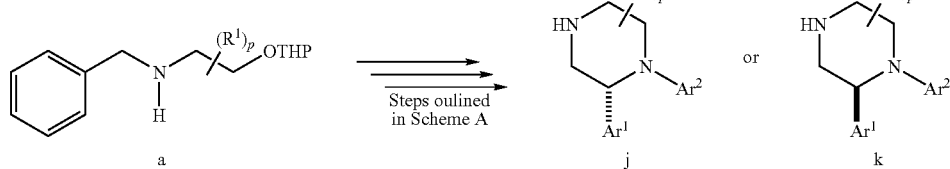

Further functionalization of piperazine g into compounds is illustrated in Scheme C. Piperazine g can be transformed into the alkylated derivatives such as l and m via reductive alkylation (Na(AcO)$_3$BH/XC(O)R$^2$) and/or direct alkylation (base/X(R$^2$)$_2$OMs) conditions. Also, the piperazine g can be converted into an amide or sulfonamide using standard techniques (e.g. n and o). Hydroxy-ethyl analogs p can be made via reaction of a hydroxy-mesylate or epoxide with piperazine g.

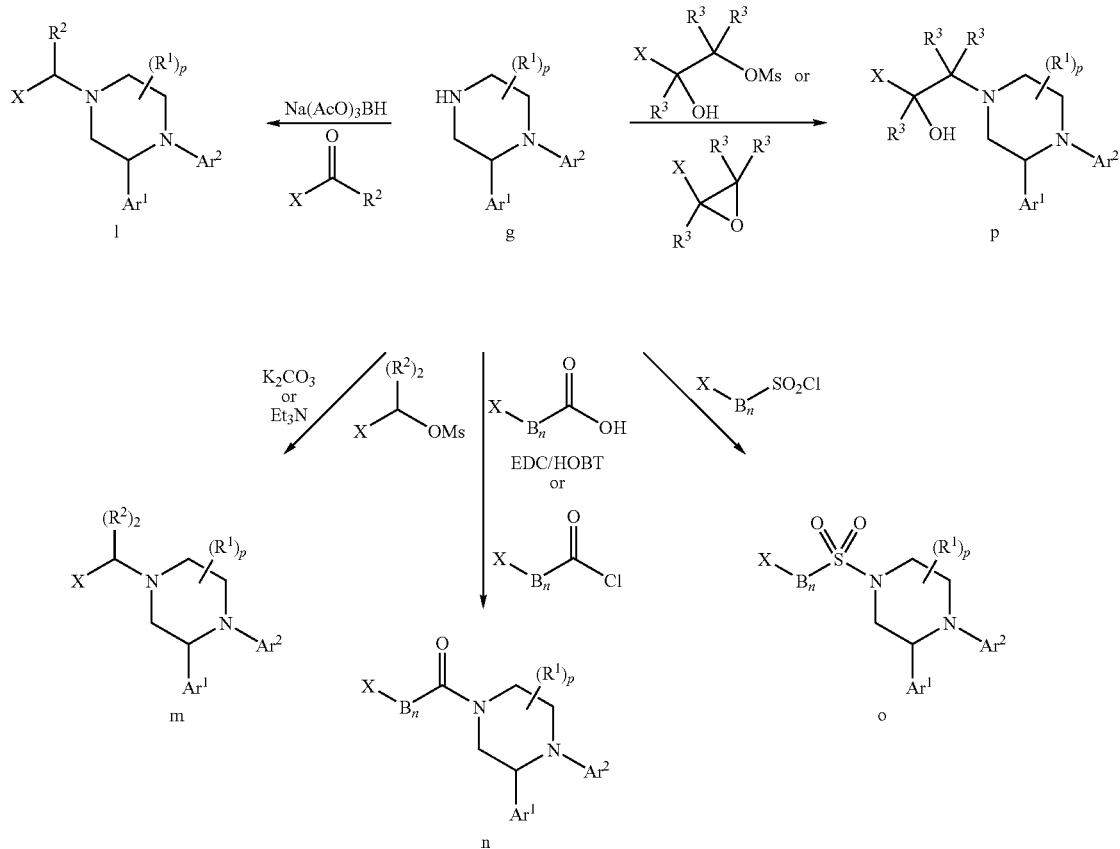

Also, the chiral piperazine j can be functionalized according to the transformations outlined in Scheme C to furnish the corresponding chiral derivatives (Scheme D).

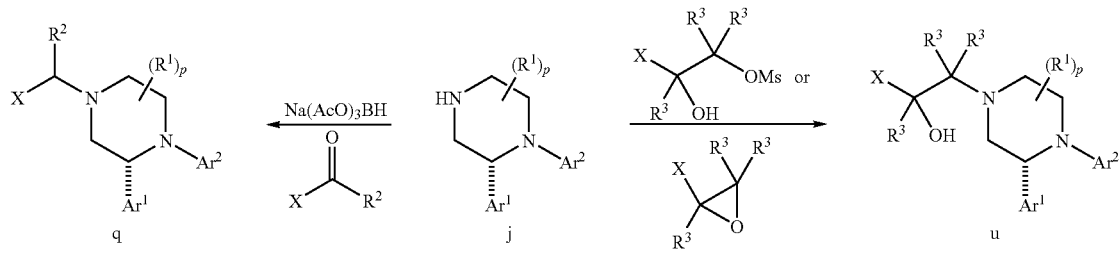

-continued

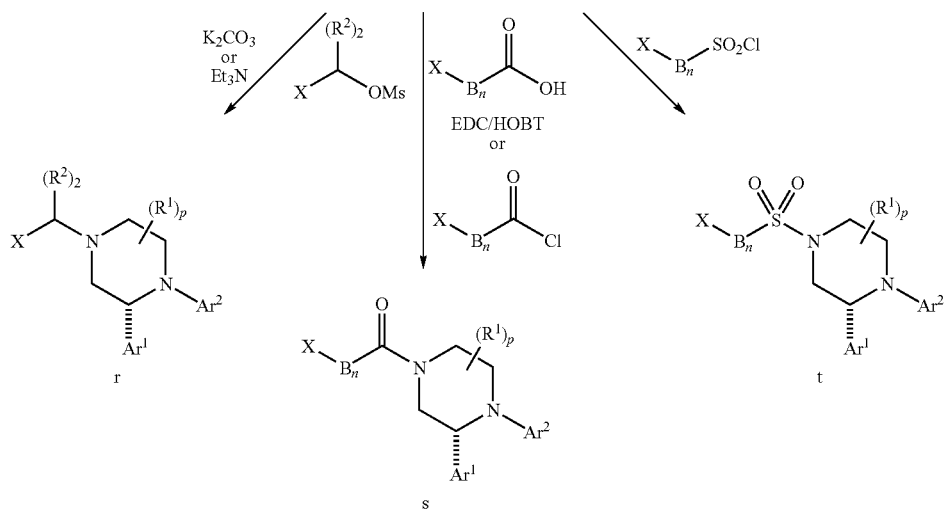

Also, the chiral piperazine k can be functionalized according to the transformations outlined in Scheme C to furnish the corresponding chiral derivatives (Scheme E).

Scheme E

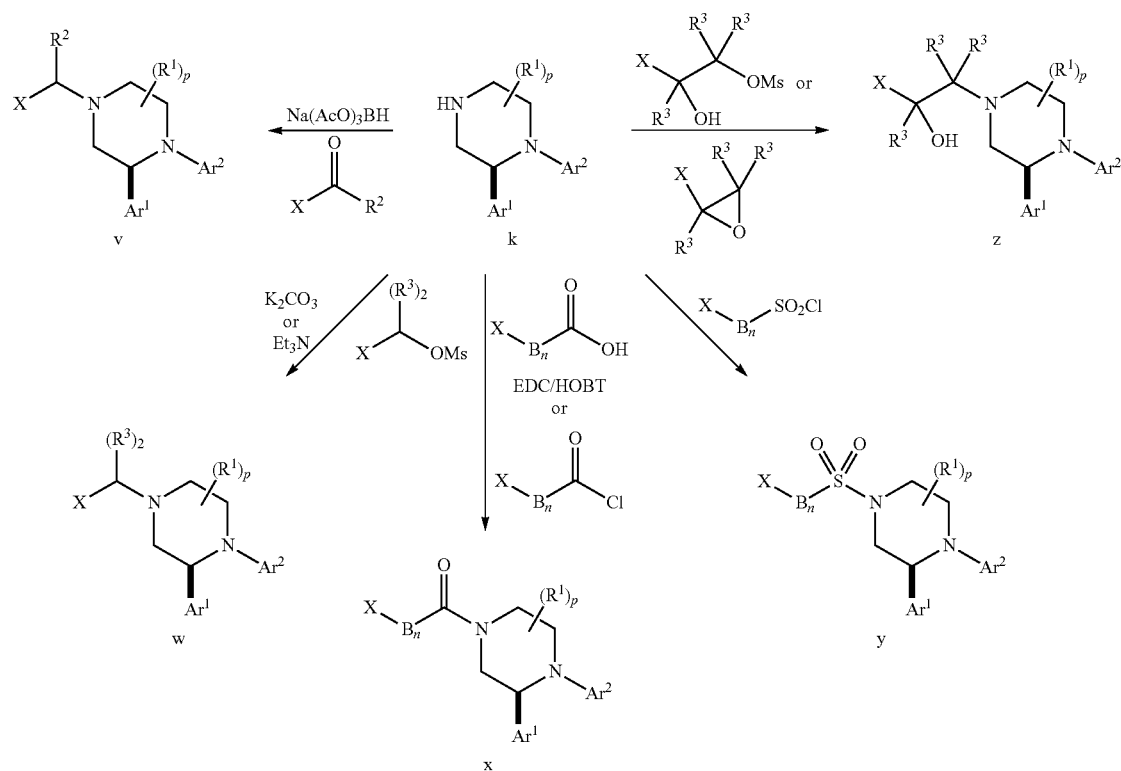

Certain reagents for functionalization of the piperazine core can be prepared in chiral form. These reagents can be prepared by known procedures in the art, and non-limiting examples are illustrated below.

A ketone can be transformed into either enantiomer of the corresponding alcohol by several methods (1.reduction 2 enzymatic resolution or chiral reduction). Activation of the alcohol (MsCl/Et$_3$N) provides the either enantiomer of the mesylate which can be coupled to either enantiomer of the piperazine (j or k) which provides access to four possible diastereomers in pure form (e.g. aa, ab, ac, or ad; Scheme F).

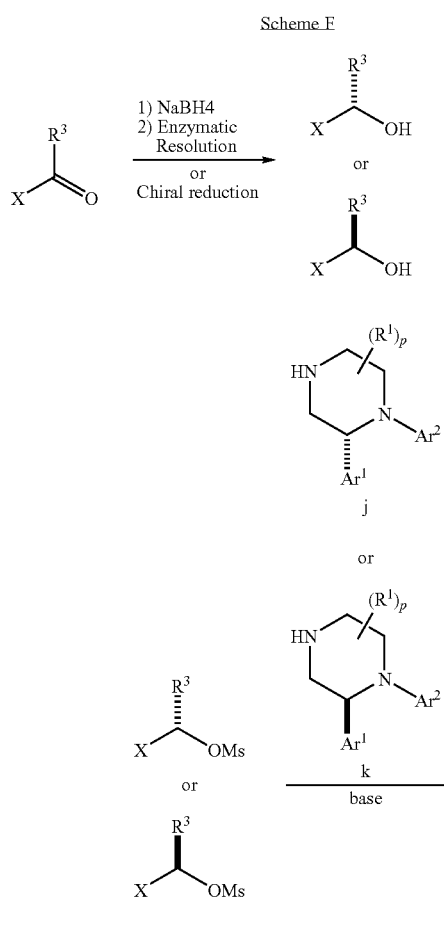

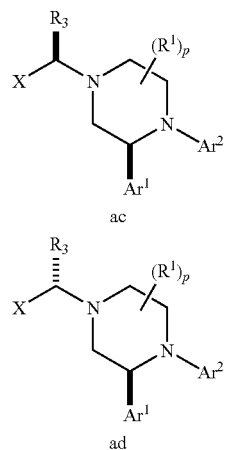

Using procedures known in the art, substituted alkenes can be prepared from olefination of ketones (Wittig) and/or transition metal mediated methods (Pd(0)/metal-alkenyl derivative). These can be transformed into chiral diols via asymmetric methods (e.g. Sharpless AD mix α or β). The formed chiral diol can be transformed into the corresponding mesylate and/or epoxide. These can be reacted with the chiral piperazines, j and k, to provide four possible diastereomers in pure form (e.g. ae, af, ag, and ah; Scheme G).

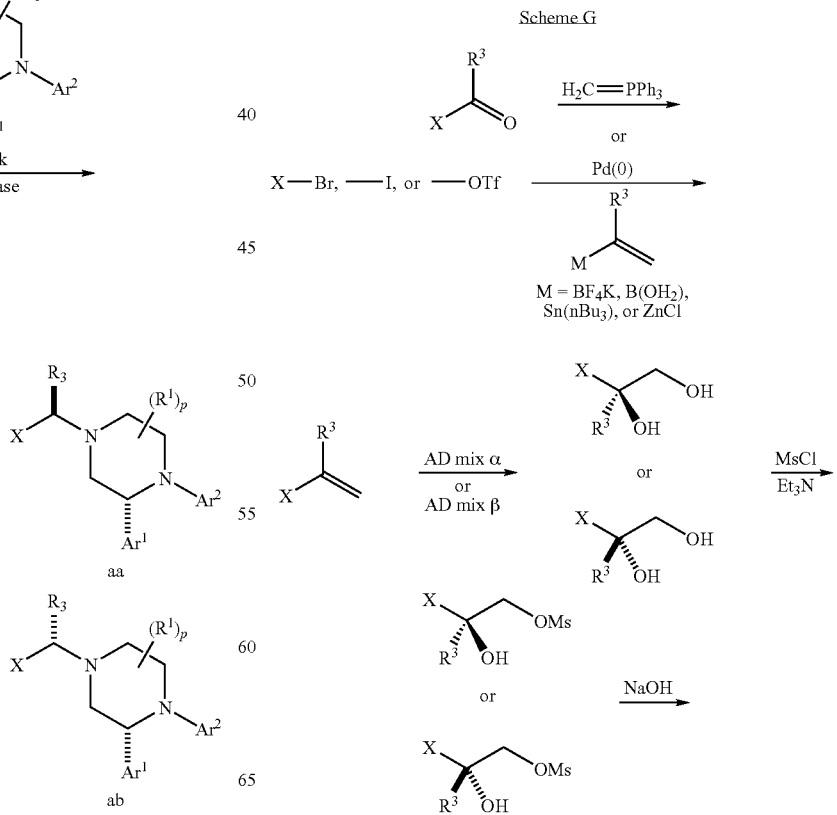

-continued
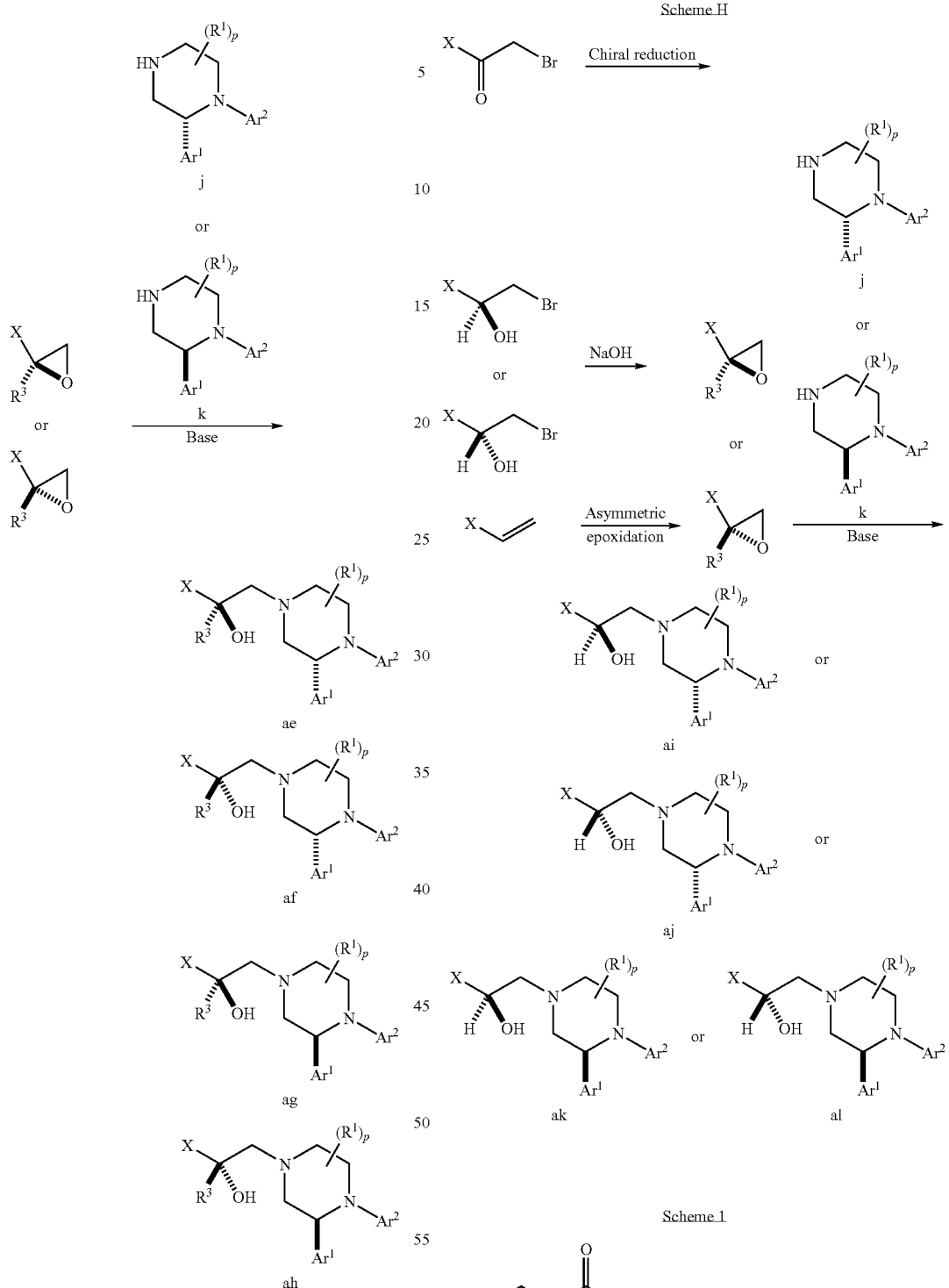
Also, the chiral piperazine cores, j and k, can be reacted with chiral epoxides to produce chiral piperazine-alcohol derivatives ai, aj, ak, and al (Scheme H). The requisite chiral epoxides can be prepared by procedures known in the art (e.g. chiral reduction of a bromo-ketone and/or asymmetric epoxidation of an alkene).
Scheme H
Scheme 1

-continued

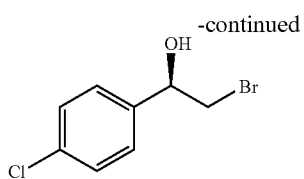

Step 1

To 2-bromo-4'-chloroacetophenone (233 g, 1000 mmol) in THF (1L) at 0° C. was added (R)-2-methyl-CBS-oxazaborolidine (1.0 M in THF, 200 mL, 200 mmol) through an addition funnel. The BH$_3$.SMe$_2$ (2.0 M in THF, 300 mL, 600 mL) was added slowly over 25 min. The reaction was stirred at room temperature for 2 h. The reaction was cooled to 0° C. and MeOH (200 mL) was added slowly (gas evolution). The resulting solution was concentrated in vacuo and then diluted with CH$_2$Cl$_2$ (3.5 L). The organic layer was washed with 1N HCl, water, and brine. Dried (MgSO$_4$), filtered, and concentrated in vacuo to provide the bromoalcohol as an oil that solidified on standing (237 g).

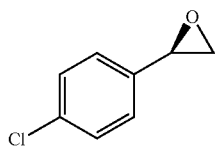

Step 2

Dissolved the bromoalcohol from Step 1 (237 g; 1000 mmol) in toluene (3.5 L) and added 3N NaOH (3.5 L). Stirred the reaction vigorously at room temperature for 3h. Washed the organic layer with water and brine and dried (MgSO$_4$). Filtered and concentrated in vacuo to provide the epoxide (154 g, 1000 mmol). The ee of the epoxide was found to be ≥96% ee by HPLC [HR-Whelko-O-1, 99.75:0.25 hexane/IPA, 1 mL/min, 220 nm. Isomer A retention time 10.5 min, isomer B (major) 14.1 min)].

Scheme 2

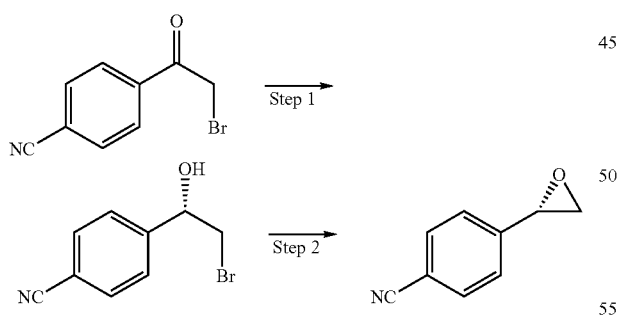

Step 1 To 2-bromo-4'-cyanoacetophenone (1.0 g, 4.5 mmol) in THF (4.5 mL) at 0° C. was added (S)-2-methyl-CBS-oxazaborolidine (1M in toluene, 0.89 mL) followed by BH$_3$.SMe$_2$ (2.0M in THF, 1.3 mL). The mixture was stirred at 0° C. for 75 minutes. MeOH (~5 mL) was added (with gas evolution) and the mixture was stirred for 15 minutes. The reaction mixture was concentrated in vacuo. The residue was taken up into CH$_2$Cl$_2$ and washed with 1N HCL, water, and brine, dried (MgSO$_4$), filtered, and concentrated in vacuo to provide the corresponding alcohol which was used directly in the next step without further purification.

Step 2 The alcohol prepared in step 1 was taken up into toluene (40 mL). 1N NaOH (40 mL) was added and the mixture was stirred at room temperature for 20 h. The organic layer was washed with water and brine, dried (MgSO$_4$), filtered, and concentrated in vacuo. The resulting residue was purified by silica gel chromatography (0-20% EtOAc/hexane) to provide the epoxide (0.52 g, 3.6 mmol).

Scheme 3

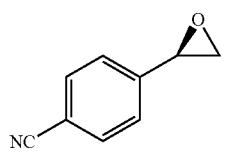

The epoxide was formed in the same manner as the 4-chlorostyrene oxide formed in Scheme 1 except that 2-bromo-4'-cyanoacetophenone was used instead of 2-bromo-4'-chloroacetophenone in Step 1

Scheme 4

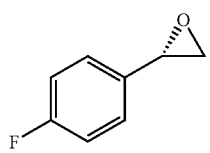

The 4-fluoroepoxide was formed in the same manner as the 4-chlorostyrene oxide formed in Scheme 1 except that 2-bromo-4'-fluoroacetophenone was used instead of 2-bromo-4'-chloroacetophenone and (S)-2-methyl-CBS-oxazaborolidine was used instead of (R)-2-methyl-CBS-oxazaborolidine in Step 1.

Scheme 5

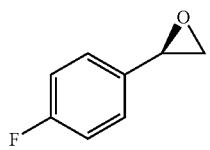

The 4-fluoroepoxide was formed in the same manner as the 4-chlorostyrene oxide formed in Scheme 1 except that 2-bromo-4'-fluoroacetophenone was used instead of 2-bromo-4'-chloroacetophenone in step 1.

Scheme 6

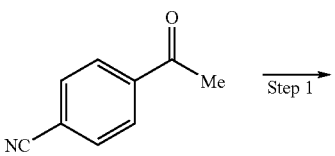

-continued

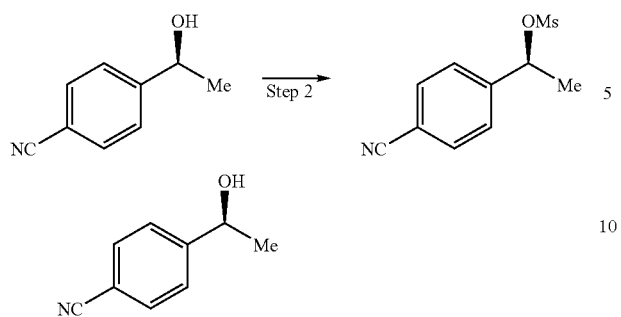

Step 1

To 4-acetylbenzonitrile (3.0 g, 20.7 mmol) in THF (21 mL) at −18 °C. (CO₂/ethylene glycol bath) was added (R-2-methyl-CBS-oxazaborolidine (1M in toluene, 2.1 mL) followed by BH₃.SMe₂ (2.0M in THF, 7.2 mL). Allowed the cold bath to expire while stirring for 18 h. Added MeOH (~10 mL) [gas evolution] and stirred for 15 minutes. Concentrated the reaction mixture in vacuo and took up into EtOAc. Washed with 1N HCL, water, and brine. Dried (MgSO₄) the organic layer, filtered, and concentrated in vacuo. Purified the residue by silica gel chromatography (5-40% EtOAc/hexanes) to provide the alcohol (1.85 g, 12.6 mmol).

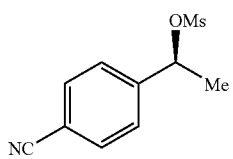

Step 2

To the alcohol from Step 1 (0.70 g, 4.8 mmol) in CH₂Cl₂ (16 mL) at 0° C. was added TEA (0,72 g, 7.1 mmol) followed by methanesulfonyl chloride (0.60 g, 5.2 mmol). Stirred the reaction at 0° C. for 1 h. Added CH₂Cl₂ and washed with 1N HCL, water, and brine. Dried (MgSO₄) the organic layer, filtered, and concentrated in vacuo to provide the mesylate (1.1 g, 4.7 mmol) that was used directly without further purification.

-continued

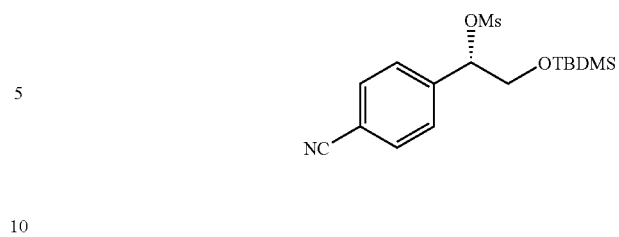

Step 1

To AD mix α (available from Aldrich) (10.8 g) in ted-butyl alcohol/water (1:1) (78 mL) at 0° C. was added 4-cyanostyrene (1.0 g, 7.7 mmol). The reaction was stirred for 20 h, allowing the cold bath to expire. The reaction was cooled to 0° C. and solid sodium sulfite (10 g) was added. The mixture was allowed to warm to room temperature while stirring for 1 h. The mixture was then extracted with EtOAc. The organic layer was washed with water and brine, dried (MgSO₄), filtered, and concentrated in vacuo. The residue was purified by silica gel chromatography (5% MeOH/CH₂Cl₂) to provide the corresponding diol (1.24 g).

Step 2

To the diol prepared in step 1 (0.62 g, 3.8 mmol) in DMF (10 mL) at 0° C. was added imidazole (0.65 g, 9.5 mmol) followed by TBDMS-Cl (i.e., tert-butyldimethylsilyl chloride) (0.69 g, 4.6 mmol). The reaction mixture was stirred for 4h while warming to room temperature. The reaction mixture was poured into brine and then extracted with EtOAc. The organic layer was washed with water, brine, dried (MgSO₄), filtered, and concentrated in vacua. The residue was purified by silica gel chromatography (20% EtOAc/hexane) to provide a tert-butyidimethylsilyl ether (0.67 g).

Step 3

To the tert-butyldimethylsilyl ether prepared in step 2 (0,67 g, 2.4 mmol) in CH₂Cl₂ (8 mL) at 0° C. was added TEA (i.e., triethylamine) (0.5 mL, 3.6 mmol) followed by MeSO₂Cl (0.22 mL, 2.9 mmol). The reaction mixture was stirred for 2 h and CH₂Cl₂ was added. The mixture was washed with saturated NaHCO₃(aq), water, and brine. The organic layer was dried (MgSO4), filtered, and concentrated in vacuo to provide a methylsulfonyl ester (0.87 g) that was used directly without further purification.

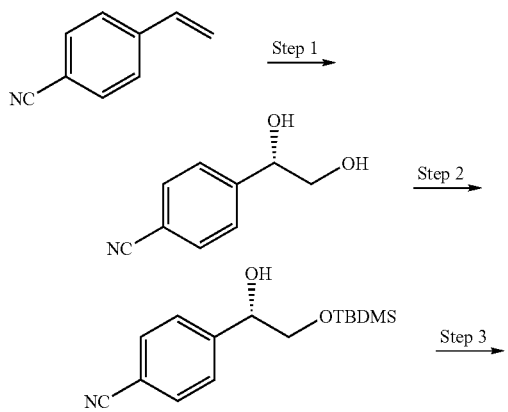

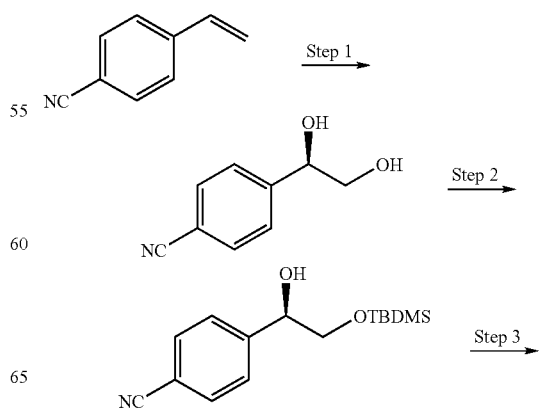

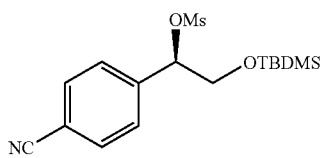

The mesylate formed in step 3 of Scheme 8 was prepared in the same manner as the mesylate in Scheme 7 except that AD mix β was used instead of AD mix α in Step 1.

Scheme 9

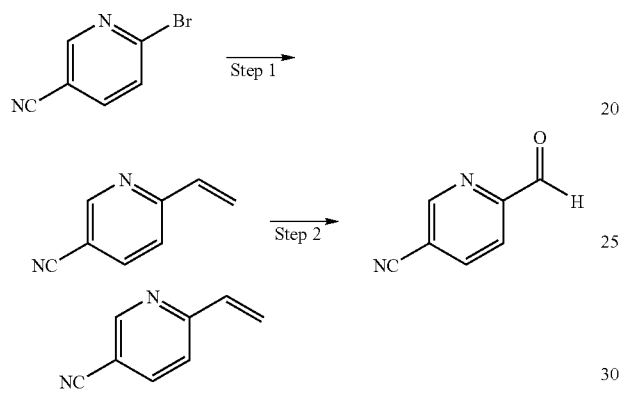

Step 1 Nitrogen was bubbled through a solution of 2-bromo-5-cyanopyridine (6.0 g, 33 mmol) in MeOH (25 mL) for 5 minutes. Potassium vinyltrifluoroborate (5.3 g, 39 mmol) and TEA (4.5 mL, 33 mmol) were added followed by Pd(dppf)$_2$Cl.CH$_2$Cl$_2$ (1.1 g, 0.04 mmol). Warmed the reaction to 80° C. in a sealed tube and stirred for 8 h. Cooled to room temperature and concentrated in vacuo. Added water and EtOAc and filtered through a bed of Celite. Washed the filtrate with water and brine. Dried the organic layer (MgSO$_4$), filtered, and concentrated in vacuo. Purified the residue by silica gel chromatography (0-20% EtOAc/Hex over 30 minutes) to proved the olefin (4.1 g, 31.5 mmol).

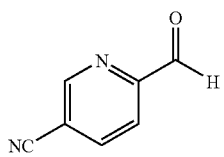

Step 2 A DCM solution (160 mL) of containing the aldehyde from step 1 (4.1 g, 31 mmol) was cooled to −78° C. Ozone was bubbled through the reaction mixture until the solution turned light blue (~30 minutes). The reaction was then purged with oxygen and then dimethylsulfide (7 mL, 95 mmol) was added. The reaction was stirred for 18 h after taking the cold bath away. Washed the mixture with water and brine. Dried (MgSO$_4$) the organic layer, filtered, and concentrated in vacuo. The residue was purified by silica gel chromatography (0-20% EtOAc/Hex) to provide the aldehyde (1.3 g, 9.7 mm Scheme 10

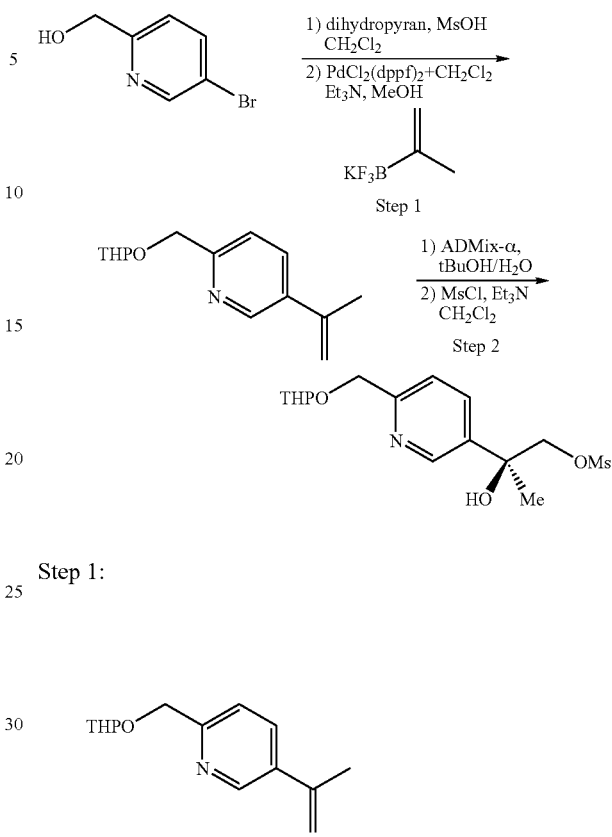

Step 1:

To a solution of 5-bromopyridin-2-yl methanol (Supplier: Biofine International, Vancouver, Canada) (5.27 g, 28.0 mmol) in CH$_2$Cl$_2$ was added methanesulfonic acid (2.82 g, 29.4 mmol) and dihydropyran (4.00 g, 47.6 mmol). The resultant solution was stirred at RT overnight. The solution was then washed with NaHCO$_3$ (aq.), dried over Na$_2$SO$_4$, filtered and concentrated. The crude product was purified via flash chromatography (SiO$_2$: gradient elution, 100:0 to 70:30 hexanes:EtOAc) to afford the ether (6.90 g) as a light yellow oil.

To a solution of the tetrahydropyranyl ether (10.4 g, 38.2 mmol) in MeOH (50 mL) in a pressure tube was added potassium trifluoro(prop-1-en-2-yl)borate (*J. Am Chem. Soc* 2003, 125, 11148-11149) (8.5 g, 57 mmol). The resultant slurry was degassed by bubbling N$_2$ through the solvent for 10 min. To this slurry was added PdCl$_2$(dppf)$_2$.CH$_2$Cl$_2$ (1.3 g, 1.6 mmol) and Et$_3$N (3.87 g, 38.2 mmol). The pressure tube was sealed and the mixture was heated to 100° C. with stirring for 16 h. The mixture was then cooled to RT, transferred to a round bottom flask and concentrated. The residue was partitioned between water and CH$_2$Cl$_2$ and the aqueous layer was extracted with CH$_2$Cl$_2$ (3×). The combined organic layers were dried over Na$_2$SO$_4$, filtered and concentrated. The crude product was purified via flash chromatography (SiO$_2$: gradient elution, 100:0 to 65:35 hexanes:EtOAc) to afford the styrene (5.0 g).

Step 2:

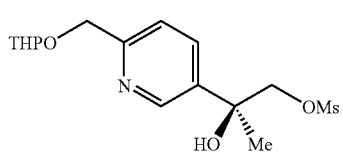

To a biphasic mixture of the styrene from step 1 (2.8 g, 12 mmol) in 1:1 tert-butanol/water (50 mL) was added AD mix α (Aldrich) (17 g) and methane sulfonamide (1.1 g, 12 mmol). The mixture was stirred vigorously at RT for 72 h. At that time, Na$_2$SO$_3$ (9.0 g, 72 mmol) was added and the resultant mixture was stirred at RT for 1 h. The mixture was then diluted with 2-propanol and stirred for an additional 1 h. The mixture was filtered through filter paper to remove the solids. The organic layer was then separated, dried over Na$_2$SO$_4$, filtered and concentrated. The residue was dissolved in CH$_2$Cl$_2$ (ca 10 mL) and Et$_3$N (1.8 g, 18 mmol) followed by methanesulfonyl chloride (1.5 g, 12 mmol) were added. The resultant solution was stirred at RT for 48 h. The solution was then diluted with CH$_2$Cl$_2$, washed with water, dried over Na$_2$SO$_4$, filtered and concentrated. The crude product was purified via flash chromatography (SiO$_2$: gradient elution, 100:0 to 0:100 hexanes:EtOAc) to afford the mesylate (1.5 g, 36% for 2 steps).

TABLE 1

The following halides were converted to mesylates using a similar method to that described in Scheme 10.

| Entry | Halides (Supplier) | Mesylate |
|---|---|---|
| 1 | ![] | ![] |
| 2 | ![] | ![] |
| 3 | ![] (Combi-Blocks: San Diego, CA) | ![] |
| 4 | ![] | ![] |

Scheme 11

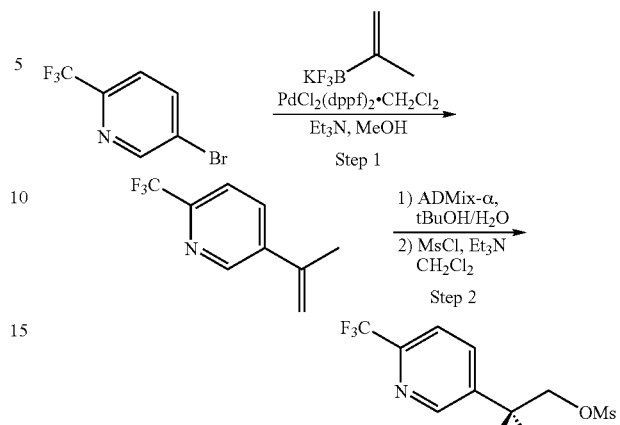

Step 1:

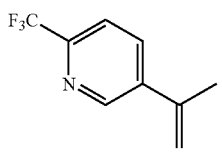

To a solution of 5-bromo-2-trifluoromethyl pyridine (4.0 g, 18 mmol) in MeOH (10 mL) in a pressure tube was added potassium trifluoro(prop-1-en-2-yl)borate (3,1 g, 21 mmol). The resultant sturry was degassed by bubbling N$_2$ through the solvent for 10 min. At that time, PdCl$_2$(dppf)$_2$.CH$_2$Cl$_2$ (0.58 g, 0.71 mmol) and Et$_3$N (1.8 g, 18 mmol) were added, the pressure tube was sealed and the mixture was heated to 100° C. with stirring for 3 h. The mixture was then cooled to RT, transferred to a round bottom flask and concentrated in vacuo. The crude residue was partitioned between water and CH$_2$Cl$_2$. The aqueous layer was then extracted with CH$_2$Cl$_2$ (3×). The combined organic layers were dried over Na$_2$SO$_4$, filtered and concentrated. The crude product was purified via flash chromatography (SiO$_2$: gradient elution, 100:0 to 85:15 hexanes:EtOAc) to afford the styrene (2.5 g, 75%).

Step 2:

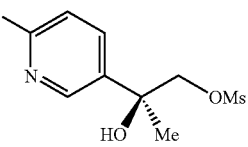

To a biphasic mixture of the styrene from Step 1 (2.5 g, 14 mmol) in 1:1 tert-butanol/water (50 mL) was added AD mix α(Aldrich) (19 g) and methane sulfonamide (1.3 g, 14 mmol). The resultant mixture was stirred vigorously at RT for 72 h. After that time, Na$_2$SO$_3$ (21 g, 165 mmol) was added and the mixture was stirred at RT for 1 h. The mixture was then diluted with 2-propanol and stirred for 1 h, at which time, the solids were removed via filtration. The organic layer was then separated, dried over Na$_2$SO$_4$, filtered and concentrated. The residue was redissolved in CH$_2$Cl$_2$ (ca 10 mL). To this solution was added Et$_3$N (1.65 g, 16.3 mmol) followed by methanesulfonyl chloride (1.7 g, 15 mmol). The solution was stirred at RT for 3 h. At that time, the solution was concentrated and the crude product was purified via flash chromatography (SiO$_2$: gradient elution, 100:0 to 45:55 hexanes: EtOAc) to afford the mesylate (3.5 g, 87% for 2 steps).

TABLE 2

The following halides were converted to mesylates using a similar method to that described in Scheme 11.

| Entry | Halide | Mesylate |
|---|---|---|
| 1 | | |
| 2 | | |
| 3 | | |
| 4 | | |
| 5 | | |
| 6 | | |
| 7 | | |
| 8 | | |
| 9 | | |
| 10 | | |

Scheme 12

Step 1:

To a slurry of 6-aminonicotinic acid (12.5 g, 90.5 mmol) in MeCN (150 mL) was added N,O-dimethylhydroxylamine hydrochloride (10.6 g, 109 mmol), HOBt (14.7 g, 109 mmol), EDCl (20.8 g, 109 mmol) and diisopropylethylamine (35.0 g, 272 mmol). The resultant mixture was stirred at RT overnight. Once the reaction was complete, the mixture was concentrated in vacuo. The residue was partitioned between 1 M NaOH (aq.) and EtOAc and the aqueous layer was extracted with EtOAc (3×). The combined organic layers were washed with brine, dried over Na₂SO₄, filtered and concentrated to afford the amide (6.7 g) as a white solid. The product was slurried in tert-butanol (100 mL) and di-tert-butyldicarbonate (8.88 g, 40.7 mmol) was added. The resultant mixture was stirred at RT overnight. Additional di-tert-butyldicarbonate (1.5 g, 6.9 mmol) was added and the mixture was stirred at RT for an additional 48 h. The reaction mixture was then concentrated to afford the amide (9.6 g, 38% yield for 2 steps) as a tan solid that was used without further purification.

Step 2:

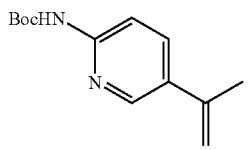 [SMILES: C=C(C)c1ccc(NC(=O)OC(C)(C)C)nc1]

To a solution of the amide from step 1 (9.6 g, 34 mmol) in THF (200 mL) at 0° C. was added a solution of MeMgBr (3 M in hexanes, 28.4 mL, 85 mmol). The solution was stirred at 0° C. for 1 h. At that time, 1 M HCl (aq.) was slowly added and the biphasic mixture was extracted with EtOAc (3×). The combined organic layers were washed sequentially with NaHCO₃ (aq.) and brine, dried over Na₂SO₄, filtered and concentrated to afford the ketone (8.0 g) as a tan solid.

To a slurry of methyltriphenylphosphonium bromide (24 g, 68 mmol) in THF (150 mL) was added dropwise a solution of n-BuLi (1.6 M in hexanes, 42.3 mL, 68 mmol). The mixture was stirred at RT for 1 h then cooled to 0° C. A solution of the ketone from above (8.0 g, 34 mmol) in THF (150 mL) was added slowly via addition funnel to the mixture. Once the addition was complete, the mixture was warmed to RT and stirred. After 16 h at RT, water was added and the aqueous layer was extracted with EtOAc (3×). The combined organic layers were washed with brine, dried over Na₂SO₄, filtered and concentrated. The crude product was purified via flash chromatography (SiO₂: gradient elution, 100:0 to 60:40 hexanes:EtOAc) to afford the styrene (6.4 g, 80% for 2 steps) as an off white solid.

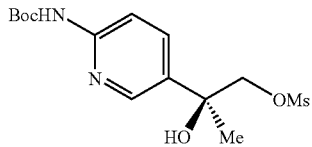 [SMILES: CC(C)(C)OC(=O)Nc1ccc([C@](C)(O)COS(C)(=O)=O)cn1]

Step 3:

The mesylate was prepared using a similar procedure to that described in Scheme 13 step 3 except the styrene from Step 2 of this example was used.

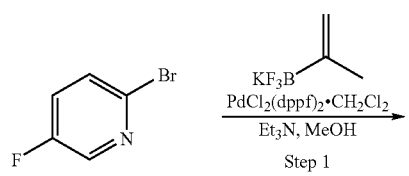

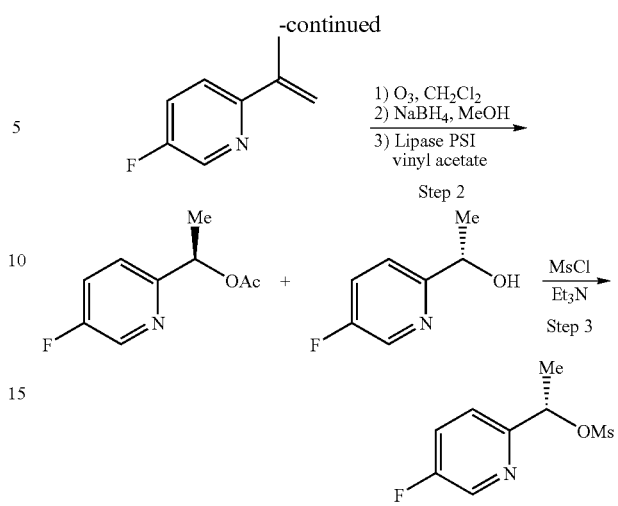

Step 1:

The styrene was prepared by using a similar method to that described in Scheme 11 step 1, except that 2-bromo-5-fluoropyridine was used.

Step 2:

To a solution of the styrene from Step 1 (4,9 g, 36 mmol) in CH₂Cl₂ (125 mL) at −78° C. was bubbled ozone until the solution turned blue (ca. 20 min). The solution was then purged with N₂. To the solution was added MeOH (50 mL) followed by the slow addition of NaBH₄ (2.0 g, 54 mmol). The resultant mixture was stirred at −78° C. for 30 min then warmed to 0° C. and stirred for an additional 2 h. After that time, 1 M HCl (aq.) was added and the mixture was stirred vigorously at RT for 10 min. The mixture was then basified with 1 N NaOH (aq.) and extracted with EtOAc (3×). The combined organic layers were washed with brine, dried over Na₂SO4, filtered and concentrated. The crude product was purified via flash chromatography (SiO₂: gradient elution, 100:0 to 50:50 hexanes:EtOAc) to afford the alcohol (3.0 g, 59%) as a light yellow oil.

To a portion of this alcohol (2.60 g, 9 18.4 mmol) in THF at 30° C. was added vinyl acetate (4.76 g, 55.3 mmol) and Lipase PS-C I (Aldrich)(1.30 g). The resultant mixture was stirred at 30° C. overnight. The mixture was then filtered through Celite and concentrated in vacuo. The crude product was purified via flash chromatography (SiO₂: gradient elution, 100:0 to 50:50 hexanes:EtOAc) to afford the acetate (1.18 g, 35%) and the alcohol (1.0 g, 38%).

Step 3:

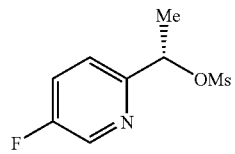

To a solution of the alcohol from step 2 (0.30 g9 2.1 mmol) in CH₂Cl₂ (20 mL) at 0° C. was added Et₃N (0.26 g9 2.4 mmol) followed by methanesulfonyl chloride (0.27 g, 2.4 mmol). The resultant solution was stirred at 0° C. for 1 h. Additional Et₃N (0.13 g, 1.3 mmol) and methanesulfonyl chloride (0.13 g, 1.2 mmol) were added and the solution was stirred at 0° C. for an additional 1 h. The solution was then diluted with CH₂Cl₂ and washed with NaHCO₃ (aq.). The organic layer was dried over Na₂SO₄ filtered and concentrated to afford the mesylate (0.45 g, 96%) as a light yellow oil that was used without further purification.

TABLE 3

The following bromide was converted to a mesylate using a similar method to that described in Scheme 13.

| Bromide | Mesylate |
|---|---|
| 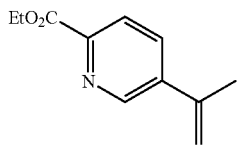 | |

Scheme 14

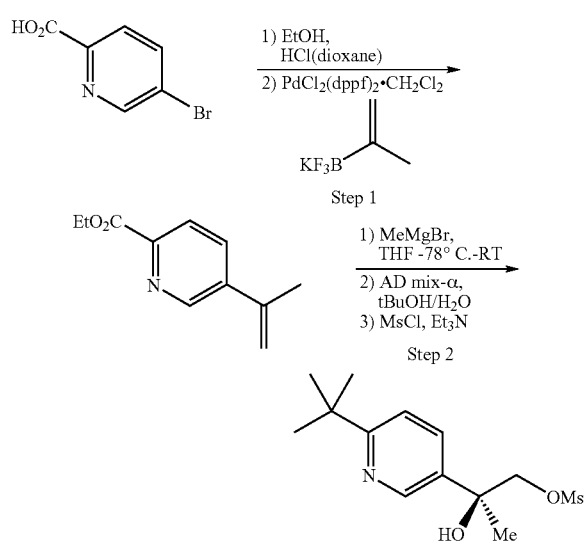

Step 1:

To a cloudy suspension of the 5-bromopicolinic acid (5.0 g, 25 mmol) in EtOH (150 mL) was added a solution of HCl in dioxane (4M, 6.8 mL, 27 mmol). The mixture was heated to reflux with stirring for 16 h. The mixture was then concentrated and the crude product was partitioned between EtOAc and NaHCO₃ (aq.). The aqueous layer was extracted with EtOAc (3×). The combined organic layers were washed with brine, dried over Na₂SO₄, filtered and concentrated to afford the ester (4.91 g) as a white crystalline solid. The ester was converted to the styrene using a similar method to that described in Scheme 11 Step 1.

Step 2:

To a solution of the ester from Step 1 (1.50 g, 7.80 mmol) in THF (25 mL) at −78° C. was added dropwise a solution of MeMgBr (3N in hexanes, 10.3 mL, 31 mmol). After the addition was complete, the solution was warmed to RT and stirred for 2 h. After that time, a solution of sodium citrate (25% w/w in water) was added and the resultant mixture was stirred vigorously at RT for 1 h. The aqueous layer was then extracted with EtOAc (3×). The combined organic layers were washed with brine, dried over Na₂SO₄, filtered and concentrated. The crude product was purified via flash chromatography (SiO₂: gradient elution, 100:0 to 75:25 hexanes:EtOAc) to afford the alcohol (1.1 g) as a clear oil, which was carried onto the mesylate using the methods described in Scheme 10 step 2.

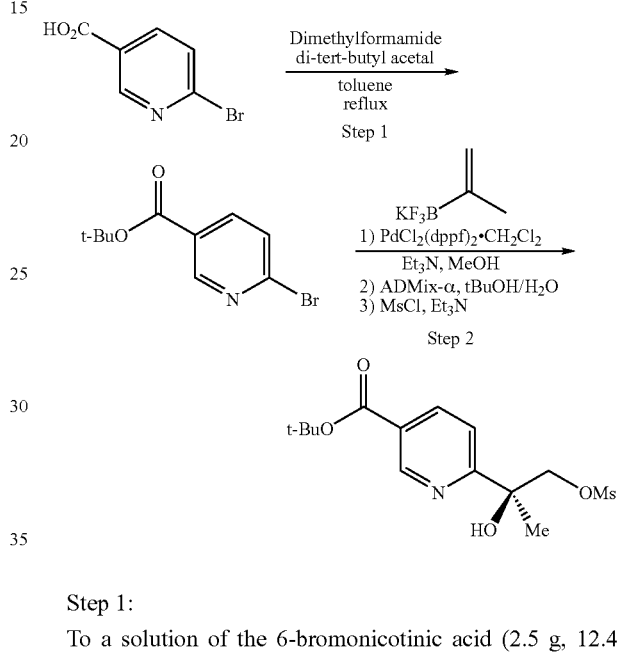

Step 1:

To a solution of the 6-bromonicotinic acid (2.5 g, 12.4 mmol) in toluene (25 mL) was added dimethylformamide di-tert-buatylcetal (5.0 g, 24.8 mmol). The solution was then heated to reflux overnight. Additional dimethylformamide di-tert-butylacetal (10.0 g, 59.6 mmol) was added in two portions over 24 h with continued stirring at reflux. The solution was stirred at reflux for a total of 72 h then cooled to RT. To the solution was added sat. NaHCO₃ (aq.) and the aqueous layer was extracted with EtOAc (3×). The combined organic layers were washed with brine, dried over Na₂SO₄, filtered and concentrated. The crude product was purified via flash chromatography (SiO₂: gradient elution, 100:0 to 92:8 hexanes:EtOAc) to afford the alcohol (1.68 g, 52%).

Step 2:

The mesylate was prepared using a similar method to that described in Scheme 11 except the bromide from step 1 was used.

Scheme 16

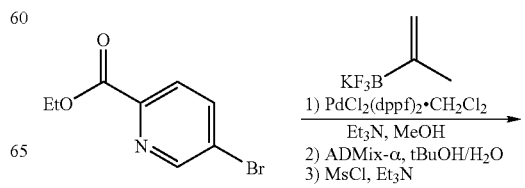

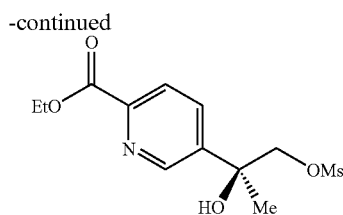

The ethyl ester from Scheme 14 step 1 was converted to the mesylate using a similar method to that described in Scheme 11.

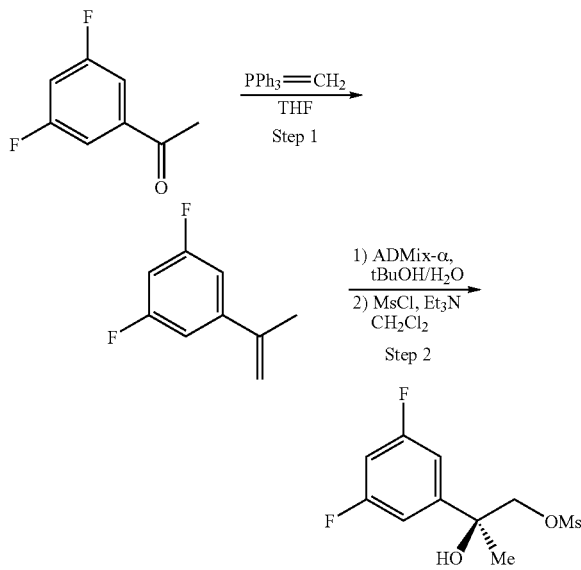

The fluorobenzyl alcohol in Scheme 17 was converted to the optically active acetate and alcohol using a similar method to that described in Scheme 20 step 2 except 1-(4-fluorophenyl)ethanol was used.

Step 1:
To a slurry of methyltriphenylphosphonium bromide (21.6 g, 57.6 mmol) in THF (100 mL) at 0° C. was added dropwise a solution of n-BuLi (1.6 M in hexanes, 36.0 mL, 57.6 mmol). The mixture was stirred at 0° C. for 30 min. After that time, a solution of 1-(3,5-difluorophenyl)ethanone (6.00 g, 38.4 mmol) in THF (100 mL) was added dropwise via addition funnel Once the addition was complete, the mixture was warmed to RT and stirred overnight. Water was then added and the aqueous layer was extracted with EtOAc (3×). The combined organic layers were washed with brine, dried over $Na_2SO_4$, filtered and concentrated. The crude product was purified via flash chromatography ($SiO_2$: gradient elution, 100:0 to 88:12 hexanes:EtOAc) to afford the styrene (4.3 g, 72%) as a clear oil.

Step 2:
The mesylate was prepared using a similar method to that described in Scheme 11 Step 2 except the styrene from Step 1 of this scheme was used.

TABLE 4

The following ketone/styrene was converted to a mesylate using a similar method to that described in Scheme 18.

| Entry | Ketone/Styrene | Mesylate |
|---|---|---|
| 1 | ![F,F-phenyl ketone] | ![F,F-phenyl mesylate] |
| 2 | ![F-phenyl styrene] | ![F-phenyl mesylate] |
| 3 | ![phenyl styrene] | ![phenyl mesylate] |

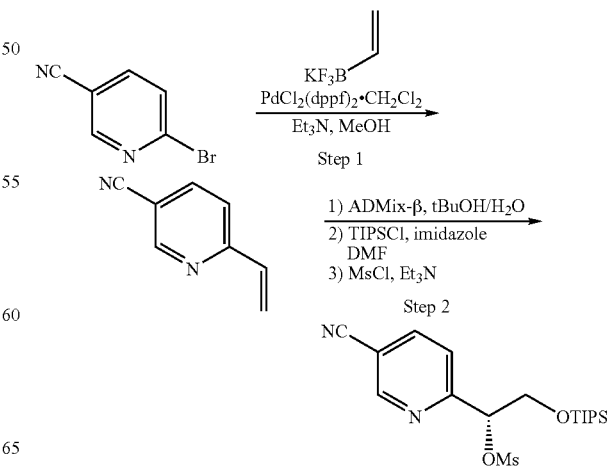

Step 1:

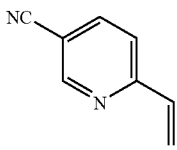

To a solution of the 2-bromo-5-cyanopyridine (6.37 g, 34.8 mmol) in MeOH (25 mL) in a pressure tube was added vinyl trifluoroborate (Aldrich) (5.60 g, 41.8 mmol). The resultant slurry was degassed by bubbling $N_2$ through the solvent for 10 min. To this slurry was added $PdCl_2(dppf)_2 \cdot CH_2Cl_2$ (1.14 g, 1.40 mmol) and $Et_3N$ (3.51 g, 34.8 mmol). The pressure tube was sealed and the mixture was heated to 80° C. with stirring for 8 h. The mixture was then cooled to RT, transferred to a round bottom flask and concentrated in vacuo. The residue was partitioned between water and EtOAc. The aqueous layer was extracted with EtOAc (3×). The combined organic layers were washed with brine, dried over $Na_2SO_4$, filtered and concentrated. The crude product was purified via flash chromatography ($SiO_2$: gradient elution, 100:0 to 80:20 hexanes: EtOAc) to afford the styrene (4.50 g, 99%).

Step 2:

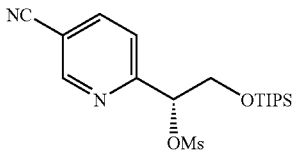

To a biphasic mixture of the styrene from Step 1 (4.50 g, 34.5 mmol) in 1:1 tert-butanol/water (150 mL) was added AD mix β (Aldrich) (48 g) and methane sulfonamide (3.3 g, 34.5 mmol). The mixture was stirred vigorously at RT for 24 h. After that time, $Na_2SO_3$ (50 g) was added and the mixture was stirred at RT for 1 h. The mixture was then diluted with 2-propanol and filtered through filter paper. The organic layer was separated, dried over $Na_2SO_4$, filtered and concentrated. The crude product was purified via flash chromatography ($SiO_2$: gradient elution, 100:0 to 95:5 $CH_2Cl_2$: MeOH) to afford the diol (4.40 g, 78%).

To a portion of the diol (1.17 g, 7.10 mmol) in DMF (10 mL) was added triisopropylsilyl chloride (1.37 g, 7.1 mmol) and imidazole (1.21 g, 17.8 mmol). The resultant solution was stirred at RT for 24 h. After that time, the solution was diluted with $Et_2O$ and washed with water (2×). The organic layer was dried over $Na_2SO_4$, filtered and concentrated. The crude product was purified via flash chromatography ($SiO_2$: gradient elution, 100:0 to 85:15 hexanes:EtOAc) to afford the silyl ether (1.60 g, 70%) as a white crystalline solid. To a solution of the ether (1.60 g) in $CH_2Cl_2$ (25 mL) was added $Et_3N$ (0.758 g, 7.50 mmol) followed by methanesulfonyl chloride (0.600 g, 5.20 mmol). After stirring at RT for 3 h, the solution was diluted with $CH_2Cl_2$ and washed with $NaHCO_3$ (aq.). The aqueous layer was back extracted with $CH_2Cl_2$ (2×). The combined organic layers were dried over $Na_2SO_4$, filtered and concentrated. The crude product was purified via flash chromatography ($SiO_2$: gradient elution, 100:0 to 75:25 hexanes: EtOAc) to afford the mesylate (1.34 g, 67%) as a mixture of enantiomers (ca 6:1 with enantiomer pictured above the major).

Scheme 20

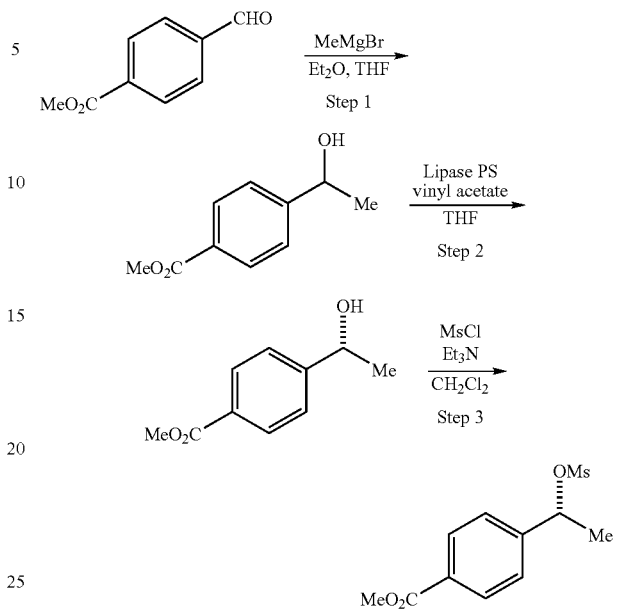

Step 1:

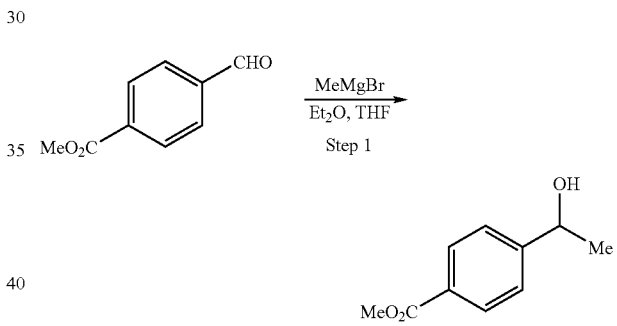

A solution of methyl, 4-formylbenzoate (8 g, 48.7 mmol, 1 eq) in THF (150 mL) was cooled to −78° C. Methyl magnesium bromide (3M in $Et_2O$ 16.2 mL, 48.7 mmol, 1 eq) was added dropwise to the solution over 15 min. The resulting mixture was stirred 16h, allowing it to warm to room temperature. Upon quenching the reaction with saturated $NH_4Cl$, the organic layer was removed, washed with saturated $NH_4Cl$, dried over anhydrous $MgSO_4$, filtered and evaporated to afford a crude yellow oil which was subjected to silica gel chromatography (0% to 50% EtOAc in hexanes) to afford the desired product as a free-flowing pale yellow oil.

Step 2:

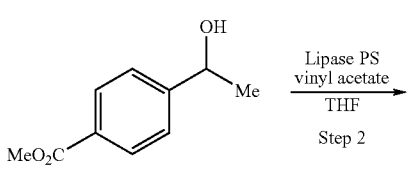

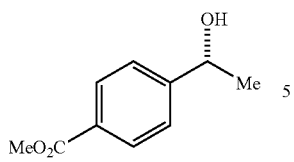

The racemic alcohol prepared in Step 1 (1.8 g, 10.0 mmol, 1 eq) and vinyl acetate (2.8 mL, 30.0 mmol, 3 eq) were dissolved in THF (60 mL). Lipase PS (900 mg) was added, and the reaction heated at 30° C. for 16h. The resulting mixture was filtered through a pad of silica, and the pad was subsequently washed with 200 mL EtOAc. The combined filtrates were evaporated and the crude residue purified via silica gel chromatography (0% to 100% EtOAc in hexanes) to afford the enantiomerically pure (R) alcohol (99.7:0.3 er, Chiracel OJ column, 90:10 hexanes:IPA, 10.7 min (minor), 13.7 min (major)) (900 mg).

Step 3:

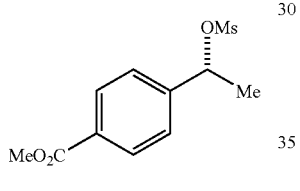

A solution of the enantiopure alcohol described in Step 2 (900 mg, 4.99 mmol, 1 eq) and Et$_3$N (0.84 mL, 5.99 mmol, 1.2 eq) in CH$_2$Cl$_2$ (20 mL) was cooled to 0° C. and treated with MsCl (0.43 mL, 5.49 mmol, 1.1 eq). After stirring 30 min at 0° C. and 30 min at r.t., the reaction was partitioned with slightly acidified brine. The organic layer was removed and washed with saturated Na$_2$CO$_3$ and brine, dried over anhydrous MgSO$_4$, filtered and evaporated to afford the product as a white crystalline solid (1 g) that contained ~13% of unconverted alcohol. This material was used without further purification.

Scheme 21

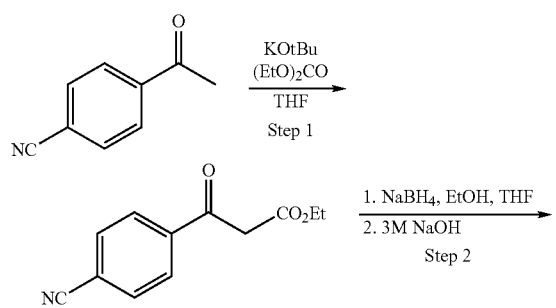

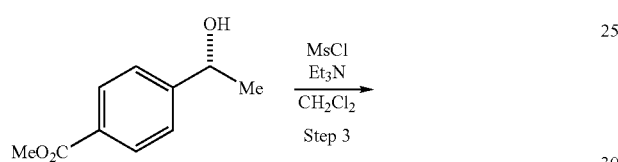

Step 1:


Potassium tert-butoxide (23.7 g, 211.2 mmol, 2 eq) was suspended in THF (100 mL) with stirring. A solution of 4-cyanoacetophenone (15.4 g, 106.1 mmol, 1 eq) and diethylcarbonate (19.6 mL, 161.7 mmol, 1.5 eq) in THF (50 mL) was added dropwise with stirring to the potassium tert-butoxide suspension. The suspension was stirred for 16h, during which time a large amount of precipitate formed. An additional amount of THF (250 mL) was added and the reaction stirred for 24h more. The resulting suspension was poured into a stirred solution of ice and aqueous HCl. The quenched reaction was partitioned with EtOAc, the organic layer was removed, and the aqueous layer was extracted twice more with EtOAc. The combined organic extracts were washed twice with brine, dried over anhydrous MgSO$_4$, filtered, and evaporated to afford a dark red solid. Purification via silica gel chromatography (10% to 90% EtOAc in hexanes) afforded the desired ketoester as a yellow solid (14.7g).

Step 2:

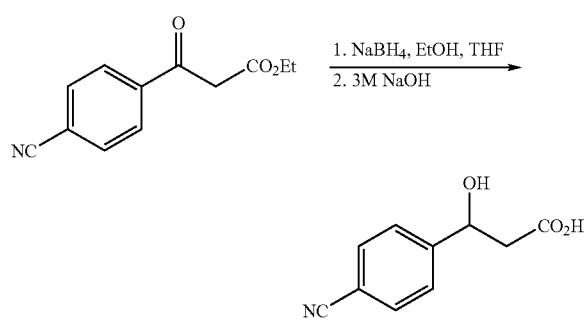

The ketoester prepared in Step 1 (10.2 g, 47.0 mmol, 1 eq) was dissolved in a mixture of ethanol (77 mL) and THF (128 mL) and treated with slow addition of NaSH$_4$ (890 mg, 23.5 mmol, 0.5 eq). After stirring for 2 h, a second portion of NaBH$_4$ (890 mg, 23.5 mmol, 0.5 eq) was added and stirred for an additional 2 h. The mixture was then carefully acidified with 3N HCl and stirred for 30 min. The solution was then adjusted to pH 14 with 3M NaOH and stirred for 1 h. The solution of hydrolyzed ester was acidified to pH 1 with conc. HCl, water was added, and the organic layer was removed. The aqueous layer was then extracted twice with EtOAc. The combined organic extracts were washed three times with brine, dried over MgSO4, filtered and evaporated to afford the crude hydroxy acid as a pale orange oil that was used without further purification (9.1 g).

Step 3:

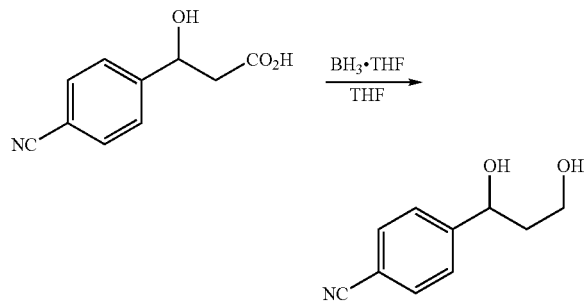

The hydroxy acid prepared in Step 2 (9 g, 47.1 mmol, 1 eq) was dissolved in THF (100 mL) and cooled to 0° C. A solution of BH$_3$.THF (1M in THF, 57 mL, 56.5 mmol, 1.2 eq) was added dropwise with stirring over 30 min. After stirring for 30 min. the reaction was allowed to warm to room temperature and was stirred for 16h. The solution was again cooled to 0° C. and treated with water then 3N NaOH The quenched reaction was partitioned between EtOAc and diluted brine. Removal of the organic layer was followed by extraction of the aqueous layer with EtOAc. The combined organic extracts were washed with brine, dried over anhydrous Na$_2$SO$_4$, filtered, and evaporated to afford a yellow oil which was subjected to silica gel chromatography (05 to 20% MeOH in CH$_2$Cl$_2$) to furnish the desired diol as a free-flowing yellow oil (5.7 g).

Step 4:

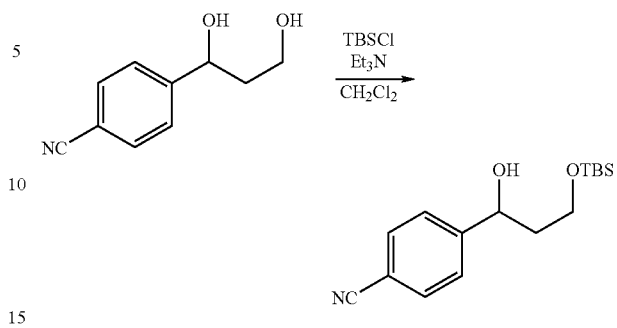

A solution of the diol (232 mg, 1.31 mmol 1 eq) in DMF (2 mL) was cooled to 0° C. TBSCl (217 mg, 1.44 mmol, 1.1 eq) and imidazole (134 mg, 1.97 mmol, 1.5 eq) were added and the reaction was stirred 16h, allowing it to warm to room temperature. The completed reaction was partitioned between CH$_2$Cl$_2$ and brine. The aqueous layer was extracted again with CH$_2$Cl$_2$. The combined organic extracts were evaporated and purified via silica gel chromatography (0% to 100% EtOAc in hexanes) to provide the mono-TBS protected diol as a clear viscous oil (243 mg).

Step 5:

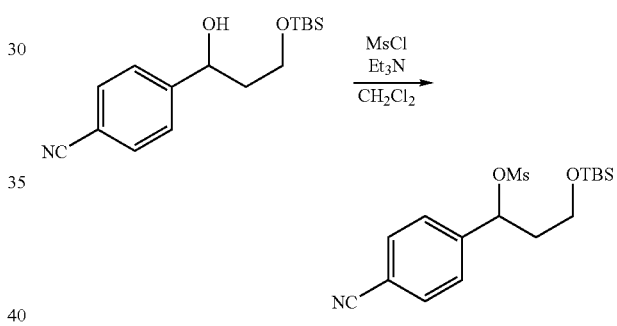

A solution of the silyl ether (263 mg, 0.90 mmol, 1 eq) and Et$_3$N (0.19 mL, 1.35 mmol, 1.5 eq) in CH$_2$Cl$_2$ (2 mL) was treated with MsCl (0.08 mL, 0.99 mmol, 1.1 eq) and stirred for 1 h. The reaction was then loaded directly onto a silica gel column and purified (0% to 80% EtOAc in hexanes) to afford the desired mesylate as a clear film (51 mg).

Scheme 22

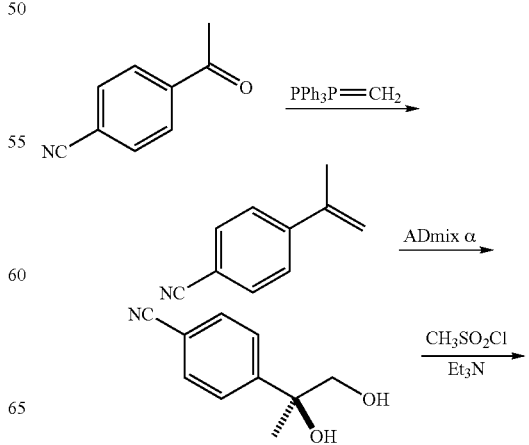

Step 3

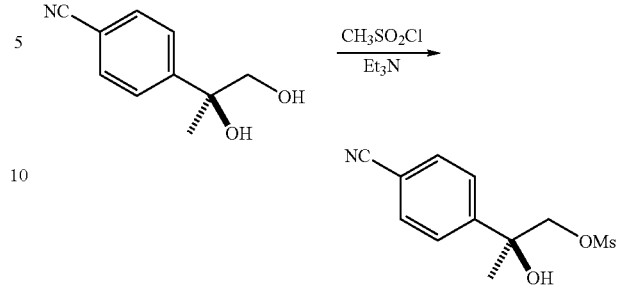

Step 1

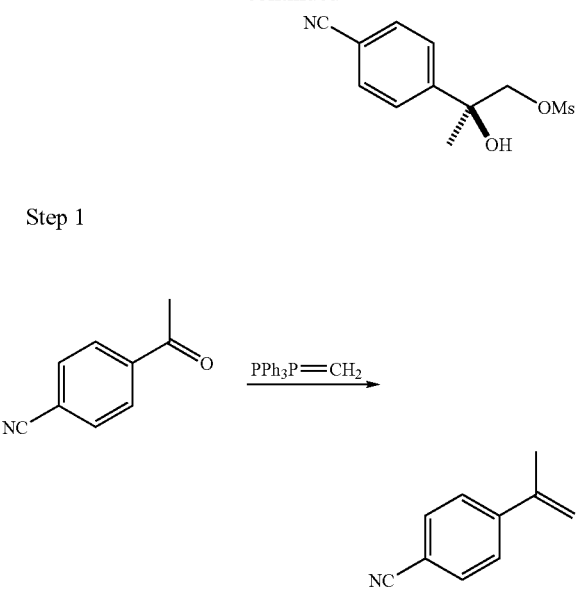

Methyl triphenylphosponium bromide (35.4 g, 99 mmol) was suspended in THF (300 mL) at 0° C. n-Butyllithium (36.3 mL of a 2.5 M solution in hexanes) was added dropwise at 0° C. The yellow solution was stirred at 0° C. (1 h). The ketone (12 g, 82.7 mmol) was added, and the resulting slurry was stirred at 25° C. (3.5 h). The mixture was quenched with water, and the mixture was extracted with EtOAc. The combined EtOAc layers were concentrated. The residue was partitioned between hexanes and water. The aqueous layer was extracted with hexanes. The combined hexane layers were washed with brine and dried (MgSO$_4$). The mixture was filtered and concentrated. The residue was purified via gradient flash chromatography (1/1 hexanes/CH$_2$Cl$_2$, SiO$_2$) which furnished 9.5 g (80%) of the alkene as a colorless oil.

Step 2

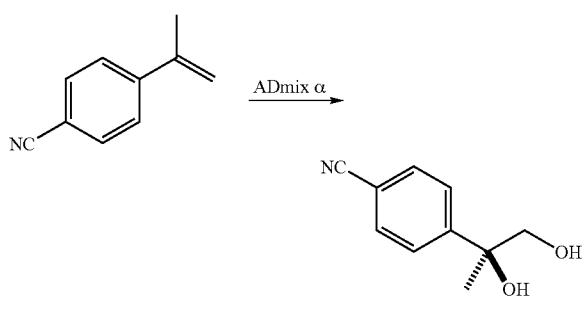

The alkene (9.5 g, 66.4 mmol) and AD mix α (76 g) were taken up in tert-butanol/water (1/1, 360 mL), and the mixture was stirred at 25° C. (4 days). The mixture was cooled to 0° C., and water (150 mL) was added. Solid Na$_2$SO$_3$ (75g) was added slowly to the mixture at 0° C. The solution was stirred at 0° C. (1 h) and then at 25° C. (1 h). The mixture was extracted with EtOAc. The combined organic layers were washed with brine and dried (MgSO$_4$). The solution was filtered and concentrated to give 11.7 g (99%) of the diol as a thick gum.

The diol (11.7 g, 66 mmol) and Et$_3$N (8 g) were taken up in CH$_2$Cl$_2$ at 0° C. Methanesulfonyl chloride (7.2 g, 63 mmol) in CH$_2$Cl$_2$ (20 mL) was added dropwise at 0° C. The solution was stirred at 0° C. for 15 minutes. The solution was washed with sat. NaHCO$_{3(aq.)}$. The aqueous layer was extracted with CH$_2$Cl$_2$. The combined organic layers were dried (MgSO$_4$), filtered, and concentrated. The mesylate was recrystallized from CH$_2$Cl$_2$.

Scheme 22A

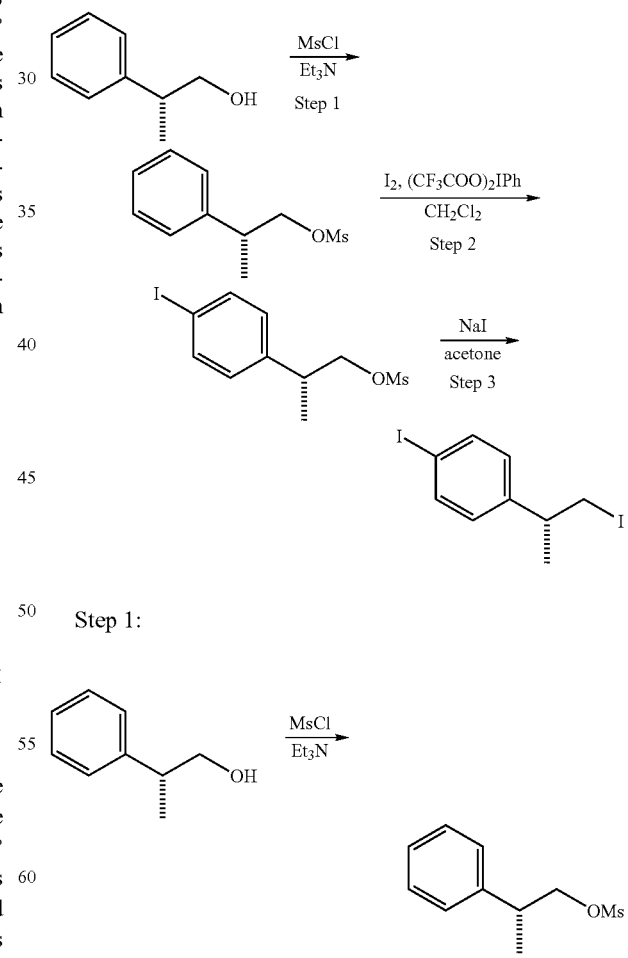

Step 1:

A solution of (R)-2-phenyl-propan-1-ol (1 g, 7.35 mmol) and triethylamine (1.2 mL, 8.82 mmol) in CH$_2$Cl$_2$ was cooled to 0° C. Methanesulfonyl chloride (0.63 mL, 8.1 mmol) was added dropwise and the solution was subsequently warmed to room temperature with stirring. After 2h, the reaction was partitioned between CH₂Cl₂ and 1N NaOH (aq). The organic layer was removed and the aqueous layer was extracted with CH₂Cl₂. The combined organic layers were dried over anhydrous MgSO₄, filtered, and evaporated to afford the mesylate as a yellow oil that was used without further purification (1.66 g).

Step 2:

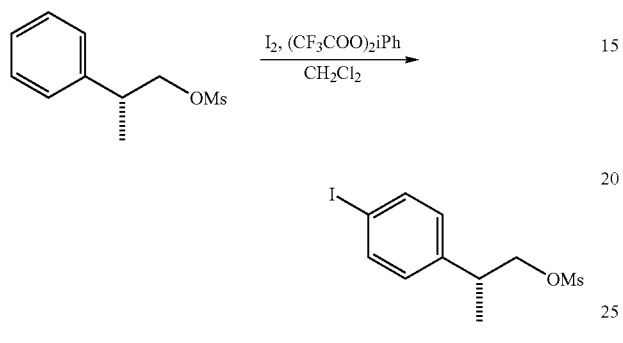

A solution of the mesylate prepared in Step 1 (1.66 g, 7.76 mmol) in CH₂Cl₂ was treated with iodine (985 mg, 3.88 mmol) and bis(trifluoroacetoxy)iodobenzene (2 g, 4.66 mmol). After stirring for 16h in the dark, the reaction was poured into a stirred solution of NaHCO₃ (2 g) and NaHSO₃ (700 mg) in water. Upon stirring for 0.5h, the organic layer was removed and the aqueous layer was extracted with CH₂Cl₂. The combined organic layers were dried over anhydrous MgSO₄, filtered, and evaporated to afford a crude oil which was subjected to silica gel chromatography (gradient elution, 0% to 25% EtOAc in hexanes) to afford the aryl iodide as a colorless oil (1.73 g).

Step 3:

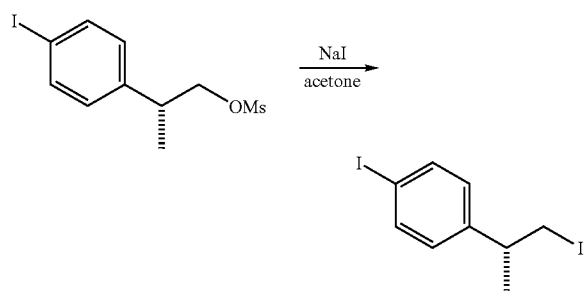

The aryl iodide prepared in Step 2 (1.73 g, 5.09 mmol) and sodium iodide (7.6 g, 50 mmol) were taken up in acetone (80 mL) and heated at reflux 16h. The reaction was partitioned between Et₂O and water and the organic layer was removed. The aqueous layer was extracted with Et₂O. After combining the ether layers, they were washed with 10% Na₂S₂O₃, dried over anhydrous MgSO₄, filtered, and evaporated to afford the diiodide as a yellow oil that was used without further purification (1.86 g).

Scheme 22B

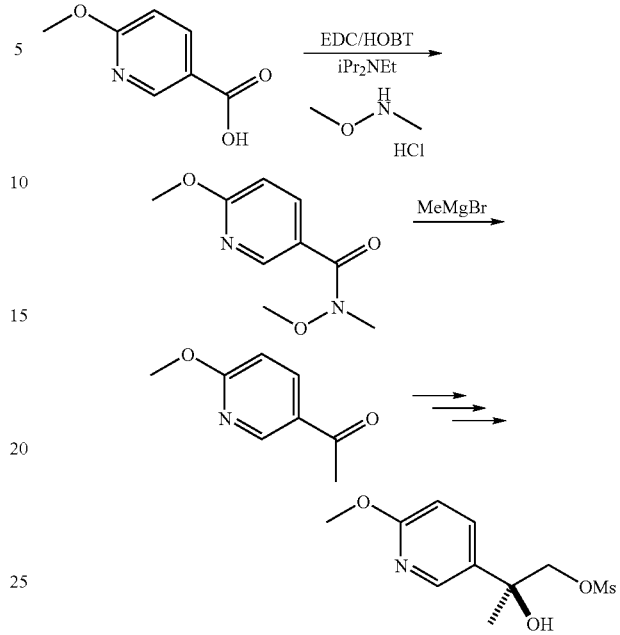

Step 1

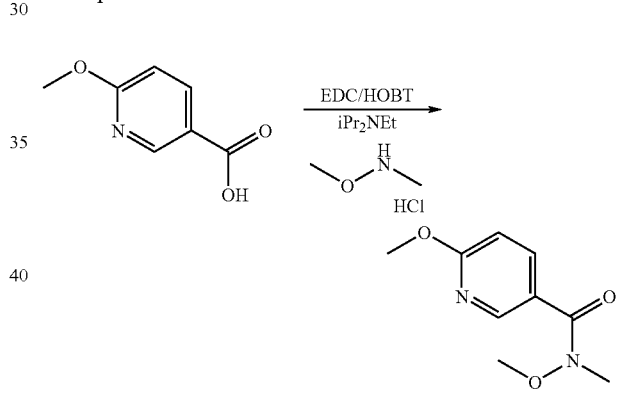

The acid (10 g, 65 mmol), EDOC (15 g), HOBT (10.6 g), and iPr₂NEt (25 g), and N,O-dimethyl-hydroxylamine hydrochloride (7.65 g) were taken up in CH₃CN and stirred at 25° C. for 18 h. The solution was partitioned between EtOAc and 1 N NaOH ₍aq₎. The aqueous layer was extracted with EtOAc. The combined organic layers were washed with brine and dried (MgSO₄). Filtration and concentration gave a yellow oil. The residue was purified via gradient flash chromatography (20-40% EtOAc in hexanes, SiO₂) which gave 10.4 g (61%) of the amide as a yellow oil.

Step 2

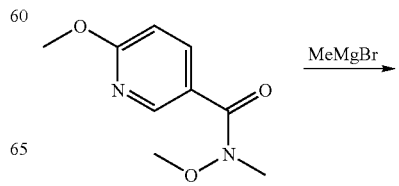

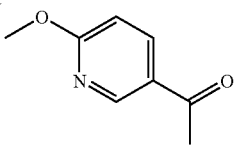

The amide (10.4 g, 53 mmol) was taken up in THF (100 mL) and cooled to 0° C. Methylmagnesium bromide (26.5 mL of a 3 M solution in Et$_2$O) was added dropwise at 0° C. After the addition, the reaction was stirred at 0° C. for 1 h. The solution was quenched slowly with 1 M HCl (aq.). The mixture was extracted with EtOAc. The combined organic layers were washed with brine and dried (MgSO$_4$). Filtration and concentration provided 7.8 g (97%) of the ketone as a colorless solid.

The ketone from Step 2 of Scheme 22B was transformed into the mesylate according to the procedures outlined previously in Scheme 22.

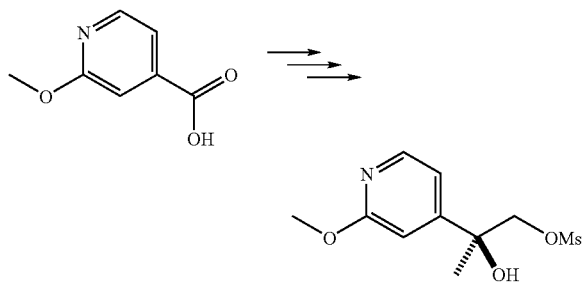

Scheme 22C

The mesylate in Scheme 22C was prepared in a similar fashion as that shown in Scheme 22B using the appropriately substituted carboxylic acid.

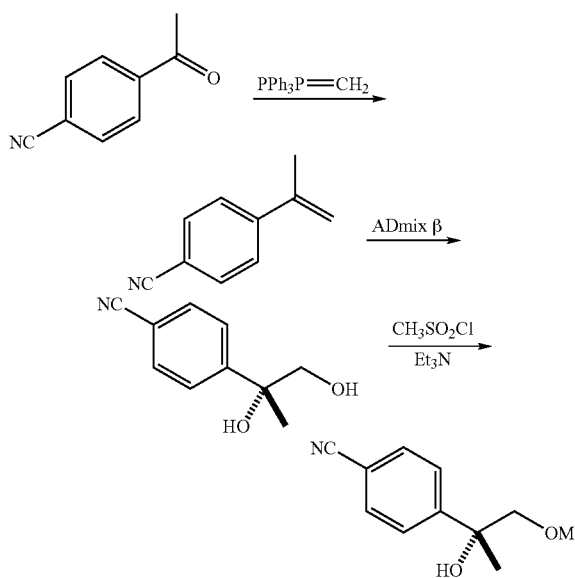

Scheme 22D

The mesylate in Scheme 22D was prepared in a similar fashion as that shown in Scheme 22 using the appropriate antipode of the AD mix reagent.

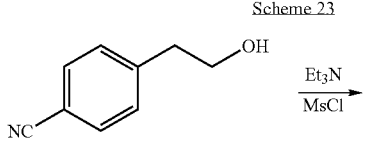

Scheme 23

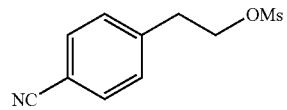

4-(2-Hydroxy-ethyl)-benzonitrile (5 g, 34 mmol) and Et$_3$N (4.5 g) were taken up in DCM and cooled to 0° C. Methanesulfonyl chloride (4.1 g) was added dropwise to the solution at 0° C. The solution was stirred at 0° C for 30 minutes. The solution was diluted with DCM and washed with sat. NaHCO$_{3(aq.)}$. The aqueous layer was extracted with DCM. The combined organic layers were dried (MgSO$_4$). Filtration and concentration gave a yellow solid. The residue was recrystallized from diethyl ether which gave 6.92 g (90%) of the mesylate as a white solid.

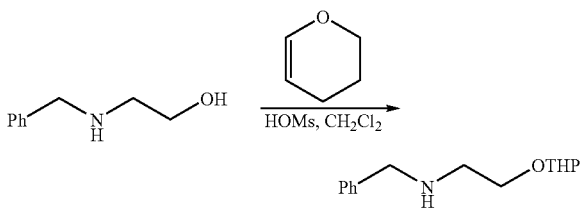

Scheme 24

2-Benzylamino-ethanol (18.8 mL, 132.3 mmol, 1 eq) was slowly added to a solution of methanesulfonic acid (9 mL, 139.4 mmol, 1.05 eq) in CH$_2$Cl$_2$ (325 mL) while stirring with a reflux condenser attached. The resulting mixture was stirred for 5 min, followed by slow addition of 3,4-dihydro-2H-pyran (21 mL, 230.2 mmol, 1.7 eq). After 2 h, the reaction was slowly poured into a stirred 10% aqueous K$_2$CO$_3$ solution (400 mL). The organic layer was removed, dried over anhydrous Na$_2$SO$_4$, filtered and evaporated to afford a pale orange oil that was subjected to short path distillation to afford 1-1 (24 9) as a clear oil (~1 mmHg, 132° C.).

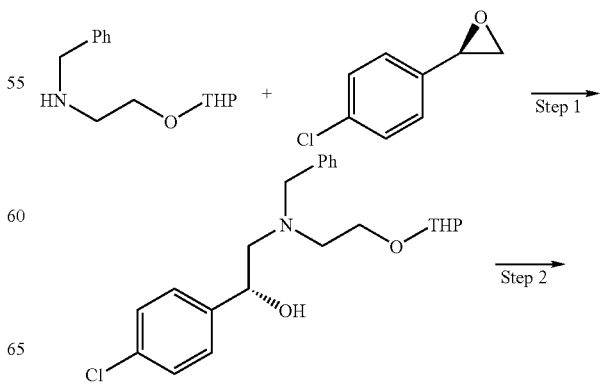

Scheme 25

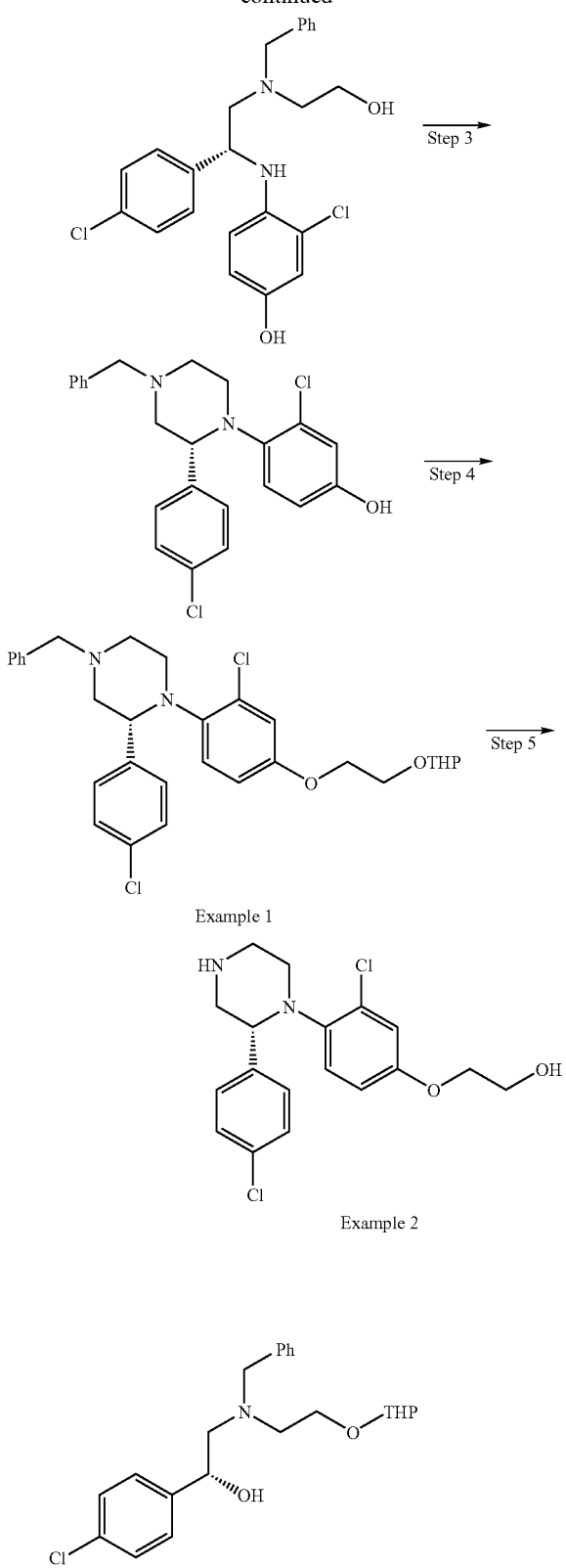

Example 1

Example 2

Step 1 To the amine (200 g, 0.86 mol-synthesis described below in Scheme 24) was added the epoxide (140 g, 0,86 mol-synthesis described below in Scheme 1). Heated the reaction neat to 100° C. and stirred overnight. Cooled to room temperature and purified directly by silica gel chromatography (2-8% MeQH/CH$_2$Cl$_2$) to provide the alcohol (310 g, 0.79 mmol).

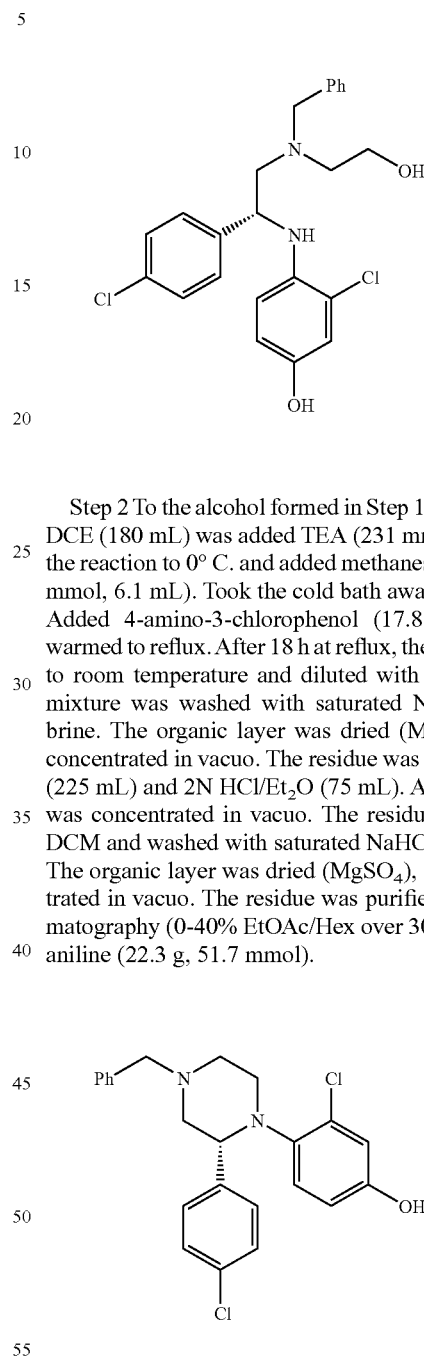

Step 2 To the alcohol formed in Step 1 (25.8 g, 66 mmol) in DCE (180 mL) was added TEA (231 mmol, 32 mL). Cooled the reaction to 0° C. and added methanesulfonyl chloride (79 mmol, 6.1 mL). Took the cold bath away and stirred for 2 h. Added 4-amino-3-chlorophenol (17.8 g, 99 mmol) and warmed to reflux. After 18 h at reflux, the reaction was cooled to room temperature and diluted with DCM. The reaction mixture was washed with saturated NaHCO$_3$, water, and brine. The organic layer was dried (MgSO$_4$), filtered, and concentrated in vacuo. The residue was taken up into MeOH (225 mL) and 2N HCl/Et$_2$O (75 mL). After 2 h, the reaction was concentrated in vacuo. The residue was taken up into DCM and washed with saturated NaHCO$_3$, water and brine. The organic layer was dried (MgSO$_4$), filtered, and concentrated in vacuo. The residue was purified by silica gel chromatography (0-40% EtOAc/Hex over 30 min) to provide the aniline (22.3 g, 51.7 mmol).

Step 3 To the aniline from Step 2 (22.3 g, 52 mmol) in DCM (200 mL) was added TEA (18 mL, 129 mmol). The reaction was cooled to 0° C. and dibromotriphenylphosphine (32.7 g, 78 mmol) was added. The cold bath was taken away and the reaction was stirred for 3 h. The reaction was diluted with DCM and washed with saturated NaHCO$_3$, water, and brine. The organic layer was dried (MgSO$_4$), filtered, and concentrated in vacuo. The residue was purified by silica gel chromatography (0-40% EtOAc/Hex over 40 minutes) to provide the piperazine (15 g, 36 mmol).

Example 1

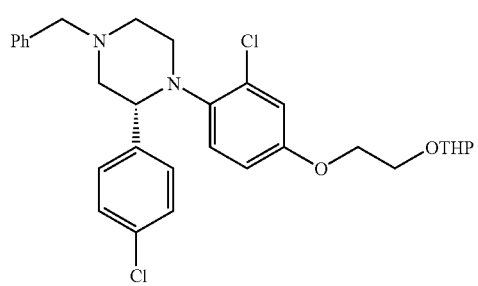

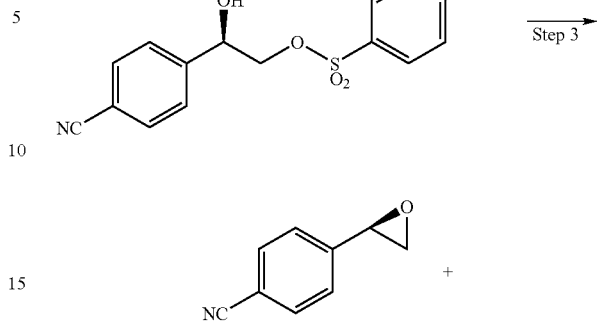

Step 4 To the piperazine from Step 3 (4.30 g, 10.5 mmol) in DMF (35 mL) was added K₂CO₃ (3.63 g, 26.3 mmol) and 2-(2-bromoethoxy)tetrahydro-2H-pyran (available from Aldrich Chemical Co.) (2.74 g, 13.1 mmol). Warmed the reaction to 100° C. and stirred for 18 h. Cooled the reaction to room temperature and added water. Extracted with EtOAc. Combined the organic layers and washed with water and brine. Dried (MgSo₄), filtered, and concentrated in vacuo. Purified the residue by column chromatography (0-40% EtOAc/Hex over 30 minutes) to provide Example 1 (4.19 g, 7.73 mmol).

Example 2

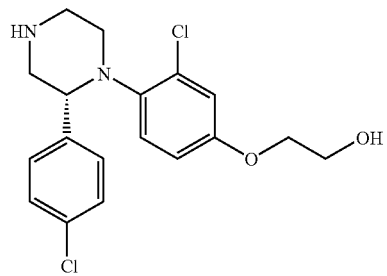

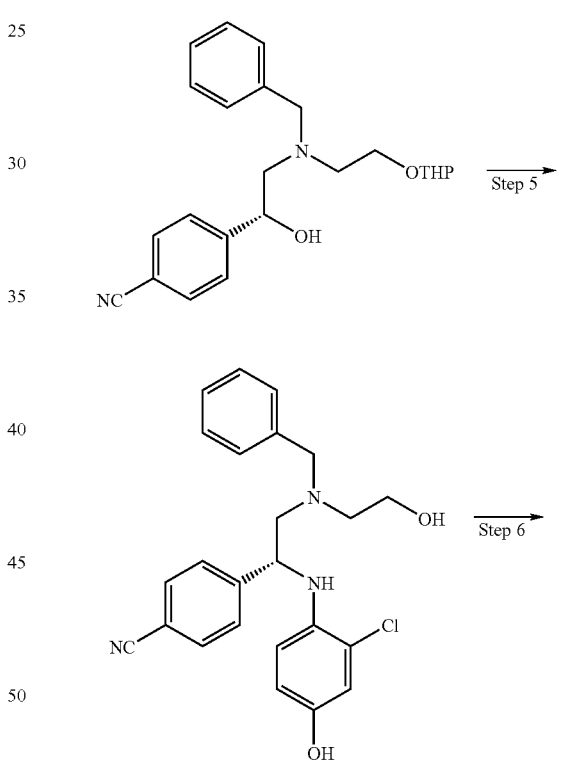

Step 5 To Example 1 (0.6 g, 1.1 mmol) in DCM (5 mL) was added 1-chloroethylchloroformate (0.2 mL, 1.9 mmol) and proton sponge (0.05 g, 0.22 mmol). Stirred at room temperature for 2.5 h and concentrated in vacuo. Added MeOH (5 mL) and warmed to reflux. Stirred for 1 h and concentrated in vacuo. The residue was taken up into DCM and washed with saturated NaHCO₃, water, and brine. Dried (MgSO₄), filtered, and concentrated in vacuo. The residue was purified by silica gel chromatography (5-10% MeOH/DCM over 20 minutes) to provide Example 2 (0.37 g, 1.0 mmol).

Scheme 25.1

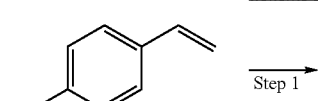

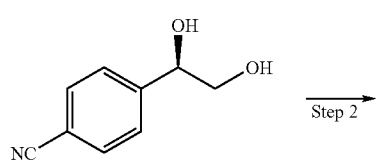

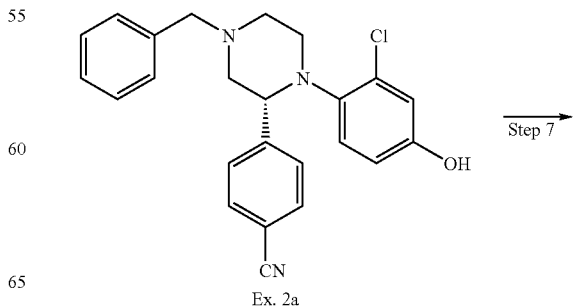

Ex. 2a

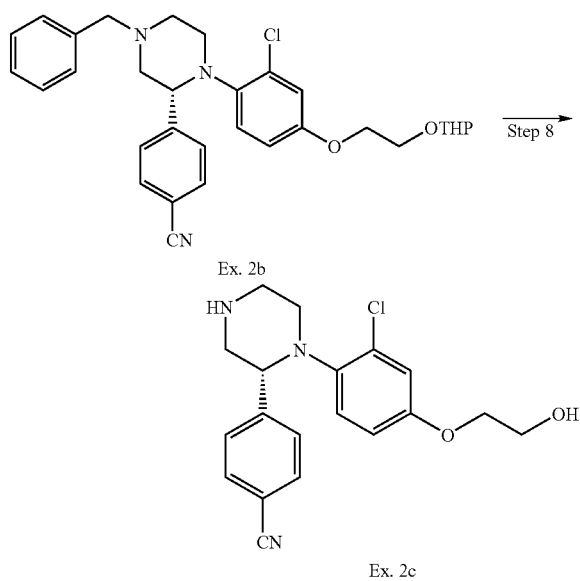

Ex. 2b

Ex. 2c chromatography (0-25% EtOAc/Hex over 30 minutes) to provide the epoxide (8.2 g, 56 mmol).

Step 4 To the epoxide prepared in step 3 (8.2 g, 56 mmol) was added the N-benzyl amine prepared in scheme 24 (14.5 g, 62 mmol). Warmed the reaction to 100° C. and stirred for 24 h. Cooled the reaction to room temperature and purified directly by silica gel chromatography (0-5% MeOH/DCM over 30 minutes) to provide the alcohol (19.4 g, 51 mmol).

Step 5 The alcohol prepared in step 4 was subjected to the conditions in step 2 of scheme 25 to provide the diamine product.

Step 6 The diamine prepared in step 5 was subjected to the conditions in step 3 of scheme 25 to provide the piperazine Ex. 2a.

Step 7 Ex. 2a was subjected to the conditions found in step 4 of scheme 25 to provide Ex. 2b.

Step 8 Ex. 2b prepared in step 7 was subjected to the conditions found in step 5 of scheme 25 to provide Ex. 2c.

Using the requisite styrene oxide and a procedure similar to that described in Scheme 25, the following piperazine cores were prepared,

TABLE 4.1

| styrene oxide | Example Number | piperazine core |
|---|---|---|
| ![styrene oxide structure] Prepared in Scheme 36 | 28 | ![piperazine core structure] |

Step 1 To 4-cyanostyrene (12.5 g, 97 mmol) in tert-butanol/water 1:1 (968 mL) at 0° C. was added AD mix β (135 g). Allowed the cold bath to expire while stirring for 24 h. Cooled the reaction to 0° C. and added sodium sulfite (~40 g). Stirred the mixture for 1 h and then extracted with EtOAc. Washed the organic layer with water and brine. Dried the organic layer (MgSO$_4$), filtered, and concentrated in vacuo. Purified the crude oil by silica gel chromatography (0-5% MeOH/EtOAc over 30 minutes) to provide the diol (11.9 g).

Step 2 To the diol prepared in step 1 (11.9 g, 73 mmol) in DCM (350 mL) at room temperature was added TEA (10.2 mL), dibutyloxostannane (0.36 g, 1.5 mmol), and p-toluenesulfonyl chloride (13.9 g, 73 mmol). Stirred for 24 h allowing the cold bath to expire. Washed the reaction with 1 N HCl, water, and brine Dried (MgSO$_4$) the organic layer, filtered, and concentrated in vacuo to provide a white solid (21 g) that was carried on directly without further purification.

Step 3 To the tosylate prepared in step 2 (21 g, 65 mmol) in DCM (210 mL) was added 1 N NaOH (100 mL). Stirred vigorously for 3 h. Added DCM to the reaction and washed with water and brine. Dried (MgSO$_4$) the organic layer, filtered, and concentrated in vacuo. Purified the oil by silica gel Scheme 26

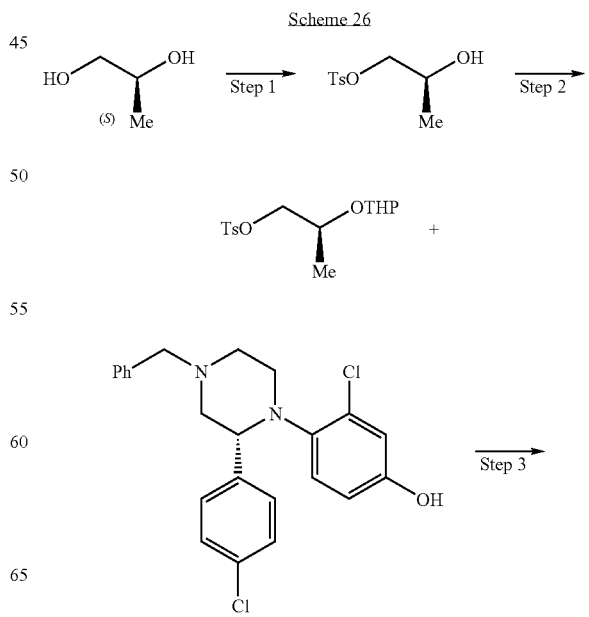

Example 3

Step 3 To the THP-protected alcohol from Step 2 (1.02 g, 2.47 mmol) in DMAF (8 mL) was added the piperazine from Step 3 Scheme Y (1.17 g, 3.71 mmol) and K₂CO₃ (0.68 g, 4.94 mmol). Warmed the reaction to 100° C. and stirred for 20 h. Cooled to room temperature and added brine. Extracted with EtOAc. Washed the organic layer with water and brine. Dried (MgSO₄), filtered, and concentrated in vacuo. Purified the residue by silica gel chromatography (0-20% EtOAc/Hex over 30 minutes then 20-30% EtOAc/Hex over 10 minutes) to provide the Example 3 (0.86 g, 1.56 mmol).

Example 4

Step 1 To (S)-propane diol (4-89 g, 64.2 mmol) in DCM (20 mL) at −20 ° C. (CO₂/ethylene glycol bath) was added TEA (11.2 mL, 80.3 mmol) followed by p-toluenesulfonyl chloride (12.3 g, 64.3 mmol) in DCM (26 mL) dropwise over 30 minutes. Allowed the cold bath to expire while stirring for 26 h. Added DCM and washed the reaction with 1N HCl, water, and brine. Dried (MgSO₄) the organic layer, filtered, and concentrated in vacuo. The residue was purified by silica gel chromatography (0-40% EtOAc/Hex over 40 minutes) to provide the tosylate (8.37 g, 36.4 mmol)

Step 4 Example 3 from Step 3 was subjected to the conditions of Step 5 in Scheme 25 to provide Example 4.

Step 2 To the tosylate from Step 1 (8.37 g, 36.4 mmol) in DCM (120 mL) at 0° C. was added 3,4-2H-dihydropyran (6.38 g, 76 mmol) and p-toluenesulfonic acid (0.69 g, 3,64 mmol). Allowed the cold bath to expire whine stirring for 19 h. Added DCM and washed with saturated NaHCO₃, water, and brine, Dried (MgSO₄) the organic layer, filter, and concentrated in vacuo. Purified the residue by silica gel chromatography (0-25% EtOAc/Hex over 35 minutes) to provide the THP-protected alcohol (7.85 g, 25 mmol).

Example 5

Example 5 was prepared in a similar manner to Example 3 except that (R)-propane dial was used instead of (S)-propane diol in Step 1 of Scheme 26.

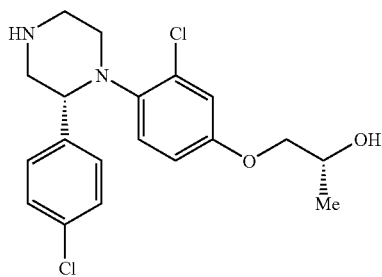

Example 6

Example 6 was prepared in a similar manner as Example 4 except that (R)-propane diol was used instead of (S)-propane diol in Step 1 of Scheme 26.

Scheme 27

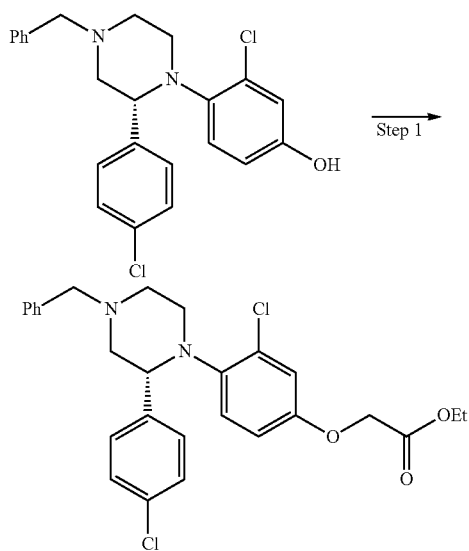

Example 7

Example 8

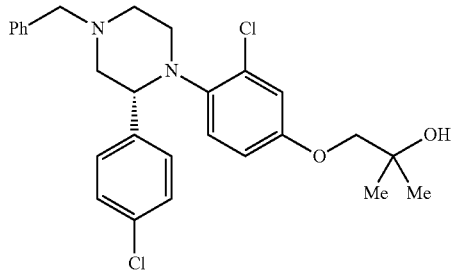

Example 9

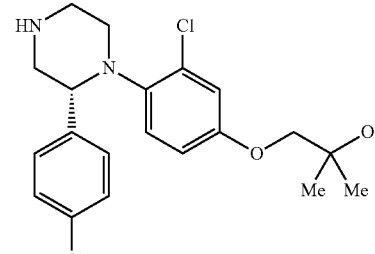

Step 1 To the piperazine prepared in Step 3 Scheme 25 (0.21 g, 0.5 mmol) in DMF (2 mL) was added ethyl bromoacetate (0.08 mL, 0.75 mmol) and potassium carbonate (0.21 g, 1.5 mmol). Warmed the reaction to 50° C. and stirred for 18 h. Cooled the reaction to room temperature and added the reaction to brine. Extracted the mixture with EtOAc. Combined the organic layers and washed with water and brine. Dried (MgSO$_4$) the organic layer, filtered, and concentrated in vacua. The residue was purifed by silica gel chromatography (25% EtOAc/Hex) to provide Example 7 (0.16 g, 0.64 mmol).

Step 2 To Example 7 (0.14 g, 0.28 mmol) in THF at —78° C. was added MeMgBr (3M in Et$_2$O, 0.38 mL, 0.84 mmol) dropwise. The cold bath was taken away and the reaction was stirred for 2h. To the reaction was added 25% sodium citrate (5 mL). The mixture was extracted with EtOAc. The organics were combined and washed with water and brine. The organic layer was dried (MgSO$_4$), filtered, and concentrated in vacuo. The residue was purified by silica gel chromatography (40% EtOAc/Hex) to provide Example 8 (0.12 g, 0.24 mmol)

Step 3 To Example 8 (1,22 g, 2.5 mmol) in DCM (8 mL) at room temperature was added proton sponge (0.11 g, 0.5 mmol) and 1-chloroethylchloroformate (0.33 mL, 3 mmol). Stirred at room temperature for 1 h and concentrated the reaction in vacuo. Added MeOH (8 mL) and stirred at reflux for 1 h. Concentrated the reaction in vacuo and added DCM. Washed the mixture with saturated NaHCO$_3$, water, and brine. Dried (MgSO$_4$) the organic layer, filtered, and concentrated in vacuo. The residue was purified by silica gel chromatography (0-10% MeOH/DCM over 25 minutes) to provide Example 9 (0.86 g, 2.2 mmol).

Scheme 28

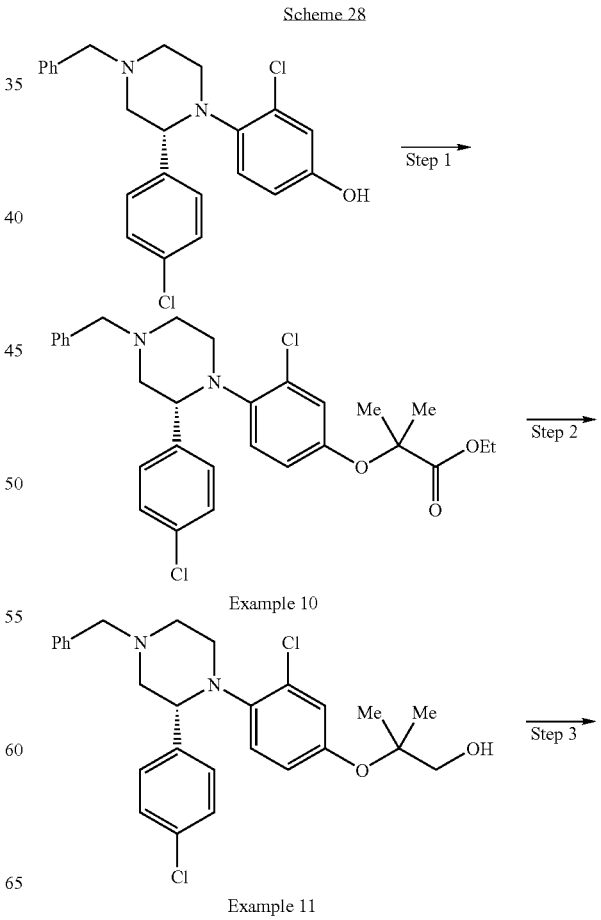

Example 10

Example 11

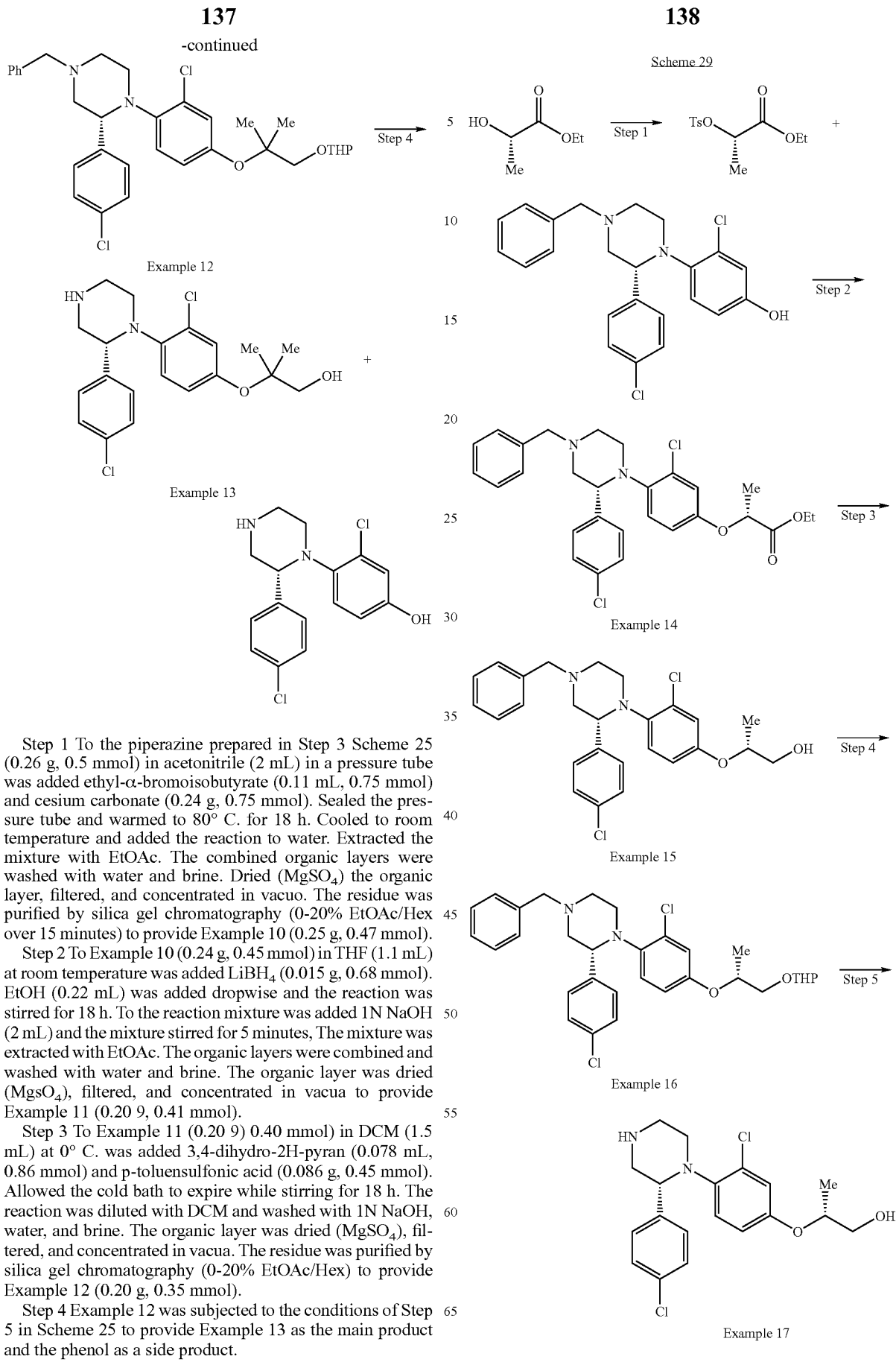

Step 1 To the piperazine prepared in Step 3 Scheme 25 (0.26 g, 0.5 mmol) in acetonitrile (2 mL) in a pressure tube was added ethyl-α-bromoisobutyrate (0.11 mL, 0.75 mmol) and cesium carbonate (0.24 g, 0.75 mmol). Sealed the pressure tube and warmed to 80° C. for 18 h. Cooled to room temperature and added the reaction to water. Extracted the mixture with EtOAc. The combined organic layers were washed with water and brine. Dried (MgSO$_4$) the organic layer, filtered, and concentrated in vacuo. The residue was purified by silica gel chromatography (0-20% EtOAc/Hex over 15 minutes) to provide Example 10 (0.25 g, 0.47 mmol).

Step 2 To Example 10 (0.24 g, 0.45 mmol) in THF (1.1 mL) at room temperature was added LiBH$_4$ (0.015 g, 0.68 mmol). EtOH (0.22 mL) was added dropwise and the reaction was stirred for 18 h. To the reaction mixture was added 1N NaOH (2 mL) and the mixture stirred for 5 minutes. The mixture was extracted with EtOAc. The organic layers were combined and washed with water and brine. The organic layer was dried (MgsO$_4$), filtered, and concentrated in vacua to provide Example 11 (0.20 9, 0.41 mmol).

Step 3 To Example 11 (0.20 9) 0.40 mmol) in DCM (1.5 mL) at 0° C. was added 3,4-dihydro-2H-pyran (0.078 mL, 0.86 mmol) and p-toluensulfonic acid (0.086 g, 0.45 mmol). Allowed the cold bath to expire while stirring for 18 h. The reaction was diluted with DCM and washed with 1N NaOH, water, and brine. The organic layer was dried (MgSO$_4$), filtered, and concentrated in vacua. The residue was purified by silica gel chromatography (0-20% EtOAc/Hex) to provide Example 12 (0.20 g, 0.35 mmol).

Step 4 Example 12 was subjected to the conditions of Step 5 in Scheme 25 to provide Example 13 as the main product and the phenol as a side product.

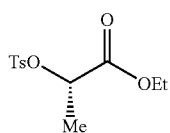

Step 1 Ethyl (8)-lactate was converted to the tosylate according to the reference *Tetrahedron*, 1985, 41) 541-546.

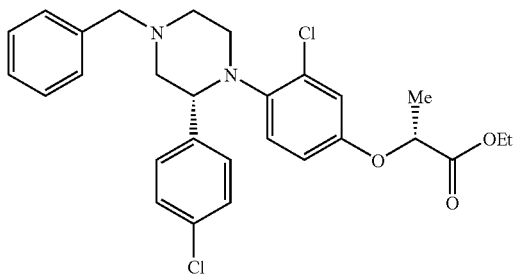

Example 14

Step 2 To the piperazine (3.0 g, 7.3 mmol) formed in Step 3 Scheme 25 in DMF (20 mL) was added the tosylate (3.0 g, 10.9 mmol) prepared in Step 1 followed by potassium carbonate (2.0 g, 14.6 mmol). Warmed the reaction to 100° C. and stirred for 18 h. Cooled the reaction to room temperature and poured the reaction into brine. Extracted with EtOAc. Combined the organics and washed with water and brine. Dried (MgSO$_4$) the organic layer, filtered, and concentrated in vacuo. The residue was purified by silica gel chromatography (0-30% EtOAc/Hex over 25 minutes) to provide Example 14 (3.6 g, 7.0 mmol).

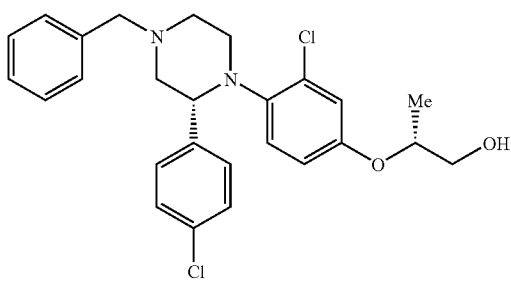

Example 15

Step 3 To Example 14 (3.6 g, 7.0 mmol) in THF (17.5 mL) was added LiBH$_4$ (0.23 g, 10.5 mmol) followed by the dropwise addition of EtOH (3.5 mL). The mixture was stirred for 1 h at room temperature. To the reaction mixture was added 1N NaOH (5 mL) and the resultant mixture was stirred for 30 minutes. The mixture was then extracted with EtOAc. The combined organic layers were washed with water and brine. The organic layer was dried (MgSO$_4$), filtered, and concentrated in vacuo. The residue was purified by silica gel chromatography (0-50% EtOAc/Hex over 25 minutes) to provide Example 15 (2.5 g, 5.3 mmol).

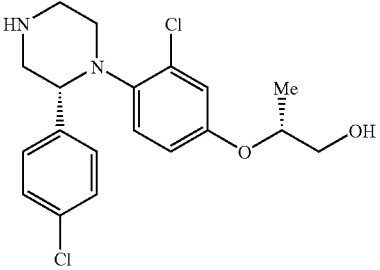

Example 16

Step 4 Example 15 was subjected to the same conditions as in Step 3 Scheme 28 to provide Example 16.

Example 17

Step 5 Example 16 was subjected to the same conditions as in Step 5 Scheme 25 to provide Example 17.

Example 18

Example 18 was prepared in a similar manner as Example 6 except that the piperazine formed in step 6 of scheme 50 was used instead of the piperazine found in step 3 of scheme 25.

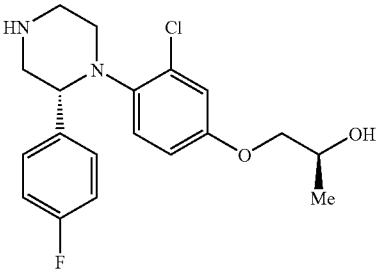

Example 19

Example 19 was prepared in a similar manner as Example 4 except that the piperazine formed in step 6 of scheme 50 was used instead of the piperazine found in step 3 of scheme 25.

Scheme 30
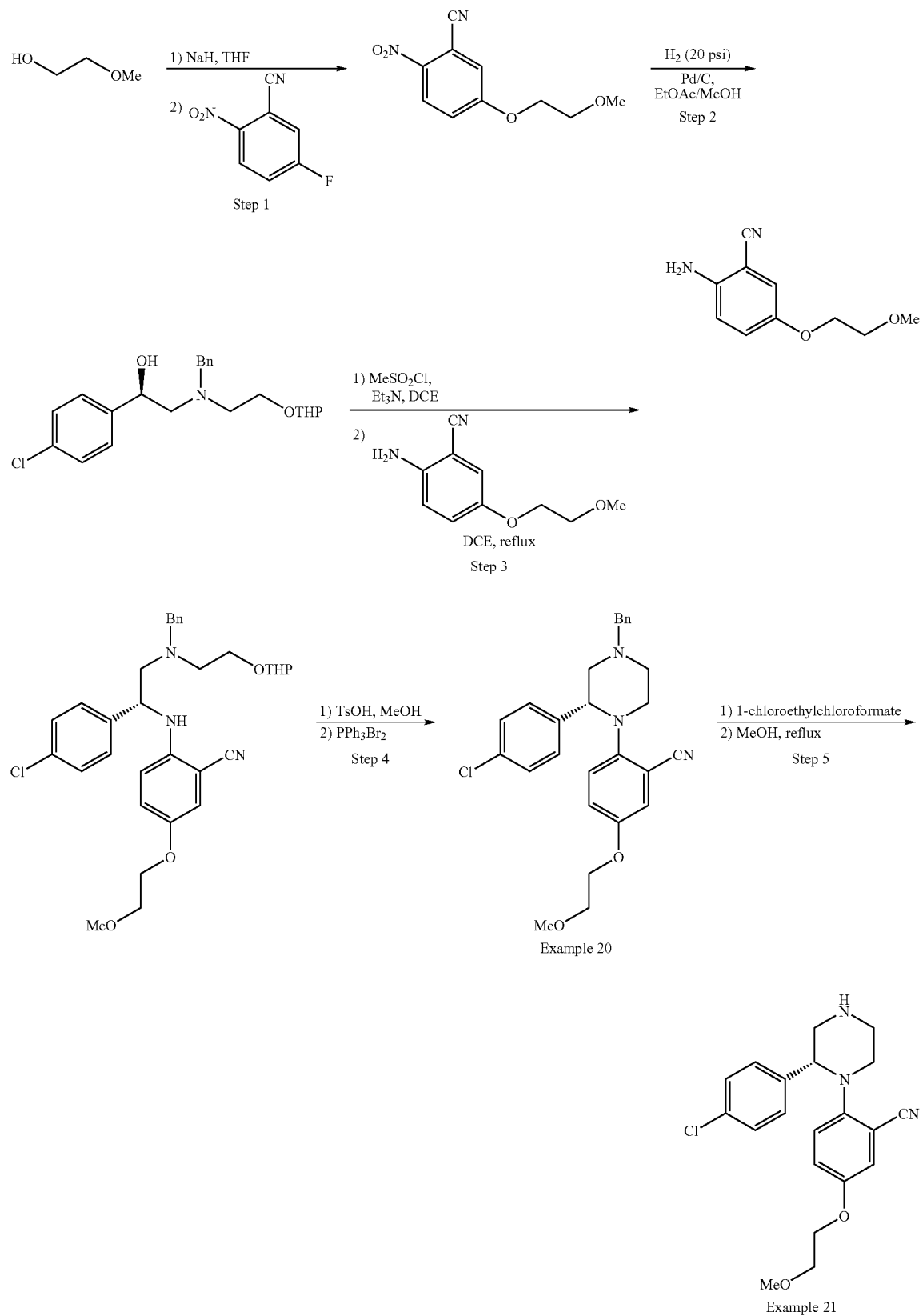

Step 1:

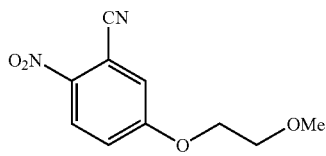 [SMILES: COCCOc1ccc([N+](=O)[O-])c(C#N)c1]

To a solution of 2-methoxyethanol (9.6 mL, 122 mmol) in THF at 0° C. was added NaH (60% in oil, 4.8 g, 122 mmol). The mixture was stirred at 0° C. for 15 min. To this solution was added 5-fluoro-2-nitrobenzonitrile (15.0 g, 103 mmol). The solution was then allowed to warm to RT and stirred at ambient temperature for 48 hours. The solution was partitioned between EtOAc and water. The water layer was extracted with EtOAc. The organic layer was dried over $Na_2SO_4$, filtered and concentrated. The crude product was purified via flash chromatography ($SiO_2$: gradient elution, 100:0 to 10:90 hexanes:EtOAc) to afford the ether (21.7 g, 95%) as a light yellow liquid.

Step 2:

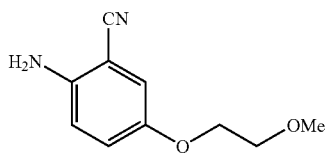

A solution of the nitro compound from step 1 (18 g, 81 mmol) in 4:1 EtOAc/MeOH (100 mL) divided between two pressure vessels was degassed by bubbling $N_2$ through the solution for 10 min. To each vessel was added 10% Pd/C (400 mg) and the vessels were sealed. The vessels were pressurized with $H_2$ (20 psi) and the vessels were shaken at RT for 20 min. The vessels were then purged with $N_2$ and the catalyst was removed by filtration through Celite and the solvent was removed in vacuo. The crude product was purified via flash chromatography ($SiO_2$: gradient elution, 100:0 to 20:80 hexanes:EtOAc) to afford aniline (14.3 g, 92%) as a light yellow solid.

Step 3:

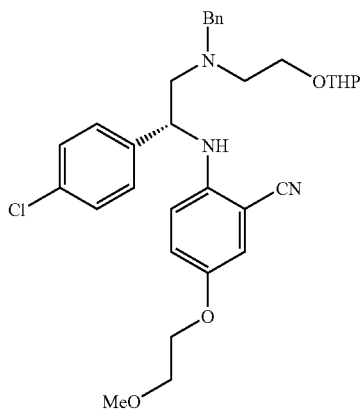

To a solution of the alcohol from Scheme 25 Step 1 (5.52 g, 14.2 mmol) in DCE (30 mL) at 0° C. was added $Et_3N$ (5.0 mL, 35.5 mmol) followed by methanesulfonyl chloride (133 mL, 17.0 mmol). The solution was allowed to slowly warm to RT over 2 h. After that time, the aniline from step 2 (3.0 g, 15.6 mmol) was added and the solution was heated to reflux. After 16 h at reflux, the solution was cooled to RT and allowed to stir at ambient temperature for an additional 48 h. The reaction mixture was then partitioned between $CH_2Cl_2$ and $NaHCO_3$(aq.). The organic layer was separated, dried over $Na_2SO4$, filtered and concentrated. The crude product was purified via flash chromatography ($SiO_2$: gradient elution, 100:0 to 75:25 hexanes:EtOAc) to afford aniline (6.5 g, 81%) as a light yellow oil.

Step 4:

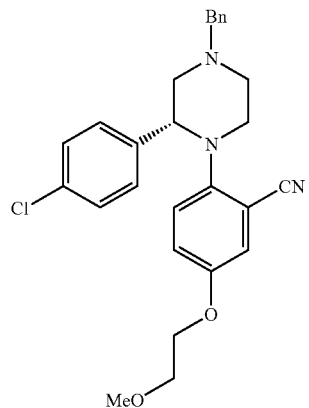 [SMILES: COCCOc1ccc(N2CCN(Cc3ccccc3)C[C@H]2c2ccc(Cl)cc2)c(C#N)c1]

To a solution of aniline from step 3 (6.5 g, 11.5 mmol) in MeOH was added $TsOH.H_2O$ (2.97 g, 17.3 mmol). The solution was stirred at RT overnight. After that time, the solution was concentrated and the residue was partitioned between $NaHCO_3$ (aq.) and $CH_2Cl_2$. The aqueous layer was extracted with $CH_2Cl_2$ (3×). The combined organic layers were dried over $Na_2SO_4$, filtered and concentrated. The crude product was purified via flash chromatography ($SiO_2$: gradient elution, 100:0 to 45:55 hexanes:EtOAc) to afford the intermediate alcohol (ca, 5.4 g). To a solution of the alcohol (5.4 g, 11 mmol) in $CH_2Cl_2$ (30 mL) at 0° C. was added $Et_3N$ (3.90 mL, 28.1 mmol) followed by triphenylphosphine dibromide (7.1 g, 17 mmol). The mixture was stirred at 0° C. for 3 h. The mixture was then allowed to warm to RT and stir for an additional 48 h. After that time, $NaHCO_3$ (aq.) was added to the mixture and the aqueous layer was extracted with $CH_2Cl_2$. The organic layer was dried over $Na_2SO_4$, filtered and concentrated. The crude product was purified via flash chromatography ($SiO_2$: gradient elution, 100:0 to 11:89 hexanes:EtOAc) to afford Example 20 (5 g).

Step 5:

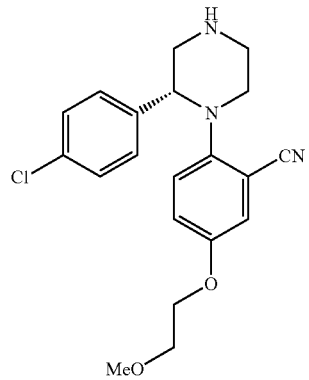 [SMILES: COCCOc1ccc(N2CCNC[C@H]2c2ccc(Cl)cc2)c(C#N)c1]

To a solution of Example 20 from step 4 (1.3 g, 2.8 mmol) in DCE was added 1chloroethyl-chloroformate (0.33 mL, 3.1 mmol). The resultant solution was stirred at RT for 1 h. Additional 1-chloroethylchloroformate (0.03 mL, 0.30 mmol) was added and the solution was stirred at RT for an additional 16 h. The solution was then concentrated in vacuo.

To the residue was added MeOH and the resultant solution was heated to reflux with stirring for 1 h. The solution was then concentrated and the residue was partitioned between CH$_2$Cl$_2$ and NaHCO$_3$ (aq.). The aqueous layer was extracted with CH$_2$Cl$_2$. The organic layer was dried over Na$_2$SO$_4$, filtered and concentrated. The crude product was purified via flash chromatography (SiO$_2$: gradient elution, 100:0:0 to 93:7:1 CH$_2$Cl$_2$: MeOH: 7N NH$_3$ (in MeOH)) to afford the Example 21 (400 mg, 38%).

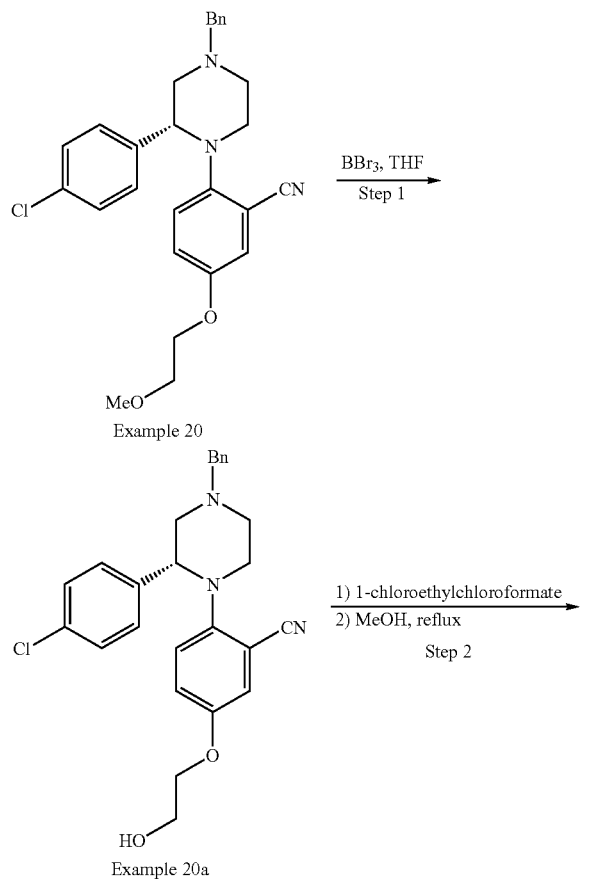

at RT overnight. The mixture was then partitioned between NaHCO$_3$ (aq.) and CH$_2$Cl$_2$. The organic layer was separated, dried over Na$_2$SO$_4$, filtered and concentrated. The crude product was purified via flash chromatography (SiO$_2$: gradient elution, 100:0 to 25:75 hexanes:EtOAc) to afford Example 20a.

Step 2:
To a solution of the alcohol (2.0 g, 4.5 mmol) in DCE was added 1-chloroethylchloroformate (1.2 mL, 11.2 mmol). The solution was stirred at RT for 1 h. Additional 1-chloroethylchloroformate (0.30 mL, 3.0 mmol) was added and the solution was stirred at RT for an additional 16 h. The solution was then concentrated in vacuo To the residue was added MeOH and the solution was heated to reflux with stirring for 1 h. After that time, the solution was concentrated and the residue was partitioned between CH$_2$Cl$_2$ and NaHCO$_3$ 5 (aq.) The organic layer was separated, dried over Na$_2$SO$_4$, filtered and concentrated The crude product was purified via flash chromatography (SiO$_2$: gradient elution, 100:0:0 to 93:7:1 CH$_2$Cl$_2$: MeOH: 7N NH$_3$ (in MeOH)) to afford the Example 22 (800 mg, 50%).

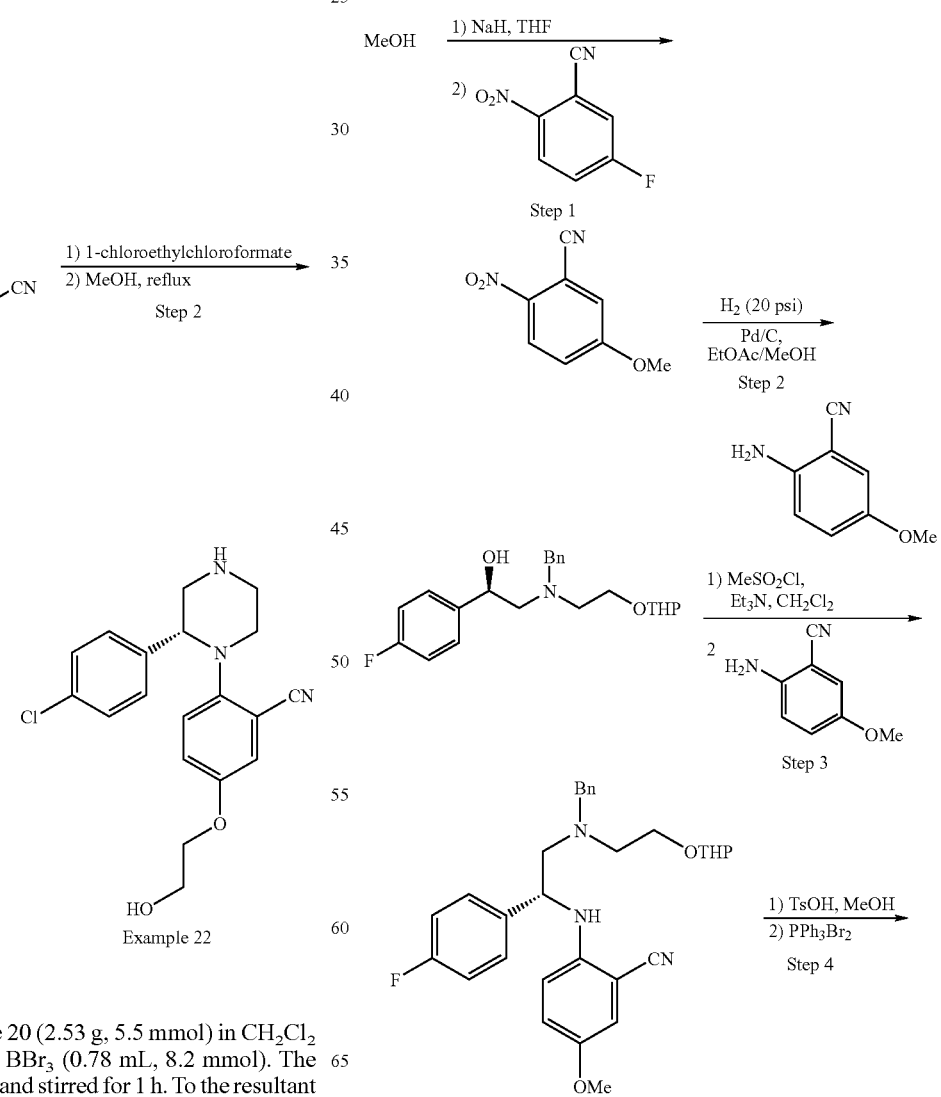

Step 1:
To a solution of Example 20 (2.53 g, 5.5 mmol) in CH$_2$Cl$_2$ (5 mL) at 0° C. was added BBr$_3$ (0.78 mL, 8.2 mmol). The solution was warmed to RT and stirred for 1 h. To the resultant red solution was added 1 M NaOH and the mixture was stirred

Step 1:

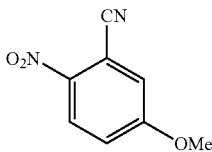

To a slurry of NaH (60% in oil)(7.2g, 181 mmol) in anhydrous THF (300 mL) at 0° C. was added dropwise anhydrous MeOH (5.8 g, 181 mmol). Once the addition was complete, the resultant mixture was stirred at 0° C. for an additional 20 min. The slurry was added slowly via cannula to a solution of 5-fluoro-2-benzonitrile (25 g, 150 mmol) in THF (100 mL). The green solution was allowed to slowly warm to RT and stir overnight. Water was slowly added and the aqueous layer was extracted with EtOAc (3×). The combined organic layers were washed with brine, dried over $Na_2SO_4$, filtered and concentrated. The crude product was purified via flash chromatography ($SiO_2$: gradient elution, 100:0 to 60:40 hexanes: EtOAc) to afford the nitro compound (23.2 g, 87%) as a light yellow solid.

Step 2:

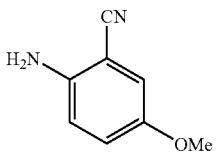 [SMILES: COc1ccc(N)c(C#N)c1]

A solution of the nitro compound from Step 1 (6.5 g, 36 mmol) in 4:1 EtOAc: MeOH (150 mL) in a pressure vessel was degassed with by bubbling $N_2$ through the solution for 10 min. To this solution was added 10% Pd/C (300 mg). The vessel was sealed and pressurized with $H_2$ to 25 psi. The vessel was then shaken at RT for 20 min. Once the reaction was complete, the vessel was purged with $N_2$. The mixture was filtered through Celite and concentrated. The crude product was purified via flash chromatography ($SiO_2$: gradient elution, 100:0 to 60:40 hexanes:EtOAc) to afford the aniline (6.4 g, 100%) as a light yellow solid.

Step 3:

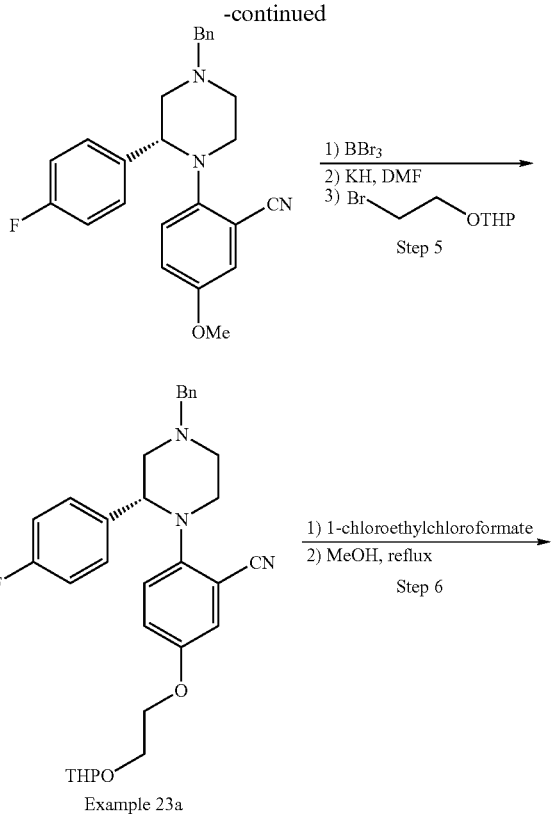

Example 23a

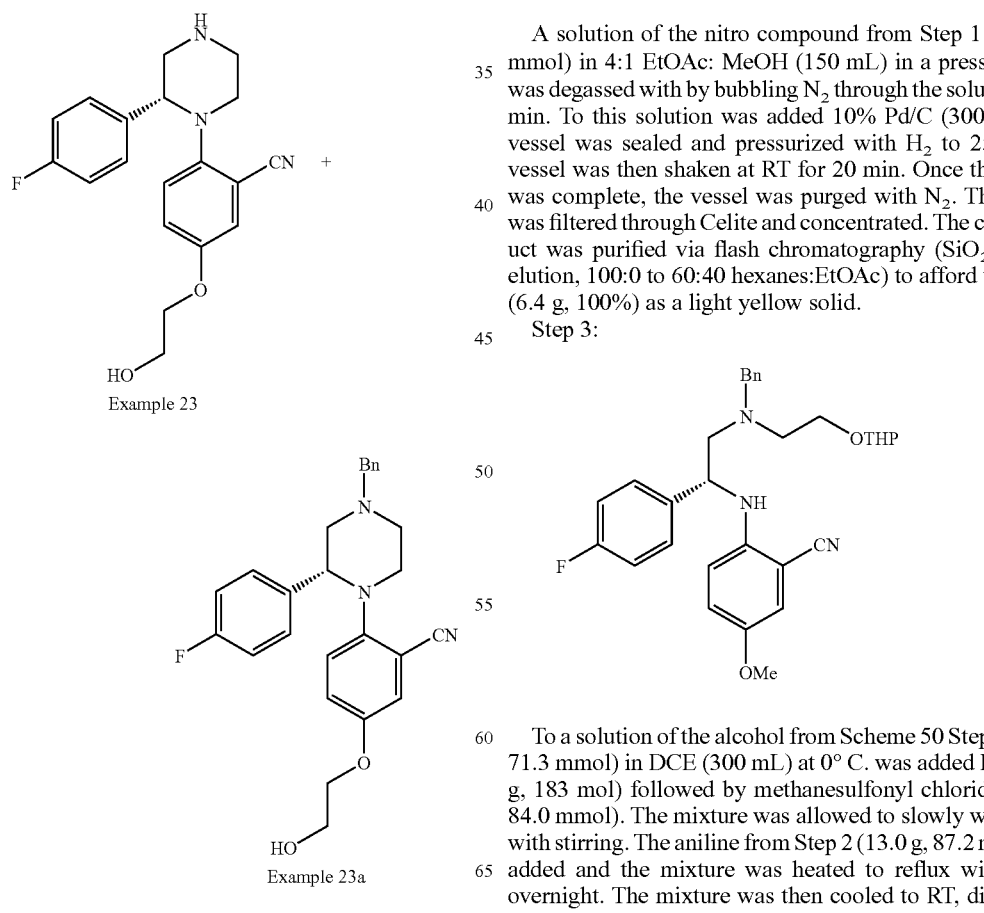

Example 23

Example 23a

To a solution of the alcohol from Scheme 50 Step 3 (27.3 g, 71.3 mmol) in DCE (300 mL) at 0° C. was added $Et_3N$ (18.5 g, 183 mol) followed by methanesulfonyl chloride (9.60 g, 84.0 mmol). The mixture was allowed to slowly warm to RT with stirring. The aniline from Step 2 (13.0 g, 87.2 mmol) was added and the mixture was heated to reflux with stirring overnight. The mixture was then cooled to RT, diluted with $CH_2Cl_2$ and washed with $NaHCO_3$ (aq.). The aqueous layer was back extracted with CH$_2$Cl$_2$ (2×). The combined organic layers were dried over Na$_2$SO$_4$, filtered and concentrated. The crude product was purified via flash chromatography (SiO$_2$: gradient elution, 100:0 to 75:25 hexanes:EtOAc) to afford the diamine product (28.7 g, 80%) as a yellow oil.

Step 4:

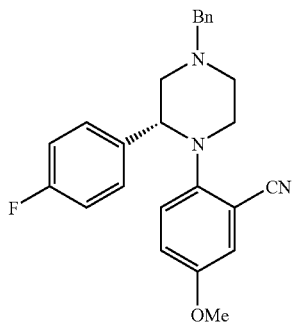 [SMILES: COc1ccc(N2CCN(Cc3ccccc3)C[C@H]2c2ccc(F)cc2)c(C#N)c1]

To a solution of the THP ether from step 3 (28.6 g, 56.9 mmol) in MeOH (400 mL) was added methanesulfonic acid (6.52, 67.8 mmol). The resultant solution was stirred at RT for 5.5 h. The solution was concentrated and the residue was partitioned between EtOAc and sat, NaHCO$_3$ (aq.) and the aqueous layer was extracted with EtOAc (3×). The combined organic layers were washed with brine, dried over Na$_2$SO$_4$, filtered and concentrated. The residue (ca. 24.1 g, 57.6 mmol) was dissolved in DCE (400 mL) and cooled to 0° C. To this solution was added Et$_3$N (14.5 g, 144 mmol) and triphenylphosphine dibromide (36.5 g, 86.4 mmol). The solution was slowly warmed to RT over 1 h with stirring, then heated to 60° C. for 6 hr. The reaction mixture was cooled to RT and allowed to stir for an additional 48 h at ambient temperature. After this time, the reaction mixture was partitioned between CH$_2$Cl$_2$, and NaHCO$_3$ (aq.) and the aqueous layer was then extracted with CH$_2$Cl$_2$ (2×) The combined organic layers were dried over Na$_2$SO$_4$, filtered and concentrated. The crude product was purified via flash chromatography (SiO$_2$: gradient elution. 90:10 to 60:40 hexanes:EtOAc) to afford the piperazine (19.2 9, 84%) as a yellow foam.

Step 5:

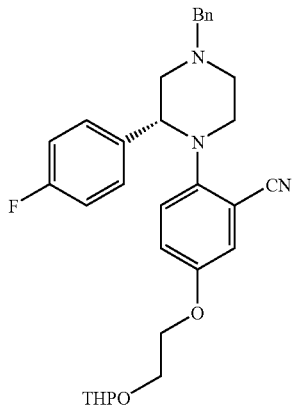

To a solution of the methyl ether from Step 4 (1.35 g, 3.4 mmol) in CH$_2$Cl$_2$ (50 mL) at 0° C. was added BBr$_3$ (0.48 mL, 5.0 mmol). The mixture was allowed to slowly warm to RT with stirring over 4 h. Additional BBr$_3$ (0.48 mL, 5.0 mmol) was added and the mixture was stirred at RT overnight. The reaction mixture was then slowly poured into sat. NaHCO$_3$ (aq.). After the addition was complete, the aqueous layer was extracted with CH$_2$Cl$_2$ (3×). The combined organic layers were dried over Na$_2$SO$_4$, filtered and concentrated. The crude product was purified via flash chromatography (SiO$_2$: gradient elution, 100:0 to 50:50 hexanes:EtOAc) to afford the phenol (1.2 g, 91%) as a yellow foam.

To a solution of the phenol (1.20 g, 3.10 mmol) in anhydrous DMF (35 mL) at 0° C. was added KH (30% in oil, 0.62 g, 4.64 mmol) and the resultant mixture was stirred at 0° C. for 20 min. To this mixture was added 2-(2-bromoethoxy) tetrahydro-2H-pyran (Aldrich) (1.30 g, 6.20 mmol). The resultant mixture was stirred at 0° C. for 15 min followed by an additional 16 h at ambient temperature. After that time, water was added slowly to the mixture and the aqueous layer was extracted with EtOAc. The organic layer was washed sequentially with water and brine, then dried over Na$_2$SO$_4$, filtered and concentrated. The crude product was purified via flash chromatography (SiO$_2$: gradient elution, 100:0 to 50:50 hexanes:EtOAc) to afford example 23a (1.33 g, 83%).

Step 6:

To a solution of the benzyl amine (1.20 g, 2.3 mmol) in CH$_2$Cl$_2$ (15 mL) was added 1-chloroethyl chloroformate (490 mg, 3.4 mmol). The resultant solution was heated to reflux for 2 h. At that time, additional 1-chloroethyl chloroformate (200 mg, 1.4 mmol) was added and the solution was heated to reflux with stirring for an additional 1 h. The solution was then concentrated in vacuo and to the residue was added MeOH (15 mL). The resultant solution was heated to reflux for 1 h. The solution was concentrated and the residue was partitioned between CH$_2$Cl$_2$ and NaHCO$_3$ (aq.). The aqueous layer was extracted with CH$_2$Cl$_2$ (3×). The combined organic layers were dried over Na$_2$SO$_4$, filtered and concentrated. The crude products were purified via flash chromatography [SiO$_2$: gradient elution, 100:0:0 to 95:5:1 CH$_2$Cl$_2$:MeOH: 7N NH$_3$ (in MeOH)] to afford Example 23 (690 mg) and Example 23a (30 mg).

Scheme 32.1

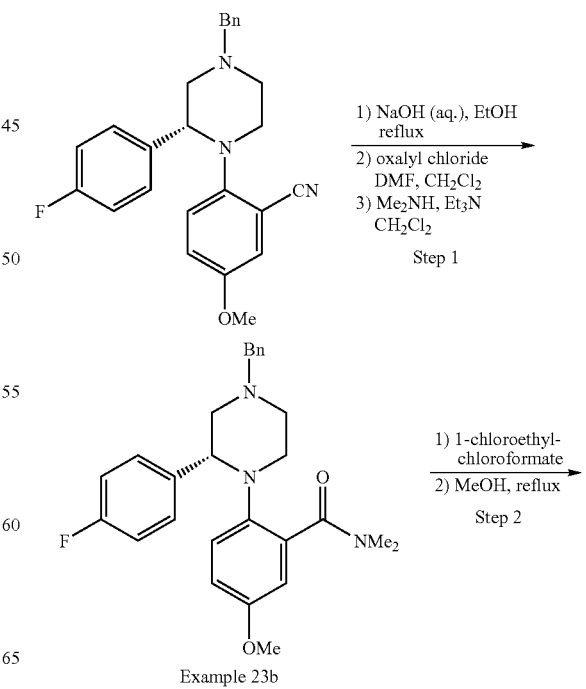

Example 23b

-continued

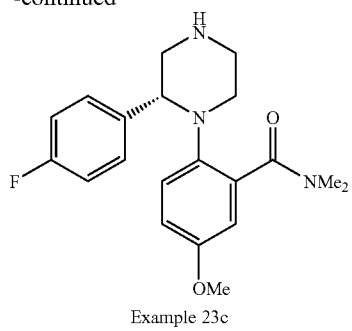

Example 23c

Step 1:

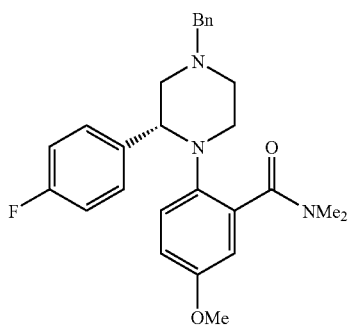

Example 23b

To a solution of the piperazine from Scheme 32 Step 4 (8.0 g, 19.9 mmol) in EtOH was added 3 N NaOH (aq.) (53 mL, 159 mmol). The resultant solution was heated to reflux with stirring for 4 days. After that time, the organic solvent was removed in vacuo and the aqueous layer was adjusted to pH 8.5. The aqueous layer was then extracted with EtOAc. The organic layer was dried over $Na_2SO_4$, filtered and concentrated. The crude product was purified via flash chromatography ($SiO_2$: gradient elution 100:0 to 30:70 hexanes:EtOAc) to afford the intermediate carboxylic acid (3.6 g).

To a slurry of the acid (3.46 g, 8.2 mmol) in anhydrous $CH_2Cl_2$ was added oxalyl chloride (1.15 g, 9.1 mmol) followed by DMF (1 drop). The resultant mixture was stirred at RT for 2 h. The solvent was removed in vacuo to afford the acid chloride (ca 8.2 mmol) which was dissolved in anydrous $CH_2Cl_2$. To this solution was added a solution of diethylamine (2 M in THF, 24.6 mmol) and $Et_3N$ (6.2 mL, 12.3 mmol). The resultant solution was stirred at RT overnight. After that time, the solution was washed with $NaHCO_3$ (aq.) and the organic layer was dried over $Na_2SO_4$, filtered and concentrated. The crude product was purified via flash chromatography ($SiO_2$: gradient elution 100:0 to 50:50 hexanes: EtOAc) to afford Example 23b (3.70 g).

Example 23c

Step 2:

To a solution of Example 23b (3.65 g, 8.2 mmol) in $CH_2Cl_2$ was added 1-chloroethylchloroformate (1.75 g, 12.2 mmol). The resultatant solution was stirred at RT for 1 h. The solution was then concentrated. The residue was dissolved in MeOH and heated to reflux for 1 h. The solution was concentrated and the resiude was partitioned between $CH_2Cl_2$ and $NaHCO_3$ (aq.). The organic layer was dried over $Na_2SO_4$, filtered and concentrated. The crude product was purified via flash chromatography [$SiO_2$: gradient elution 100:0:0 to 90:10:1 $CH_2Cl_2$: MeOH: conc. $NH_4OH$ (aq.)] to afford Example 23c (2.6 g).

Scheme 33

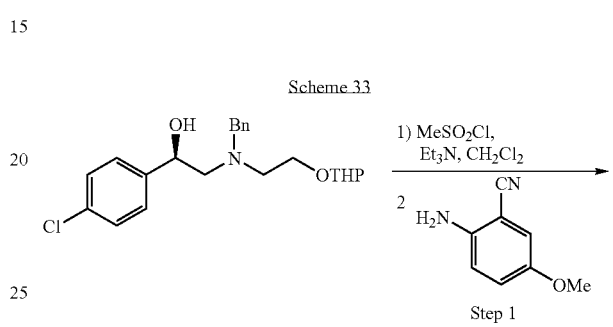

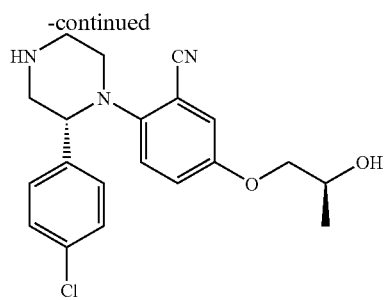

Example 24

Step 1:
The diamine was prepared using a similar method to that described in Scheme 32 Step 3.

Step 2:
The piperazine was prepared using a similar method to that described in Scheme 32 Step 4, except the diamine from Step 1 of this scheme was used.

Step 3:
To a solution of the piperazine from Step 2 (7.64 g, 18.3 mmol) in DCE was added allyl chloroformate (3.3 g, 27 mmol) and iPr$_2$NEt (4.73 g, 36.6 mmol). The resultant solution was heated to reflux for 16 h. Additional allyl chloroformate (1,70 g, 14 mmol) and iPr$_2$NEt (2.47 g, 18.4 mmol) were added and the solution was stirred at reflux for an additional 3 h. The solution was then concentrated and the crude product was purified via flash chromatography (SiO$_2$: gradient elution, 100:0 to 70:30 hexanes:EtOAc) to afford the allyl carbamate (6.85 g, 91%).

To a solution of a portion of the carbamate from above (2.3 g, 5.6 mmol) in CH$_2$Cl$_2$ (15 mL) at 0° C. was added BBr$_3$ (3.5 g, 14 mmol). The mixture was allowed to warm to RT and stir for 16 h. To the mixture was added sat. NaHCO$_3$ (aq.) and the mixture was stirred vigorously at RT for 1 h. After that time, allyl chloroformate (1.0 g, 8.4 mmol) was added and the mixture was stirred at RT for 1.5 h. The mixture was then partitioned between CH$_2$Cl$_2$ and sat NaHCO$_3$ (aq.) and the aqueous layer was extracted with CH$_2$Cl$_2$ (3×). The combined organic layers were dried over Na$_2$SO$_4$, filtered and concentrated. The crude products were purified via flash chromatography (SiO$_2$: gradient elution. 100:0 to 70:30 hexanes:EtOAc) to afford the free phenol (0.45 g) and the allyl carbonate (1.7 g).

To a solution of the allyl carbonate (1.7 g, 3.5 mmol) in MeOH was treated with an aqueous solution of LiOH (2 M, 2.6 mL, 5.2 mmol). The solution was stirred at RT for 1.5 h. The solution was then adjusted to pH 6.5 by the slow addition of 1 M HCl (aq) and the resultant mixture was extracted with CH$_2$Cl$_2$. The organic layer was dried over Na$_2$SO$_4$, filtered and concentrated. The crude product was purified via flash chromatography (SiO$_2$: gradient elution, 100:0 to 70:30 hexanes:EtOAc) to afford the phenol (ca 1.30 g).

Step 4:
To a solution of the phenol from Step 3 (1.75 g, 4.5 mmol) in DMF in a pressure tube was added K$_2$CO$_3$ (1.3 g, 9.1 mmol) and (2S)-2-(tetrahydro-2H-pyran-2-yloxy)propyl 4-methylbenzenesulfonate (prepared in Scheme 26 Step 2, 2.2 g, 6.7 mmol). The tube was sealed and the mixture was heated to 100° C. with stirring for 16 h. The mixture was then cooled to RT, transferred to a round bottom flask and concentrated. The residue was partitioned between water and CH$_2$Cl$_2$. The organic layer was separated, dried over Na$_2$SO$_4$, filtered and concentrated. The crude product was purified via flash chromatography (SiO$_2$: gradient elution, 100:0 to 55:45 hexanes:EtOAc) to afford the ether (1.42 g, 58% yield).

To a solution of the ether (1.42 g, 2.6 mmol) in a 1:1 mixture of MeCN/H$_2$O was added was added diethylamine (38 g, 52 mmol), Pd(OAc)$_2$ (6.6 mg, 0.026 mmol) and trisodium triphenylphosphine 3,3',3"-trisulfonate (Aldrich) (30 mg, 0.052 mmol). The resultant mixture was stirred at RT for 3 h. After that time, the mixture was concentrated and the crude product was purified via flash chromatography [SiO$_2$: gradient elution, 100:0:0 to 97:2.5:0.25 CH$_2$Cl$_2$:MeOH: conc NH$_4$OH (aq.)] to afford the amine (1.16 g, 98% yield).

To a solution of the amine (1.16 g, 2.5 mmol) in MeOH was added p-toluene sulfonic acid (0.88 g, 5.1 mmol). The resultant solution was stirred at RT for 1 h. The solution was then concentrated and the residue was partitioned between CH$_2$Cl$_2$ and NaHCO$_3$ (aq.). The aqueous layer was extracted with CH$_2$Cl$_2$ (3×). The combined organic layers were dried over Na$_2$SO$_4$, filtered and concentrated. The crude product was purified via flash chromatography [SiO$_2$: gradient elution, 100:0:0 to 90:10:1 CH$_2$Cl$_2$:MeOH: conc NH$_4$OH (aq.)] to afford the piperazine.

Scheme 34

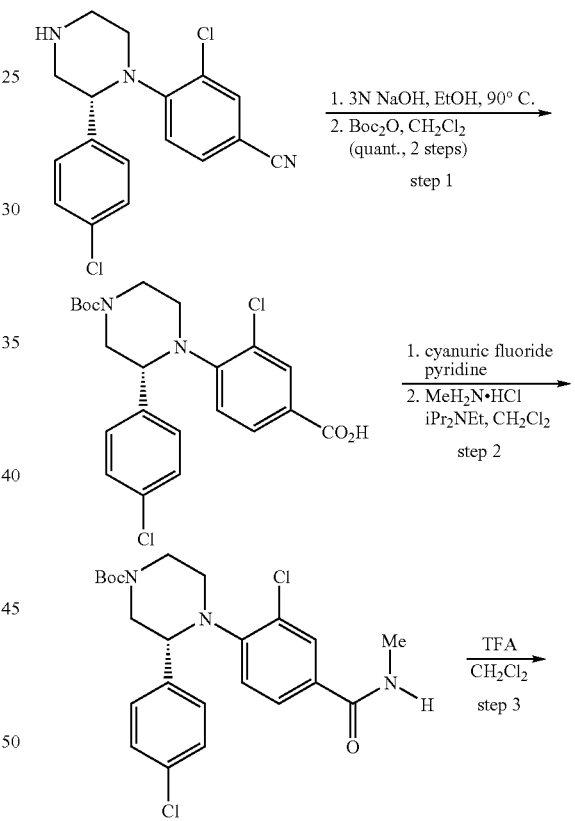

Example 25

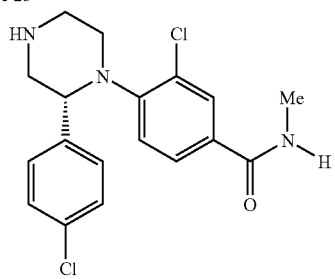

Example 25a

Step 1:

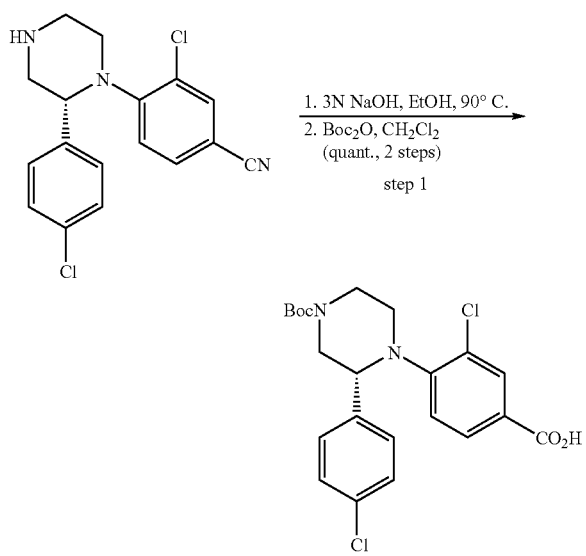

1. 3N NaOH, EtOH, 90° C.
2. Boc₂O, CH₂Cl₂
(quant., 2 steps)

step 1

To a solution of the starting nitrile (10.3 g, 31.0 mmol, 1 eq) in EtOH (40 mL) was added 3M NaGH (60 mL) with stirring. The reaction was heated with a 90° C. oil bath for 4 h, at which point the oil bath was removed and the solution cooled to room temperature. After letting the reaction sit for 16h, the volume was reduced to ca. ½ via rotary evaporation. A solution of di-tert-butyl dicarbonate (6.98 g, 32.0 mmol, 1.03 eq) in CH₂Cl₂ (50 mL) was then added to the crude hydrolysis product and the reaction stirred for 3 h. EtOAc (150 mL) was added to the reaction and the reaction acidified to pH 1-2 with 3N HCl. The aqueous layer was removed and the organic layer washed three times with brine. The organic layer was then dried over anhydrous Na₂SO₄, filtered and evaporated to afford the desired Boc-protected amino acid (14 g) as a dark tan foam that was used in the following step without further purification.

Step 2:

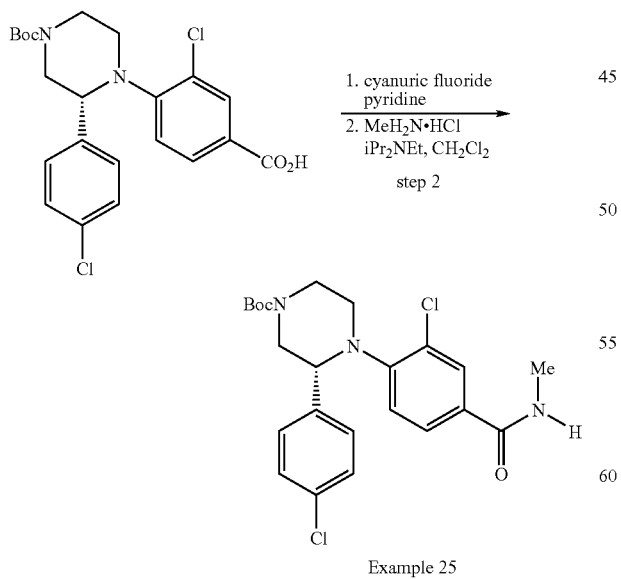

1. cyanuric fluoride
pyridine
2. MeH₂N·HCl
iPr₂NEt, CH₂Cl₂ step 2

Example 25

A solution of the benzoic acid (3 g, 6.65 mmol, 1 eq) and pyridine (2.2 mL) in CH₂Cl₂ (100 mL) was cooled to 0° C. Cyanuric fluoride (1.2 mL) was then added dropwise with stirring. After 1 h, additional amounts of pyridine (2.2 mL) and cyanuric fluoride (1.2 mL) were added and the reaction stirred an additional 2 h. The mixture was then poured into a cold solution of saturated aqueous NaHCO₃. The organic layer was removed, and the aqueous layer extracted with CH₂Cl₂. The two organic extracts were combined, dried over anhydrous Na₂SO₄, filtered and evaporated to afford the acid fluoride as an orange foam that was used in the following step without further purification.

One half of the crude acid fluoride was dissolved in CH₂Cl₂ (20 mL) and cooled to 0° C. iPr₂NEt (1.7 mL, 9.97 mmol, 3 eq) was added to the solution, followed by methylamine hydrochloride (449 mg, 6.65 mmol, 2 eq). The reaction was stirred for 16h, allowing it to warm to room temperature, then partitioned between CH₂CO₂ and saturated aqueous NaHCO₃. Removal of the organic layer was followed by extraction of the aqueous layer with CH₂Cl₂. After combining the two organic extracts, the volatiles were removed in vacuo to afford a crude product which was purified via silica gel chromatography (0% to 100% EtOAc in hexanes over 10 column volumes) to afford Example 25 (1.02 g) as a clear viscous oil.

Step 3:

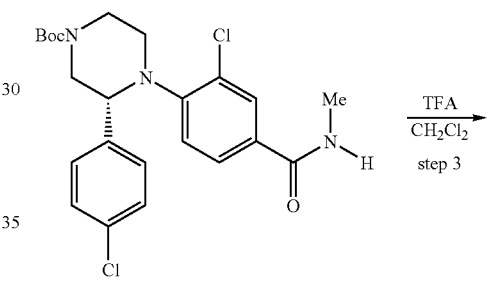

TFA
CH₂Cl₂ step 3

Example 25

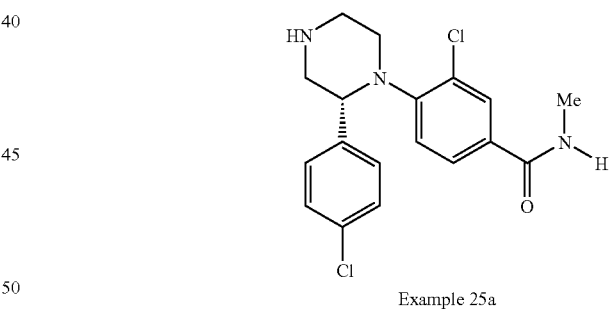

Example 25a

Trifluoroacetic acid (5 mL) was added to a stirred solution of Example 25 (1.02 g, 2.20 mmol) in CH₂Cl₂ (20 mL). After 3 d, the reaction was slowly poured into a mixture of CH₂Cl₂ and saturated aqueous NaHCO₃. The quenched reaction was stirred for 3h then the organic layer was removed. The aqueous layer was extracted twice with CH₂Cl₂. The three organic extracts were then combined and evaporated to afford a crude residue which was purified via silica gel chromatography (0% to 40% MeOH in CH₂Cl₂) to afford Example 25a (750 mg) as a yellow solid.

Using the method described above, substituting various amines for methylamine hydrochloride in Step 2, the following piperazine core compounds were prepared:

TABLE 4.2

| Amine | Example | piperazine core |
|---|---|---|
| Me₂NH•HCl | 25b | (structure) |
| HOCH₂CH₂NHMe | 25c | (structure) |

Scheme 35

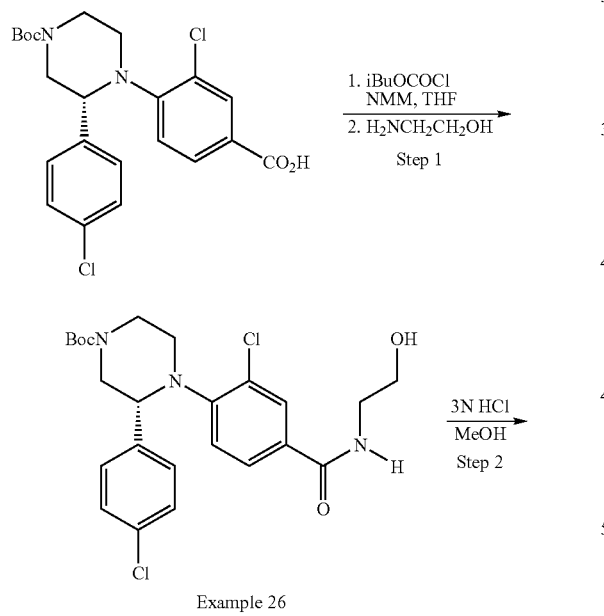

Example 26

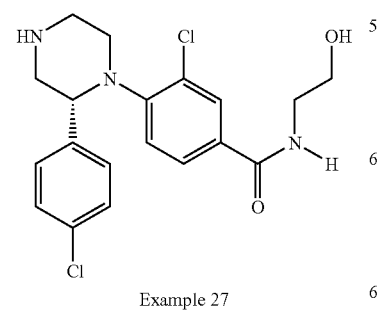

Example 27

Step 1:

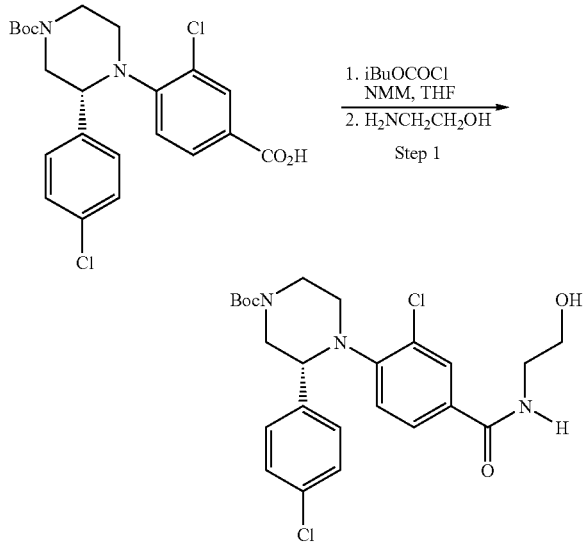

Example 26

The Boc-protected amino acid prepared in Scheme 34, Step 1 (900 mg, 2.00 mmol, 1 eq) and N-methylmorpholine (660 μL, 6.00 mmol, 3 eq) were dissolved in THF (10 mL) and cooled to 0° C. Isobutyl chloroformate (337 μL, 2.60 mmol, 1.3 eq) was added dropwise with stirring, allowing the reaction to slowly warm to room temperature over 1.5 h. A filter with vacuum adapter was attached to a flask cooled to 0° C. containing ethanolamine (241 μL, 4.00 mmol, 2 eq) in THF (5 mL). The mixed anhydride reaction was then filtered into the ethanolamine solution with stirring. After 2h, the reaction was partitioned between EtOAc and saturated aqueous NaHCO₃. The aqueous layer was removed and the organic layer was washed with brine and evaporated to provide a crude residue, which was subjected to silica gel chromatography (15% to 100% EtOAc in hexanes gradient) to afford Example 26 as a clear film (660 mg), Step 2

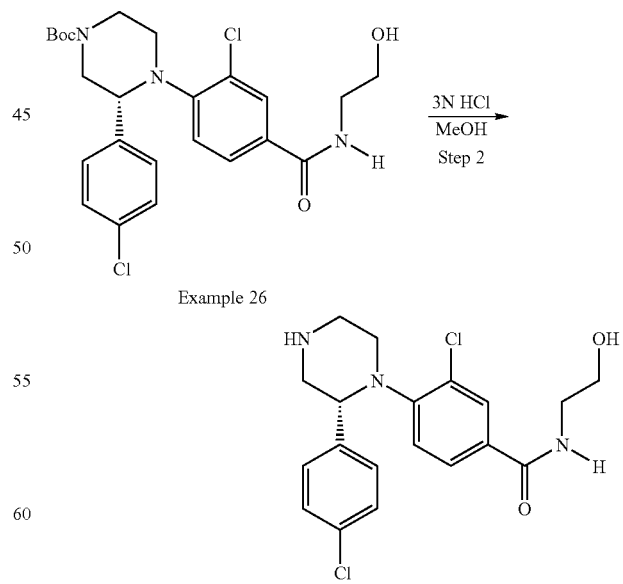

Example 26

Example 27

A solution of Example 26 (630 mg, 1.27 mmol, 1 eq) in methanol (15 mL) was treated with 3N HCl (7 mL) and stirred for 30 min. A second amount of 3N HCl (8 mL) was added and the reaction stirred for 16h. The reaction was then quenched with saturated aqueous NaHCO₃ and partitioned with CH₂Cl₂. The organic layer was removed and the aqueous layer extracted with CH₂Cl₂. The solids remaining in the aqueous layer were filtered off, dissolved in MeOH, combined with the two organic extracts, and evaporated to afford a crude residue that was subjected to silica gel chromatography (0% to 40% MeOH in CH₂Cl₂) to afford Example 27 as a clear film.

Scheme 36

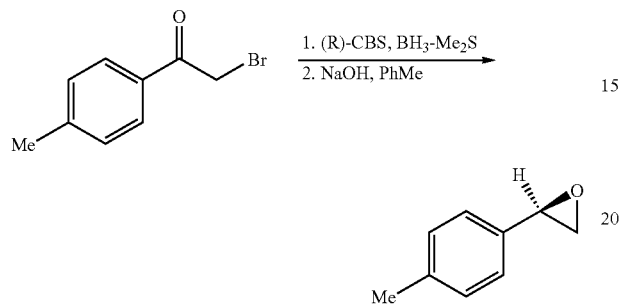

To a solution of 2-bromo-4'methylacetophenone (29.9 g, 140.3 mmol, 1 eq) in THF (140 mL) at 0° C. was added (R)-2-methyl-CBS-oxazaborolidine (1M in toluene, 28 mL, 28.1 mmol, 0.2 eq). An additional amount of toluene (50 mL) was used to wash any remaining oxazaborolidine into the reaction. Borane dimethylsulfide complex (2M in THF, 42 mL, 84.2 mmol, 0.6 eq) was added dropwise with stirring, and the resulting mixture stirred 30 min at 0° C. and 1.5 h at room temperature. Methanol (28 mL) was added dropwise, the quenched reaction was stirred 30 min and evaporated to afford a pale yellow oil. The resulting bromo-alcohol was dissolved in CH₂Cl₂ (400 mL) and treated with 3M NaOH (300 mL). After stirring for 3h, the organic layer was removed, washed with brine, dried over anhydrous MgSO₄, filtered, and evaporated to afford a pale yellow oil which was subjected to short path distillation (130° C., ~10 mmHg) to afford the title compound as a clear oil (17 g).

Scheme 37

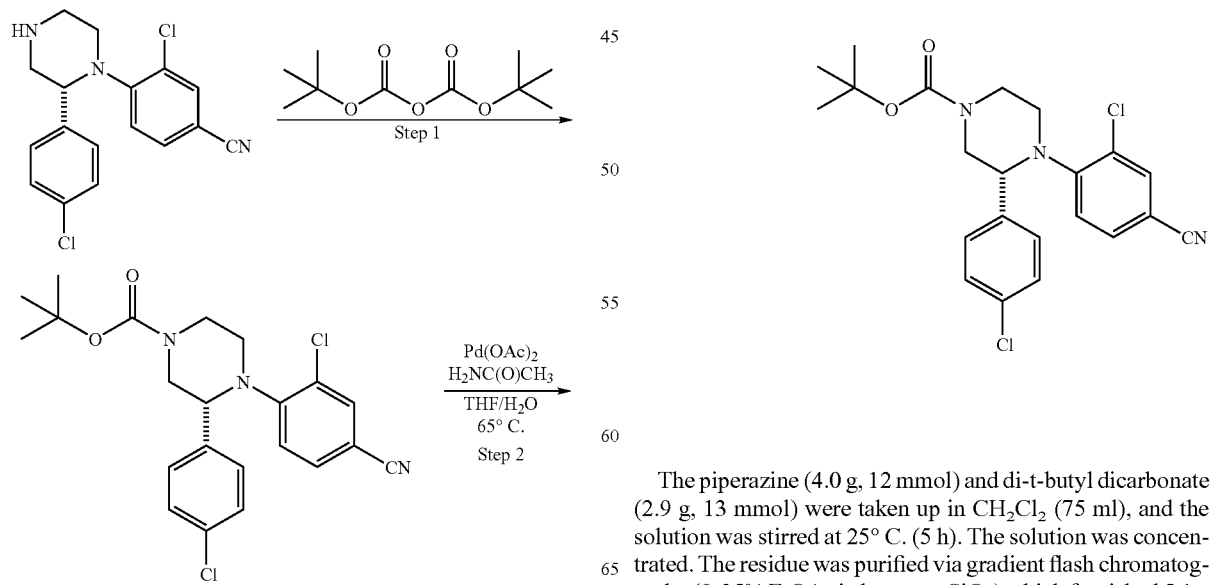

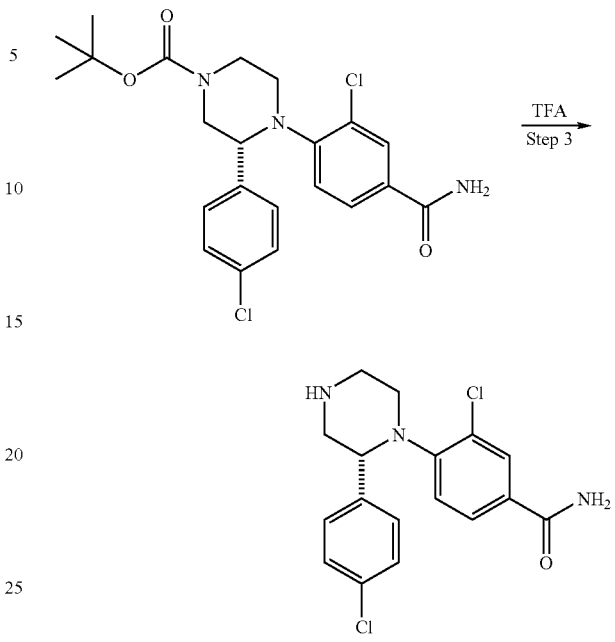

Step 1

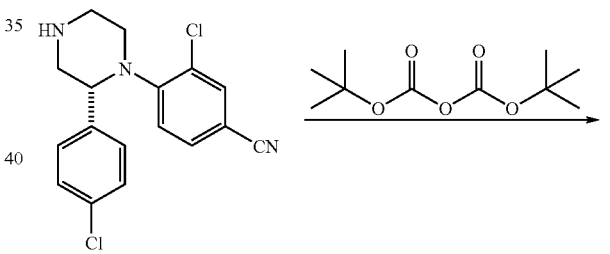

The piperazine (4.0 g, 12 mmol) and di-t-butyl dicarbonate (2.9 g, 13 mmol) were taken up in CH₂Cl₂ (75 ml), and the solution was stirred at 25° C. (5 h). The solution was concentrated. The residue was purified via gradient flash chromatography (0-25% EtOAc in hexanes, SiO₂) which furnished 5.1 g (97%) of the Boc protected piperazine.

Step 2

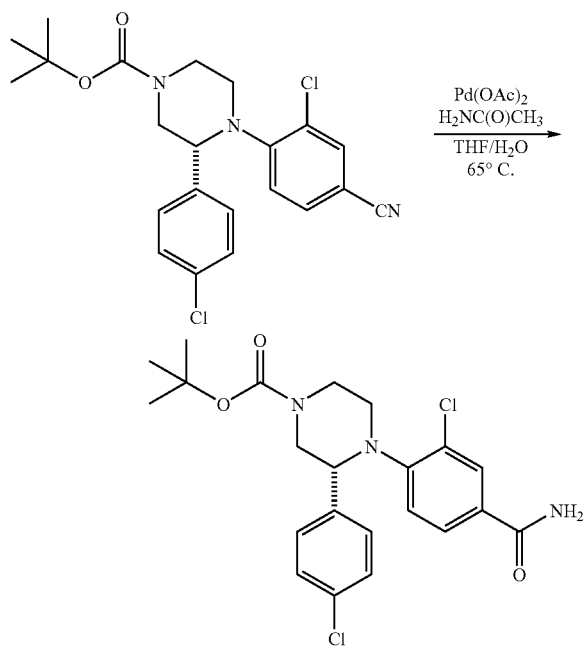

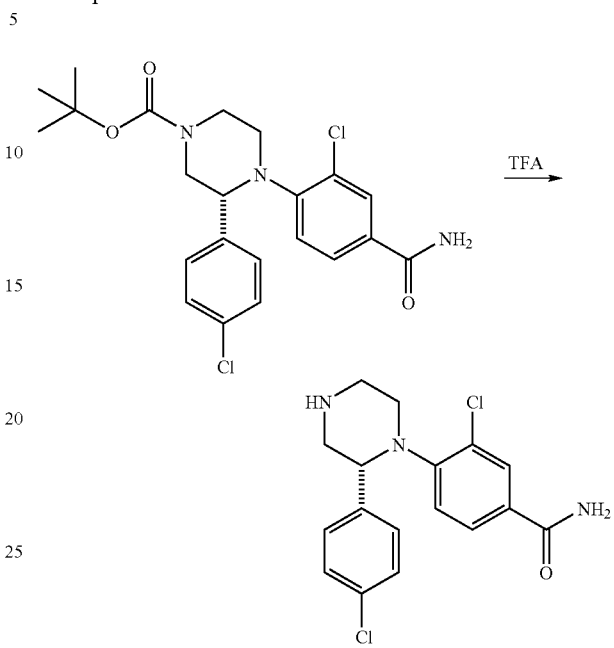

The Boc protected piperazine (1 g, 2.3 mmol), acetamide (580 mg), and Pd(OAc)$_2$ (52 mg) were taken up in THF/H$_2$O (3/1, 40 mL). The solution was stirred at 25 °C. for 17 h. After TLC analysis (4/1 hexanes/EtOAc), the hydrolysis was not complete. Pd(OAc)$_2$ (50 mg) and acetamide (500 mg) were added, and the solution was heated to 65° C. (4.5 h). After TLC analysis, the starting material was consumed. The solution was cooled and concentrated. The residue was partitioned between EtOAc and H$_2$O. The aqueous layer was extracted with EtOAc. The combined EtOAc layers were dried (MgSO$_4$), filtered, and concentrated. The residue was purified via gradient flash chromatography (0-30% EtOAc in CH$_2$Cl$_2$) which furnished 1 g (100%) of the piperazine as a brown oil.

Step 3

The Boc protected piperazine (1.0 g, 2.2 mmol) was taken up in CH$_2$Cl$_2$. TFA was added at 25° C., and the resulting solution was stirred at 25° C. (12 h). The solution was evaporated. The residue was partitioned between 2N NaOH(aq,) and EtOAc. The aqueous layer was extracted with EtOAc. The combined EtOAc layers were washed with brine and dried (MgSO$_4$). The mixture was filtered and concentrated which furnished 0.65 g (84%) of the piperazine Example 29 as a solid.

Scheme 38

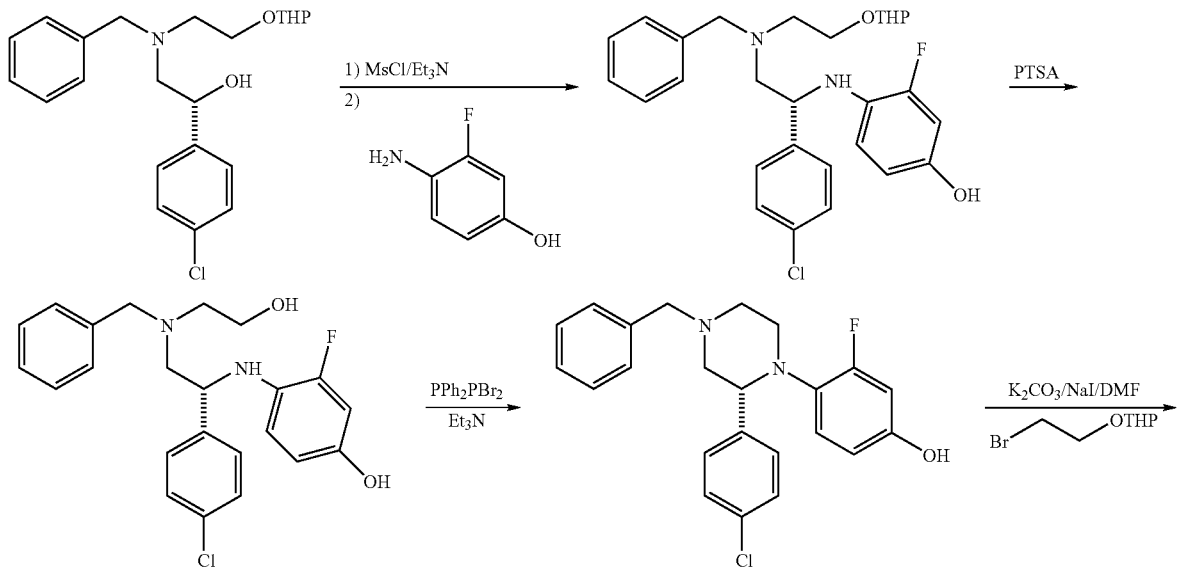

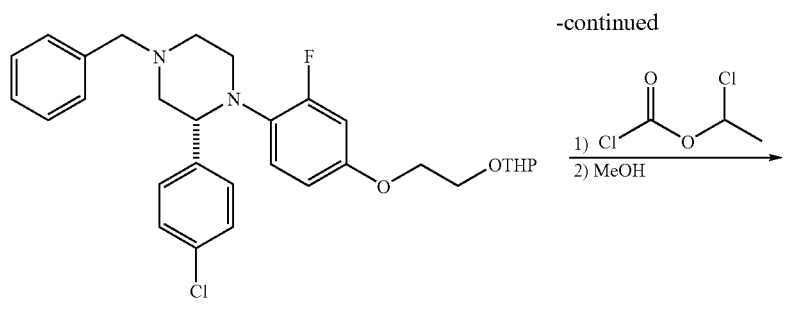

Example 30

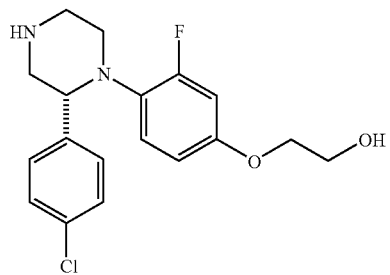

Example 31

Step 1

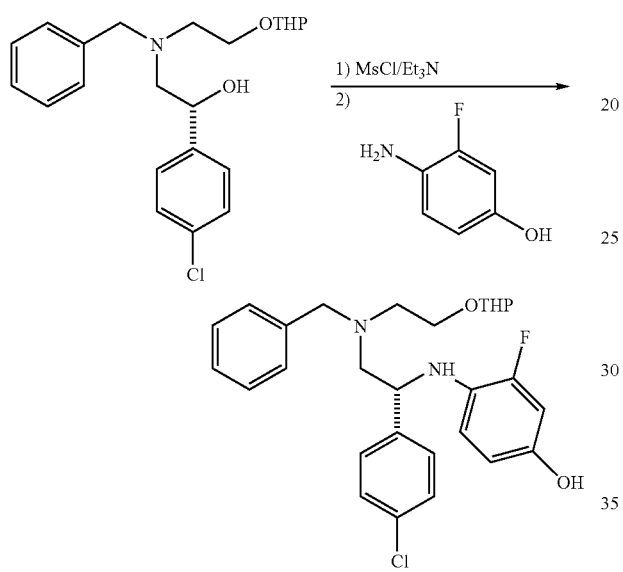

The alcohol (16 g, 41 mmol) and Et$_3$N (10.4 g, 104 mmol) were taken up in 1,2-DCE (130 mL) at 0° C. Methanesulfonyl chloride was added (4.9 g, 43 mmol) at 0° C., and the resulting solution was stirred at 25° C. (2 h). 4-Amino-3-fluoro phenol (5.7 g, 45 mmol) was added, and the resulting solution was heated at reflux (85° C., 12 h). The solution was cooled and washed with sat. NaHCO$_{3(aq.)}$. The aqueous layer was extracted with EtOAc. The combined EtOAc layers were washed with brine and dried over MgSO$_4$. Filtration and concentration gave a brown oil. The residue was purified via gradient flash chromatography (0-20% EtOAc/hexanes, SiO$_2$) which furnished 17.9 g (87%) of the THP protected aniline as a thick gum.

Step 2

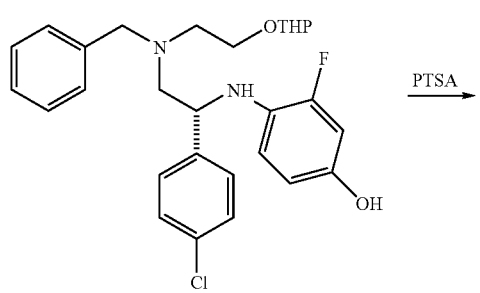

The THP protected alcohol (17.9 g, 36 mmol) and PTSA (8.5 g) were taken up in MeOH (120 mL), and the solution was stirred at 25° C. (12 h). The solution was evaporated. The residue was partitioned between EtOAc and NaHCO$_{3(aq.)}$. The aqueous layer was extracted with EtOAc. The combined EtOAc layers were washed with brine and dried (MgSO$_4$). Filtration and concentration furnished a yellow oil. The residue was purified via gradient flash chromatography (0-40% EtOAc/hexanes, SiO$_2$) which furnished 7.15 g (48%) of the alcohol as a yellow gum.

Step 3

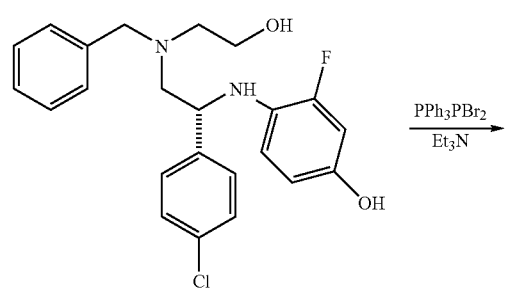

The alcohol (7.15 g, 17.2 mmol) and Et$_3$N (4.37 g) were taken up in DCM (100 mL) at 0° C. Triphenylphospine dibromide (10.18 g, 24 mmol) was added to the solution at 0° C., and the resulting solution was stirred at 0° C. for 1 h. The reaction was quenched with sat. NaHCO$_{3(aq.)}$. The aqueous layer was extracted with DCM. The combined organic layers were dried (MgSO$_4$), filtered, and concentrated, The residue was purified via gradient flash chromatography (0-40% EtOAc/hexanes, SiO$_2$) which furnished 5.5 g (81%) of the piperazine as a colorless foam.

Step 4

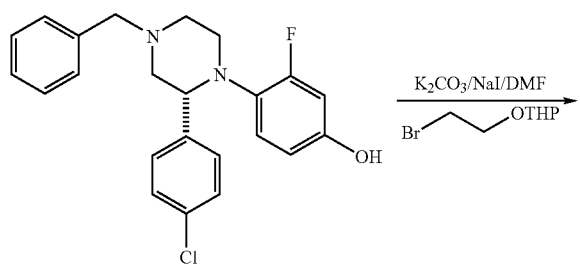

Example 30

The phenol (3 g, 7.56 mmol), BrCH$_2$CH$_2$OTHP (1.98 g), K$_2$CO$_3$ (2.61 g), and NaI (0.23 g) were taken up in DMF (25 mL), and the resulting solution was stirred at 100° C. (12 h). The solution was partitioned between EtOAc and water. The aqueous layer was extracted with EtOAc. The combined organic layers were washed with brine and dried (MgSO$_4$). Filtration and concentration gave a brown oil. The residue was purified via gradient flash chromatography (0-25% EtOAc/hexanes, SiO$_2$) which furnished 1.8 g (45%) of Example 30 as a foam.

Step 5

Example 30 (1.8 g, 3.4 mmol) and proton sponge (147 mg) were taken up in DCM (20 mL) at 25° C. 1-Chloroethyl chloroformate (0.65 mL) was added, and the resulting solution was stirred at 25° C. for 2 h. The solution was evaporated. The residue was taken up in MeOH and heated at reflux (65° C.) for 1 h. The solution was evaporated, and the residue was partitioned between EtOAc and sat. NaHCO$_{3(aq.)}$. The aqueous layer was extracted with EtOAc. The combined EtOAc layers were washed with brine and dried (MgSO$_4$). Filtration and concentration gave a brown oil. The residue was purified via gradient flash chromatography (0-10% MeOH/CH$_2$Cl$_2$, SiO$_2$) which furnished 0.54 g (45%) of Example 31 as a foam.

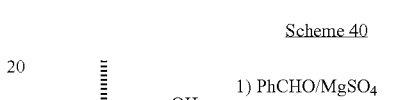

Scheme 40

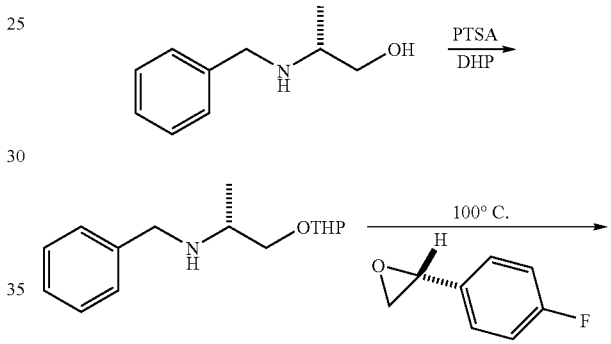

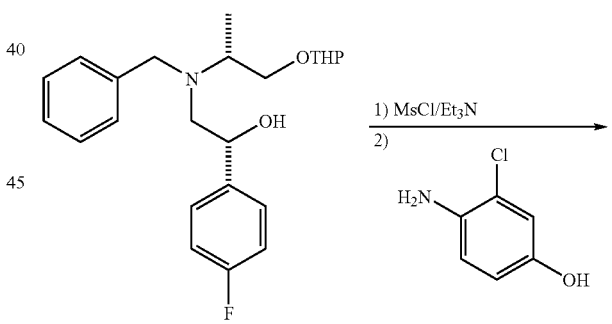

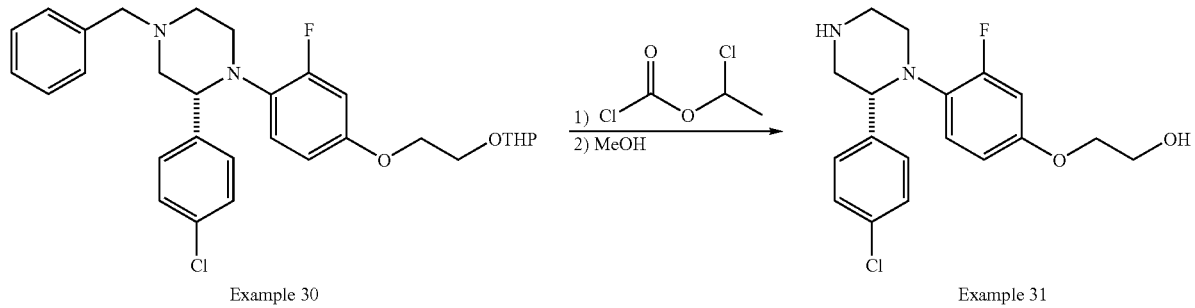

Example 30 → Example 31

-continued

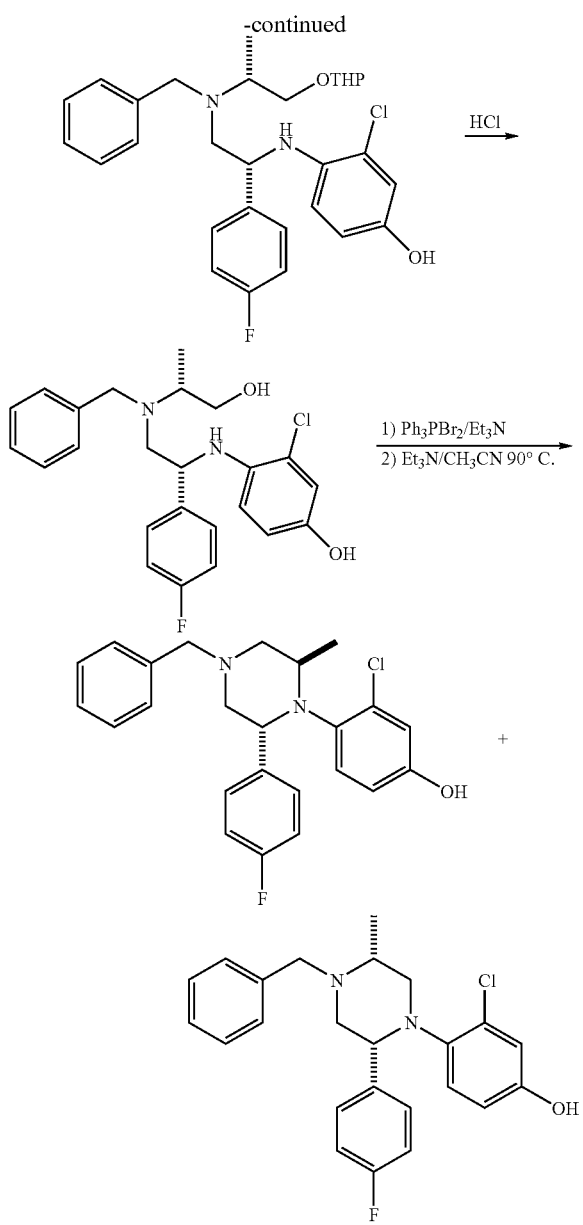

C. for 18 h. The solution was concentrated, and the residue was quenched carefully with 3 M HCl $_{(aq.)}$ (gas evolution/exotherm). The aqueous acidic layer was extracted with Et$_2$O (4×200 mL). The aqueous layer was cooled to 0° C. and made basic via addition of NaOH pellets (pH=11-12). The aqueous layer was extracted with DCM. The combined DCM layers were dried (MgSO$_4$). Filtration and concentration gave 30.4 g (79%) of the amino-alcohol as a white solid.

Step 2

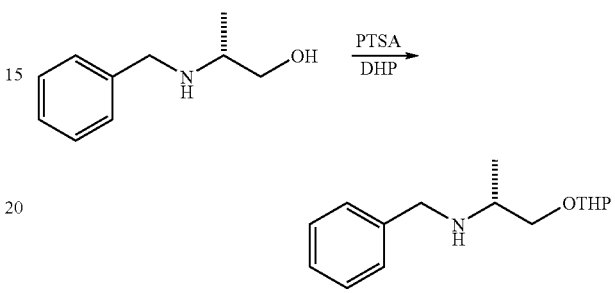

The amino-alcohol (20 g, 121 mmol), PTSA (28 g, 145 mmol), and DHP (20.3 g, 242 mmol) were taken up in DCM and stirred at 25° C. for 17 h. The solution was concentrated, and the residue was washed with K$_2$CO$_3$/water solution (50 g/200 ml). The mixture was stirred at 25° C. for 0.5 h. The layers were separated, and the aqueous layer was extracted with DCM. The combined DCM layers were dried (MgSO$_4$). Filtration and concentration gave a yellow oil. The residue was purified via gradient flash chromatography (0-10% MeOH in DCM, SiO$_2$) which furnished 30g (Quant.) of the THP protected alcohol as a yellow oil.

Step 3

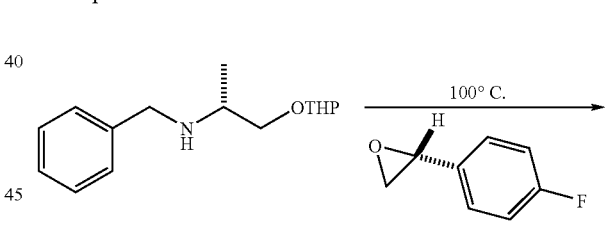

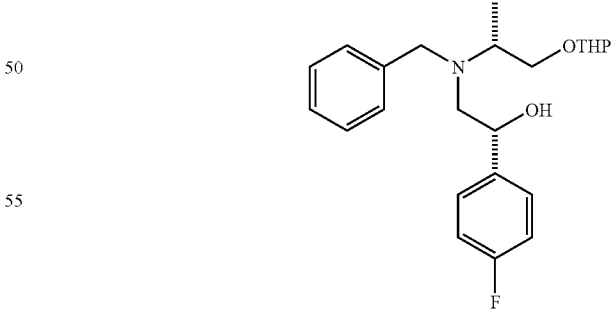

Step 1

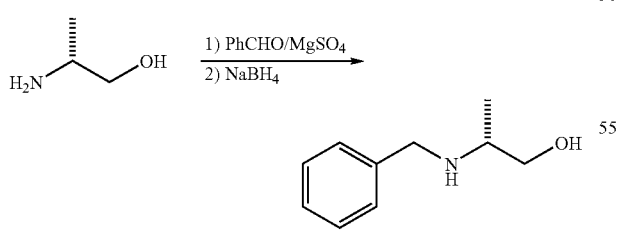

(R)-Alaninol (17.5 g, 233 mmol), PhCHO (30 g, 280 mmol), and MgSO$_4$ (40 g) were taken up in DCM and stirred at 25° C. for 19 h. The solution was filtered and concentrated which furnished a yellow solid. The residue was taken up in MeOH and cooled to 0° C. Sodium borohydride (11 g, 288 mmol) was added in portions to the solution at 0° C. (gas evolution). After the addition, the solution was stirred at 25°

The THP protected alcohol (18 g, 72 mmol) and epoxide (10 g, 72 mmol) were heated neat in a sealed tube at 100° C. for 18 h. The residue was purified via gradient flash chromatography (0-25% EtOAc/hexanes, SiO$_2$) which gave 10.6 g (38%) of the amino-alcohol as a yellow oil.

Step 4

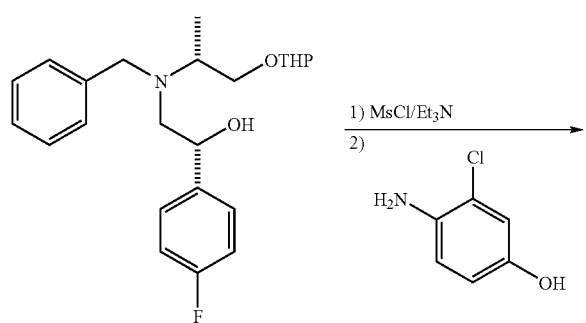

The amino-alcohol (10.6 g, 27.4 mmol) and Et₃N (3.9 g, 39 mmol) were taken up in DCE (100 mL), and the solution was cooled to 0° C. Methansulfonyl chloride (2.3 mL, 30 mmol) was added dropwise to the solution at 0° C. After 15 minutes, more Et3N (5.5 g) and 4-amino-3-chloro phenol (4.5 g, 31.5 mmol) were added, and the resulting solution was heated at 85° C. for 3 h. The solution was diluted with DCM and washed with sat. NaHCO₃ $_{(aq)}$. The aqueous layer was extracted with DCM. The combined organic layers were dried (MgSO₄). Filtration and concentration gave a brown oil. Ther residue was purified via gradient flash chromatography (0-25% EtOAc/hexanes, SiO₂) which gave 13.3 g, (95%) of the aniline as a thick oil.

Step 5

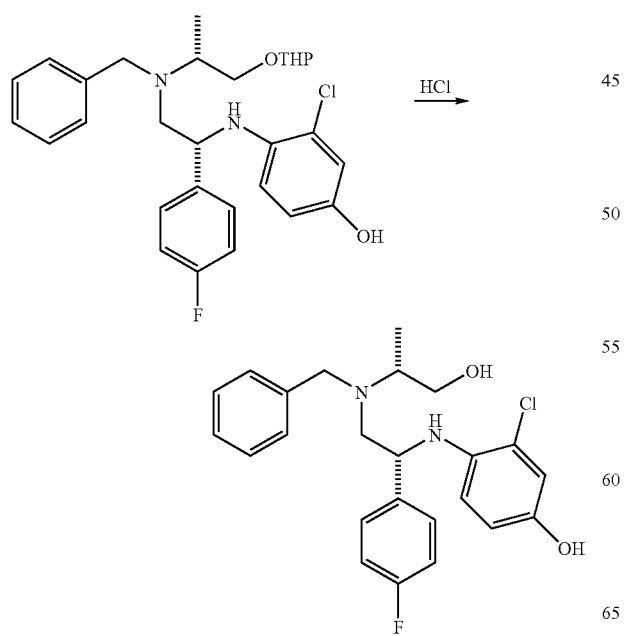

The THP protected alcohol (13.3 g, 26 mmol) was taken up in MeOH (60 mL) and 3 N HCl $_{(aq.)}$ (40 mL), and the resulting solution was stirred at 25° C. for 3 h. The solution was concentrated. The residue was partitioned between EtOAc and water. Solid Na₂CO₃ was added until the aqueous layer was basic (pH=8, gas evolution). The aqueous layer was extracted with EtOAc. The combined EtOAc layers were washed with brine and dried (MgSO₄). Filtration and concentration gave a yellow oil. The residue was purified via gradient flash chromatography (0-35% EtOAc/hexanes, SiO₂) which gave 9.1 g (82%) of the alcohol as a thick oil.

Step 6

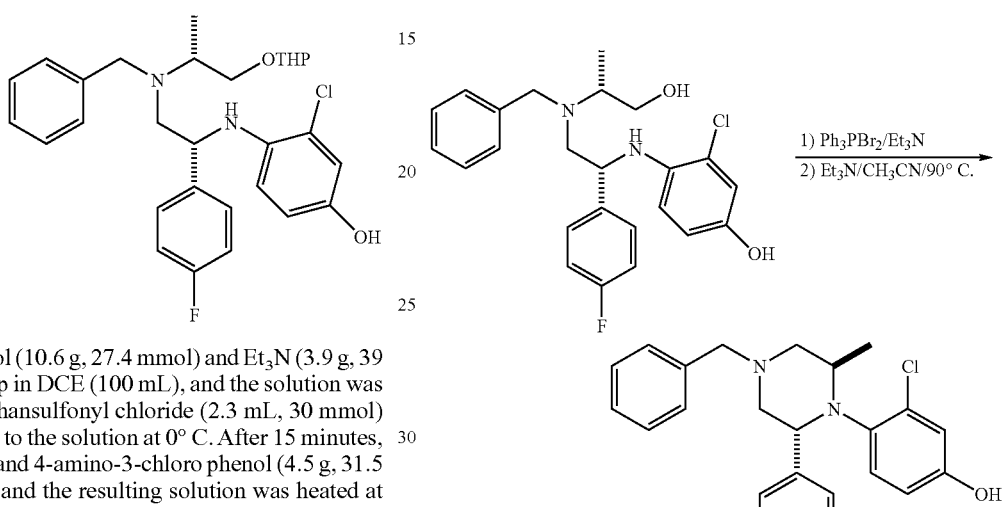

The alcohol (9.1 g, 21.3 mmol) and Et₃N (3 g) were taken up in DCM (100 mL) at 0° C. Triphenylphosphine dibromide (11.2 g, 26.6 mmol) was added at 0° C. The solution was warmed to 25° C. and stirred at that temperature for 1 h. The solution was concentrated. The residue and Et₃N (5.9 mL) were taken up in CH₃CN (100 mL), and the solution was heated at 90° C. for 18 h. The solution was concentrated, and the residue was partitioned between EtOAc and sat. NaHCO₃ $_{(aq)}$. The aqueous layer was extracted with EtOAc. The combined organic layers were washed with brine and dried (MgSO₄). Filtration and concentration gave a brown oil. The residue was purified via gradient flash chromatography (0-5% EtOAc/hexanes, SiO₂) which provided 2.1 g (24%) of the 2,6-subsituted piperazine and 2.9 g (34%) of the 2,5-substituted piperazine as foams.

Scheme 41
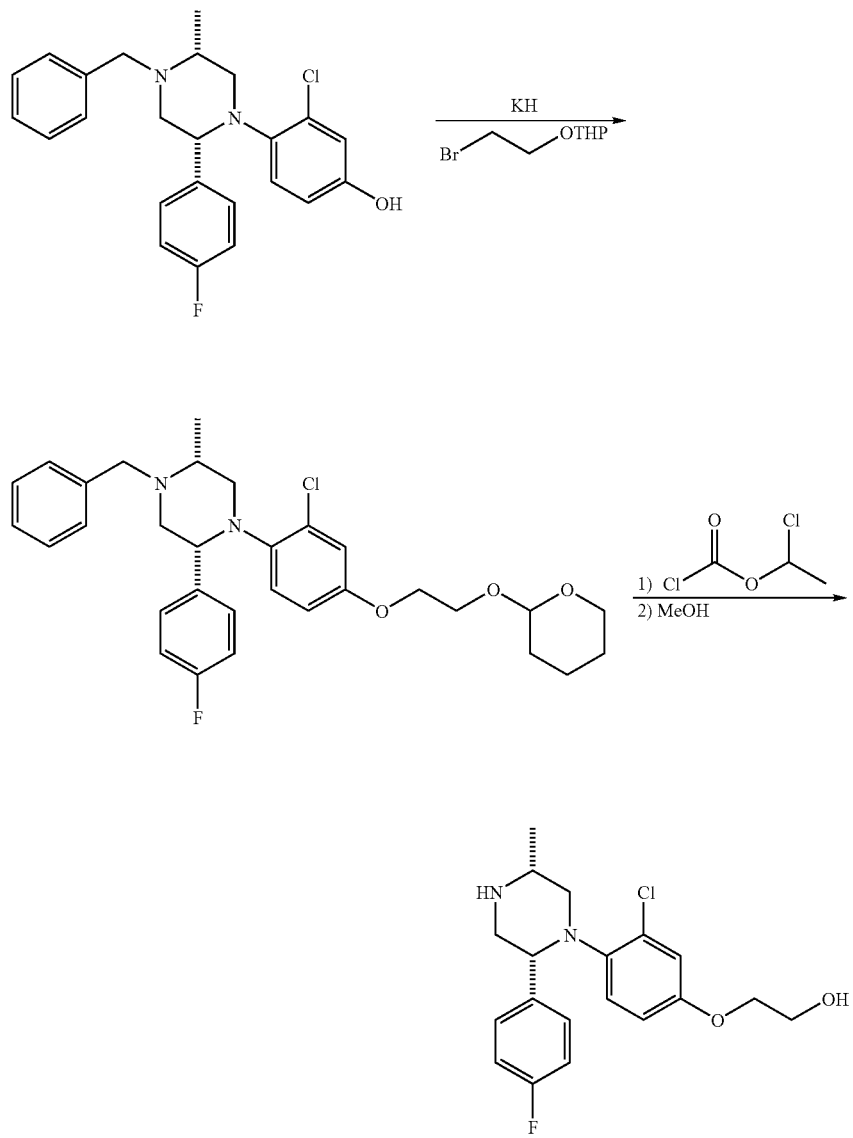
Example 32
Step 1
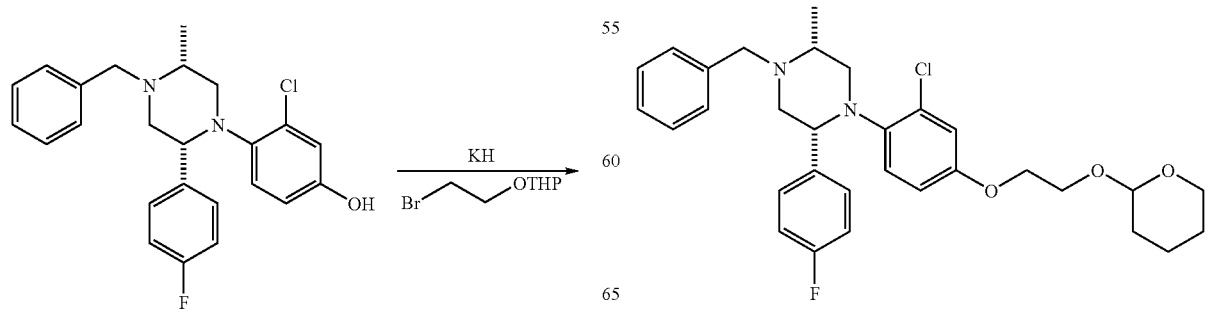
-continued

The 2,5-disubstituted piperazine (2.9 g, 7.07 mmol) was taken up in DMF (20 mL) and cooled to 0° C. Potassium hydride (1.4 g of a 30% wt. dispersion in oil) was added at 0° C. The solution was stirred at 0° C. for 15 minutes. The bromide (2.2 g, 10.6 mmol) was added at 0° C. The solution was warmed to 25° C. and stirred at that temperature for 2 h. The reaction was quenched with water (gas evolution). The mixture was extracted with EtOAc. The combined EtOAc layers were washed with brine and dried (MgSO$_4$). Filtration and concentration gave a yellow oil. The residue was purified via gradient flash chromatography (0-30% EtOAc/hexanes, SiO$_2$) which provided 3-35 g (88%) of the THDP protected alcohol as a yellow oil.

Step 2

10.9 mmol) were taken up in DCE (50 mL) and heated at 90° C. for 2 h. The solution was stirred an additional 18 hours at 25° C. The solution was evaporated, and the residue was taken up in MeOH and heated at 85° C. for 1 h. Aqueous 4 M HCl (3 mL) was added, and the resulting solution was heated at 85° C. for 2 h. The solution was concentrated. The residue was partitioned between sat. NaHCO$_3$ $_{(aq.)}$ and EtOAc. The aqueous layers was extracted with EtOAc. The combined EtOAc layers were washed with brine and dried (MgSO$_4$). Filtration and concentration gave a brown oil. The residue was purified via gradient flash chromatography (0-10% MeOH/DCM, SiO$_2$) which furnished 660 mg (29%) of Example 32 as a yellow foam.

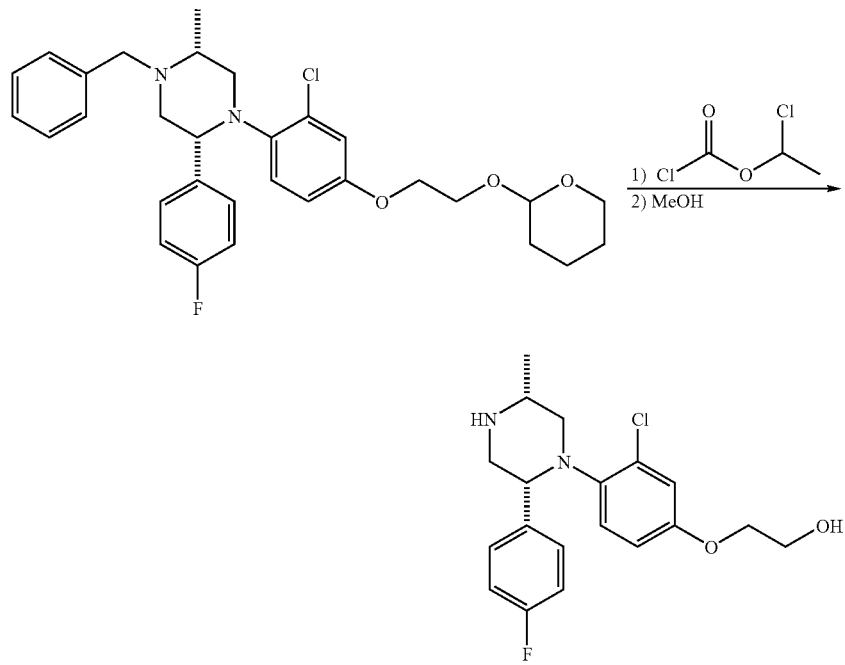

The THP protected alcohol (3.35 g, 6.22 mmol), proton sponge (400 mg), and 1-chloroethyl-chloroformate (1.56 g,

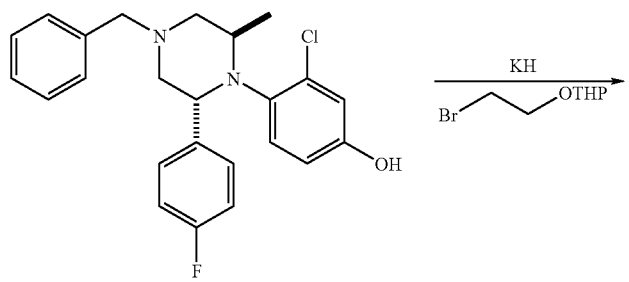

Scheme 42

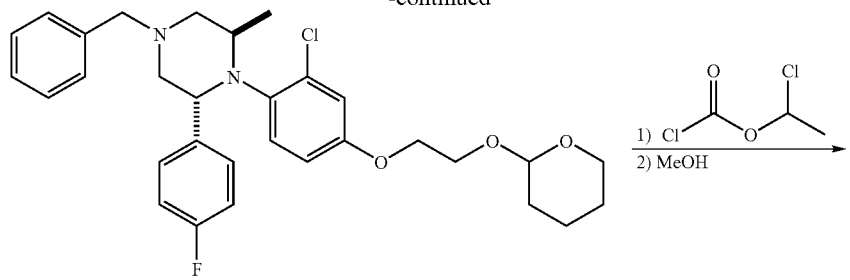
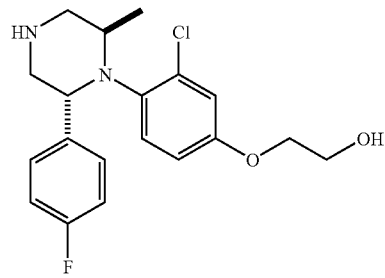
Example 33
Step 1
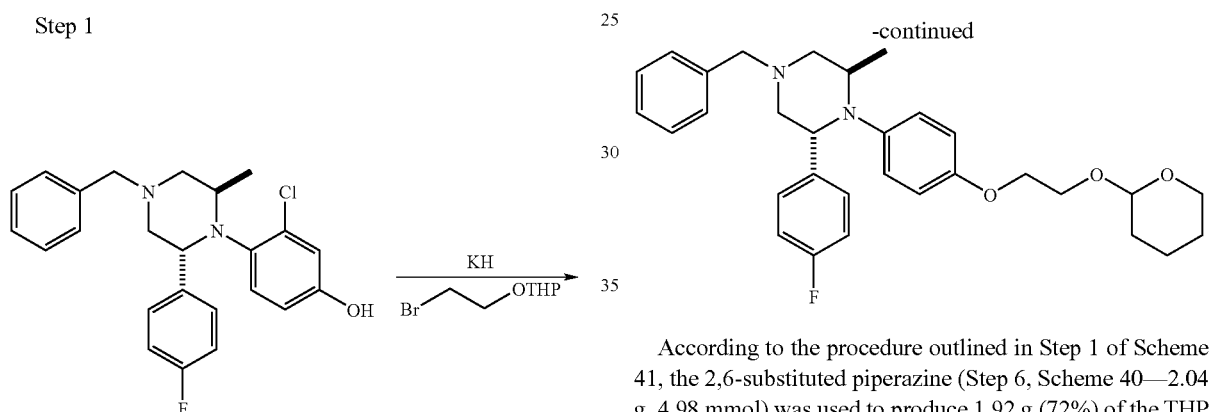
According to the procedure outlined in Step 1 of Scheme 41, the 2,6-substituted piperazine (Step 6, Scheme 40—2.04 g, 4.98 mmol) was used to produce 1.92 g (72%) of the THP protected alcohol as a yellow oil.
Step 2
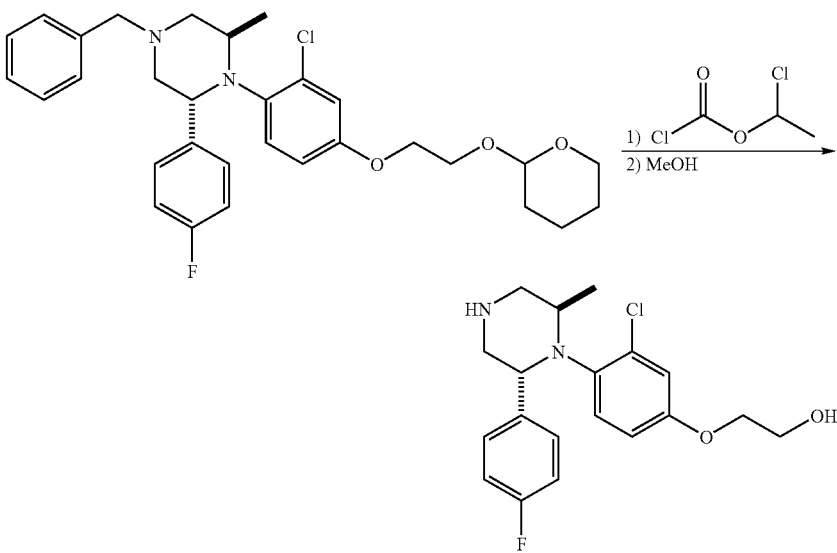
Example 33

According to the procedure outlined in Step 2 of Scheme 41, the THP alcohol (1.9 g, 3.5 mmol) was used to produce 0.68 g (53%) of Example 33 as a foam.
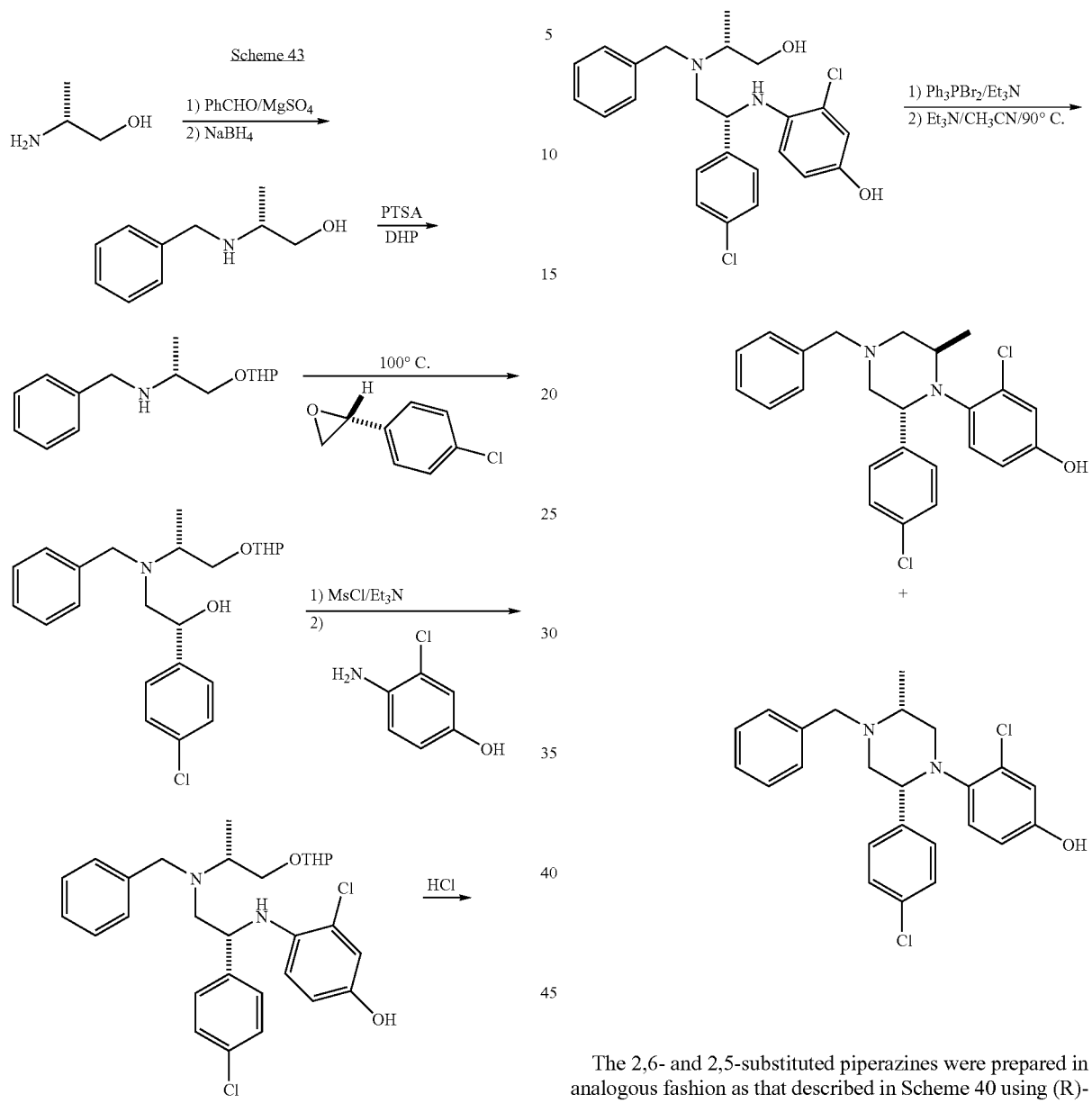
The 2,6- and 2,5-substituted piperazines were prepared in analogous fashion as that described in Scheme 40 using (R)-2-(4-Chloro-phenyl)-oxirane in Step 3 (Scheme 43).
Scheme 44
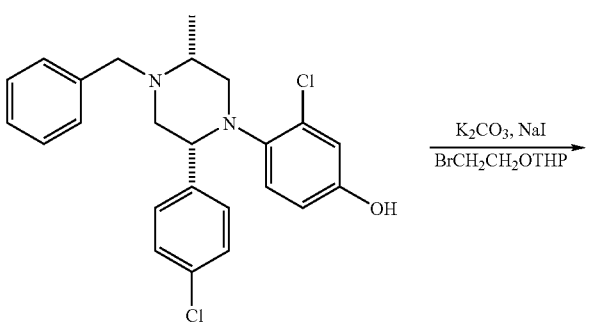

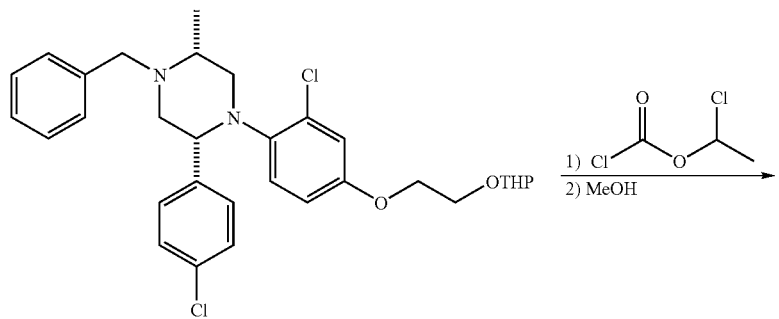

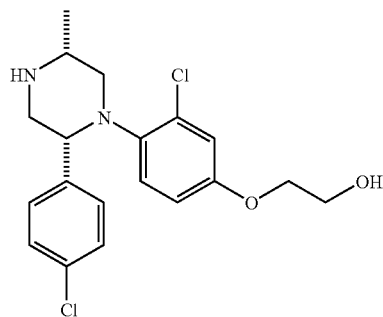

Example 34

Step 1

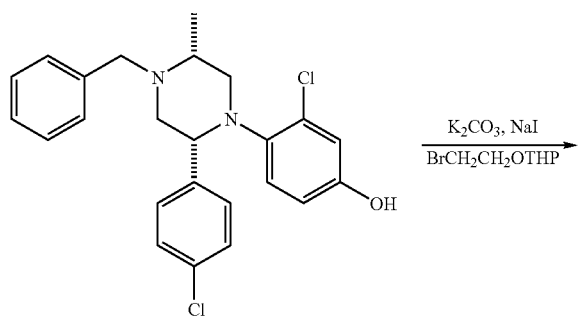

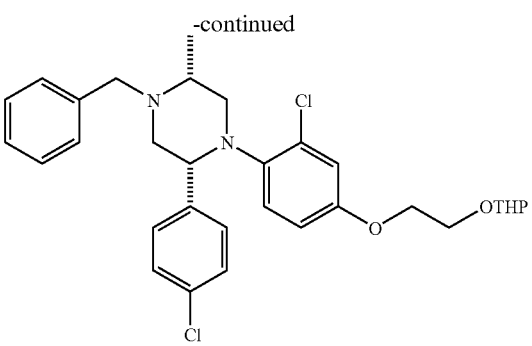

The phenol (3.3 g, 7.8 mmol), BrCH$_2$CH$_2$OTHP (2.5 g), K$_2$CO$_3$ (2.7 g), and NaI (230 mg) were taken up in DMF (20 mL) and heated to 100° C. for 30 h. The mixture was partitioned between EtOAc and water. The aqueous layer was extracted with EtOAc. The combined organic layers were washed with brine and dried (MgSO4). Filtration and concentration gave a brown oil. The residue was purified via gradient flash chromatography (0-30% EtOAc/hexanes, SiO$_2$) which gave 2.76 g (64%) of the THP protected alcohol as a foam.

Step 2

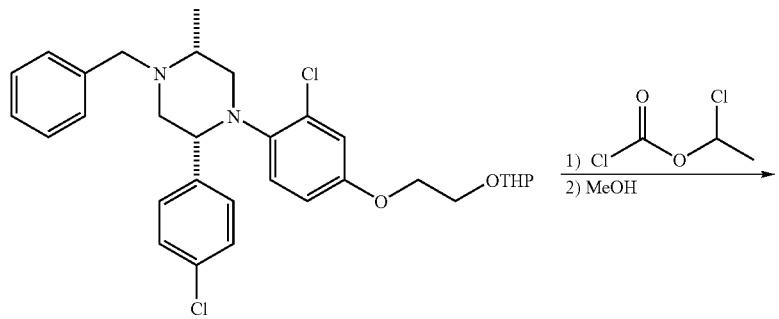

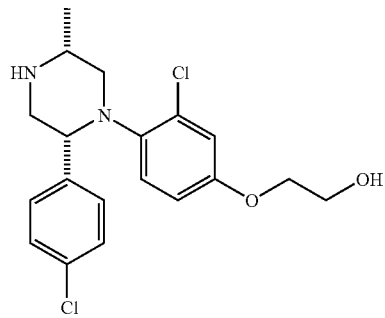

Example 34

The THP protected alcohol (2.76 g, 4.99 mmol), 1-chloroethyl chloroformate (1 25 g), and proton sponge (300 mg) were taken up in DCE (40 mL) and heated at 90° C. for 2 h. The solution was concentrated, and the residue was taken up in MeOH. The solution was heated at 85° C. for 1 h. The solution was concentrated. The residue was partitioned between DCM and sat. NaHCO$_3$ $_{(aq.)}$. The aqueous layer was extracted with DCM. The combined organic layers were washed with brine and dried (MSgSO$_4$). Filtration and concentration gave a brown oil. The residue was purified via gradient flash chromatography (0-10 MeOH/DCM, SiO$_2$) which gave 1.47 g (77%) of Example 34 as a yellow foam.

Scheme 45

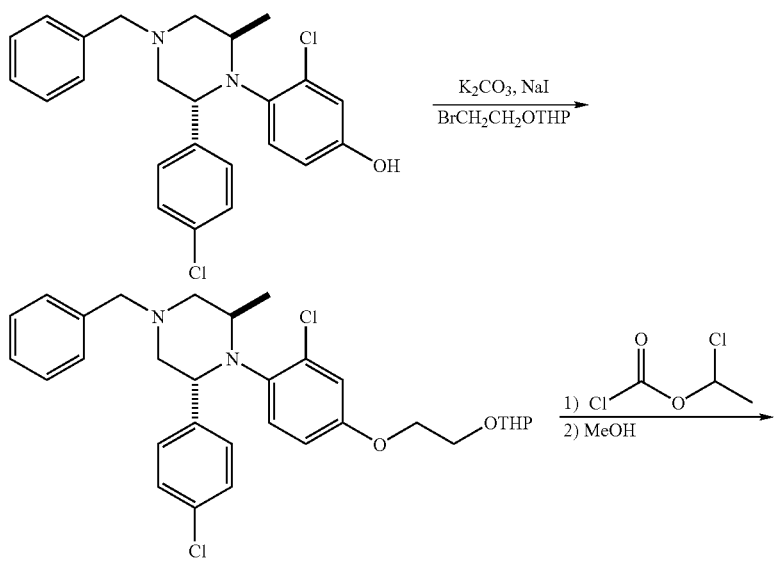

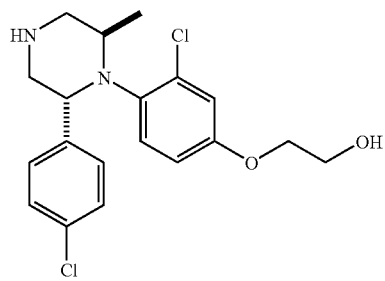

Example 35

Step 1

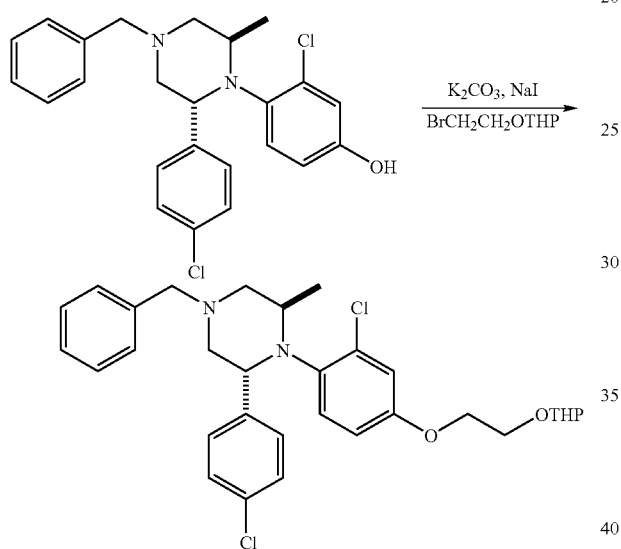

The phenol (2.15 g, 5.04 mmol), BrCH$_2$CH$_2$OTHP (1.37 g, 6.55 mmol), K$_2$CO$_3$ (1.74 g, 12.6 mmol), and NaI (151 mg) were taken up in DMF (10 mL) and heated to 100° C. for 18 h. More of the bromide was added (0.5 mL), and the solution was heated an additional 24 hours at 100° C. The mixture was partitioned between EtOAc and water. The aqueous layer was extracted with EtOAc. The combined organic layers were washed with brine and dried (MgSO4). Filtration and concentration gave a brown oil. The residue was purified via gradient flash chromatography (0-10% EtOAc/hexanes, SiO$_2$) which gave 2.05 g (73%) of the THP protected alcohol as a foam.

Step 2

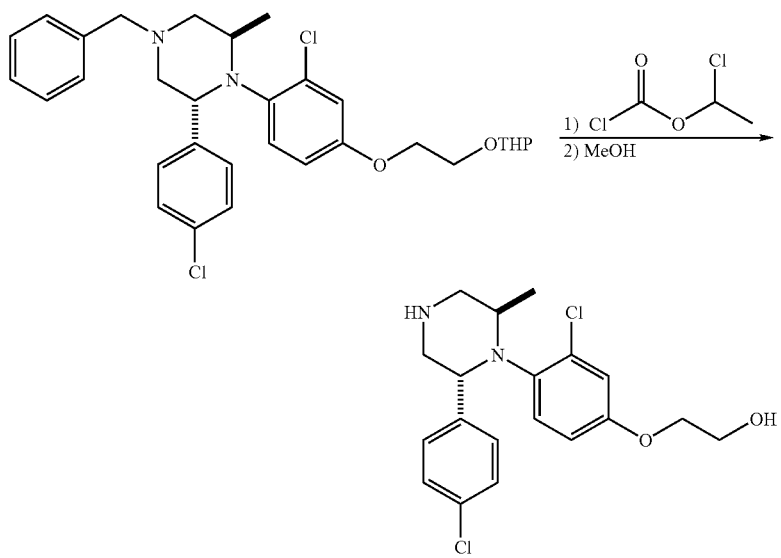

Example 35

The THP protected alcohol (2.05 g, 3.69 mmol), 1-chloroethyl chloroformate (0.84 g, 5.9 mmol), and proton sponge (160 mg) were taken up in DOCE (20 mL) and heated at 80° C. for 2 h. The solution was concentrated, and the residue was taken up in MeOH. The solution was heated at 85° C. for 1 h. The solution was concentrated. The residue was partitioned between DCM and sat. NaHCO$_{3(aq.)}$. The aqueous layer was extracted with DCMe. The combined organic layers were washed with brine and dried (MgSO$_4$). Filtration and concentration gave a brown oil. The residue was purified via gradient flash chromatography (0-10% MeOH/DCM, SO$_2$) which gave 0.85 g (61%) of Example 35 as a yellow foam.

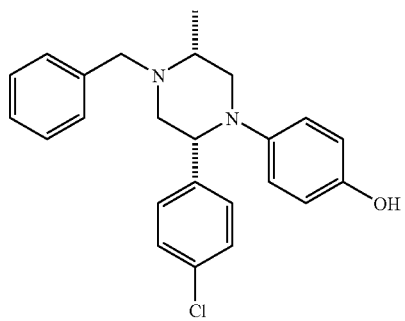 [SMILES: C[C@@H]1CN(c2ccc(O)cc2Cl)[C@H](c2ccc(Cl)cc2)CN1Cc1ccccc1]

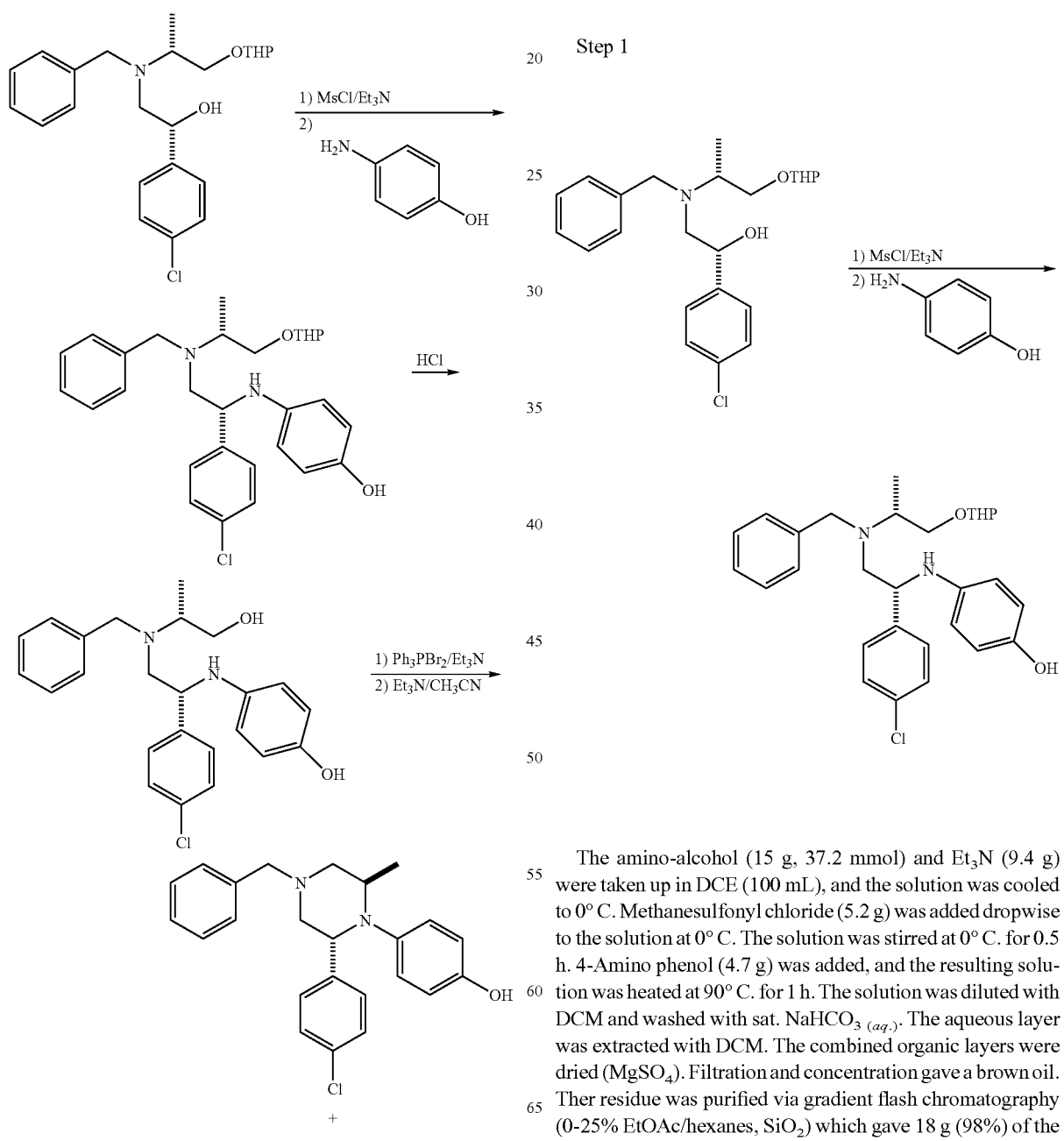

The amino-alcohol (15 g, 37.2 mmol) and Et$_3$N (9.4 g) were taken up in DCE (100 mL), and the solution was cooled to 0° C. Methanesulfonyl chloride (5.2 g) was added dropwise to the solution at 0° C. The solution was stirred at 0° C. for 0.5 h. 4-Amino phenol (4.7 g) was added, and the resulting solution was heated at 90° C. for 1 h. The solution was diluted with DCM and washed with sat. NaHCO$_3$ $_{(aq.)}$. The aqueous layer was extracted with DCM. The combined organic layers were dried (MgSO$_4$). Filtration and concentration gave a brown oil. Ther residue was purified via gradient flash chromatography (0-25% EtOAc/hexanes, SiO$_2$) which gave 18 g (98%) of the aniline as a thick oil.

Step 2

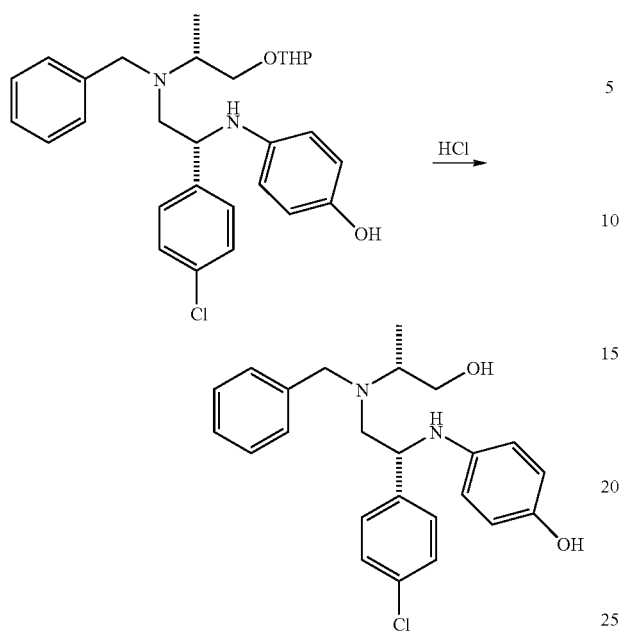

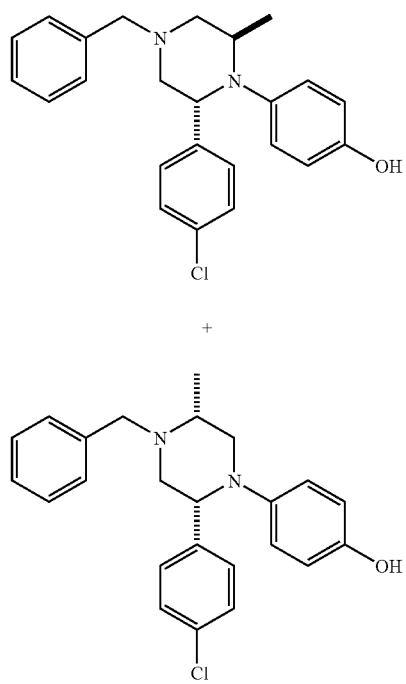

The THP protected alcohol (18 g, 36.4 mmol) was taken up in MeOH (60 mL) and 3 N HCl $_{(aq.)}$ (40 mL), and the resulting solution was stirred at 25° C. for 18 h. The solution was concentrated. The residue was partitioned between EtOAc and water. Solid Na$_2$CO$_3$ was added until the aqueous layer was basic (pH=8, gas evolution). The aqueous layer was extracted with EtOAc. The combined EtOAc layers were washed with brine and dried (MgSO$_4$). Filtration and concentration gave a yellow oil. The residue was purified via gradient flash chromatography (0-25% EtOAc/DCM, SiO$_2$) which gave 5.15 g (35%) of the alcohol as a thick oil.

Step 3

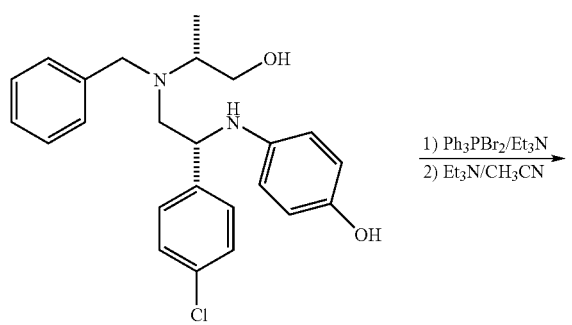

The alcohol (5.15 g, 12.6 mmol) and Et$_3$N (3.2 g) were taken up in DCM (100 mL) at 0° C. Triphenylphosphine dibromide (7.0 g) was added at 0 ° C. The solution was warmed to 25° C. and stirred at that temperature for 2 h. The solution was concentrated. The residue and Et$_3$N (1.9 g) were taken up in CH$_3$CN (100 mL), and the solution was heated at 90° C. for 3 h. The solution was concentrated, and the residue was partitioned between EtOAc and sat. NaHCO$_3$ $_{(aq.)}$. The aqueous layer was extracted with EtOAc. The combined organic layers were washed with brine and dried (MgSO$_4$). Filtration and concentration gave a brown oil. The residue was purified via gradient flash chromatography (0-10% EtOAc/hexanes, SiO$_2$) which provided 1.56 g (32%) of the 2,6-subsituted piperazine and 2.46 g (50%) of the 2,5-subsituted piperazine as foams.

Scheme 47

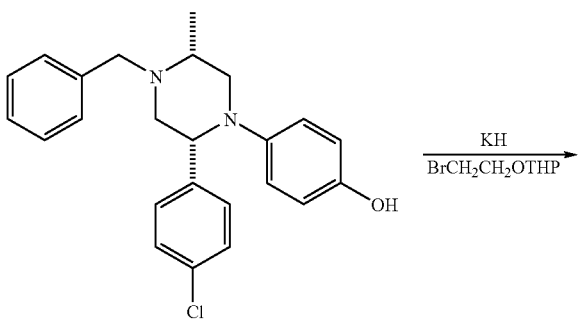

189

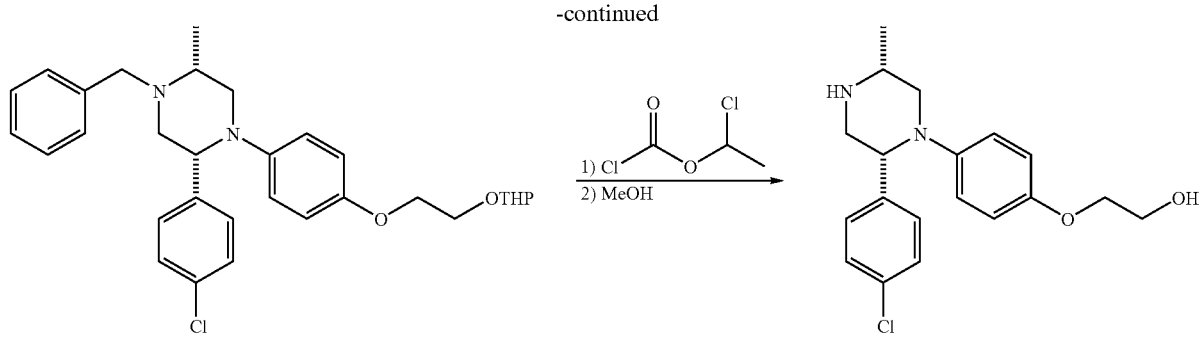

Example 36

Step 1

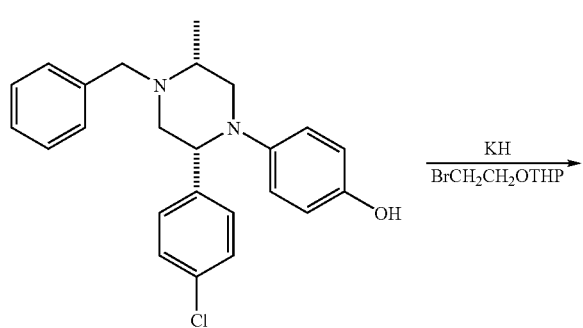

Step 2

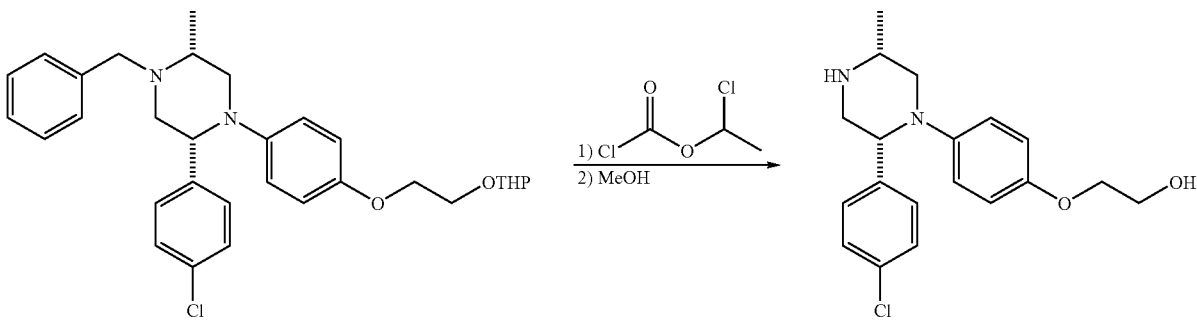

Example 36

-continued

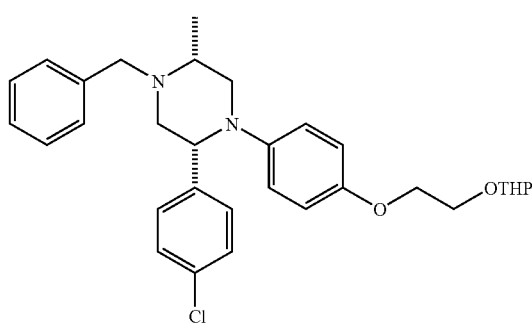

The 2,5-disubstituted piperazine (2.46 g, 6.3 mmol) was taken up in DMF (20 mL) and cooled to 0° C. Potassium hydride (1.7 g of a 30% wt. dispersion in oil) was added at 0° C. The solution was stirred at 0° C. for 15 minutes. The bromide (2.6 g) was added at 0° C. The solution was warmed to 25° C. and stirred at that temperature for 2 h. The reaction was quenched with water (gas evolution). The mixture was extracted with EtOAc. The combined EtOAc layers were washed with brine and dried (MgSO$_4$). Filtration and concentration gave a yellow oil. The residue was purified via gradient flash chromatography (0-30% EtOAc/hexanes, SiO$_2$) which provided 2.68 g (82%) of the THP protected alcohol as a yellow oil.

The THP protected alcohol (2.68 g 5.15 mmol), 1-chloroethyl chloroformate (1.3 g), and proton sponge (330 mg) were taken up in DCE (20 mL) and heated at 90° C. for 2 h. The solution was concentrated, and the residue was taken up in MeOH and 3 mL of 4 M HCl in dioxane was added. The solution was heated at 85° C. for 1 h. The solution was concentrated. The residue was partitioned between DCM and sat. NaHCO$_{3(aq.)}$. The aqueous layer was extracted with DCM. The combined organic layers were washed with brine and dried (MgSO$_4$). Filtration and concentration gave a brown oil. The residue was purified via gradient flash chromatography (0-10% MeOH/DCM, SiO$_2$) which gave 1.25 g (70%) of Example 36 as a yellow foam.

Scheme 48

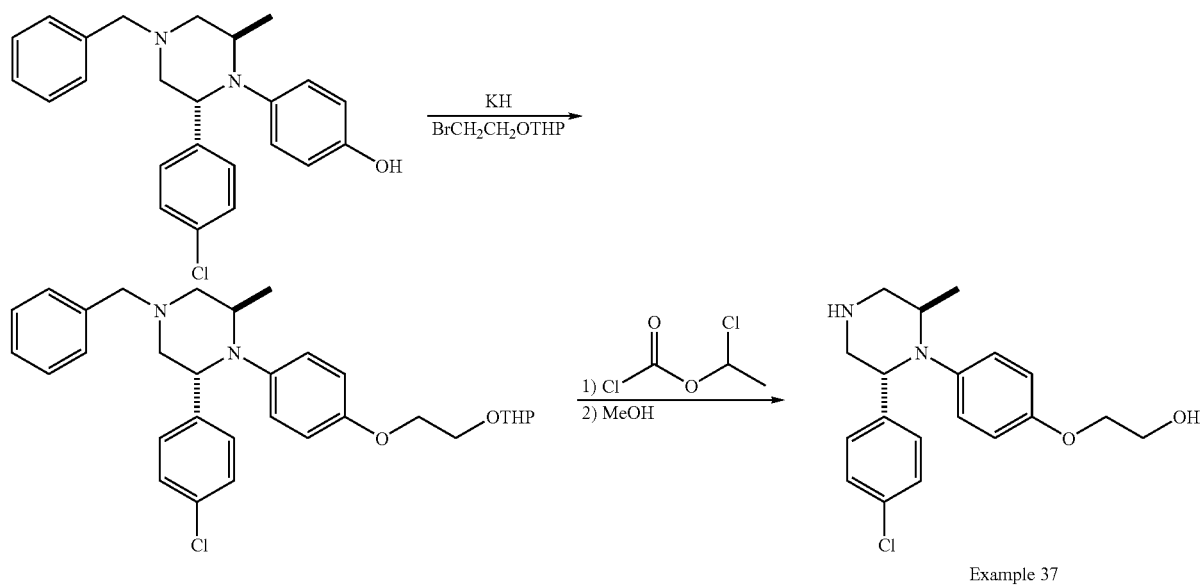

Step 1

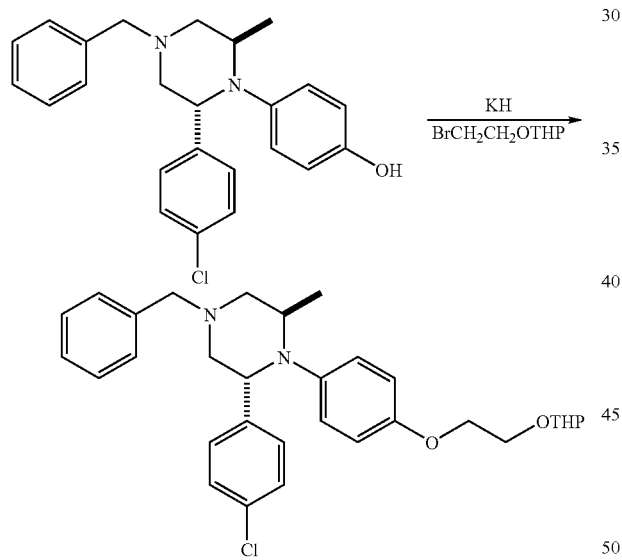

The 2,6-disubstituted piperazine (1.6 g, 4.08 mmol) was taken up in DMF (15 mL) and cooled to 0° C. Potassium hydride (1.1 g of a 30% wt. dispersion in oil) was added at 0° C. The solution was stirred at 0° C. for 15 minutes. The bromide (1.7 g) was added at 0° C. The solution was warmed to 25° C. and stirred at that temperature for 2 h. The reaction was quenched with water (gas evolution). The mixture was extracted with EtOAc. The combined EtOAc layers were washed with brine and dried (MgSO$_4$). Filtration and concentration gave a yellow oil. The residue was purified via gradient flash chromatography (0-30% EtOAc/hexanes, SiO$_2$) which provided 1,26 g (59%) of the THP protected alcohol as a yellow oil.

Step 2

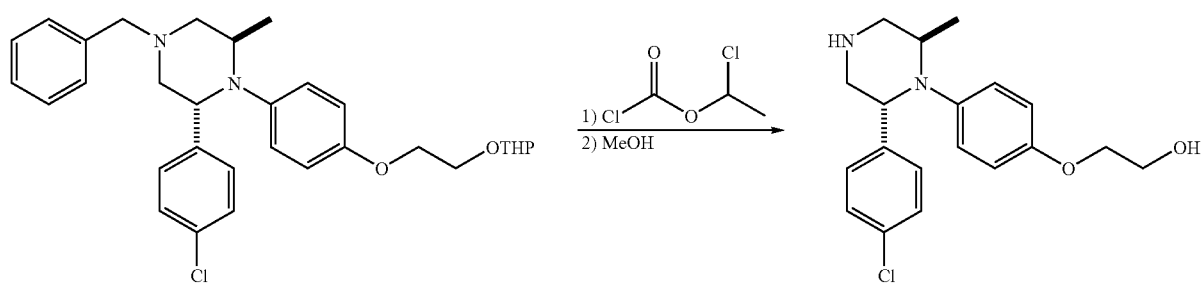

Example 37

The THP protected alcohol (1.26 g, 2.4 mmol), 1-chloroethyl chloroformate (0.6 g), and proton sponge (155 mg) were taken up in DOE (10 mL) and heated at 90° C. for 2 h. The solution was concentrated, and the residue was taken up in MeOH and 1.5 mL of 4 M HCl in dioxane was added. The solution was heated at 85° C. for 1 h. The solution was concentrated. The residue was partitioned between DCM and water. The aqueous layer was extracted with DCM. The combined organic layers were washed with brine and dried (MgSO$_4$). Filtration and concentration gave a brown oil. The residue was purified via gradient flash chromatography (0-10% MeOH/DCM, SiO$_2$) which gave 0.42 g (51%) of Example 37 as a yellow foam.

Scheme 49

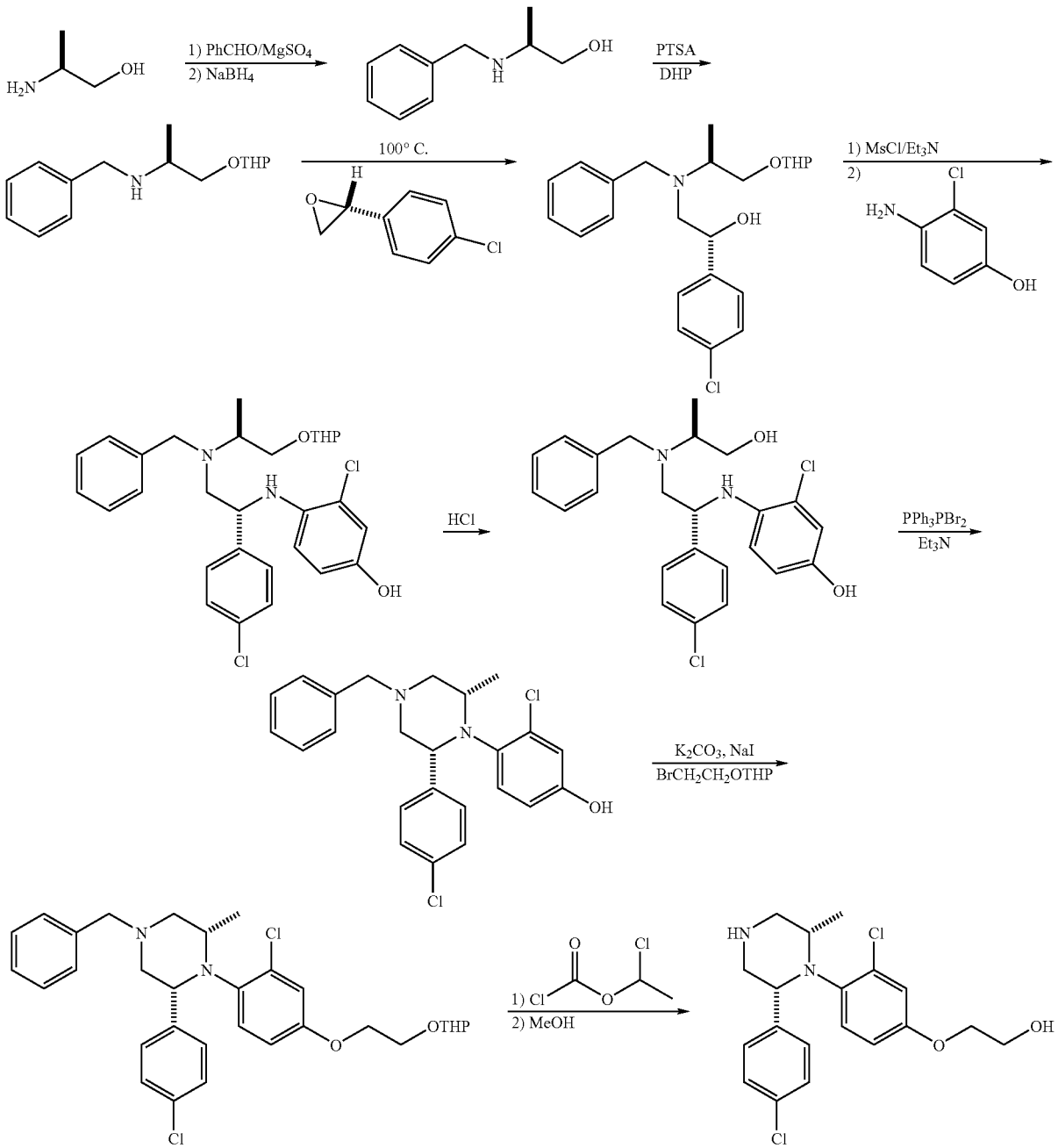

Step 1

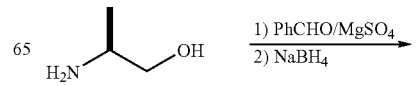

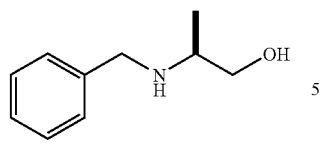

(S)-Alininol (17.5 g, 233 mmol), PhCHO (26 g), and MgSO$_4$ (70 g) were taken up in DCM and stirred at 25° C. for 19 h. The solution was filtered and concentrated which furnished a yellow solid. The residue was taken up in MeOH and cooled to 0° C. Sodium borohydride (11 g, 288 mmol) was added in portions to the solution at 0° C. (gas evolution). After the addition, the solution was stirred at 25° C. for 18 h. The solution was concentrated, and the residue was quenched carefully with 3 M HCl $_{(aq.)}$ (gas evolution/exotherm). The aqueous acidic layer was extracted with Et$_2$O (4×200 mL). The aqueous layer was cooled to 0° C. and made basic via addition of NaOH pellets (pH=11-12). The aqueous layer was extracted with DCM. The combined DCM layers were dried (MgSO$_4$). Filtration and concentration gave 23.2 g (60%) of the amino-alcohol as a white solid.

Step 2

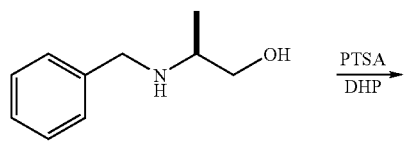

The amino-alcohol (23,2 g, 141 mmol), PTSA (32 g), and DHP (14.2 g) were taken up in DCM and stirred at 25° C. for 17 h. The solution was concentrated, and the residue was washed with K$_2$CO$_3$/water solution (50 g, 200 ml). The mixture was stirred at 25° C. for 0.5 h. The layers were separated, and the aqueous layer was extracted with DCM. The combined DCM layers were dried (MgSO$_4$). Filtration and concentration gave a yellow oil. The residue was purified via gradient flash chromatography (0-10% MeOH in DCM, SiO$_2$) which furnished 23 g (66%.) of the THP protected alcohol as a yellow oil.

Step 3

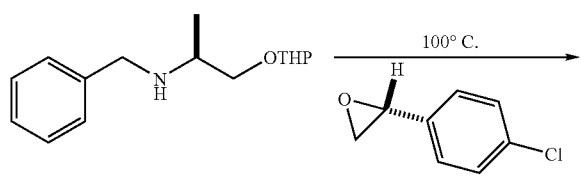

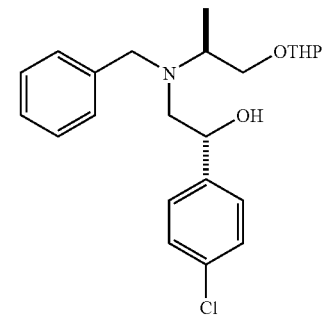

The THP protected alcohol (15 g, 64.7 mmol) and epoxide (10 g, 64.7 mmol) were heated neat in a sealed tube at 100° C. for 18 h. The residue was purified via gradient flash chromatography (0-25% EtOAc/hexanes, SiO$_2$) which gave 15.1 g (58%) of the amino-alcohol as a yellow oil.

Step 4

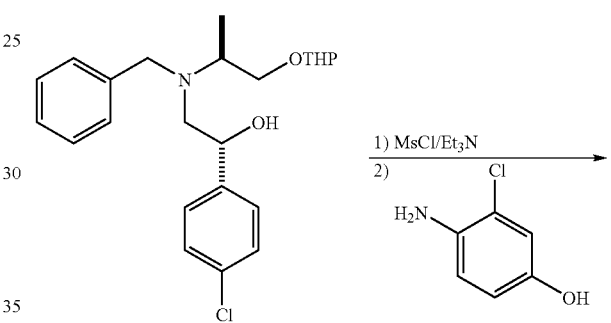

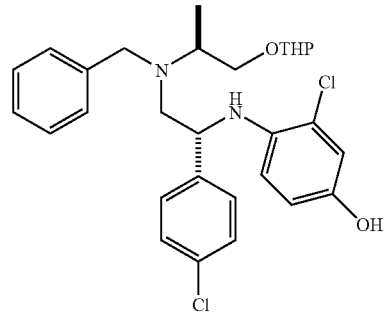

The alcohol (11.2 g, 27.9 mmol) and Et$_3$N (4.2 g) were taken up DCM and cooled to 0° C., Methanesulfonyl chloride (3.4 g) was added to the solution at 0° C. After stirring at 0° C. for 30 minutes, the reaction was diluted with DCM and washed with sat. NaHC$_3$ $_{(aq.)}$. The aqueous layer was extracted with DCM. The combined DCM layers were dried (MgSO$_4$). Filtration and concentration gave a yellow oil. The residue and 4-amino-3-chloro-phenol (4 g) were taken up in DCE and heated at 85° C. for 3 h. The reaction was washed with sat. NaHCO$_3$ $_{(aq.)}$. The aqueous layer was extracted with DCM. The combined organic layers were dried (MgSO$_4$). Filtration and concentration gave a brown oil. The residue was purified via gradient flash chromatography (0-25% EtOAc/hexanes, SIO$_2$) which gave 11.48 g (78%) of the aniline as a foam.

Step 5

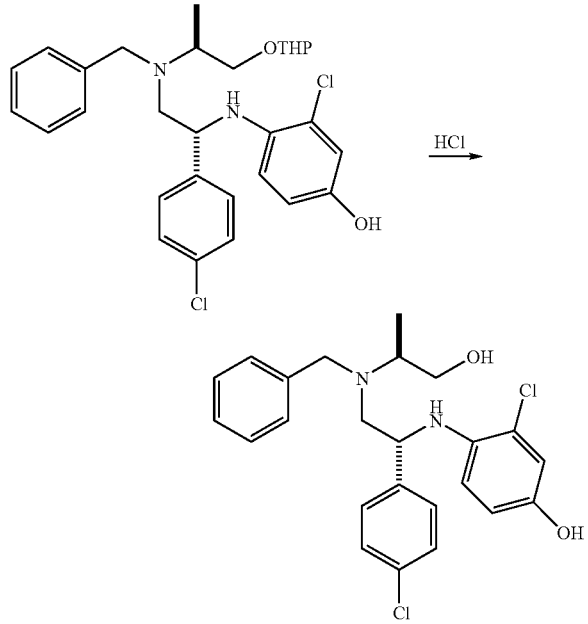

The THP protected alcohol (11.48 g, 21.6 mmol) was taken up in 3 M HCl$_{(aq.)}$ (35 mL) and MeOH (70 mL). The solution was stirred at 25° C. for 2 h. The solution was concentrated. The residue was partitioned between EtOAc and water. Solid Na$_2$CO$_3$ (6 g) was added in portions until the aqueous pH=8-9. The aqueous layer was extracted with EtOAc. The combined organic layers were washed with brine and dried (MgSO$_4$). Filtration and concentration gave a yellow oil. The residue was purified via gradient flash chromatography (15-30% EtOAc/hexanes, SiO$_2$) which provided 8.15 g (85%) of the alcohol as yellow foam.

Step 6

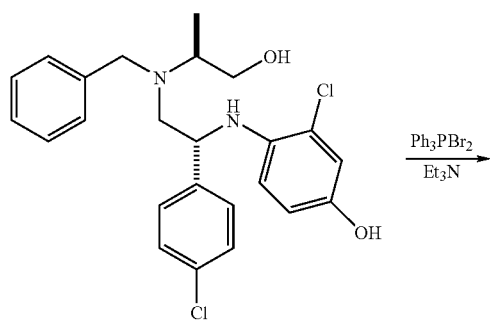

-continued

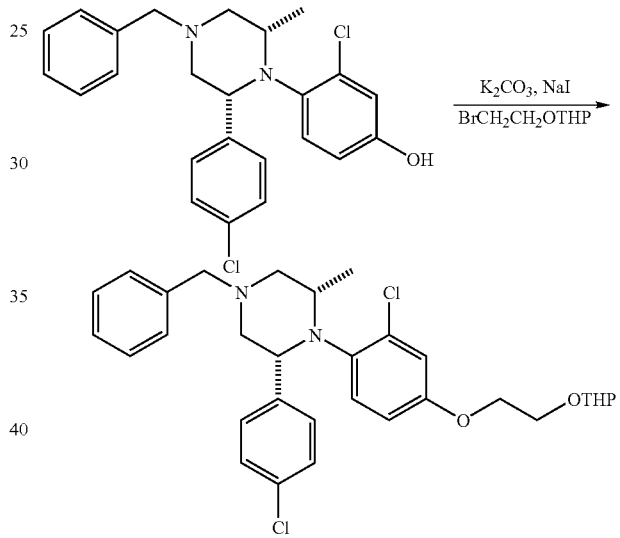

The alcohol (8.15 g, 18.4 mmol) and Et$_3$N (4.64 g) were taken up in DCE (150 mL) at 0° C. Triphenylphosphine dibromide (10.8 g) was added to the solution at 0° C. in portions. After the addition, the reaction was stirred at 25° C. for 2 h. The solution was then heated at 90° C. for 2 h. The solution was diluted with DCM and washed with sat. NaHCO$_3$ $_{(aq.)}$. The aqueous layer was extracted with DCM. The combined organic layers were dried (MgSO$_4$). Filtration and concentration gave a brown oil. The residue was purified via gradient flash chromatography (0-30% EtOAc/hexanes, SiO$_2$) which provided 4.5 g (57%) of the piperazine as a foam.

Step 7

The phenol (4.5 g, 10.6 mmol), BrCH$_2$CH$_2$OTHP (2.7 g), K$_2$CO$_3$ (3.6 g), and NaI (320 mg) were taken up in DMF (15 mL) and heated at 100° C. for 48 h. The mixture was partitioned between EtOAc and water. The aqueous layer was extracted with EtOAc. The combined organic layers were washed with brine and dried (MgSO$_4$). Filtration and concentration gave a brown oil. The residue was purified via gradient flash chromatography (0-30% EtOAc/hexanes, SiO$_2$) which furnished 3.96 g (67%) of the THP protected alcohol as a foam.

Step 8

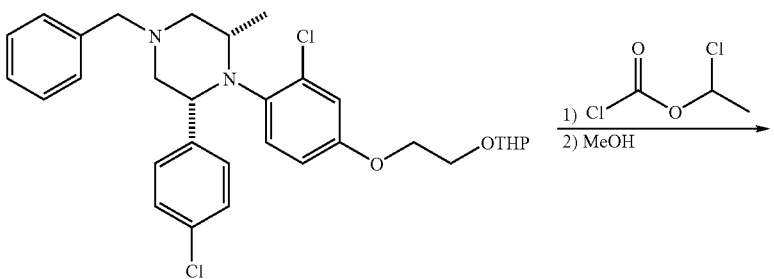

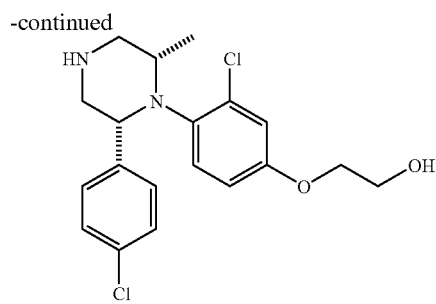

Example 38

The THP protected alcohol (3.0 g, 5,4 mmol) and proton sponge (240 mg) were taken up in DOCE at 25° C. 1-Chloroethyl chloroformate (0.41 g) was added, and the solution was stirred at 25° C. for 3 h. The solution was concentrated, and the residue was heated in MeOH (85° C.) for 1 h. The solution was concentrated. The residue was partitioned between EtOAc and water. The aqueous layer was extracted with EtOAc. The combined organic layers were washed with brine and dried (MgSO$_4$). Filtration and concentration gave a brown oil. The residue was purified via gradient flash chromatography (0-10% MeOH/DCM, SiO$_2$) which gave 1.59 g (77%) of Example 38 as a yellow foam.

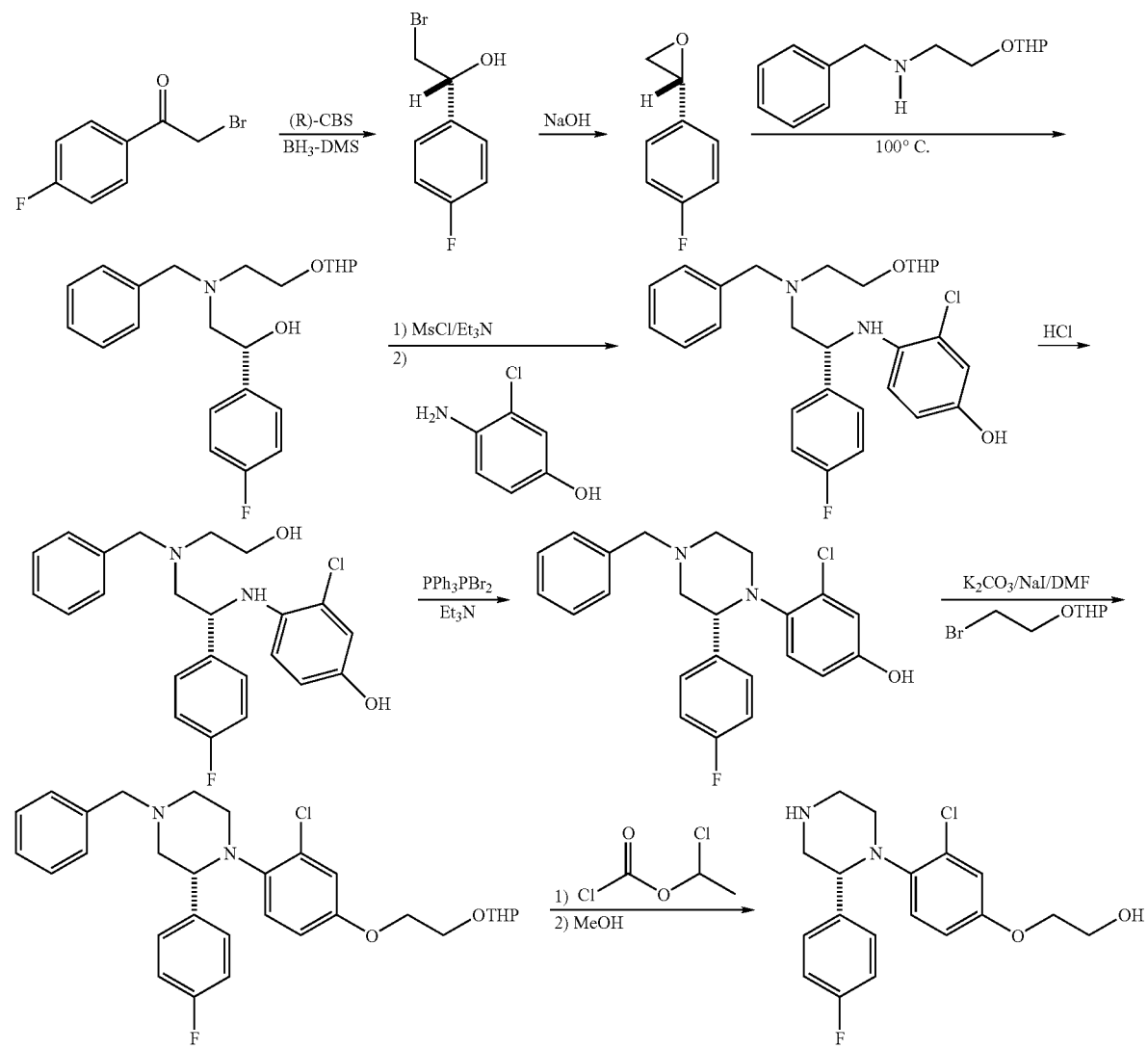

Scheme 50

Example 39

Step 1

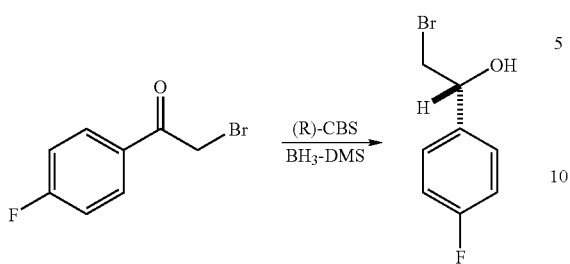

The bromo-acetophenone (15 g, 69 mmol) was taken up in THF (75 mL) at 0° C. (R)-CBS (14 mL of a 1.0 M solution in toluene) was added to the solution at 0° C. Borane-dimethyl sulfide (21 mL of a 2.0 M solution in THE) was added dropwise to the solution at 0° C. The solution was allowed to warm to 25° C. and stir at that temperature for 12 h. The solution was quenched with careful addition of MeOH (15 mL, gas evolution). The solution was concentrated. The residue was partitioned between $CH_2Cl_2$ and 1 N $NaOH_{(aq.)}$. The aqueous layer was extracted with $CH_2Cl_2$. The combined organic layers were dried ($MgSO_4$), filtered, and concentrated. The residue was filtered through a plug of $SiO_2$ rinsing with hexanes/EtOAc (4/1, 1 L). The solution was concentrated to yield 13.8 g (91 %) of the alcohol as a yellow oil.

Step 2

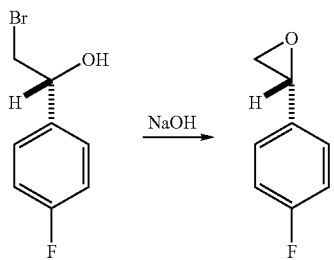 [SMILES: O[C@@H](CBr)c1ccc(F)cc1 ; "NaOH" ; Fc1ccc([C@@H]2CO2)cc1]

The bromo-alcohol (13.8 g, 63 mmol) was partitioned between 3 $NaOH_{(aq.)}$ and $CH_2Cl_2$ (1/1, 360 mL). The mixture was stirred at 25° C. for 4 h. The layers were separated, and the aqueous layer was extracted with $CH_2Cl_2$. The combined organic layers were dried ($MgSO_4$), filtered and concentrated. This yielded 8.7 g (Quant.) of the epoxide as a yellow oil.

Step 3

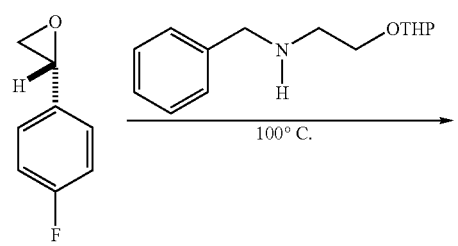

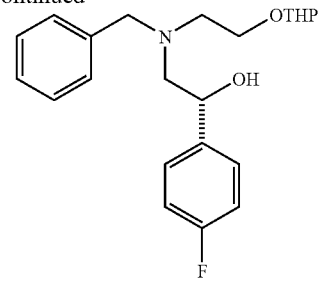

The epoxide (10.5 g, 65 mmol) and the amine (15.3 g, 65 mmol) were heated neat in a sealed tube at 100° C. for 23 h. The residue was purified via gradient flash chromatography (0-35% EtOAc/hexanes, $SiO_2$) which gave 23.7 g (98%) of the amrino-acohol as a yellow oil.

Step 4

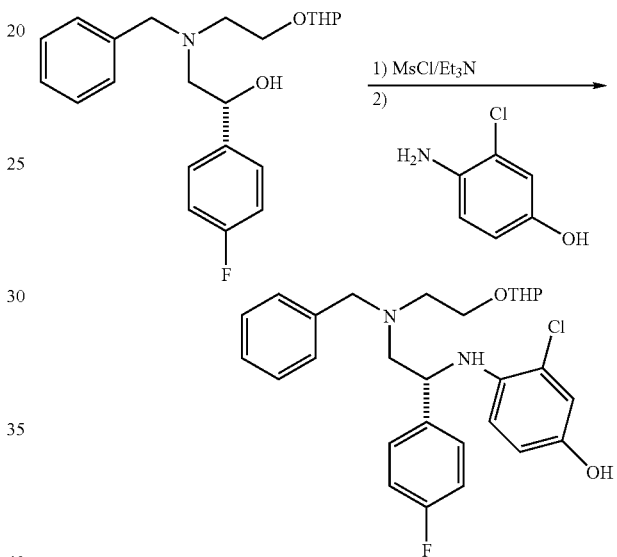

The alcohol (23.7 g, 63.5 mmol) and $Et_3N$ (22 mL, 159 mmol) were taken up in DCE (200 mL) and cooled to 0° C. Methanesulfonyl chloride (5.2 mL, 66.6 mmol) was added dropwise to the solution at 0° C. After the addition, the solution was stirred at 25° C. for 3h. 4-Amino-3-chloro-phenol (10 g, 70 mmol) was added, and the resulting solution was stirred at reflux (90° C.) for 18 h. The solution was diluted with $CH_2Cl_2$ and washed with sat. $NaHCO_{3(aq.)}$. The aqueous layer was extracted with $CH_2Cl_2$. The combined organic layers were dried ($MgSO_4$), filtered, and concentrated. The residue was purified via gradient flash chromatography (0-25% EtOAc/hexanes, $SiO_2$) which gave 29.3 g (92%) of the amine as a yellow oil.

Step 5

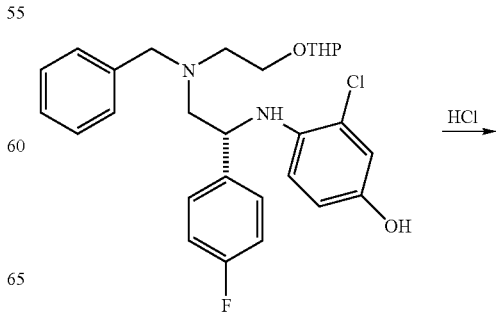

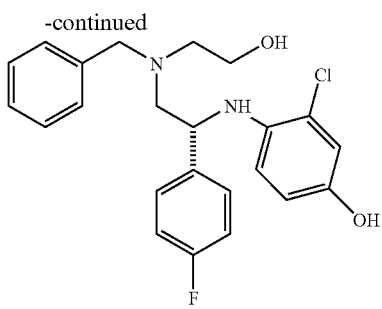

The amine (27.5 g, 55.1 mmol) was taken up in 3 M HCl$_{(aq.)}$ (90 mL) and MeOH (150 mL) and the solution was stirred at 25° C. for 3.5 h. The solution was concentrated. The residue was partitioned between EtOAc and water. Solid Na$_2$CO$_3$ (16 g) was added in portions to the mixture until the aqueous layer pH=8 (gas evolution). The layers were separated, and the aqueous layer was extracted with EtOAc. The combined organic layers were washed with brine and dried (MgSO$_4$). Filtration and concentration gave a yellow oil. The residue was purified via gradient flash chromatography (0-40% EtOAc/hexanes, SiO$_2$) which gave 16 g (70%) of the amino-alcohol as a thick gum.

Step 6

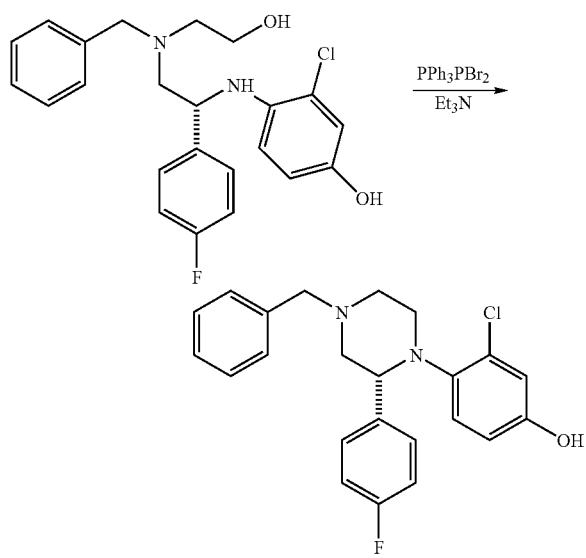

The amino-alcohol (16.7 g, 40 mmol) and Et$_3$N (14 mL, 100 mmol) were taken up in CH$_2$Cl$_2$ (200 mL) and cooled to 0° C. Triphenylphosphine dibromide (22 g, 52 mmol) was added to the solution in portions at 0° C. (slight exotherm). After the addition, the solution was stirred at 25° C. for 3 h. The solution was diluted with CH$_2$Cl$_2$ and washed with sat. NaHCO$_{3(aq.)}$. The aqueous layer was extracted with CH$_2$Cl$_2$. The combined organic layers were dried (MgSO$_4$), filtered, and concentrated. The residue was purified via gradient flash chromatography (0-35% EtOAc/hexanes, SiO$_2$) which provided 14.9 g (93%) of the piperazine as a yellow foam.

Step 7

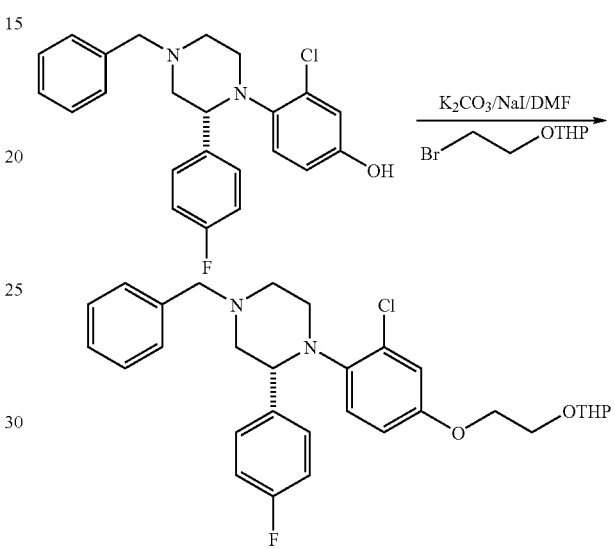

The phenol (3 g, 7.6 mmol), BrCH$_2$CH$_2$OTHP (1.4 mL, 9.45 mmol), K$_2$CO$_3$ (2.6 g, 18.9 mmol), and NaI (230 mg) were taken up in DMF (10 mL) and heated at 100° C. for 17 h. The solution was partitioned between EtOAc and water. The aqueous layer was extracted with EtOAc. The combined EtOAc layers were washed with brine and dried (MgSO$_4$). Filtration and concentration gave a brown oil. The residue was purified via gradient flash chromatography (0-40% EtOAc/hexanes, SiO$_2$) which provided 3.18 g (80%) of the The THP protected alcohol as a thick gum.

Step 8

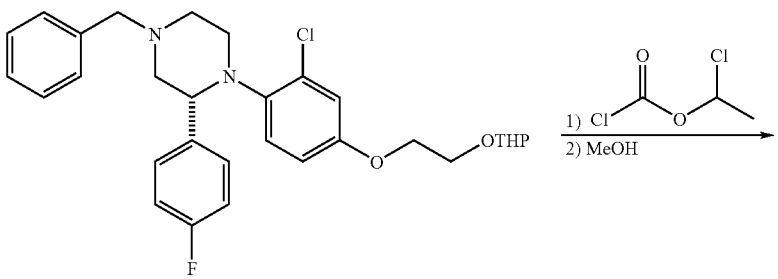

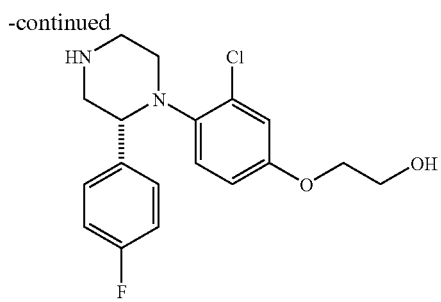

Example 39

The THP protected alcohol (3.2 g, 6.1 mmol) and proton sponge (260 mg) were taken up in CH$_2$Cl$_2$ at 25° C. 1-Chloroethyl chloroformate (1.1 mL, 9.7 mmol) was added, and the solution was stirred at 25° C. for 1.5 h. The solution was concentrated. The residue was taken up in MeOH and heated at 75° C. for 1.5 h. The solution was concentrated. The residue was partitioned between CH$_2$Cl$_2$ and sat. NaHCO$_{3(aq.)}$. The aqueous layer was extracted with CH$_2$Cl$_2$. The combined organic layers were dried (MgSO$_4$). Filtration and concentration gave a brown oil. The residue was purified via gradient flash chromatography (0-10% MeOH/CH$_2$Cl$_2$, SiO$_2$) which provided 1.32 g (62%) of Example 39 as a white foam.

Step 1

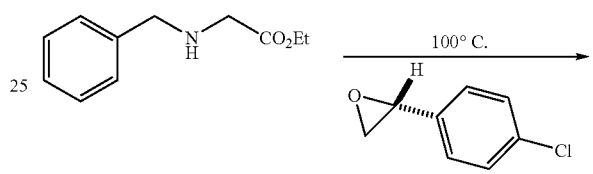

Scheme 51

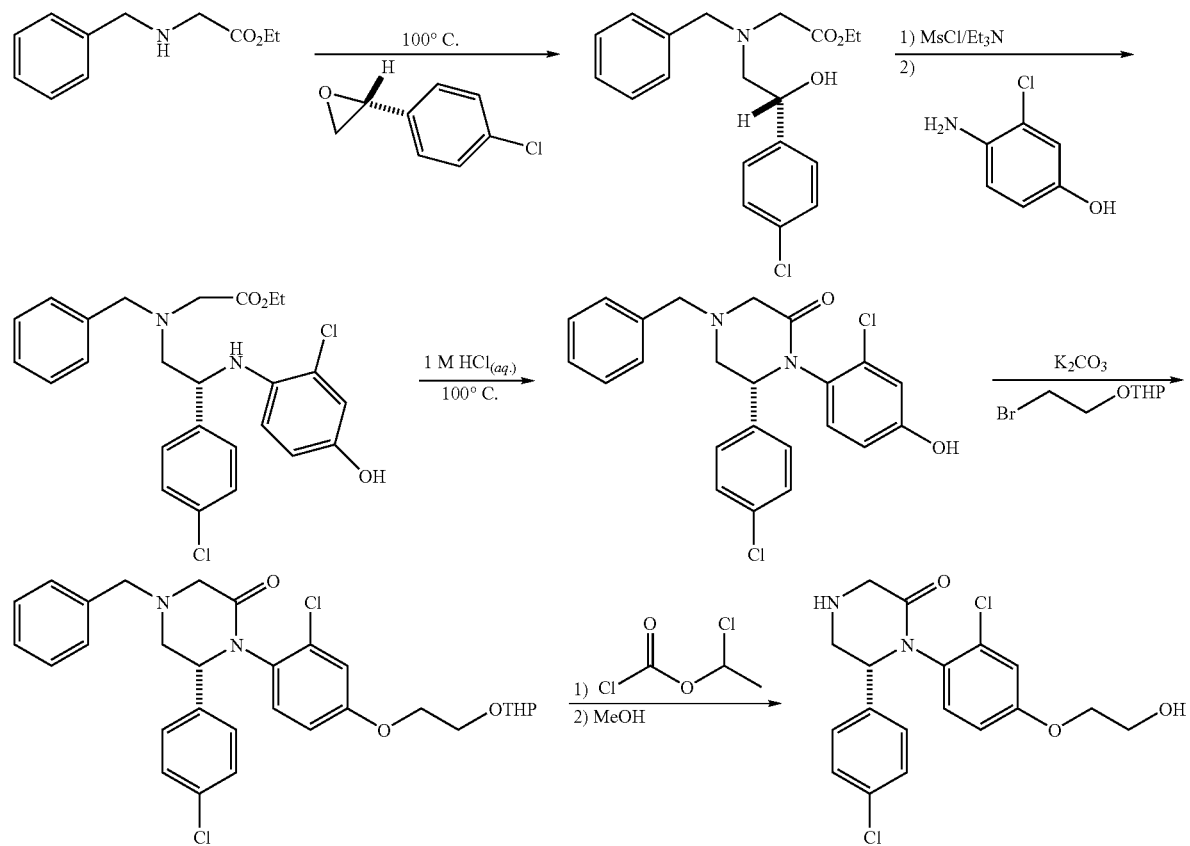

Example 40

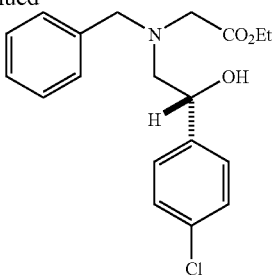

N-Benzyl glycine, ethyl ester (6.2 g, 32 mmol) and (R)-2-(4-chloro-phenyl)-oxirane (5.0 g, 32 mmol) were heated neat in a sealed tube at 110° C. for 19 h.

The residue was purified via gradient flash chromatography (0-15% EtOAc/hexanes, SiO$_2$) which provided 3.9 g (35%) of the alcohol as a yellow oil.

Step 2

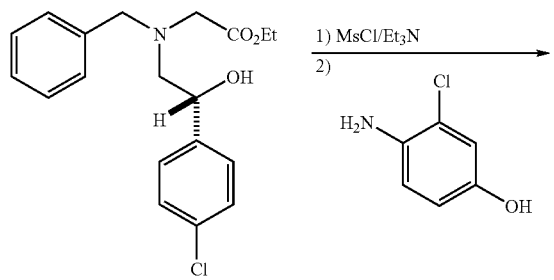

The alcohol (3.4 g, 9.8 mmol) and Et$_3$N (3.4 mL, 24.5 mmol) were taken up in DCE (100 mL) and cooled to 0° C. Methanesulfonyl chloride (0.8 mL, 10 mmol) was added dropwise to the solution at 0° C. After the addition, the solution was stirred at 25° C. for 15 minutes. 4-Amino-3-chloro-phenol (1.5 g, 11 mmol) was added, and the resulting solution was stirred at reflux (90° C.) for 18 h. The solution was diluted with DCM and washed with sat. NaHCO$_{3(aq.)}$. The aqueous layer was extracted with DCM. The combined organic layers were dried (MgSO$_4$), filtered, and concentrated. The residue was purified via gradient flash chromatography (0-20% EtOAc/hexanes, SiO$_2$) which gave 3.9 g (84%) of the amine as a yellow oil.

Step 3

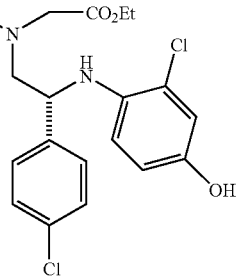

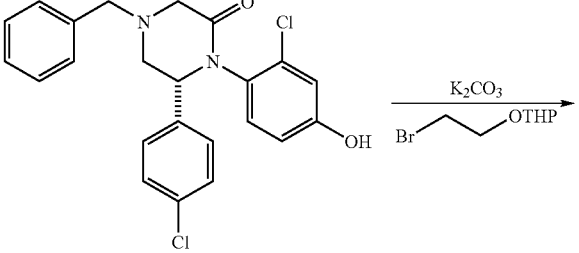

The amine (2.86 g, 6 mmol) was taken up in 1 M HCl$_{(aq.)}$/dioxane (1/1, 60 mL), and the resulting solution was heated at 100° C. for 19 h. The solution was concentrated. The residue was partitioned between EtOAc and sat. NaHCO$_{3(aq.)}$. Solid NaHCO$_3$ was added to ensure complete quench of aq. HCl.

The mixture was stirred at 25° C. for 1 h. The aqueous layer was extracted with EtOAc. The combined organic layers were washed with brine and dried (MgSO$_4$). Filtration and concentration furnished a yellow oil. The residue was purified via gradient flash chromatography (0-35% EtOAc/DCM, SiO$_2$) which gave 2.15 g (83%) of the keto-piperazine as a foam.

Step 4

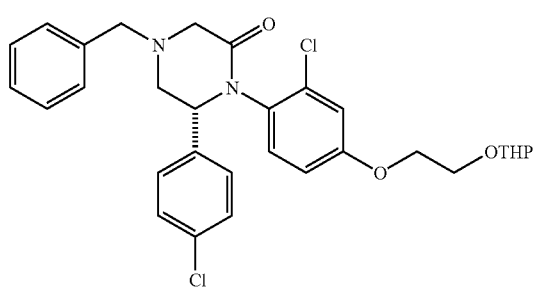

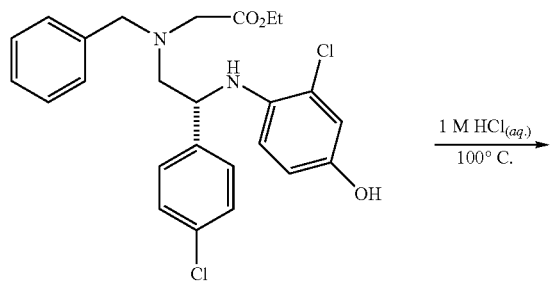

The phenol (2.73 g, 6.4 mmol), K$_2$CO$_3$ (2.64 g), and BrCH$_2$CH$_2$OTHP (2.68 g) were taken up in acetone (20 mL) and heated at 70° C. for 18 h. The solution was concentrated. The residue was partitioned between EtOAc and water. The aqueous layer was extracted with EtOAc. The combined organic layers were washed with brine and dried (MgSO$_4$). Filtration and concentration gave a yellow oil. The residue was purified via gradient flash chromatography (0-25% EtOAc/DCM, SiO$_2$) which provided 2.9 g (82%) of the THP protected alcohol as a yellow foam.

Step 5

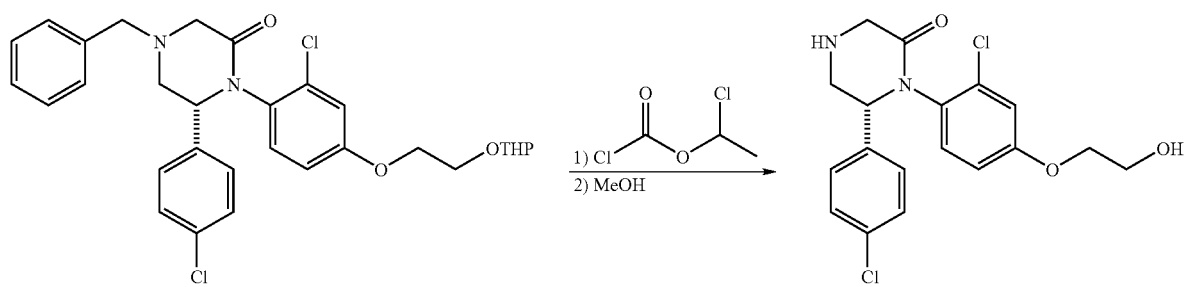

Example 40

The THP protected alcohol (2.9 g, 5.2 mmol), 1-chloroethyl chloroformate (1.3 g), and i-Pr$_2$NEt (1.35 g) were taken up in DCE (10 mL) and heated at 90° C. for 7 h. The solution was concentrated, and the residue was taken up in MeOH and 2 mL of 4 M HCl in dioxane was added. The solution was heated at 85° C. for 1 h. The solution was concentrated. The residue was partitioned between EtOAc and sat. NaHCO$_{3(aq)}$. The aqueous layer was extracted with EtOAc. The combined organic layers were washed with brine and dried (MgSO$_4$). Filtration and concentration gave a brown oil. The residue was purified via gradient flash chromatography (0-10% MeOH/DCM, SiO$_2$) which gave 10 g (50%) of Example 40 as a yellow foam.

Step 1

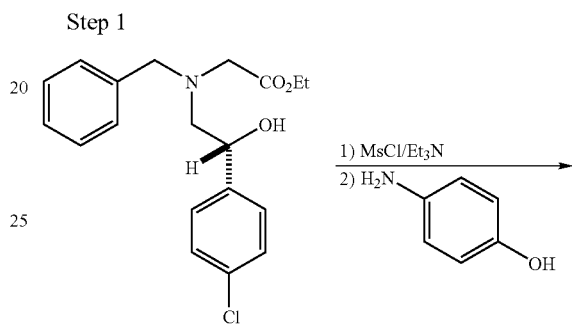

Scheme 52

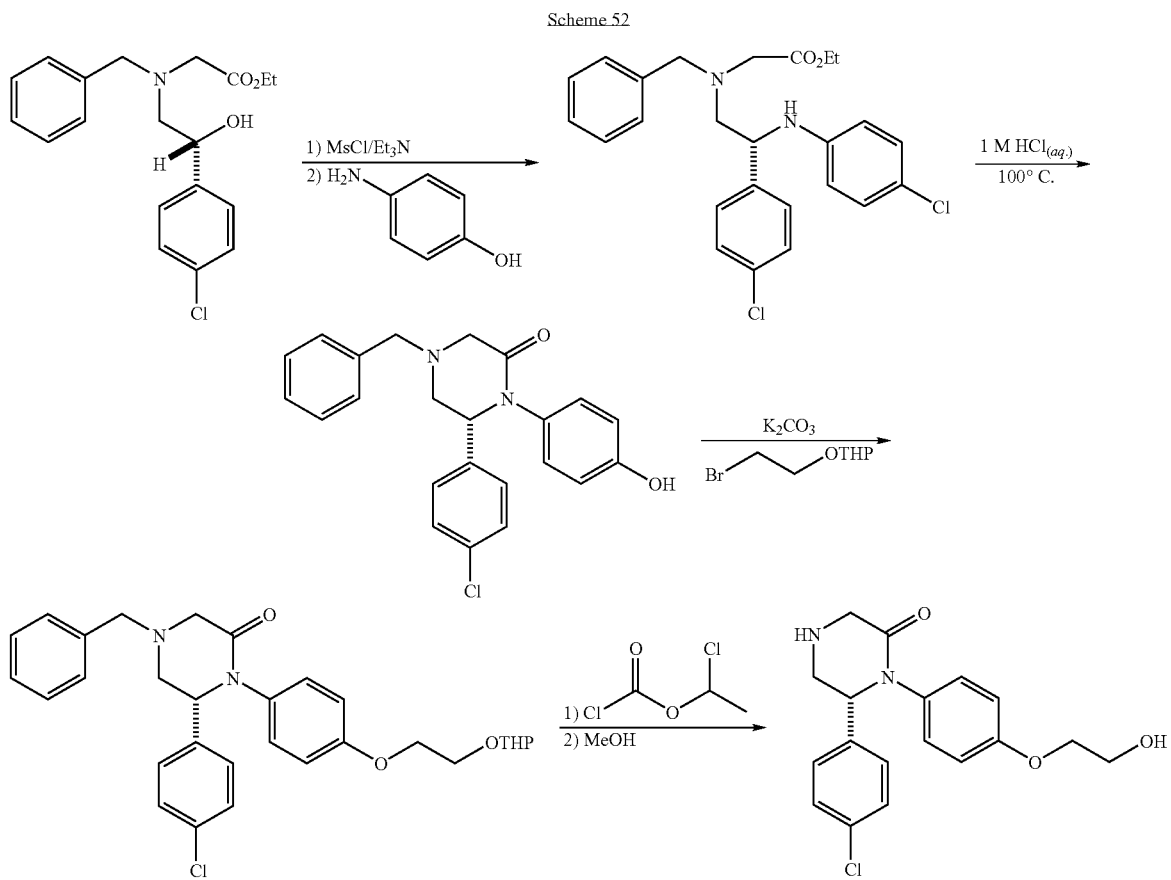

Example 41

-continued

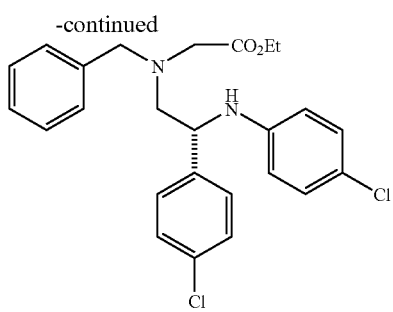

The alcohol (3.9 g, 11 mmol) and Et₃N (3.9 mL, 28 mmol) were taken up in DCE (80 mL) and cooled to 0° C. Methanesulfonyl chloride (0.92 mL, 12 mmol) was added dropwise to the solution at 0° C. After the addition, the solution was stirred at 0° C. for 20 minutes. 4-Amino-phenol (1.35 g, 12 mmol) was added, and the resulting solution was stirred at reflux (85° C.) for 18 h. The solution was diluted with DCM and washed with sat. NaHCO₃(aq). The aqueous layer was extracted with DCM. The combined organic layers were dried (MgSO₄), filtered, and concentrated. The residue was purified via gradient flash chromatography (0-25% EtOAc/hexanes, SiO₂) which gave 4.15 g (84%) of the amine as a yellow oil.

Step 2

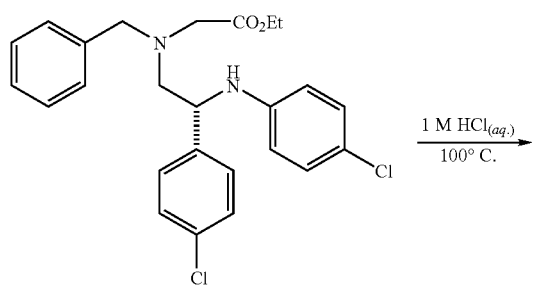

The amine (4.0 g, 9.1 mmol) was taken up in 1 M HCl(aq.)/dioxane (1/1, 80 mL), and the resulting solution was heated at 100° C. for 19 h. The solution was concentrated. The residue was partitioned between EtOAc and sat. NaHCO₃(aq.). Solid NaHCO₃ was added to ensure complete quench of aq. HCl.

The mixture was stirred at 25° C. for 1 h. The aqueous layer was extracted with EtOAc. The combined organic layers were washed with brine and dried (MgSO₄). Filtration and concentration furnished a yellow oil. The residue was purified via gradient flash chromatography (0-50% EtOAc/DCM, SiO₂) which gave 2.96 g (82%) of the keto-piperazine as a foam.

Step 3

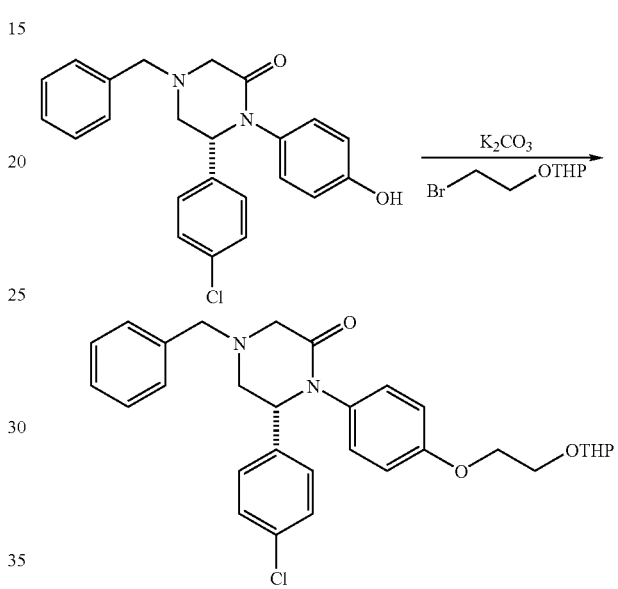

The phenol (2.84 g, 7.2 mmol), K₂CO₃ (3.0 g, 21 mmol), and BrCH₂CH₂OTHP (3.0 g, 14 mmol) were taken up in acetone (80 mL) and heated at 70° C. for 18 h. Sodium iodide (500 mg) and more bromide (0.5 mL) were added, and the resulting mixture was heated at 70° C. for 18 h. The solution was filtered through Celite and concentrated. The residue was purified via gradient flash chromatography (0-35% EtOAc/DCM, SiO₂) which provided 2.65 g (71%) of the THP protected alcohol as a yellow foam.

Step 4

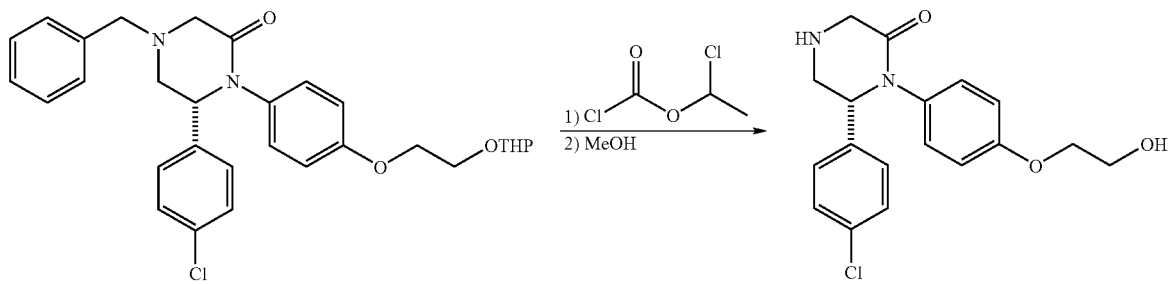

Example 41

The THP protected alcohol (2.65 g, 5.1 mmol), 1-chloroethyl chloroformate (0.9 mL, 8 mmol), and proton sponge (220 mg) were taken up in DCE (10 mL) and heated at 90° C. for 3 h. Additional 1-chloroethyl chloroformate (0.35 mL) and iPr$_2$EtN (2.6 mL) was added, and the solution was heated at 90° C. for 3 h. The solution was concentrated, and the residue was taken up in MeOH. The solution was heated at 85° C. for 1 h. A solution of 4 M HCl/dioxane (5 mL) was added, and the solution was stirred at 25° C. for 2.5h. The solution was concentrated. The residue was partitioned between EtOAc and sat. NaHCO$_{3(aq.)}$. Solid NaHCO$_3$ was added to ensure complete quench of aq. HCl. The aqueous layer was extracted with EtOAc. The combined organic layers were washed with brine and dried (MgSO$_4$). Filtration and concentration gave a brown oil. The residue was purified via gradient flash chromatography (0-15% MeOH/DCM, SiO$_2$) which gave 1.49 g (84%) of Example 41 as a yellow foam.

stirred for 24 h. The EtOH was removed in vacuo. To the aqueous solution was added CH$_2$Cl$_2$ (4 mL) and di-tert-butyl dicarbonate (0.57 g, 2.6 mmol). Stirred at room temperature for 18 h. Acidified the reaction mixture to pH-2 with 1 N HCl, Extracted with DCM. Combined the organics and washed with water and brine. Dried (MgSO$_4$), filtered, and conc. in vacuo. Purified by silica gel chromatography (0-3% MeOH/EtOAc over 30 min.) to provide Ex. 41a as the major product (0.47 g)

Step 2 To Ex. 41a (0.34 g, 0.72 mmol) in DCM (3 mL) at 0° C. was added oxalyl chloride (0.125 mL, 1.4 mmol). Stirred the reaction for 2 h. Added an additional equivalent (0.062 mL) of oxalyl chloride and a drop of DMF. Stirred for another 1 h and added excess ammonium hydroxide. Stirred for 30 minutes. Extracted with EtOAc. Combined organics and washed with water and brine. Dried (MgSO$_4$), filtered, and concentrated in vacuo. The residue was purified by silica gel chromatography (0-10% MeOH/EtOAc over 35 minutes) to provide Ex. 41 b (0.26 g).

Step 3 To Ex. 41 b (0.28 g, 0.6 mmol) in DCM (2 mL) was added 2N HCl/ether (5 mL). Stirred for 18 h and concentrated in vacuo to provide Ex. 41c (0.24 g).

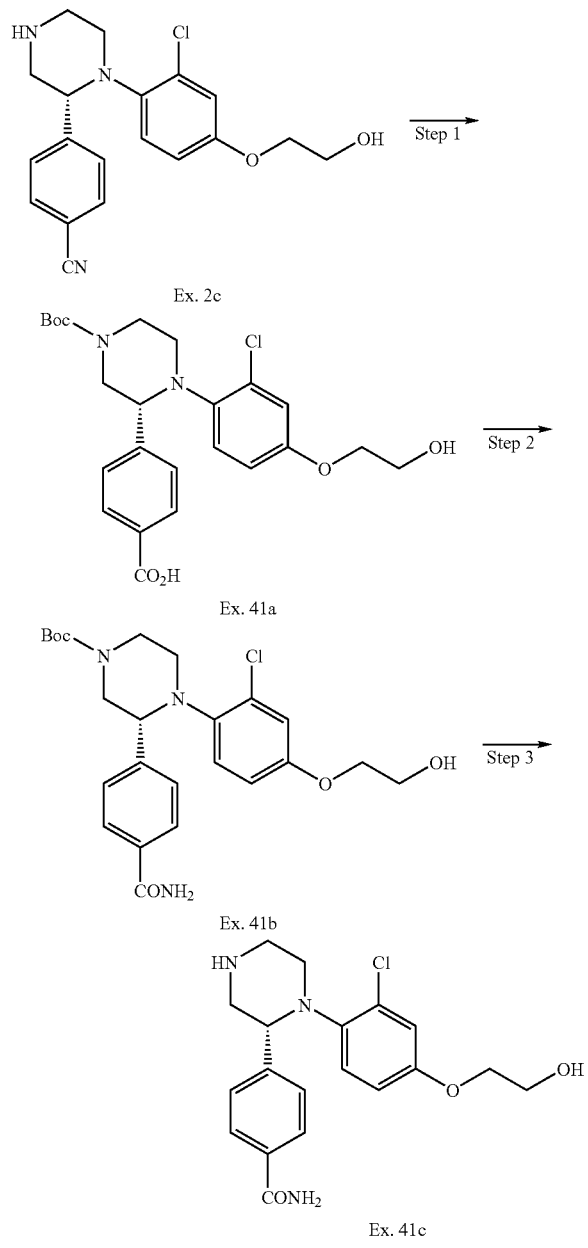

Scheme 52.1

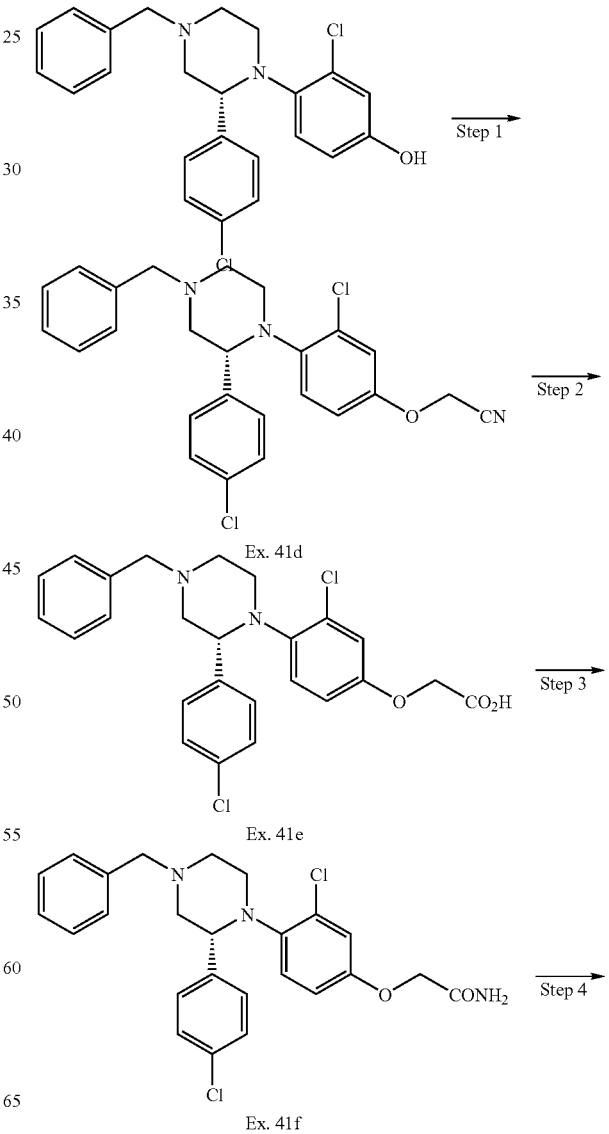

Scheme 52.2

Step 1 To Ex. 2c (0.75 g, 2.1 mmol) in EtOH (3 mL) was added 3N NaOH (5 mL). Warmed the reaction to 90° C. and

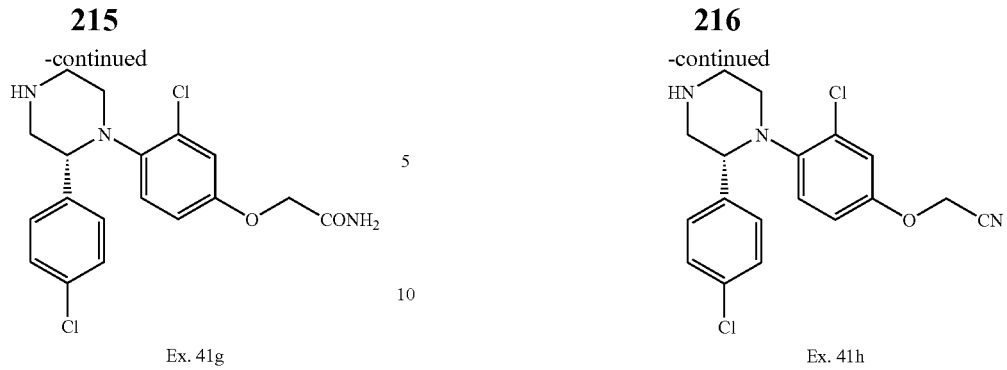

Ex. 41g

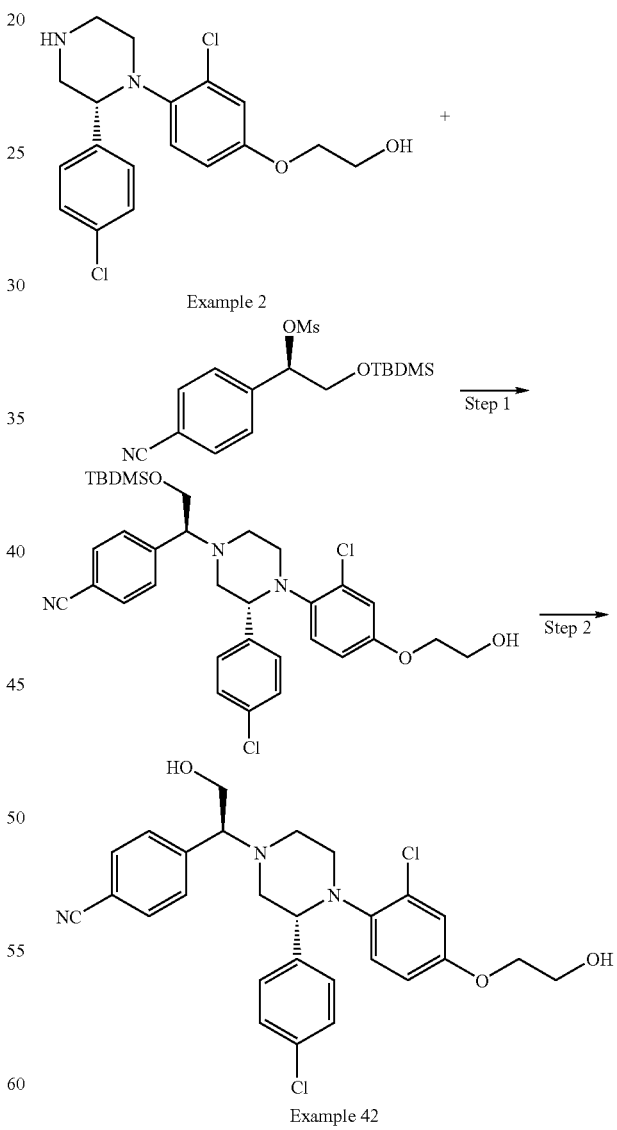

Ex. 41h

Step 1 To the intermediate formed in step 3 of scheme 25 (2.9 g, 7.1 mmol) in acetone (24 mL) was added 2-bromoacetonitrile (0.49 mL, 7.1 mmol) and potassium carbonate (1.2 g, 8.8 mmol). Warmed to 50° C. and stirred for 20 h. Cooled to room temperature and added water. Extracted with EtOAc. Combined organic layers and washed with water and brine. Dried (MgSO$_4$), filtered, and concentrated in vacuo. Purified the residue by silica gel chromatography (0-40% EtOAc/hex over 30 minutes) to provide Ex. 41d (2.2 g, 4.9 mmol).

Step2 To Ex. 41d (0.98 g, 2.2 mmol) in THF (2 mL) was added 50% NaOH (5 mL) and benzyltriethylammonium chloride (0.01 g, 0.04 mmol). Warmed the reaction to 45° C. and stirred for 18 h. Cooled to room temperature and neutralized with 6 N HCl. Extracted with EtOAc. Combined the organics and washed with water and brine. Dried (MgSO$_4$), filtered, and concentrated in vacuo to provide Ex. 41e (0.60 g).

Step 3 To Ex. 41e (0.6 g, 1.3 mmol) in DCM (5 mL) was added oxalyl chloride (0.28 mL, 3.2 mmol) and a drop of DMF. Stirred for 2 h allowing to warm to room temperature. Added NH$_4$OH (2 mL) and stirred for 15 min. Added water and extracted with EtOAc. Combined the organics and washed with water and brine. Dried (MgSO$_4$), filtered, and concentrated in vacuo. The residue was purified by silica gel chromatography (0-5% MeOH/EtOAc over 25 min.) to provide Ex. 41f (0.49 g).

Step 4 To Ex. 41f (0.48 g, 1.0 mmol) in DCM (3 mL) was added proton sponge (0.04 g, 0.2 mmol) followed by 1-chloroethylchloroformate (0.19 mL, 1.8 mmol). The reaction was stirred at room temperature for 2h and then concentrated in vacuo. The residue was taken up into MeOH (3 mL) and warmed to reflux. The reaction was stirred at reflux for 1 h and then concentrated in vacuo. The residue was taken up into DCM and washed with saturated NaHCO$_3$, water, and brine. The organic layer was dried (MgSO$_4$), filtered, and concentrated in vacuo. The residue was purified by silica gel chromatography (0-10% MeOH/DCM over 30 minutes) to provide Ex. 41 g (0.17 g).

Scheme 52.3

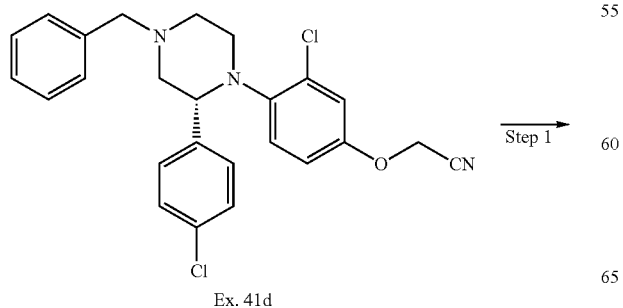

Ex. 41d

Ex. 41h was prepared from Ex. 41d using the conditions in step 5 of scheme 25.

Scheme 53

Example 42

Step 1 To Example 2 (0.10 g, 0.27 mmol) in acetonitrile (1 mL) was added potassium carbonate (0.09 g, 0.68 mmol) and the mesylate (0.12 g, 0.33 mmol) formed in Scheme 8. The reaction mixture was warmed to 80° C. and stirred for 18 h.

The reaction was then cooled to room temperature and water was added. The mixture was extracted with EtOAc. The combined organic layers were washed with water and brine. The organic layer was dried (MgSO$_4$), filtered, and concentrated in vacuo. The residue was purified by silica gel chromatography (0-50% EtOAc/Hex over 15 minutes) to provide the tert-butyldimethylsilyl protected alcohol (0.14 g9 0.23 mmol).

Step 2 To the tert-butyldimethylsilyl protected alcohol prepared in Step 1 (0.14 g, 0.23 mmol) in THF (1 mL) was added tetrabutylammonium fluoride (1.0 M in THF, 0.25 mL, 0.25 mmol). The reaction was stirred at room temperature for 1 8 h. Water was added to the reaction and the mixture was extracted with EtOAc. The combined organic layers were washed with water and brine. The organic layer was dried (MgSO$_4$), filtered, and concentrated in vacuo. The residue was purified by silica gel chromatography (0-40% EtOAc/Hex over 20 minutes) to provide Example 42 (0.10 g, 0.20 mmol).

The compounds in Table 5 were prepared in a similar manner as Ex. 42 in Scheme 53.

TABLE 5

| Ex. | Piperazine | Mesylate |
|---|---|---|
| 31 | [structure] | [structure] (Scheme 8) |
| 2 | [structure] | [structure] (Scheme 7) |
| 21 | [structure] | [structure] (Scheme 8) |
| 22 | [structure] | [structure] (Scheme 8) |

TABLE 5-continued
| 6 | 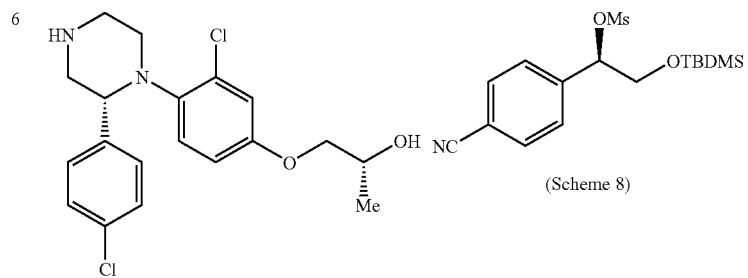 (Scheme 8) |
| 4 | 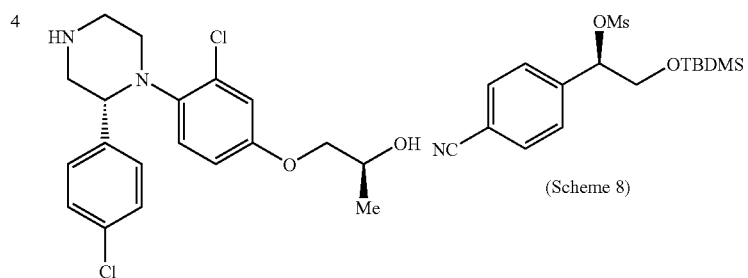 (Scheme 8) |
| 4 | 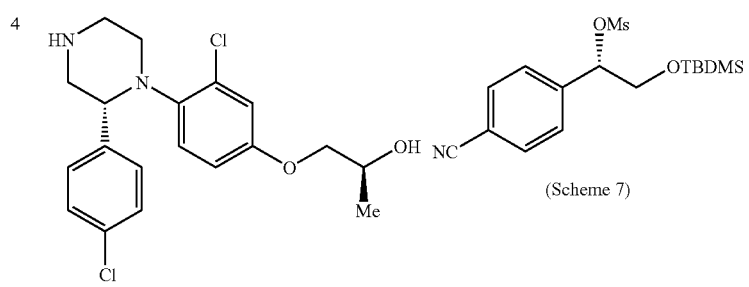 (Scheme 7) |
| 6 | 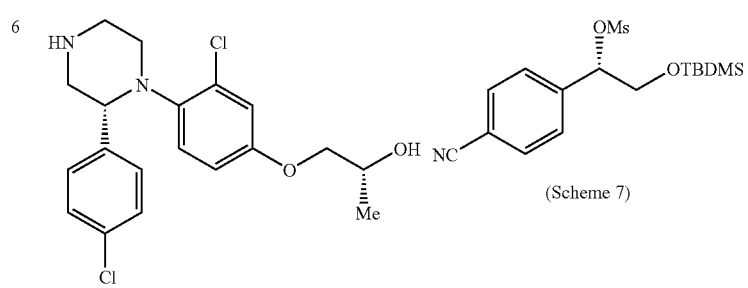 (Scheme 7) |
| 39 | 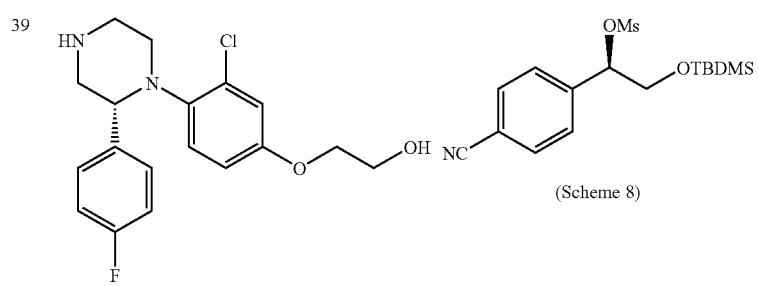 (Scheme 8) |

TABLE 5-continued
| | | |
|---|---|---|
| 9 | 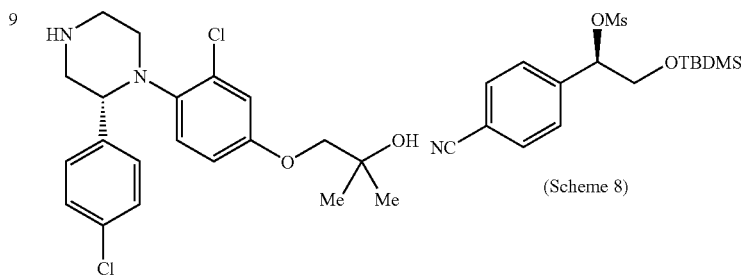 | (Scheme 8) |
| 13 | 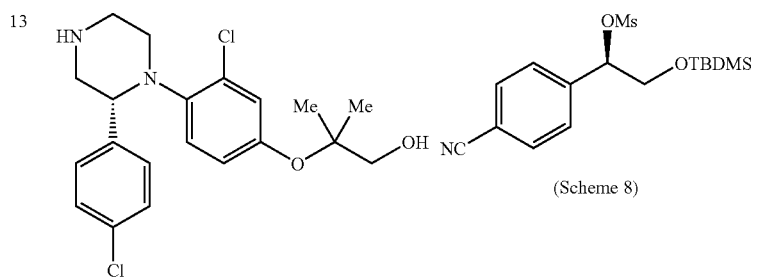 | (Scheme 8) |
| 13 | 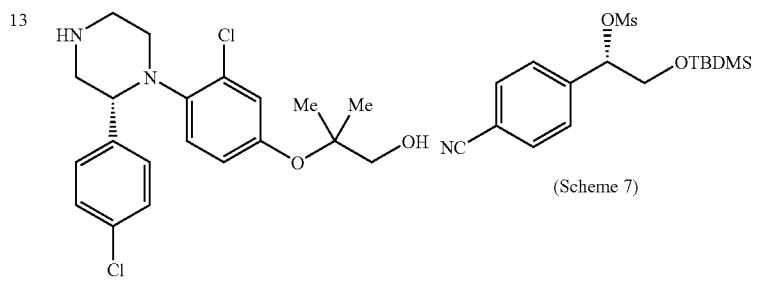 | (Scheme 7) |
| 9 | 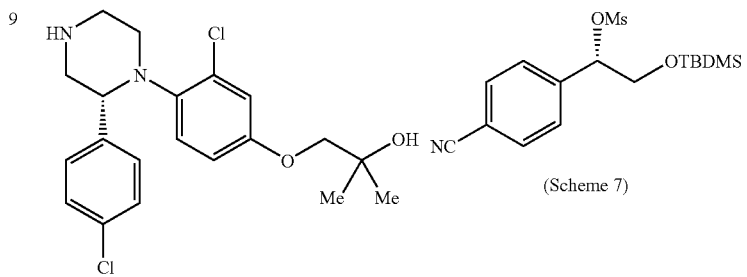 | (Scheme 7) |
| 38 | 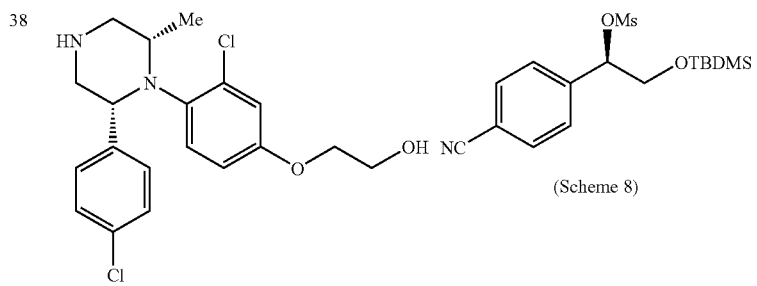 | (Scheme 8) |

TABLE 5-continued
| | | |
|---|---|---|
| 29 | 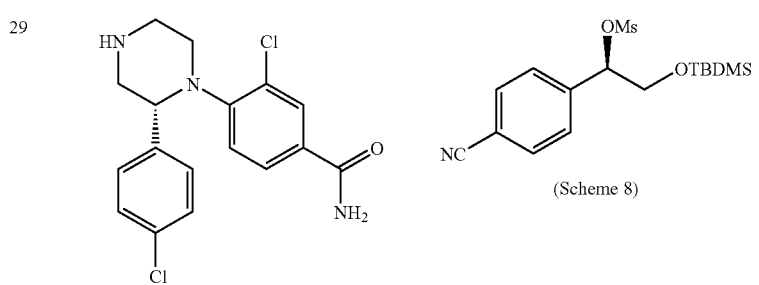 | (Scheme 8) |
| 2c | 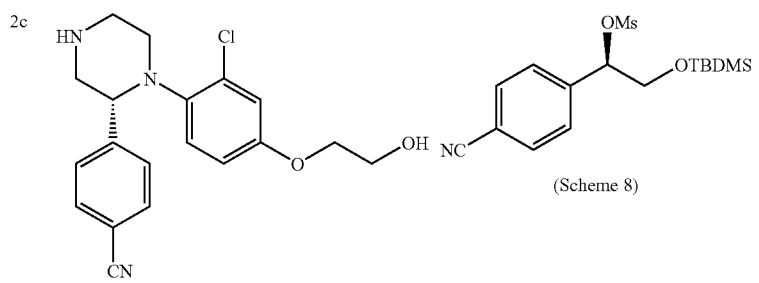 | (Scheme 8) |
| 2c | 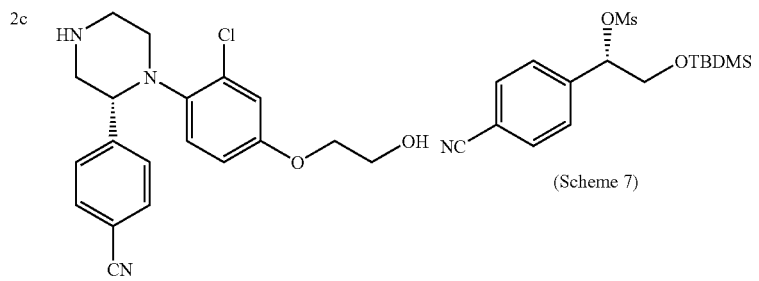 | (Scheme 7) |
| 25a | 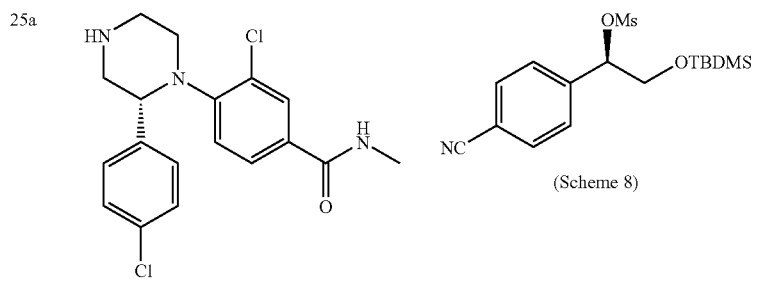 | (Scheme 8) |
| Ex. | Structure |
|---|---|
| 43 | 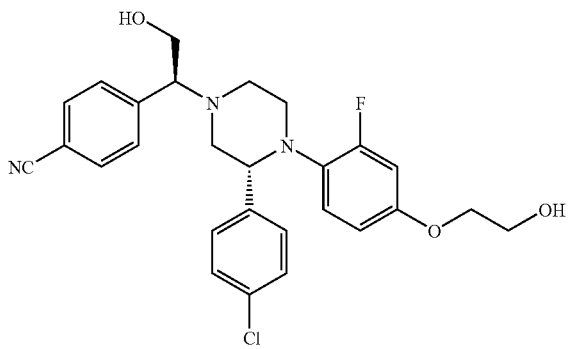 |

TABLE 5-continued
| 44 | 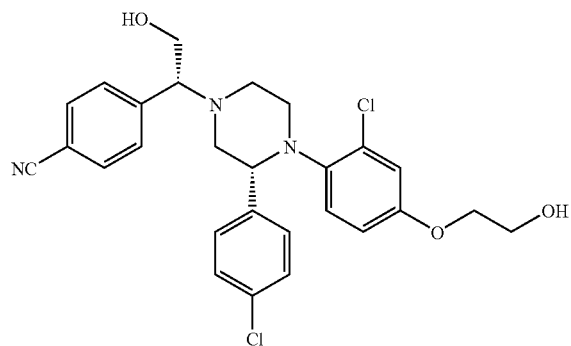 |
|---|---|
| 45 | 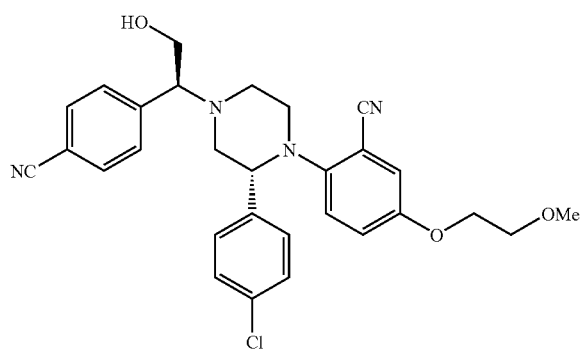 |
| 46 | 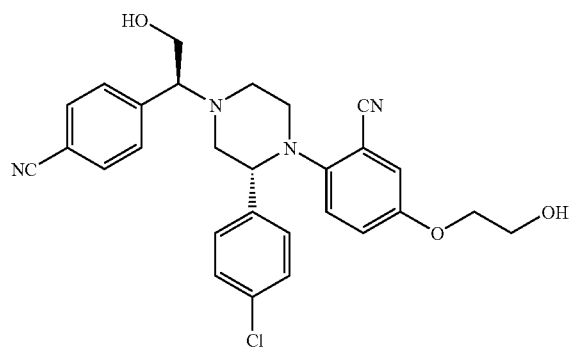 |
| 47 | 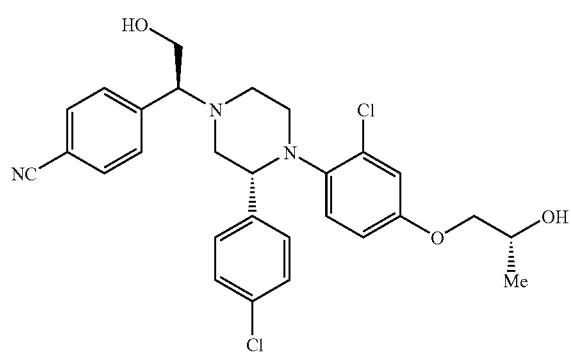 |

TABLE 5-continued
48
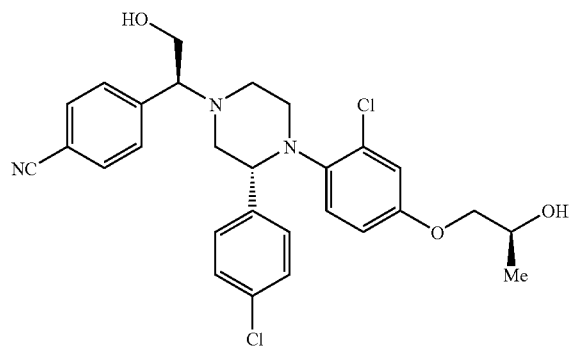
49
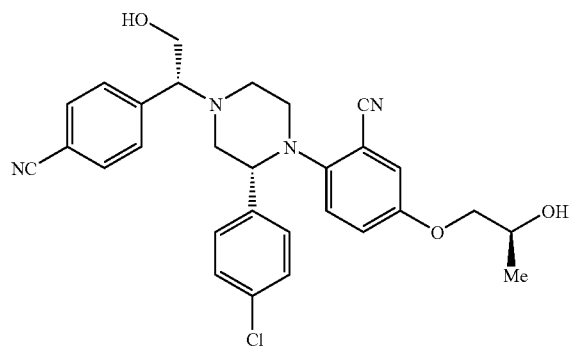
50
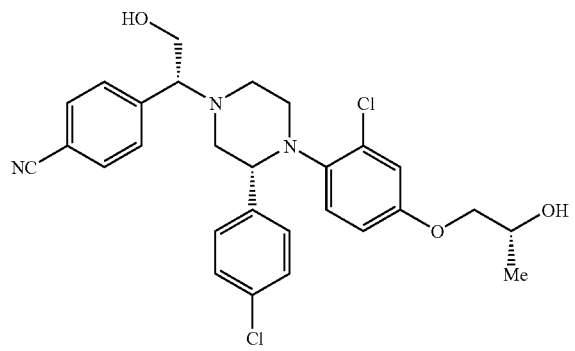
51
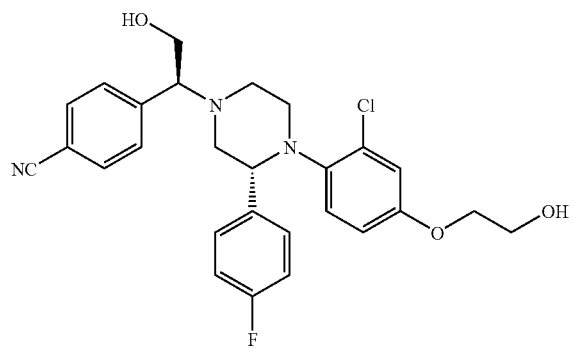

TABLE 5-continued
52
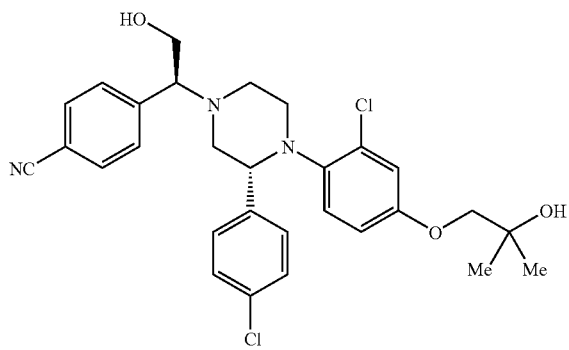
53
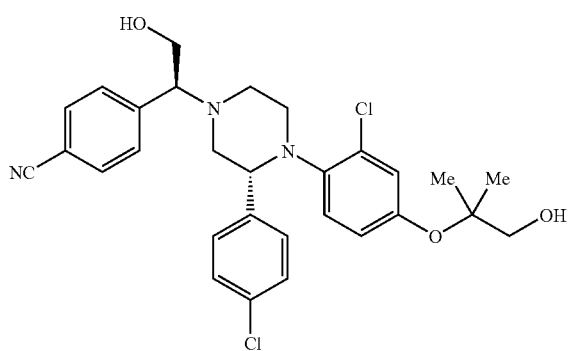
54
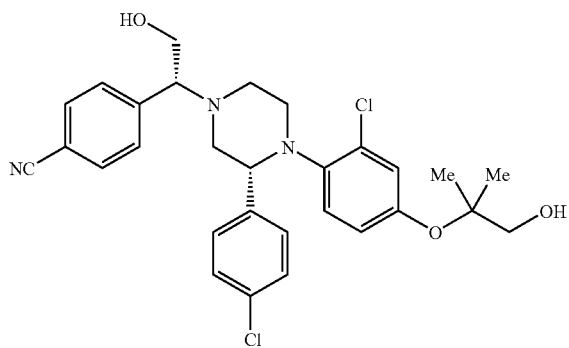
55
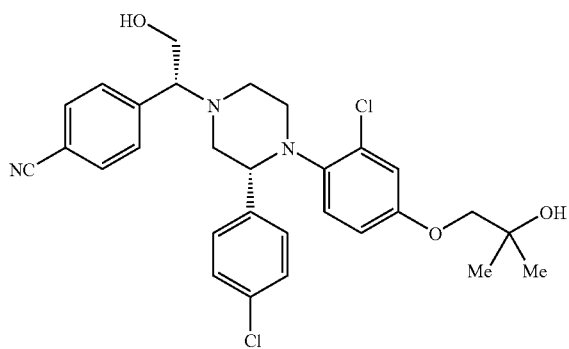

TABLE 5-continued
56 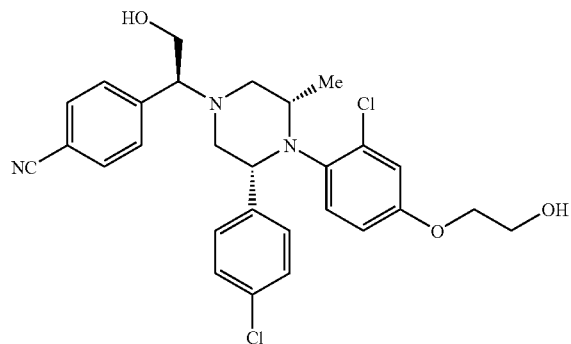
57 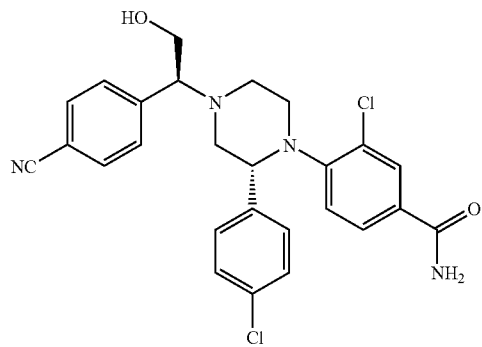
57a 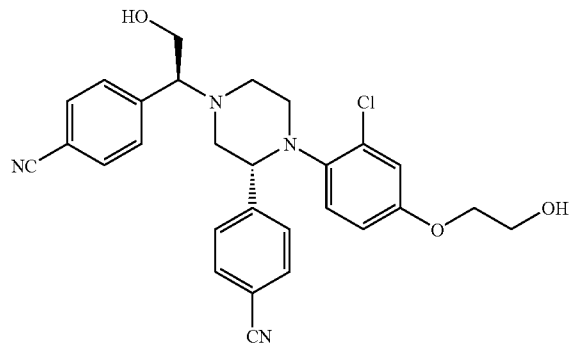
57b 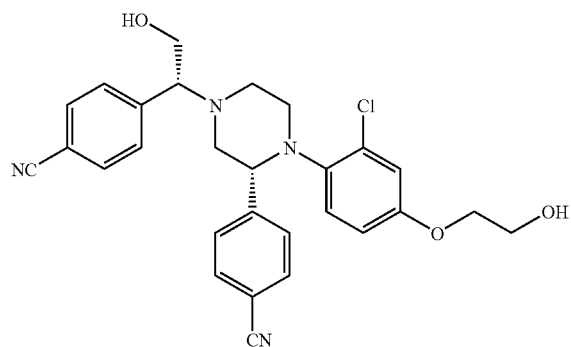

TABLE 5-continued

| | |
|---|---|
| 57c | 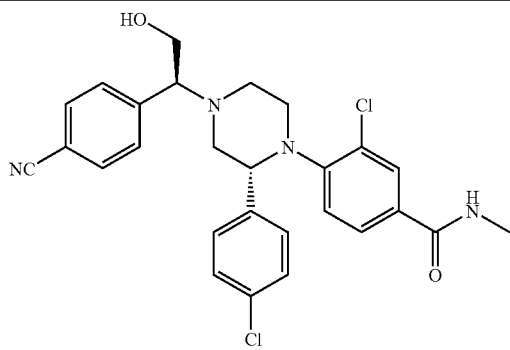 |

Scheme 54

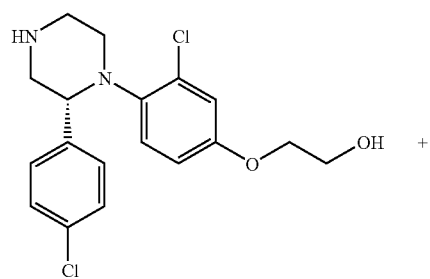

Example 2

+

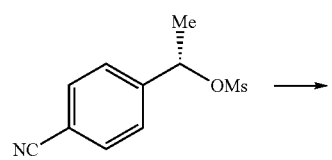

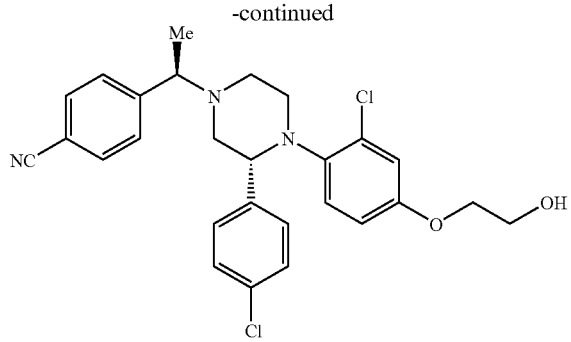

Example 58

-continued

To Example 2 (0.21 g, 0.57 mmol) in acetonitrile (2 mL) was added potassium carbonate (0.12 g, 0.86 mmol) and the mesylate prepared in Step 2 of Scheme 6 (0.21 g, 0.93 mmol). The reaction was warmed to 90° C. and stirred for 19 h. The reaction was cooled to room temperature and water was added. The mixture was extracted with EtOAc. The combined organic layers were washed with water and brine. The organic layer was dried (MgSO$_4$), filtered, and concentrated in vacuo. The residue was purified by silica gel chromatography (0-70% EtOAc/Hex over 30 minutes) to provide Example 58 (0-24 g, 0.49 mmol) as a 8:1 mixture of diastereomers as determined by $^1$H NMR.

Target compounds in Table 6 were prepared in a similar manner as Ex. 58 in Scheme 54.

TABLE 6

| Ex | Piperazine | Ex. | Structure |
|---|---|---|---|
| 31 | ![piperazine structure] | 59 | ![structure] |

TABLE 6-continued

| Ex | Piperazine | Ex. | Structure |
|---|---|---|---|
| 21 | | 60 | 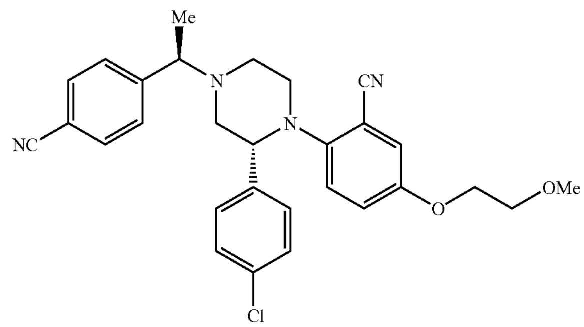 |
| 6 | | 61 | 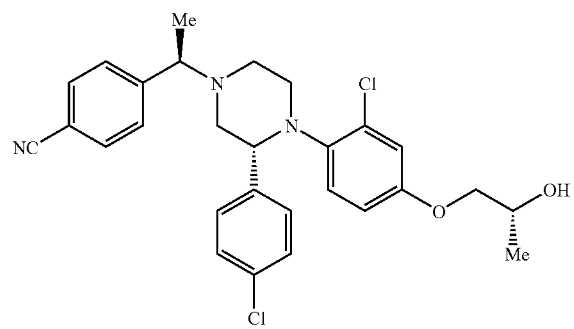 |
| 4 | | 62 | 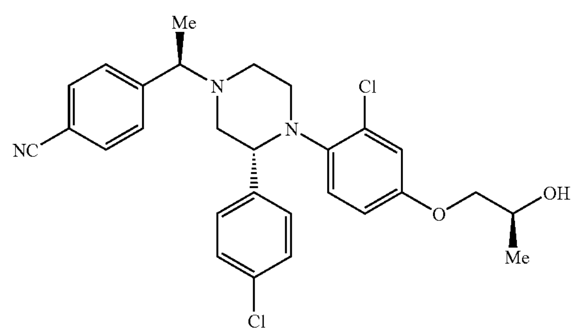 |
| 28 | | 63 | 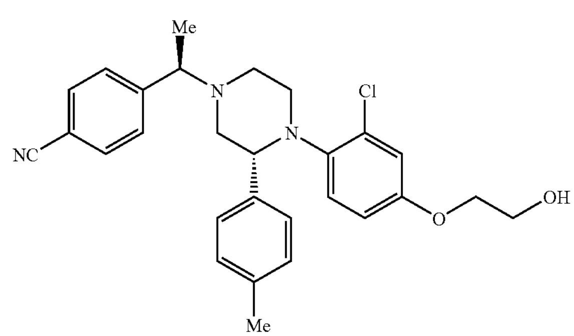 |

TABLE 6-continued

| Ex | Piperazine | Ex. | Structure |
|---|---|---|---|
| 39 | | 64 | 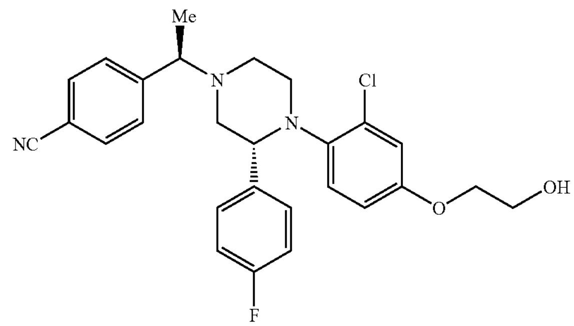 |
| 9 | | 65 | 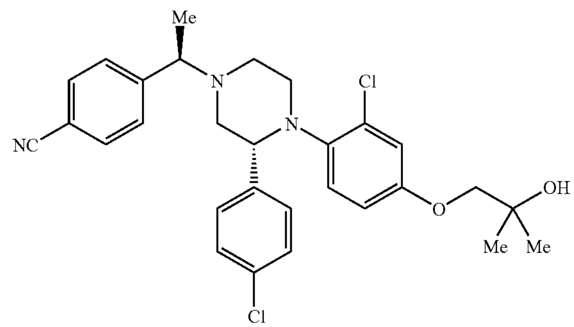 |
| 38 | | 66 | 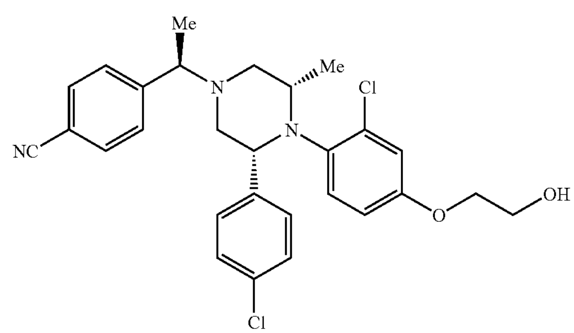 |
| 18 | | 67 | 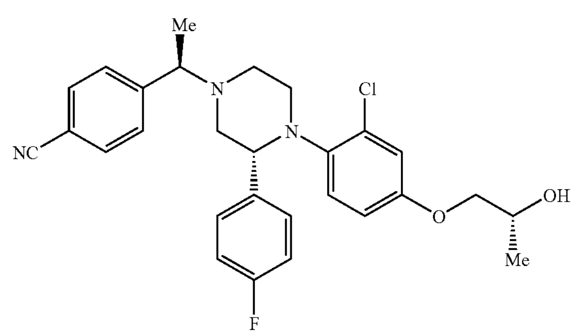 |

TABLE 6-continued

| Ex | Piperazine | Ex. | Structure |
| --- | --- | --- | --- |
| 34 | | 68 | |
| 19 | | 69 | 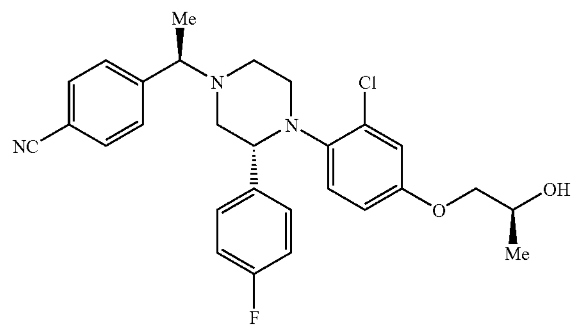 |
| 35 | | 70 | 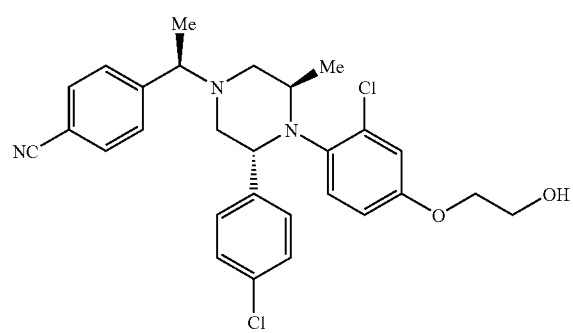 |
| 34 | | 71 | |

TABLE 6-continued
| Ex | Piperazine | Ex. | Structure |
| --- | --- | --- | --- |
| 17 | 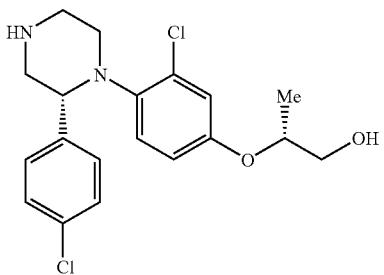 [SMILES: C[C@H](CO)Oc1ccc(N2CCNC[C@H]2c2ccc(Cl)cc2)c(Cl)c1] | 72 | 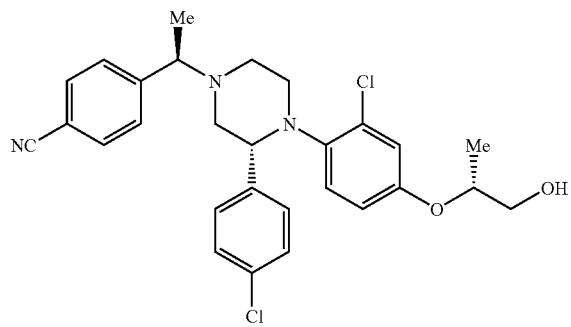 |
| 24 | 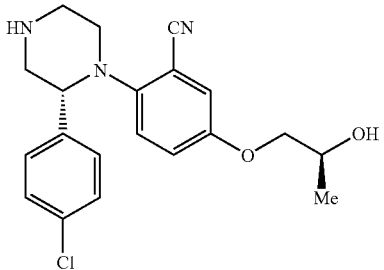 | 73 | 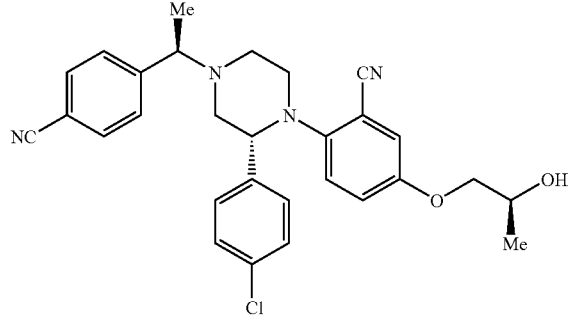 |
| 33 | 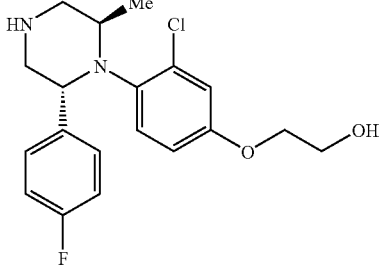 | 74 | 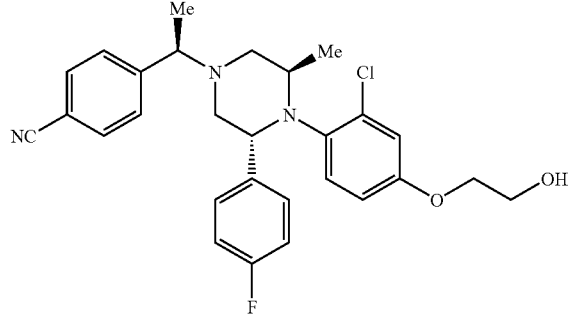 |
| 29 | 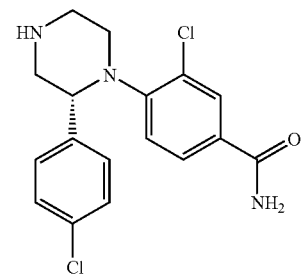 [SMILES: NC(=O)c1ccc(N2CCNC[C@H]2c2ccc(Cl)cc2)c(Cl)c1] | 75 | 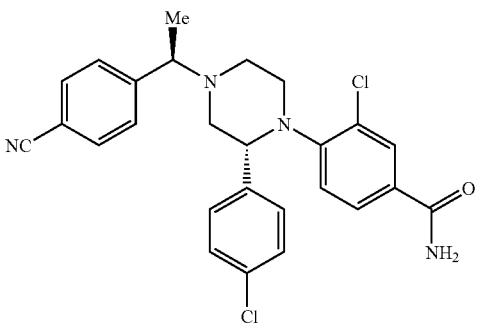 |

TABLE 6-continued

| Ex | Piperazine | Ex. | Structure |
|---|---|---|---|
| 27 | | 76 | 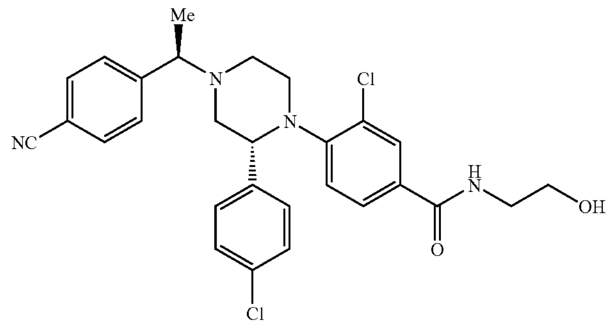 |
| 25c | | 77 | 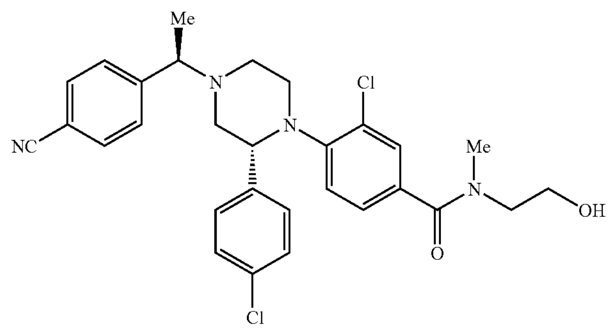 |
| 25b | | 78 | 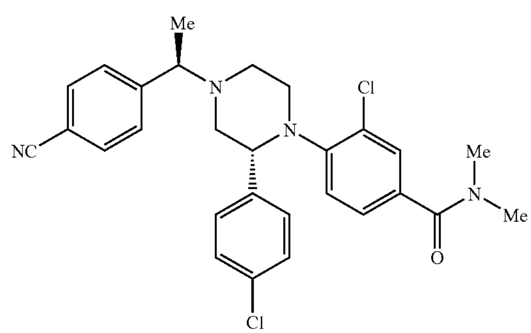 |
| 25a | | 79 | 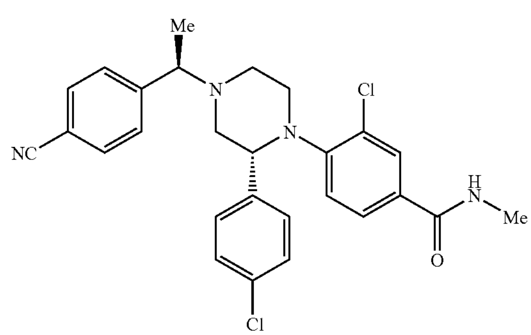 |

TABLE 6-continued

| Ex | Piperazine | Ex. | Structure |
|---|---|---|---|
| 22 | | 80 | 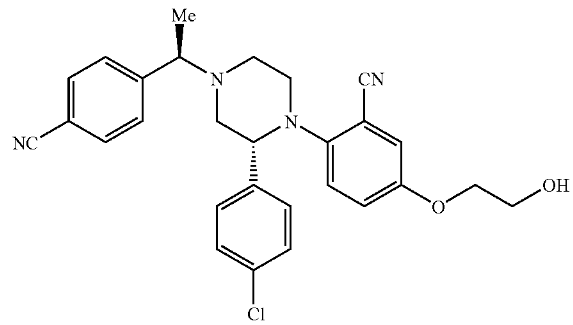 |
| 2c | | 80a | 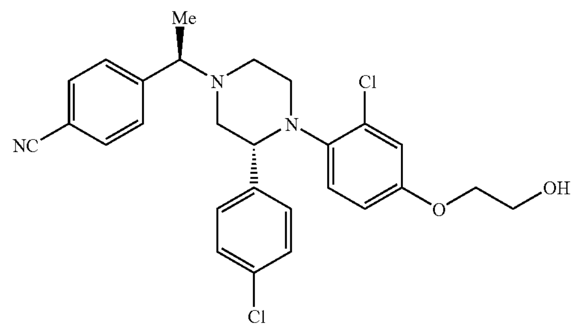 |
| 37 | | 80b | 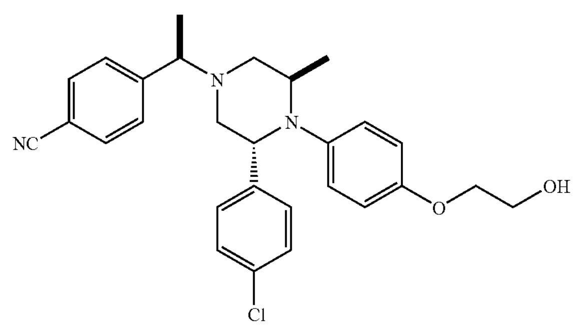 |
| 36 | | 80c | 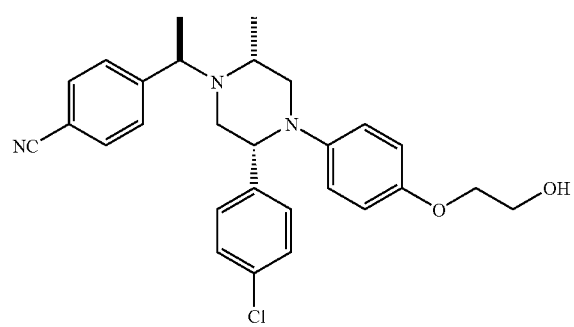 |

TABLE 6-continued

| Ex | Piperazine | Ex. | Structure |
| --- | --- | --- | --- |
| 40 | | 80d | 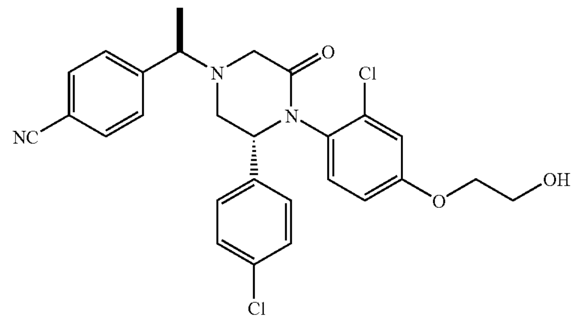 |
| 41c | | 80e | 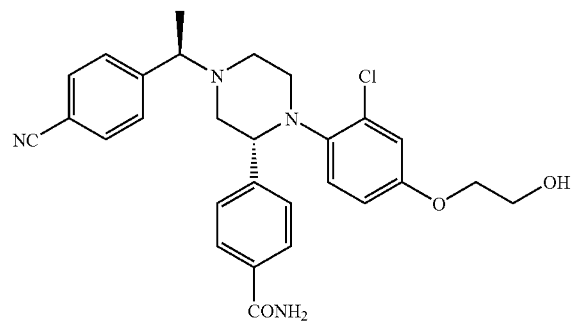 |
| 41g | | 80f | 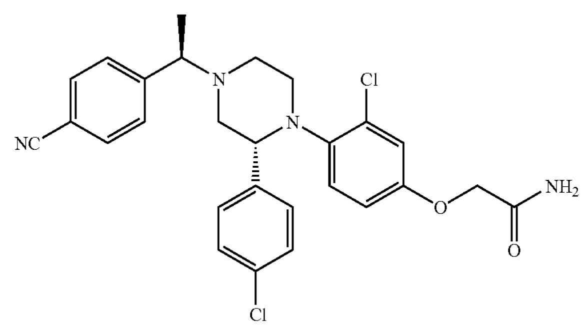 |

Scheme 55

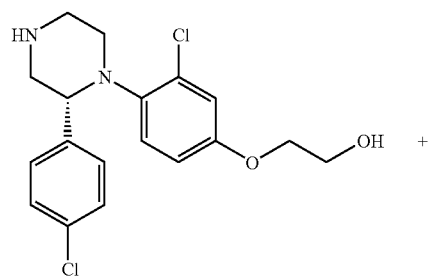

Example 2

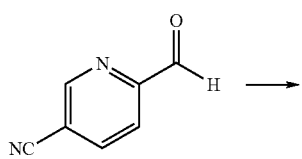

Example 81

To Example 2 (0.1 g, 0.3 mmol) in DCE (1.1 mL) was added the aldehyde from Scheme 9 (0.05 g, 0.3 mmol) and Na(OAc)$_3$BH (0.09 g, 0.4 mmol). The reaction was stirred for 18 h at room temperature. DCM was added and the mixture was washed with saturated NaHCO$_3$, water, and brine. The residue was purified by silica gel chromatography (0-90% EtOAc/Hex over 30 minutes) to provide Example 81 (0.96 g, 0.195 mmol).

Target compounds in Table 7 were prepared in a similar manner as Ex. 81 in Scheme 55.

TABLE 7
| Aldehyde | Ex. | Piperazine |
|---|---|---|
| 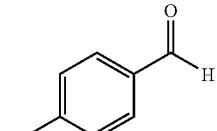 | 2 | 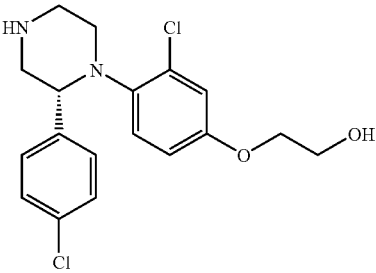 |
| 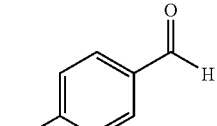 | 31 | 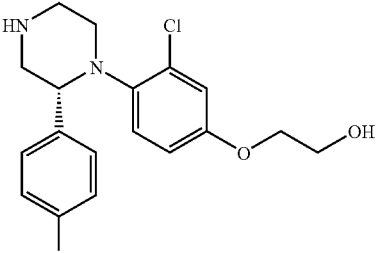 |
| 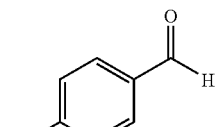 | 9 | 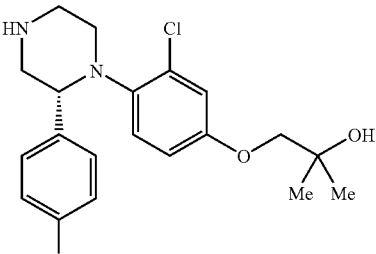 |
| 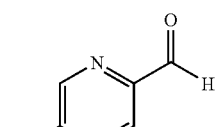 | 9 | 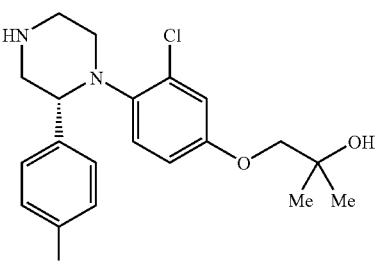 |
| 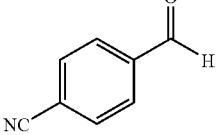 | 6 | 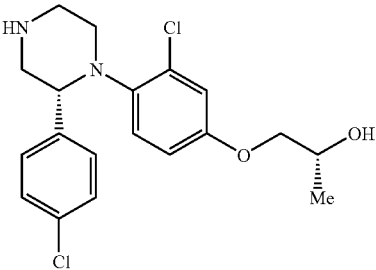 [SMILES: C[C@@H](O)COc1ccc(N2CCNC[C@H]2c2ccc(Cl)cc2)c(Cl)c1] |

TABLE 7-continued
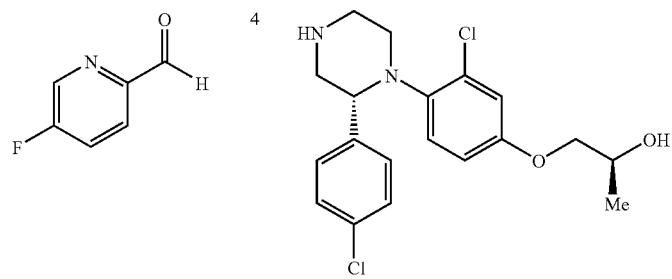
4
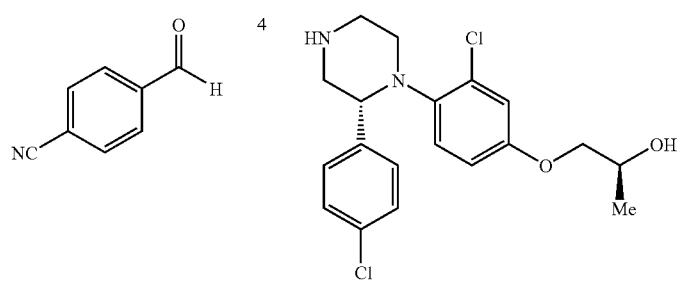
4
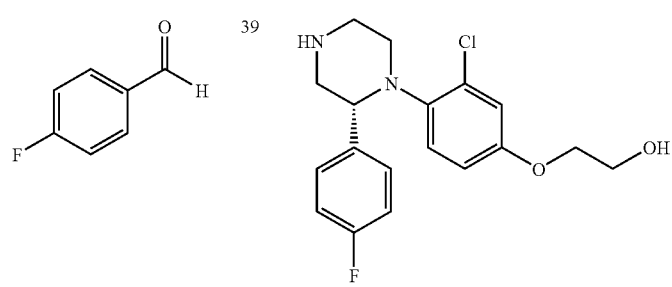
39
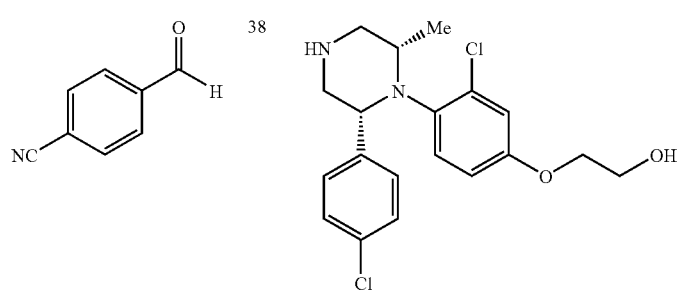
38
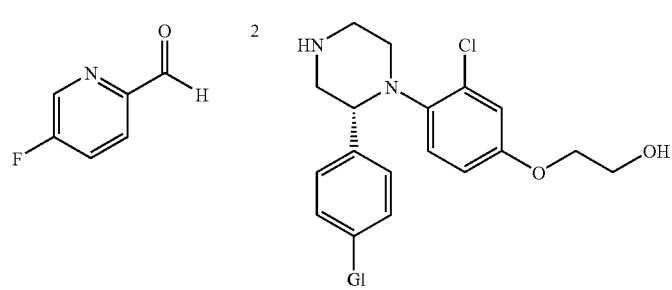
2

TABLE 7-continued
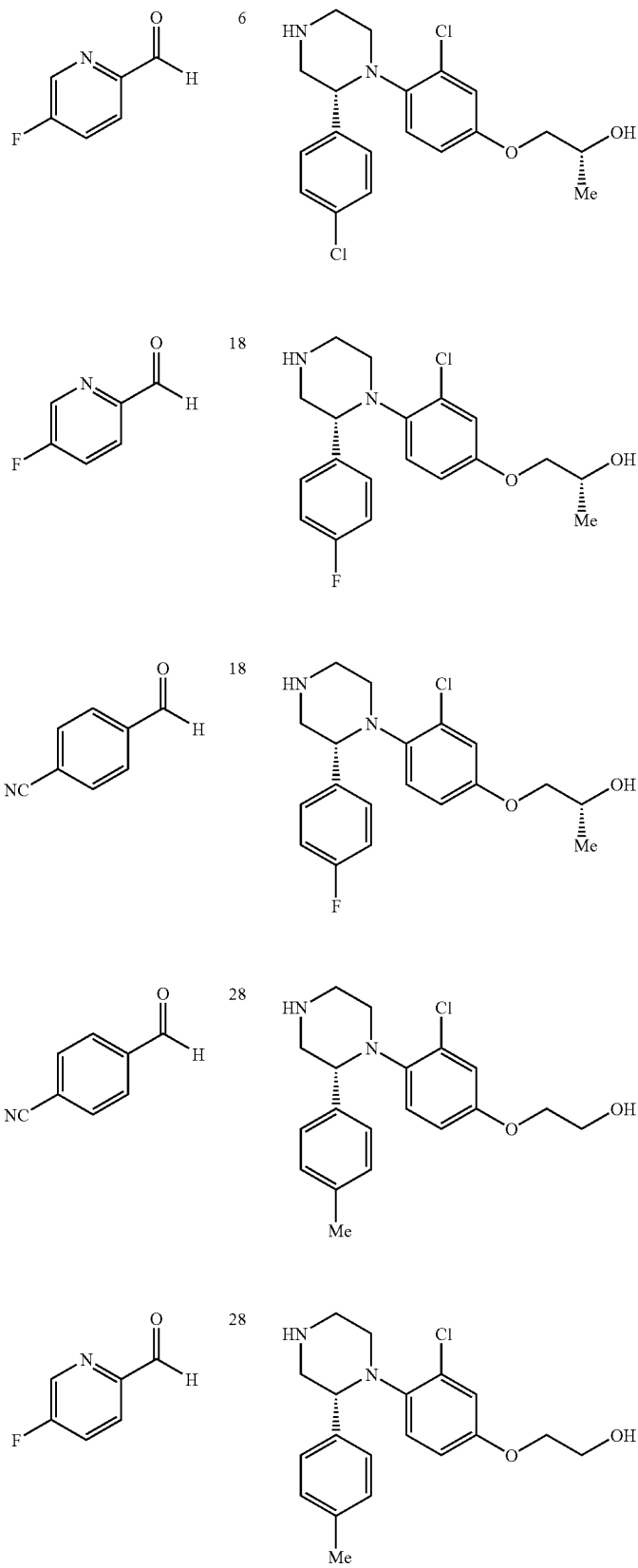

TABLE 7-continued
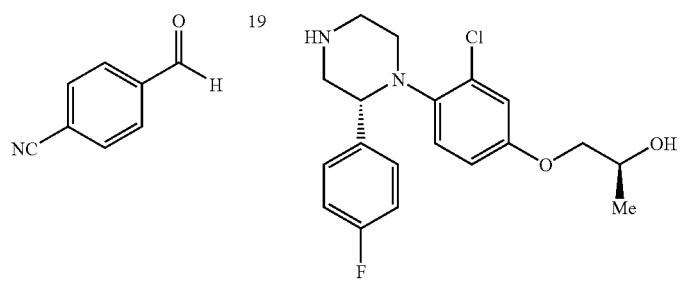
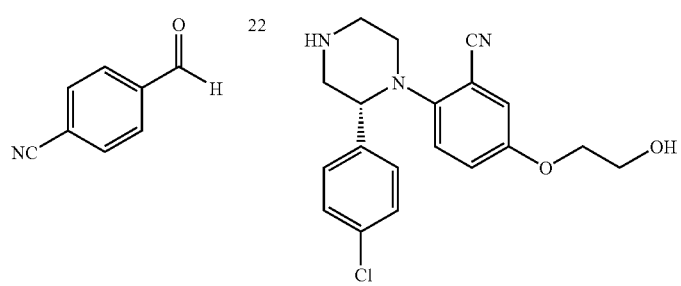
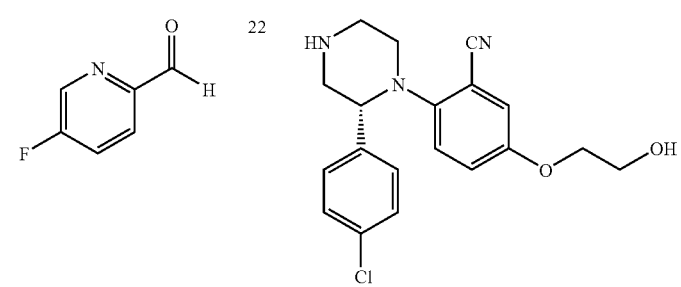
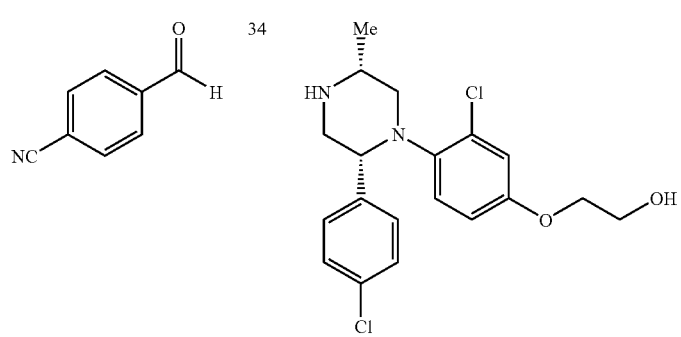
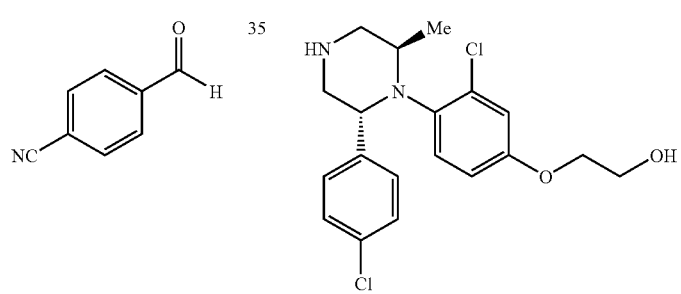

TABLE 7-continued
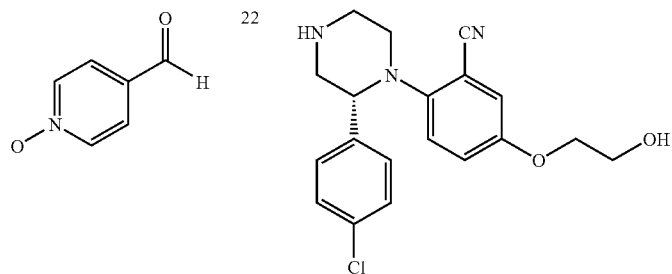 22
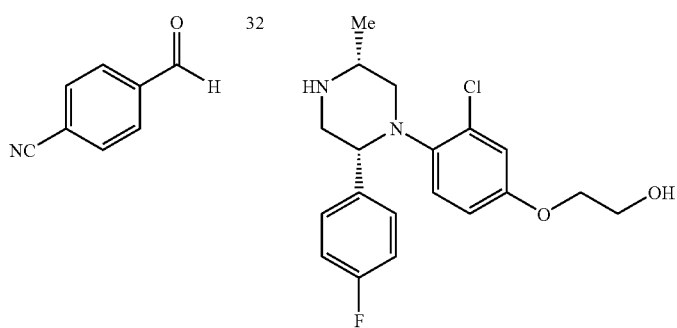 32
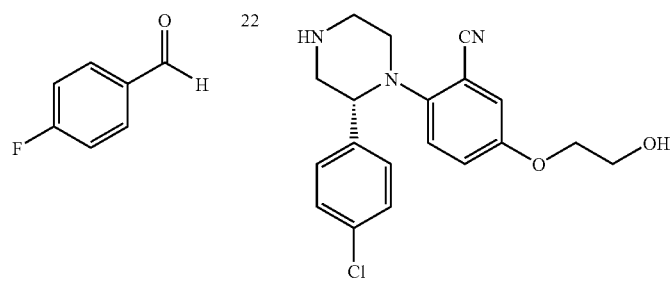 22
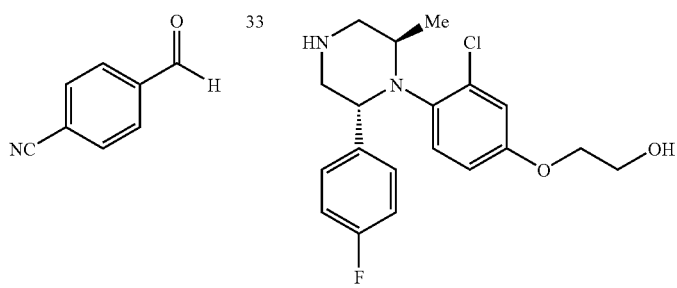 33
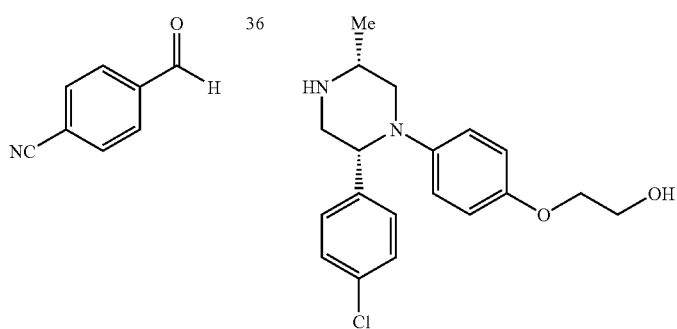 36

TABLE 7-continued
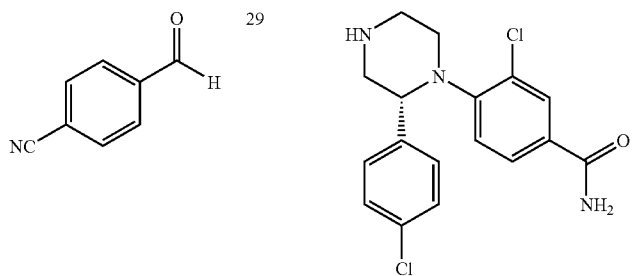
29
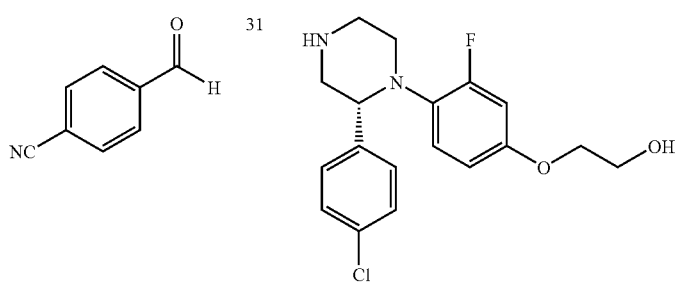
31
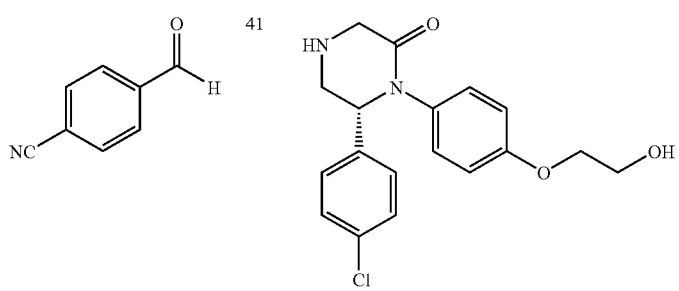
41
| Ex. | Structure |
|---|---|
| 82 | 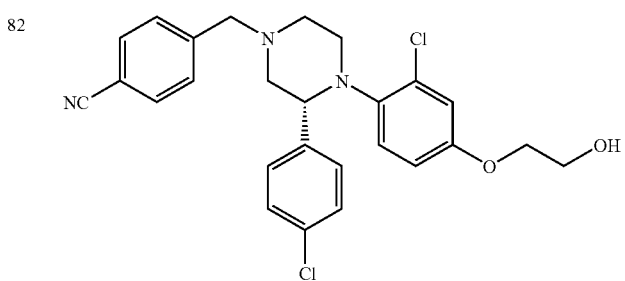 |
| 83 | 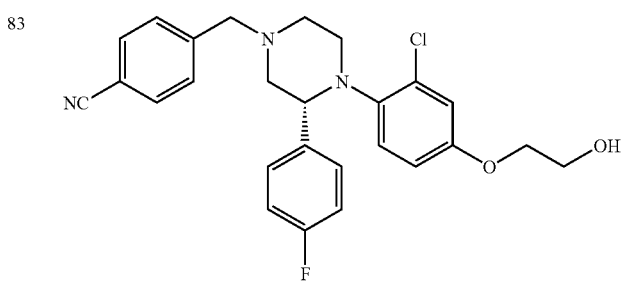 |

TABLE 7-continued
84 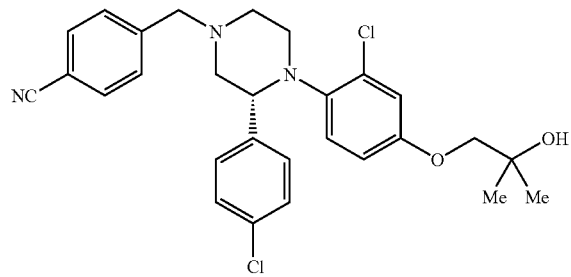
85 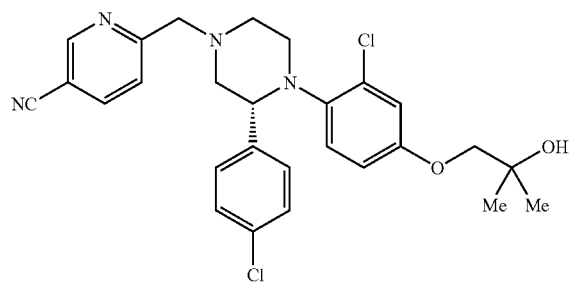
86 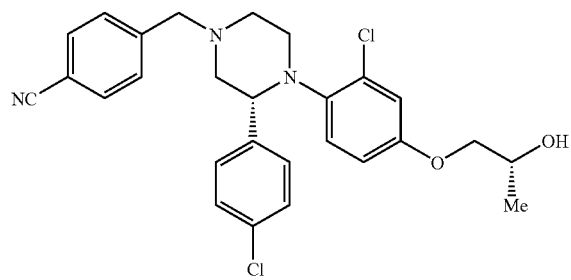
87 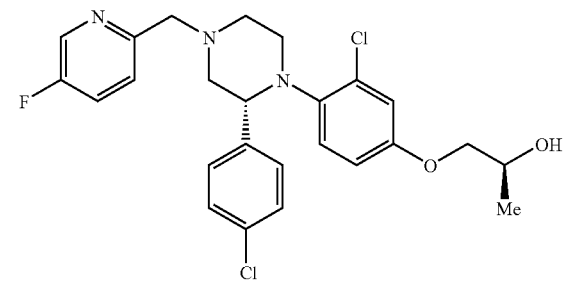 [SMILES: C[C@H](O)COc1ccc(N2CCN(Cc3ccc(F)cn3)C[C@H]2c2ccc(Cl)cc2)c(Cl)c1]
88 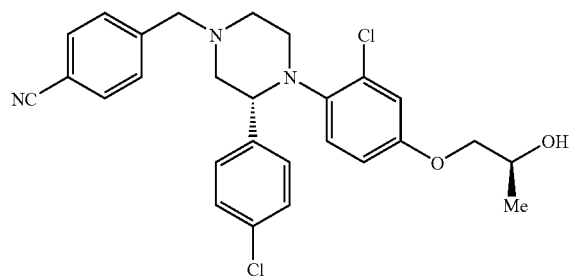

TABLE 7-continued
| 89 | 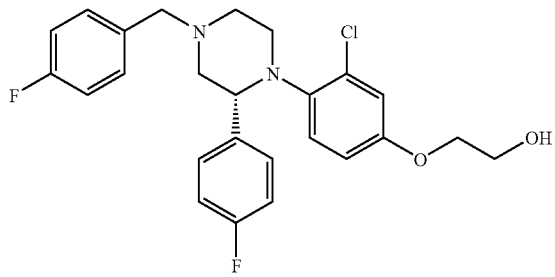 [SMILES: OCCOc1ccc(N2CCN(Cc3ccc(F)cc3)C[C@H]2c2ccc(F)cc2)c(Cl)c1] |
| 90 | 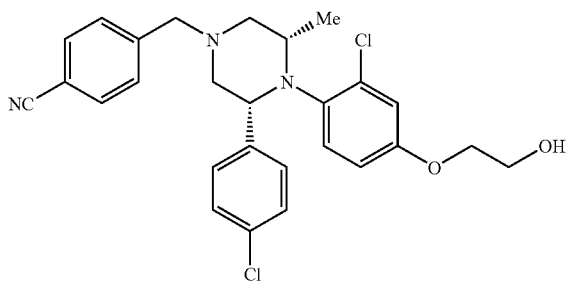 |
| 91 | 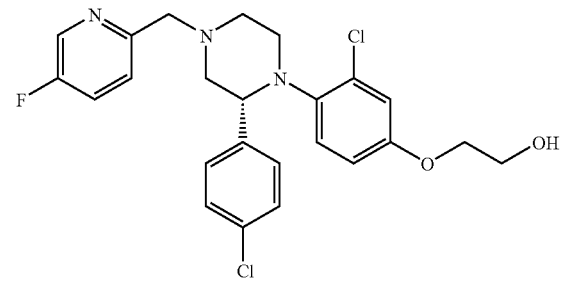 [SMILES: OCCOc1ccc(N2CCN(Cc3ccc(F)cn3)C[C@H]2c2ccc(Cl)cc2)c(Cl)c1] |
| 92 | 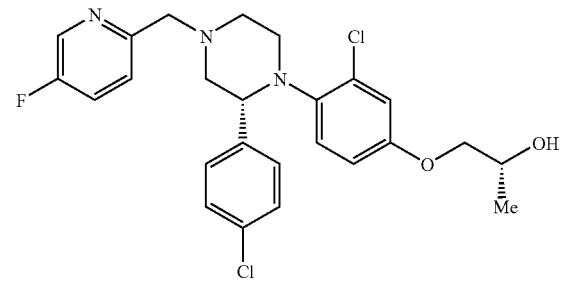 [SMILES: C[C@@H](O)COc1ccc(N2CCN(Cc3ccc(F)cn3)C[C@H]2c2ccc(Cl)cc2)c(Cl)c1] |
| 93 | 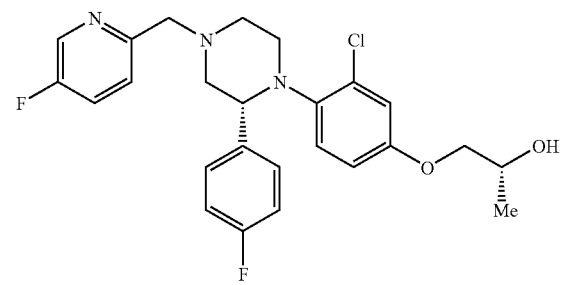 [SMILES: C[C@@H](O)COc1ccc(N2CCN(Cc3ccc(F)cn3)C[C@H]2c2ccc(F)cc2)c(Cl)c1] |

TABLE 7-continued
94 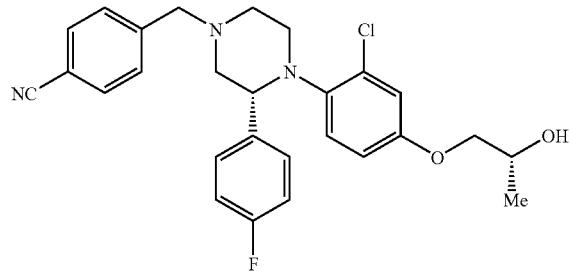
95 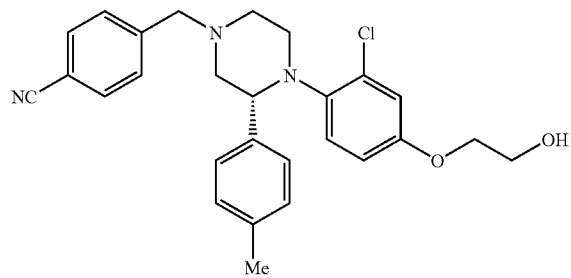
96 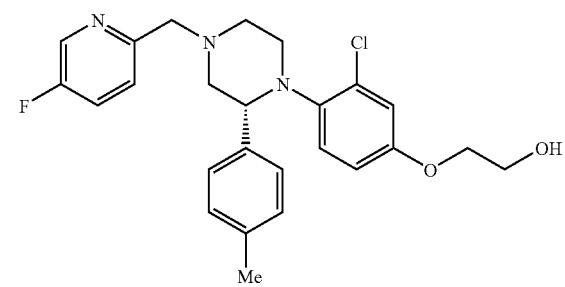 [SMILES: Cc1ccc([C@@H]2CN(Cc3ccc(F)cn3)CCN2c2ccc(OCCO)cc2Cl)cc1]
97 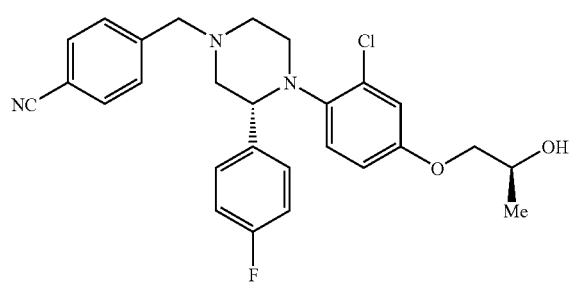
98 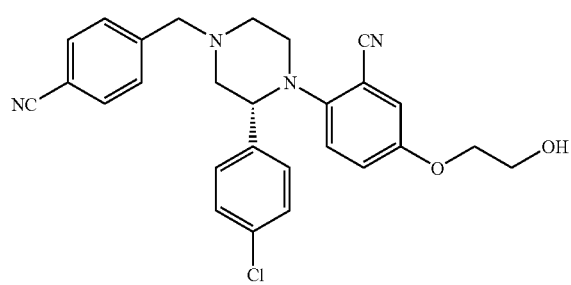

TABLE 7-continued
99 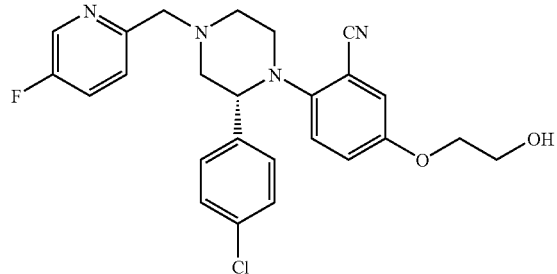
100 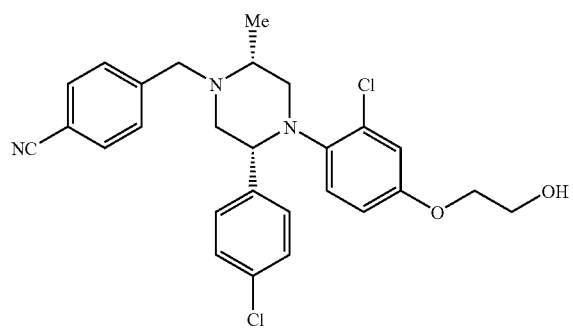
101 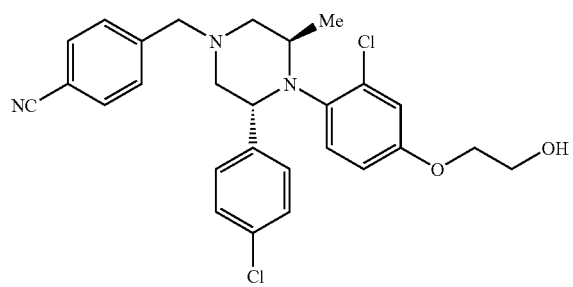
102 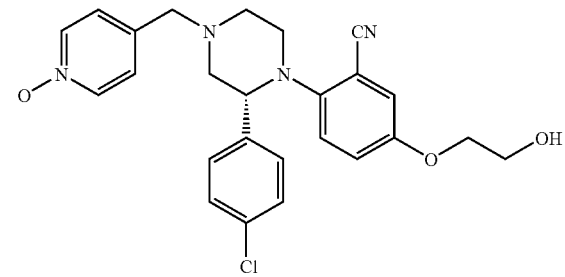
103 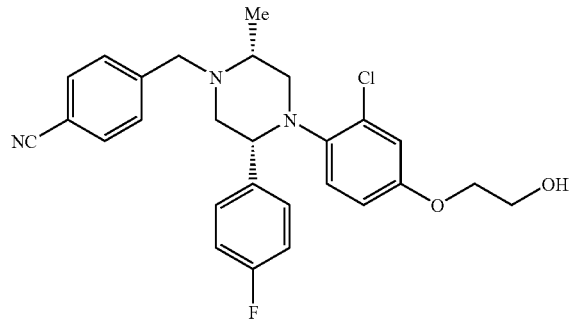

TABLE 7-continued
| 104 | 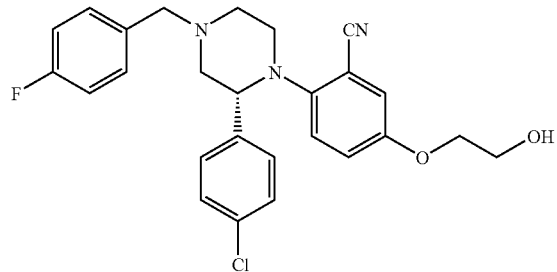 [SMILES: N#Cc1cc(OCCO)ccc1N1CCN(Cc2ccc(F)cc2)C[C@H]1c1ccc(Cl)cc1] |
| --- | --- |
| 105 | 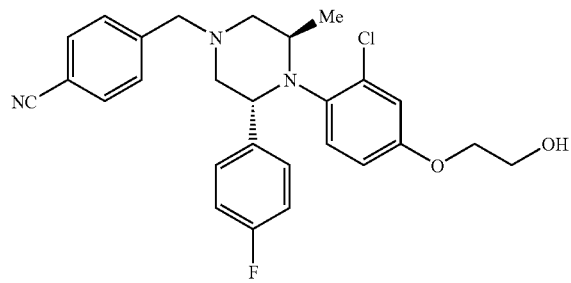 |
| 106 | 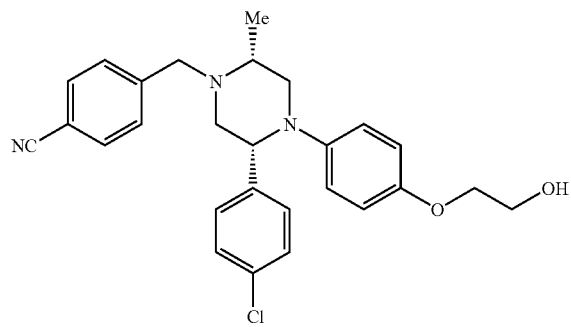 |
| 107 | 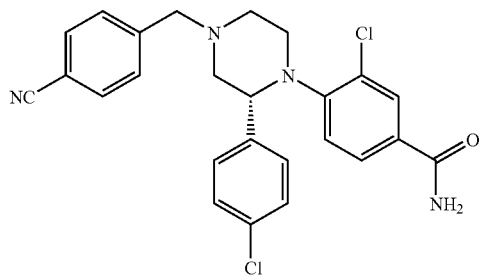 |
| 108 | 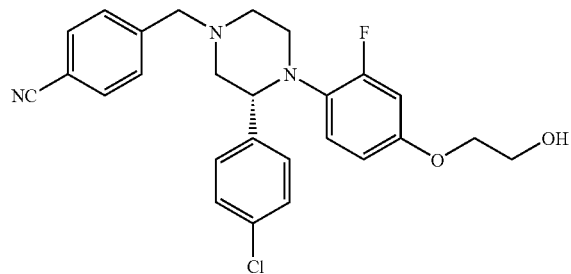 |

TABLE 7-continued

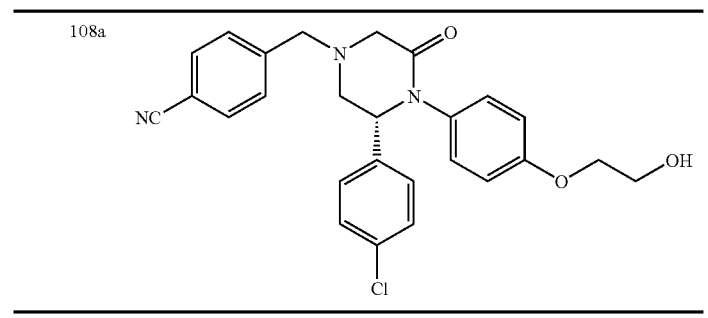
108a

Scheme 56

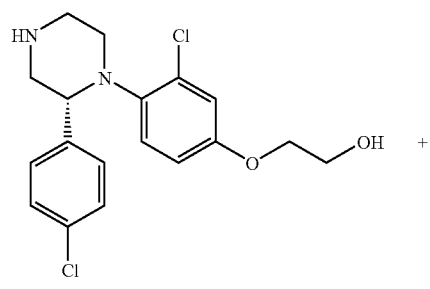
Example 2

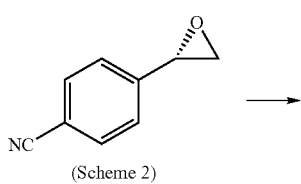
(Scheme 2)

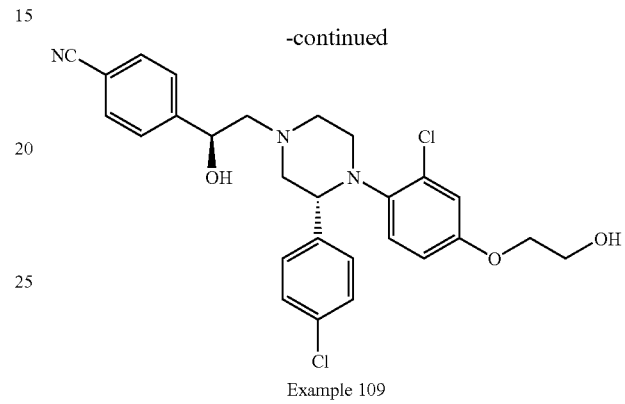
Example 109

To Example 2 (0.08 g, 0.22 mmol) was added the 4-cyanostyrene oxide (0.035 g, 0.24 mmol). Heated the mixture neat to 100° C. and stirred for 20 h. Cooled to room temperature and purified the mixture directly by silica gel chromatography (40-100% EtOAc/Hex over 25 min.) to provide Example 109 (0.06 g, 0.13 mmol).

Target compounds in Table 8 were prepared in a similar manner as Ex. 109 in Scheme 56.

TABLE 8

| Epoxide | Ex. | Piperazine |
|---|---|---|
|  | 6 |  |
|  | 22 |  |

TABLE 8-continued
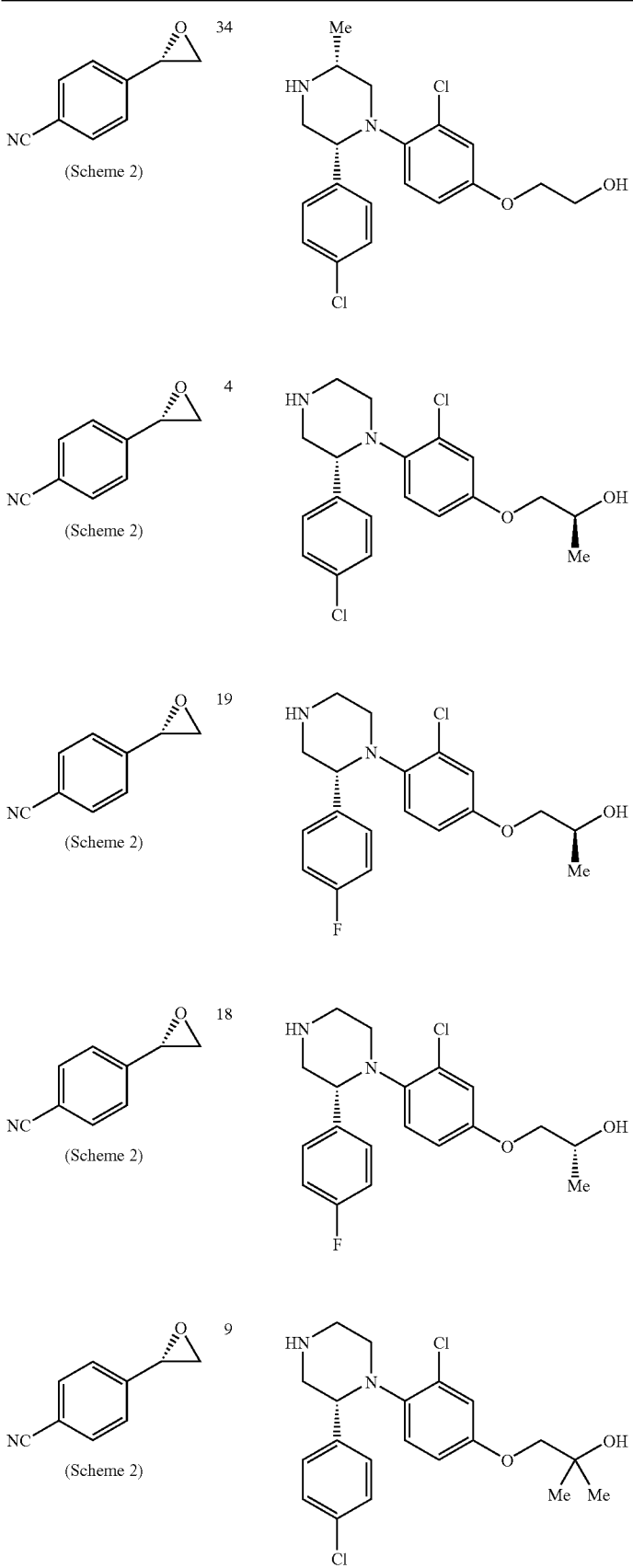

TABLE 8-continued
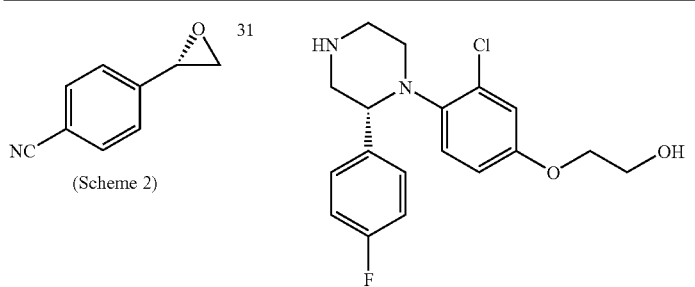
31
(Scheme 2)
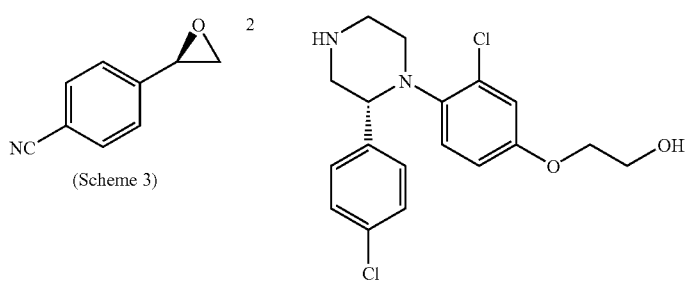
2
(Scheme 3)
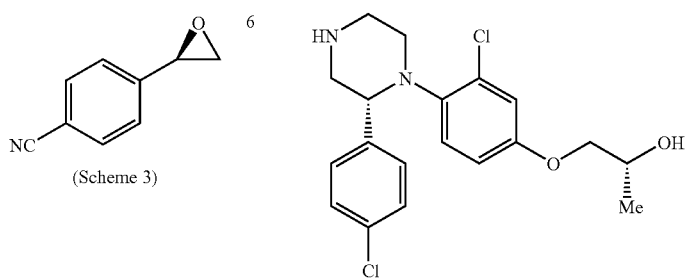
6
(Scheme 3)
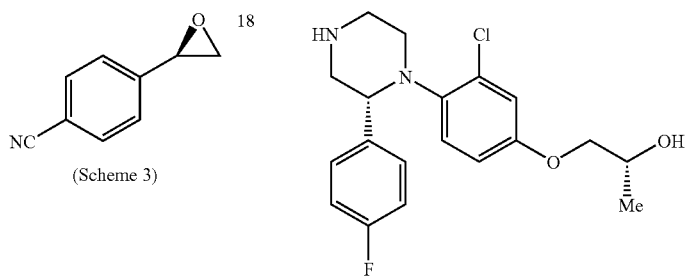
18
(Scheme 3)
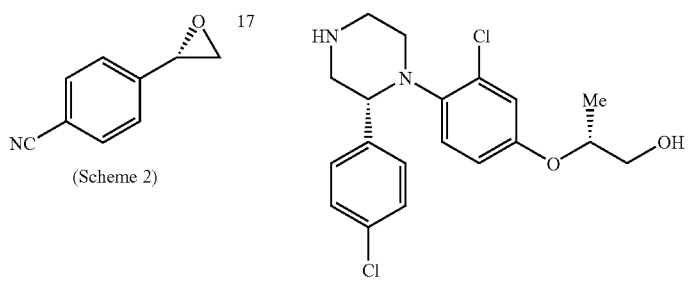
17
(Scheme 2)

TABLE 8-continued
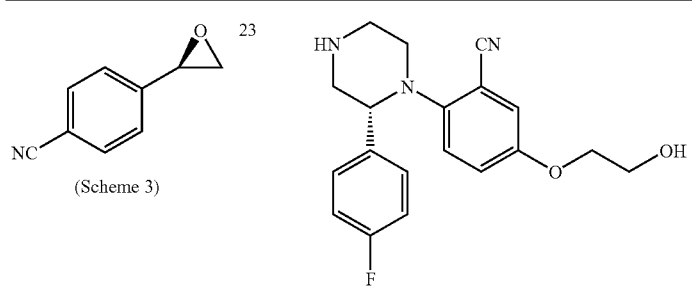
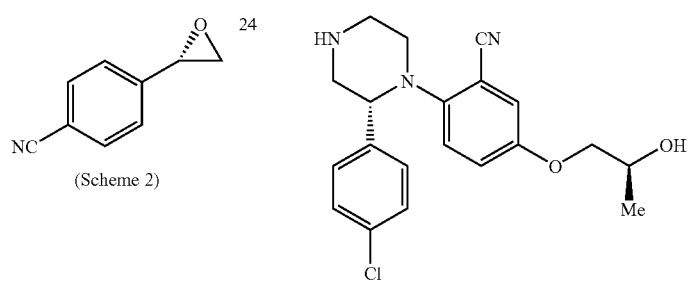
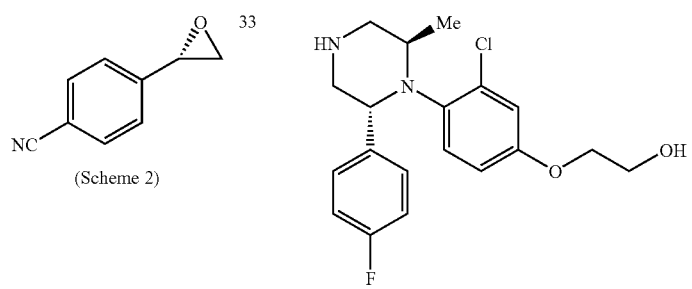
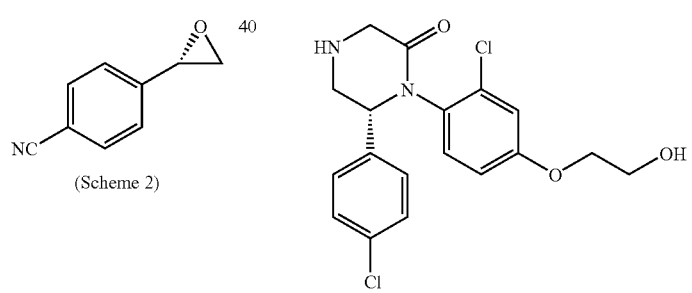
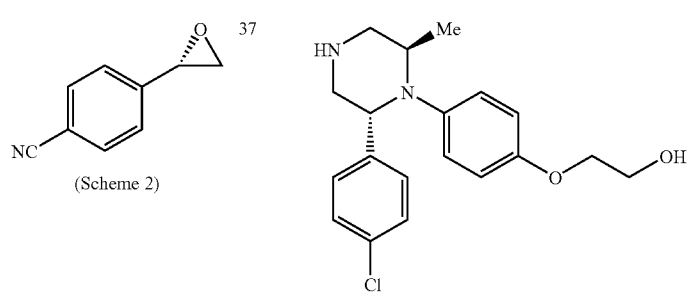

TABLE 8-continued
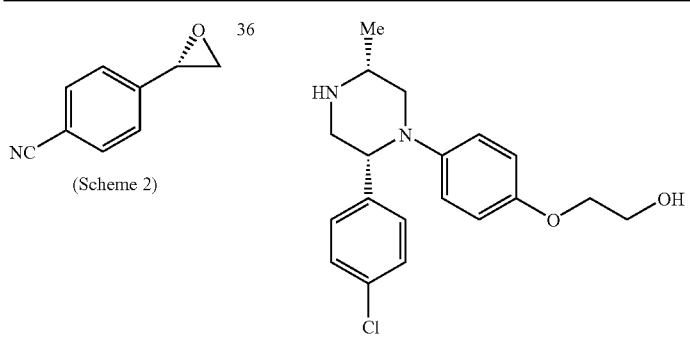
36
(Scheme 2)
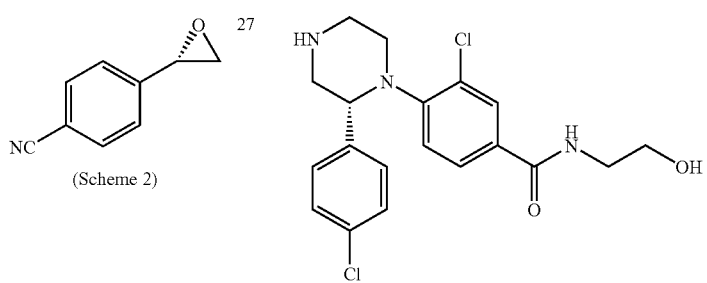
27
(Scheme 2)
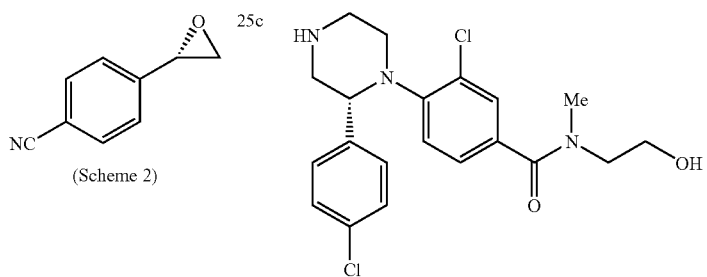
25c
(Scheme 2)
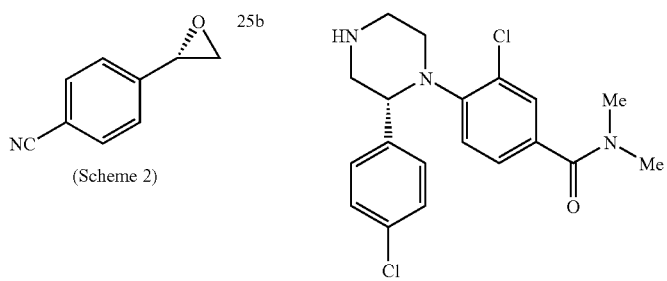
25b
(Scheme 2)
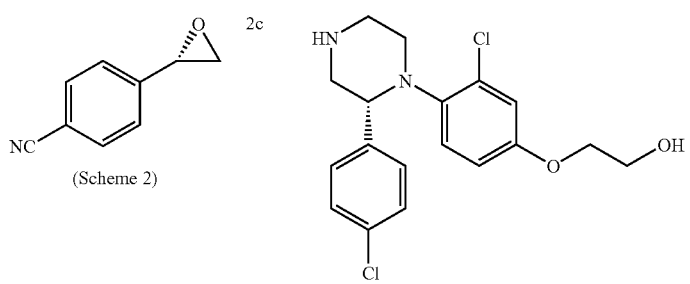
2c
(Scheme 2)

TABLE 8-continued
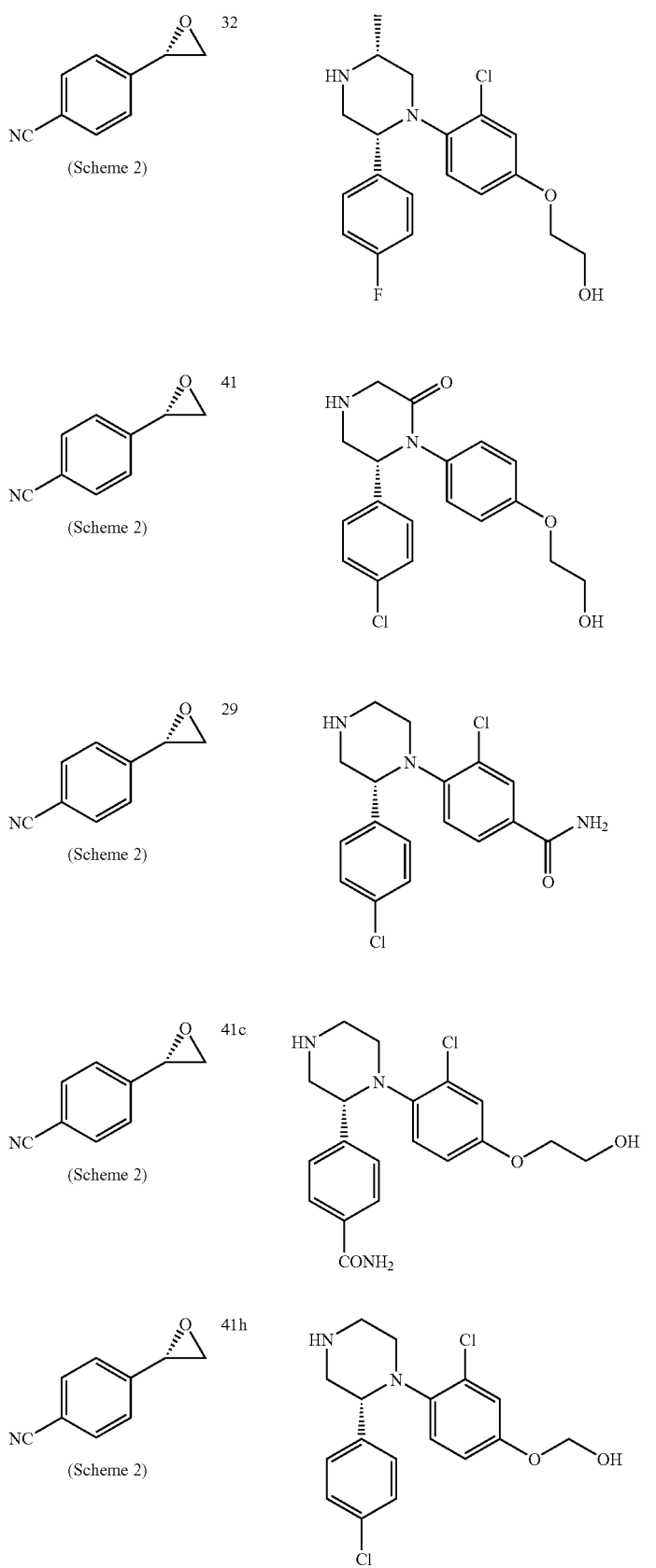

TABLE 8-continued
| | | |
|---|---|---|
| | 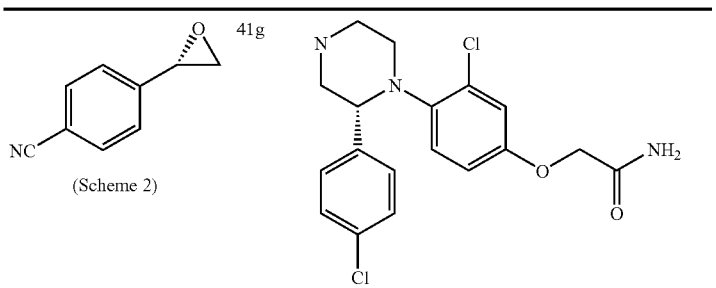 | 41g (Scheme 2) |
| | 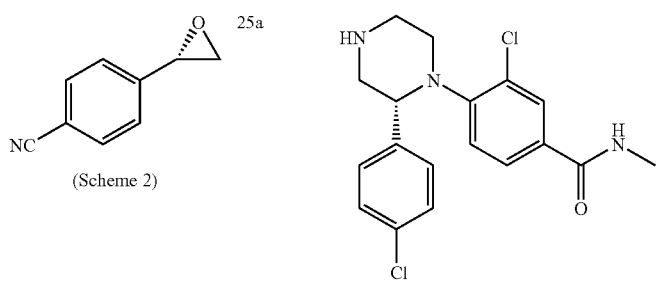 | 25a (Scheme 2) |
| Ex. | Structure |
|---|---|
| 110 | 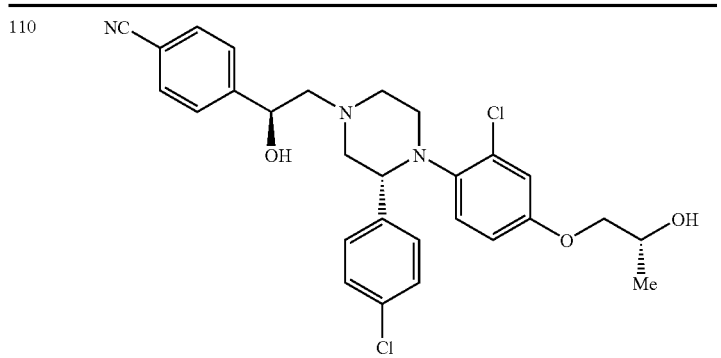 |
| 111 | 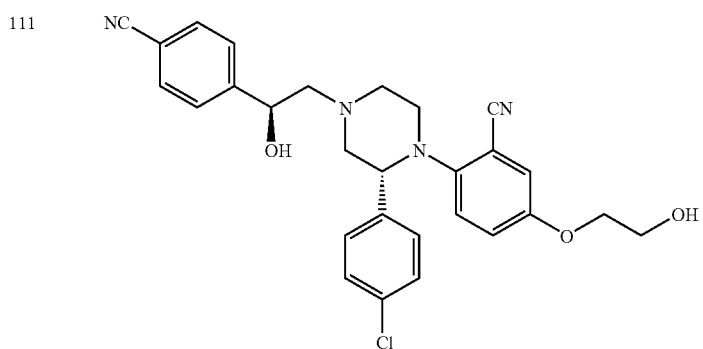 |
| 112 | 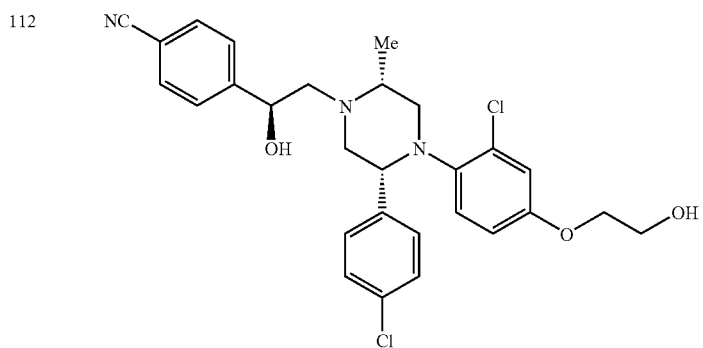 |

TABLE 8-continued
113 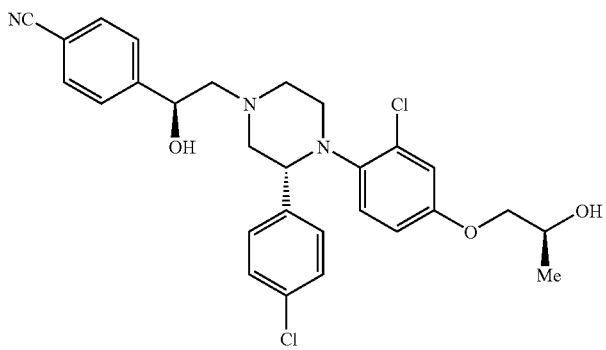
114 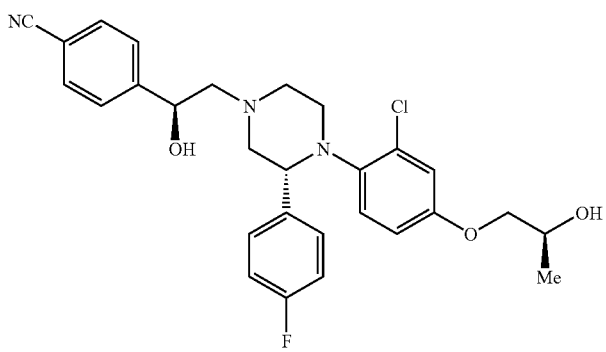
115 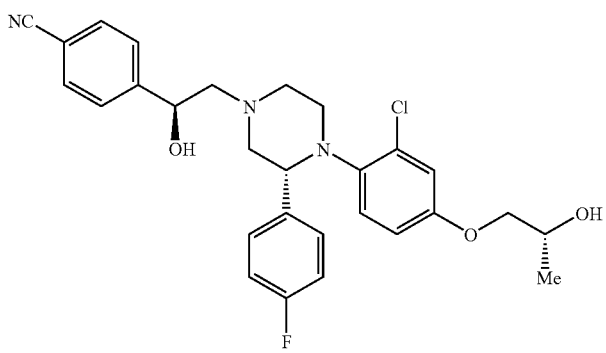
116 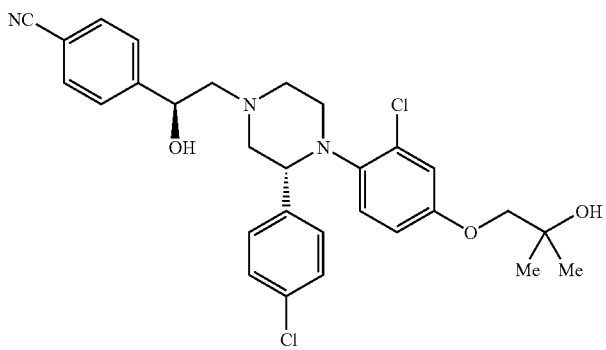

TABLE 8-continued
| 117 | 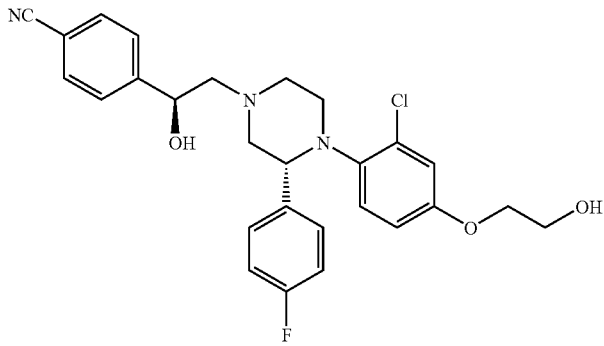 |
| 118 | 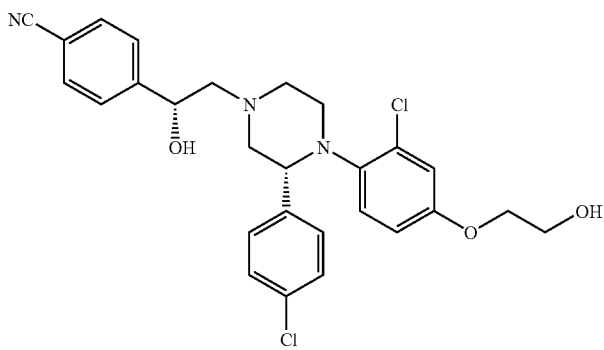 |
| 119 | 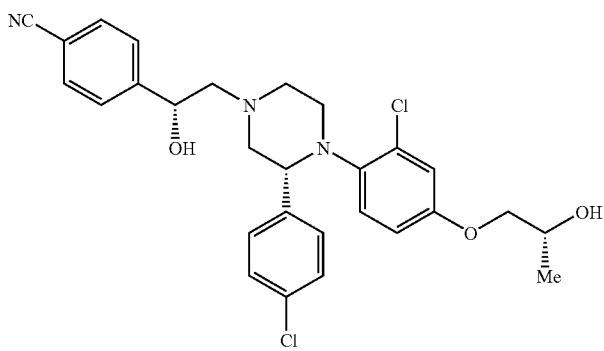 |
| 120 | 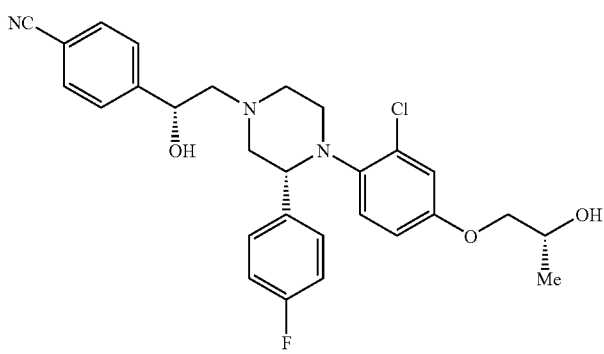 |

TABLE 8-continued
| 121 | 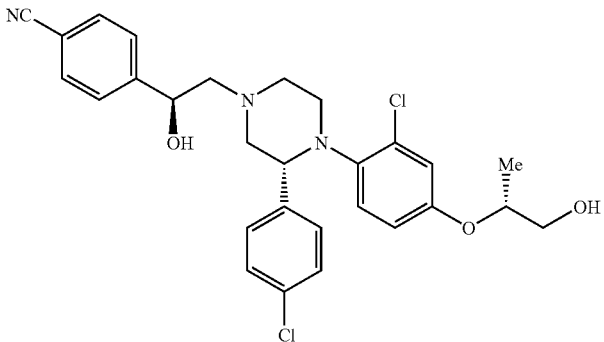 |
| 122 | 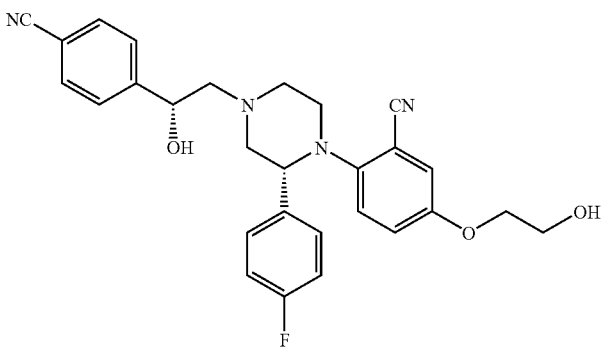 |
| 123 | 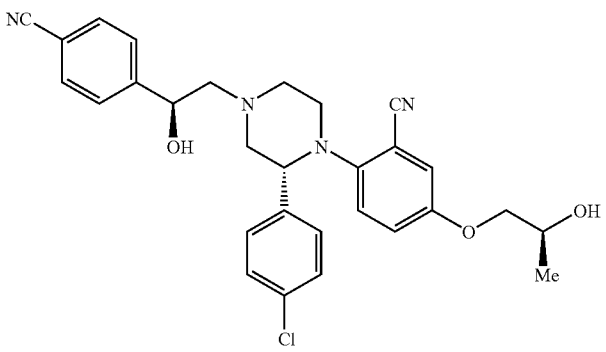 |
| 124 | 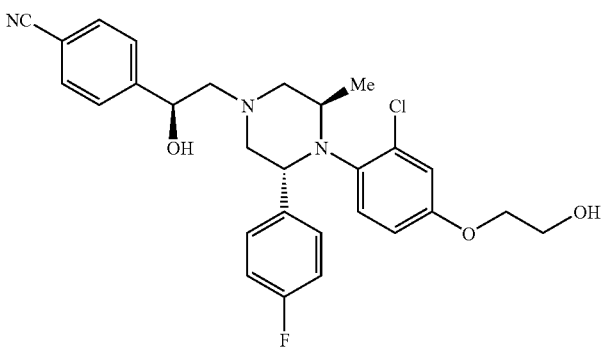 |

TABLE 8-continued
125 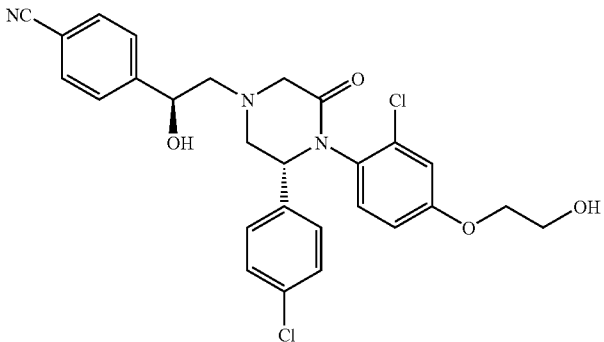
126 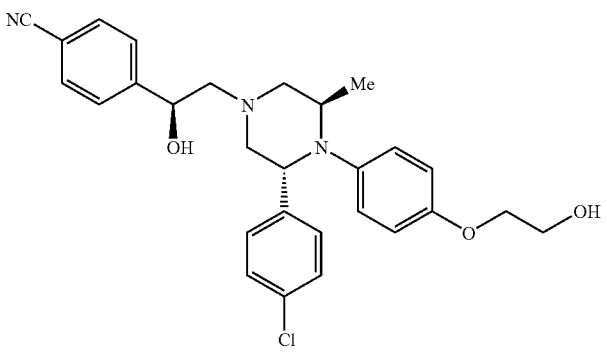
127 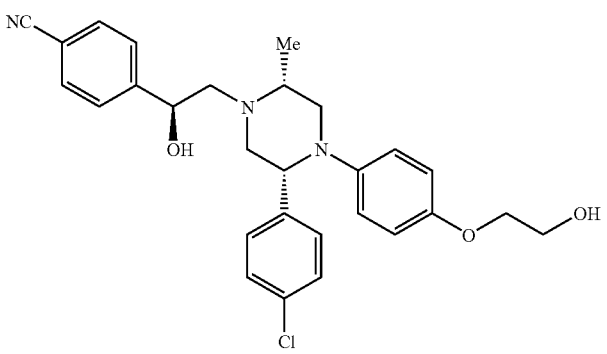
128 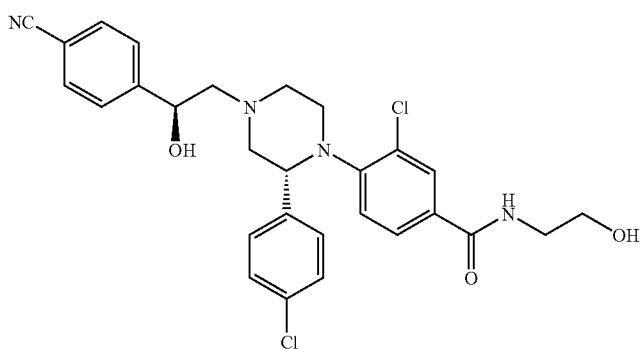

TABLE 8-continued
| 129 | 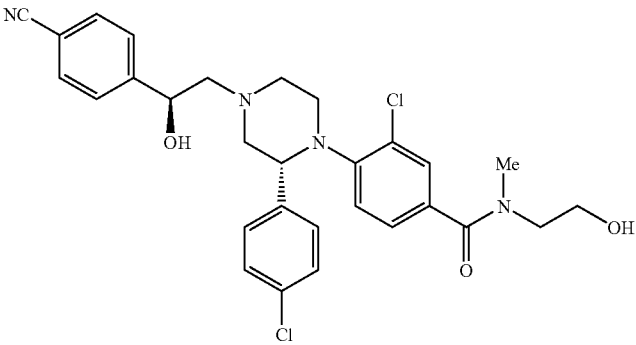 |
| 130 | 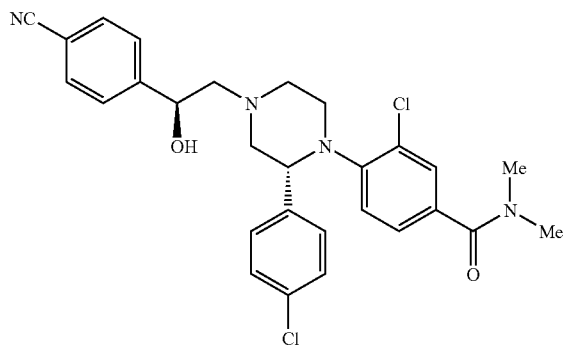 |
| 131 | 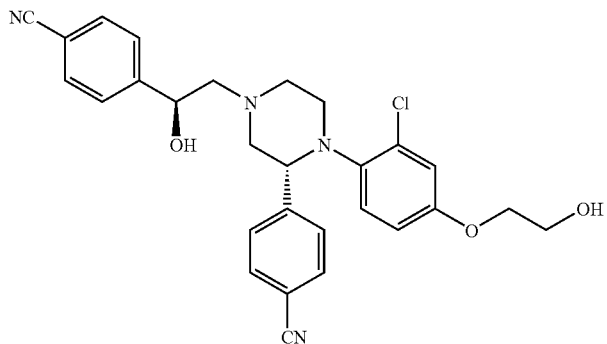 |
| 131a | 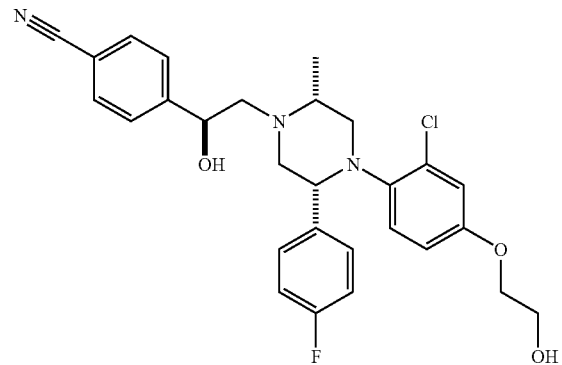 [SMILES: C[C@@H]1CN(c2ccc(OCCO)cc2Cl)[C@H](c2ccc(F)cc2)CN1C[C@@H](O)c1ccc(C#N)cc1] |

TABLE 8-continued
131b
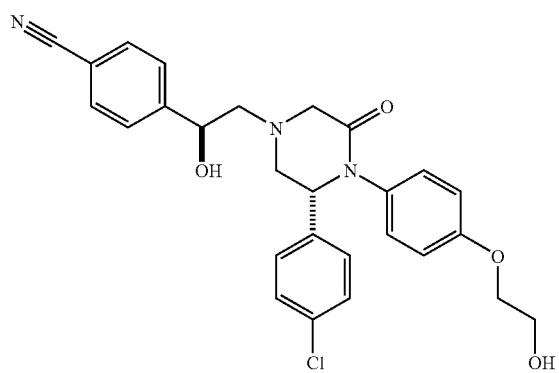 [SMILES: N#Cc1ccc([C@H](O)CN2CC(=O)N(c3ccc(OCCO)cc3)[C@H](c3ccc(Cl)cc3)C2)cc1]
131c
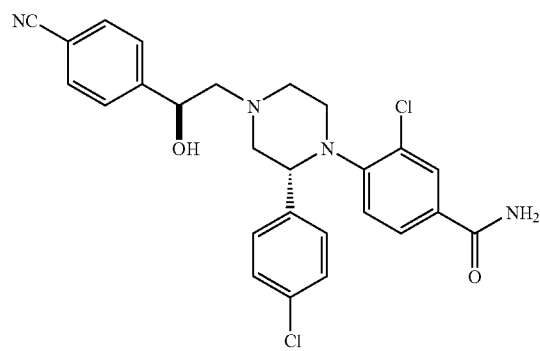
131d
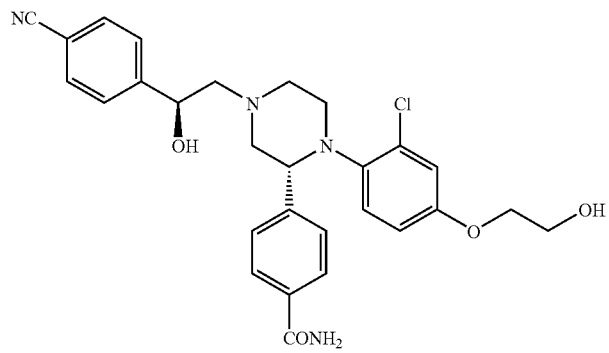
131e
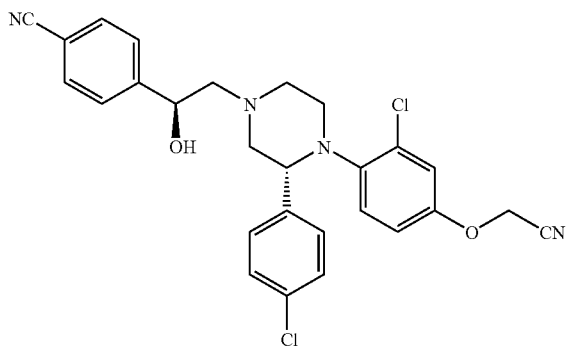

TABLE 8-continued
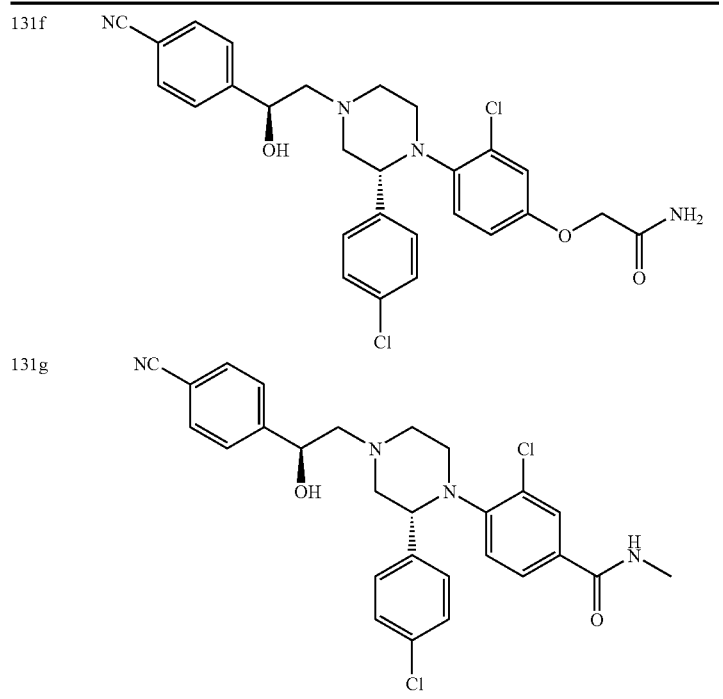
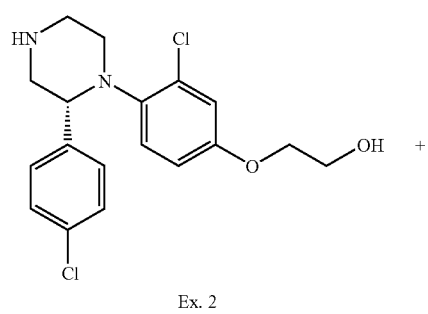
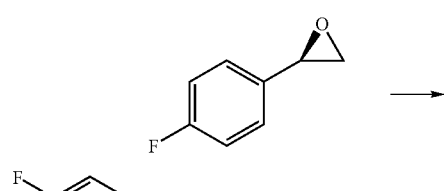
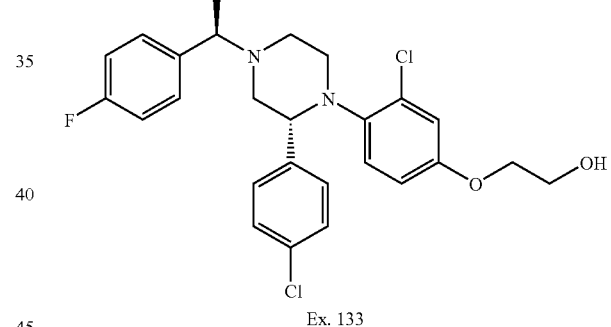
To the piperazine Ex. 2 (0.12 g, 0.33 mmol) in a pressure tube was added the fluoroepoxide (prepared in Scheme 5). Capped the pressure tube and warmed to 100° C. Heated for 15 h. Cooled to room temperature and purified directly by silica gel chromatography (0-100% EtOAc/Hex over 30 minutes) to provide Ex. 132 (0.99 mg, 0.2 mmol) and Ex. 133 (0.30 g, 0.06 mmol).
Scheme 58
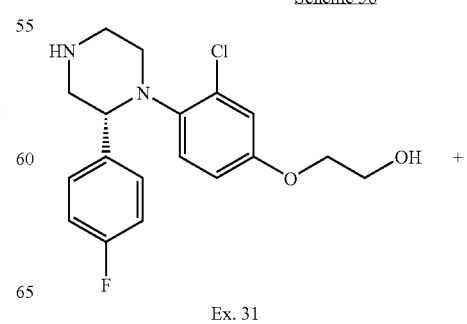

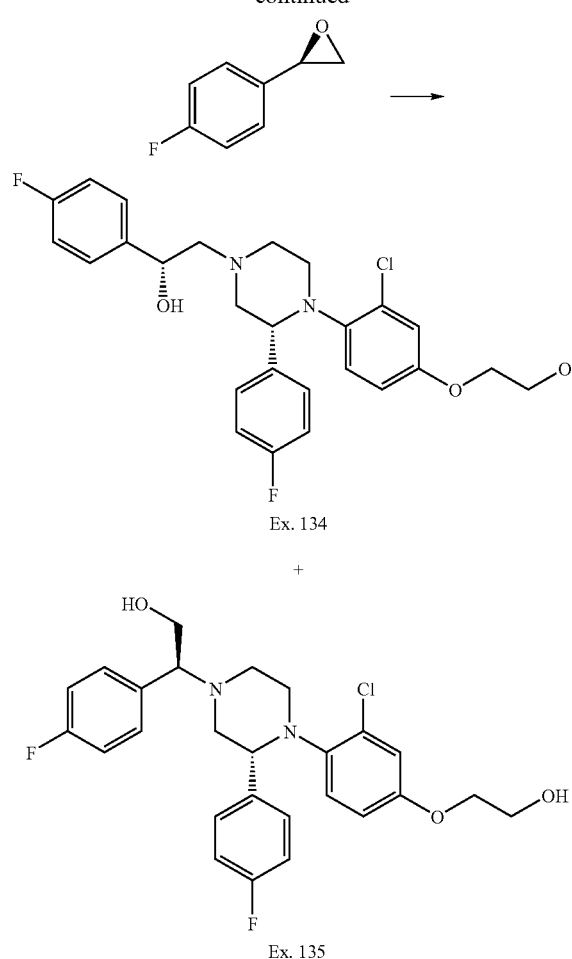

Ex. 134 and Ex. 135 were prepared in the same manner as Ex. 132 and Ex. 133 in Scheme 57 except that piperazine Ex. 31 was used instead of piperazine Ex. 2.

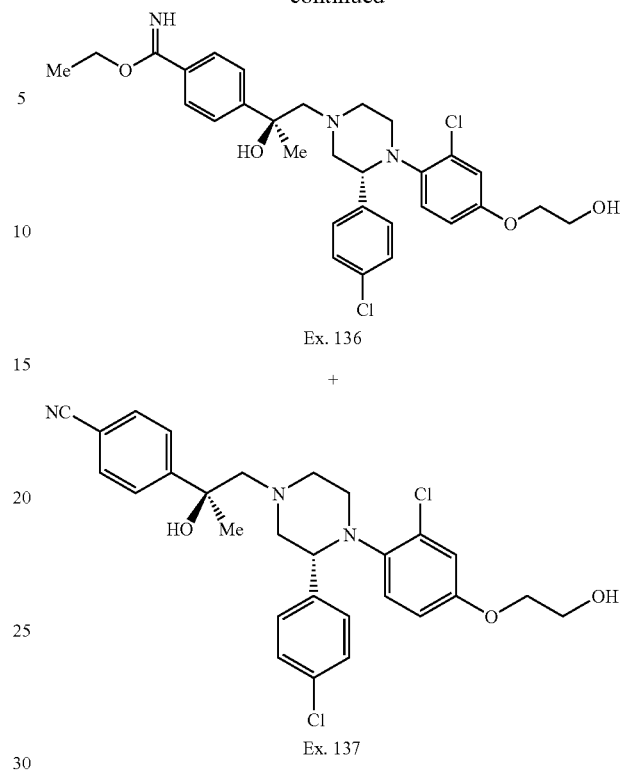

To Ex. 2 (0.03 g, 0.08 mmol) in ethanol (1 mL) was added the mesylate (prepared in Scheme 22) and $K_2CO_3$ (0.034 g, 0.24 mmol). Warmed to 75° C. and stirred for 18 h. Added an additional mesylate (0.01 g, 0.04 mmol) and continued to heat at 75° C. for 24 h. Cooled the reaction to room temperature and concentrated in vacuo. Added water and extracted with EtOAc. Combined organics and washed with water and brine. Dried ($MgSO_4$) the organic layer, filtered, and concentrated in vacuo. Purified the residue by prep plate chromatography (2000μ $SiO_2$, 50%EtOAc/Hex) to provide the imidate Ex. 136 (0.028 g) and Ex. 137 (0.005 g).

Scheme 59

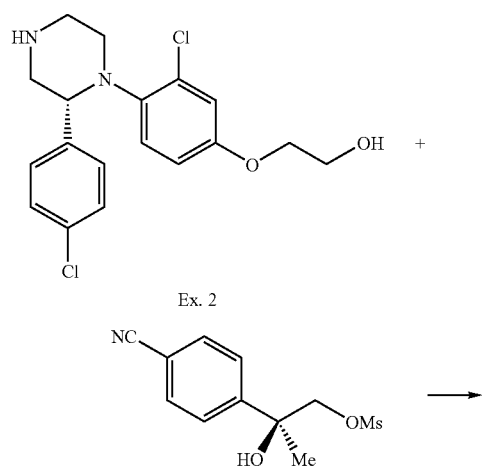

Scheme 60

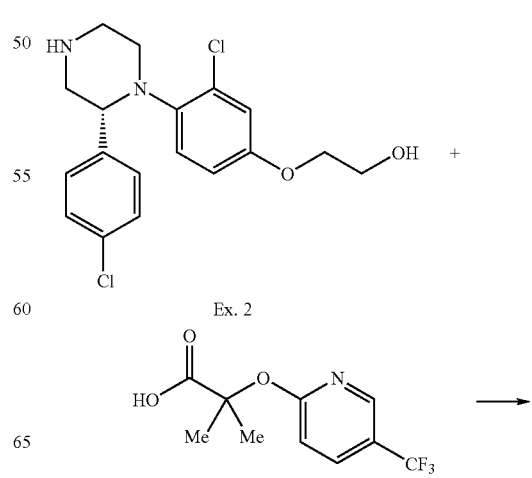

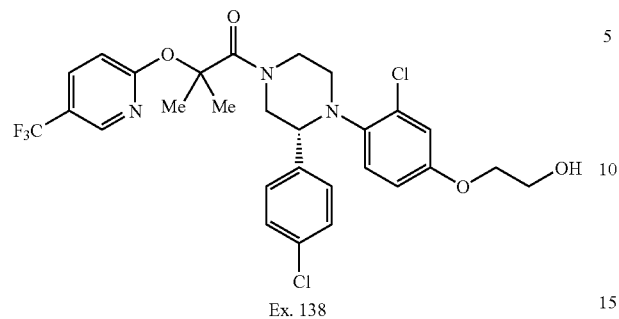

Ex. 138

To the piperzine Ex. 2 (0.10 g, 0.27 mmol) in acetonitrile (1 mL) was added the acid (preparation described in WO03077847) (0.25 g, 0.41 mmol). HOBt (0.07 g, 0.54 mmol), TEA (0.11 mL) and EDCl (0.10 g, 0.54 mmol). Warmed the reaction to 80° C. Stirred for 18 h and cooled to room temperature. Added EtOAc and washed with 1N NaOH, water, and brine. Dried (MgSO$_4$) the organic layer, filtered, and concentrated in vacuo. Purified the residue by silica gel chromatography (0-50% EtOAc/Hex over 25 minutes) to provide the amide Ex. 138 (0.11 g, 0.18 mmol).

Scheme 61

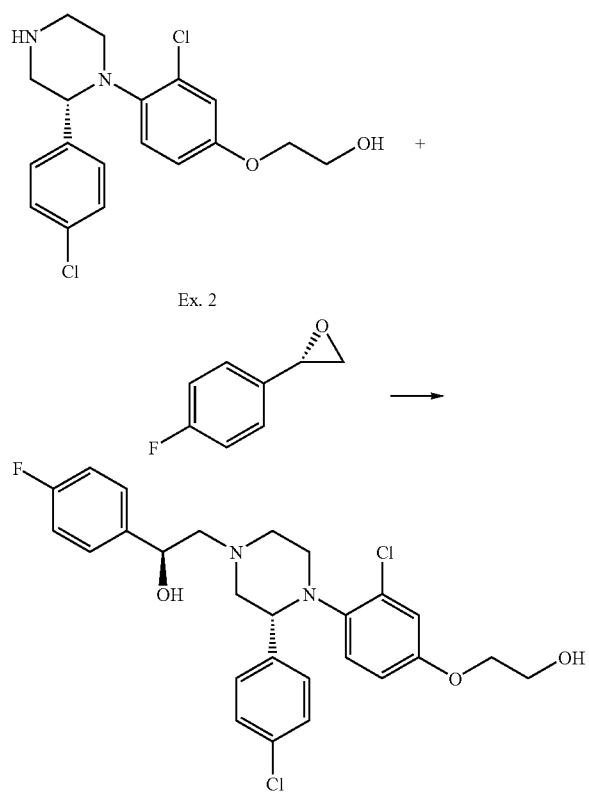

Ex. 2

Ex. 139

Example 139 and Example 140 were formed in the same manner as Example 132 and Example 133 in Scheme 57 except that the epoxide formed in Scheme 4 was used.

Scheme 62

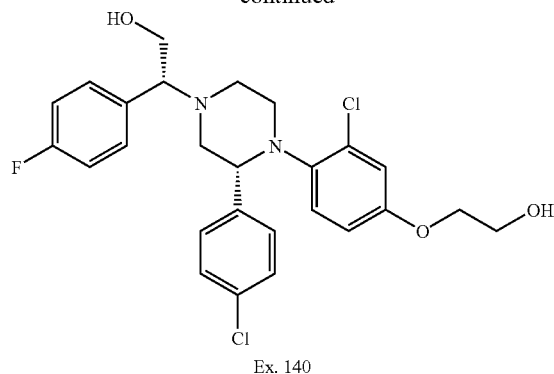

Ex. 140

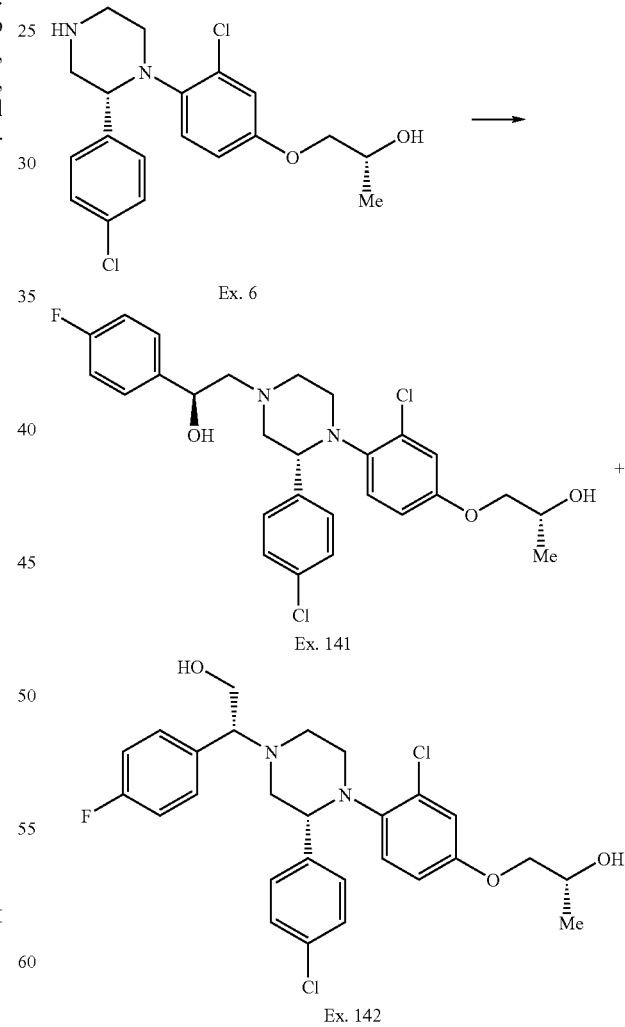

Ex. 6

Ex. 141

Ex. 142

Ex. 141 and Ex. 142 were prepared using the conditions in Scheme 61 except that piperazine Ex. 6 was used instead of Ex. 2.

Scheme 63

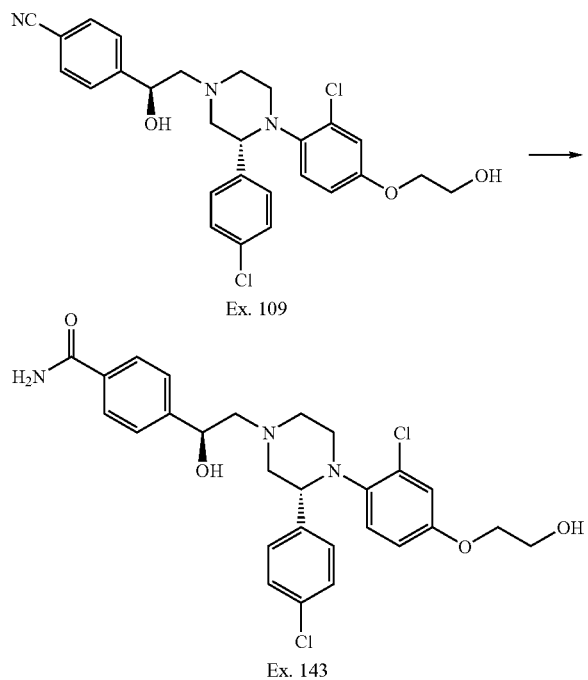

Ex. 109 was converted to Ex. 143 using the procedure described in Step 2 of Scheme 37.

Scheme 64

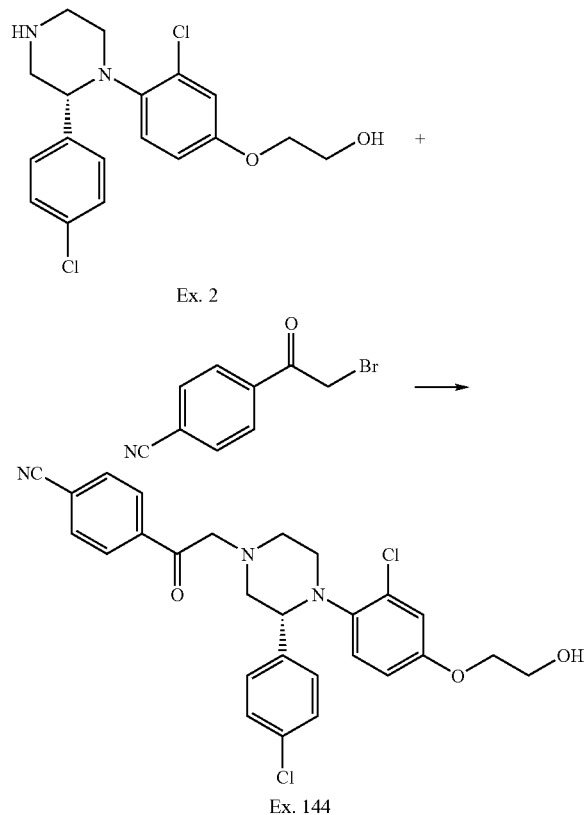

To Ex. 2 (0.25 g, 0.68 mmol) in THF (2 mL) was added N,N-diisopropyl amine (0.27 mL) followed by 2-bromo-4'-cyanoacetophenone (0.17 g, 0.75 mmol). The reaction was stirred at room temperature for 2 h. The reaction mixture was taken up into EtOAc and washed with saturated NaHCO$_3$, water, and brine. Dried (MgSO$_4$) the organic layer, filtered, and concentrated in vacuo. Purified the residue by silica gel chromatography (0-40% EtOAc/Hex over 10 min.) to provide Ex. 144 (0.31 g, 0.61 mmol).

Scheme 65

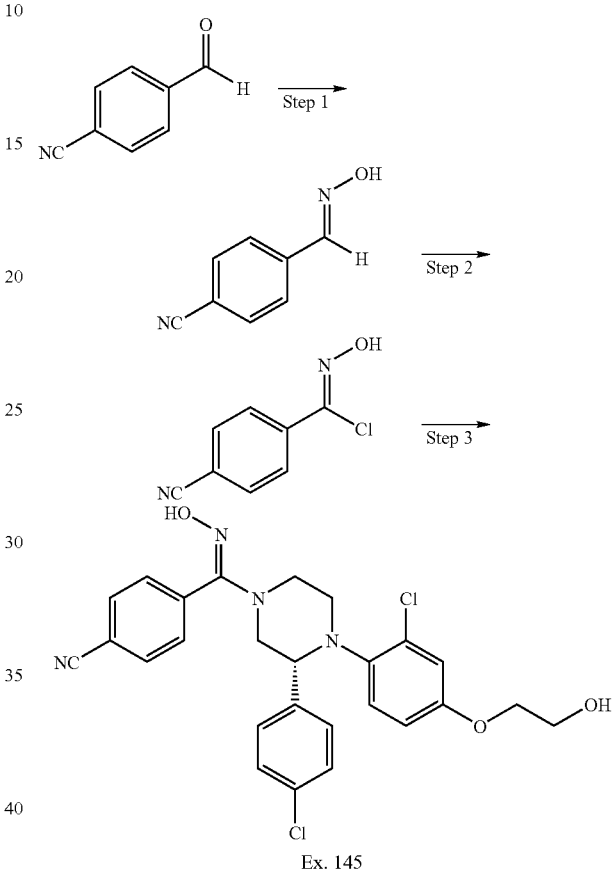

Step 1 To 4-formylbenzonitrile (2.0 g, 15 mmol) in ethanol (20 mL) was added pyridine (3.1 mL) and hydroxylamine hydrochloride (2.1 g, 30 mmol). Warmed the reaction to reflux and stirred for 18 h. Concentrated the reaction in vacuo. Took up the mixture into dichloromethane and washed with water and brine Dried (MgSO$_4$) the organic layer, filtered, and concentrated in vacuo to provide the oxime (1.0 g, 6.6 mmol).

Step 2 To the oxime (1.0 g, 6.6 mmol) in DMF at room temperature was added N-chlorosuccinimide (0.9 g, 6.6 mmol). Stirred at room temperature for 20 h. Added water and extracted with ether. Combined the organic layers and washed with water and brine Dried (MgSO$_4$) the organic layer, filtered, and concentrated in vacuo to provide 4-cyano-N-hydroxybenzimidoylchloride (1.0 g, 5.8 mmol).

Step 3 To the piperazine Ex. 2 (0.20 g, 0.56 mmol) in dichloromethane (1.7 mL) was added N,N-diisopropylamine (0.2 mL) and the 4-cyano-N-hydroxybenzimidoylchloride (0.15 g, 0.82 mmol) prepared in step 2. Stirred at room temperature for 18 h. Added dichloromethane and washed with saturated NaHCO$_3$, water, and brine. Dried (MgSO$_4$) the organic layer, filtered, and concentrated in vacuo. Purified by silica gel chromatography (0-75%EtOAc/hex over 30 minutes to provide Ex. 145 (0.085 g, 0.16 mmol).

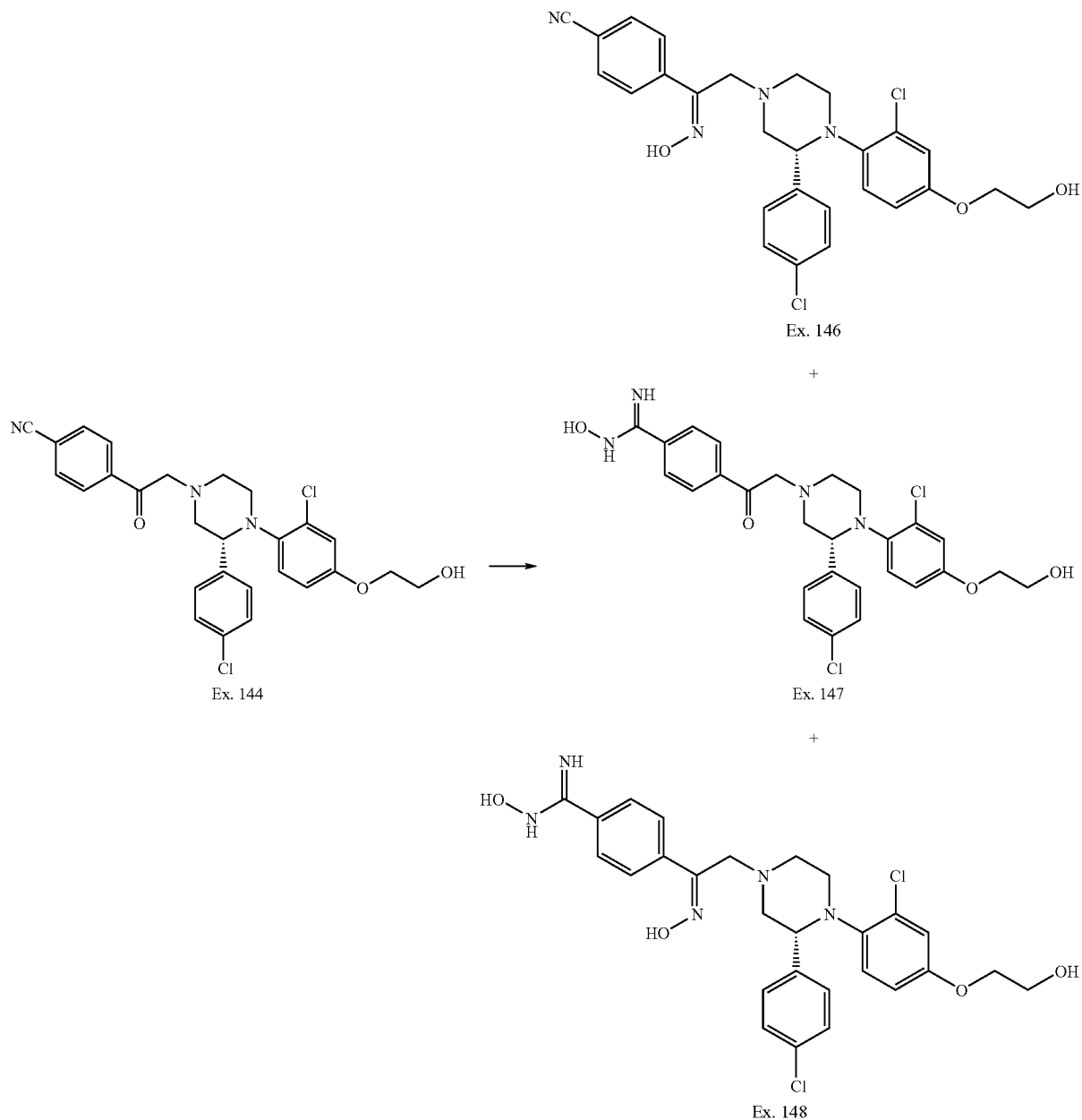

Scheme 66

Ex. 146

Ex. 144

Ex. 147

Ex. 148

To Ex. 144 (0.27 g, 0.53 mmol) in ethanol (0.6 mL) was added hydroxylamine hydrochloride (0.07 g, 1.1 mmol) and pyridine (0.1 mL). Warmed the reaction to reflux and stirred for 18 h. Concentrated in vacuo. Took up the residue into EtOAc and washed with water and brine. Dried (MgSO$_4$) the organic layer, filtered, and concentrated in vacuo. Purified the residue by silica gel chromatography (0-100% EtOAc/hex over 30 minutes) to provide Ex. 146 as the major product (0.045 g, 0.09 mmol), and Ex. 147 (0.010 g) and Ex.148 (0.011 g) as side products.

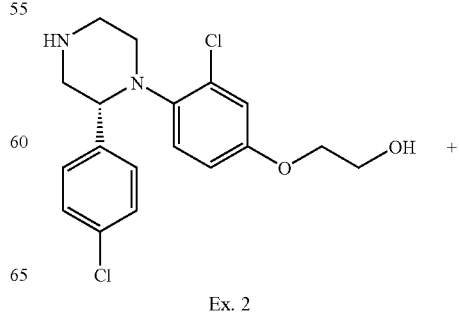

Scheme 67

Ex. 2

-continued

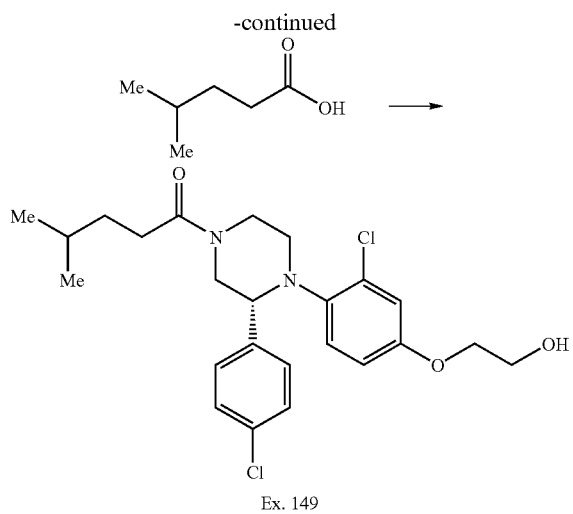

Ex. 149

To Ex. 2 (0.10 g, 0.27 mmol) in dichloroethane (1 mL) was added 4-methylvaleric acid (0.047 9, 0.41 mmol), HOBt (0.02mg, 0.14 mmol), and EDCl (0.10 g, 0.54 mmol). Stirred the reaction at room temperature for 18 h. Added methylene chloride and washed with saturated NaHCO$_3$, water, and brine. Dried (MgSO$_4$) the organic layer, filtered, and concentrated in vacuo. Purified the residue by silica gel chromatography (0-40% EtOAc/hex over 25 minutes) to provide Ex. 149 (0.033 g, 0.07 mmol).

Scheme 67.1

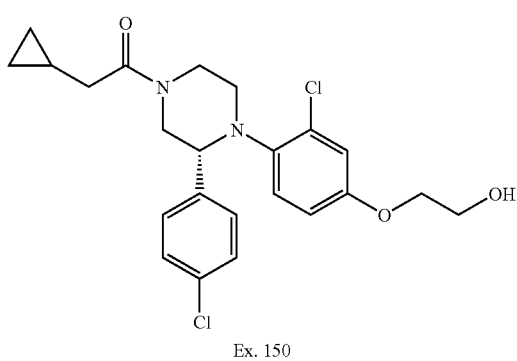

Ex. 150

Ex. 150 was prepared in the same manner as Ex. 149 in Scheme 67 except that cyclopropylacetic acid was used instead of 4-methylvaleric acid Scheme 68

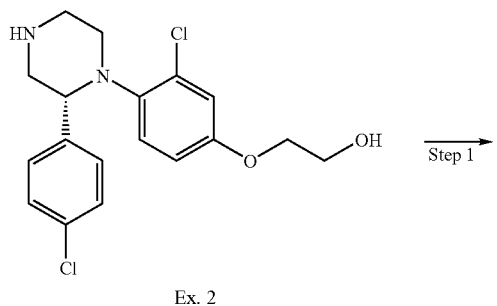

Ex. 2

-continued

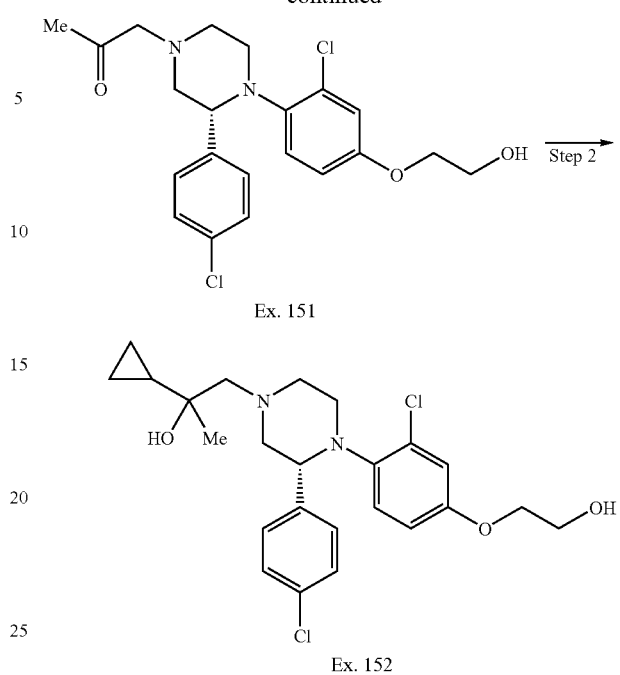

Ex. 151

Ex. 152

Step 1 To Ex. 2 (0.20 g, 0.54 mmol) in acetonitrile (2 mL) at 0° C. was added potassium carbonate (0.15 g, 1.1 mmol), sodium iodide (0.02 g, 0.14 mmol), and chloroacetone (0.05 mL). Stirred for 2 h and added water. Extracted with EtOAc. Washed the organic layer with water and brine. Dried (MgSO$_4$) the organic layer, filtered, and concentrated in vacuo. Purified the residue by silica gel chromatography (0-5% MeOH/EtOAc over 25 minutes) to provide Ex. 151 (0.23 g, 0.54 mmol).

Step 2 To Ex. 2 (0.20 g, 0.47 mmol) in THF (1 mL) at room temperature was added cyclopropylmagnesium bromide (0.5 M solution in THF, 1.9 mL, 0.9 mmol). Stirred at room temperature for 18 h. Added aqueous saturated Rochelle's salt solution and extracted with EtOAc. Washed the organic layer with water and brine. Dried (MgSO$_4$) the organic layer, filtered, and concentrated in vacua. Purified the residue by silica gel chromatography (0-100% EtOAc/hex over 30 minutes) to provide Ex. 152 (0.09 g, 0.19 mmol) as a 1:1 mixture of diastereomers.

Scheme 69

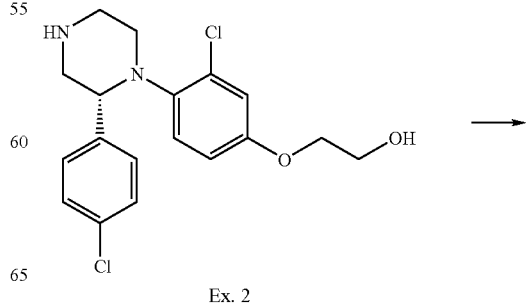

Ex. 2

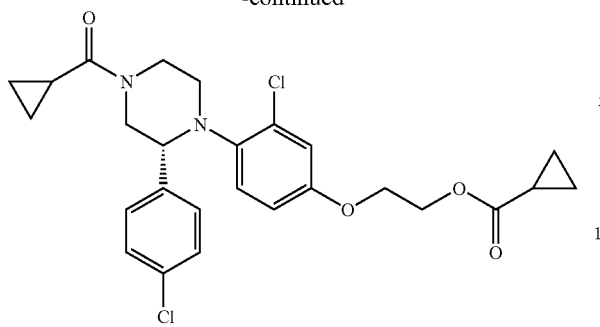

Ex. 153

To Ex. 2 (0.10 g, 0.27 mmol) in dichloromethane (2 mL) was added triethylamine (0.095 mL, 0.68 mmol) and cyclopropanecarboxylic acid (2 equivalents). Stirred at room temperature for 18 h. Added dichloromethane and washed with saturated NaHCO₃, water, and brine. Dried (MgSO₄) the organic layer, filtered, and concentrated in vacuo to provide Ex. 153 (0.13 g).

Scheme 69.1

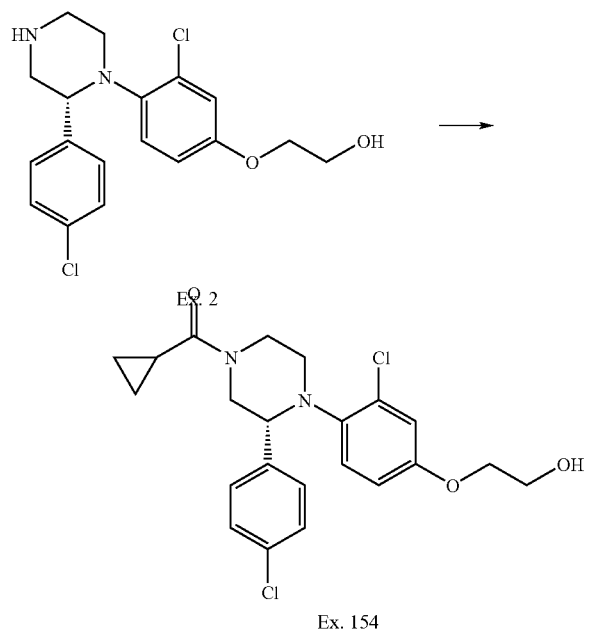

Ex. 154

Example 154 was prepared using the same conditions to prepare Ex 153 in Scheme 69 except that only 1 equivalent of cyclopropylcarbonyl chloride was used instead of 2 equivalents.

Scheme 69.2

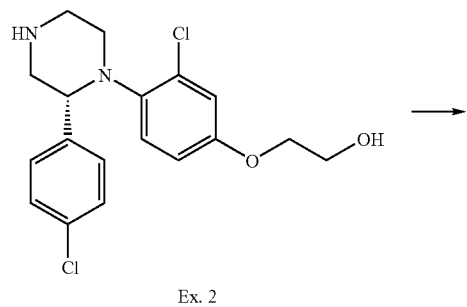

Ex. 2

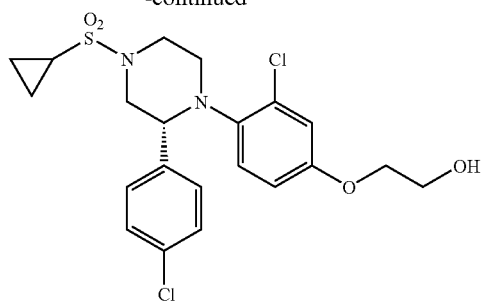

Ex. 155

To Ex. 2 (0.10 g, 0.27 mmol) in DCM (1 mL) was added TEA (0.056, 0.4 mmol) and cyclopropylsulfonyl chloride (0.027 mL, 0,27 mmol). The reaction was stirred at room temperature for 18 h. The reaction was diluted with DCM and washed with water and brine. The organic layer was dried (MgSO₄), filtered, and concentrated in vacua. The residue was purified by silica gel chromatography (0-50% EtOAc/Hex over 25 minutes) to provide Ex. 155 (0.10 g).

Scheme 70

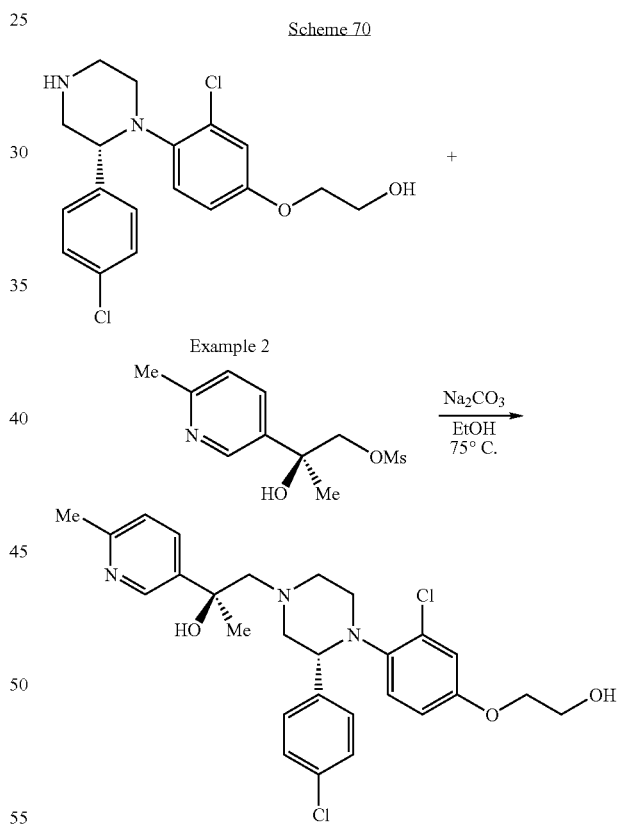

Example 156

To a solution of Example 2 (110 mg, 0.30 mmol) in EtOH (1 mL) in a pressure tube was added the mesylate from Table 2—entry 6 (88 mg, 036 mmol) and Na₂CO₃ (80 mg, 0.75 mmol). The pressure tube was sealed and the mixture was heated to 75° C. with stirring for 24 h. After that timer the mixture was concentrated in vacuo and the residue partitioned between EtOAc and water. The organic layer was separated, washed with brine, dried over MgSO₄, filtered and concentrated. The crude product was purified via flash chromatography (SiO₂: gradient elution, 100:0 to 0:100 hexanes:EtOAc) to afford Example 156 (110 mg, 71%) as a white foam.

TABLE 9
The following examples were prepared using a similar method to that described for Example 156 above.
| Ex. | Piperazine Core | Mesylate |
|---|---|---|
| 2 | 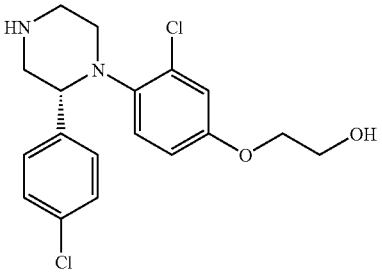 [SMILES: OCCOc1ccc(N2CCNC[C@H]2c2ccc(Cl)cc2)c(Cl)c1] | 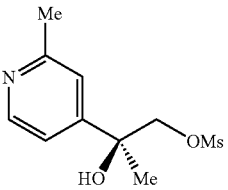 (Table 2, entry 5) |
| 31 | 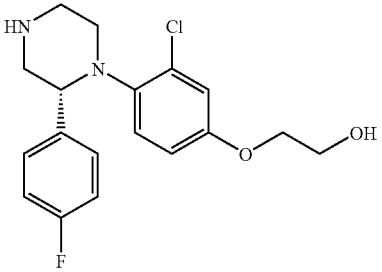 | 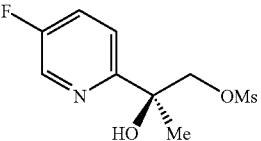 (Table 2, entry 1) |
| 22 | 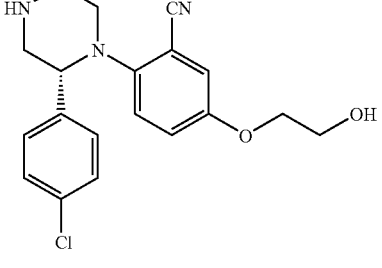 | 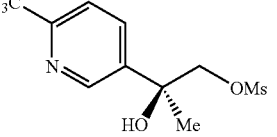 (Scheme 11) |
| 2 | 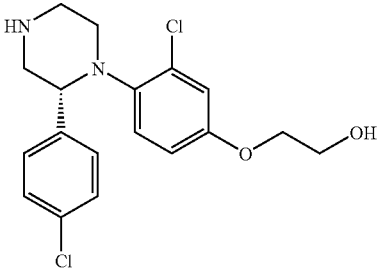 | 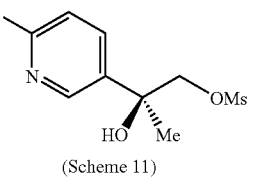 (Scheme 11) |
| 6 | 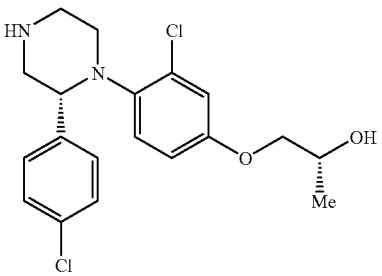 [SMILES: C[C@@H](O)COc1ccc(N2CCNC[C@H]2c2ccc(Cl)cc2)c(Cl)c1] | 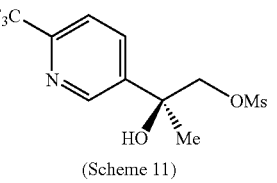 (Scheme 11) |

TABLE 9-continued
The following examples were prepared using a similar method to that described for Example 156 above.
| | | |
|---|---|---|
| 18 | 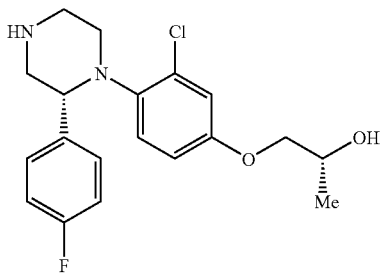 [SMILES: C[C@@H](O)COc1ccc(N2CCNC[C@H]2c2ccc(F)cc2)c(Cl)c1] | 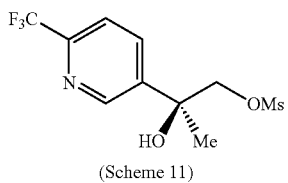 [SMILES: C[C@@](O)(COS(C)(=O)=O)c1ccc(C(F)(F)F)nc1] (Scheme 11) |
| 31 | 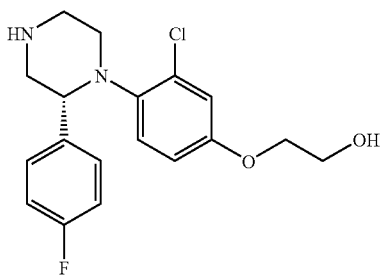 | 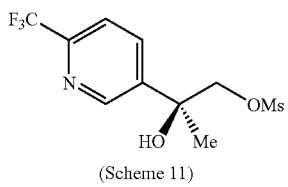 (Scheme 11) |
| 22 | 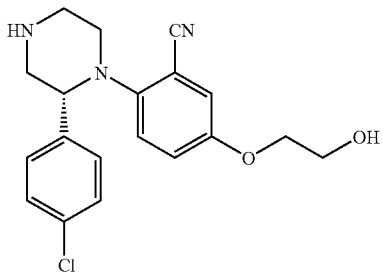 | 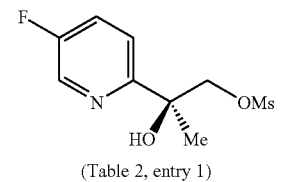 [SMILES: C[C@@](O)(COS(C)(=O)=O)c1ccc(F)cn1] (Table 2, entry 1) |
| 22 | 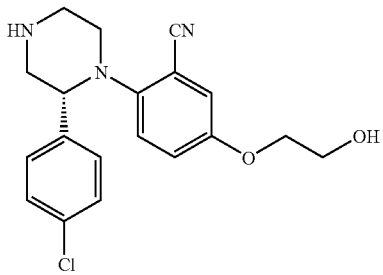 | 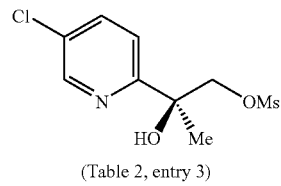 [SMILES: C[C@@](O)(COS(C)(=O)=O)c1ccc(Cl)cn1] (Table 2, entry 3) |
| 22 | 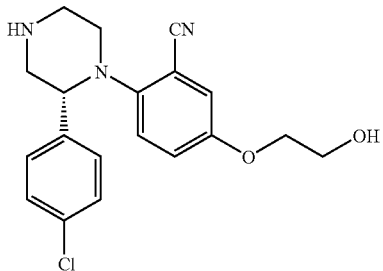 | 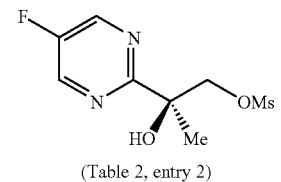 [SMILES: C[C@@](O)(COS(C)(=O)=O)c1ncc(F)cn1] (Table 2, entry 2) |

TABLE 9-continued
The following examples were prepared using a similar method to that described for Example 156 above.
| | | |
|---|---|---|
| 19 | 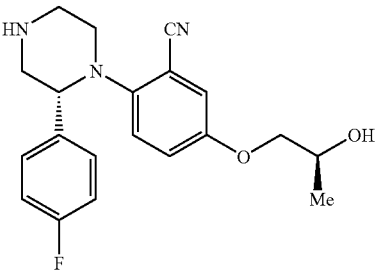 | 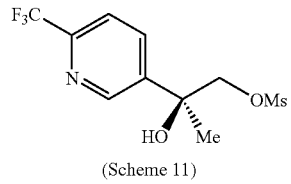 [SMILES: C[C@@](O)(COS(C)(=O)=O)c1ccc(C(F)(F)F)nc1]
(Scheme 11) |
| 4 | 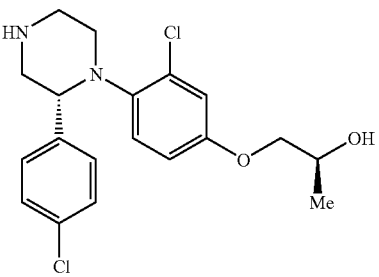 [SMILES: C[C@H](O)COc1ccc(N2CCNC[C@H]2c2ccc(Cl)cc2)c(Cl)c1] | 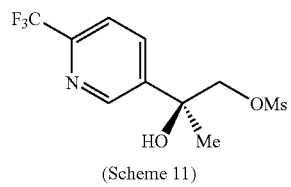 [SMILES: C[C@@](O)(COS(C)(=O)=O)c1ccc(C(F)(F)F)nc1]
(Scheme 11) |
| 31 | 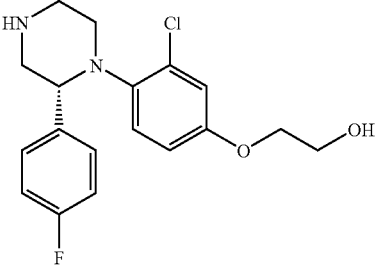 [SMILES: OCCOc1ccc(N2CCNC[C@H]2c2ccc(F)cc2)c(Cl)c1] | 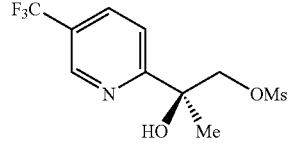
(Table 2, entry 4) |
| 22 | 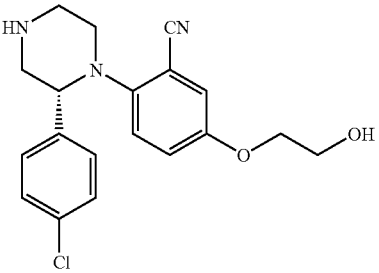 | 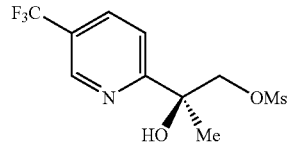
(Table 2, entry 4) |
| 31 | 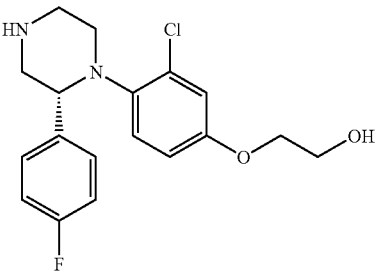 [SMILES: OCCOc1ccc(N2CCNC[C@H]2c2ccc(F)cc2)c(Cl)c1] | 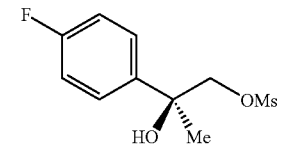
(Table 4, entry 2) |

TABLE 9-continued
The following examples were prepared using a similar method to that described for Example 156 above.
2 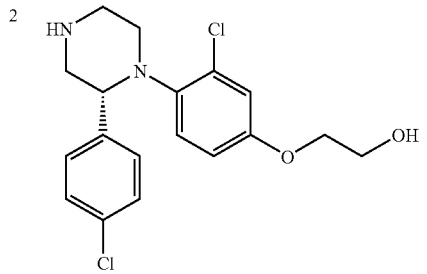 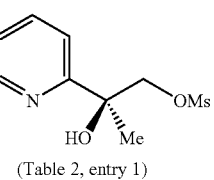
(Table 2, entry 1)
22 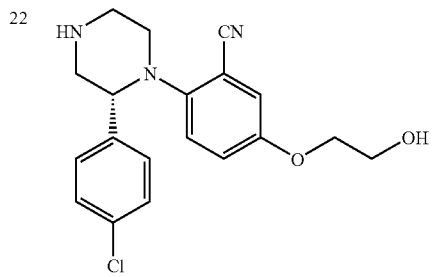 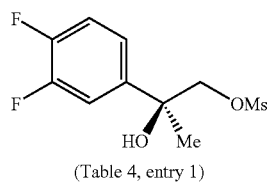
(Table 4, entry 1)
22 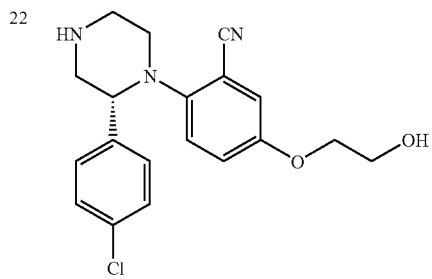 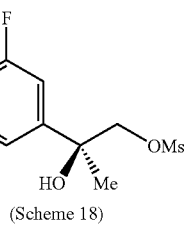
(Scheme 18)
2 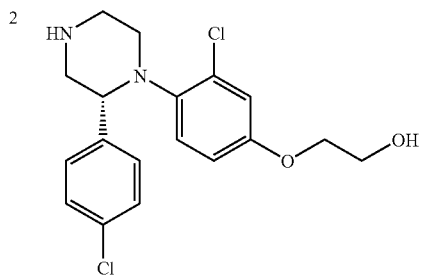 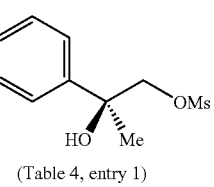
(Table 4, entry 1)
2 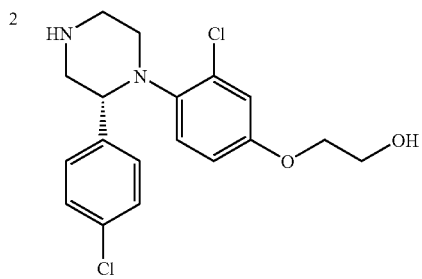 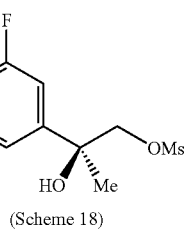
(Scheme 18)

TABLE 9-continued
The following examples were prepared using a similar method to that described for Example 156 above.
| 31 | 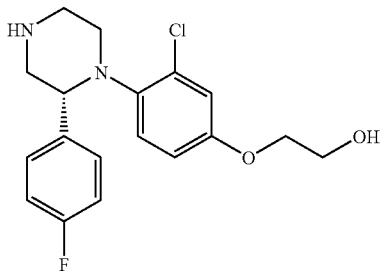 [SMILES: OCCOc1ccc(N2CCNC[C@H]2c2ccc(F)cc2)c(Cl)c1] | 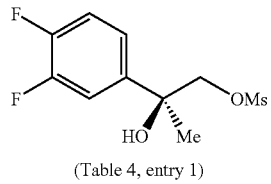 [SMILES: C[C@@](O)(COS(C)(=O)=O)c1ccc(F)c(F)c1] (Table 4, entry 1) |
| 31 | 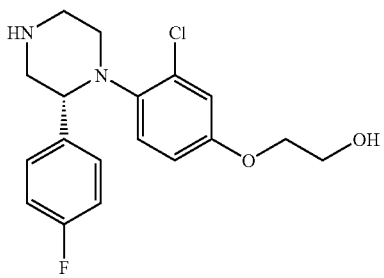 [SMILES: OCCOc1ccc(N2CCNC[C@H]2c2ccc(F)cc2)c(Cl)c1] | 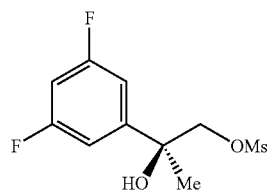 (Scheme 18) |
| 23 | 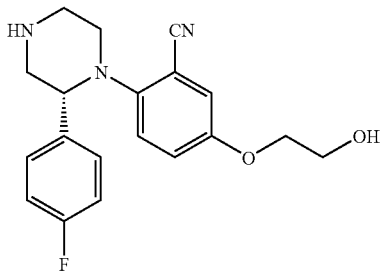 [SMILES: N#Cc1cc(OCCO)ccc1N1CCNC[C@H]1c1ccc(F)cc1] | 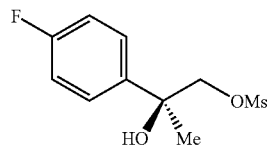 (Table 4, entry 2) |
| 22 | 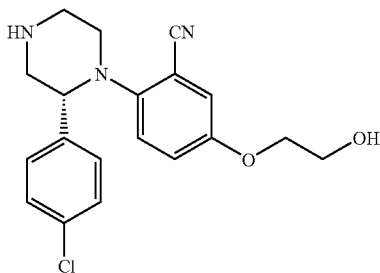 | 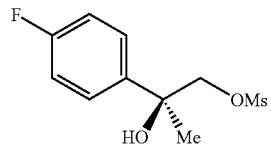 (Table 4, entry 2) |
| 36 | 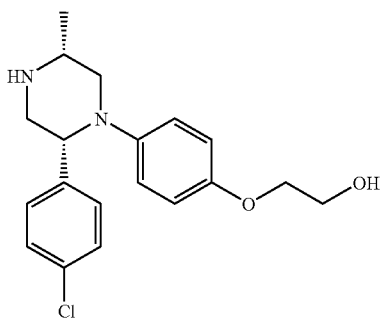 [SMILES: C[C@@H]1CN(c2ccc(OCCO)cc2)[C@H](c2ccc(Cl)cc2)CN1] | 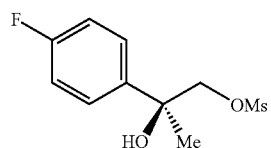 (Table 4, entry 2) |

TABLE 9-continued
The following examples were prepared using a similar method to that described for Example 156 above.
| 33 | 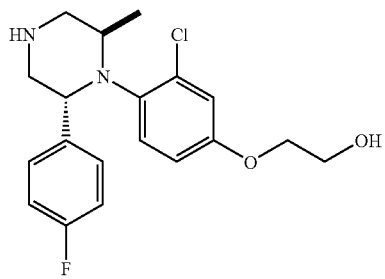 [SMILES: C[C@@H]1CNC[C@@H](c2ccc(F)cc2)N1c1ccc(OCCO)cc1Cl] | 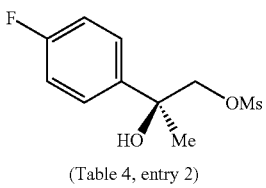 [SMILES: C[C@@](O)(COS(C)(=O)=O)c1ccc(F)cc1] (Table 4, entry 2) |
| 40 | 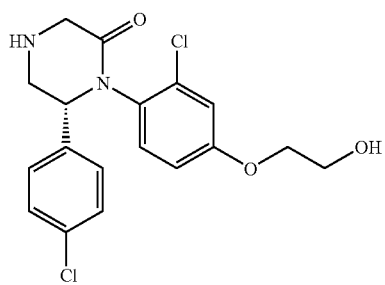 [SMILES: O=C1CNC[C@@H](c2ccc(Cl)cc2)N1c1ccc(OCCO)cc1Cl] | 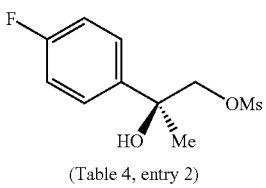 [SMILES: C[C@@](O)(COS(C)(=O)=O)c1ccc(F)cc1] (Table 4, entry 2) |
| 29 | 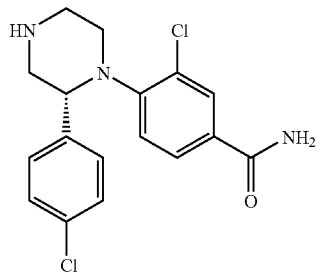 [SMILES: NC(=O)c1ccc(N2CCNC[C@H]2c2ccc(Cl)cc2)c(Cl)c1] | 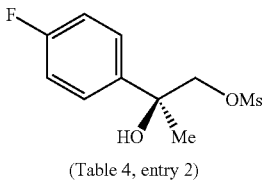 (Table 4, entry 2) |
| 24 | 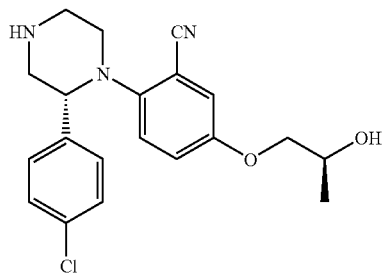 [SMILES: C[C@H](O)COc1ccc(N2CCNC[C@H]2c2ccc(Cl)cc2)c(C#N)c1] | 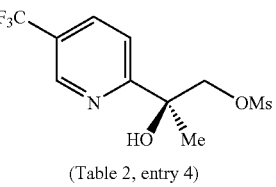 (Table 2, entry 4) |
| 24 | 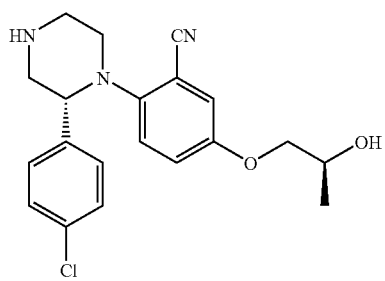 [SMILES: C[C@H](O)COc1ccc(N2CCNC[C@H]2c2ccc(Cl)cc2)c(C#N)c1] | 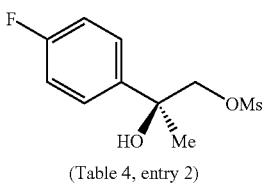 [SMILES: C[C@@](O)(COS(C)(=O)=O)c1ccc(F)cc1] (Table 4, entry 2) |

TABLE 9-continued
The following examples were prepared using a similar method to that described for Example 156 above.
| 24 | 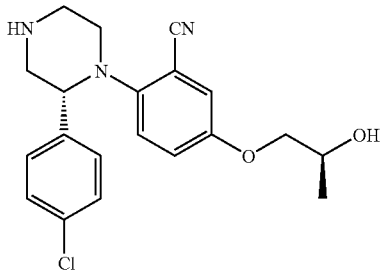 [SMILES: C[C@H](O)COc1ccc(N2CCNC[C@H]2c2ccc(Cl)cc2)c(C#N)c1] | 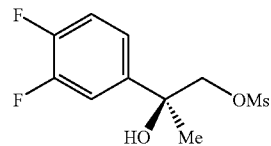 (Table 4, entry 1) |
| --- | --- | --- |
| 31 | 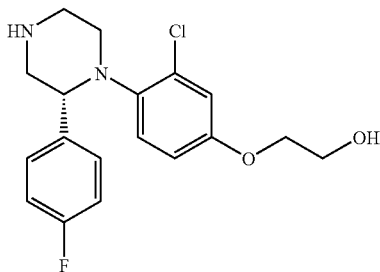 [SMILES: OCCOc1ccc(N2CCNC[C@H]2c2ccc(F)cc2)c(Cl)c1] | 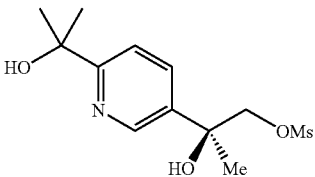 (Scheme 14) |
| 2 | 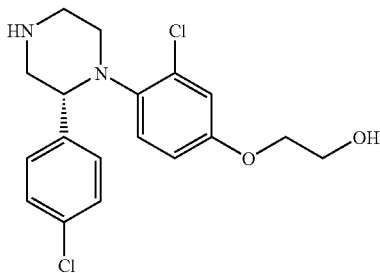 [SMILES: OCCOc1ccc(N2CCNC[C@H]2c2ccc(Cl)cc2)c(Cl)c1] | 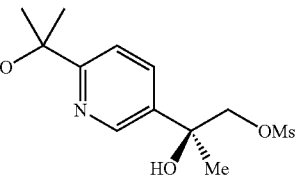 (Scheme 14) |
| 22 | 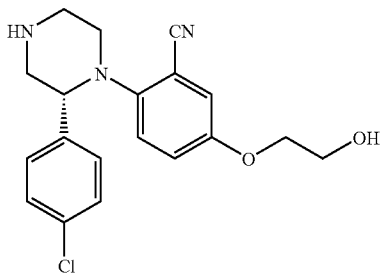 [SMILES: N#Cc1cc(OCCO)ccc1N1CCNC[C@H]1c1ccc(Cl)cc1] | 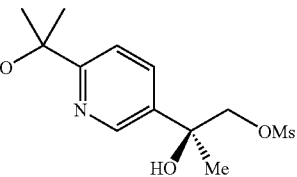 (Scheme 14) |
| 24 | 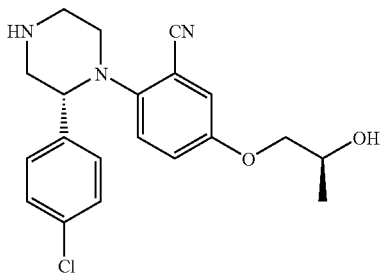 [SMILES: C[C@H](O)COc1ccc(N2CCNC[C@H]2c2ccc(Cl)cc2)c(C#N)c1] | 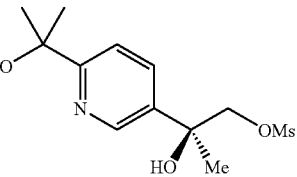 (Scheme 14) |

TABLE 9-continued
The following examples were prepared using a similar method to that described for Example 156 above.
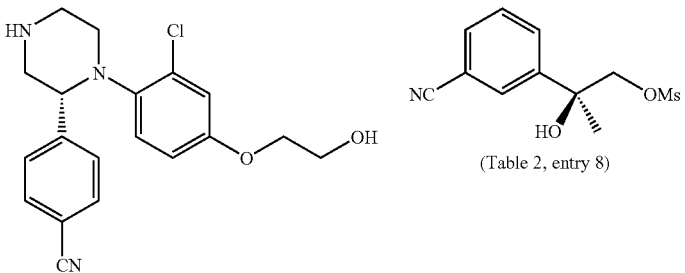
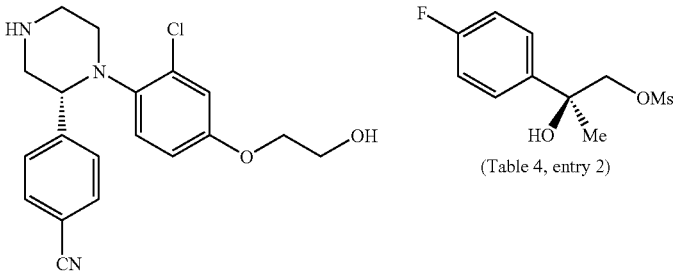
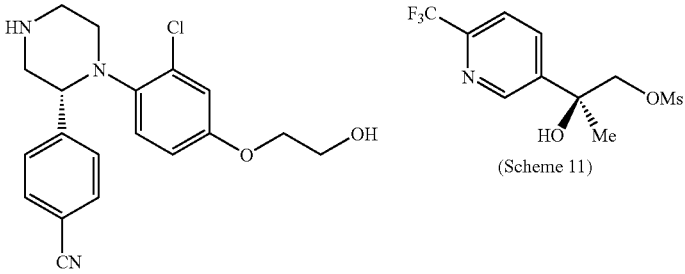
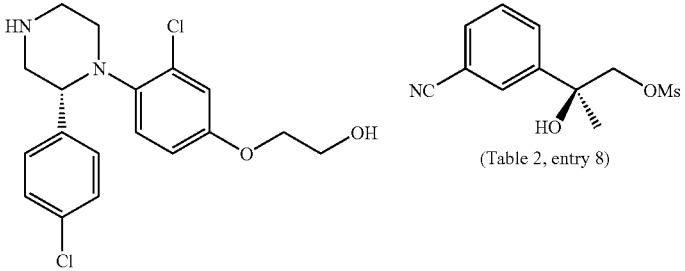
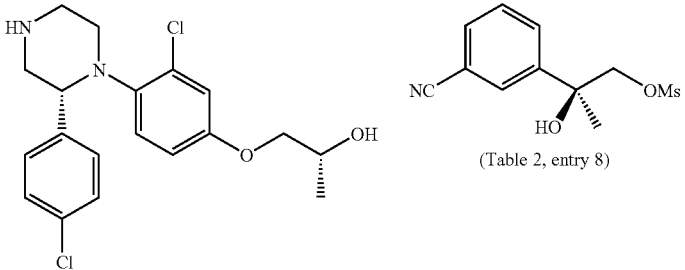

TABLE 9-continued
The following examples were prepared using a similar method to that described for Example 156 above.
| 41 | 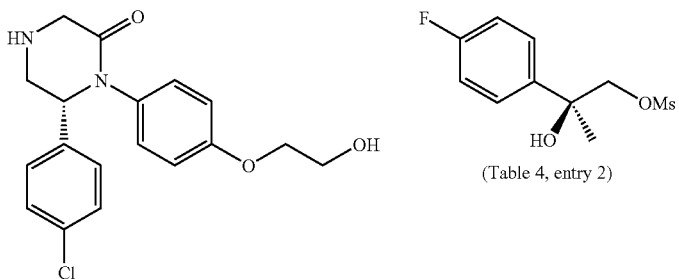 | (Table 4, entry 2) |
| 41 | 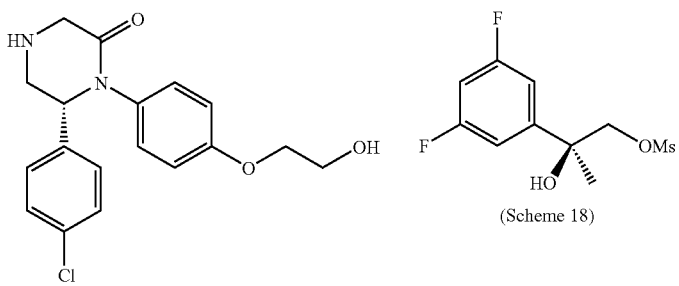 | (Scheme 18) |
| 41 | 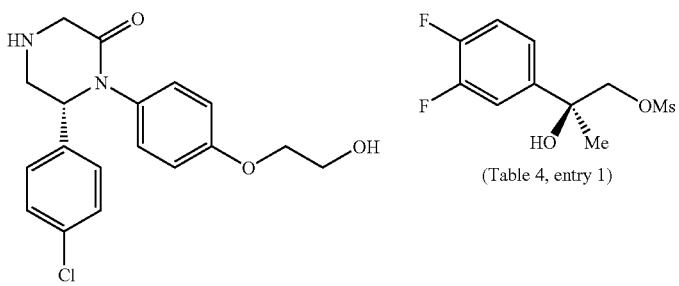 | (Table 4, entry 1) |
| 31 | 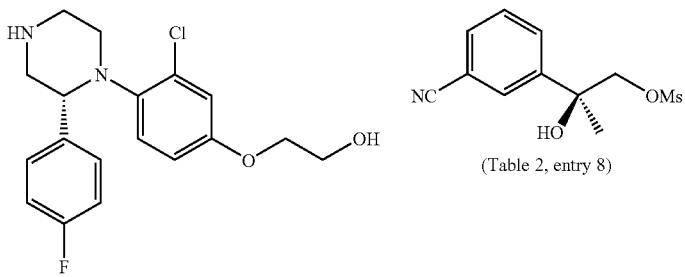 | (Table 2, entry 8) |
| 4  | 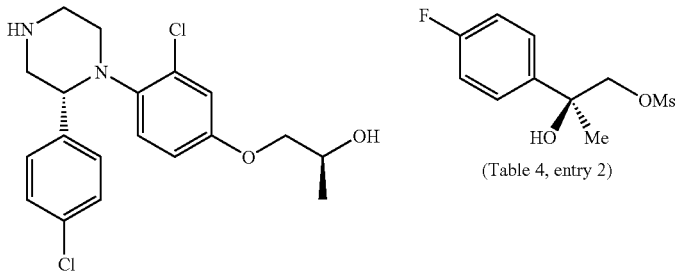 | (Table 4, entry 2) |

TABLE 9-continued
The following examples were prepared using a similar method to that described for Example 156 above.
| 19 | 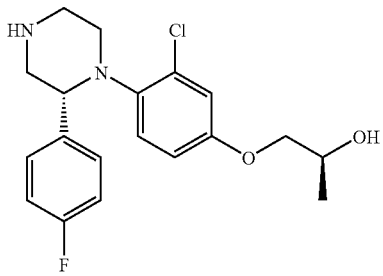 [SMILES: C[C@H](O)COc1ccc(N2CCNC[C@H]2c2ccc(Cl)cc2)c(Cl)c1] | 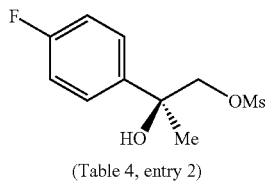 (Table 4, entry 2) |
| 6 | 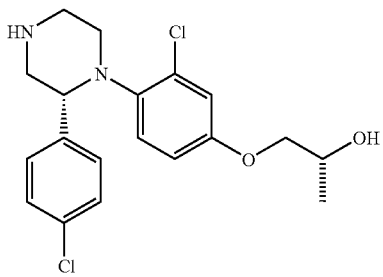 | 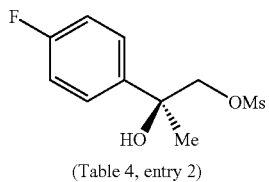 [SMILES: C[C@@](O)(COS(C)(=O)=O)c1ccc(F)cc1] (Table 4, entry 2) |
| 18 | 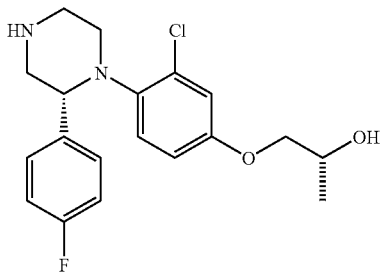 [SMILES: C[C@@H](O)COc1ccc(N2CCNC[C@H]2c2ccc(F)cc2)c(Cl)c1] | 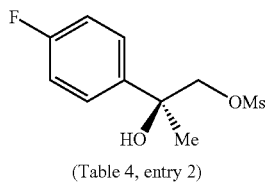 [SMILES: C[C@@](O)(COS(C)(=O)=O)c1ccc(F)cc1] (Table 4, entry 2) |
| 2 | 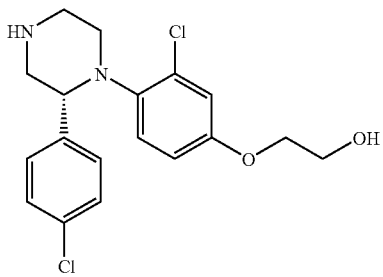 [SMILES: OCCOc1ccc(N2CCNC[C@H]2c2ccc(Cl)cc2)c(Cl)c1] | 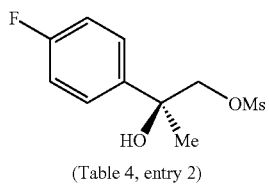 (Table 4, entry 2) |
| 2 | 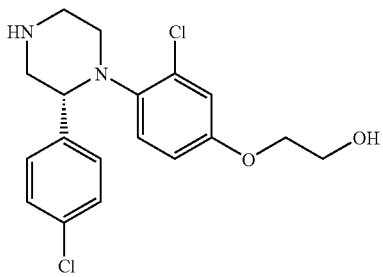 [SMILES: OCCOc1ccc(N2CCNC[C@H]2c2ccc(Cl)cc2)c(Cl)c1] | 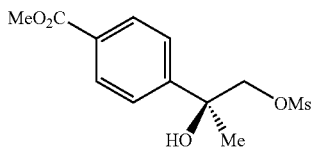 [SMILES: COC(=O)c1ccc([C@](C)(O)COS(C)(=O)=O)cc1] |

TABLE 9-continued
The following examples were prepared using a similar method to that described for Example 156 above.
| | | |
|---|---|---|
| 23 | 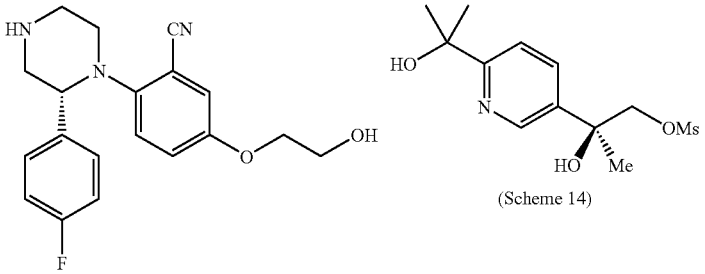 | (Scheme 14) |
| 23 | 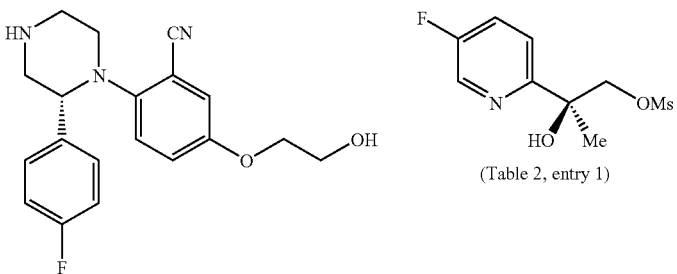 | (Table 2, entry 1) |
| 22 | 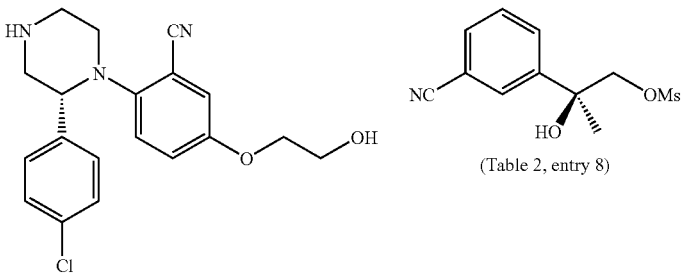 | (Table 2, entry 8) |
| 2 | 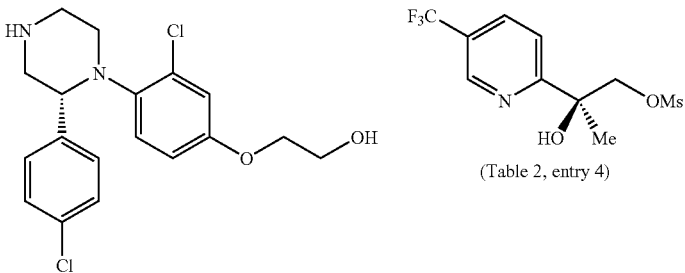 | (Table 2, entry 4) |
| 29 | 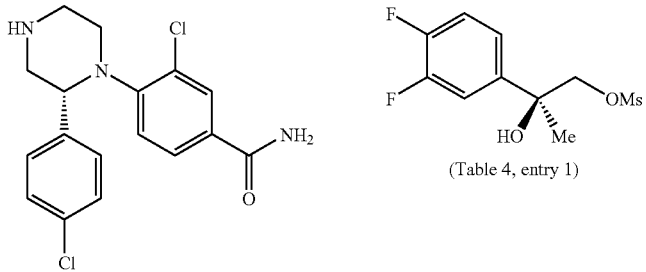 | (Table 4, entry 1) |

TABLE 9-continued
The following examples were prepared using a similar method to that described for Example 156 above.
| 29 | 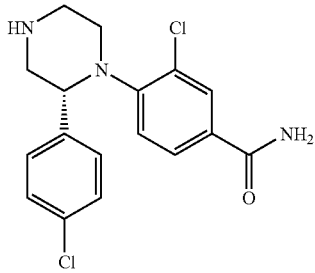 [SMILES: NC(=O)c1ccc(N2CCNC[C@H]2c2ccc(Cl)cc2)c(Cl)c1] | 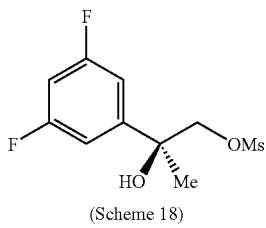 [SMILES: C[C@@](O)(COS(C)(=O)=O)c1cc(F)cc(F)c1] (Scheme 18) |
| 37 | 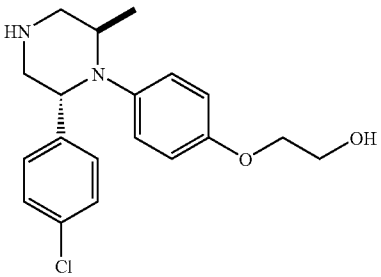 [SMILES: C[C@@H]1CNC[C@@H](c2ccc(Cl)cc2)N1c1ccc(OCCO)cc1] | 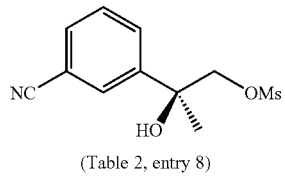 (Table 2, entry 8) |
| 29 | 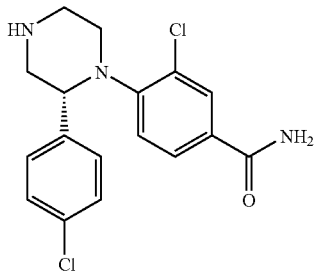 [SMILES: NC(=O)c1ccc(N2CCNC[C@H]2c2ccc(Cl)cc2)c(Cl)c1] | 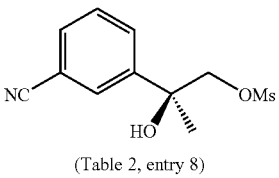 (Table 2, entry 8) |
| 2 | 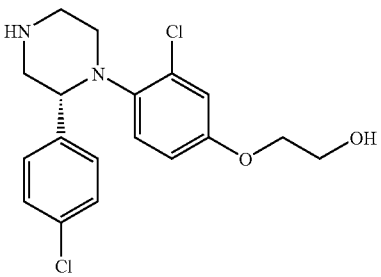 [SMILES: OCCOc1ccc(N2CCNC[C@H]2c2ccc(Cl)cc2)c(Cl)c1] | 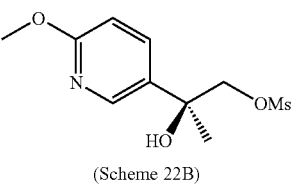 [SMILES: COc1ccc([C@](C)(O)COS(C)(=O)=O)cn1] (Scheme 22B) |
| 2 | 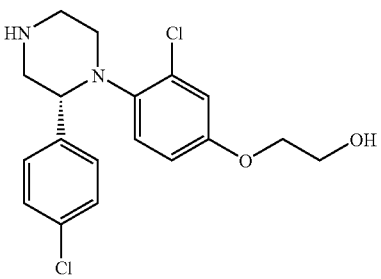 | 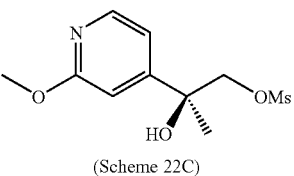 [SMILES: COc1cc([C@](C)(O)COS(C)(=O)=O)ccn1] (Scheme 22C) |

TABLE 9-continued
The following examples were prepared using a similar method to that described for Example 156 above.
| 31 | 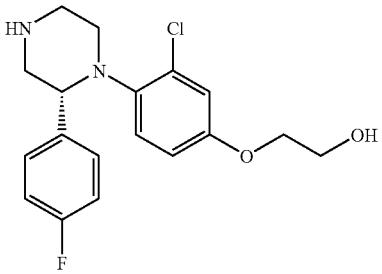 | 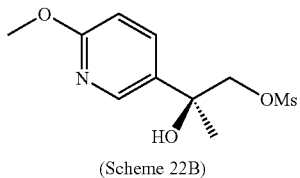 [SMILES: COc1ccc([C@](C)(O)COS(C)(=O)=O)cn1]
(Scheme 22B) |
| --- | --- | --- |
| 38 | 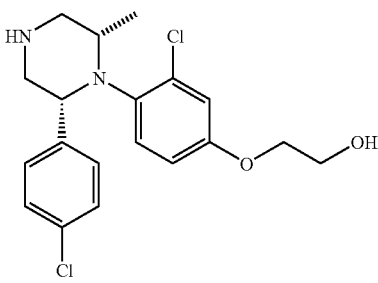 [SMILES: C[C@H]1CNC[C@@H](c2ccc(Cl)cc2)N1c1ccc(OCCO)cc1Cl] | 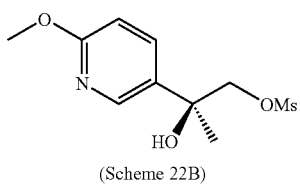 [SMILES: COc1ccc([C@](C)(O)COS(C)(=O)=O)cn1]
(Scheme 22B) |
| 29 | 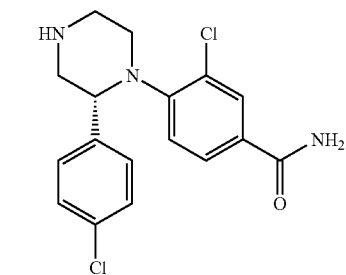 [SMILES: NC(=O)c1ccc(N2CCNC[C@H]2c2ccc(Cl)cc2)c(Cl)c1] | 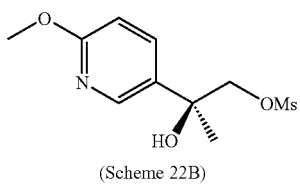 [SMILES: COc1ccc([C@](C)(O)COS(C)(=O)=O)cn1]
(Scheme 22B) |
| 24 | 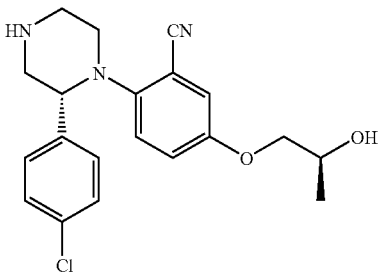 [SMILES: C[C@H](O)COc1ccc(N2CCNC[C@H]2c2ccc(Cl)cc2)c(C#N)c1] | 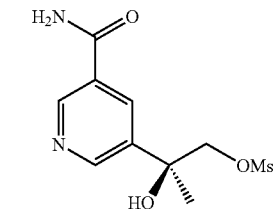
(Table 2, Entry 9) |
| 2 | 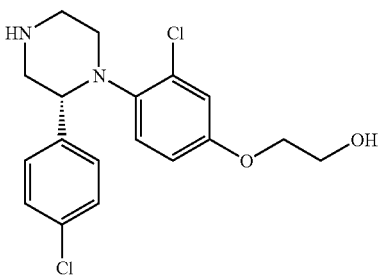 | 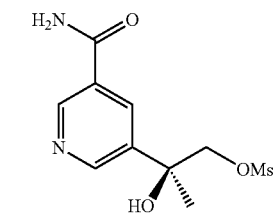
(Table 2, Entry 9) |

TABLE 9-continued
The following examples were prepared using a similar method to that described for Example 156 above.
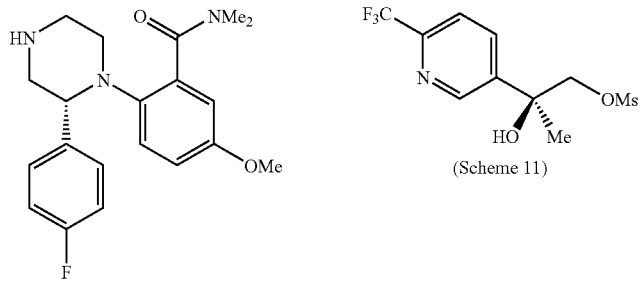
32c (Scheme 11)
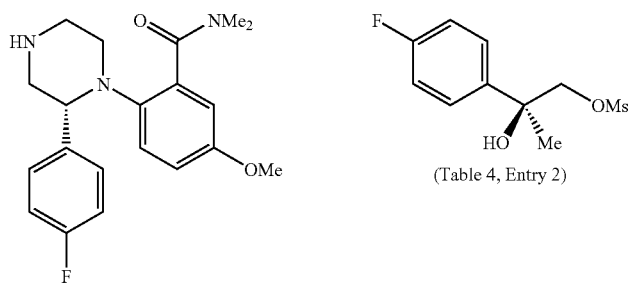
32c (Table 4, Entry 2)
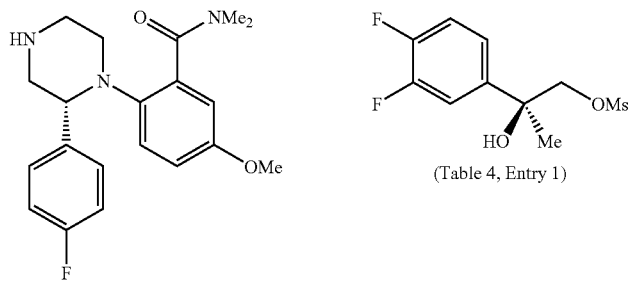
32c (Table 4, Entry 1)
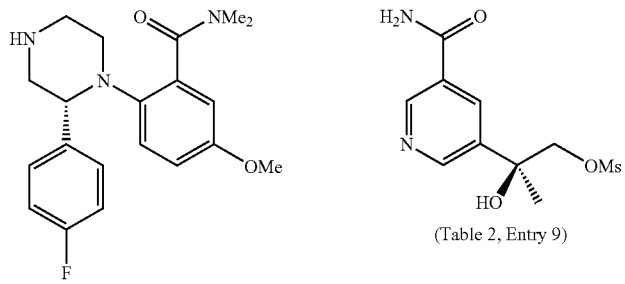
32c (Table 2, Entry 9)
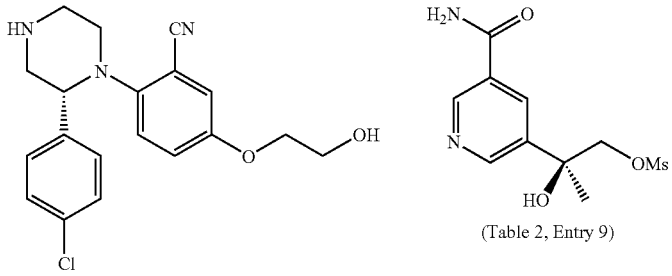
22 (Table 2, Entry 9)

TABLE 9-continued
The following examples were prepared using a similar method to that described for Example 156 above.
| | | |
|---|---|---|
| 32c | 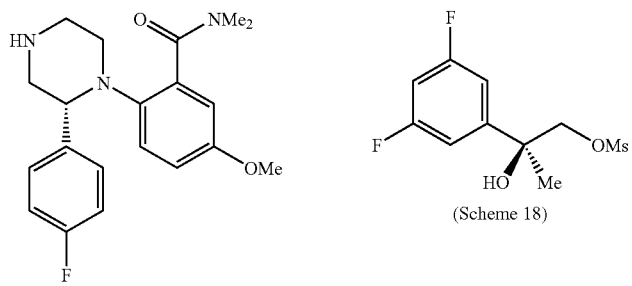 | (Scheme 18) |
| 31 | 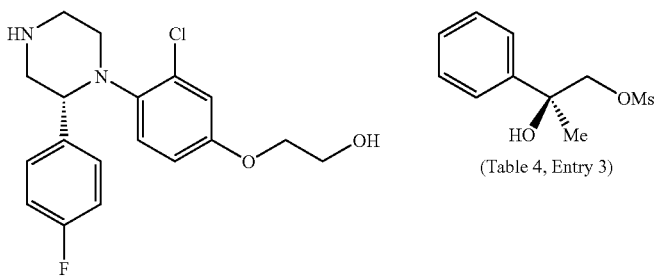 | (Table 4, Entry 3) |
| 2 | 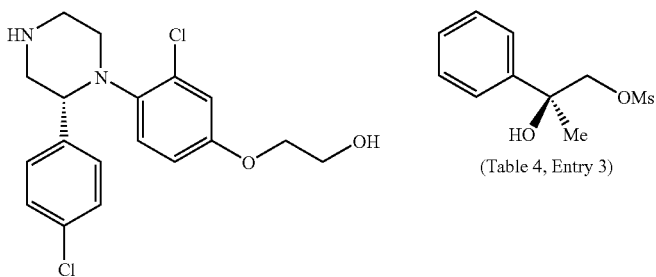 | (Table 4, Entry 3) |
| 31 | 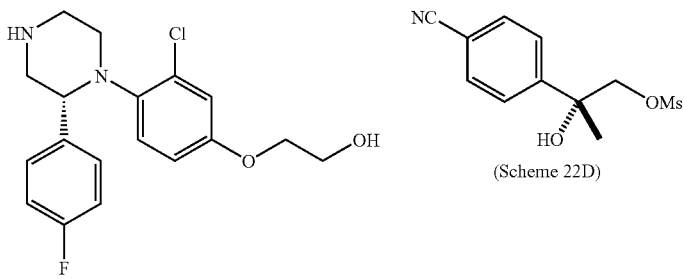 | (Scheme 22D) |
| 2 | 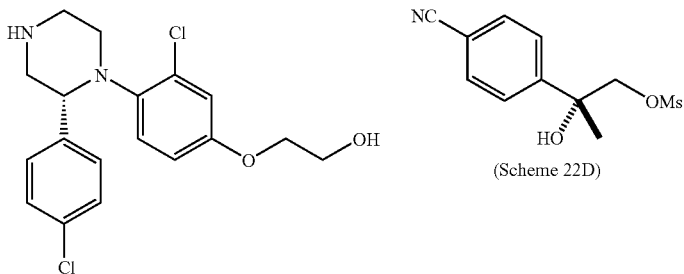 | (Scheme 22D) |

TABLE 9-continued
The following examples were prepared using a similar method to that described for Example 156 above.
| | | |
|---|---|---|
| 2c | 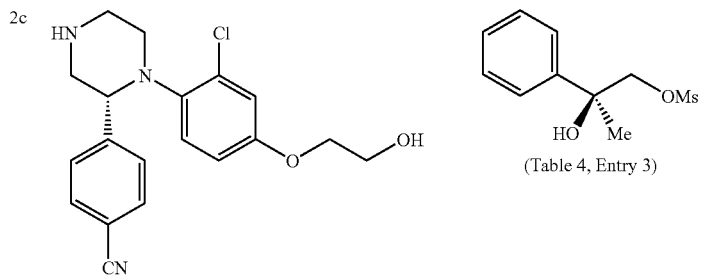 | (Table 4, Entry 3) |
| 6 | 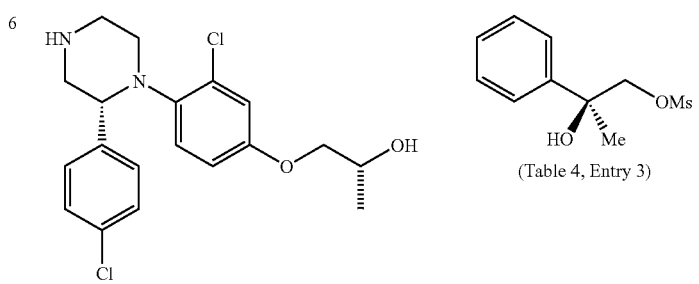 | (Table 4, Entry 3) |
| 6 | 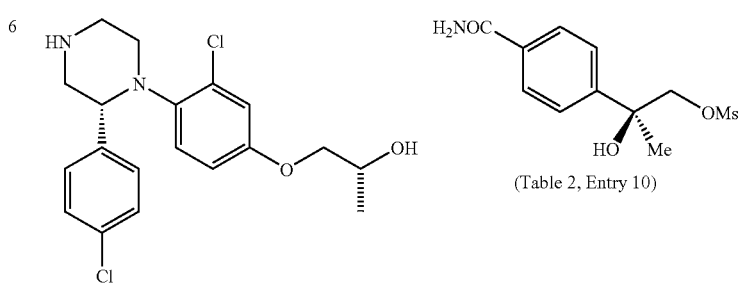 | (Table 2, Entry 10) |
| 32c | 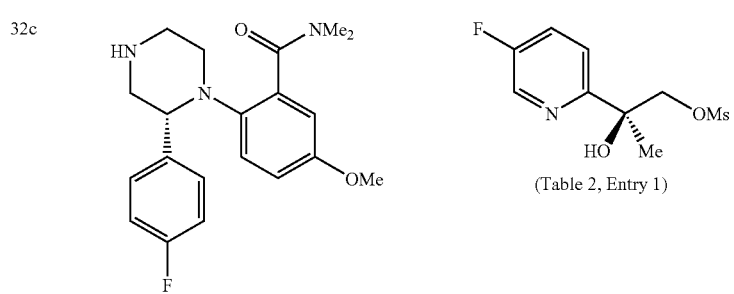 | (Table 2, Entry 1) |
| Ex. | Structure |
|---|---|
| 157 |

TABLE 9-continued
The following examples were prepared using a similar method to that described for Example 156 above.
158 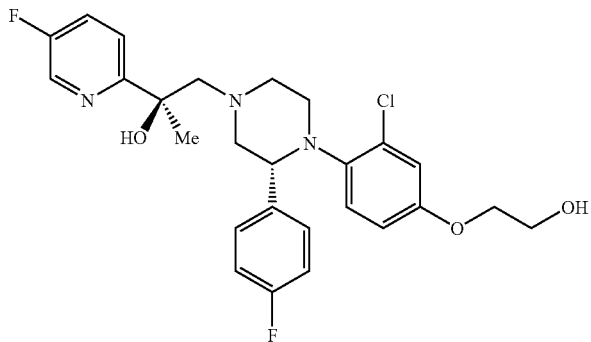 [SMILES: C[C@@](O)(CN1CCN(c2ccc(OCCO)cc2Cl)[C@H](c2ccc(F)cc2)C1)c1ccc(F)cn1]
159 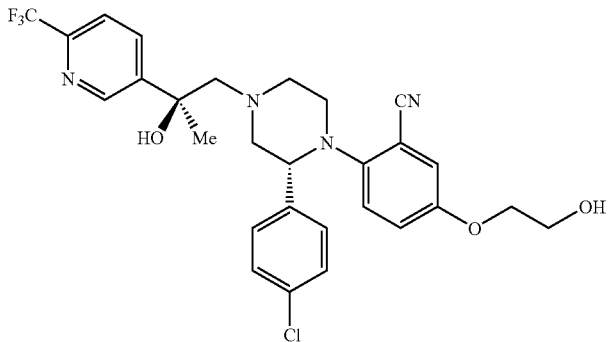 [SMILES: C[C@@](O)(CN1CCN(c2ccc(OCCO)cc2C#N)[C@H](c2ccc(Cl)cc2)C1)c1ccc(C(F)(F)F)nc1]
160 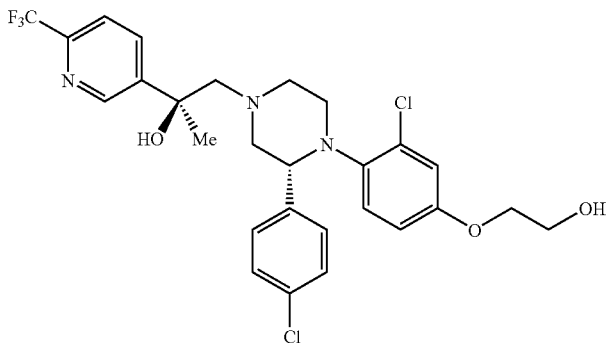 [SMILES: C[C@@](O)(CN1CCN(c2ccc(OCCO)cc2Cl)[C@H](c2ccc(Cl)cc2)C1)c1ccc(C(F)(F)F)nc1]
161 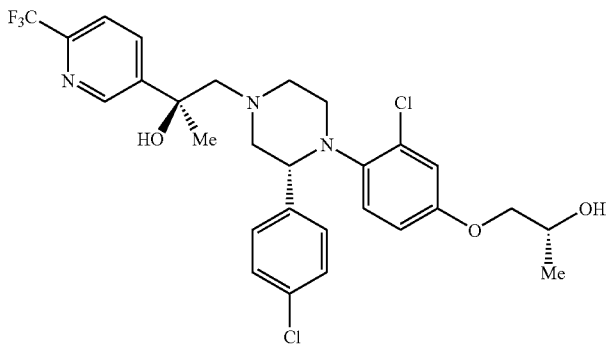

TABLE 9-continued
The following examples were prepared using a similar method to that described for Example 156 above.
162 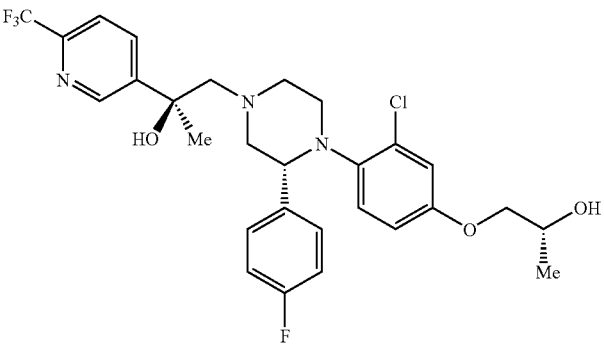 [SMILES: C[C@@H](O)COc1ccc(N2CCN(C[C@@](C)(O)c3ccc(C(F)(F)F)nc3)C[C@H]2c2ccc(F)cc2)c(Cl)c1]
163 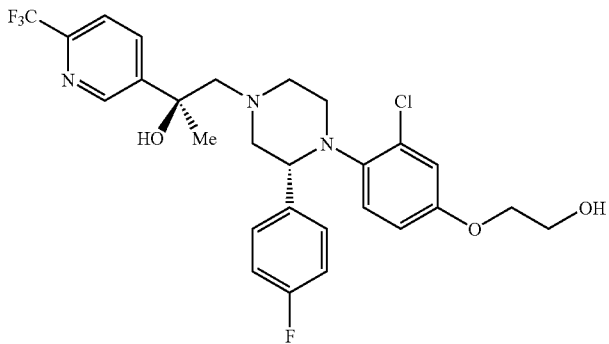
164 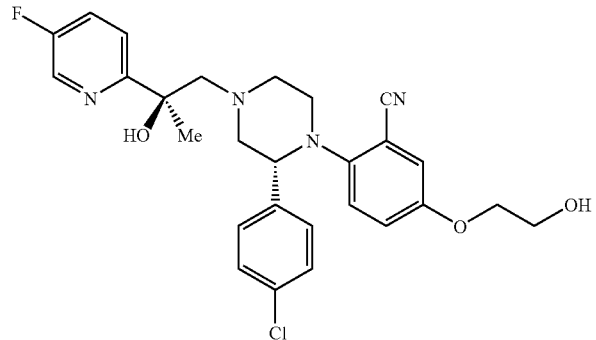 [SMILES: C[C@@](O)(CN1CCN(c2ccc(OCCO)cc2C#N)[C@H](c2ccc(Cl)cc2)C1)c1ccc(F)cn1]
165 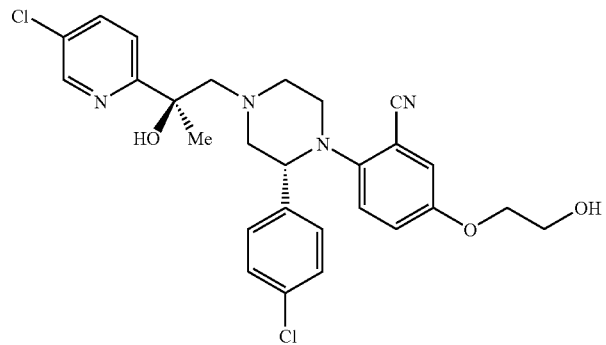 [SMILES: C[C@@](O)(CN1CCN(c2ccc(OCCO)cc2C#N)[C@H](c2ccc(Cl)cc2)C1)c1ccc(Cl)cn1]

TABLE 9-continued
The following examples were prepared using a similar method to that described for Example 156 above.
166 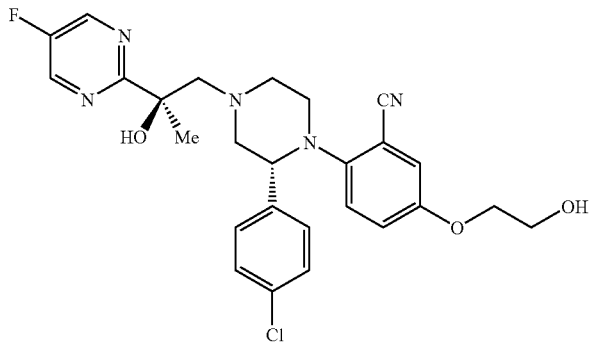
167 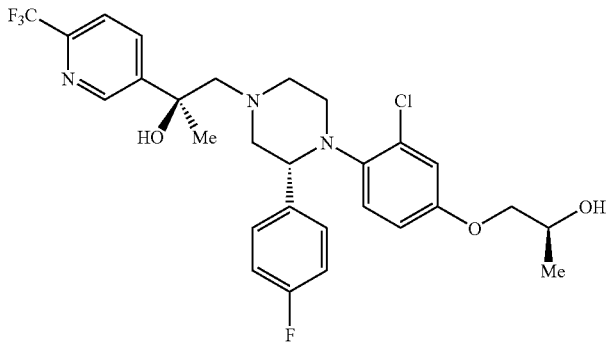
168 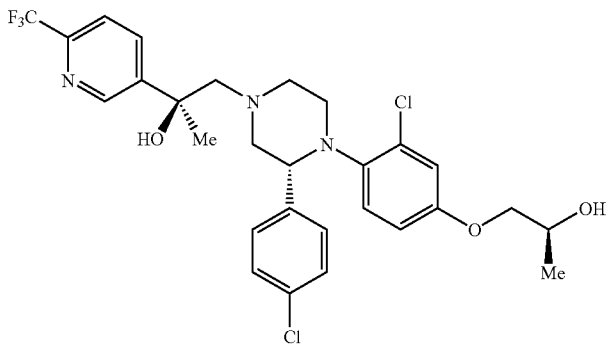 [SMILES: C[C@H](O)COc1ccc(N2CCN(C[C@@](C)(O)c3ccc(C(F)(F)F)nc3)C[C@H]2c2ccc(F)cc2)c(Cl)c1]
169 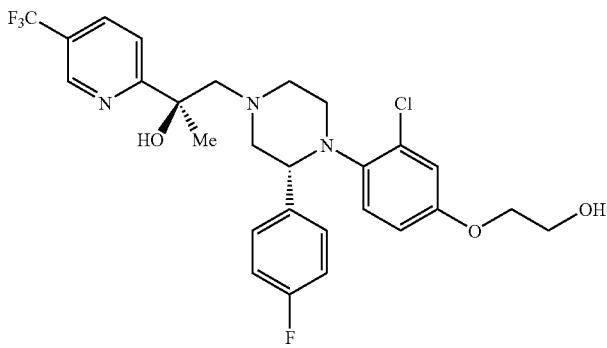 [SMILES: C[C@@](O)(CN1CCN(c2ccc(OCCO)cc2Cl)[C@H](c2ccc(F)cc2)C1)c1ccc(C(F)(F)F)cn1]

TABLE 9-continued
The following examples were prepared using a similar method to that described for Example 156 above.
170 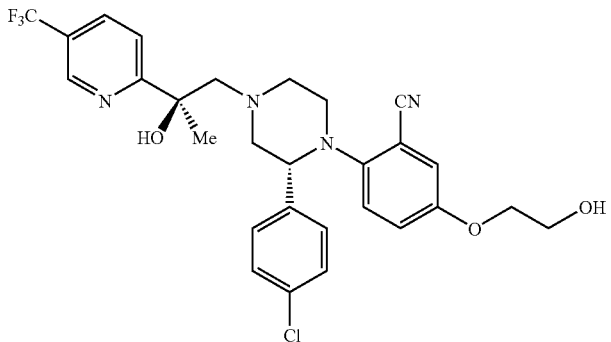 [SMILES: C[C@@](O)(CN1CCN(c2ccc(OCCO)cc2C#N)[C@H](c2ccc(Cl)cc2)C1)c1ccc(C(F)(F)F)cn1]
171 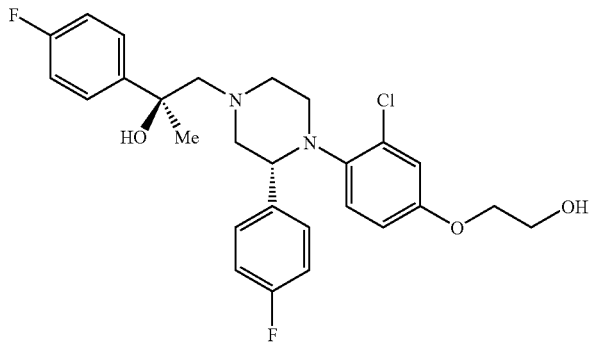
172 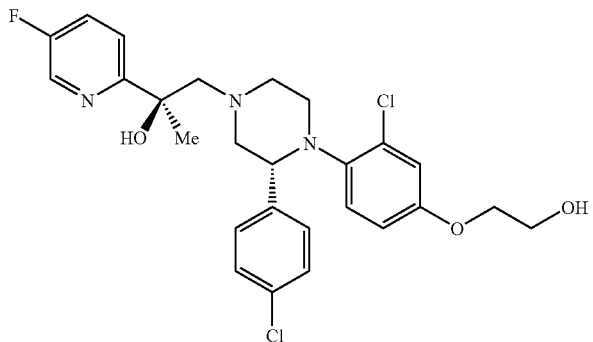
173 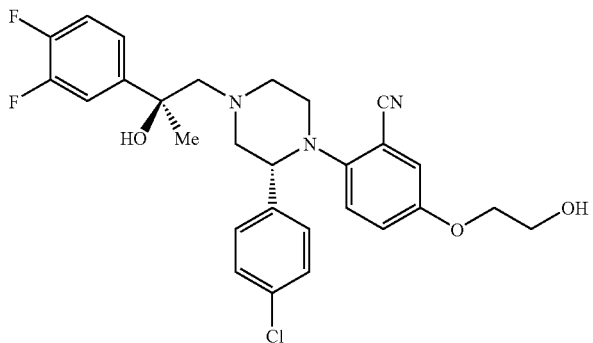

TABLE 9-continued
The following examples were prepared using a similar method to that described for Example 156 above.
174 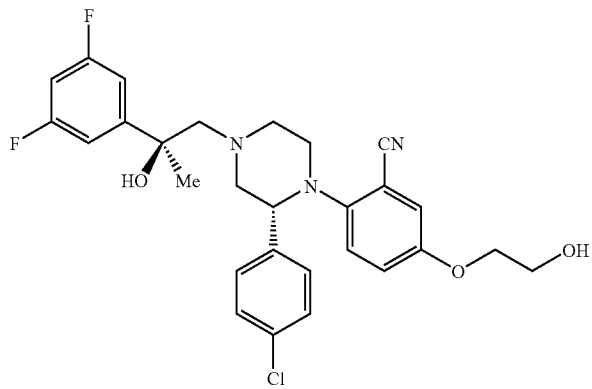 [SMILES: C[C@@](O)(CN1CCN(c2ccc(OCCO)cc2C#N)[C@H](c2ccc(Cl)cc2)C1)c1cc(F)cc(F)c1]
175 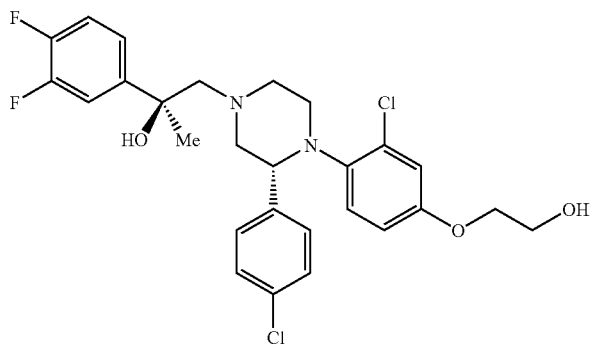 [SMILES: C[C@@](O)(CN1CCN(c2ccc(OCCO)cc2Cl)[C@H](c2ccc(Cl)cc2)C1)c1ccc(F)c(F)c1]
176 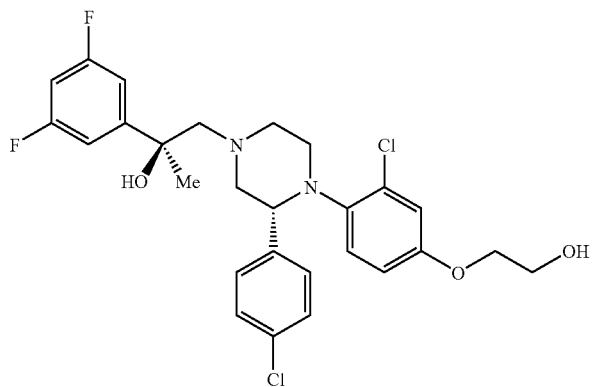
177 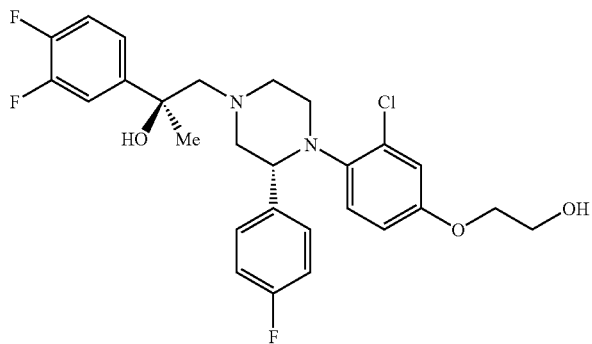

TABLE 9-continued
The following examples were prepared using a similar method to that described for Example 156 above.
178 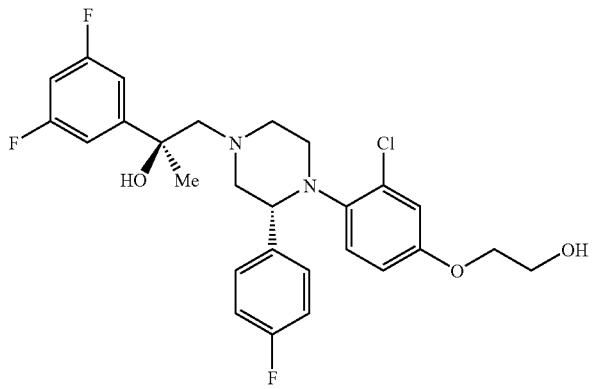
179 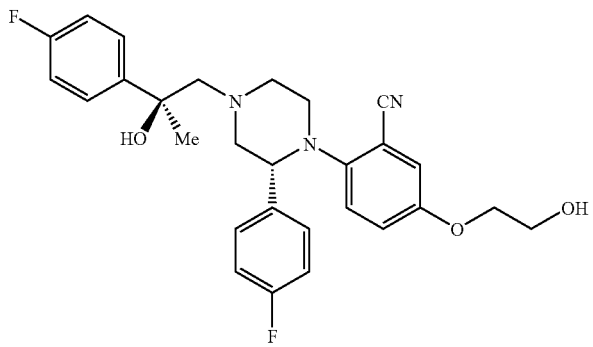
180 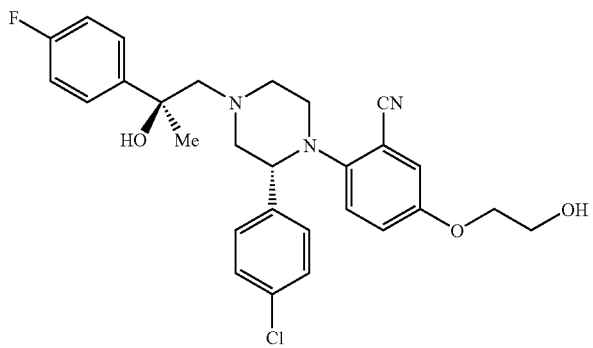 [SMILES: C[C@@](O)(CN1CCN(c2ccc(OCCO)cc2C#N)[C@H](c2ccc(Cl)cc2)C1)c1ccc(F)cc1]
181 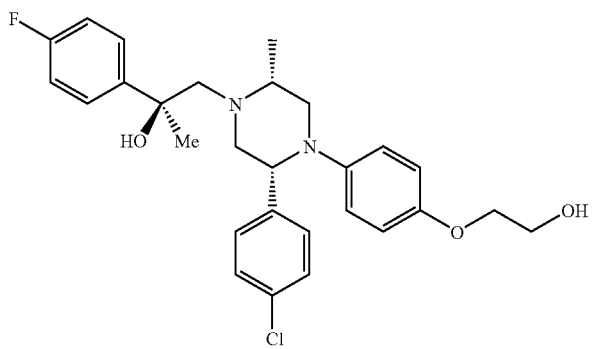 [SMILES: C[C@@H]1CN(c2ccc(OCCO)cc2)[C@H](c2ccc(Cl)cc2)CN1C[C@@](C)(O)c1ccc(F)cc1]

TABLE 9-continued
The following examples were prepared using a similar method to that described for Example 156 above.
182 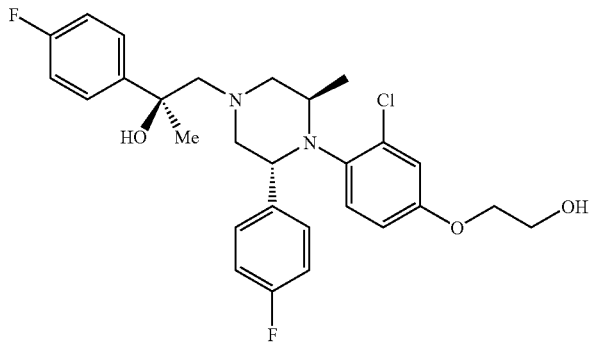 [SMILES: C[C@@H]1CN(C[C@@](C)(O)c2ccc(F)cc2)C[C@@H](c2ccc(F)cc2)N1c1ccc(OCCO)cc1Cl]
183 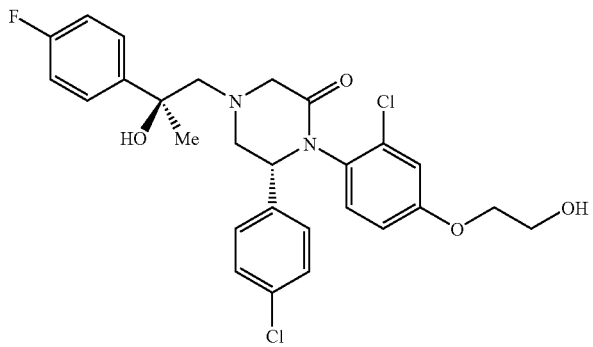 [SMILES: C[C@@](O)(CN1CC(=O)N(c2ccc(OCCO)cc2Cl)[C@H](c2ccc(Cl)cc2)C1)c1ccc(F)cc1]
184 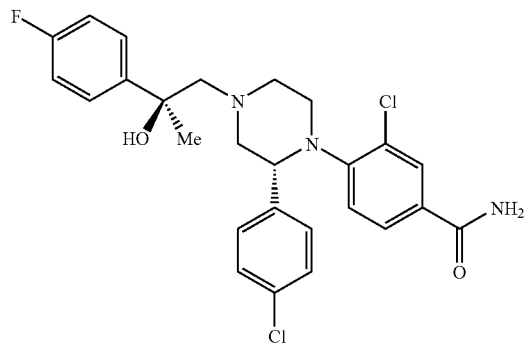 [SMILES: C[C@@](O)(CN1CCN(c2ccc(C(N)=O)cc2Cl)[C@H](c2ccc(Cl)cc2)C1)c1ccc(F)cc1]
185 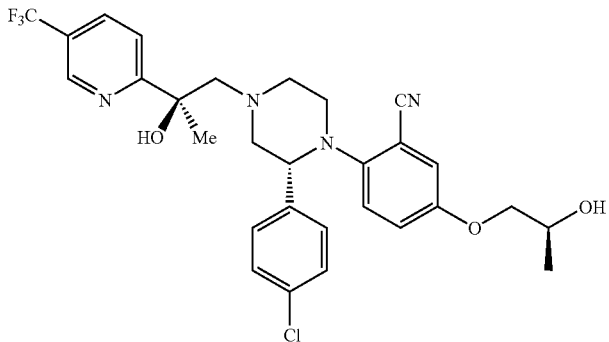 [SMILES: C[C@H](O)COc1ccc(N2CCN(C[C@@](C)(O)c3ccc(C(F)(F)F)cn3)C[C@H]2c2ccc(Cl)cc2)c(C#N)c1]

TABLE 9-continued
The following examples were prepared using a similar method to that described for Example 156 above.
| 186 | 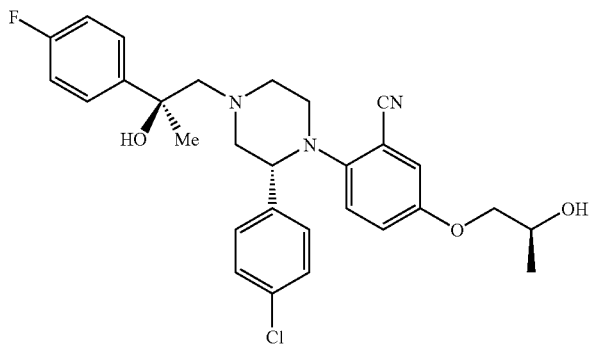 [SMILES: C[C@H](O)COc1ccc(N2CCN(C[C@@](C)(O)c3ccc(F)cc3)C[C@H]2c2ccc(Cl)cc2)c(C#N)c1] |
| --- | --- |
| 187 | 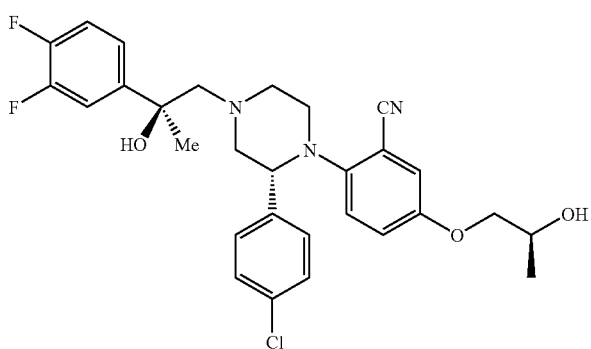 [SMILES: C[C@H](O)COc1ccc(N2CCN(C[C@@](C)(O)c3ccc(F)c(F)c3)C[C@H]2c2ccc(Cl)cc2)c(C#N)c1] |
| 188 | 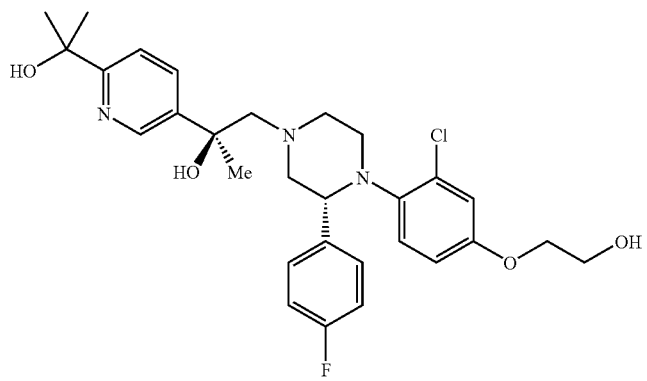 |
| 189 | 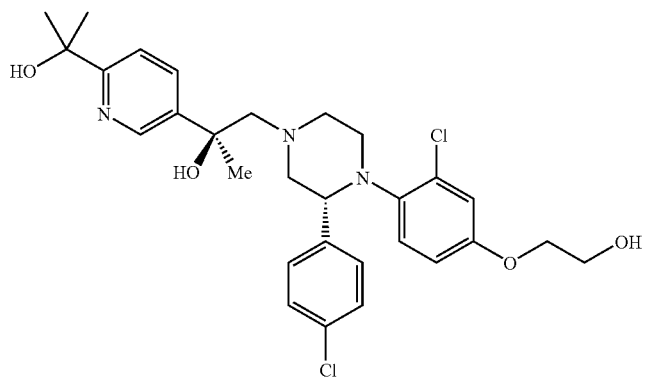 [SMILES: CC(C)(O)c1ccc([C@](C)(O)CN2CCN(c3ccc(OCCO)cc3Cl)[C@H](c3ccc(Cl)cc3)C2)cn1] |

TABLE 9-continued
The following examples were prepared using a similar method to that described for Example 156 above.
190
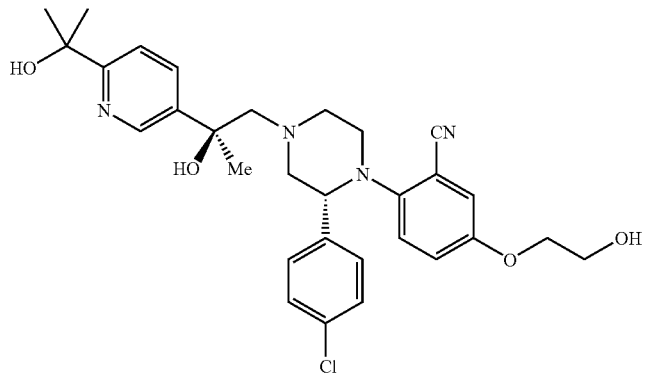 [SMILES: CC(C)(O)c1ccc([C@](C)(O)CN2CCN(c3ccc(OCCO)cc3C#N)[C@H](c3ccc(Cl)cc3)C2)cn1]
191
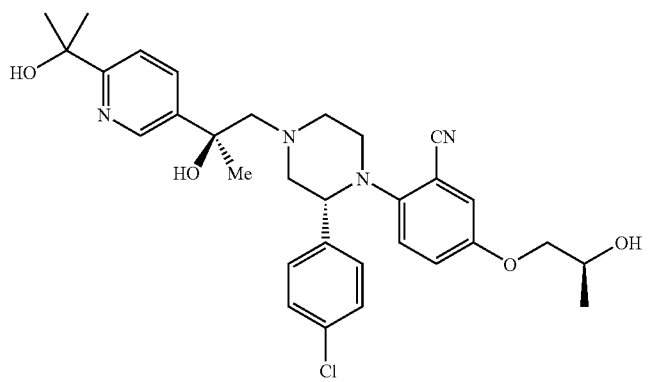 [SMILES: C[C@H](O)COc1ccc(N2CCN(C[C@@](C)(O)c3ccc(C(C)(C)O)nc3)C[C@H]2c2ccc(Cl)cc2)c(C#N)c1]
192
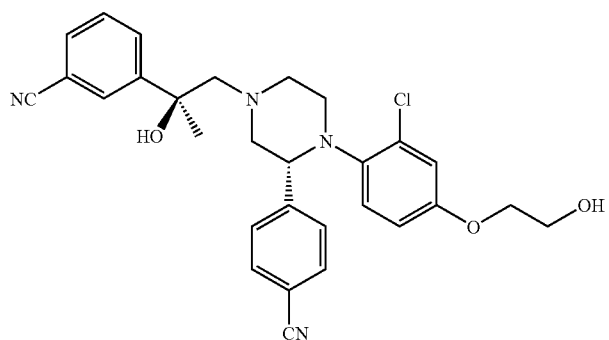
193
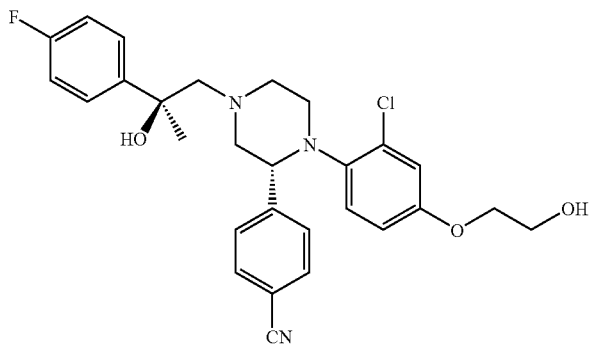 [SMILES: C[C@@](O)(CN1CCN(c2ccc(OCCO)cc2Cl)[C@H](c2ccc(C#N)cc2)C1)c1ccc(F)cc1]

TABLE 9-continued
The following examples were prepared using a similar method to that described for Example 156 above.
194 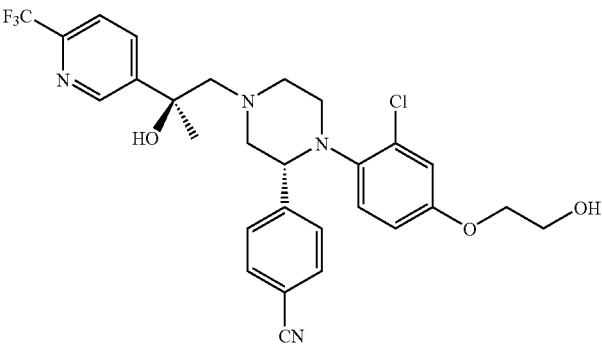 [SMILES: C[C@@](O)(CN1CCN(c2ccc(OCCO)cc2Cl)[C@H](c2ccc(C#N)cc2)C1)c1ccc(C(F)(F)F)nc1]
195 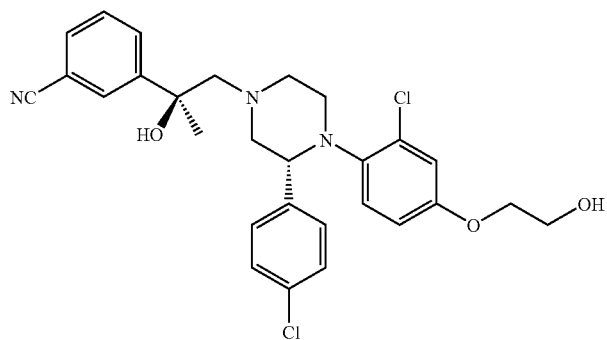
196 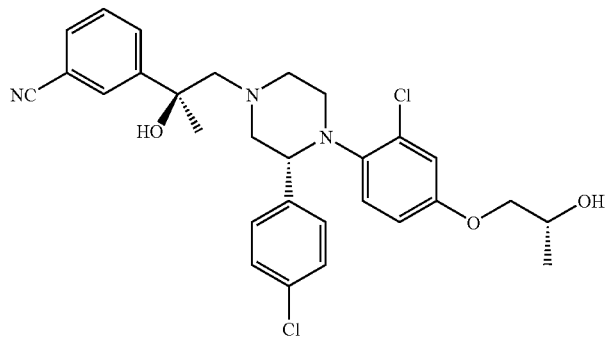
197 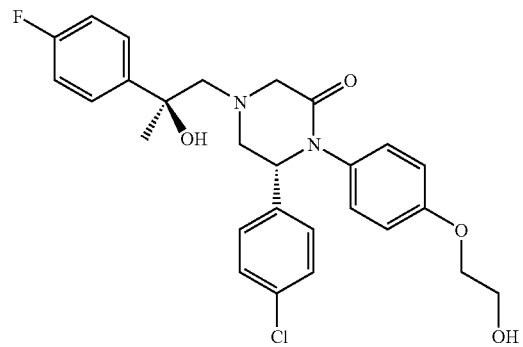 [SMILES: C[C@@](O)(CN1CC(=O)N(c2ccc(OCCO)cc2)[C@H](c2ccc(Cl)cc2)C1)c1ccc(F)cc1]

TABLE 9-continued
The following examples were prepared using a similar method to that described for Example 156 above.
198 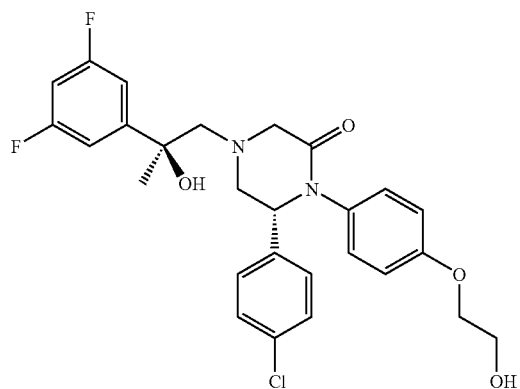 [SMILES: C[C@@](O)(CN1CC(=O)N(c2ccc(OCCO)cc2)[C@H](c2ccc(Cl)cc2)C1)c1cc(F)cc(F)c1]
199 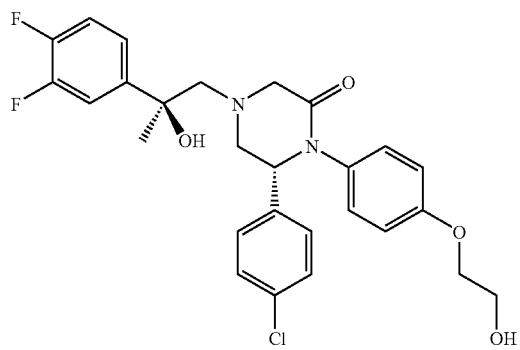 [SMILES: C[C@@](O)(CN1CC(=O)N(c2ccc(OCCO)cc2)[C@H](c2ccc(Cl)cc2)C1)c1ccc(F)c(F)c1]
200 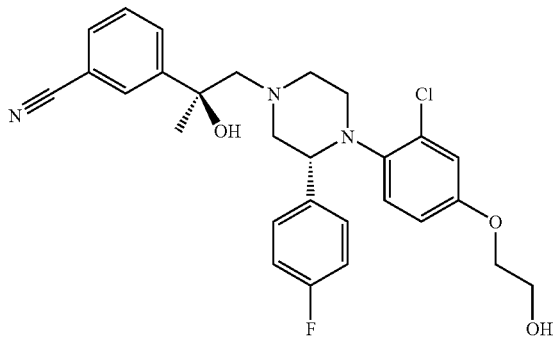 [SMILES: C[C@@](O)(CN1CCN(c2ccc(OCCO)cc2Cl)[C@H](c2ccc(F)cc2)C1)c1cccc(C#N)c1]
200a 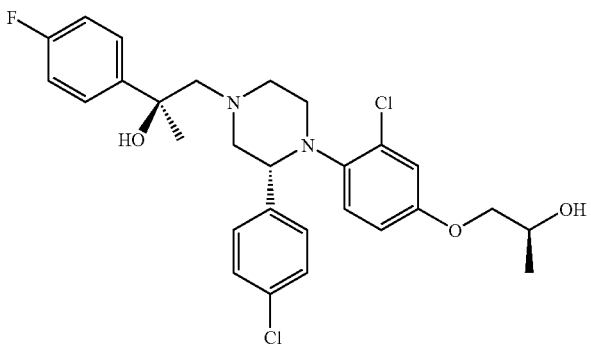

TABLE 9-continued
The following examples were prepared using a similar method to that described for Example 156 above.
200b
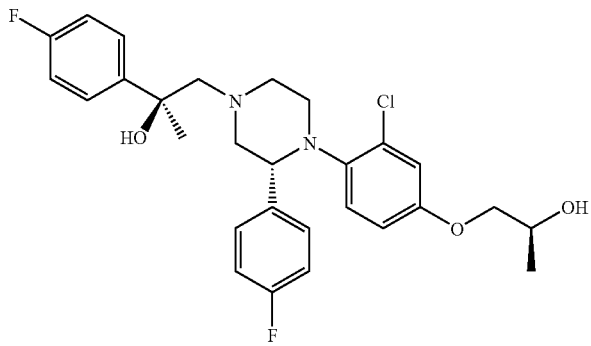 [SMILES: C[C@H](O)COc1ccc(N2CCN(C[C@@](C)(O)c3ccc(F)cc3)C[C@H]2c2ccc(F)cc2)c(Cl)c1]
200c
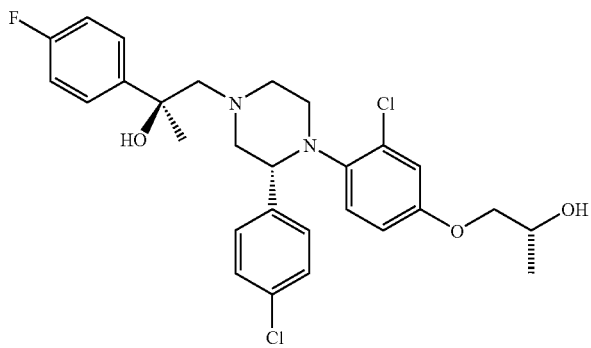 [SMILES: C[C@@H](O)COc1ccc(N2CCN(C[C@@](C)(O)c3ccc(F)cc3)C[C@H]2c2ccc(F)cc2)c(Cl)c1]
200d
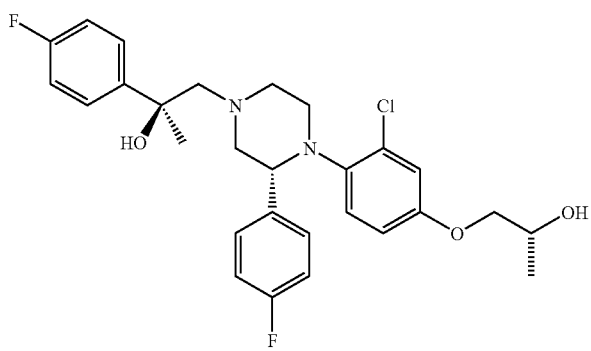
200e
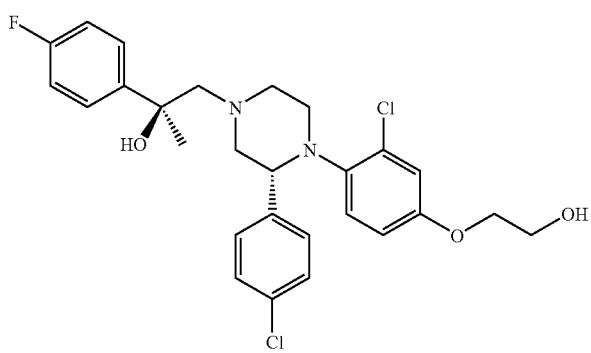 [SMILES: C[C@@](O)(CN1CCN(c2ccc(OCCO)cc2Cl)[C@H](c2ccc(Cl)cc2)C1)c1ccc(F)cc1]

TABLE 9-continued
The following examples were prepared using a similar method to that described for Example 156 above.
200f
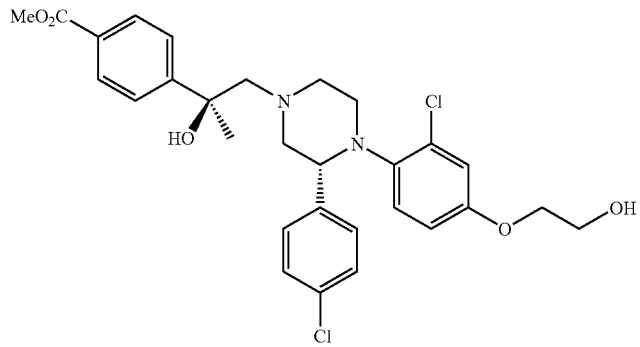 [SMILES: COC(=O)c1ccc([C@](C)(O)CN2CCN(c3ccc(OCCO)cc3Cl)[C@H](c3ccc(Cl)cc3)C2)cc1]
200g
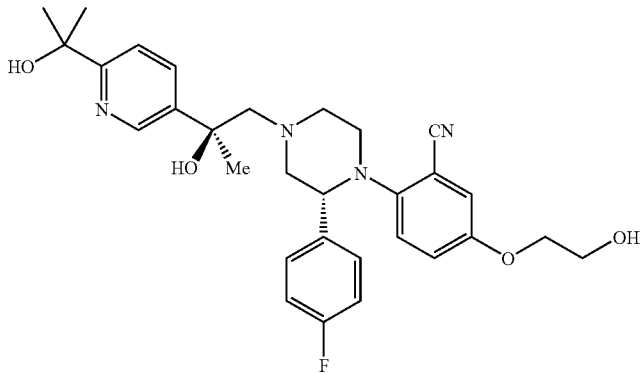
200h
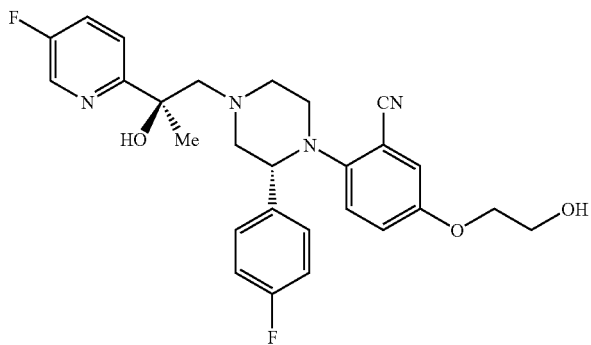 [SMILES: C[C@@](O)(CN1CCN(c2ccc(OCCO)cc2C#N)[C@H](c2ccc(F)cc2)C1)c1ccc(F)cn1]
200i
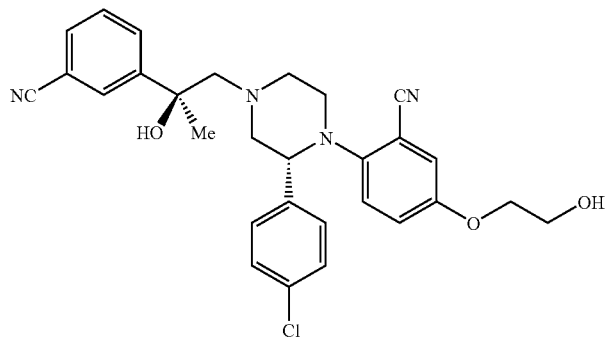

TABLE 9-continued
The following examples were prepared using a similar method to that described for Example 156 above.
200j
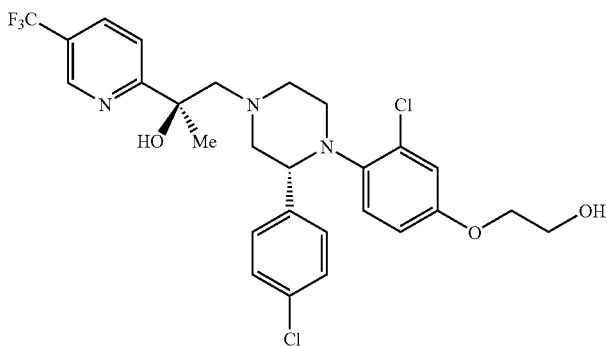 [SMILES: C[C@@](O)(CN1CCN(c2ccc(OCCO)cc2Cl)[C@H](c2ccc(Cl)cc2)C1)c1ccc(C(F)(F)F)cn1]
200k
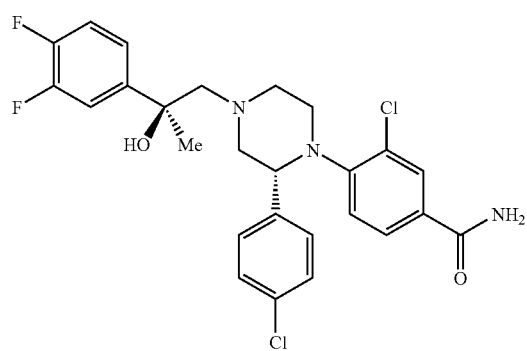 [SMILES: C[C@@](O)(CN1CCN(c2ccc(C(N)=O)cc2Cl)[C@H](c2ccc(Cl)cc2)C1)c1ccc(F)c(F)c1]
200l
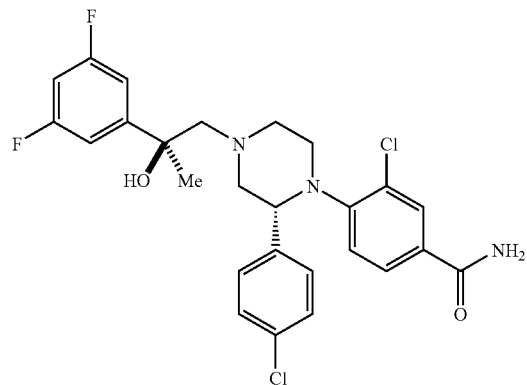 [SMILES: C[C@@](O)(CN1CCN(c2ccc(C(N)=O)cc2Cl)[C@H](c2ccc(Cl)cc2)C1)c1cc(F)cc(F)c1]
200m
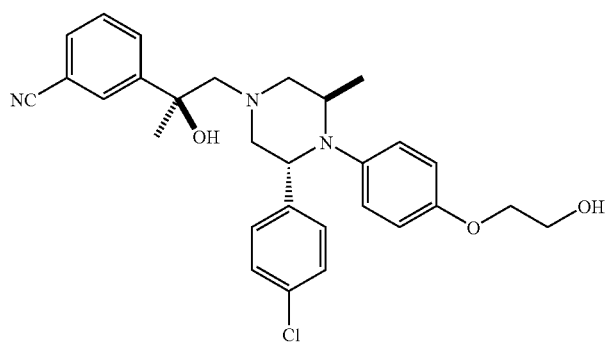

TABLE 9-continued
The following examples were prepared using a similar method to that described for Example 156 above.
200n
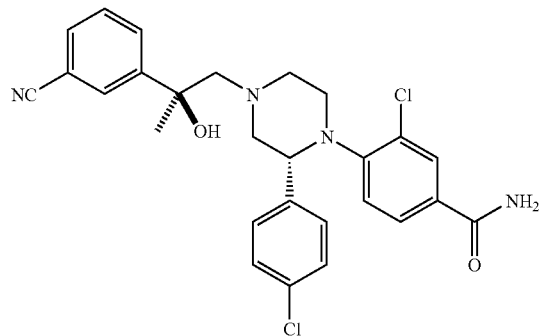
200o
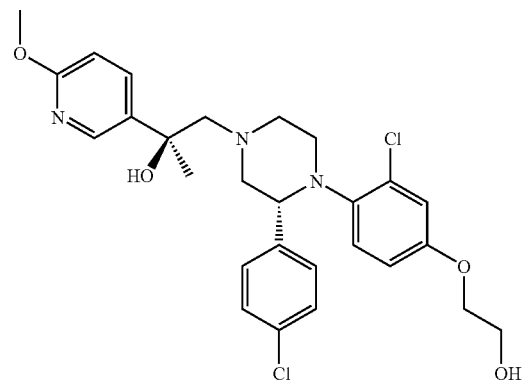 [SMILES: COc1ccc([C@](C)(O)CN2CCN(c3ccc(OCCO)cc3Cl)[C@H](c3ccc(Cl)cc3)C2)cn1]
200p
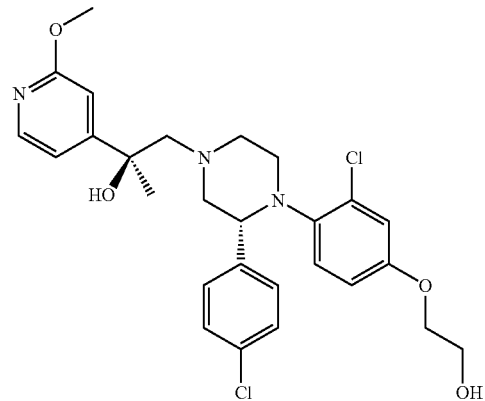 [SMILES: COc1cc([C@](C)(O)CN2CCN(c3ccc(OCCO)cc3Cl)[C@H](c3ccc(Cl)cc3)C2)ccn1]
200q
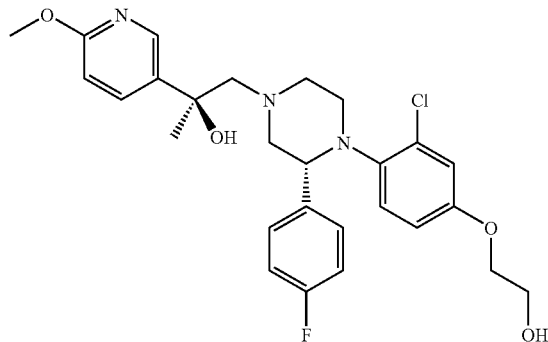 [SMILES: COc1ccc([C@](C)(O)CN2CCN(c3ccc(OCCO)cc3Cl)[C@H](c3ccc(F)cc3)C2)cn1]

TABLE 9-continued
The following examples were prepared using a similar method to that described for Example 156 above.
200r 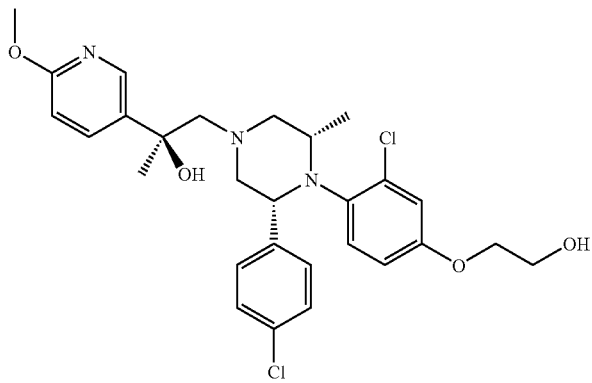 [SMILES: COc1ccc([C@](C)(O)CN2C[C@H](C)N(c3ccc(OCCO)cc3Cl)[C@H](c3ccc(Cl)cc3)C2)cn1]
200s 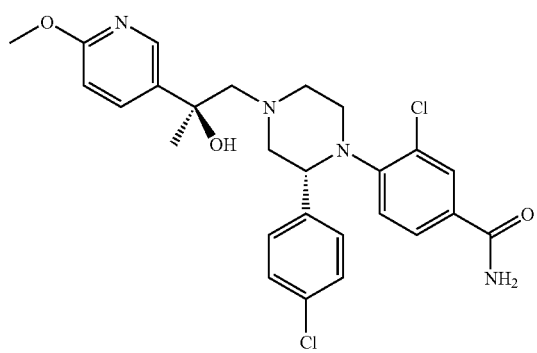 [SMILES: COc1ccc([C@](C)(O)CN2CCN(c3ccc(C(N)=O)cc3Cl)[C@H](c3ccc(Cl)cc3)C2)cn1]
200t 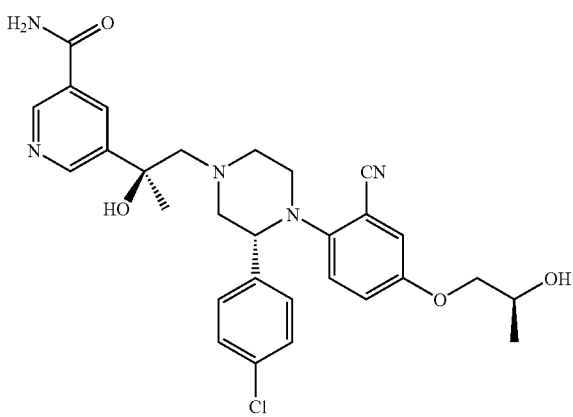 [SMILES: C[C@H](O)COc1ccc(N2CCN(C[C@@](C)(O)c3cncc(C(N)=O)c3)C[C@H]2c2ccc(Cl)cc2)c(C#N)c1]
200u 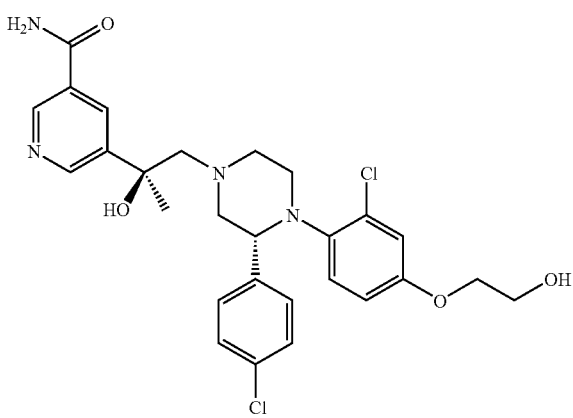 [SMILES: C[C@@](O)(CN1CCN(c2ccc(OCCO)cc2Cl)[C@H](c2ccc(Cl)cc2)C1)c1cncc(C(N)=O)c1]

TABLE 9-continued
The following examples were prepared using a similar method to that described for Example 156 above.
200v 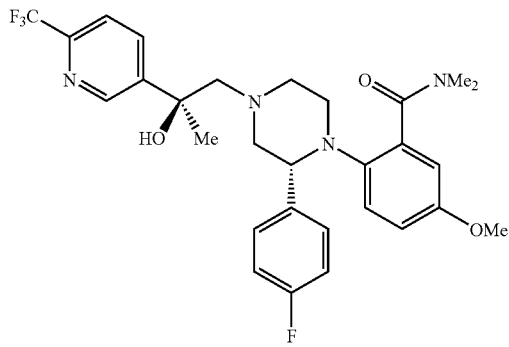 [SMILES: COc1ccc(N2CCN(C[C@@](C)(O)c3ccc(C(F)(F)F)nc3)C[C@H]2c2ccc(F)cc2)c(C(=O)N(C)C)c1]
200w 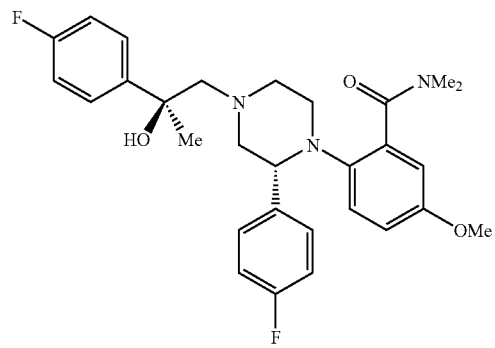 [SMILES: COc1ccc(N2CCN(C[C@@](C)(O)c3ccc(F)cc3)C[C@H]2c2ccc(F)cc2)c(C(=O)N(C)C)c1]
200x 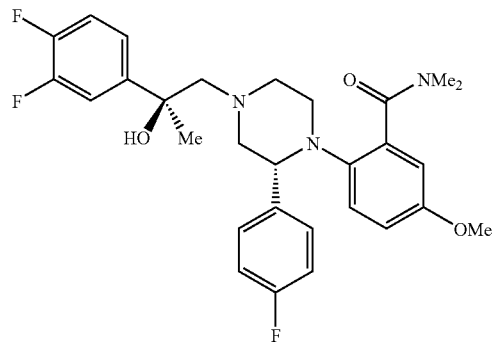 [SMILES: COc1ccc(N2CCN(C[C@@](C)(O)c3ccc(F)c(F)c3)C[C@H]2c2ccc(F)cc2)c(C(=O)N(C)C)c1]
200y 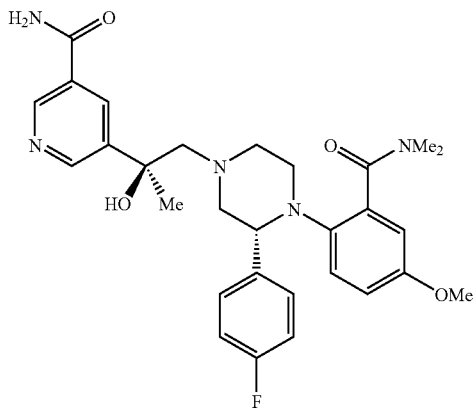 [SMILES: COc1ccc(N2CCN(C[C@@](C)(O)c3cncc(C(N)=O)c3)C[C@H]2c2ccc(F)cc2)c(C(=O)N(C)C)c1]

TABLE 9-continued
The following examples were prepared using a similar method to that described for Example 156 above.
200z 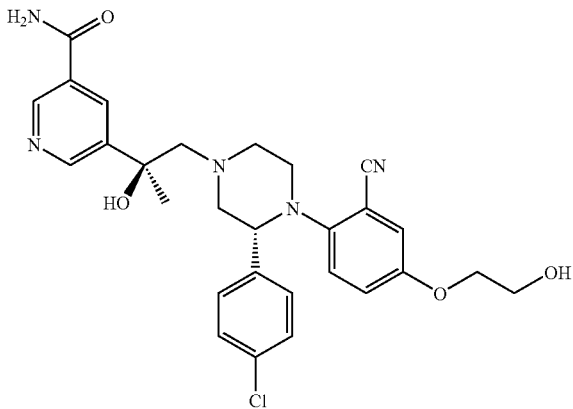 [SMILES: C[C@@](O)(CN1CCN(c2ccc(OCCO)cc2C#N)[C@H](c2ccc(Cl)cc2)C1)c1cncc(C(N)=O)c1]
200aa 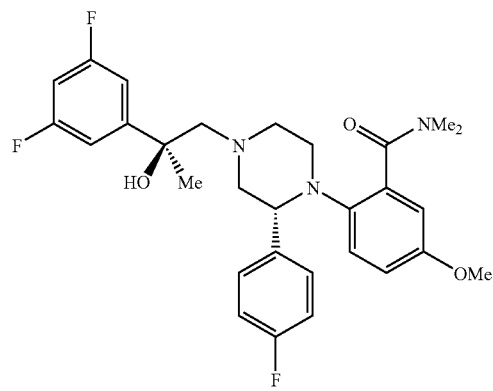 [SMILES: COc1ccc(N2CCN(C[C@@](C)(O)c3cc(F)cc(F)c3)C[C@H]2c2ccc(F)cc2)c(C(=O)N(C)C)c1]
200ab 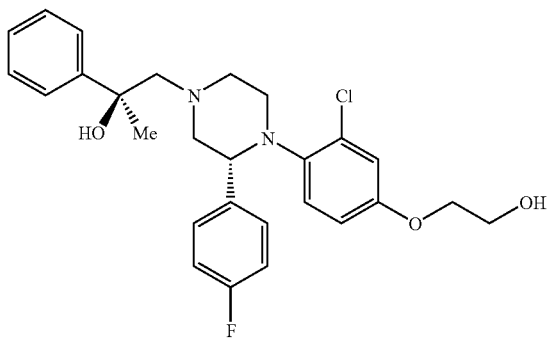 [SMILES: C[C@@](O)(CN1CCN(c2ccc(OCCO)cc2Cl)[C@H](c2ccc(F)cc2)C1)c1ccccc1]
200ac 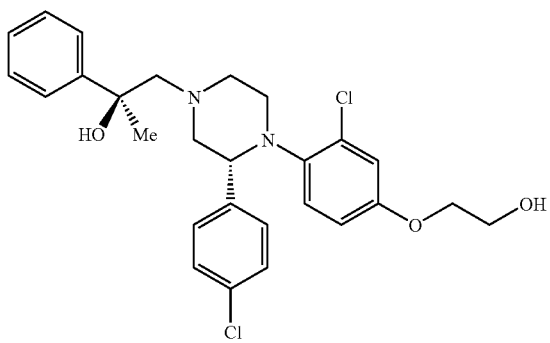

381
TABLE 9-continued
The following examples were prepared using a similar method to that described for Example 156 above.
200ad 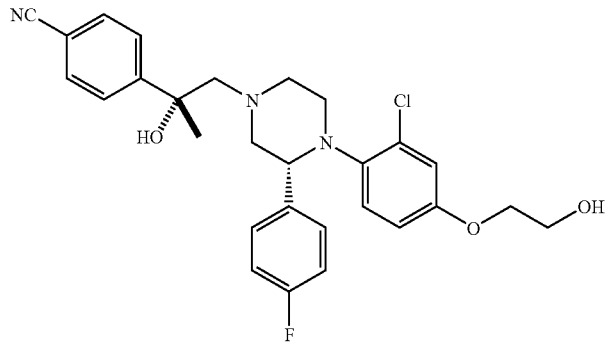
200ae 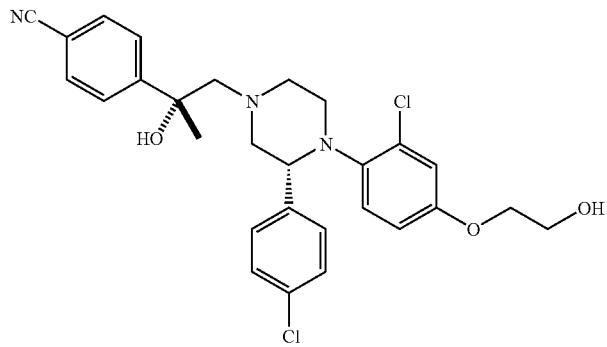
200af 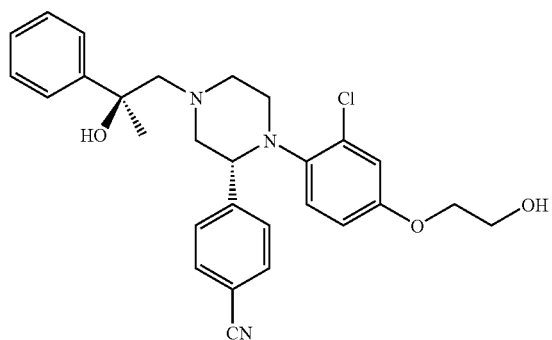 [SMILES: C[C@@](O)(CN1CCN(c2ccc(OCCO)cc2Cl)[C@H](c2ccc(C#N)cc2)C1)c1ccccc1]
200ag 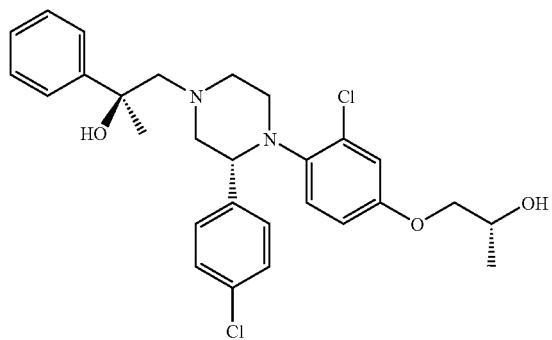 [SMILES: C[C@@H](O)COc1ccc(N2CCN(C[C@@](C)(O)c3ccccc3)C[C@H]2c2ccc(Cl)cc2)c(Cl)c1]

TABLE 9-continued

The following examples were prepared using a similar method to that described for Example 156 above.

| | |
|---|---|
| 200ah | 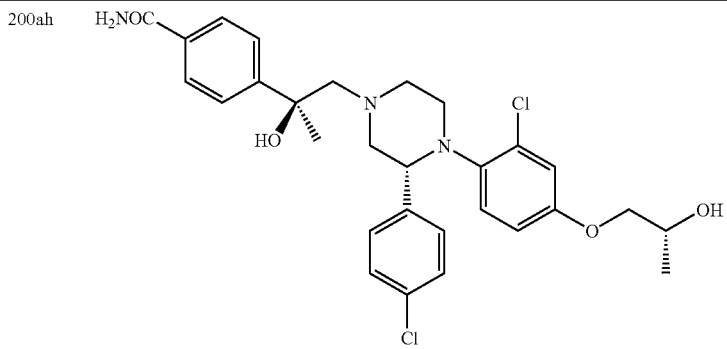 |
| 200ai | 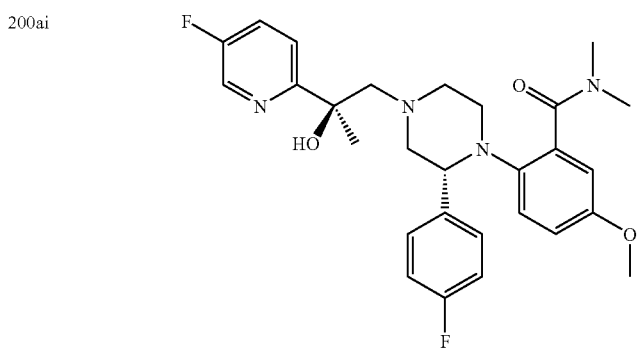 |

Scheme 71

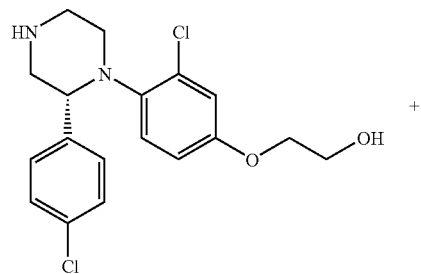

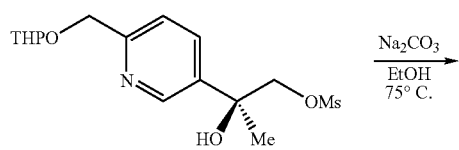

Example 201

To a solution of Example 2 (110 mg, 0.30 mmol) in EtOH (1 mL) in a pressure tube was added the mesylate from Scheme 10 (124 mg, 0.36 mmol) and Na$_2$CO$_3$ (80 mg, 0.75 mmol). The pressure tube was sealed and the mixture was heated to 75° C. with stirring for 24 h. After that time, the mixture was concentrated in vacuo and the residue partitioned between EtOAc and water. The organic layer was separated, washed with brine, dried over MgSO$_4$, filtered and concentrated. The crude product was purified via flash chromatography (SiO$_2$: gradient elution, 1 00:0 to 0:1 00 hexanes: EtOAc) to afford Example 201 (126 mg, 68%) as a white foam.

TABLE 10
The following examples in Table 10 were prepared using a similar method to that described for Example 201 above.
| Ex. | Piperazine Core | Mesylate |
|---|---|---|
| 2 | 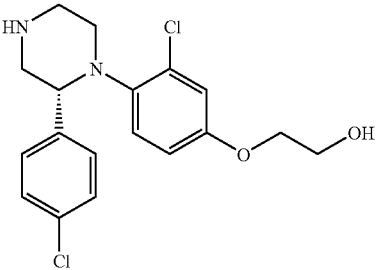 | 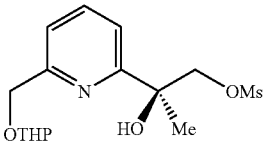<br>Table 1, entry 1 |
| 6 | 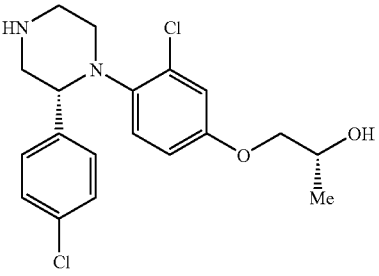 | 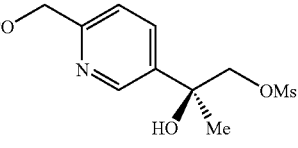<br>Scheme 10 |
| 2 | 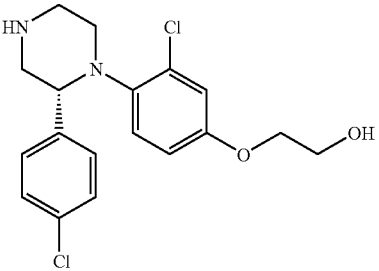 | 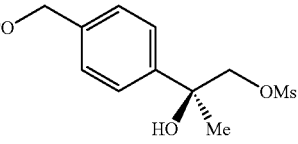<br>Entry 4, Table 1 |
| Ex. | Structure |
|---|---|
| 202 | 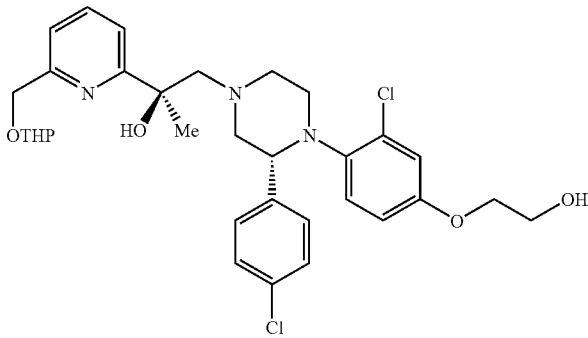 |

TABLE 10-continued
The following examples in Table 10 were prepared using a similar method to that described for Example 201 above.
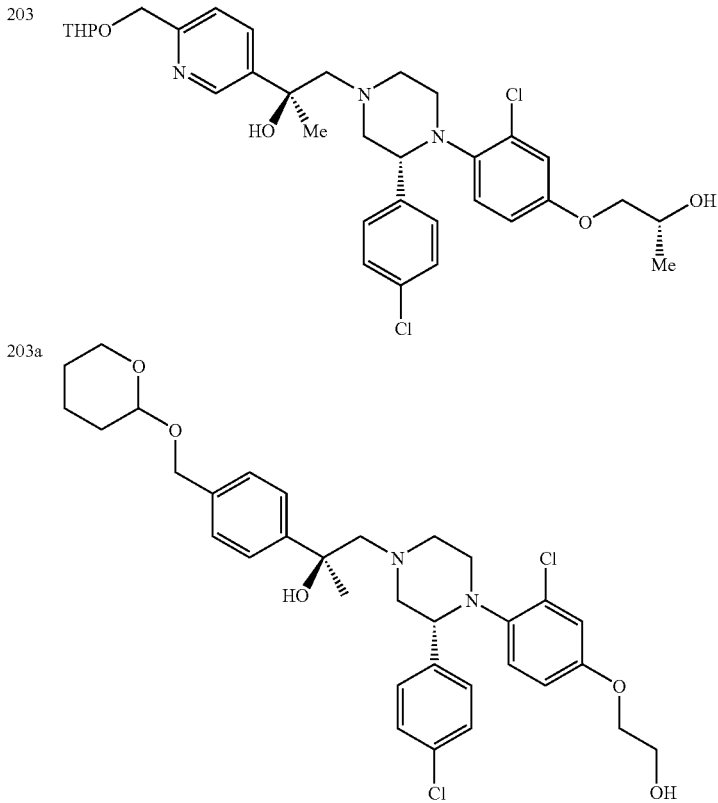
Scheme 72
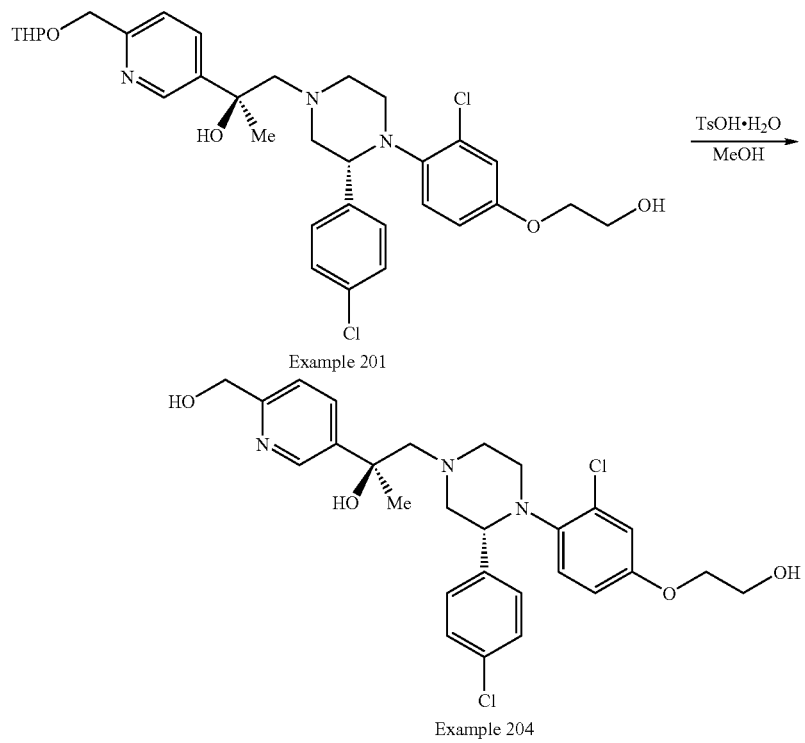

To a solution of Example 201 (116 mg, 0.19 mmol) in methanol (1 mL) was added p-toluenesulfonic acid monohydrate (45 mg, 0.23 mmol). The resultant solution was stirred at RT overnight. Additional p-toluenesulfonic acid monohydrate (36 mg, 0.19 mmol) was added and the solution was allowed to stir at RT for an additional 3 h. The solution was then concentrated and the residue was partitioned between 1 M NaOH (aq.) and EtOAc. The organic layer was separated, washed with brine, dried over MgSO$_4$, filtered and concentrated. The crude product was purified via flash chromatography (SiO$_2$: gradient elution, 100:0 to 0:100 hexanes:EtOAc) to afford Example 204 (97 mg, 97%) as a white foam.

TABLE 11

The following examples were prepared using a similar method to that described for Ex. 204 above.

| Ex. | Piperazine Core |
|---|---|
| 202 | 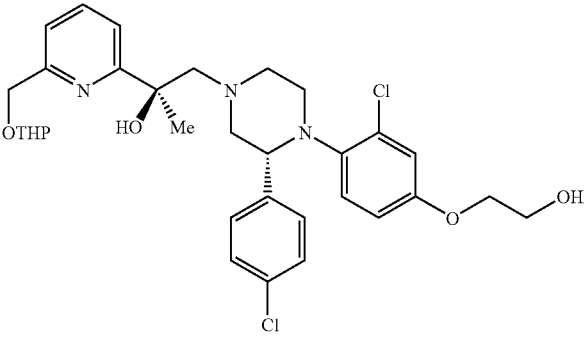 |
| 203 | 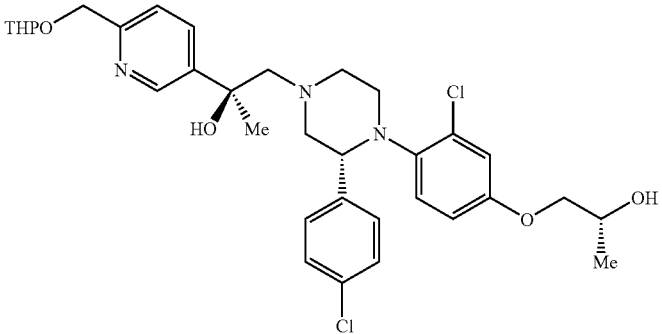 |
| 203a | 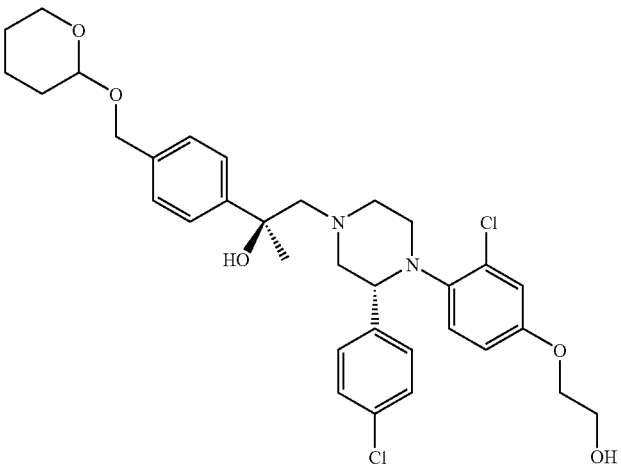 [SMILES: C[C@@](O)(CN1CCN(c2ccc(OCCO)cc2Cl)[C@H](c2ccc(Cl)cc2)C1)c1ccc(COC2CCCCO2)cc1] |

TABLE 11-continued
The following examples were prepared using a similar method to that described for Ex. 204 above.
| Ex. | Structure |
|---|---|
| 205 | 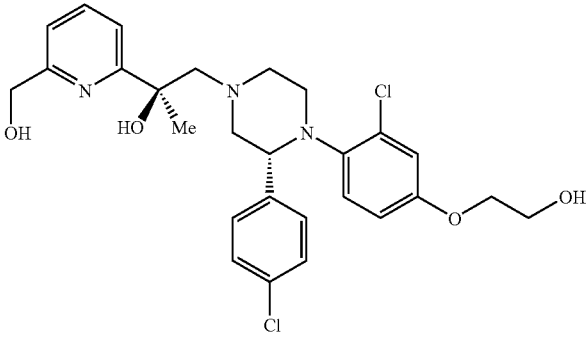 [SMILES: C[C@@](O)(CN1CCN(c2ccc(OCCO)cc2Cl)[C@H](c2ccc(Cl)cc2)C1)c1cccc(CO)n1] |
| 206 | 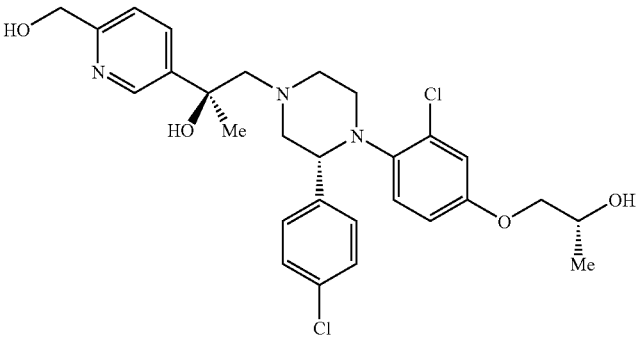 |
| 206a | 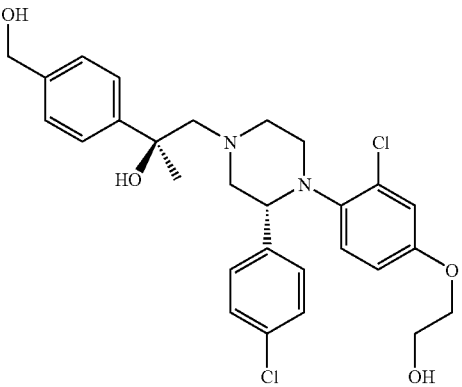 [SMILES: C[C@@](O)(CN1CCN(c2ccc(OCCO)cc2Cl)[C@H](c2ccc(Cl)cc2)C1)c1ccc(CO)cc1] |
Scheme 73
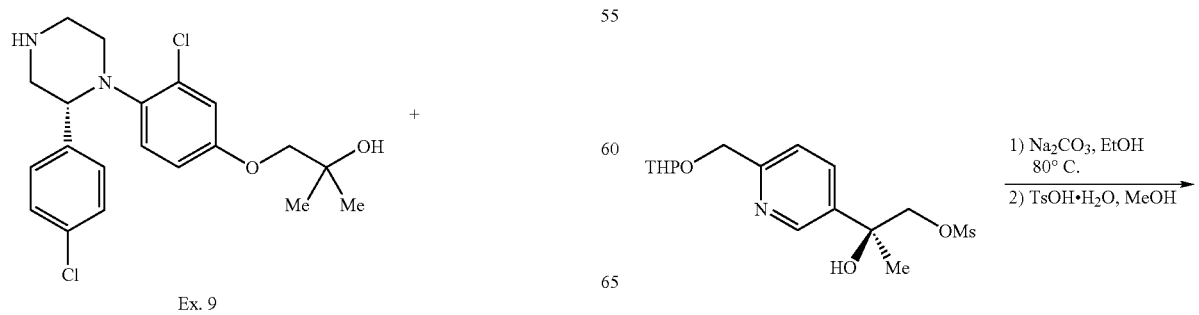

-continued

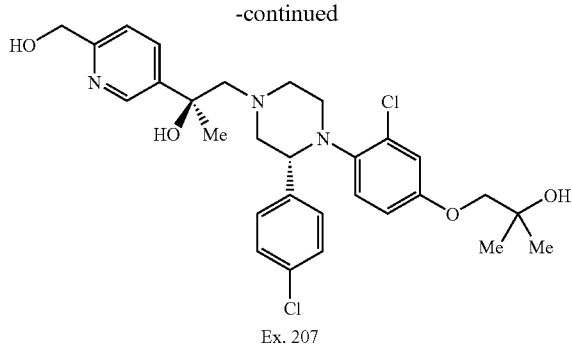

Ex. 207

To a solution of Example 9 (100 mg, 0.25 mmol) in EtOH (1 mL) in a pressure tube was added the mesylate from Scheme 10 (105 mg, 0.30 mmol) and $Na_2CO_3$ (67 mg, 0.63 mmol). The pressure tube was sealed and the mixture was heated to 80° C. with stirring for 24 h. After that time, the mixture was concentrated and the residue partitioned between EtOAc and water. The organic layer was separated, washed with brine, dried over $MgSO_4$, filtered and concentrated. The residue was dissolved in methanol (1 mL) and p-toluenesulfonic acid monohydrate (107 mg, 0.56 mmol) was added. The solution was stirred at RT overnight. The solution was then concentrated in vacuo and the residue was partitioned between 1 M NaOH (aq.) and $CH_2Cl_2$. The organic layer was separated, washed with water then brine, dried over $MgSO_4$, filtered and concentrated. The crude product was purified via flash chromatography ($SiO_2$: gradient elution, 100:0 to 0:100 hexanes:EtOAc) to afford Example 207 (140 mg, 70%) as a pale foam.

TABLE 12

The following examples were prepared using a similar method to that described for Example 207 above.

| Ex. | Piperazine Core | Mesylate |
|---|---|---|
| 31 | | Scheme 10 |
| 22 | | Scheme 10 |
|  | | Scheme 10 |
| 4 | | Table 1, entry 2 |

TABLE 12-continued
The following examples were prepared using a similar method
to that described for Example 207 above.
22 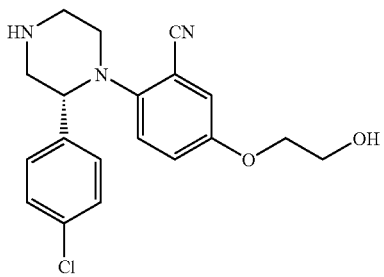 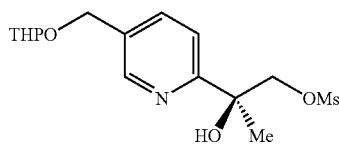
Table 1, entry 2
31 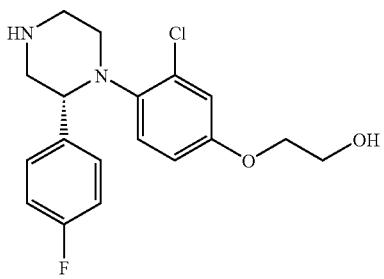 [SMILES: OCCOc1ccc(N2CCNC[C@H]2c2ccc(F)cc2)c(Cl)c1] 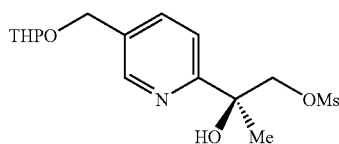
Table 1, entry 2
28 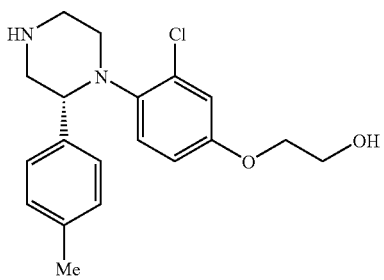 [SMILES: Cc1ccc([C@@H]2CNCCN2c2ccc(OCCO)cc2Cl)cc1] 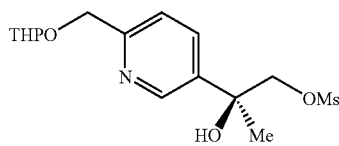
Scheme 10
38 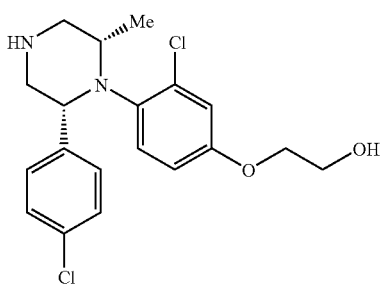 [SMILES: C[C@H]1CNC[C@@H](c2ccc(Cl)cc2)N1c1ccc(OCCO)cc1Cl] 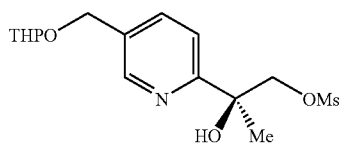
Table 1, entry 2
4 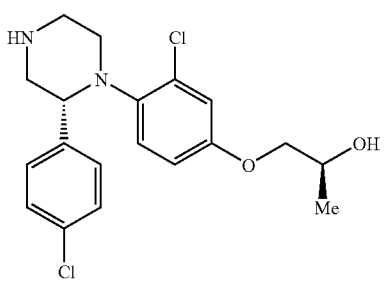 [SMILES: C[C@H](O)COc1ccc(N2CCNC[C@H]2c2ccc(Cl)cc2)c(Cl)c1] 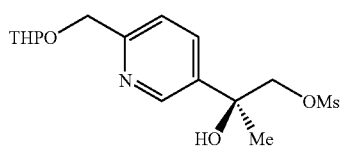
Scheme 10

TABLE 12-continued
The following examples were prepared using a similar method
to that described for Example 207 above.
38 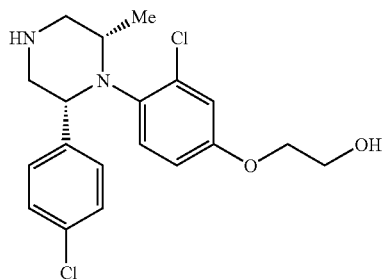 [SMILES: C[C@H]1CNC[C@@H](c2ccc(Cl)cc2)N1c1ccc(OCCO)cc1Cl] 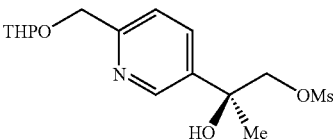
Scheme 10
18 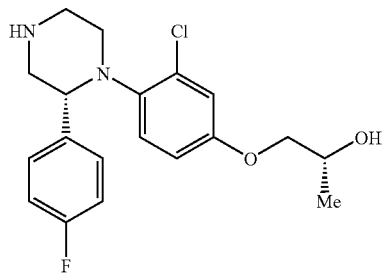 [SMILES: C[C@@H](O)COc1ccc(N2CCNC[C@H]2c2ccc(F)cc2)c(Cl)c1] 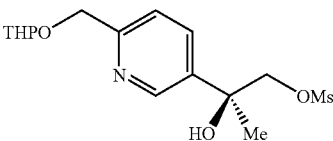
Scheme 10
34 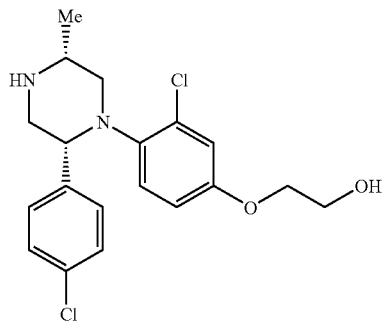 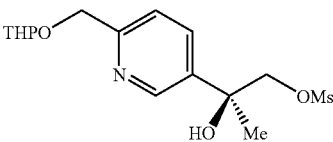
Scheme 10
19 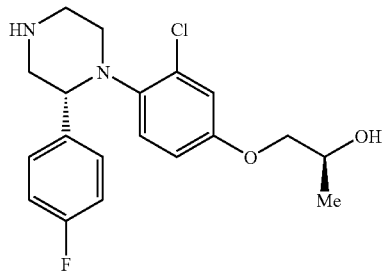 [SMILES: C[C@H](O)COc1ccc(N2CCNC[C@H]2c2ccc(F)cc2)c(Cl)c1] 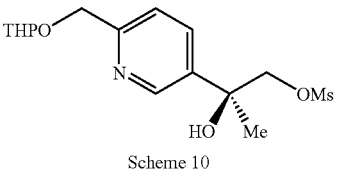
Scheme 10
35 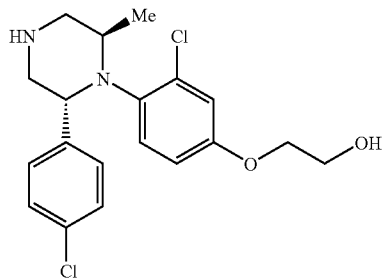 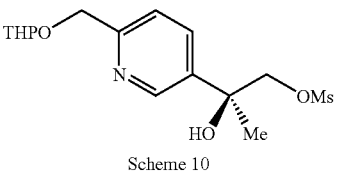
Scheme 10

TABLE 12-continued
The following examples were prepared using a similar method
to that described for Example 207 above.
24 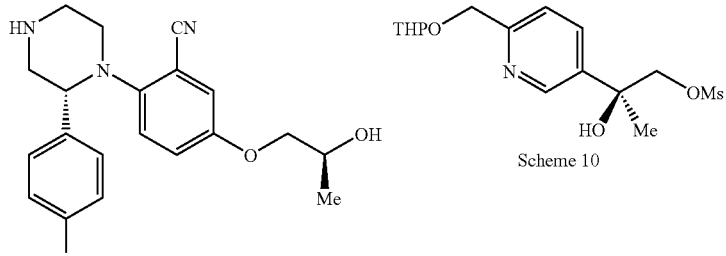
32 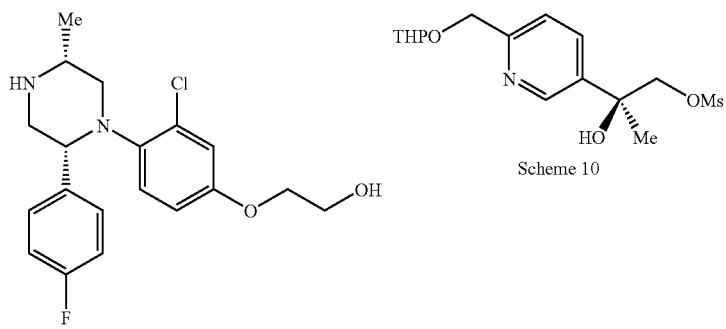
33 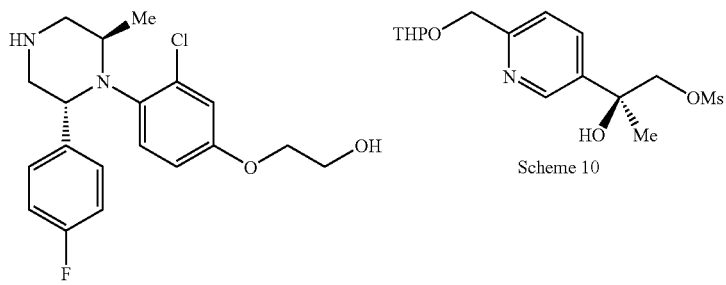
17 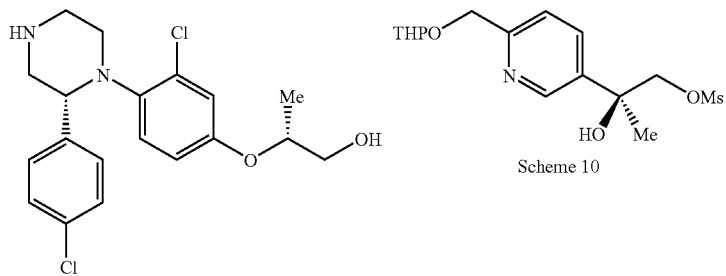
34 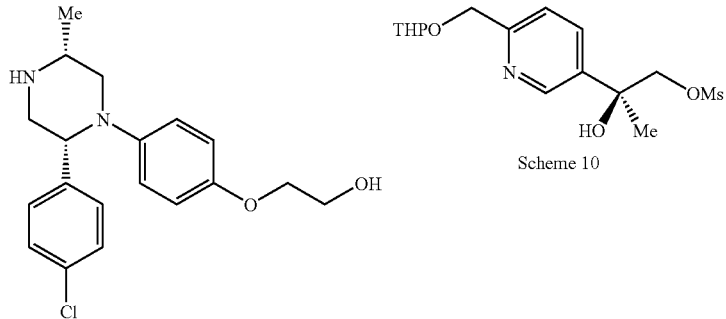

TABLE 12-continued
The following examples were prepared using a similar method
to that described for Example 207 above.
| | | |
|---|---|---|
| 29 | 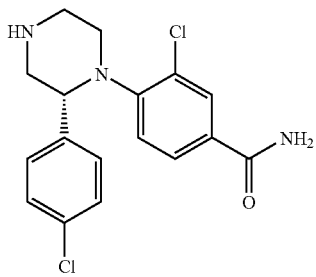 [SMILES: NC(=O)c1ccc(N2CCNC[C@H]2c2ccc(Cl)cc2)c(Cl)c1] | 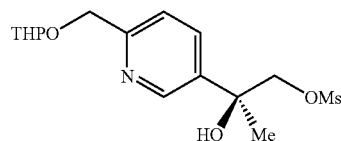
Scheme 10 |
| 27 | 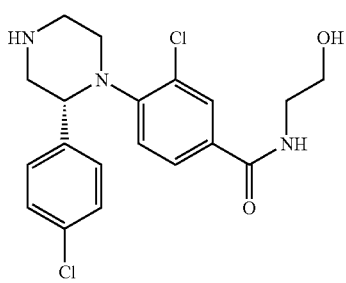 [SMILES: O=C(NCCO)c1ccc(N2CCNC[C@H]2c2ccc(Cl)cc2)c(Cl)c1] | 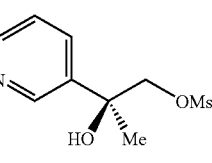
Scheme 10 |
| 25c | 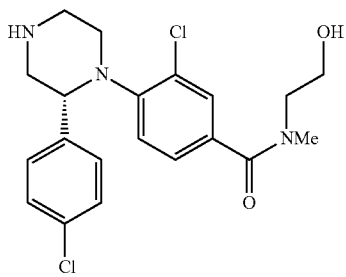 [SMILES: CN(CCO)C(=O)c1ccc(N2CCNC[C@H]2c2ccc(Cl)cc2)c(Cl)c1] | 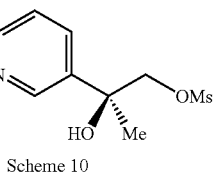
Scheme 10 |
| 25a | 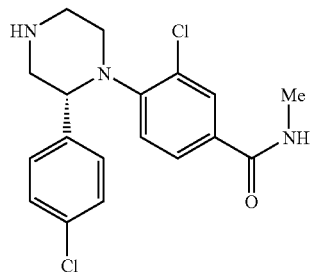 [SMILES: CNC(=O)c1ccc(N2CCNC[C@H]2c2ccc(Cl)cc2)c(Cl)c1] | 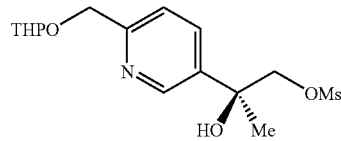
Scheme 10 |
| 25b | 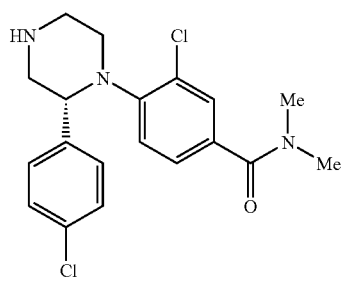 [SMILES: CN(C)C(=O)c1ccc(N2CCNC[C@H]2c2ccc(Cl)cc2)c(Cl)c1] | 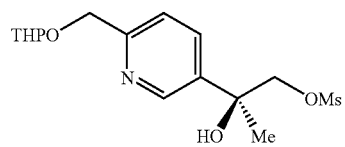
Scheme 10 |

TABLE 12-continued
The following examples were prepared using a similar method to that described for Example 207 above.
22 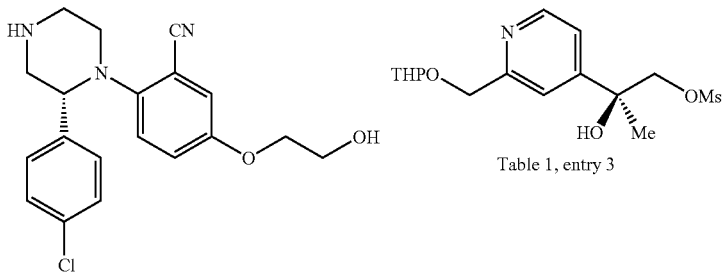
Table 1, entry 3
2 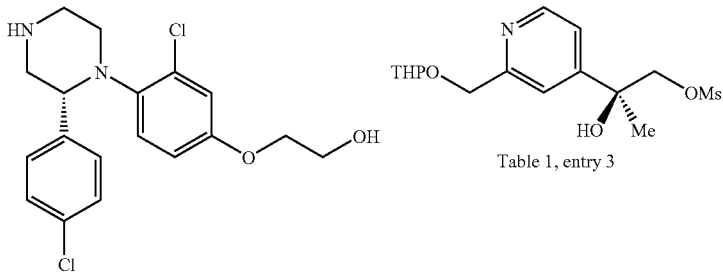
Table 1, entry 3
4 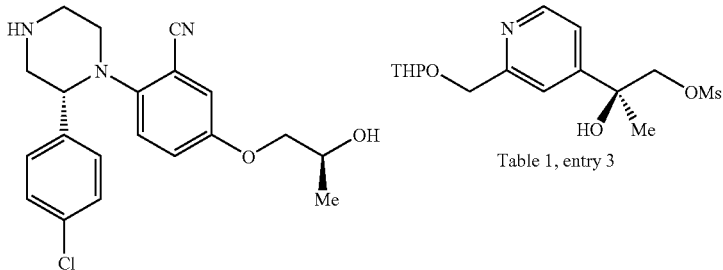
Table 1, entry 3
2c 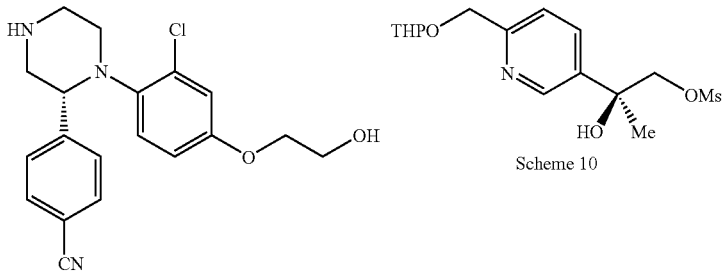
Scheme 10
31 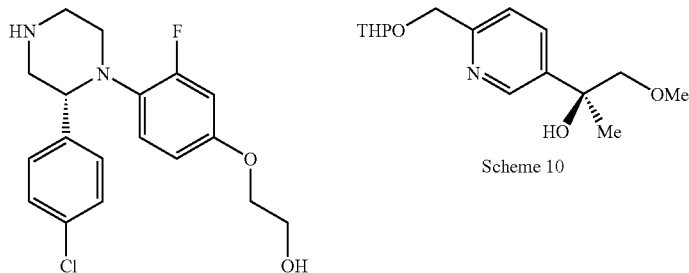
Scheme 10

TABLE 12-continued
The following examples were prepared using a similar method
to that described for Example 207 above.
| | | | |
|---|---|---|---|
| 37 | 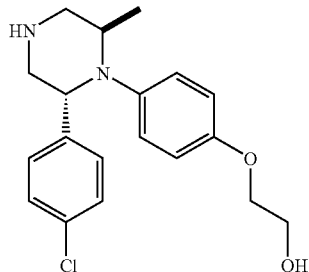 [SMILES: C[C@@H]1CNC[C@@H](c2ccc(Cl)cc2)N1c1ccc(OCCO)cc1] | 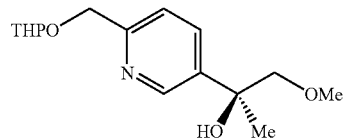 Scheme 10 | |
| 31 | 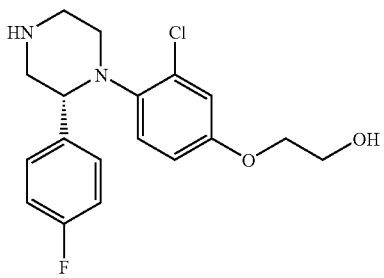 | 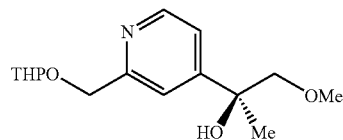 Table 1, entry 3 | |
| 23 | 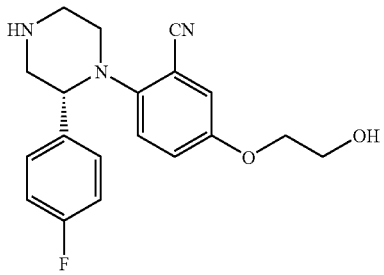 [SMILES: N#Cc1cc(OCCO)ccc1N1CCNC[C@H]1c1ccc(F)cc1] | 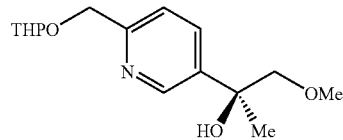 Scheme 10 | |
| 32c | 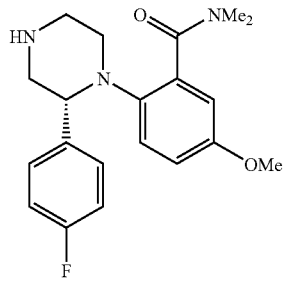 [SMILES: COc1ccc(N2CCNC[C@H]2c2ccc(F)cc2)c(C(=O)N(C)C)c1] | 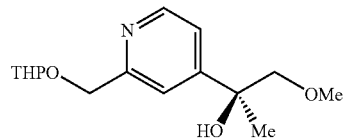 Table 1, entry 3 | |
| 32c | 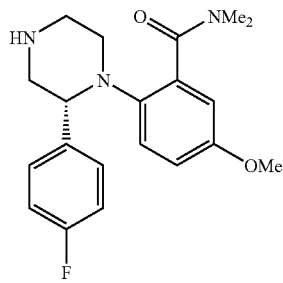 [SMILES: COc1ccc(N2CCNC[C@H]2c2ccc(F)cc2)c(C(=O)N(C)C)c1] | 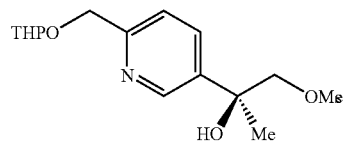 Scheme 10 | |

TABLE 12-continued
The following examples were prepared using a similar method
to that described for Example 207 above.
| Ex. | Final Structure |
|---|---|
| 208 | 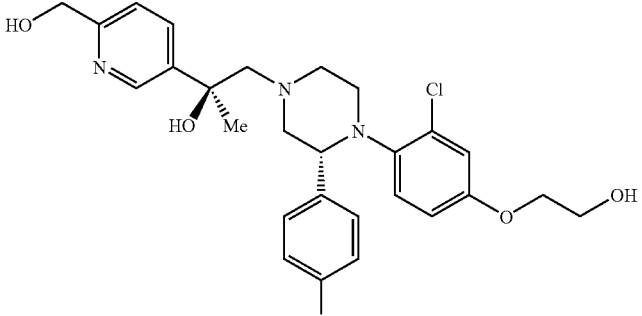 |
| 209 | 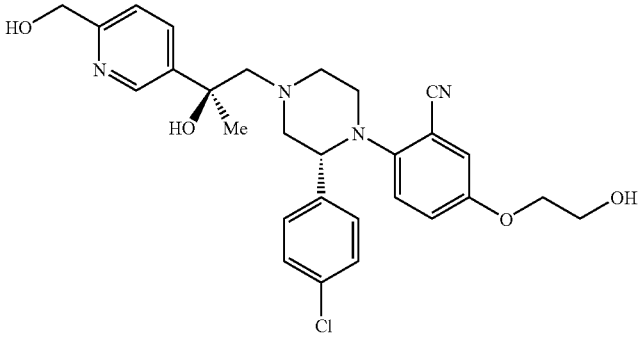 |
| 210 | 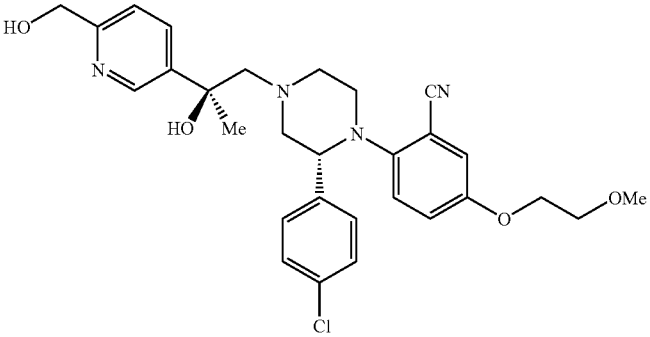 [SMILES: COCCOc1ccc(N2CCN(C[C@@](C)(O)c3ccc(CO)nc3)C[C@H]2c2ccc(Cl)cc2)c(C#N)c1] |
| 211 | 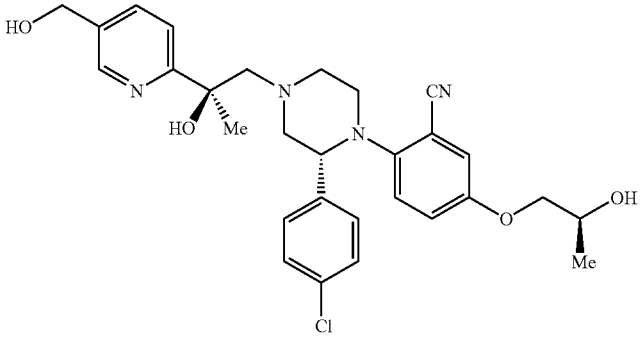 |

TABLE 12-continued
The following examples were prepared using a similar method to that described for Example 207 above.
212 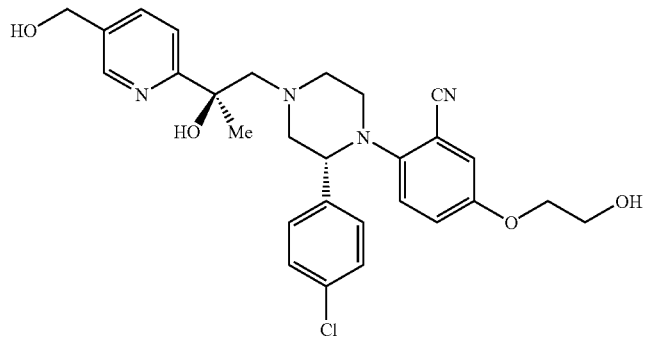
213 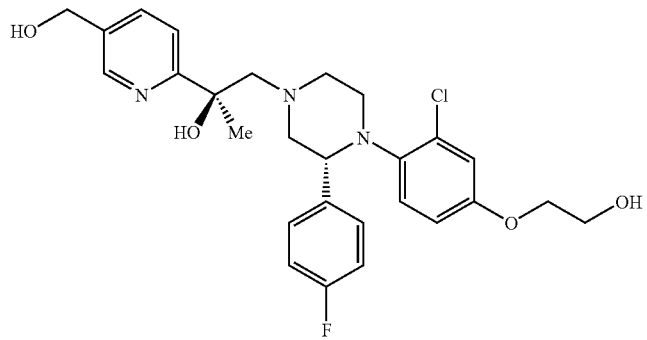 [SMILES: C[C@@](O)(CN1CCN(c2ccc(OCCO)cc2Cl)[C@H](c2ccc(F)cc2)C1)c1ccc(CO)cn1]
214 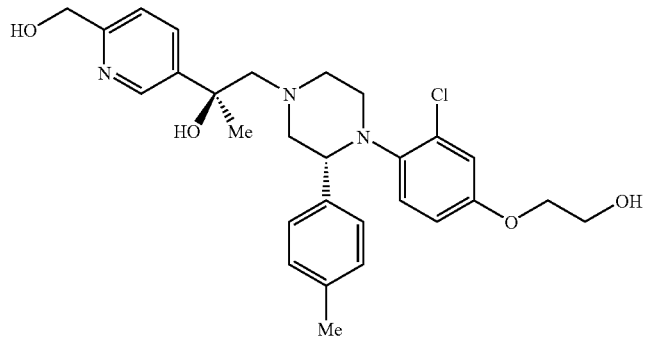 [SMILES: Cc1ccc([C@@H]2CN(C[C@@](C)(O)c3ccc(CO)nc3)CCN2c2ccc(OCCO)cc2Cl)cc1]
215 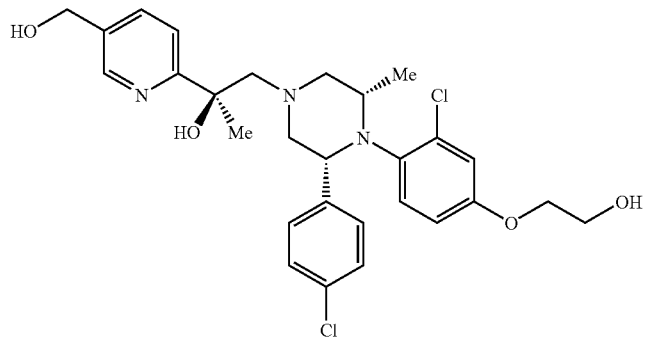 [SMILES: C[C@H]1CN(C[C@@](C)(O)c2ccc(CO)cn2)C[C@@H](c2ccc(Cl)cc2)N1c1ccc(OCCO)cc1Cl]

TABLE 12-continued
The following examples were prepared using a similar method
to that described for Example 207 above.
216 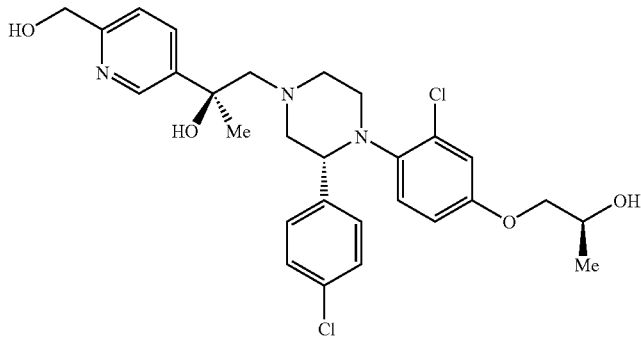 [SMILES: C[C@H](O)COc1ccc(N2CCN(C[C@@](C)(O)c3ccc(CO)nc3)C[C@H]2c2ccc(Cl)cc2)c(Cl)c1]
217 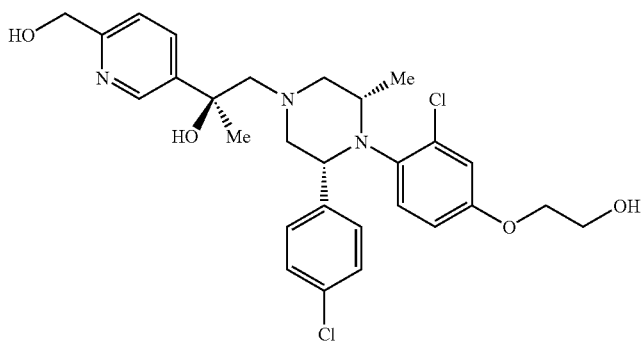 [SMILES: C[C@H]1CN(C[C@@](C)(O)c2ccc(CO)nc2)C[C@@H](c2ccc(Cl)cc2)N1c1ccc(OCCO)cc1Cl]
218 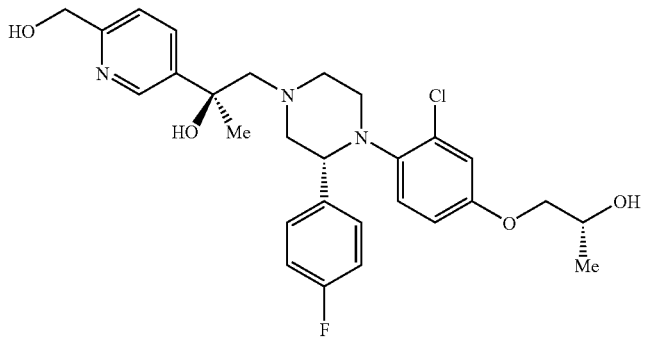
219 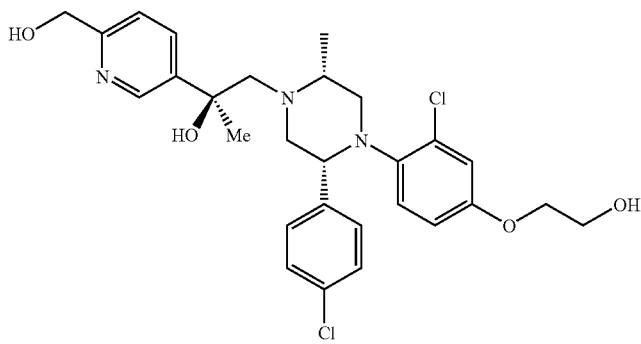 [SMILES: C[C@@H]1CN(c2ccc(OCCO)cc2Cl)[C@H](c2ccc(Cl)cc2)CN1C[C@@](C)(O)c1ccc(CO)nc1]

TABLE 12-continued
The following examples were prepared using a similar method
to that described for Example 207 above.
220 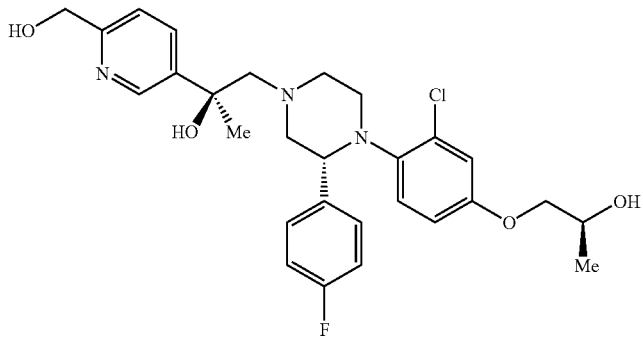
221 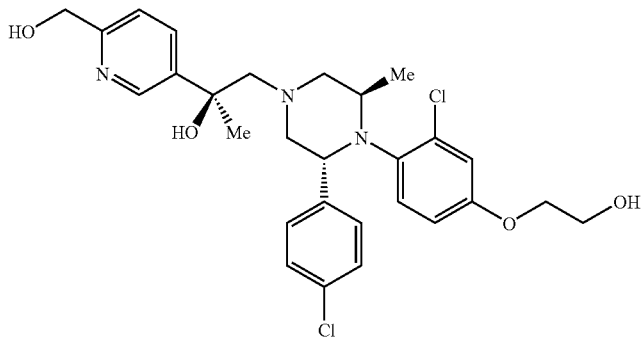
222 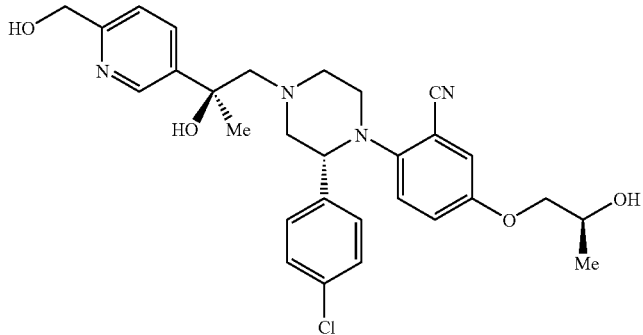
223 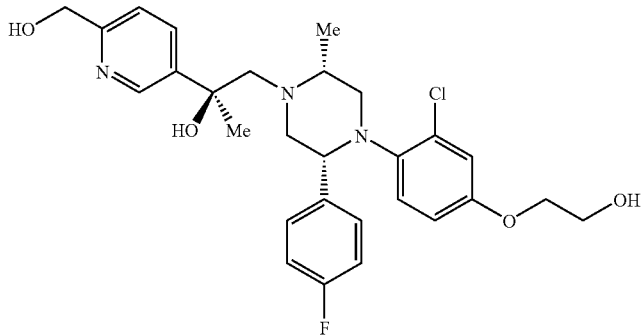 [SMILES: C[C@@H]1CN(c2ccc(OCCO)cc2Cl)[C@H](c2ccc(F)cc2)CN1C[C@@](C)(O)c1ccc(CO)nc1]

TABLE 12-continued
The following examples were prepared using a similar method to that described for Example 207 above.
224 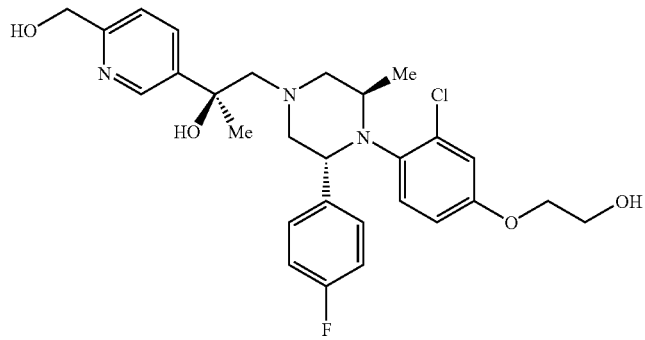 [SMILES: C[C@@H]1CN(C[C@@](C)(O)c2ccc(CO)nc2)C[C@@H](c2ccc(F)cc2)N1c1ccc(OCCO)cc1Cl]
225 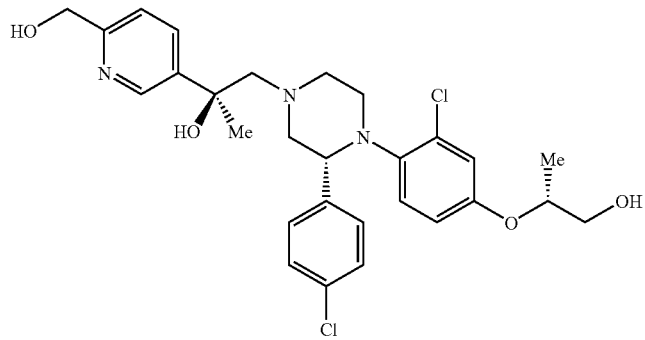 [SMILES: C[C@H](CO)Oc1ccc(N2CCN(C[C@@](C)(O)c3ccc(CO)nc3)C[C@H]2c2ccc(Cl)cc2)c(Cl)c1]
226 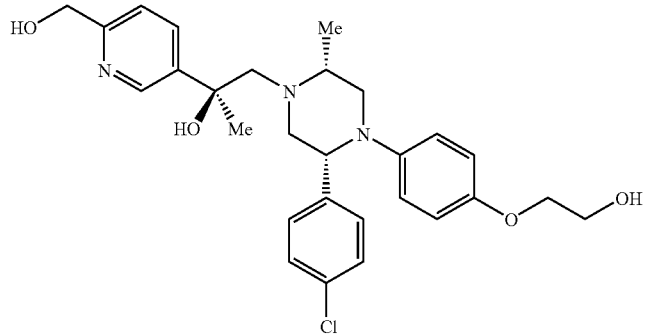 [SMILES: C[C@@H]1CN(c2ccc(OCCO)cc2)[C@H](c2ccc(Cl)cc2)CN1C[C@@](C)(O)c1ccc(CO)nc1]
227 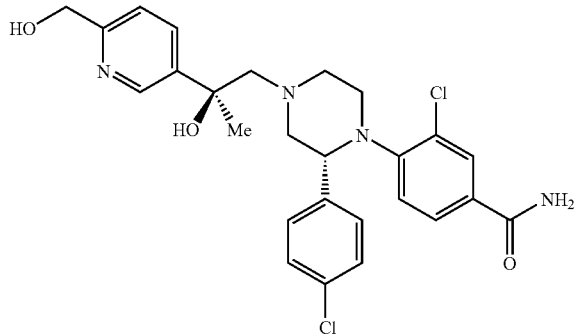 [SMILES: C[C@@](O)(CN1CCN(c2ccc(C(N)=O)cc2Cl)[C@H](c2ccc(Cl)cc2)C1)c1ccc(CO)nc1]

TABLE 12-continued
The following examples were prepared using a similar method to that described for Example 207 above.
228 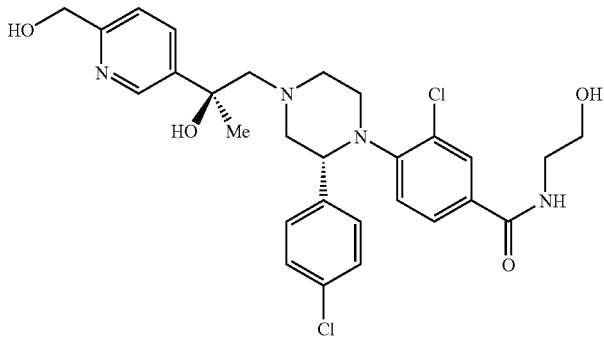 [SMILES: C[C@@](O)(CN1CCN(c2ccc(C(=O)NCCO)cc2Cl)[C@H](c2ccc(Cl)cc2)C1)c1ccc(CO)nc1]
229 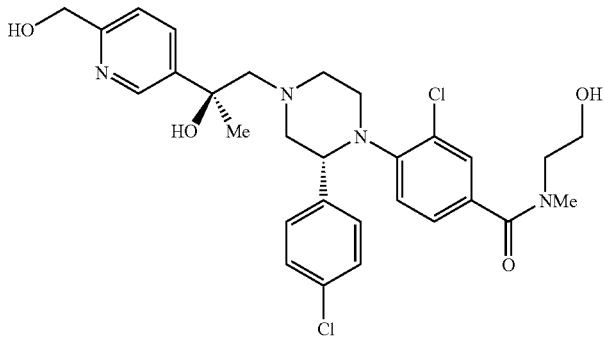 [SMILES: CN(CCO)C(=O)c1ccc(N2CCN(C[C@@](C)(O)c3ccc(CO)nc3)C[C@H]2c2ccc(Cl)cc2)c(Cl)c1]
230 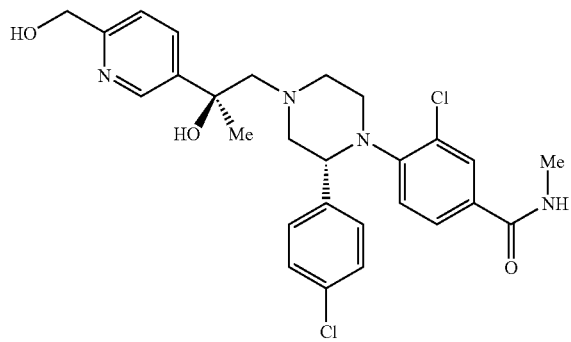 [SMILES: CNC(=O)c1ccc(N2CCN(C[C@@](C)(O)c3ccc(CO)nc3)C[C@H]2c2ccc(Cl)cc2)c(Cl)c1]
231 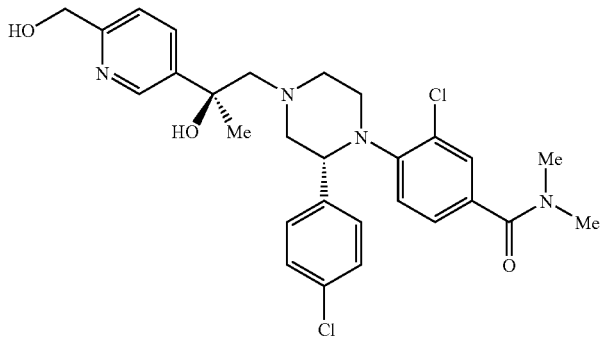 [SMILES: CN(C)C(=O)c1ccc(N2CCN(C[C@@](C)(O)c3ccc(CO)nc3)C[C@H]2c2ccc(Cl)cc2)c(Cl)c1]

TABLE 12-continued
The following examples were prepared using a similar method to that described for Example 207 above.
232 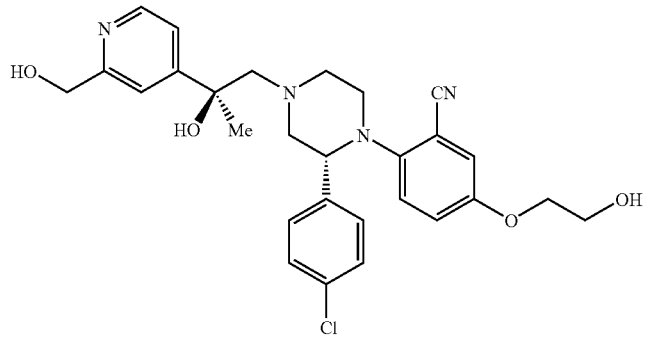
233 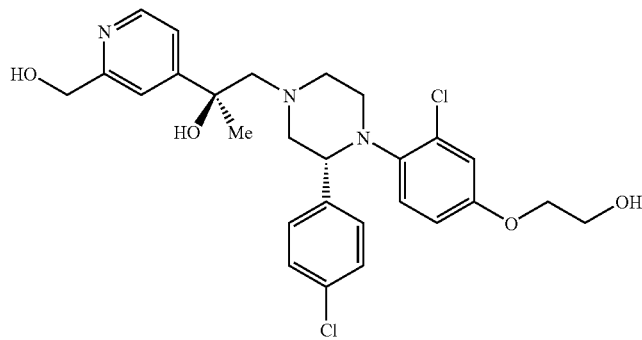
234 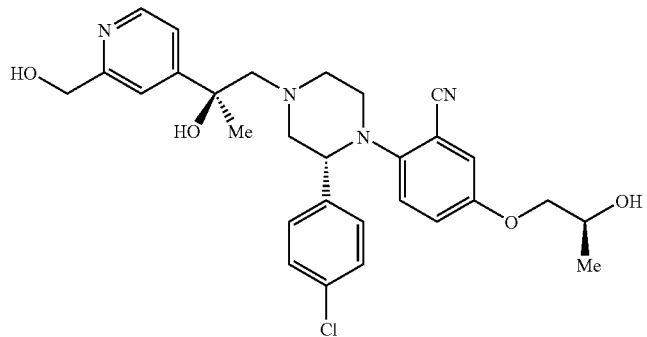 [SMILES: C[C@H](O)COc1ccc(N2CCN(C[C@@](C)(O)c3ccnc(CO)c3)C[C@H]2c2ccc(Cl)cc2)c(C#N)c1]
235 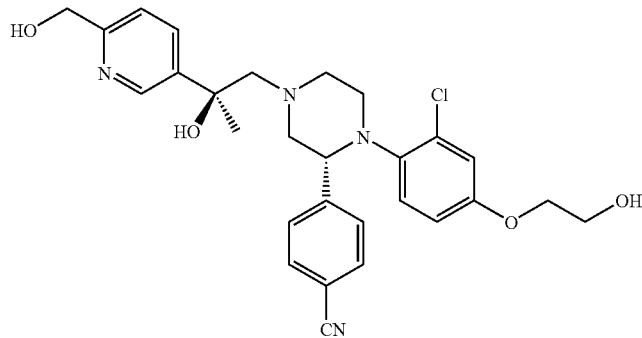 [SMILES: C[C@@](O)(CN1CCN(c2ccc(OCCO)cc2Cl)[C@H](c2ccc(C#N)cc2)C1)c1ccc(CO)nc1]

TABLE 12-continued
The following examples were prepared using a similar method
to that described for Example 207 above.
235a
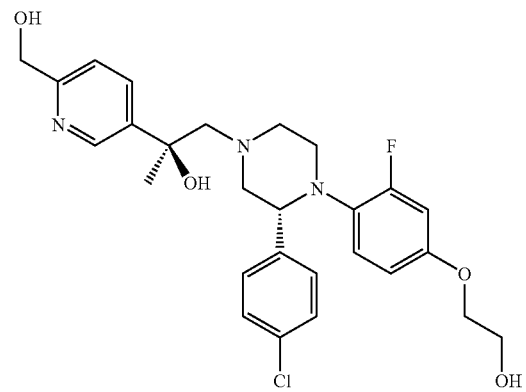 [SMILES: C[C@@](O)(CN1CCN(c2ccc(OCCO)cc2F)[C@H](c2ccc(Cl)cc2)C1)c1ccc(CO)nc1]
235b
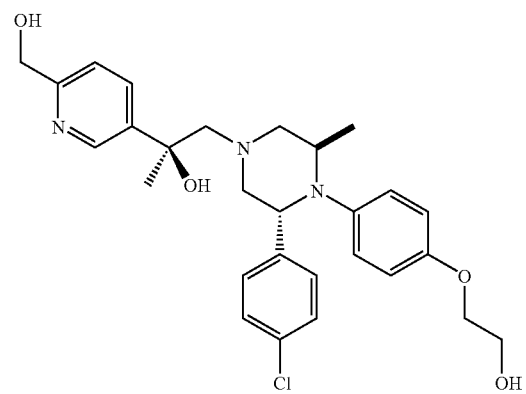 [SMILES: C[C@@H]1CN(C[C@@](C)(O)c2ccc(CO)nc2)C[C@@H](c2ccc(Cl)cc2)N1c1ccc(OCCO)cc1]
235c
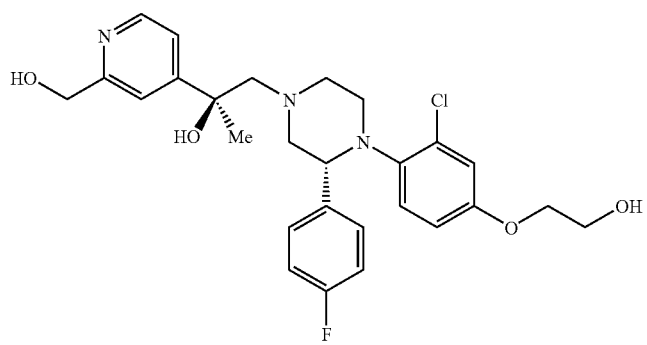 [SMILES: C[C@@](O)(CN1CCN(c2ccc(OCCO)cc2Cl)[C@H](c2ccc(F)cc2)C1)c1ccnc(CO)c1]
235d
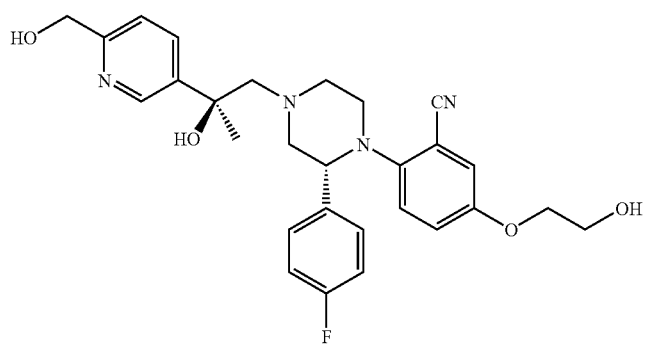 [SMILES: C[C@@](O)(CN1CCN(c2ccc(OCCO)cc2C#N)[C@H](c2ccc(F)cc2)C1)c1ccc(CO)nc1]

TABLE 12-continued
The following examples were prepared using a similar method to that described for Example 207 above.
235e
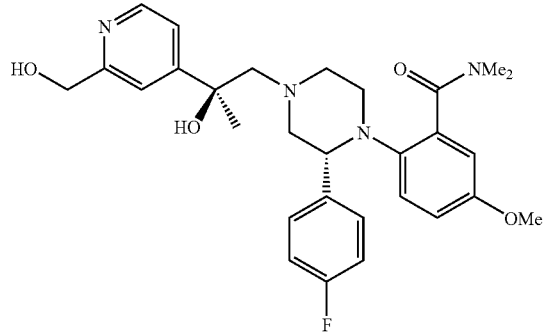 [SMILES: COc1ccc(N2CCN(C[C@@](C)(O)c3ccnc(CO)c3)C[C@H]2c2ccc(F)cc2)c(C(=O)N(C)C)c1]
235f
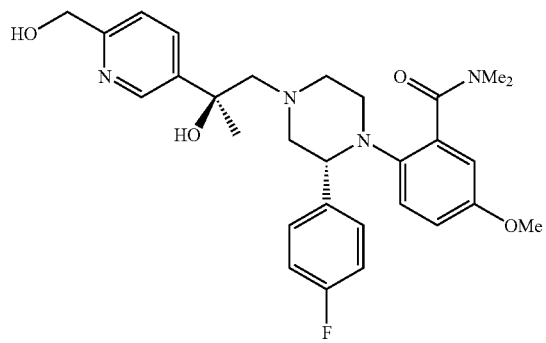 [SMILES: COc1ccc(N2CCN(C[C@@](C)(O)c3ccc(CO)nc3)C[C@H]2c2ccc(F)cc2)c(C(=O)N(C)C)c1]
Scheme 74
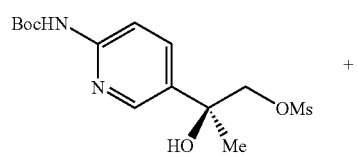
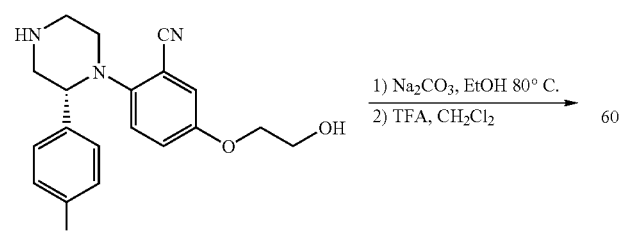
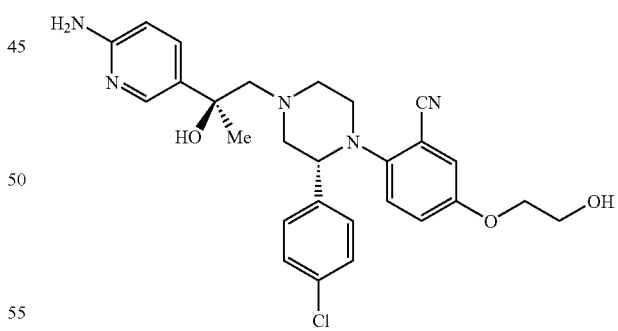
Example 236
To a solution of Example 22 (75 mg, 0.20 mmol) in EtOH (5 mL) in a pressure tube was added the mesylate from Scheme 12 (87 mg, 0.25 mmol) and $Na_2CO_3$ (100 mg). The tube was sealed and the mixture was heated to 80° C. with stirring overnight. The mixture was then concentrated and the residue was partitioned between CH$_2$Cl$_2$ and water. The organic layer was separated, dried over Na$_2$SO$_4$, filtered and concentrated. The crude product was purified via flash chromatography [SiO$_2$: gradient elution, 100:0:0 to 93:7:1 CH$_2$Cl$_2$:MeOH:7 N NH$_3$ (in MeOH)] to afford the intermediate. This intermediate was dissolved in CH$_2$Cl$_2$ and TFA 1 mL was added. The resultant solution was stirred at RT for 3 hours. The solution was concentrated and the residue was partitioned between CH$_2$Cl$_2$ and NaHCO$_3$ (aq.). The organic layer was separated, dried over Na$_2$SO$_4$, filtered and concentrated. The crude product was purified by preparative TLC (SiO$_2$: 95:5:0.5 CH$_2$Cl$_2$: MeOH: concentrated NH$_4$OH) to afford Example 236 (30 mg).

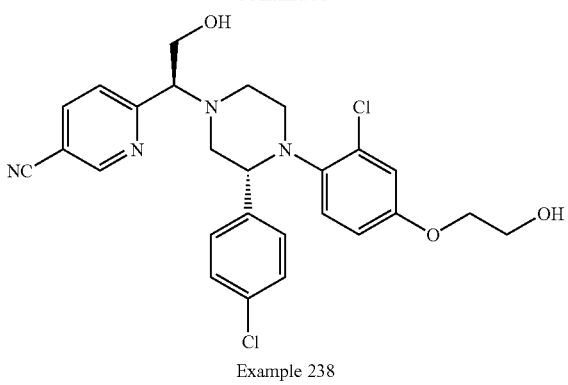
Example 238

TABLE 13

The following example was prepared using a similar method to that described for Example 236.

| Ex. | Piperazine Core | Mesylate | Ex. | Final Structure |
|---|---|---|---|---|
| 21 | | (Scheme 12) | 237 | |

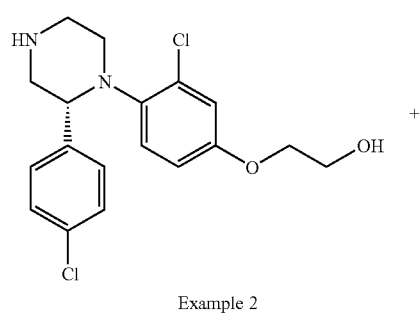
Example 2

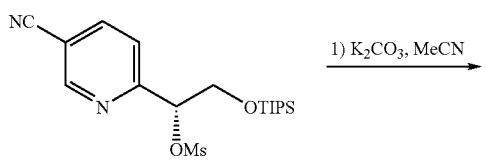

1) K$_2$CO$_3$, MeCN

To a solution of Example 2 (110 mg, 0.30 mmol) and the mesylate from Scheme 19 (179 mg, 0.45 mmol) in acetonitrile (0.5 mL) in a pressure tube was added K$_2$CO$_3$ (104 mg, 0.75 mmol). The pressure tube was sealed and heated to 100° C. for 2.5 days. The reaction mixture was then partitioned between EtOAc and water and the aqueous layer was extracted with EtOAc (3×). The combined organic layers were washed with brine, dried over MgSO$_4$, filtered and concentrated. The crude product was purified via flash chromatography (SiO$_2$: gradient elution, 100:0 to 60:40 hexanes: EtOAc) to afford the silyl ether intermediate (67 mg) as a pale yellow oil.

To a solution of the silyl ether (67 mg, 0.1 mmol) in THF (0.5 mL) was added a solution of TBAF (1 M in THF, 0.11 mL). The resultant red solution was stirred at RT overnight. After that time, the reaction mixture was partitioned between EtOAc and water. The aqueous layer was extracted with EtOAc (3×). The combined organic layers were washed with water and brine, dried over MgSO$_4$, filtered and concentrated. The crude product was purified via flash chromatography (SiO$_2$: gradient elution, 100:0 to 0:100 hexanes:EtOAc) to afford Example 238 (42 mg, 27% yield) (as a mixture of diastereomers ca. 6:1) as a pale yellow oil.

TABLE 14

The following examples were prepared using a similar method to that described for Example 238.

| Ex. | Piperazine Core | Ex. | Final Structure |
|-----|-----------------|-----|-----------------|
| 31 | | 239 | major diastereomer |
| 31 | | 240 | minor diastereomer |
| 22 | | 241 | major diastereomer |
| 22 | | 242 | minor diastereomer |

Scheme 76

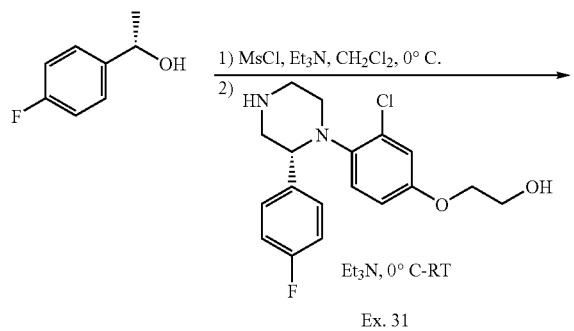

Ex. 31

Scheme 77

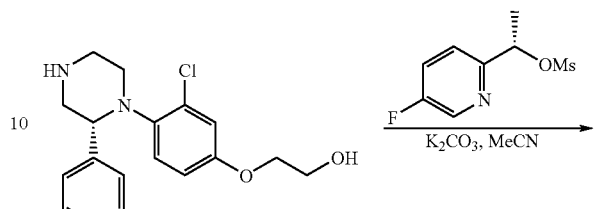

Example 31

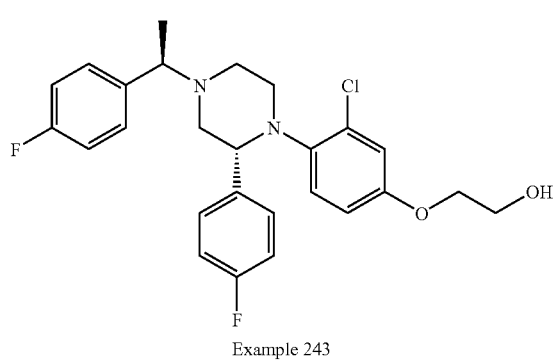

Example 243

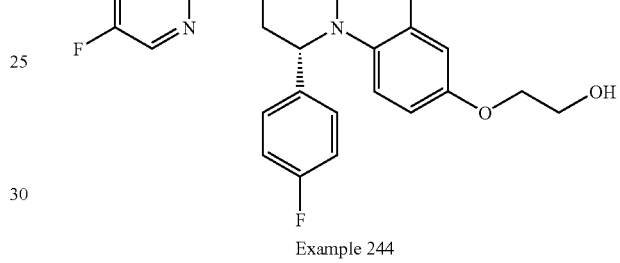

Example 244

To a solution of the alcohol from Scheme 17 (41 mg, 0.29 mmol) in $CH_2Cl_2$ (2 mL) at 0° C. was added $Et_3N$ (29 mg. 0.29 mmol) followed by methanesulfonyl chloride (33 mg, 0.29 mmol). The resultant solution was stirred at 0° C. for 20 min. To this solution was added Example 31 (85 mg, 0.24 mmol) followed by $Et_3N$ (29 mg, 0.29 mmol). The resultant solution was slowly allowed to warm to RT overnight with stirring. The solution was then concentrated and the crude product was purified via flash chromatography (1:1 EtOAc: hexanes) to afford Example 243 (9 mg, 8% yield).

A solution of the Example 31 (148 mg, 0.42 mmol), the mesylate from Scheme 13 (120 my, 0.55 mmol) and $K_2CO_3$ (58 mg, 0.42 mmol) in MeCN (2 mL) in a sealed pressure tube was heated to 80° C. with stirring for 16 h. After that time, the mixture was cooled to RT, transferred to a round bottom flask and concentrated in vacua. The residue was partitioned between EtOAc and brine. The organic layer was then separated, dried over $Na_2SO_4$, filtered and concentrated. The crude product was purified via flash chromatography ($SiO_2$: gradient elution, 100:0 to 30:70 hexanes:EtOAc) to afford Example 244 (22 mg, 11% yield).

TABLE 15

The following examples were prepared using a similar method to that described for Example 244 above.

| Ex. | Piperazine Core | Mesylate | Ex. | Final Structure |
|---|---|---|---|---|
| 22 | | Scheme 13 | 245 | |

TABLE 15-continued

The following examples were prepared using a similar method to that described for Example 244 above.

| Ex. | Piperazine Core | Mesylate | Ex. | Final Structure |
|---|---|---|---|---|
| 31 | | Table 3 | 246 | |
| 22 | | Table 3 | 247 | |

Scheme 78

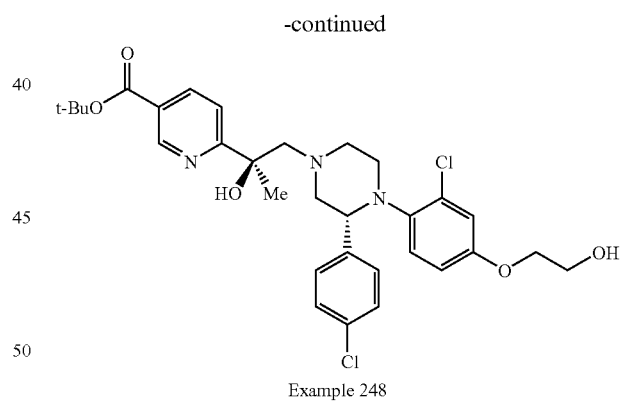

Example 248

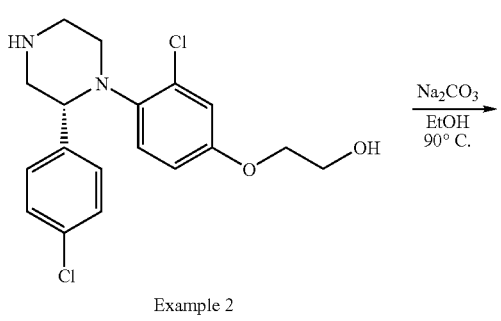

To a solution of the mesylate from Scheme 15 (397 mg, 1.20 mmol) in EtOH (5 mL) in a pressure tube was added Example 2 (400 mg, 1.09 mmol) and $Na_2CO_3$ (127 mg, 1.20 mmol). The tube was sealed and the mixture heated to 90° C. with stirring for 16 h. After that time, the mixture was cooled to RT, transferred to a round bottom flask and concentrated in vacuo. The residue was then partitioned between EtOAc and brine. The aqueous layer was extracted with EtOAc (3×). The combined organic layers were dried over $Na_2SO_4$, filtered and concentrated. The crude product was purified via flash chromatography ($SiO_2$: gradient elution, 100:0 to 50:50 hexanes:EtOAc) to afford Example 248 (630 mg, 96% yield) as a light yellow foam.

Scheme 79
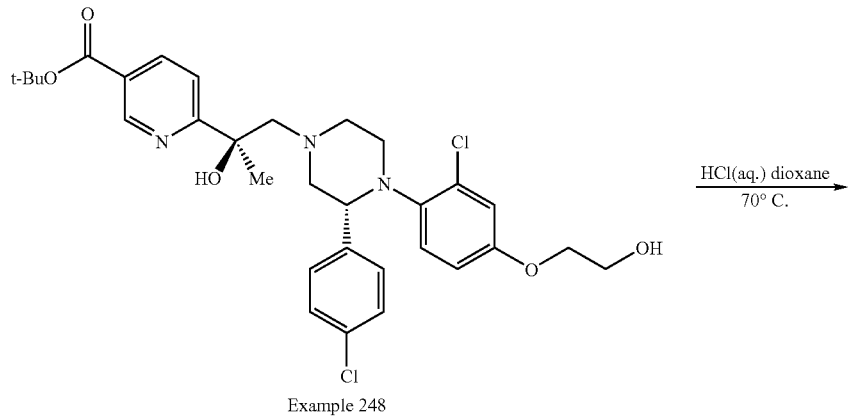
Example 248
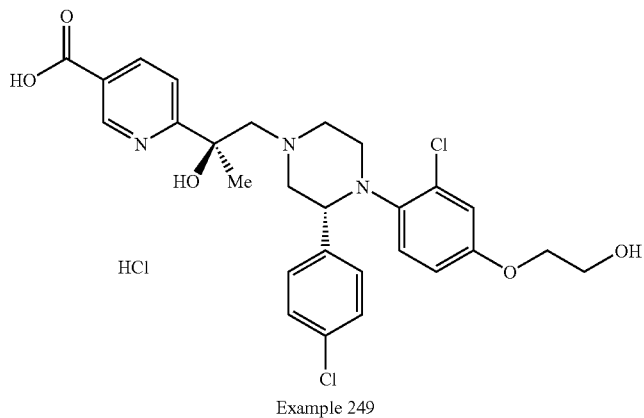
Example 249
To a solution of Example 248 (610 mg, 1.00 mmol) in dioxane (10 mL) was added a solution of HCl(aq.) (4N, 2.80 mL, 11.2 mmol). The solution was heated to 70° C. with stirring for 16h. The solution was then concentrated in vacuo followed by concentration from toluene (2×) to afford Example 249 (560 mg, 95% yield) as the HCl salt.
Scheme 80
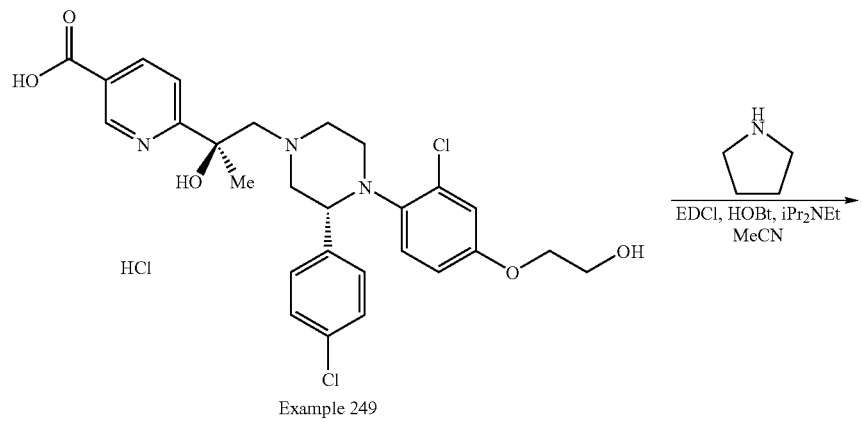
Example 249

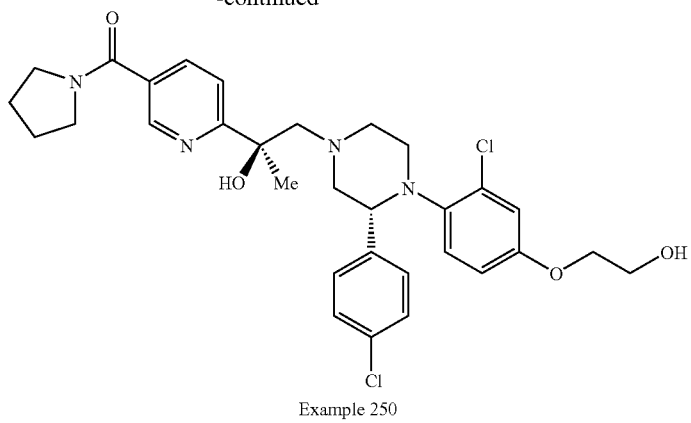

Example 250

To a suspension of Example 249 (105 mg, 0.180 mmol) in MeCN (1 mL) was added EDCl (86.3 mg, 0.45 mmol), HOBt (69.0 mg, 0.45 mmol), iPr₂NEt (69.8 mg, 0.54 mmol) and pyrrolidine (38.4 mg, 0.54 mmol). The resultant solution was stirred at RT for 16 h. After that time, the solution was concentrated, the residue was partitioned between EtOAc and 1 M NaOH (aq.) and the aqueous layer was extracted with EtOAc (3×). The combined organic layers were washed with brine, dried over Na₂SO₄, filtered and concentrated. The crude product was purified via preparative TLC (SiO₂: 95:5 CH₂Cl₂:MeOH) to afford Example 250 (36 mg, 33% yield) as a clear oil.

TABLE 16

The following examples were prepared using a similar method to that described for Example 250.

| Amine | Ex. | Final Structure |
|---|---|---|
| H-N(Me)Me · HCl | 251 | (structure) |
| MeNH₂ · HCl | 252 | (structure) |

TABLE 16-continued

The following examples were prepared using a similar method to that described for Example 250.

| Amine | Ex. | Final Structure |
|---|---|---|
| 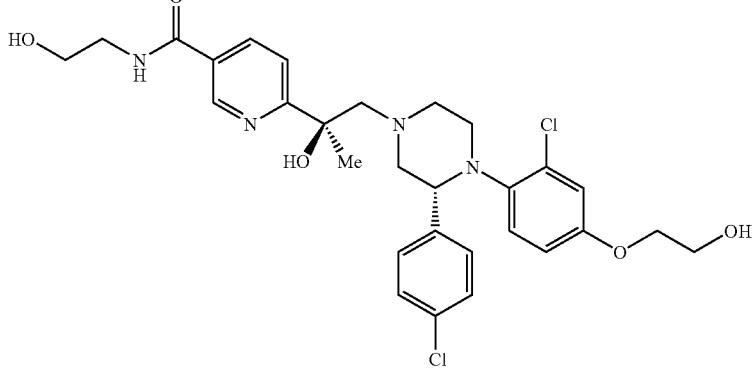 | 253 | 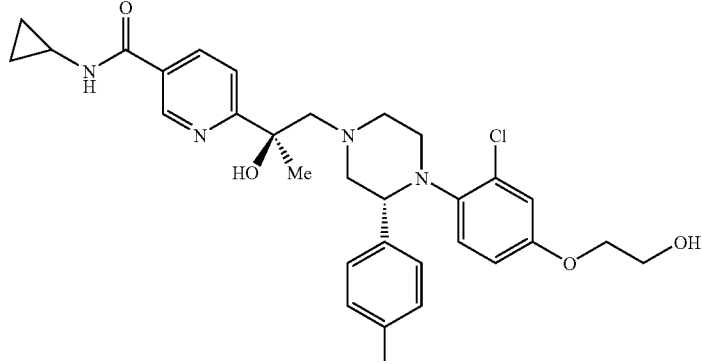 |
| | 254 | |

Scheme 81

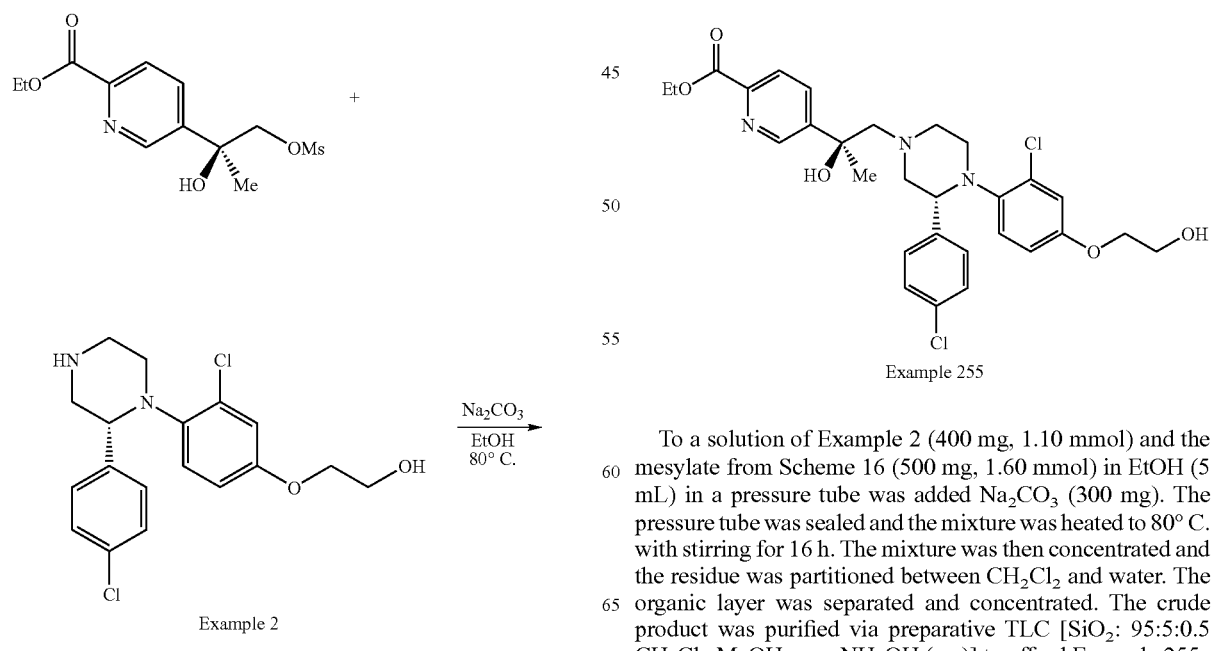

Example 2

Example 255

To a solution of Example 2 (400 mg, 1.10 mmol) and the mesylate from Scheme 16 (500 mg, 1.60 mmol) in EtOH (5 mL) in a pressure tube was added $Na_2CO_3$ (300 mg). The pressure tube was sealed and the mixture was heated to 80° C. with stirring for 16 h. The mixture was then concentrated and the residue was partitioned between $CH_2Cl_2$ and water. The organic layer was separated and concentrated. The crude product was purified via preparative TLC [$SiO_2$: 95:5:0.5 $CH_2Cl_2$:MeOH:conc $NH_4OH$ (aq.)] to afford Example 255.

Scheme 82

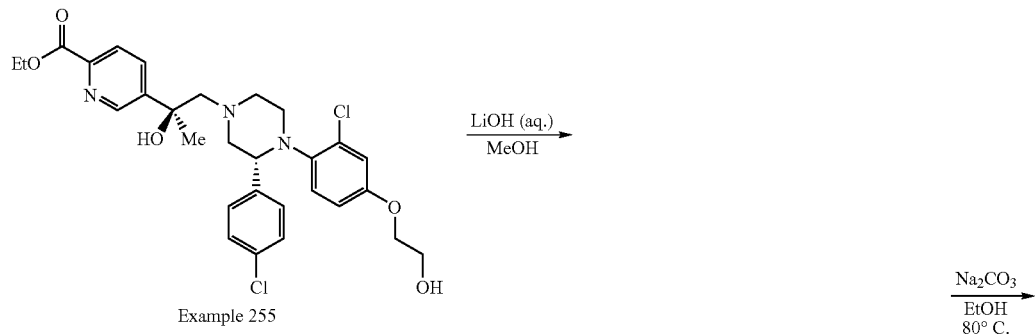

Example 255

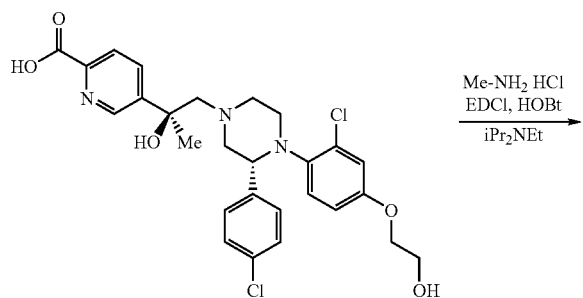

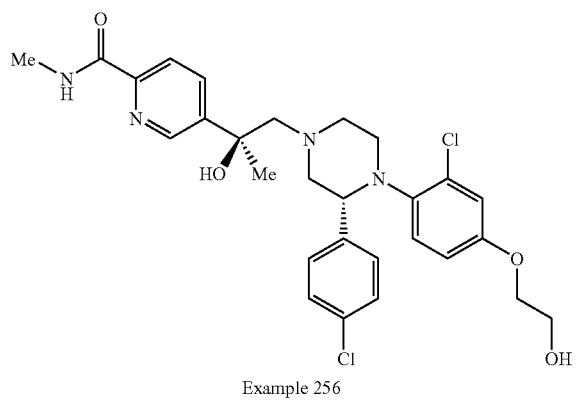

Example 256

To a solution of Example 255 (632 mg, 1.10 mmol) in MeOH was added a solution of LiOH (aq.)(2 M, 1.4 mL). The solution was stirred at RT for 2h. The solution was then concentrated and used without purification.

To a portion of the carboxylate (125 mg, 0.23 mmol) was added EDCl (66 mg, 0.35 mmol), HOBt (47 mg, 0.35 mmol), iPr$_2$NEt (2 mL) and methylamine hydrochloride (31 mg, 0.45 mmol). The mixture was stirred at RT for 16 h. After that time, the mixture was concentrated and the residue was partitioned between CH$_2$Cl$_2$ and water. The organic layer was separated, dried over Na$_2$SO$_4$, filtered and concentrated. The crude product was purified via preparative TLC [SiO$_2$: 95:5:0.5 CH$_2$Cl$_2$:MeOH:conc NH$_4$OH (aq.)] to afford Example 256 (35 mg, 27% yield).

TABLE 17

The following examples was prepared using a similar method to that described for Example 256.

| Amine | Ex. | Final Structure |
|---|---|---|
| 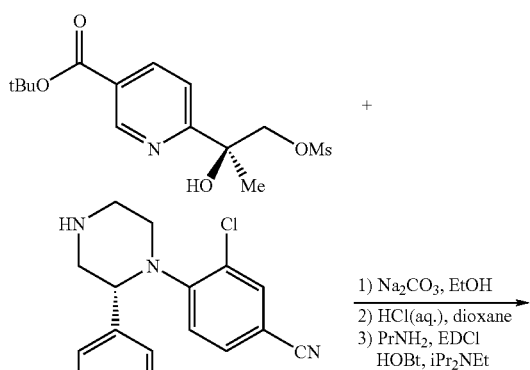 HCl | 257 | |

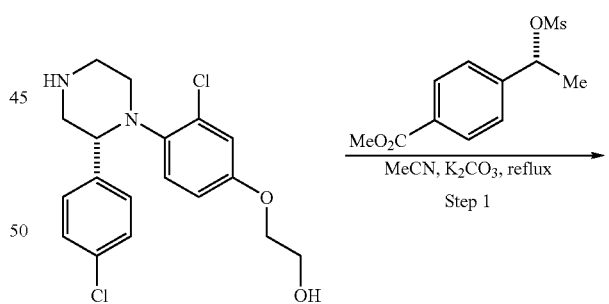

Scheme 83

Example 258

To a solution of the mesylate from Scheme 15 (500 mg, 1.50 mmol) and the piperazine (WO2006060461) (385 mg, 1.16 mmol) in EtOH (5 mL) in a pressure tube was added Na$_2$CO$_3$ (160 mg, 1.50 mmol). The tube sealed and the mixture was heated to 80° C. with stirring for 16 h. After that time, the mixture was cooled to RT, transferred to a round bottom flask and concentrated in vacuo. The residue was partitioned between EtOAc and water and the aqueous layer was extracted with EtOAc (3×). The combined organic layers were washed with brine, dried over Na$_2$SO$_4$, filtered and concentrated. The crude product was purified via flash chromatography (SiO$_2$: gradient elution, 100:0 to 50:50 hexanes:

EtOAc) to afford the ester (580 mg). The ester was taken up in a solution of HCl (aq.) (4N, 3 mL) and HCl (dioxane) (4 N, 20 mL). The resultant solution was heated to 70° C. for 2 h. The solution was concentrated and used without purification. To a portion of the diacid (HCl salt) (ca 100 mg) in MoCN (1 mL) was added EDCl (77 mg, 0.40 mmol), HOBt (54 mg, 0.40 mmol), iPr$_2$NEt (77 mg, 0.60 mmol) and propyl amine (35 mg, 0.59 mmol). The resultant solution was stirred at RT for 16 h. After that time, the solution was concentrated in vacuo and the residue was partitioned between EtOAc and 1 M NaOH (aq.). The aqueous layer was extracted with EtOAc (3×). The combined organic layers were washed with brine, dried over Na$_2$SO$_4$, filtered and concentrated. The crude product was purified via preparative TLC [SiO$_2$: 75:25 EtOAc:hexanes] to afford Example 258 (19 mg).

Scheme 84

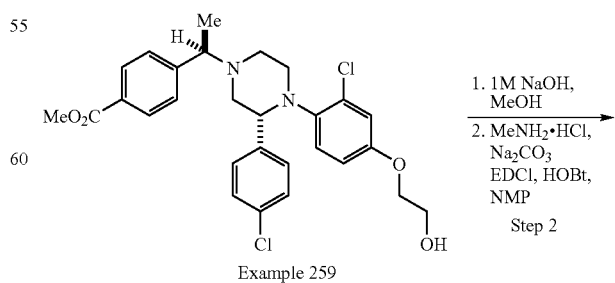

Example 259

443

-continued

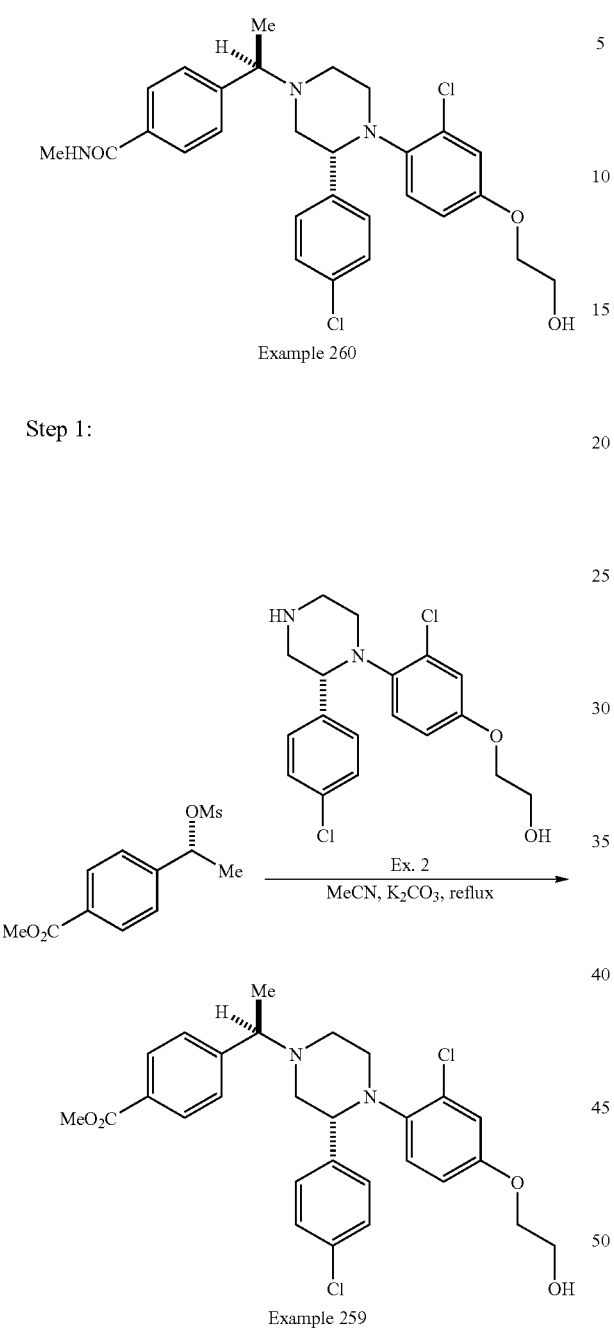

Step 1:

Step 2:

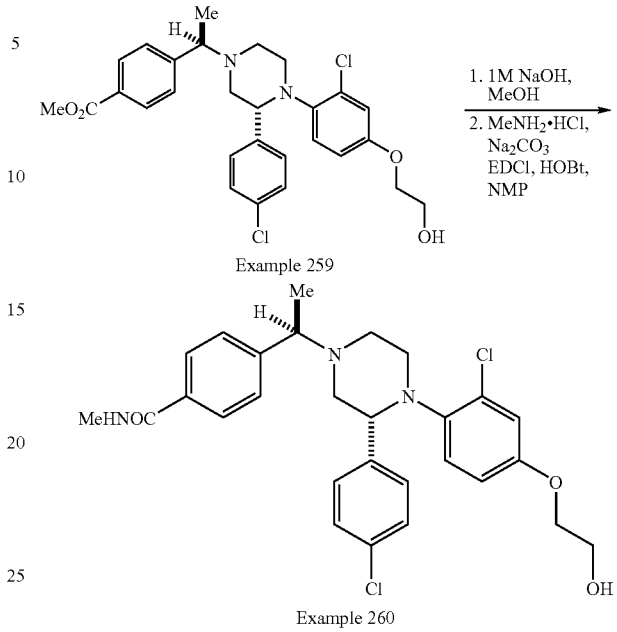

A solution of Example 259 (1 g. 1.89 mmol, 1 eq) in MeOH (4 mL) was treated with 1M NaOH (3.8 mL, 3.78 mmol, 2 eq) with stirring. A precipitate rapidly formed. MeOH (8 mL) and THF (1 mL) were added and the solution was stirred for 2 h during which time the solids dissolved. An additional amount of 1M NaOH (3 mL) was added, and the reaction stirred for 16h. The reaction was then neutralized with 2 M HCl (2.5 mL) and the volatiles removed in vacuo. A portion of the crude carboxylate (ca. 0.2 mmol), EDCl (43 mg, 0.22 mmol, 1.1 eq), HOBt (30 mg, 0.22 mmol, 1.1 eq), sodium carbonate (153 mg, 1.44 mmol, 7.2 eq), and methylamine hydrochloride (54 mg, 0.8 mmol, 4 eq) were dissolved in NMP (3 mL) and stirred 72 h. The reaction was partitioned between EtOAc and water and the aqueous layer removed. The organic layer was washed twice with brine and evaporated to afford a crude residue which was subjected to silica gel chromatography (50% to 100% EtOAc in hexanes) to afford the desired product with ~30% NMP contamination. The product was dissolved in EtOAc and washed twice with brine, filtered through a pad of silica gel, and evaporated to afford Example 260 as a clear glass (10:1 dr, 17 mg).

Combine the crude mesylate prepared in Scheme 20 (1 g, 3.87 mmol, 1.4 eq) the piperazine Ex. 2 (1.02 g, 2.78 mmol, 1 eq) and potassium carbonate (768 mg, 5.56 mmol, 2 eq) in MeCN (25 mL) and stir at reflux 16h. Over that time, the reaction became a viscous suspension. MeCN (30 mL) was added and the reaction heated at reflux for an additional 2h. The reaction was then cooled to room temperature, filtered, and the solids washed with EtOAc. The combined filtrates were evaporated to afford a crude residue that was subjected to silica gel chromatography (30% to 80% EtOAc in hexanes) to afford Example 259 (1.1 g, ~5:1 dr ($^1$H—NMR)) as a viscous oil.

Scheme 85

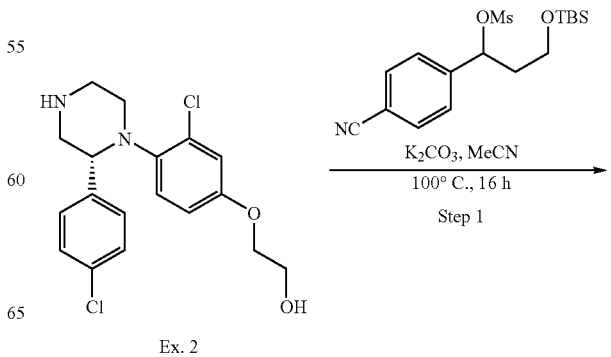

445

-continued

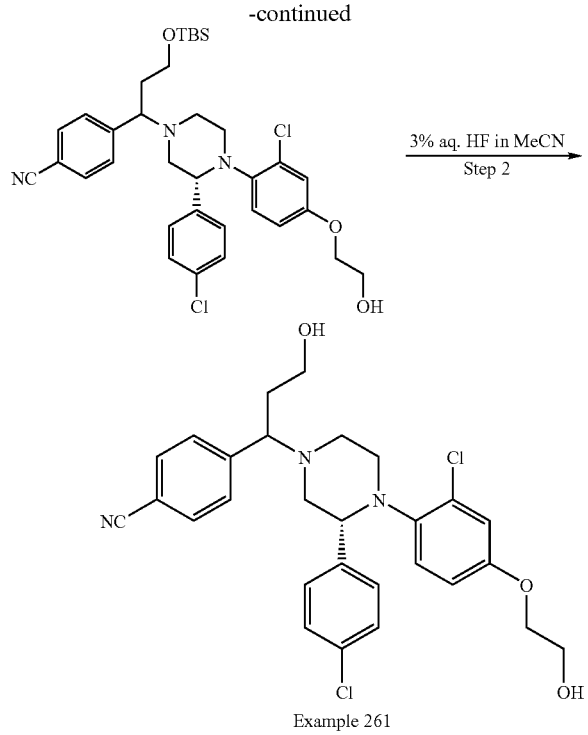

Example 261

Step 1:

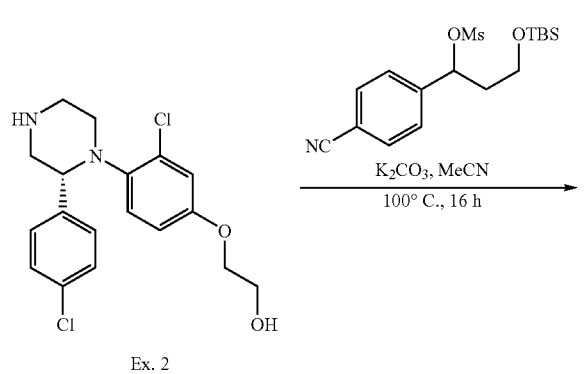

A suspension of the mesylate from Scheme 21 (51 mg, 0.14 mmol, 1 eq), Example 2 (50 mg, 0.14 mmol, 1 eq) and $K_2CO_3$ (56 mg, 0.41 mmol, 3 eq) in acetonitrile (2 mL) was heated 16 h at 100° C. with stirring. The volatiles were then removed in vacuo to afford a residue which was subjected to silica gel chromatography (20% to 80% EtOAc in hexanes) to afford the coupled product as a clear film (49 mg).

446

Step 2:

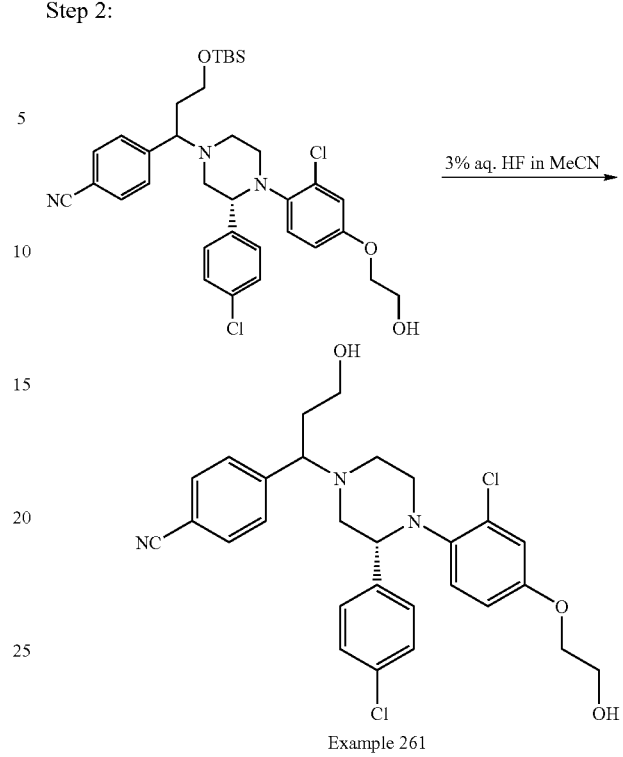

Example 261

The coupled product from Step 1 (49 mg, 0.093 mmol) was dissolved in MeCN (5 mL), treated with 5% aqueous HF in MeCN (1 mL) and stirred for 16 h. The reaction was partitioned between $CH_2Cl_2$ and saturated aqueous $NaHCO_3$. The aqueous layer was extracted with $CH_2Cl_2$ and the combined organic extracts were evaporated to afford a residue which was purified via silica gel chromatography (0% to 10% MeOH in $CH_2Cl_2$) to provide Example 261 as a clear, colorless film (1:1 dr, 34 mg).

Scheme 86

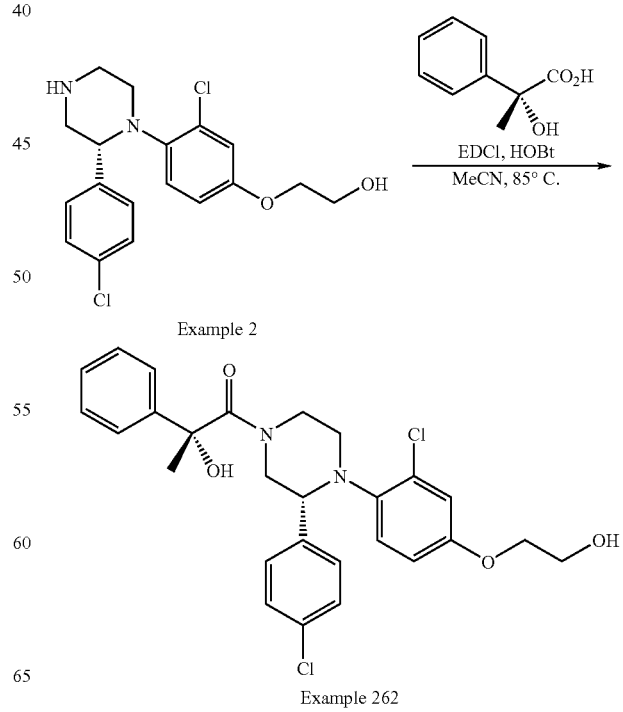

(R)-2-Hydroxy-2-phenylpropanoic acid (75 mg, 0.45 mmol, 1 eq), Example 2 (150 mg, 0.45 mmol, 1 eq), EOCl (86 mg, 0.45 mmol, 1 eq), HOBt (61 mg, 0.45 mmol, 1 eq), and i-Pr₂NEt (0.24 mL, 1.35 mmol, 3 eq) were combined in MeCN (2 mL) and heated at reflux 16 h. During that time, the solvent evaporated to afford a pale orange gum that was cooled and subjected to silica gel chromatography (50% to 100% EtOAc in hexanes) to afford Example 262 mostly pure. A second purification was conducted with a ChiralPak AD semi prep column (2 cm×25 cm, 10 μm particle size, 80:20 hexanes:i-PrOH, 12 mL/min, 30 mg/2 mL injection amount) to provide Example 262 as a clear film (83 mg).

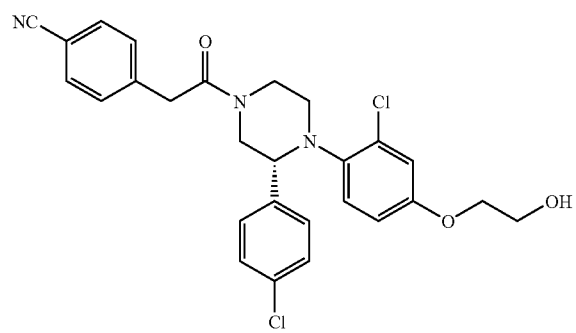

Example 263

Scheme 87

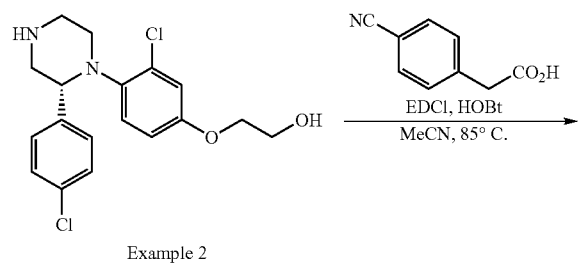

Example 2

4-Cyano-phenylacetic acid (75 mg, 0.47 mmol, 1.03 eq), Example 2 (150 mg, 0.45 mmol, 1 eq), EDCl (86 mg, 0.45 mmol, 1 eq), and HOBt (61 mg, 0.45 mmol, 1 eq) were combined in MeCN (2 mL) and heated at 70° C. for 16 h. The reaction was then partitioned between 10% MEOH in EtOAc and diluted brine. The aqueous layer was discarded and the organic layer was washed with saturated NaHCO₃, evaporated, and the resulting residue subjected to silica gel chromatography (60% to 100% EtOAc in hexanes) to afford Example 263 as a foam (110 mg).

Using the method described above and the requisite carboxylic acid, the following example were also prepared:

TABLE 18

| carboxylic acid | example | structure |
|---|---|---|
|  | 264 |  |
|  | 264a |  |

Scheme 88

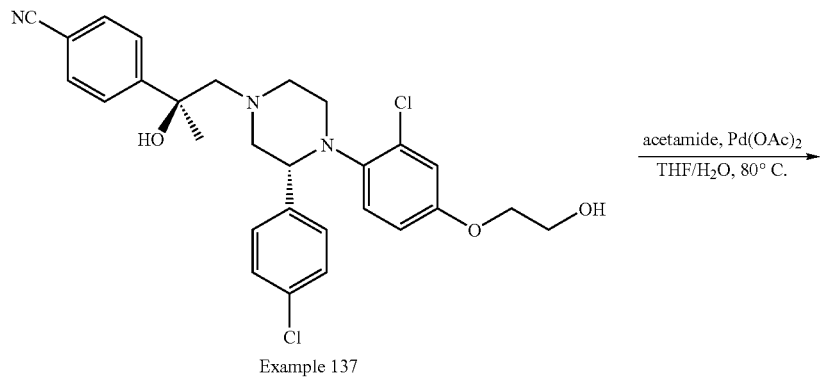

Example 137

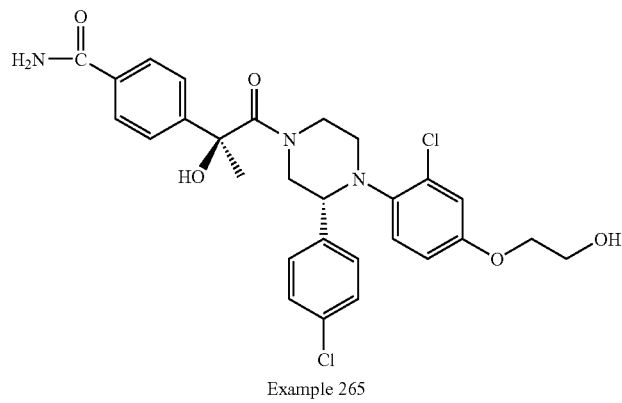

Example 265

Example 137 (200 mg, 0.38 mmol, 1 eq), Pd(OAc)$_2$ (9 mg, 0.038 mmol, 0.1 eq), and acetamide (95 mg, 1.61 mmol, 4.2 eq) were dissolved in 3:1 THF:water (7 mL) and stirred 16 h at 65° C. An additional amount of Pd(OAc)$_2$ (30 mg) was added and the reaction stirred at 80° C. for 24 h more A third portion of Pd(OAc)$_2$ (60 mg) was added along with a second portion of acetamide (230 mg) and the reaction stirred at 80° C. for 24 h more. The mixture was cooled to room temperature, partitioned between 10% MeOH in CH$_2$Cl$_2$ and saturated NaHCO$_3$, and the organic layer removed. The aqueous layer was extracted twice more with 10% MeOH in CH$_2$Cl$_2$ and all three extracts were combined and evaporated. The aqueous layer was then filtered through Celite® and the filter pad washed with water The Celite® pad was then suspended in MeOH, sonicated, filtered, and washed with MeOH. The combined MeOH filtrates were evaporated and combined with the 10% MeOH in CH$_2$Cl$_2$ extracts, loaded onto a PTLC plate (20 cm×20 cm, 1 mm thickness, and developed with 5% MeOH in CH$_2$Cl$_2$. The product band was isolated, stirred in EtOAc, filtered, and washed with EtOAc. The combined filtrates were evaporated to afford Example 265 as a foam (41 mg).

Using the method described above and the appropriate starting material, the following examples were also prepared:

TABLE 19

| example | nitrile | example | structure |
|---|---|---|---|
| 272 | (structure with NC, piperazine, Cl, F, OH) | 266 | (structure with H$_2$NOC, piperazine, Cl, F, OH) |

Scheme 89

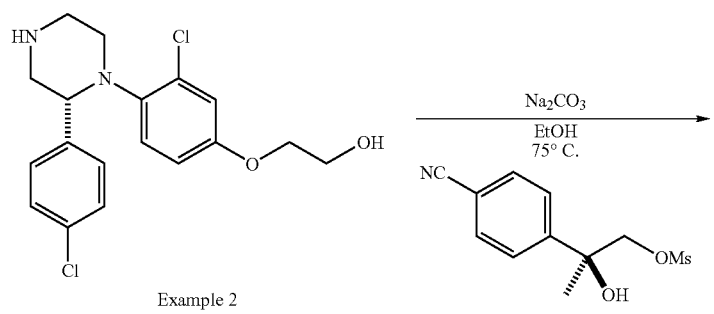

Example 2

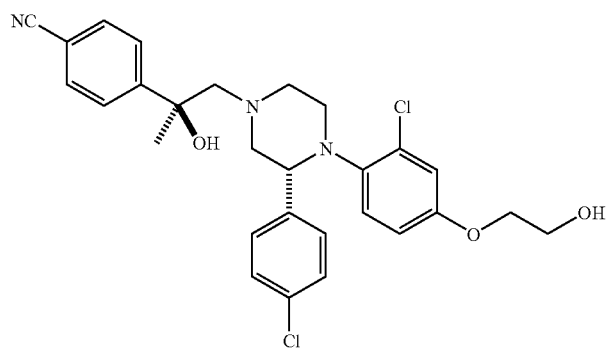

Example 137

The piperazine Ex. 2 (60 mg, 0.16 mmol), mesylate from Scheme 22 (51 mg, 0.2 mmol), and Na$_2$CO$_3$ (52 mg, 0.49 mmol) were taken up in EtOH and heated in a sealed tube (75° C., 12 h). The solution was concentrated. The residue was partitioned between EtOAc and water. The aqueous layer was extracted with EtOAc. The combined organic layers were washed with brine and dried (MgSO$_4$). The solution was filtered and concentrated. The residue was purified via gradient flash chromatography (0-50% EtOAc/hexanes, SiO$_2$) which furnished 61 mg (71%) of Example 137 as a white foam.

The following examples were prepared in a similar fashion using the appropriate piperazine core and mesylate from Scheme 22.

TABLE 20

| Ex. | Piperazine Core | Ex. | Structure |
|---|---|---|---|
| 31 | ![structure] | 267 | ![structure] |

TABLE 20-continued

| Ex. | Piperazine Core | Ex. | Structure |
|---|---|---|---|
| 22 | | 268 | 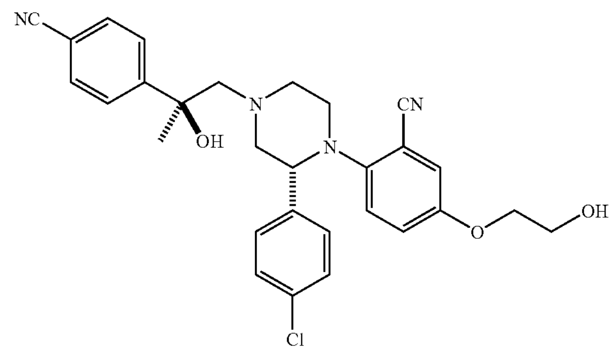 |
| 21 | | 269 | 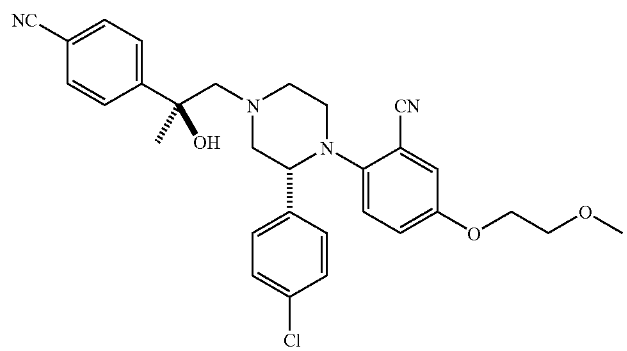 |
| 6 | | 270 | 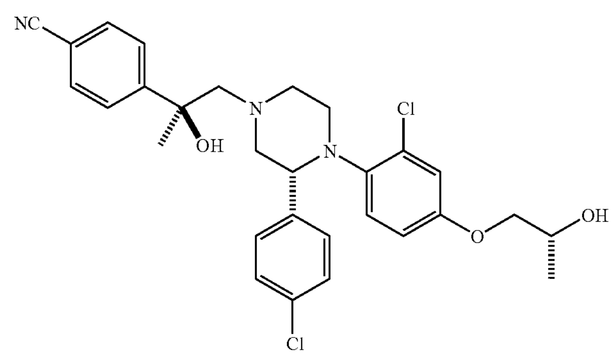 |
| 4 | | 271 | 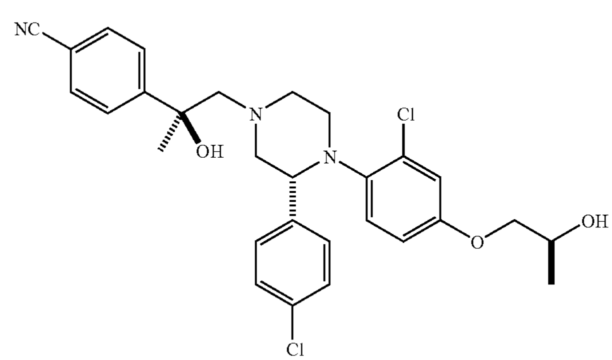 |

TABLE 20-continued

| Ex. | Piperazine Core | Ex. | Structure |
|---|---|---|---|
| 39 | | 272 | 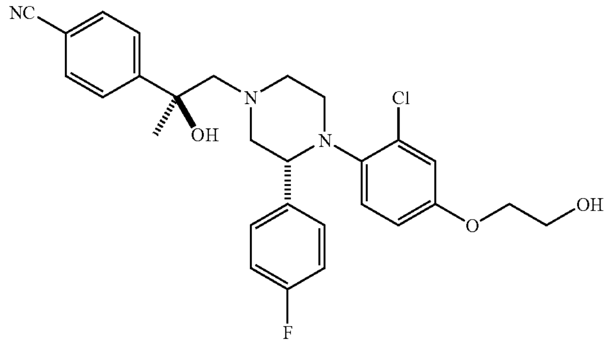 |
| 9 | | 273 | 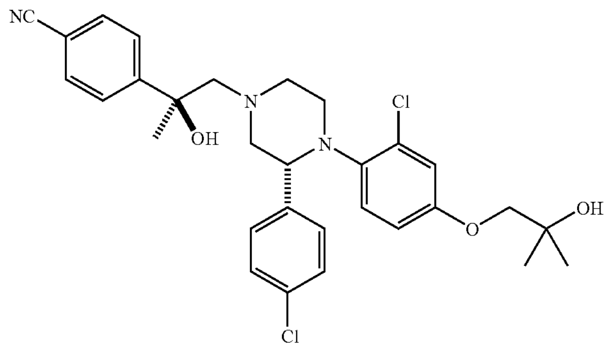 |
| 34 | | 274 | 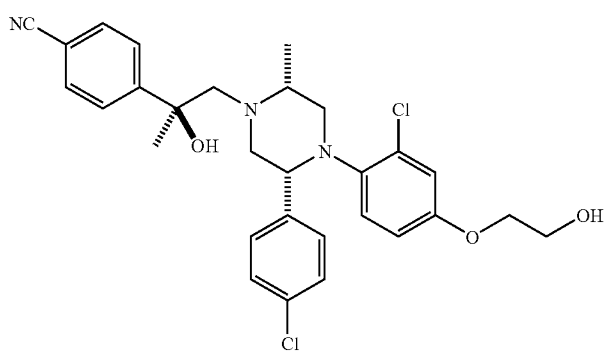 |
| 35 | | 275 | 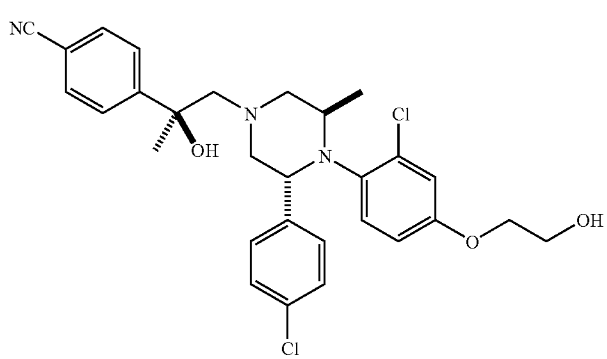 |

TABLE 20-continued

| Ex. | Piperazine Core | Ex. | Structure |
| --- | --- | --- | --- |
| 40 | | 276 | 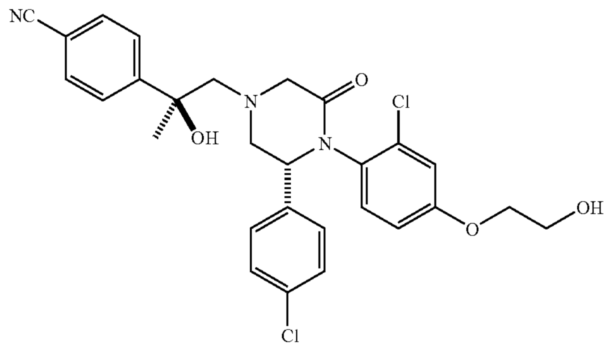 |
| 29 | | 277 | 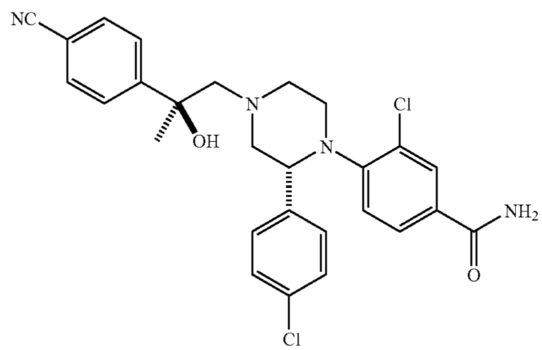 |
| 25a | | 278 | 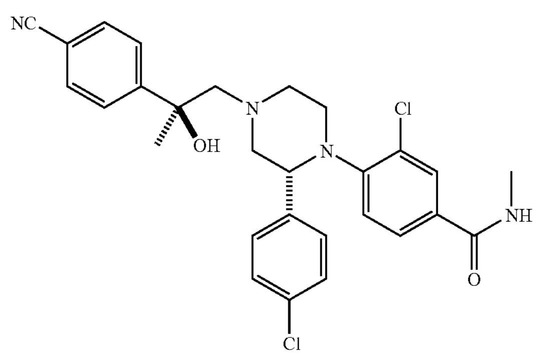 |
| 25b | | 279 | 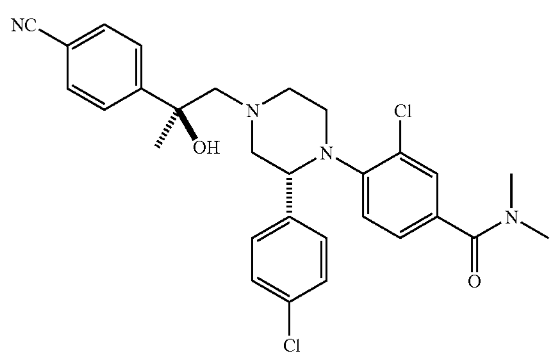 |

TABLE 20-continued

| Ex. | Piperazine Core | Ex. | Structure |
|---|---|---|---|
| 27 | | 280 | 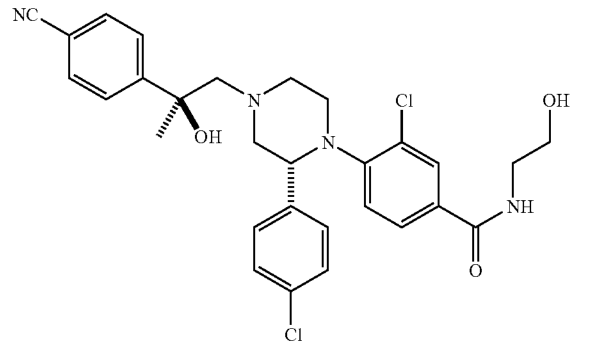 |
| 2c | | 281 | 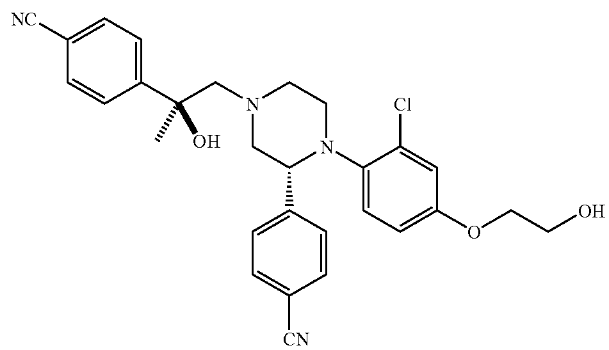 |
| 28 | | 282 | 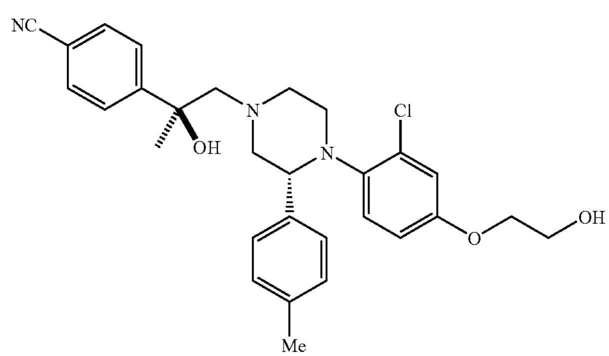 |
| 38 | | 283 | 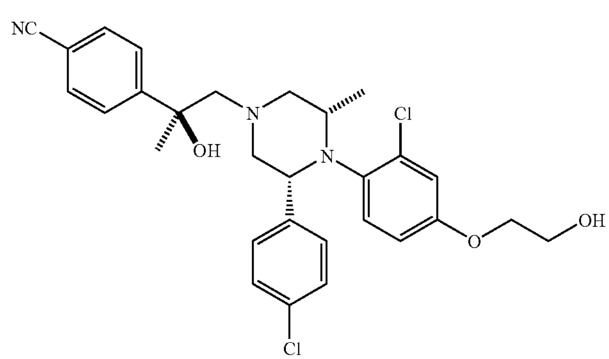 |

TABLE 20-continued

| Ex. | Piperazine Core | Ex. | Structure |
|---|---|---|---|
| 19 | | 284 | 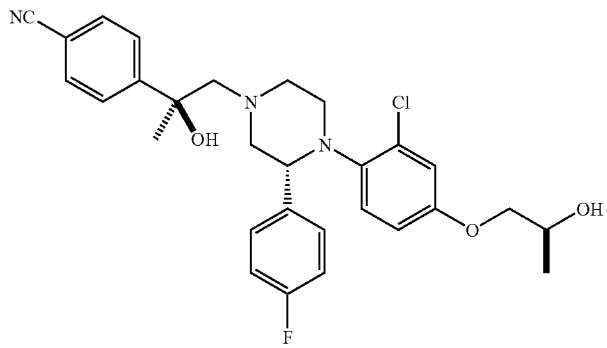 |
| 18 | | 285 | 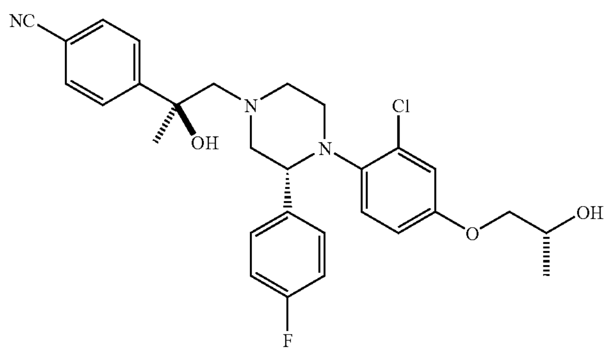 |
| 32 | | 286 | 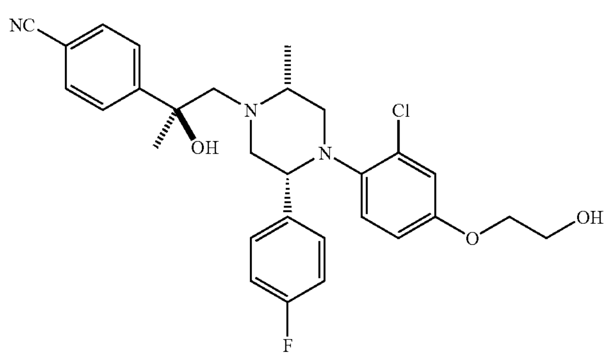 |
| 17 | | 287 | 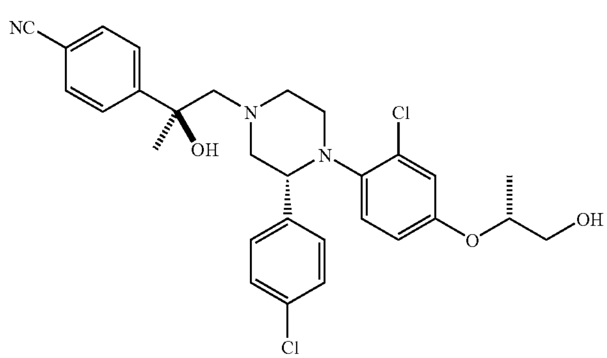 |

TABLE 20-continued

| Ex. | Piperazine Core | Ex. | Structure |
|---|---|---|---|
| 33 | | 288 | 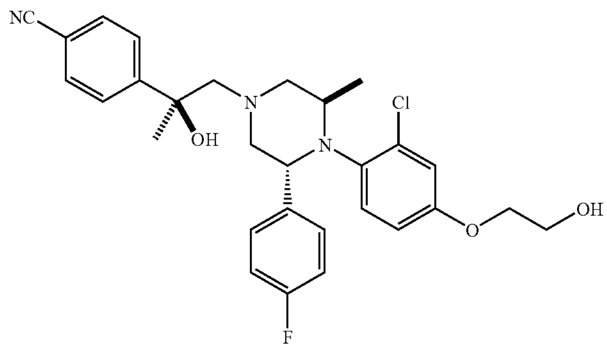 |
| 36 | | 289 | 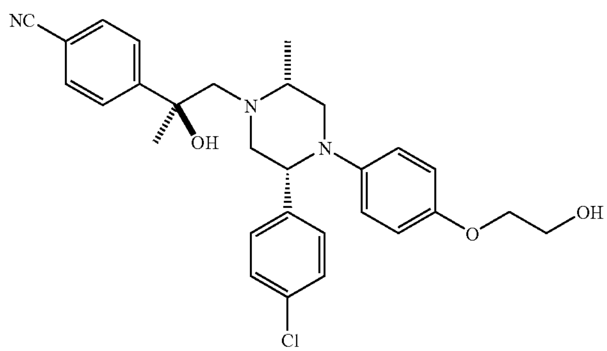 |
| 37 | | 290 | 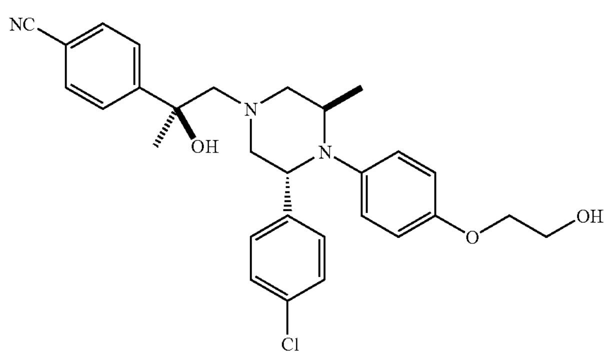 |
| 41 | | 290a | 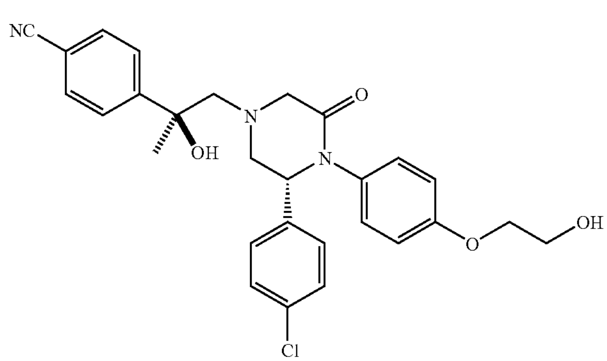 |

TABLE 20-continued

| Ex. | Piperazine Core | Ex. | Structure |
| --- | --- | --- | --- |
| 32c | | 290b | 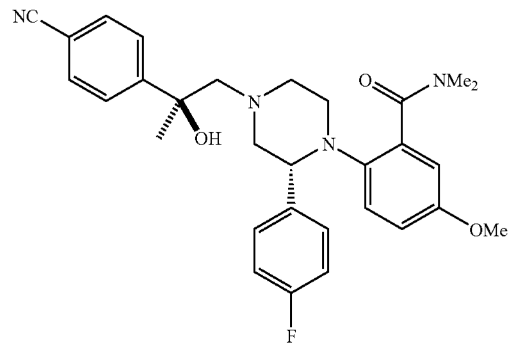 |
| 41c | | 290c | 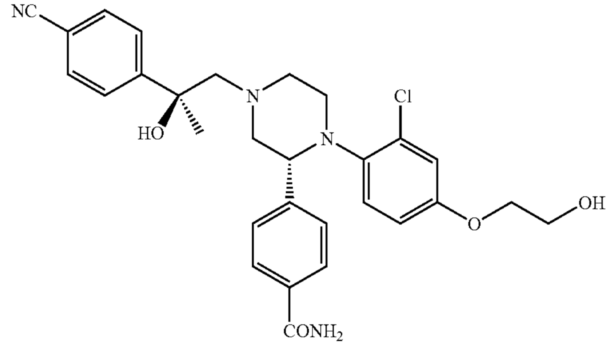 |
| 41h | | 290d | 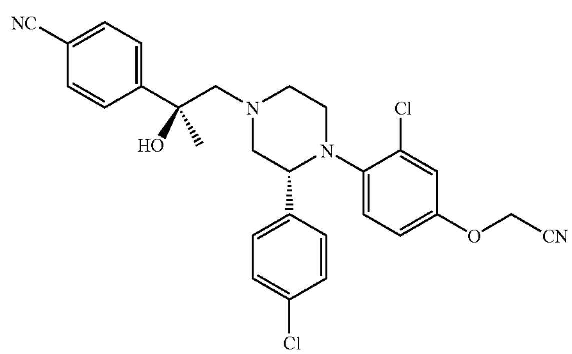 |
| 41g | | 290e | 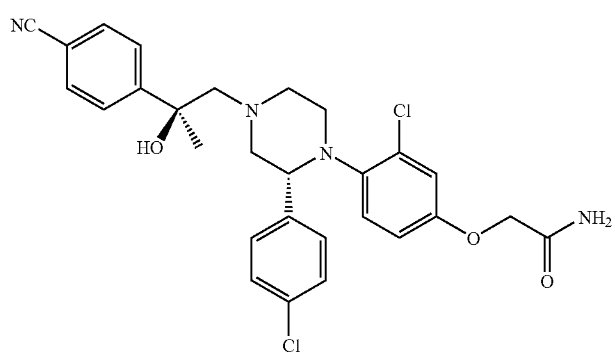 |

Scheme 90

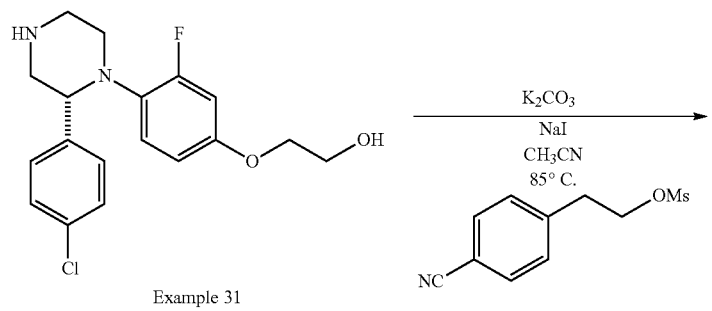

Example 31

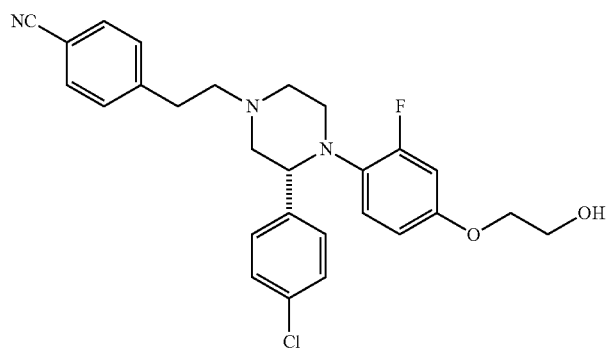

Example 291

The piperazine (Example 31; 50 mg, 0.14 mmol), mesylate from Scheme 23 (50 mg), $K_2CO_3$ (60 mg), and NaI (10 mg) were taken up in $CH_3CN$ and heated at 85° C. in a sealed tube for 18 h. More mesylate (50 mg) was added, and the solution was stirred for an additional 18 h at 85° C. The solution was diluted with EtOAc and filtered through Celite. The solution was concentrated The residue was purified via thin-layer preparative chromatography (EtOAc, $SiO_2$) which furnished 31 mg (45%) of Example 291 as a colorless oil.

The following examples were prepared in a similar fashion using the appropriate piperazine core and mesylate as Scheme 90.

TABLE 21

| Ex. | Piperazine Core | Ex. | Structure |
|---|---|---|---|
| 28 | | 292 | 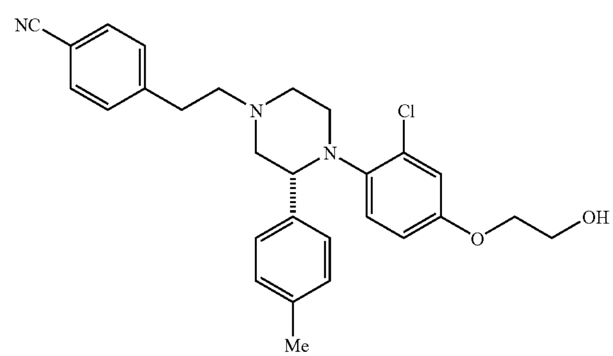 |

TABLE 21-continued

| Ex. | Piperazine Core | Ex. | Structure |
|---|---|---|---|
| 22 | | 293 | 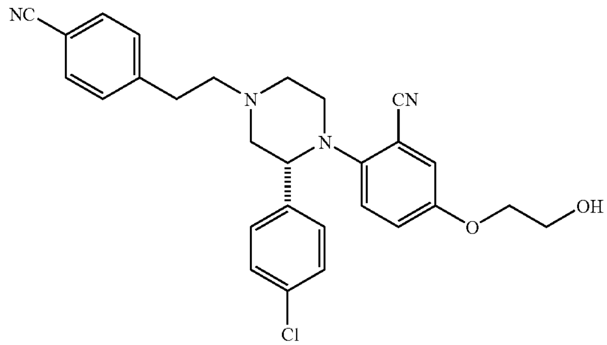 |
| 2 | | 294 | 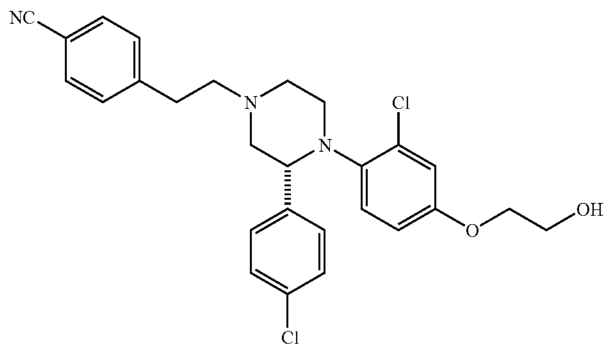 |
| 39 | | 295 | 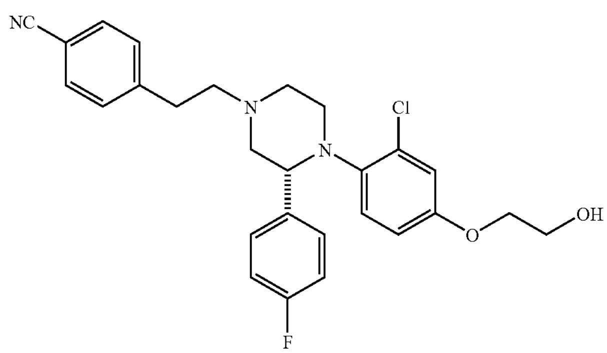 |
| 9 | | 296 | 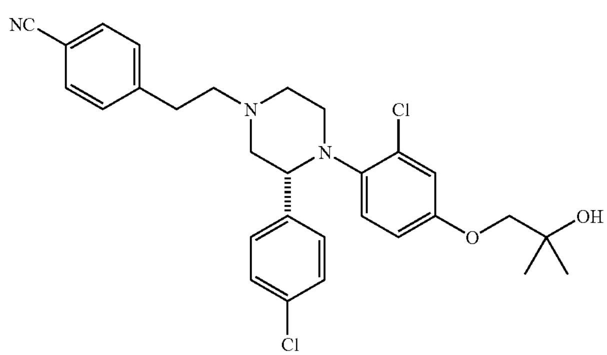 |

TABLE 21-continued

| Ex. | Piperazine Core | Ex. | Structure |
|---|---|---|---|
| 4 | | 297 | 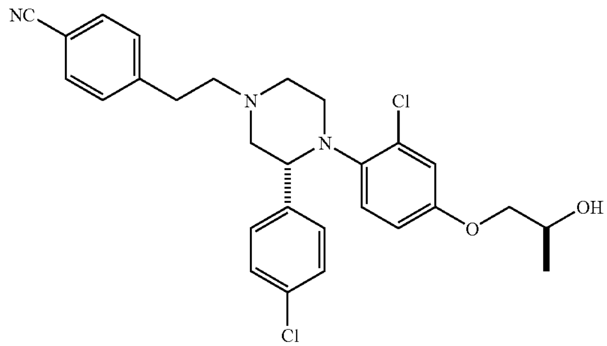 |
| 6 | | 298 | 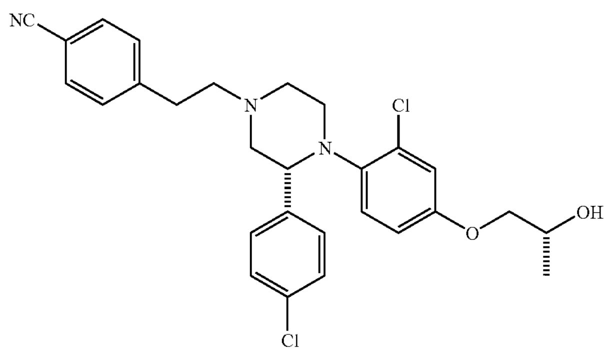 |
| 34 | | 299 | 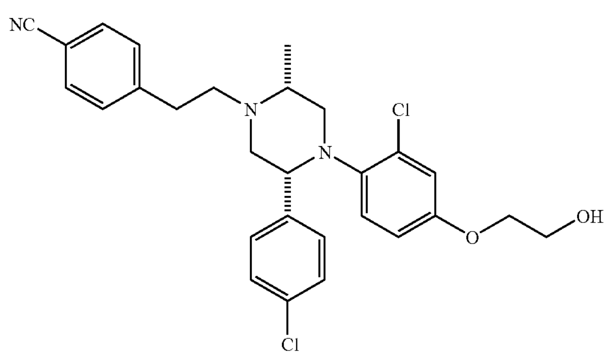 |
| 38 | | 300 | 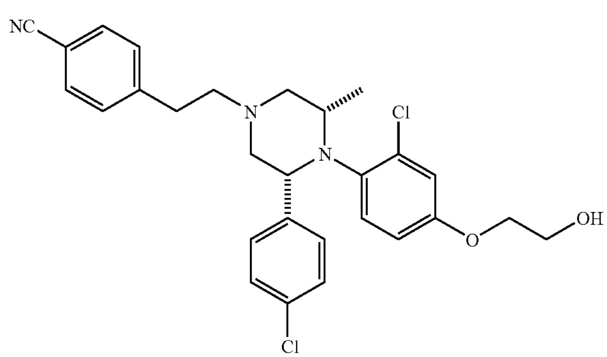 |

TABLE 21-continued

| Ex. | Piperazine Core | Ex. | Structure |
|---|---|---|---|
| 29 | | 301 | 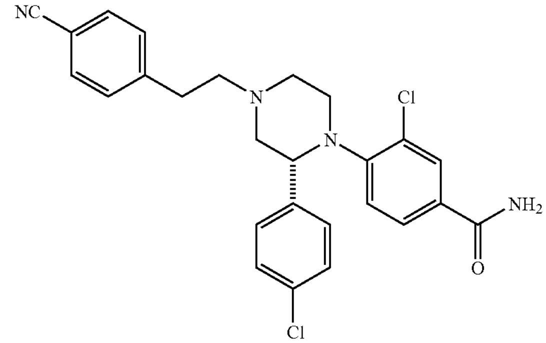 |

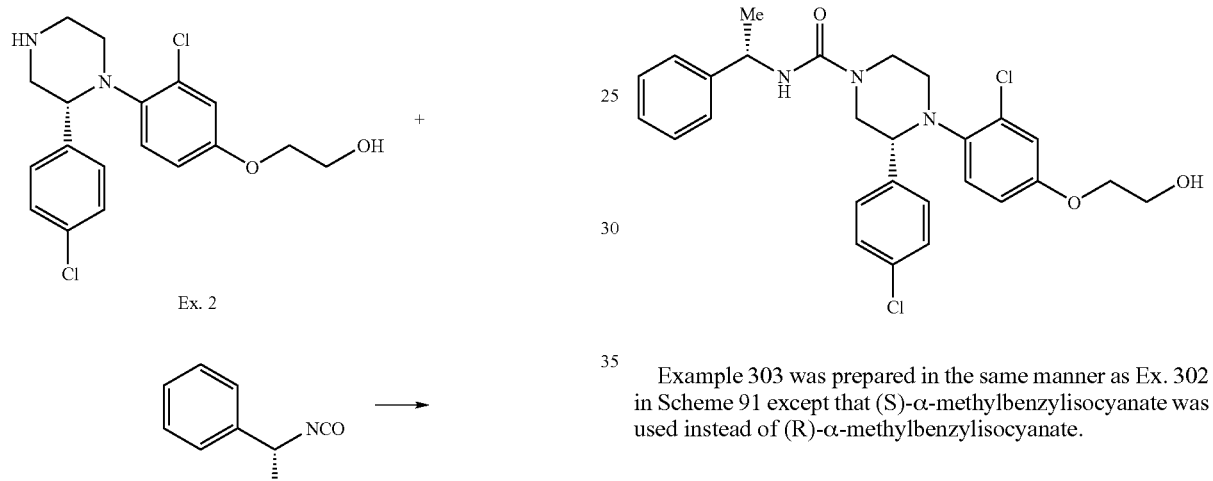

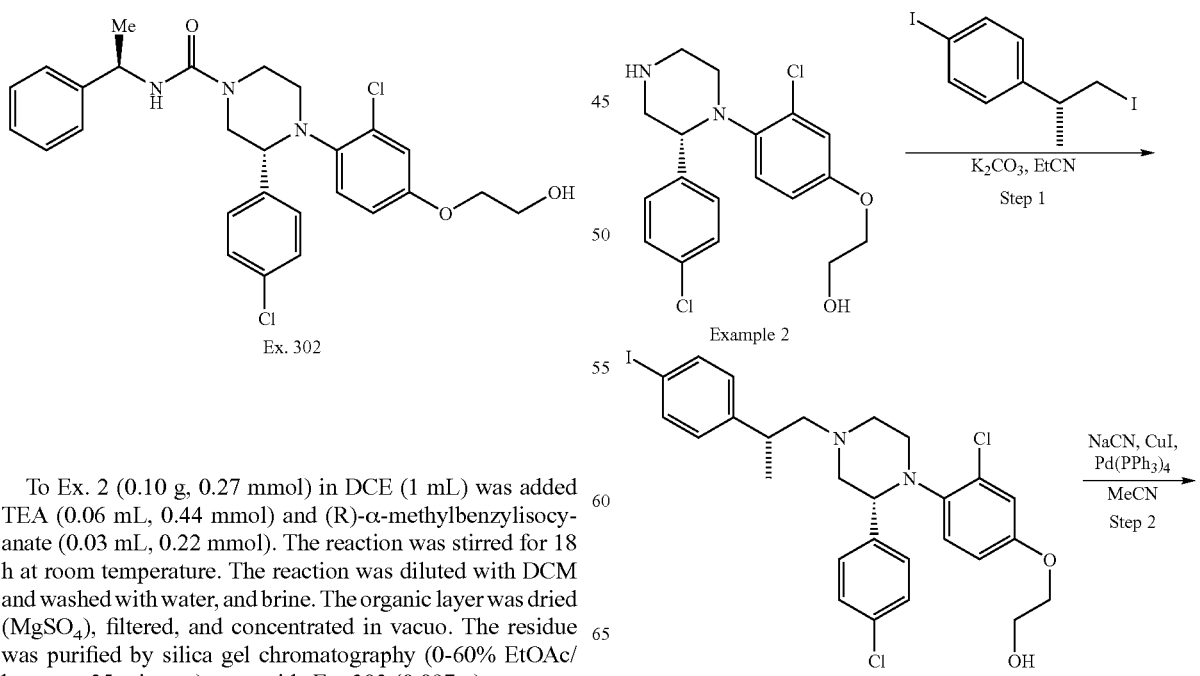

Example 303 was prepared in the same manner as Ex. 302 in Scheme 91 except that (S)-α-methylbenzylisocyanate was used instead of (R)-α-methylbenzylisocyanate.

To Ex. 2 (0.10 g, 0.27 mmol) in DCE (1 mL) was added TEA (0.06 mL, 0.44 mmol) and (R)-α-methylbenzylisocyanate (0.03 mL, 0.22 mmol). The reaction was stirred for 18 h at room temperature. The reaction was diluted with DCM and washed with water, and brine. The organic layer was dried (MgSO$_4$), filtered, and concentrated in vacuo. The residue was purified by silica gel chromatography (0-60% EtOAc/hex over 25 minutes) to provide Ex. 302 (0.097 g).

-continued

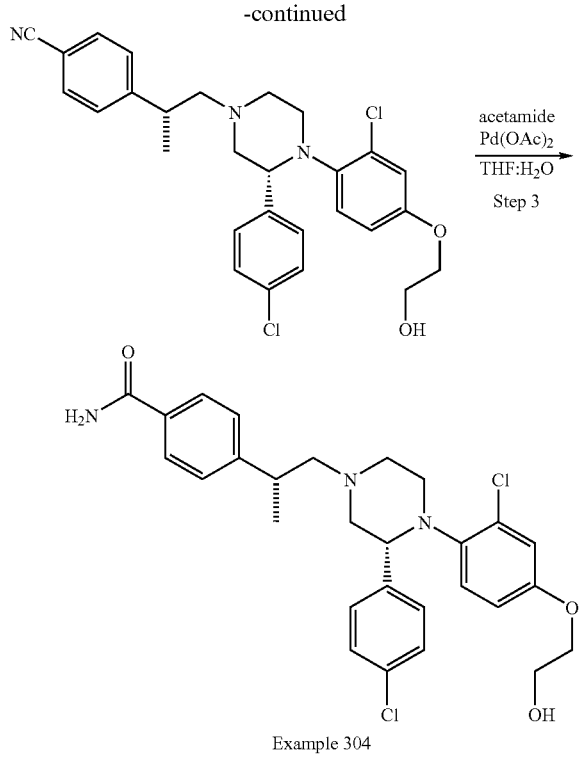

Example 304

Step 1:

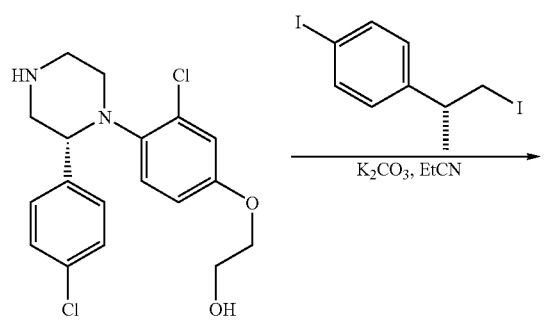

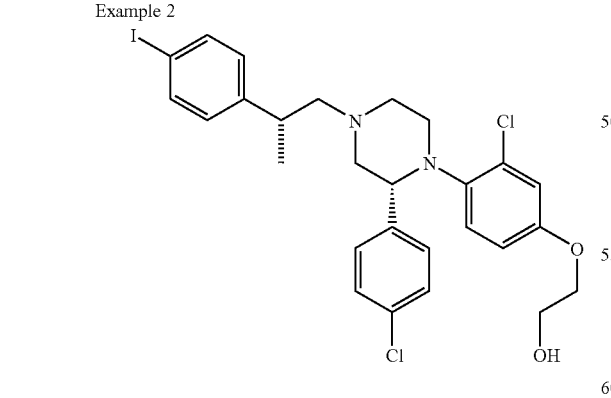

Example 2 (522 mg, 1.42 mmol, 1 eq), the diiodide prepared in Scheme 22A, Step 3 (580 mg, 1.56 mmol, 1.1 eq), and K₂CO₃ (589 mg, 4.26 mmol, 3 eq) were taken up in propionitrile (5 mL) and heated in a sealed tube (120° C., 72 h then 150° C., 24 h). The solution was partitioned between EtOAc and saturated NaHCO₃. The organic layer was removed, and the aqueous layer was extracted with EtOAc. The combined organic layers were evaporated, and the resulting residue was purified via silica gel column chromatography (0% to 100% EtOAc in hexanes) to afford the coupled product as a clear film (233 mg).

Step 2:

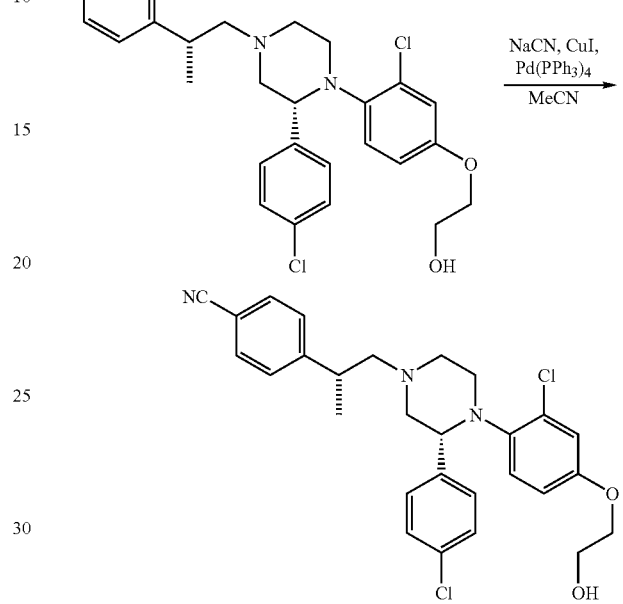

The coupled product from Step 1 (233 mg, 0.38 mmol, 1 eq), CuI (7 mg, 0.038 mmol, 0.1 eq) and NaCN (24 mg, 0.49 mmol, 1.3 eq) were combined in MeCN (5 mL), purged with nitrogen and heated to reflux under nitrogen for 1 h. The reaction was then cooled and Pd(PPh₃)₄ (44 mg, 0.38 mmol, 0.1 eq) was added. After refluxing under nitrogen for an additional 1 h, the reaction was cooled and partitioned between EtOAc and 1 N NaOH. The aqueous layer was discarded as cyanide waste, and the EtOAc layer was washed with brine, dried over anhydrous Na₂SO₄, filtered, and evaporated to afford a crude residue which was subjected to silica gel chromatography (gradient elution, 0% to 100% EtOAc in hexanes) to afford the aryl cyanide (110 mg).

Step 3:

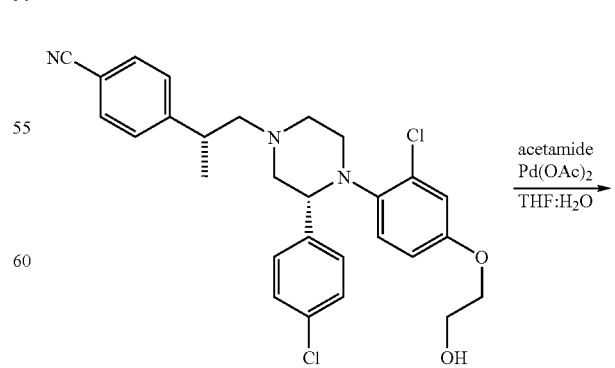

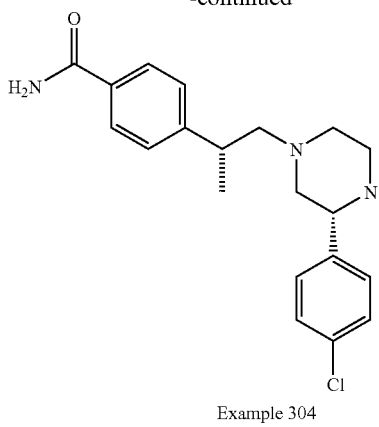

Example 304

A solution of the aryl cyanide (110 mg, 0.22 mmol, 1 eq), palladium acetate (10 mg, 0.043 mmol, 0.2 eq), and acetamide (60 mg) in a THF:water mixture (3:1, 5 mL) was heated 16 h in a 65° C. oil bath. A second portion of palladium acetate (34 mg) was added and the reaction heated 3 h at 85° C. A third portion of palladium acetate (10 mg) was added and the reaction was heated for an additional 1 h at 85° C. The reaction was cooled to room temperature and partitioned between EtOAc and saturated aqueous NaHCO$_3$. The resulting emulsion was filtered through a 0.2 micron syringe filter disc. The aqueous layer was removed and extracted with EtOAc. The combined organic layers were evaporated to afford a crude residue which was subjected to silica gel chromatography (gradient elution, 0% to 3% MeOH in EtOAc) to afford Example 304 (40 mg).

Scheme 93

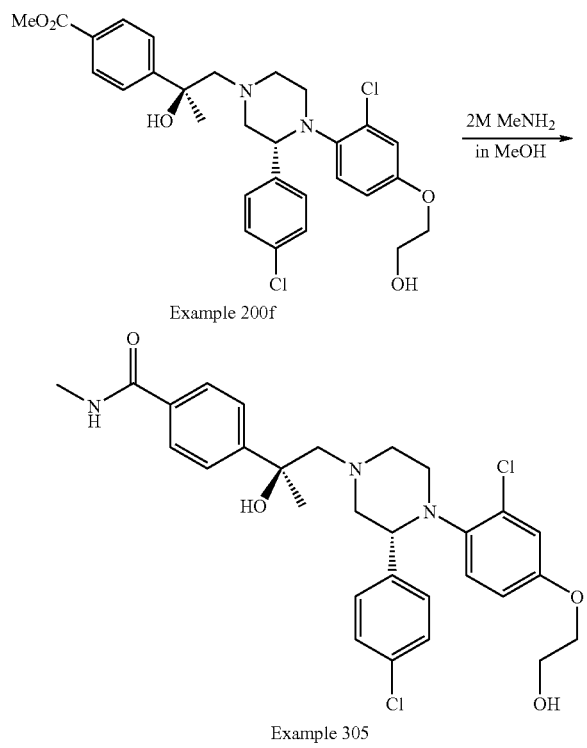

Example 200f (100 mg, 0.18 mmol) was dissolved in 2 M methylamine in methanol (8 mL), transferred to a sealed reaction vessel, sealed and heated 16 h at 100° C. The volatiles were removed in vacuo and the resulting residue was subjected to column chromatography (SiO$_2$, gradient elution 0% to 20% MeOH in EtOAc) to afford Example 305.

Scheme 94

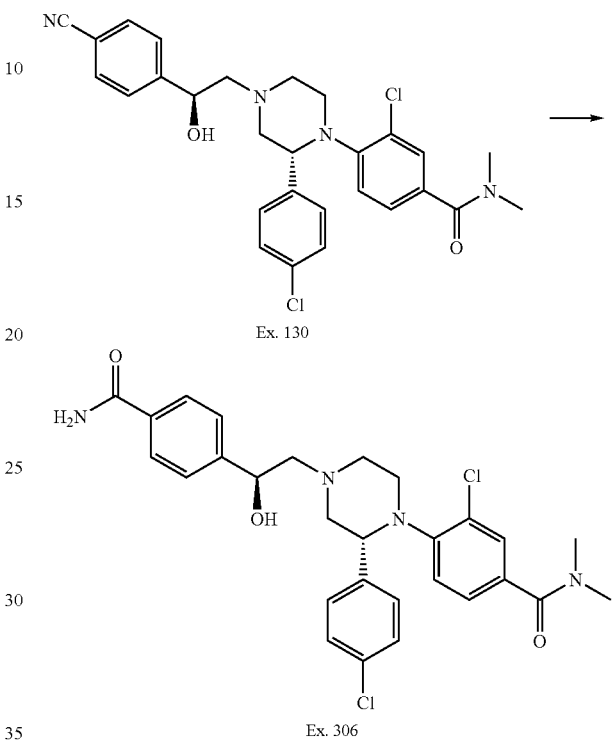

Ex. 130 was converted to Ex. 306 using a procedure similar to that described in Scheme 88.

Scheme 95

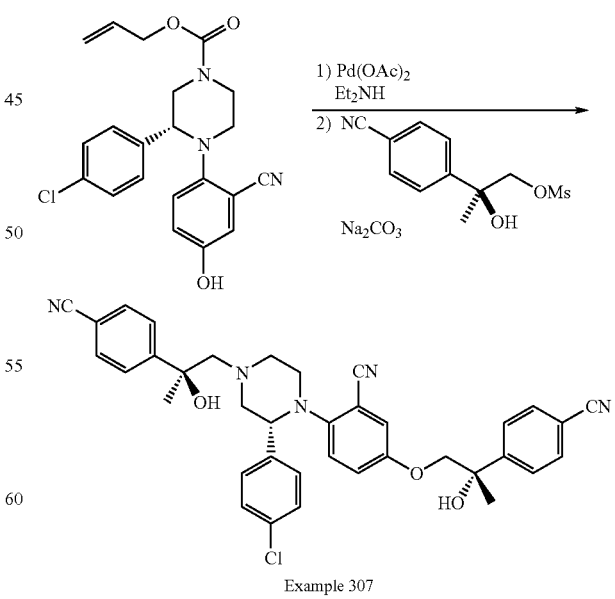

Example 307

To a solution of the phenol from Scheme 33 step 3 (500 mg, 0.57 mmol) in a 1:1 mixture of MeCN/H$_2$O was added was added diethylamine (800 mg, 11.4 mmol), Pd(OAc)$_2$ (1.4 mg, 0.0057 mmol) and trisodium triphenylphosphine 3,3',3"-trisulfonate (Aldrich) (6.5 mg, 0.011 mmol). The resultant mixture was stirred at RT for 3 h. After that time, the mixture was concentrated and the crude product was purified via flash chromatography [SiO$_2$: gradient elution, 100:0:0 to 95:5:0.5 CH$_2$Cl$_2$:MeOH: conc NH$_4$OH (aq.)] to afford the amino phenol (60 mg).

In a pressure tube, a solution of a portion of the amino phenol (ca 30 mg) in EtOH (5 mL) was added the mesylate from Scheme 22 (30 mg) and Na$_2$CO$_3$ (100 mg). The pressure tube was sealed and the mixture was heated to 100° C. with stirring. After 16 h, the mixture was cooled to RT and concentrated. The residue was purified via preparative TLC (SiO$_2$: 60:40 hexanes:EtOAc) to afford Example 307 (35 mg).

The imidazole-acid (2 g, 12.3 mmol) was taken up in 4 M HCl in dioxane (10 mL) and EtOH (120 mL) and heated at 90° C. for 18 h. The solution was concentrated. The residue was partitioned between EtOAc and sat. NaHCO$_3$ (aq.). The aqueous layer was extracted with EtOAc. The combined organic layers were washed with brine and dried (MgSO$_4$). The solution was filtered which provided 1.2 g (63%) of the imidazole-ester as a white solid.

Scheme 97

Scheme 96

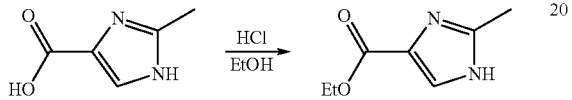

In the same manner as described in Scheme 96, the imidazole (3.78 g, 33.8 mmol) was used to prepare 2.47 g (52%) of the ester as a white solid, Scheme 98

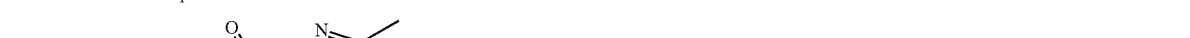

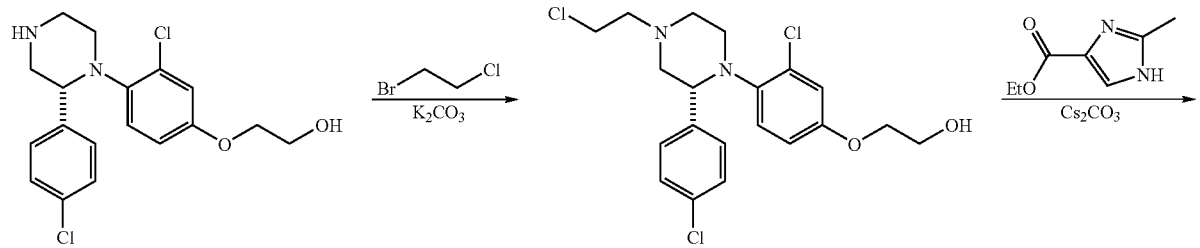

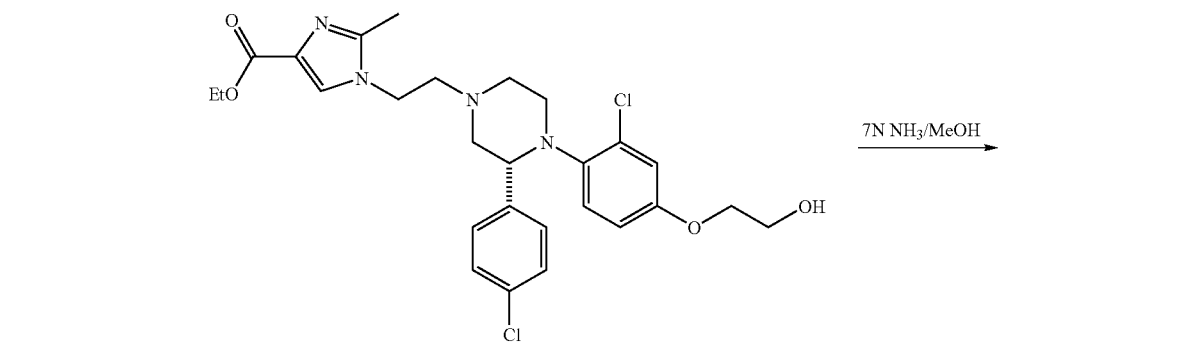

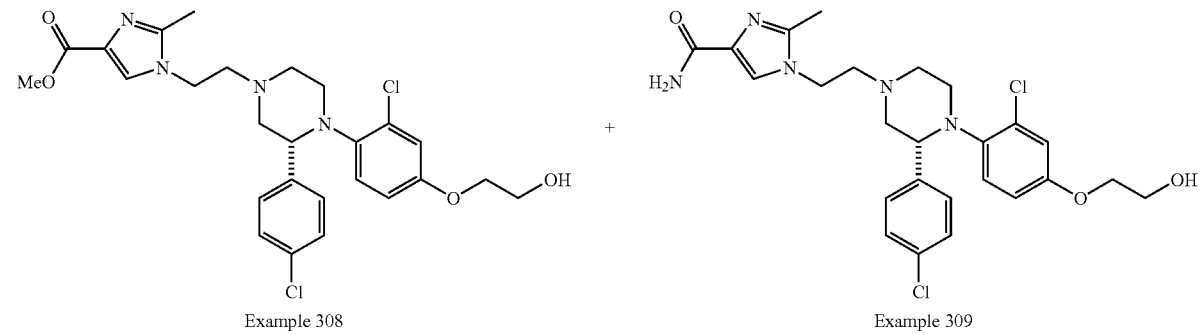

Step 1

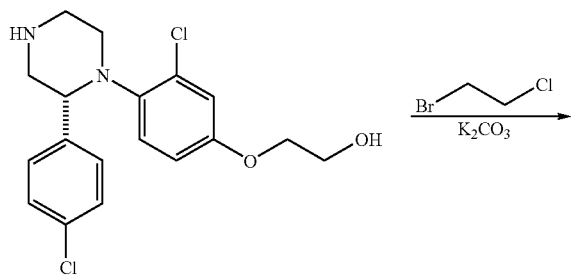

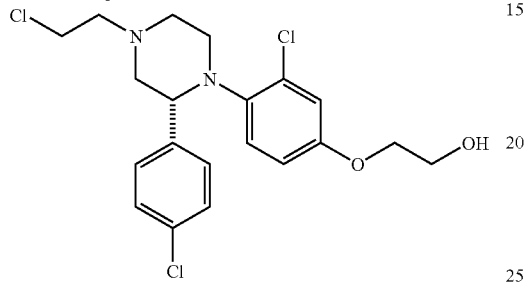

The piperazine Example 2 (500 mg, 1.36 mmol), BrCH$_2$CH$_2$Cl (0.7 mL), and K$_2$CO$_3$ (320 mg, 2.3 mmol) were taken up in CH$_3$CN (2 mL) and stirred at 25° C. for 18 h. The solution was partitioned between EtOAc and water. The aqueous layer was extracted with EtOAc. The combined organic layers were washed with brine and dried (MgSO$_4$), Filtration and concentration gave a yellow oil. The residue was purified via gradient flash chromatography (0-15% EtOAc in CH$_2$Cl$_2$, SiO$_2$) which gave 357 mg (61%) of the chloro-ethyl piperazine as a yellow oil.

Step 2

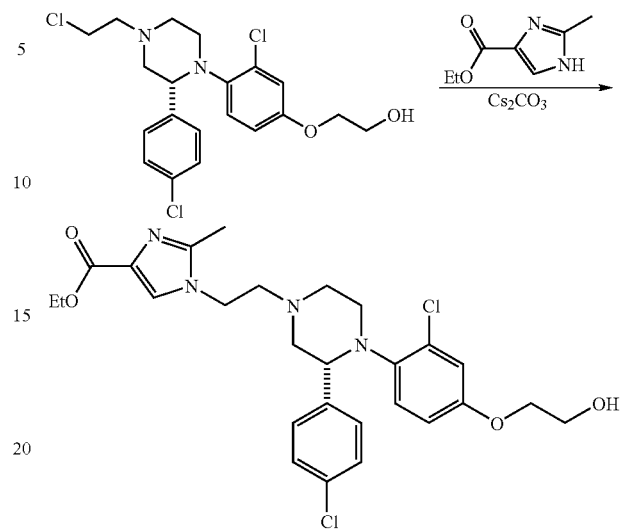

The chloro-ethyl piperazine (179 mg, 0.42 mmol), Cs$_2$CO$_3$ (272 mg, 0.83 mmol), and the imidazole from Scheme 96 (128 mg, 0.83 mmol) were taken up in CH$_3$CN (3 mL) and heated at 90° C. in a sealed tube for 18 h. The solution was partitioned between EtOAc and water. The aqueous layer was extracted with with EtOAc. The combined organic layers were washed with brine and dried (MgSO$_4$). Filtration and concentration gave a yellow oil. The residue was purified via thin-layer preparative chromatography (1/01 CH$_2$Cl$_2$/MeOH, SiO$_2$) which gave 102 mg (44%) of the imidazole as a yellow oil.

Step 3

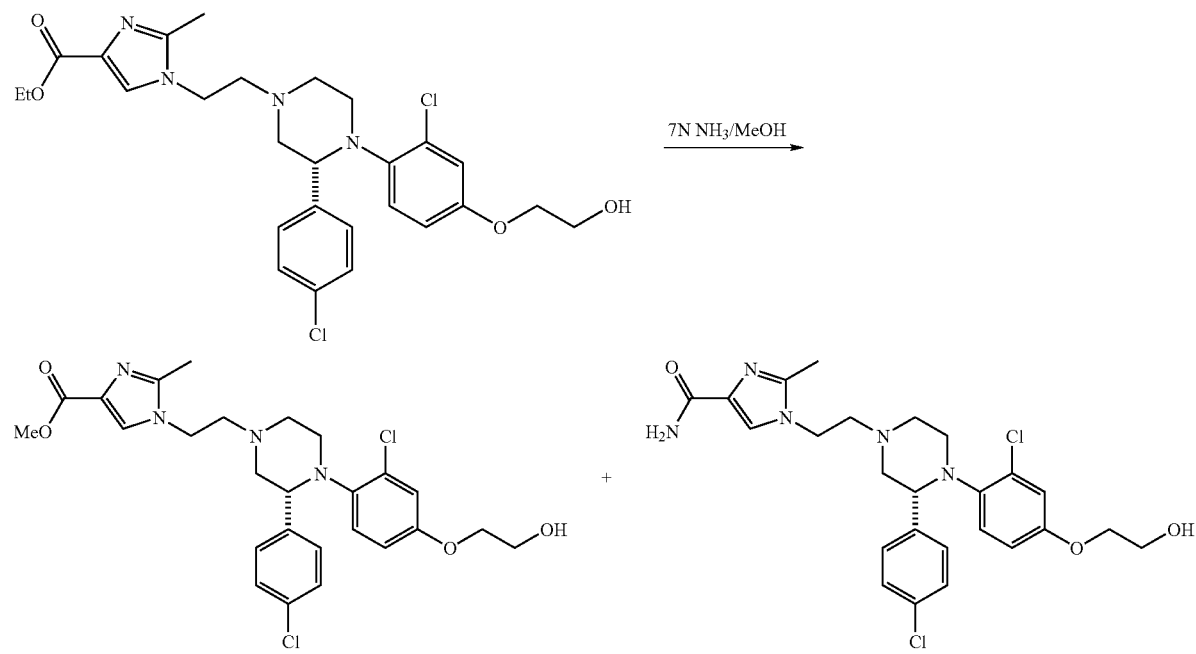

The imidazole (100 mg, 0.18 mmol) was taken up in 7 N NH₃ in MeOH. The solution was heated in a sealed tube at 90° C. for 18 h. The solution was concentrated, and fresh 7 N NH₃ in MeOH was added. The solution was heated again for 18 h. This cycle was repeated twice more. The solution was concentrated. The residue was purified via thin-layer preparative chromatography (10/1 CH₂Cl₂/MeOH, SiO₂) which gave 16 mg (17%) of Example 308 as a colorless oil and 18 mg (19%) of Example 309 as a colorless solid.

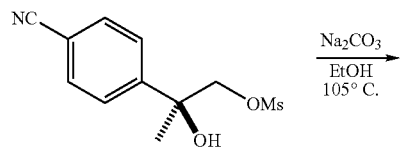

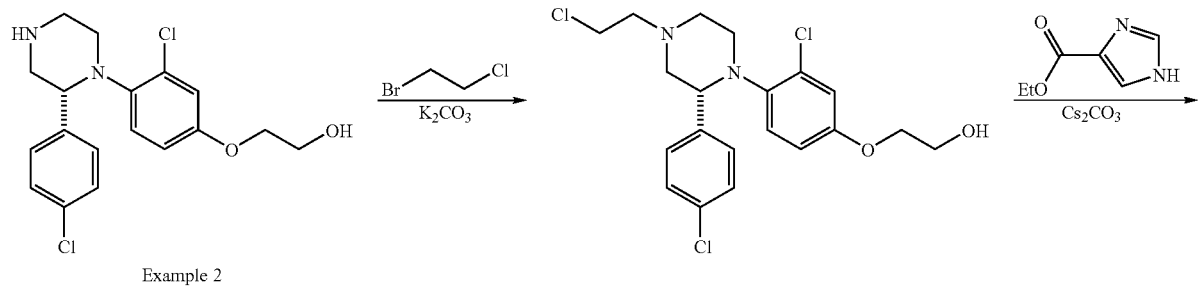

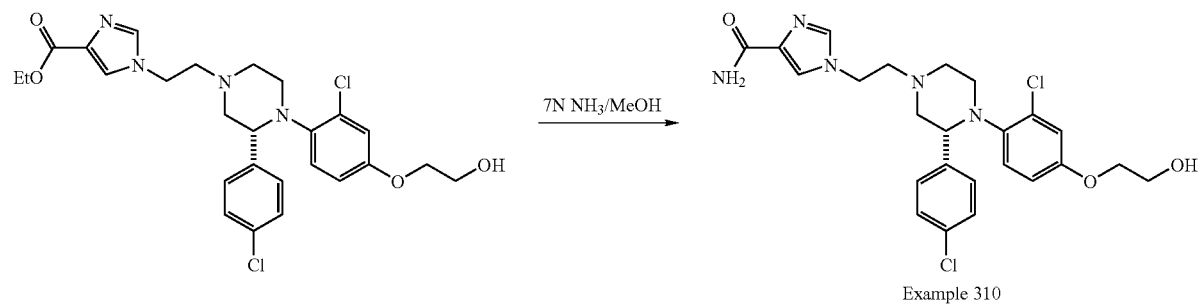

Example 310 was prepared according to the procedures illustrated in Scheme 98 using the appropriate imidazole from Scheme 97 in Step 2 (Scheme 99).

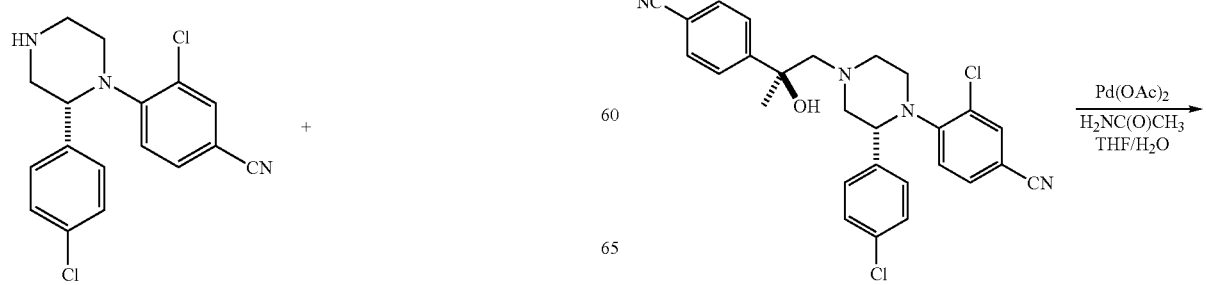

-continued

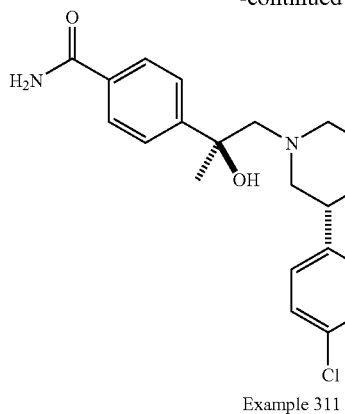

Example 311

Step 1

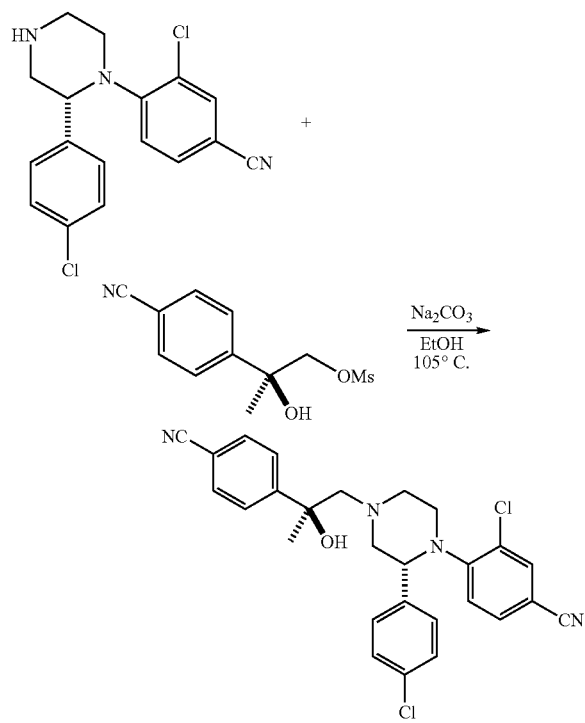

The piperazine (200 mg, 0.6 mmol), mesylate (169 mg, 0.66 mmol), and Na₂CO₃ (191 mg, 1.8 mmol) were taken up in EtOH (3.5 mL) and heated at 105° C. in a sealed tube for 17 h. The mixture was filtered through Celite. The residue was purified via thin-layer preparative chromatography (3/1 hexanes/EtOAc, SiO2) which gave 181 mg (61%) of the piperazine-alcohol as a colorless oil.

Step 2

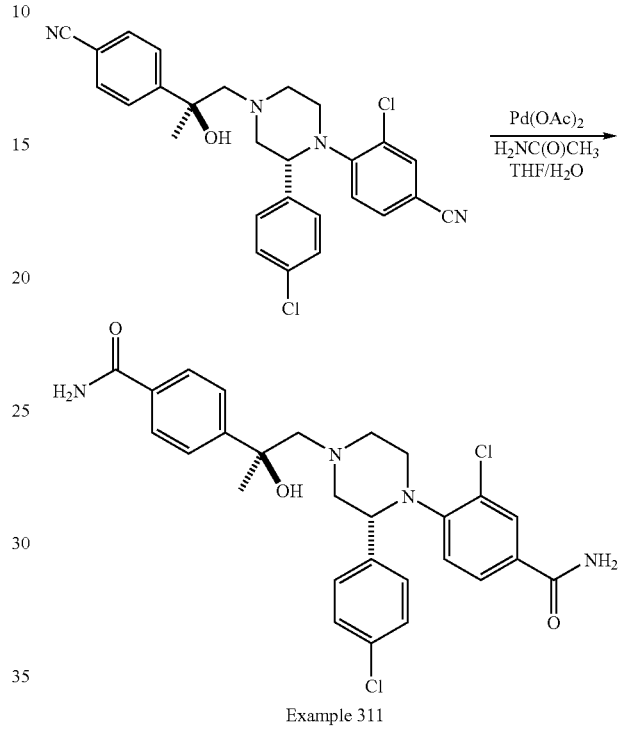

Example 311

The piperazine-alcohol (181 mg, 0.37 mmol), acetamide (200 mg), and Pd(OAc)₂ (20 mg) were taken up in THF/H₂O (3/1, 15 mL) and heated at 70° C. for 17 h. The solution was concentrated. The residue was partitioned between EtOAc and sat. NaHCO₃(aq.). The aqueous layer was extracted with EtOAc. The combined organic layers were washed with brine and dried (MgSO4). Filtration and concentration gave a brown oil. The residue was purified via thin-layer preparative chromatography (EtOAc, SiO₂) which gave 44 mg (23%) of Example 311 as a white solid.

Scheme 101

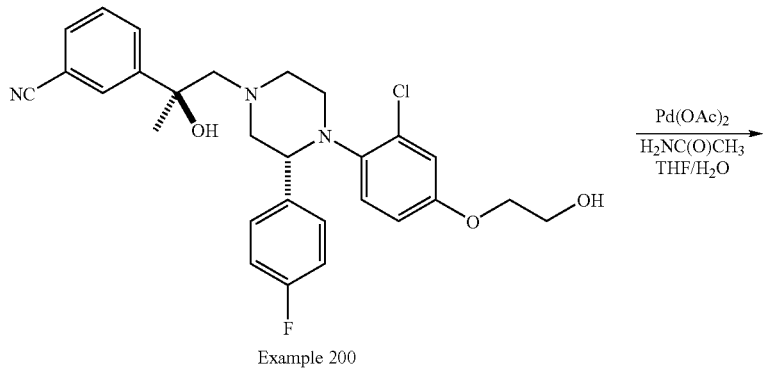

Example 200

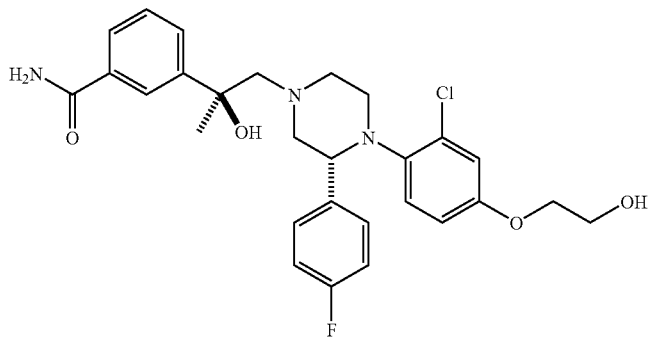

Example 312

Example 200 (200 mg, 0.39 mmol), acetamide (200 mg) and Pd(OAc)$_2$ (20 mg) were taken up in dioxane/H$_2$O (3/1, 15 mL) and heated at 75° C. for 17 h. The solution was concentrated, and the residue was partitioned between EtOAc and water. The aqueous layer was extracted with EtOAc. The combined organic layers were washed with brine and dried (MgSO$_4$). Filtration and concentration gave a brown oil. The residue was purified via thin-layer preparative chromatography (20% 7 N NH$_3$ in MeOH/CH$_2$Cl$_2$, SiO$_2$) gave 35 mg (16%) of Example 312 as colorless oil.

The following examples were prepared in a similar fashion using the appropriate starting material as illustrated in Scheme 101.

TABLE 22

| Starting Material Example | Example | Structure |
|---|---|---|
| 290 | 313 | 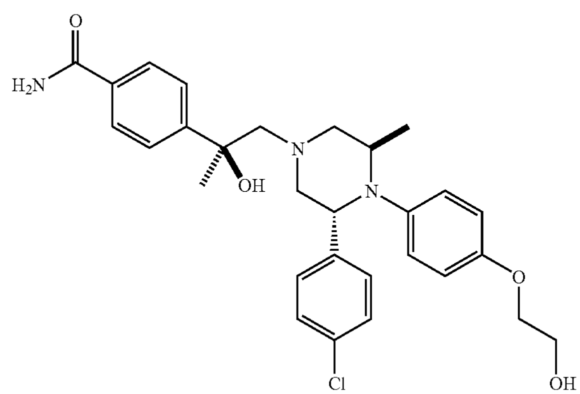 [SMILES: C[C@@H]1CN(C[C@@](C)(O)c2ccc(C(N)=O)cc2)C[C@@H](c2ccc(Cl)cc2)N1c1ccc(OCCO)cc1] |
| 200m | 314 | 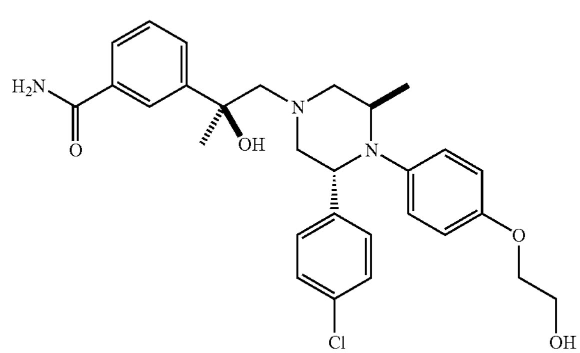 [SMILES: C[C@@H]1CN(C[C@@](C)(O)c2cccc(C(N)=O)c2)C[C@@H](c2ccc(Cl)cc2)N1c1ccc(OCCO)cc1] |

TABLE 22-continued

| Starting Material Example | Example | Structure |
|---|---|---|
| 58 | 315 | 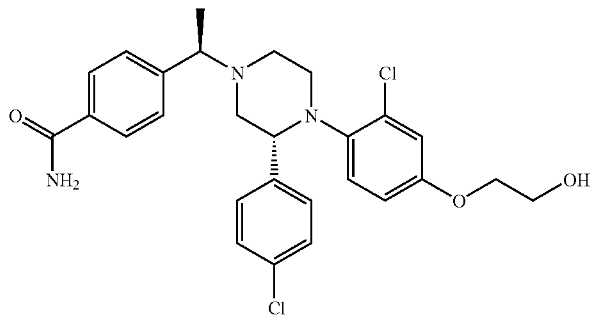 [SMILES: C[C@H](c1ccc(C(N)=O)cc1)N1CCN(c2ccc(OCCO)cc2Cl)[C@H](c2ccc(Cl)cc2)C1] |
| 200ad | 316 | 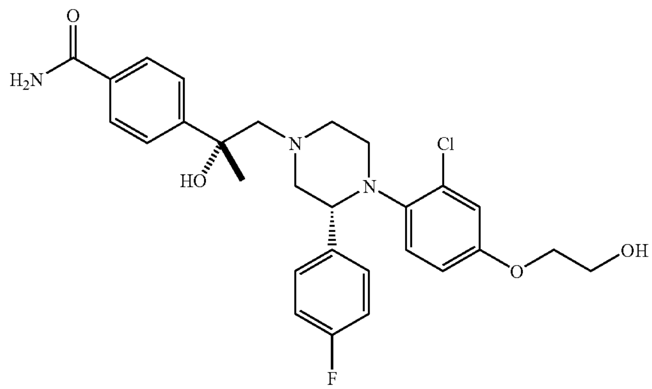 |
| 200ae | 317 | 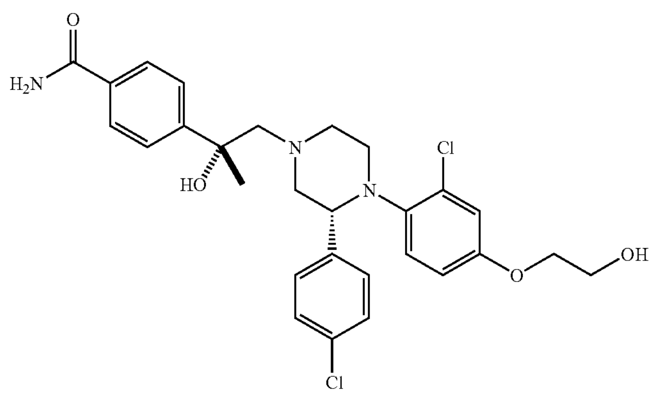 [SMILES: C[C@](O)(CN1CCN(c2ccc(OCCO)cc2Cl)[C@H](c2ccc(Cl)cc2)C1)c1ccc(C(N)=O)cc1] |

Method for Evaluating Cannabinoid $CB_1$ and $CB_2$ Affinity

Competition binding assays for cannabinoid $CB_1$ and $CB_2$ affinity were performed by incubating commercially purchased membranes prepared from cells expressing each receptor subtype (8 μg pro) with 0.5 nM $^3$H-CP55,940, a non-selective cannabinoid agonist, along with concentrations of drug ranging from 0.0001-3 μM in Buffer A (5 mM $MgCl_2$, 2.5 mM EDTA and 013% BSA). Non-specific binding was defined in the presence of 10 μM CP55,940. For saturation studies, concentrations of $^3$H-CP55,940 ranging from 0.1-5 nM were incubated with membranes in the presence and absence of 10 μM CP55,940. Assays were terminated after incubation for 1 ½ hours by rapid filtration onto 0.3% polyethylenamine treated GF/C filterplates using a BRANDEL cell harvester. The plates were dried and MICROSCINT scintillation cocktail was added, after which the bound radioactivity was quantified using a TOPCOUNT scintillation counter.

The dissociation constant ($K_d$) of $^3$H-CP55,940 at the $CB_1$ and $CB_2$ receptor were determined by plotting specific binding at each concentration of radioligand, and analysis by non-linear regression. For competition studies, the concentration of each drug that inhibited 50 percent of $^3$H-CP55,940 binding ($IC_{50}$) was determined by non-linear regression analysis of the radioligand displacement curves. Affinity constants ($K_i$) were calculated using the equation derived by Cheng and Prusoff (1973), defined as: $IC_{50}/1+$[conc. ligand/$K_d$].

GTPγS Binding Protocol

The functional efficacy of compounds to activate second messengers within the cell was determined utilizing the GTPγS binding assay. Guanine nucleotides are phosphorylated within the plasma membrane of the cell following binding and activation by agonists. A radiolabelled derivative of guanine triphosphate (GTP) is utilized in this assay as it cannot be dephosphorylated and therefore accumulates following agonist binding. The simultaneous presence of an antagonist into this system will shift the agonist concentration curve to the right, with increasing concentrations of antagonist producing a greater rightward shift in the dose-response curve of the agonist.

Commercially purchased membranes were incubated with 10 mM GDP to allow sufficient substrate for phosphorylation in the presence of agonist. The membranes were then pre-incubated with increasing concentrations of test compound for 30 minutes to determine if they were capable of stimulating phosphorylation alone. Increasing concentrations of the non-selective cannabinoid agonist WIN55,122 were then added in the presence or absence of each concentration of test compound. The assay was then incubated for 1 hour at room temperature. To complete the assay, $^{35}$S-GTPγS was added and the assay incubated for another 30 minutes. Assays were terminated by rapid filtration onto 10 mM sodium phosphate-treated GF/C filterplates using a Brandel cell harvester. The plates were dried and Microscint scintillation cocktail was added, after which the bound radioactivity was quantified using a Topcount scintillation counter.

The stimulation of $^{35}$S-GTPγS binding as a function of the concentration of the agonist WIN55,122, in the absence and presence of test compound, was plotted and the $EC_{50}$ determined by nonlinear regression analysis using GraphPad Prism software. A Schild analysis of the rightward shift in the dose response curve of WIN55,122 in the presence of test compound was determined by plotting the concentration of test compound against the negative log of the dose ratio [1-($EC_{50}$ agonist+test compound/EC50 of agonist alone)]. A linear regression analysis yields the Kb, defined as the X-intercept of the linear equation.

EXAMPLES

The following compounds of Formula (I) shown in Table 23, below, were prepared according to one or more methods reported above. The example numbers in the table correspond to the numbers of the examples described above. OBSVD LCMS MS (MH+) is the observed mass spectroscopy reading for the compound indicated.

TABLE 23

| Ex. # | MOLECULAR STRUCTURE | OBSVD LCMS MS (MH+) |
|---|---|---|
| 1 | 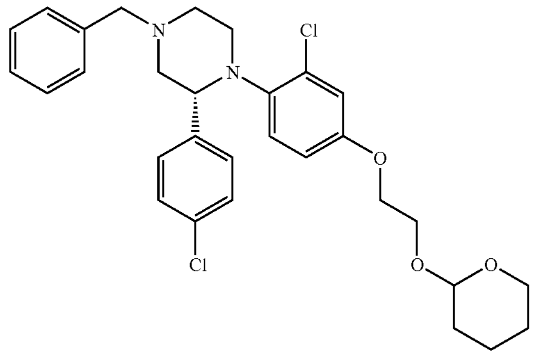 [SMILES: Clc1ccc([C@@H]2CN(Cc3ccccc3)CCN2c2ccc(OCCOC3CCCCO3)cc2Cl)cc1] | 541.3 |
| 2 | 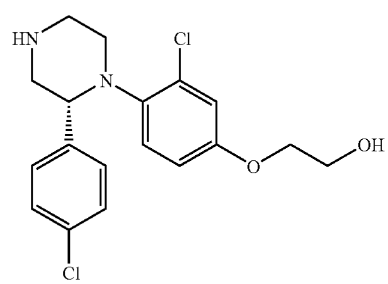 | 367.2 |
| 2b | 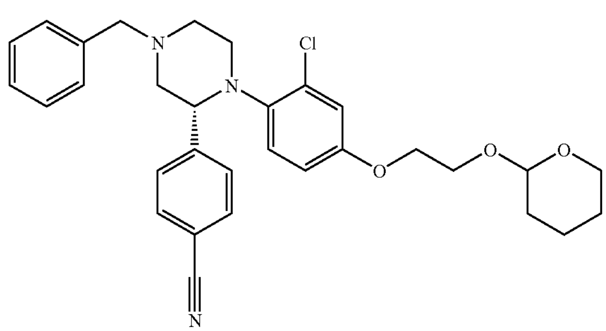 [SMILES: N#Cc1ccc([C@@H]2CN(Cc3ccccc3)CCN2c2ccc(OCCOC3CCCCO3)cc2Cl)cc1] | 532.3 |

TABLE 23-continued

| Ex. # | MOLECULAR STRUCTURE | OBSVD LCMS MS (MH+) |
|---|---|---|
| 2c | 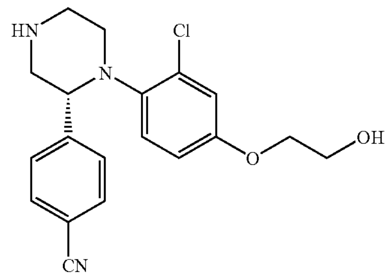 | 358.2 |
| 3 | 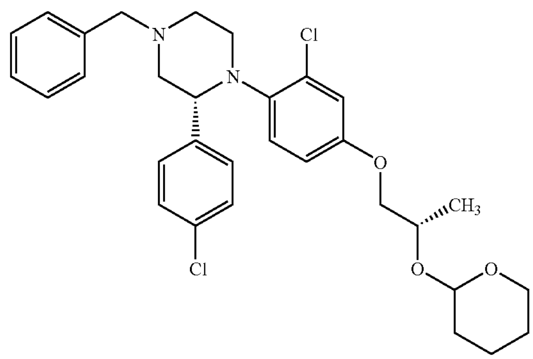 [SMILES: C[C@@H](COc1ccc(N2CCN(Cc3ccccc3)C[C@H]2c2ccc(Cl)cc2)c(Cl)c1)OC1CCCCO1] | 555.3 |
| 4 | 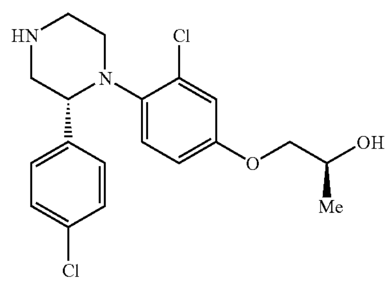 | 381.2 |
| 5 | 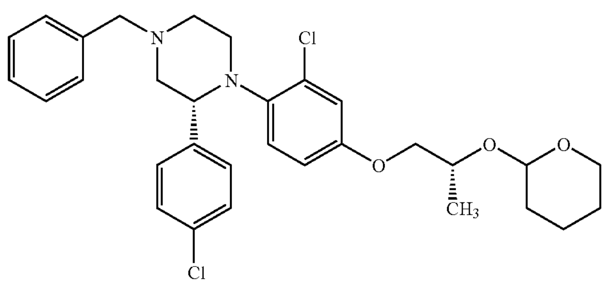 [SMILES: C[C@H](COc1ccc(N2CCN(Cc3ccccc3)C[C@H]2c2ccc(Cl)cc2)c(Cl)c1)OC1CCCCO1] | 555.3 |
| 6 | 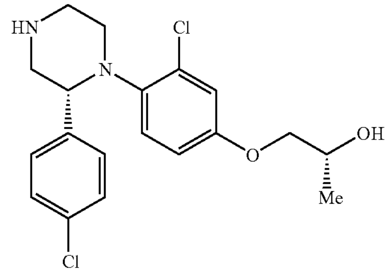 | 381.2 |

TABLE 23-continued

| Ex. # | MOLECULAR STRUCTURE | OBSVD LCMS MS (MH+) |
|---|---|---|
| 7 | 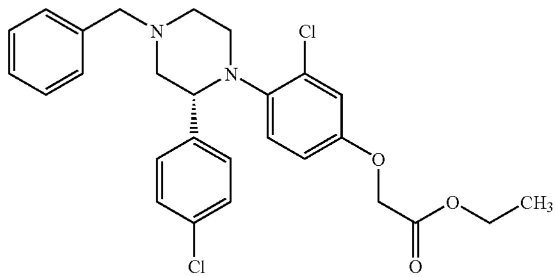 [SMILES: CCOC(=O)COc1ccc(N2CCN(Cc3ccccc3)C[C@H]2c2ccc(Cl)cc2)c(Cl)c1] | 499.3 |
| 8 | 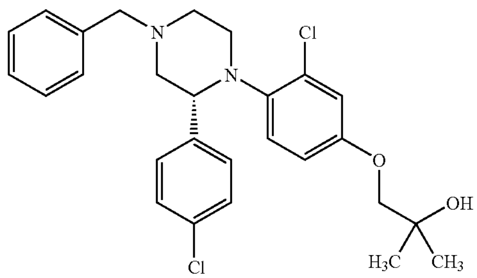 [SMILES: CC(C)(O)COc1ccc(N2CCN(Cc3ccccc3)C[C@H]2c2ccc(Cl)cc2)c(Cl)c1] | 485.3 |
| 9 | 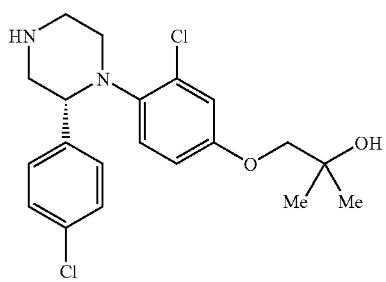 [SMILES: CC(C)(O)COc1ccc(N2CCNC[C@H]2c2ccc(Cl)cc2)c(Cl)c1] | 395.2 |
| 13 | 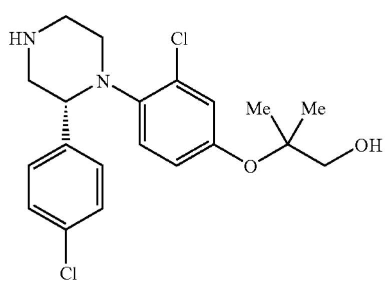 [SMILES: CC(C)(CO)Oc1ccc(N2CCNC[C@H]2c2ccc(Cl)cc2)c(Cl)c1] | 395.2 |
| 17 | 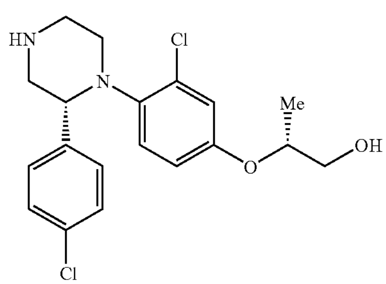 [SMILES: C[C@H](CO)Oc1ccc(N2CCNC[C@H]2c2ccc(Cl)cc2)c(Cl)c1] | 381.2 |

TABLE 23-continued

| Ex. # | MOLECULAR STRUCTURE | OBSVD LCMS MS (MH+) |
|---|---|---|
| 18 | 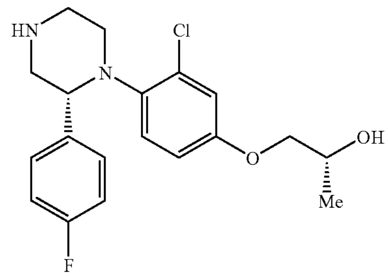 | 365.3 |
| 19 | 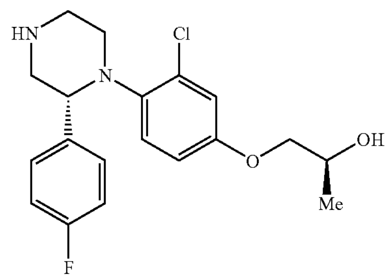 | 365.2 |
| 20a | 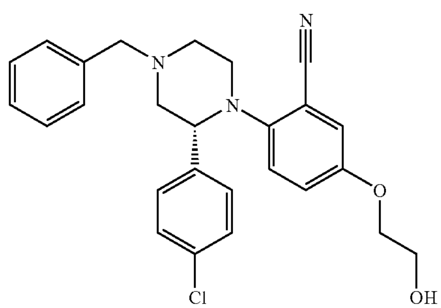 [SMILES: N#Cc1cc(OCCO)ccc1N1CCN(Cc2ccccc2)C[C@H]1c1ccc(Cl)cc1] | 448.2 |
| 20 | 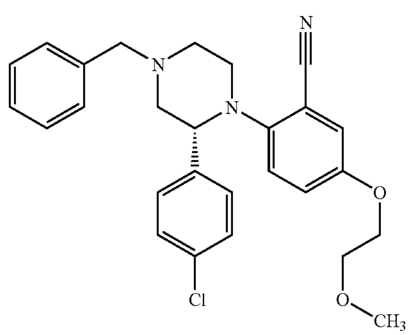 [SMILES: COCCOc1ccc(N2CCN(Cc3ccccc3)C[C@H]2c2ccc(Cl)cc2)c(C#N)c1] | 462.3 |
| 21 | 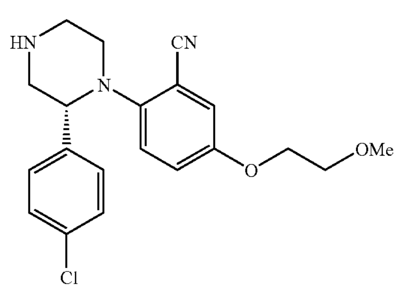 [SMILES: COCCOc1ccc(N2CCNC[C@H]2c2ccc(Cl)cc2)c(C#N)c1] | 372.2 |

TABLE 23-continued

| Ex. # | MOLECULAR STRUCTURE | OBSVD LCMS MS (MH+) |
|---|---|---|
| 22 | 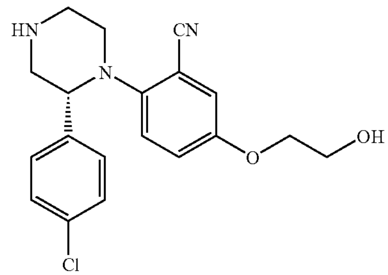 | 358.2 |
| 23a | 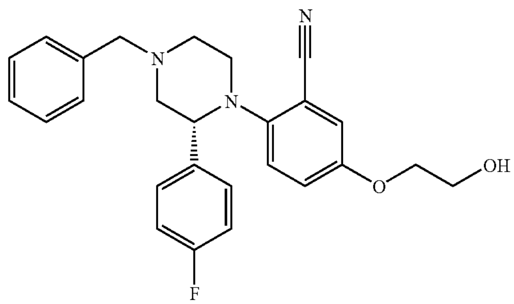 [SMILES: N#Cc1cc(OCCO)ccc1N1CCN(Cc2ccccc2)C[C@H]1c1ccc(F)cc1] | 432.2 |
| 23 | 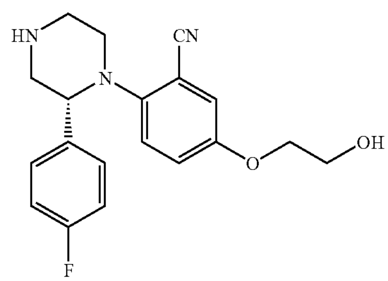 | 342.2 |
| 24 | 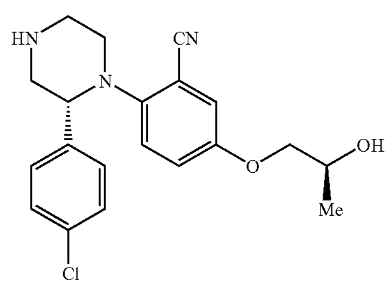 | 372.3 |
| 25a | 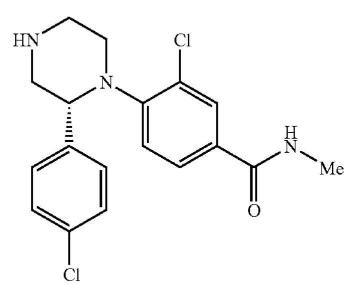 [SMILES: CNC(=O)c1ccc(N2CCNC[C@H]2c2ccc(Cl)cc2)c(Cl)c1] | 364.2 |

TABLE 23-continued

| Ex. # | MOLECULAR STRUCTURE | OBSVD LCMS MS (MH+) |
|---|---|---|
| 25 | 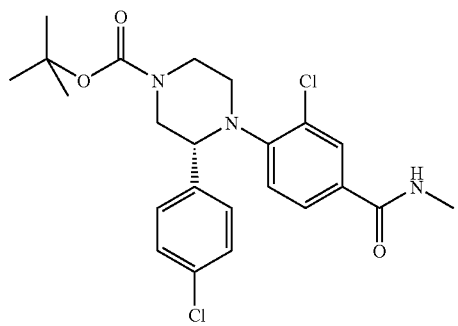 [SMILES: CNC(=O)c1ccc(N2CCN(C(=O)OC(C)(C)C)C[C@H]2c2ccc(Cl)cc2)c(Cl)c1] | 464.3 |
| 26 | 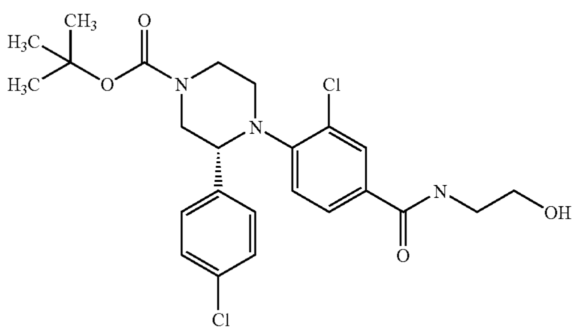 [SMILES: CC(C)(C)OC(=O)N1CCN(c2ccc(C(=O)NCCO)cc2Cl)[C@H](c2ccc(Cl)cc2)C1] | 494.3 |
| 27 | 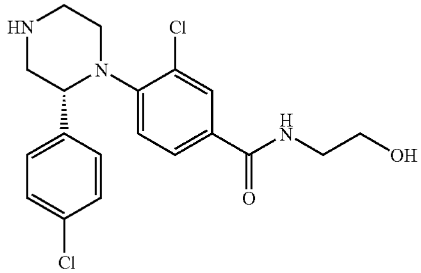 [SMILES: O=C(NCCO)c1ccc(N2CCNC[C@H]2c2ccc(Cl)cc2)c(Cl)c1] | 394.2 |
| 28 | 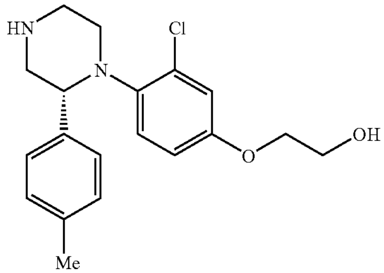 | 347.2 |
| 29 | 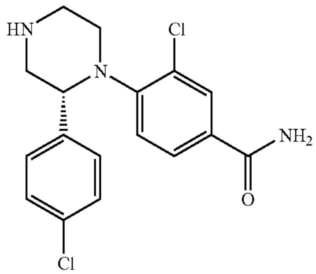 [SMILES: NC(=O)c1ccc(N2CCNC[C@H]2c2ccc(Cl)cc2)c(Cl)c1] | 350.2 |

TABLE 23-continued

| Ex. # | MOLECULAR STRUCTURE | OBSVD LCMS MS (MH+) |
|---|---|---|
| 30 | 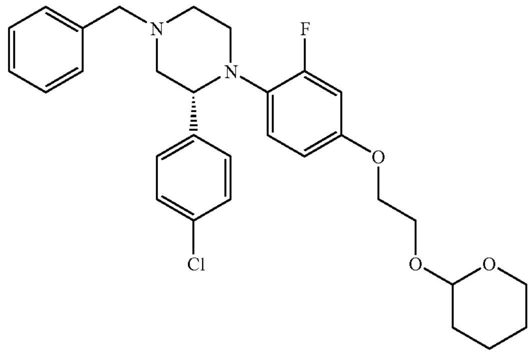 [SMILES: Fc1cc(OCCOC2CCCCO2)ccc1N1CCN(Cc2ccccc2)C[C@H]1c1ccc(Cl)cc1] | 525.3 |
| 31 | 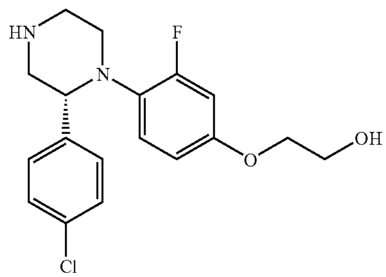 | 351.2 |
| 32 | 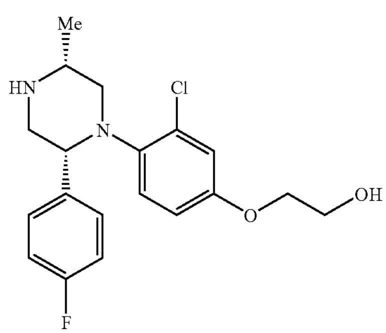 | 365.2 |
| 33 | 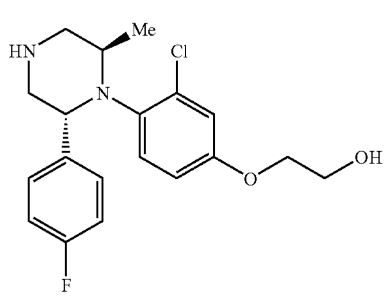 | 365.2 |

TABLE 23-continued
| Ex. # | MOLECULAR STRUCTURE | OBSVD LCMS MS (MH+) |
|---|---|---|
| 34 | 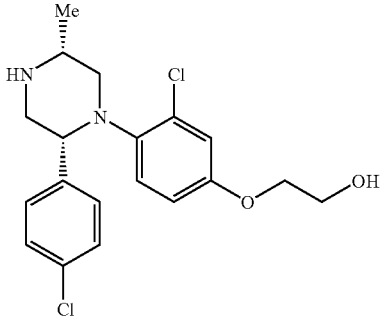 | 381.2 |
| 35 | 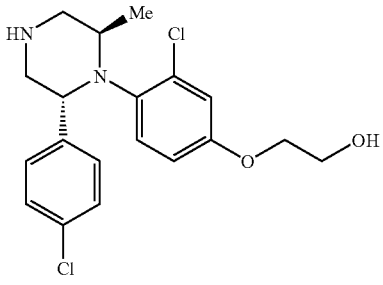 | 381.2 |
| 36 | 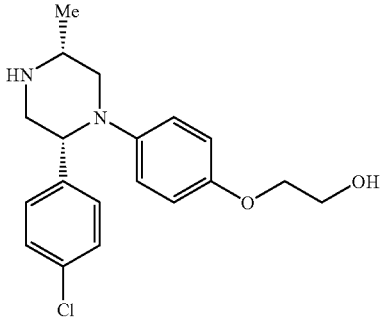 | 347.2 |
| 37 | 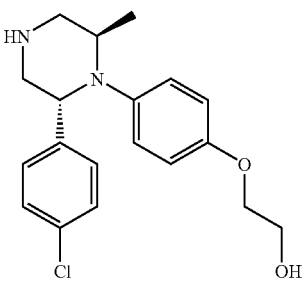 [SMILES: C[C@@H]1CNC[C@@H](c2ccc(Cl)cc2)N1c1ccc(OCCO)cc1] | 347.2 |
| 38 | 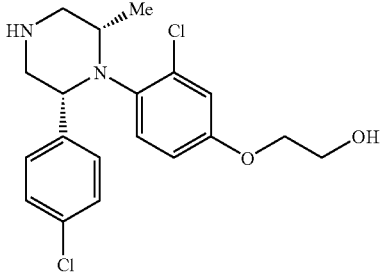 | 381.2 |

TABLE 23-continued

| Ex. # | MOLECULAR STRUCTURE | OBSVD LCMS MS (MH+) |
|---|---|---|
| 39 | 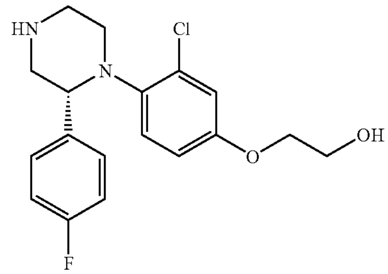 | 351.2 |
| 40 | 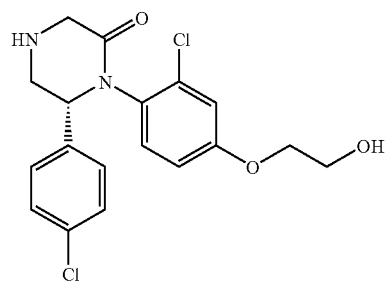 | 381.2 |
| 42 | 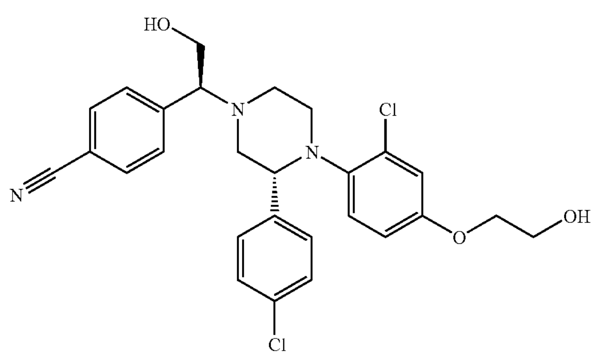 | 512.3 |
| 43 | 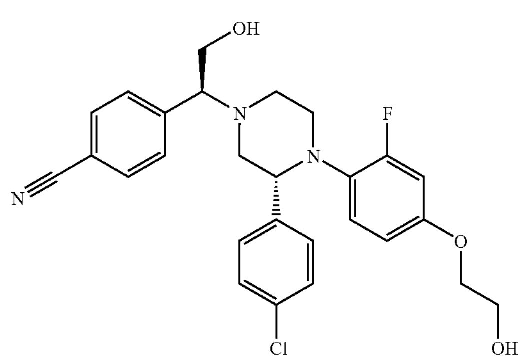 [SMILES: N#Cc1ccc([C@@H](CO)N2CCN(c3ccc(OCCO)cc3F)[C@H](c3ccc(Cl)cc3)C2)cc1] | 496.3 |

TABLE 23-continued

| Ex. # | MOLECULAR STRUCTURE | OBSVD LCMS MS (MH+) |
|---|---|---|
| 44 | 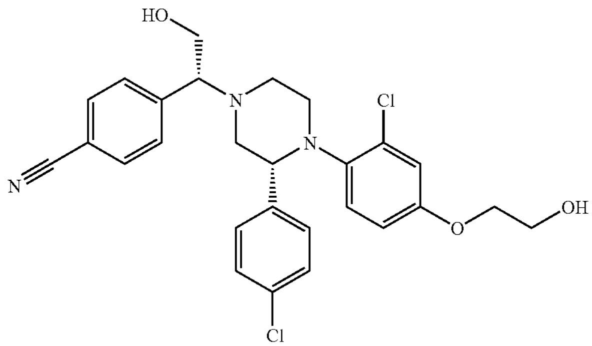 [SMILES: N#Cc1ccc([C@H](CO)N2CCN(c3ccc(OCCO)cc3Cl)[C@H](c3ccc(Cl)cc3)C2)cc1] | 512.3 |
| 45 | 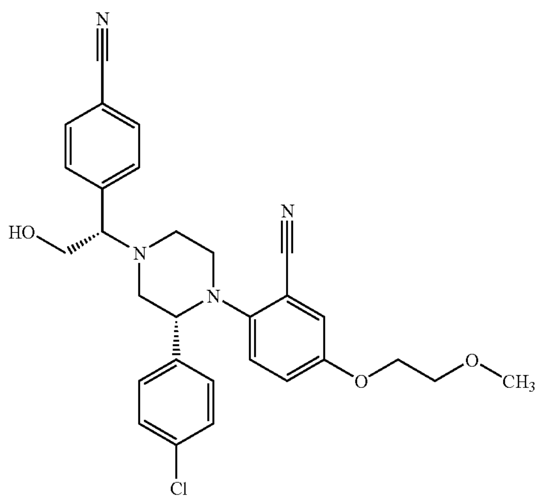 [SMILES: COCCOc1ccc(N2CCN([C@H](CO)c3ccc(C#N)cc3)C[C@H]2c2ccc(Cl)cc2)c(C#N)c1] | 517.3 |
| 46 | 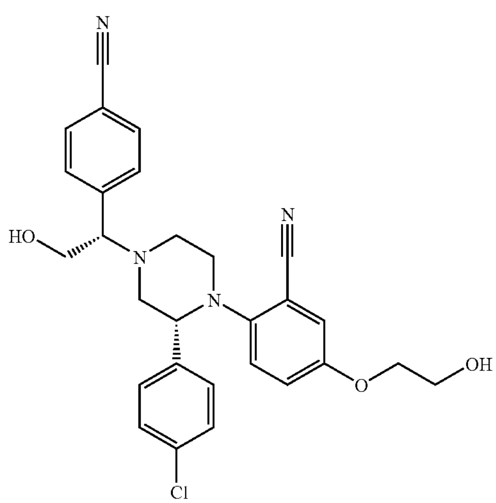 [SMILES: N#Cc1ccc([C@@H](CO)N2CCN(c3ccc(OCCO)cc3C#N)[C@H](c3ccc(Cl)cc3)C2)cc1] | 503.3 |

TABLE 23-continued

| Ex. # | MOLECULAR STRUCTURE | OBSVD LCMS MS (MH+) |
|---|---|---|
| 47 | 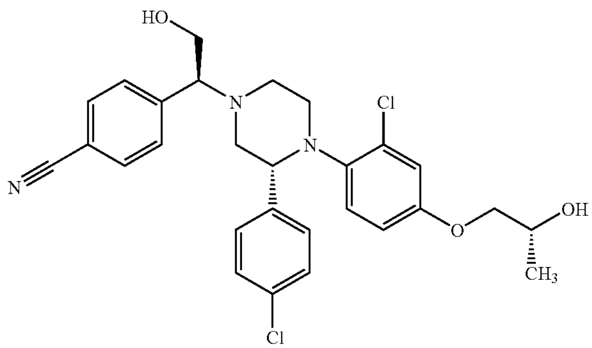 [SMILES: C[C@@H](O)COc1ccc(N2CCN([C@H](CO)c3ccc(C#N)cc3)C[C@H]2c2ccc(Cl)cc2)c(Cl)c1] | 526.3 |
| 48 | 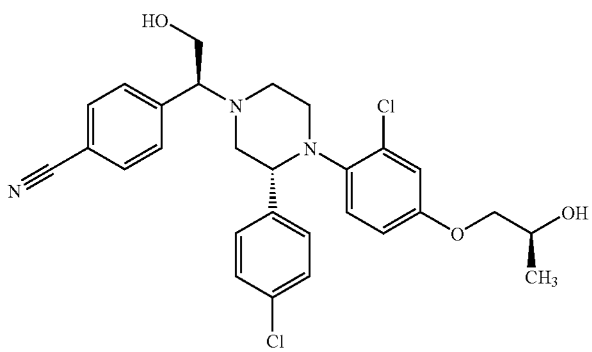 [SMILES: C[C@H](O)COc1ccc(N2CCN([C@H](CO)c3ccc(C#N)cc3)C[C@H]2c2ccc(Cl)cc2)c(Cl)c1] | 526.3 |
| 49 | 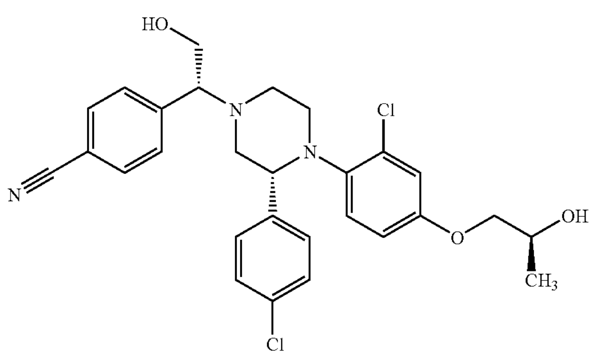 [SMILES: C[C@H](O)COc1ccc(N2CCN([C@@H](CO)c3ccc(C#N)cc3)C[C@H]2c2ccc(Cl)cc2)c(Cl)c1] | 526.3 |
| 50 | 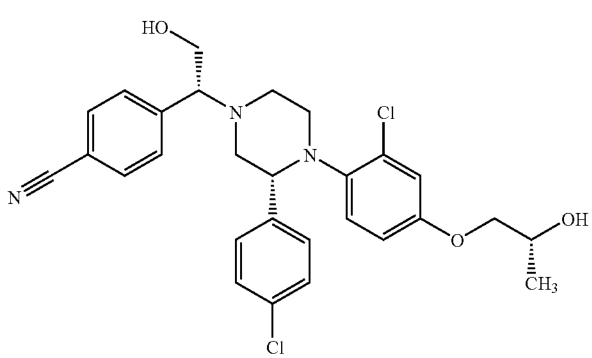 | 526.3 |

TABLE 23-continued

| Ex. # | MOLECULAR STRUCTURE | OBSVD LCMS MS (MH+) |
|---|---|---|
| 51 | 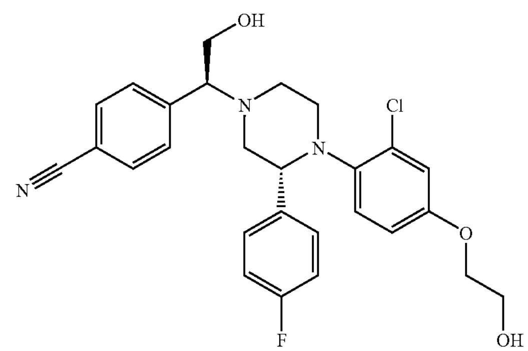 | 496.3 |
| 52 | 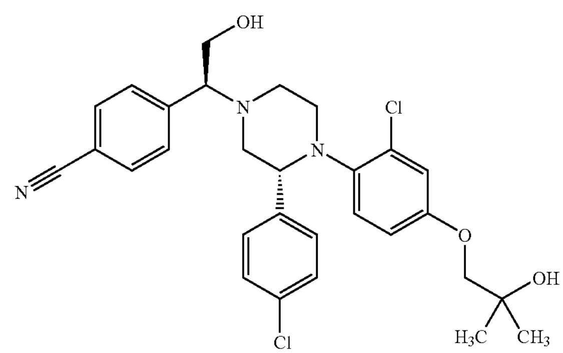 [SMILES: CC(C)(O)COc1ccc(N2CCN([C@H](CO)c3ccc(C#N)cc3)C[C@H]2c2ccc(Cl)cc2)c(Cl)c1] | 540.3 |
| 53 | 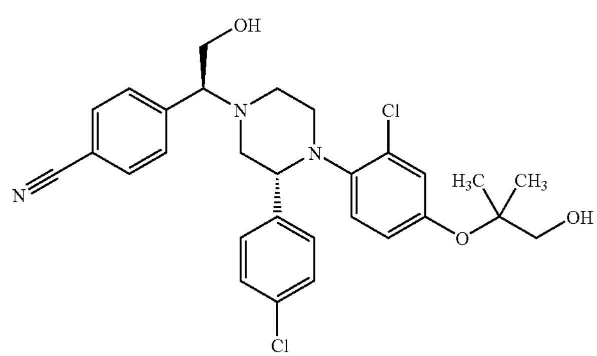 [SMILES: CC(C)(CO)Oc1ccc(N2CCN([C@H](CO)c3ccc(C#N)cc3)C[C@H]2c2ccc(Cl)cc2)c(Cl)c1] | 540.3 |
| 54 | 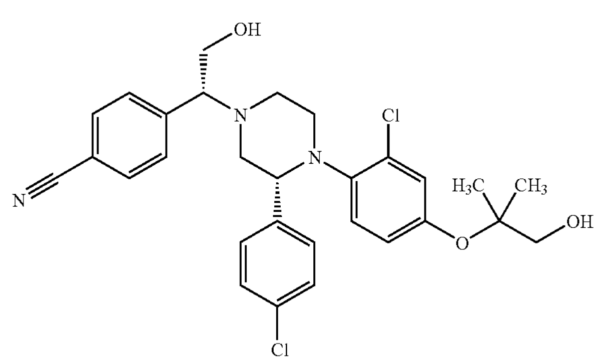 [SMILES: CC(C)(CO)Oc1ccc(N2CCN([C@@H](CO)c3ccc(C#N)cc3)C[C@H]2c2ccc(Cl)cc2)c(Cl)c1] | 540.3 |

TABLE 23-continued

| Ex. # | MOLECULAR STRUCTURE | OBSVD LCMS MS (MH+) |
|---|---|---|
| 55 | 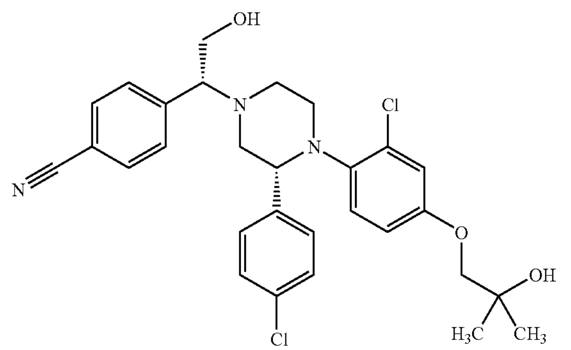 [SMILES: CC(C)(O)COc1ccc(N2CCN([C@@H](CO)c3ccc(C#N)cc3)C[C@H]2c2ccc(Cl)cc2)c(Cl)c1] | 540.3 |
| 56 | 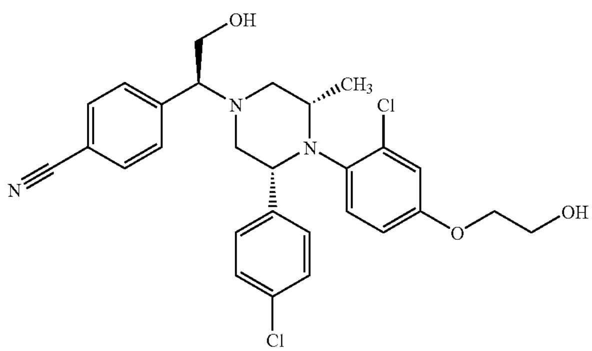 [SMILES: C[C@H]1CN([C@H](CO)c2ccc(C#N)cc2)C[C@@H](c2ccc(Cl)cc2)N1c1ccc(OCCO)cc1Cl] | 526.3 |
| 57 | 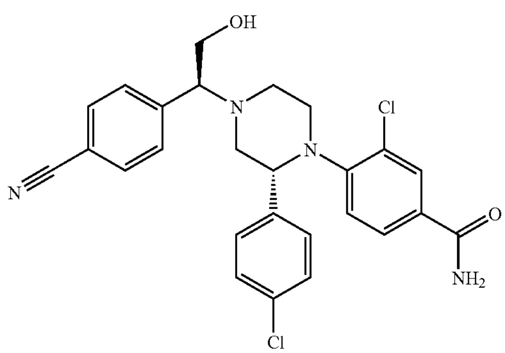 [SMILES: N#Cc1ccc([C@@H](CO)N2CCN(c3ccc(C(N)=O)cc3Cl)[C@H](c3ccc(Cl)cc3)C2)cc1] | 495.3 |
| 57b | 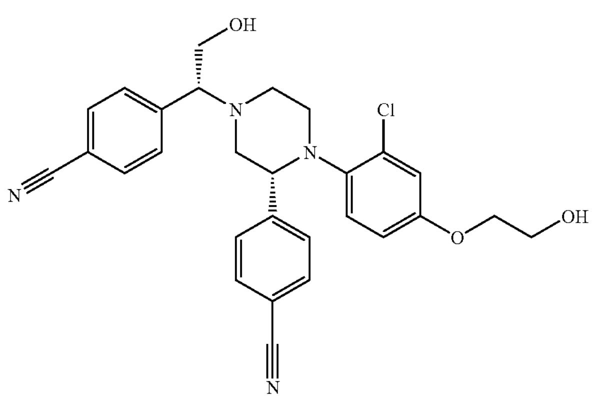 [SMILES: N#Cc1ccc([C@H](CO)N2CCN(c3ccc(OCCO)cc3Cl)[C@H](c3ccc(C#N)cc3)C2)cc1] | 503.3 |

TABLE 23-continued
| Ex. # | MOLECULAR STRUCTURE | OBSVD LCMS MS (MH+) |
|---|---|---|
| 57a | 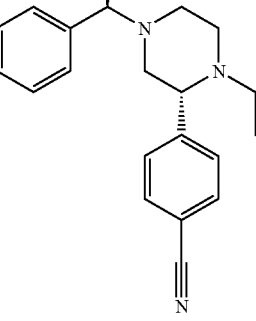 | 503.3 |
| 58 | 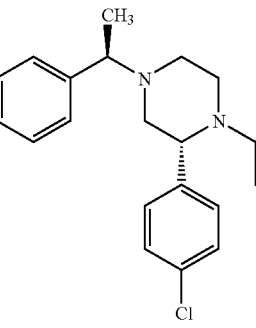 | 496.3 |
| 59 | 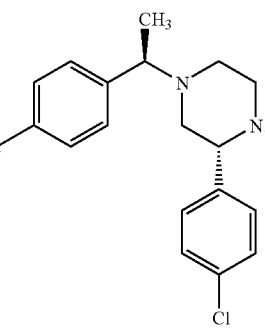 | 480.3 |
| 60 | 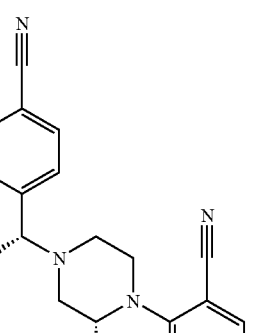 | 501.3 |

TABLE 23-continued

| Ex. # | MOLECULAR STRUCTURE | OBSVD LCMS MS (MH+) |
|---|---|---|
| 61 | 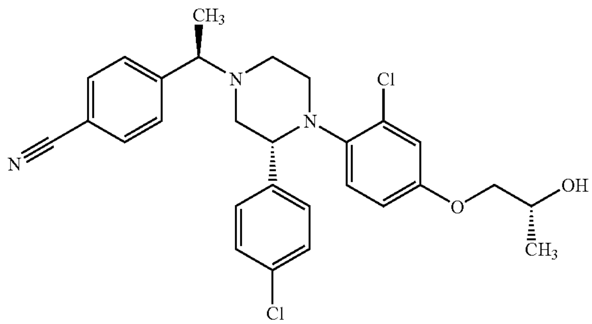 [SMILES: C[C@H](c1ccc(C#N)cc1)N1CCN(c2ccc(OC[C@@H](C)O)cc2Cl)[C@H](c2ccc(Cl)cc2)C1] | 510.3 |
| 62 | 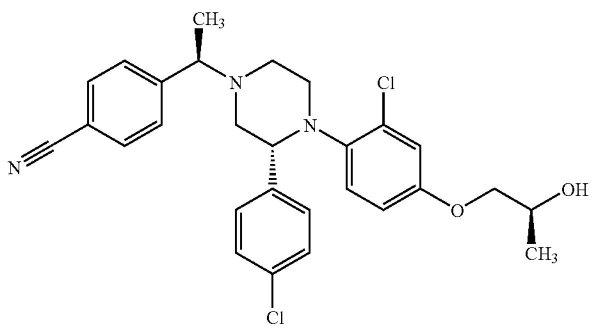 [SMILES: C[C@H](O)COc1ccc(N2CCN([C@H](C)c3ccc(C#N)cc3)C[C@H]2c2ccc(Cl)cc2)c(Cl)c1] | 510.3 |
| 63 | 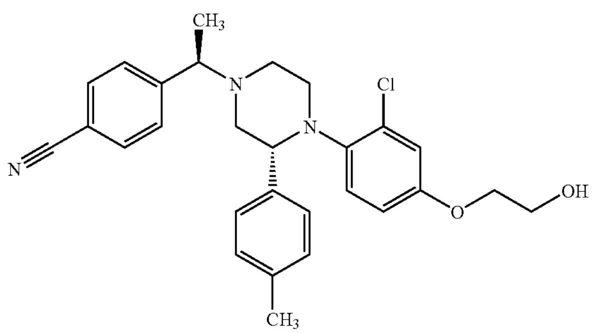 [SMILES: Cc1ccc([C@@H]2CN([C@H](C)c3ccc(C#N)cc3)CCN2c2ccc(OCCO)cc2Cl)cc1] | 476.3 |
| 64 | 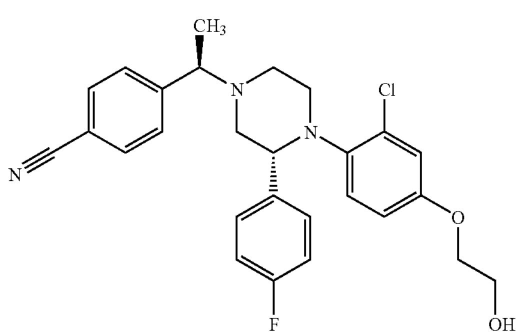 [SMILES: C[C@H](c1ccc(C#N)cc1)N1CCN(c2ccc(OCCO)cc2Cl)[C@H](c2ccc(F)cc2)C1] | 480.3 |

| Ex. # | MOLECULAR STRUCTURE | OBSVD LCMS MS (MH+) |
|---|---|---|
| 65 | 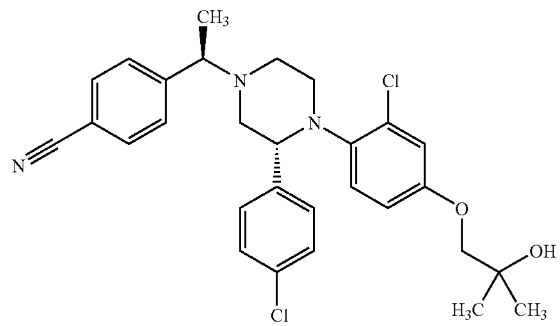 [SMILES: C[C@H](c1ccc(C#N)cc1)N1CCN(c2ccc(OCC(C)(C)O)cc2Cl)[C@H](c2ccc(Cl)cc2)C1] | 524.3 |
| 66 | 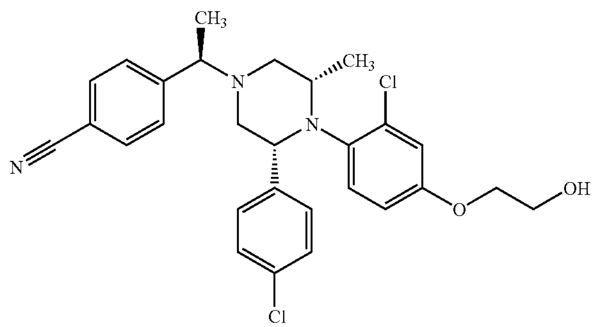 [SMILES: C[C@H](c1ccc(C#N)cc1)N1C[C@H](C)N(c2ccc(OCCO)cc2Cl)[C@H](c2ccc(Cl)cc2)C1] | 510.3 |
| 67 | 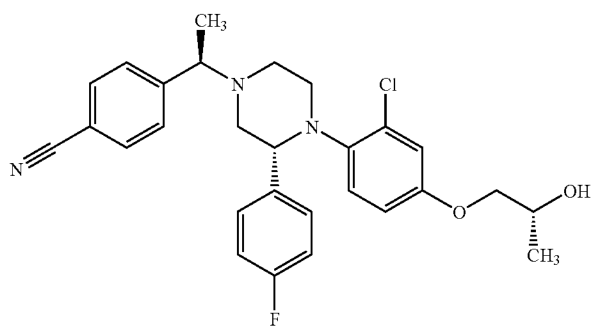 [SMILES: C[C@H](c1ccc(C#N)cc1)N1CCN(c2ccc(OC[C@@H](C)O)cc2Cl)[C@H](c2ccc(F)cc2)C1] | 494.3 |
| 68 | 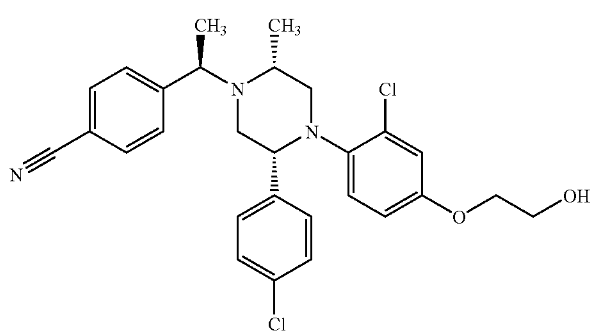 [SMILES: C[C@@H]1CN(c2ccc(OCCO)cc2Cl)[C@H](c2ccc(Cl)cc2)CN1[C@H](C)c1ccc(C#N)cc1] | 510.3 |

TABLE 23-continued

| Ex. # | MOLECULAR STRUCTURE | OBSVD LCMS MS (MH+) |
|---|---|---|
| 69 | 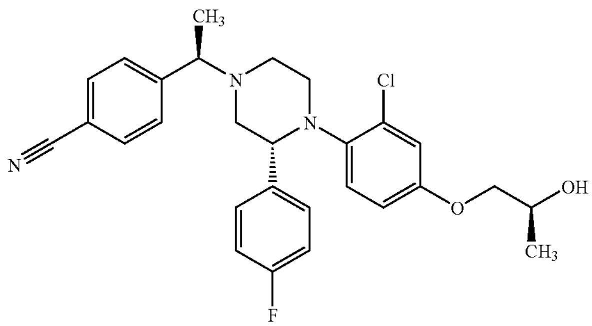 [SMILES: C[C@H](O)COc1ccc(N2CCN([C@H](C)c3ccc(C#N)cc3)C[C@H]2c2ccc(F)cc2)c(Cl)c1] | 494.3 |
| 70 | 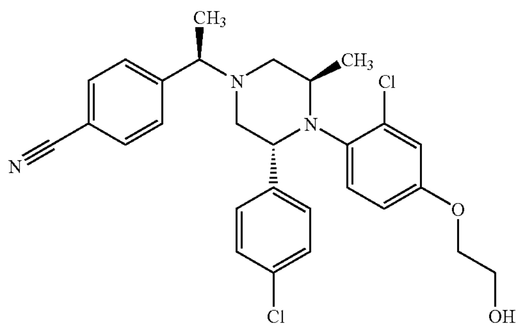 [SMILES: C[C@H](c1ccc(C#N)cc1)N1C[C@@H](C)N(c2ccc(OCCO)cc2Cl)[C@H](c2ccc(Cl)cc2)C1] | 510.3 |
| 71 | 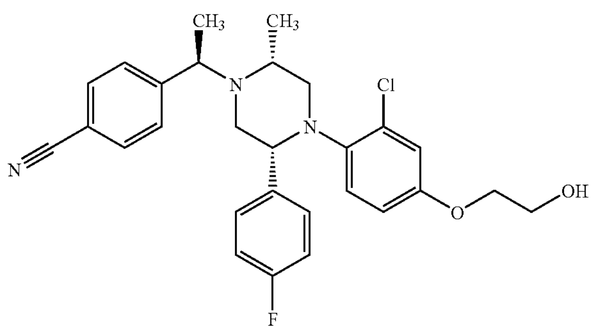 [SMILES: C[C@@H]1CN(c2ccc(OCCO)cc2Cl)[C@H](c2ccc(F)cc2)CN1[C@H](C)c1ccc(C#N)cc1] | 494.3 |
| 72 | 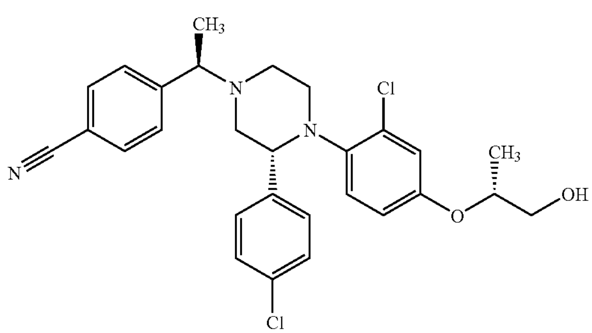 [SMILES: C[C@H](CO)Oc1ccc(N2CCN([C@H](C)c3ccc(C#N)cc3)C[C@H]2c2ccc(Cl)cc2)c(Cl)c1] | 510.3 |

TABLE 23-continued

| Ex. # | MOLECULAR STRUCTURE | OBSVD LCMS MS (MH+) |
|---|---|---|
| 73 | 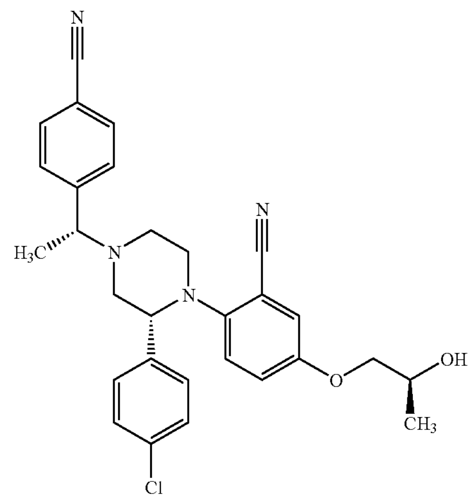 [SMILES: C[C@H](O)COc1ccc(N2CCN([C@H](C)c3ccc(C#N)cc3)C[C@H]2c2ccc(Cl)cc2)c(C#N)c1] | 501.3 |
| 74 | 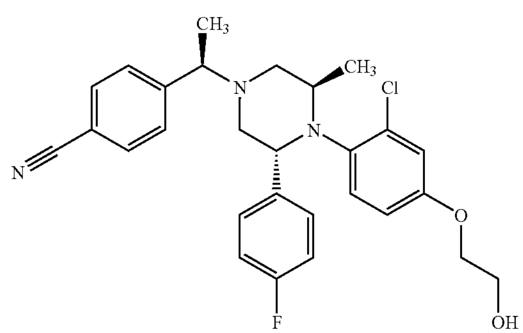 [SMILES: C[C@H](c1ccc(C#N)cc1)N1C[C@@H](C)N(c2ccc(OCCO)cc2Cl)[C@H](c2ccc(F)cc2)C1] | 494.3 |
| 75 | 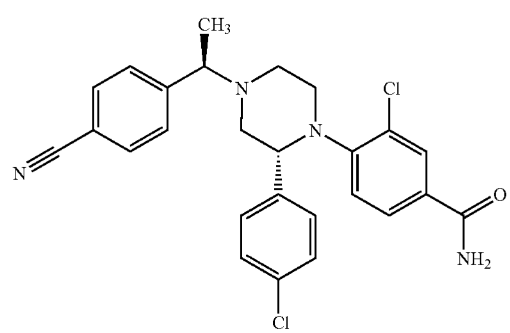 [SMILES: C[C@H](c1ccc(C#N)cc1)N1CCN(c2ccc(C(N)=O)cc2Cl)[C@H](c2ccc(Cl)cc2)C1] | 479.2 |
| 76 | 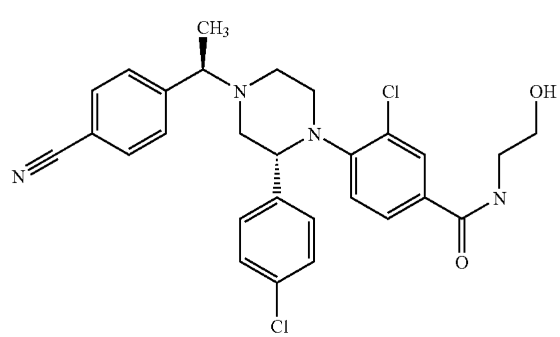 [SMILES: C[C@H](c1ccc(C#N)cc1)N1CCN(c2ccc(C(=O)NCCO)cc2Cl)[C@H](c2ccc(Cl)cc2)C1] | 523.3 |

TABLE 23-continued

| Ex. # | MOLECULAR STRUCTURE | OBSVD LCMS MS (MH+) |
|---|---|---|
| 77 | 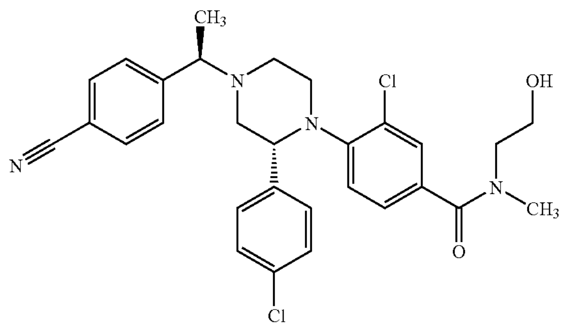 [SMILES: C[C@H](c1ccc(C#N)cc1)N1CCN(c2ccc(C(=O)N(C)CCO)cc2Cl)[C@H](c2ccc(Cl)cc2)C1] | 537.3 |
| 78 | 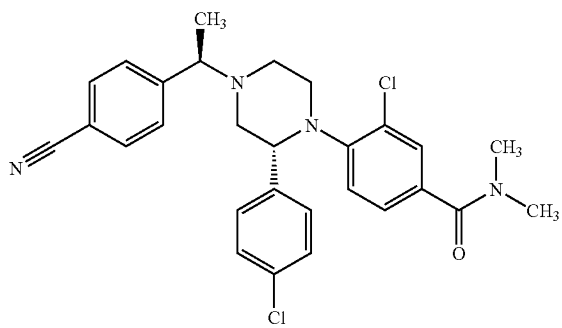 [SMILES: C[C@H](c1ccc(C#N)cc1)N1CCN(c2ccc(C(=O)N(C)C)cc2Cl)[C@H](c2ccc(Cl)cc2)C1] | 507.3 |
| 79 | 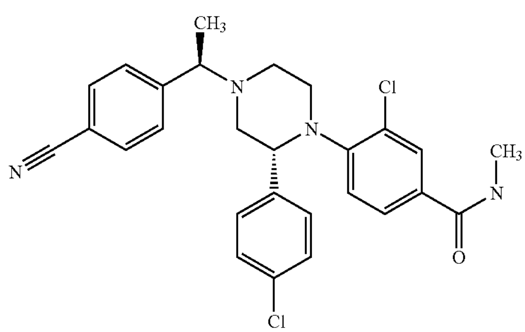 [SMILES: CNC(=O)c1ccc(N2CCN([C@H](C)c3ccc(C#N)cc3)C[C@H]2c2ccc(Cl)cc2)c(Cl)c1] | 493.3 |
| 80 | 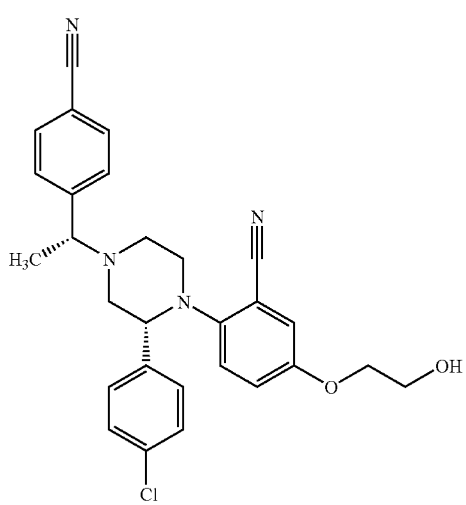 [SMILES: C[C@H](c1ccc(C#N)cc1)N1CCN(c2ccc(OCCO)cc2C#N)[C@H](c2ccc(Cl)cc2)C1] | 487.3 |

TABLE 23-continued

| Ex. # | MOLECULAR STRUCTURE | OBSVD LCMS MS (MH+) |
|---|---|---|
| 80a | 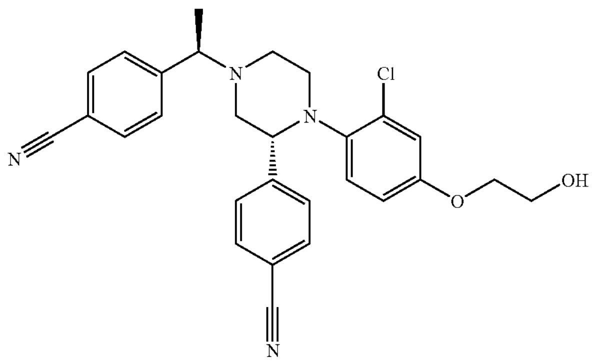 [SMILES: C[C@H](c1ccc(C#N)cc1)N1CCN(c2ccc(OCCO)cc2Cl)[C@H](c2ccc(C#N)cc2)C1] | 487.3 |
| 80b | 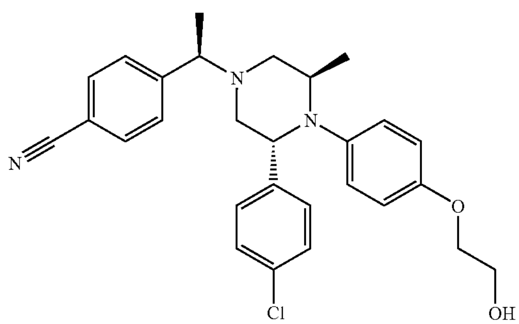 [SMILES: C[C@H](c1ccc(C#N)cc1)N1C[C@@H](C)N(c2ccc(OCCO)cc2)[C@H](c2ccc(Cl)cc2)C1] | 476.3 |
| 80c | 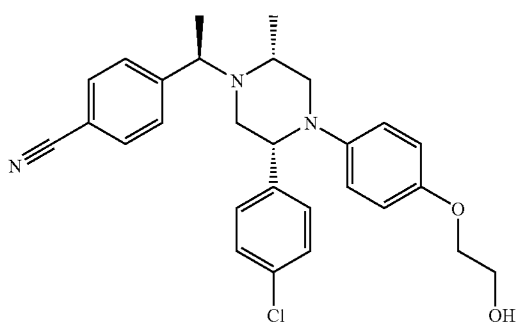 [SMILES: C[C@@H]1CN(c2ccc(OCCO)cc2)[C@H](c2ccc(Cl)cc2)CN1[C@H](C)c1ccc(C#N)cc1] | 476.3 |
| 80d | 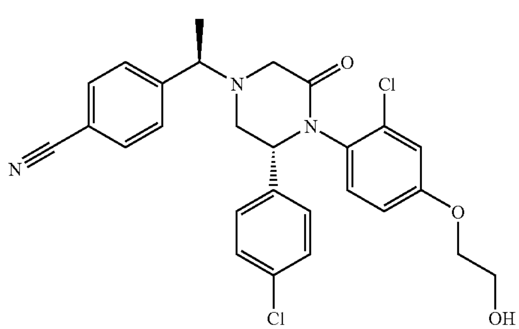 [SMILES: C[C@H](c1ccc(C#N)cc1)N1CC(=O)N(c2ccc(OCCO)cc2Cl)[C@H](c2ccc(Cl)cc2)C1] | 510.3 |

TABLE 23-continued

| Ex. # | MOLECULAR STRUCTURE | OBSVD LCMS MS (MH+) |
|---|---|---|
| 81 | 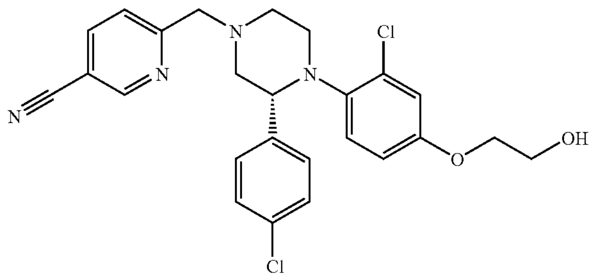 [SMILES: N#Cc1ccc(CN2CCN(c3ccc(OCCO)cc3Cl)[C@H](c3ccc(Cl)cc3)C2)nc1] | 483.3 |
| 82 | 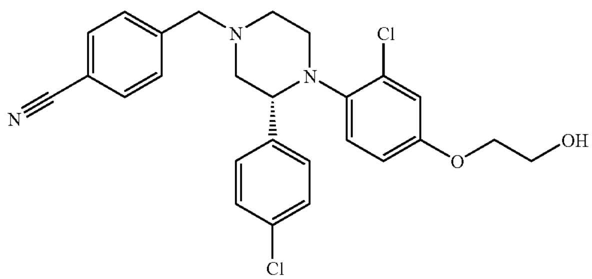 [SMILES: N#Cc1ccc(CN2CCN(c3ccc(OCCO)cc3Cl)[C@H](c3ccc(Cl)cc3)C2)cc1] | 482.3 |
| 83 | 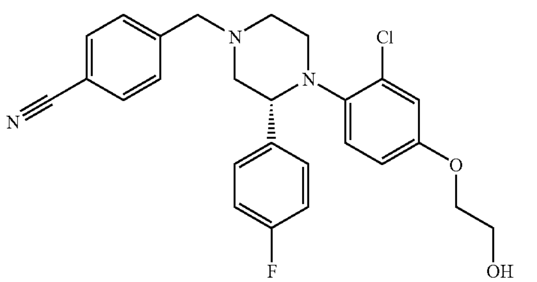 | 466.3 |
| 84 | 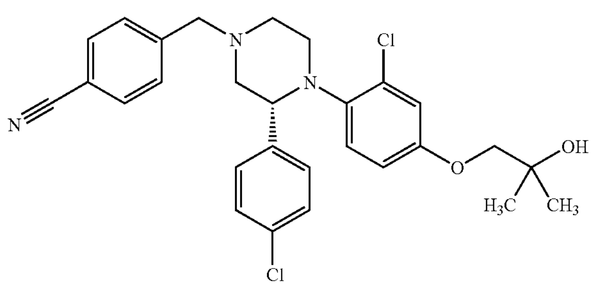 | 510.3 |
| 85 | 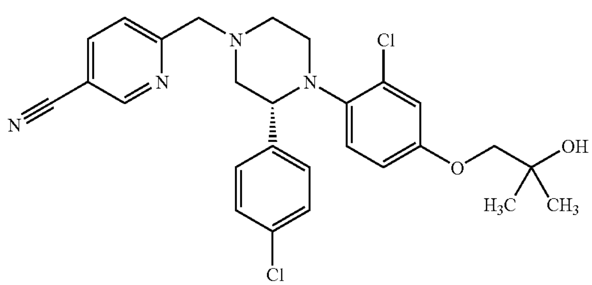 [SMILES: CC(C)(O)COc1ccc(N2CCN(Cc3ccc(C#N)cn3)C[C@H]2c2ccc(Cl)cc2)c(Cl)c1] | 511.3 |

TABLE 23-continued

| Ex. # | MOLECULAR STRUCTURE | OBSVD LCMS MS (MH+) |
|---|---|---|
| 86 | 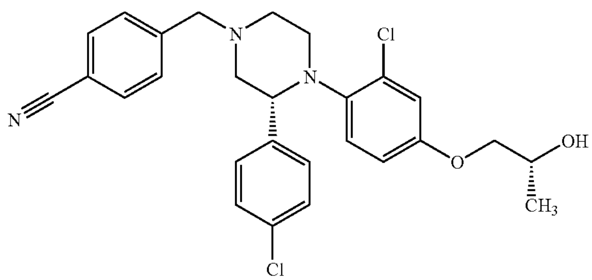 [SMILES: C[C@@H](O)COc1ccc(N2CCN(Cc3ccc(C#N)cc3)C[C@H]2c2ccc(Cl)cc2)c(Cl)c1] | 496.3 |
| 87 | 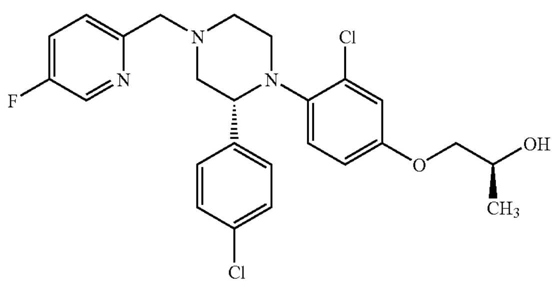 [SMILES: C[C@H](O)COc1ccc(N2CCN(Cc3ccc(F)cn3)C[C@H]2c2ccc(Cl)cc2)c(Cl)c1] | 490.3 |
| 88 | 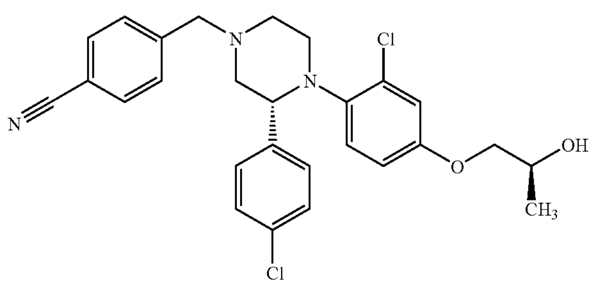 [SMILES: C[C@H](O)COc1ccc(N2CCN(Cc3ccc(C#N)cc3)C[C@H]2c2ccc(Cl)cc2)c(Cl)c1] | 496.3 |
| 89 | 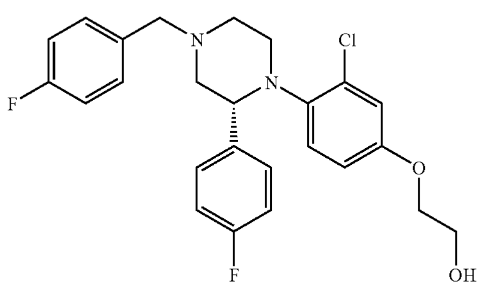 [SMILES: OCCOc1ccc(N2CCN(Cc3ccc(F)cc3)C[C@H]2c2ccc(F)cc2)c(Cl)c1] | 459.3 |
| 90 | 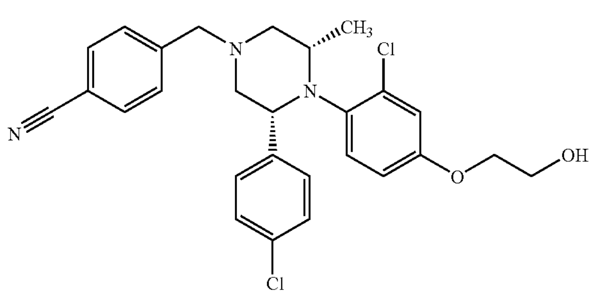 [SMILES: C[C@H]1CN(Cc2ccc(C#N)cc2)C[C@@H](c2ccc(Cl)cc2)N1c1ccc(OCCO)cc1Cl] | 496.3 |

TABLE 23-continued

| Ex. # | MOLECULAR STRUCTURE | OBSVD LCMS MS (MH+) |
|---|---|---|
| 91 | 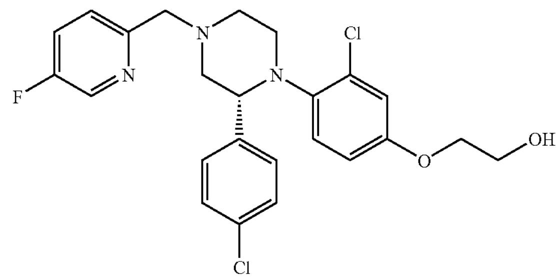 [SMILES: OCCOc1ccc(N2CCN(Cc3ccc(F)cn3)C[C@H]2c2ccc(Cl)cc2)c(Cl)c1] | 476.3 |
| 92 | 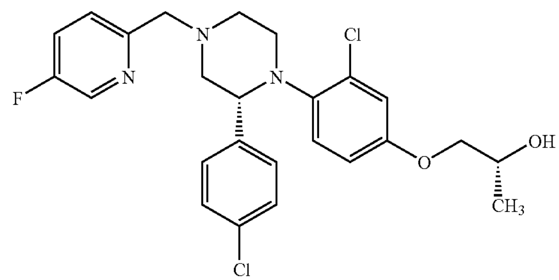 | 490.3 |
| 93 | 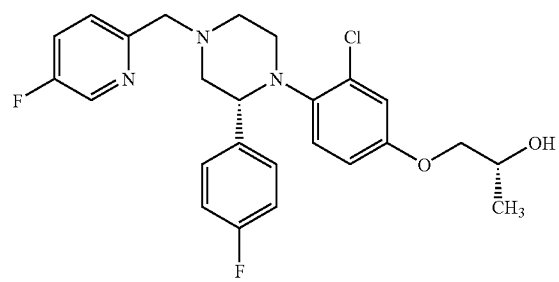 [SMILES: C[C@@H](O)COc1ccc(N2CCN(Cc3ccc(F)cn3)C[C@H]2c2ccc(F)cc2)c(Cl)c1] | 474.3 |
| 94 | 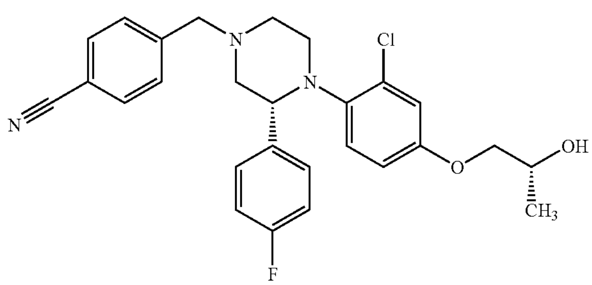 [SMILES: C[C@@H](O)COc1ccc(N2CCN(Cc3ccc(C#N)cc3)C[C@H]2c2ccc(F)cc2)c(Cl)c1] | 480.3 |
| 95 | 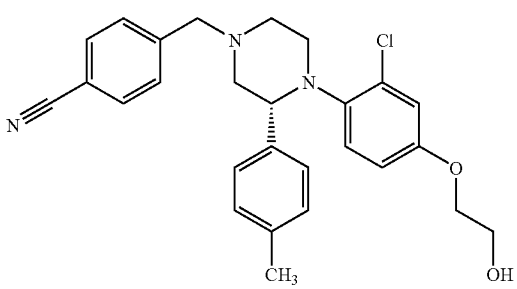 [SMILES: Cc1ccc([C@@H]2CN(Cc3ccc(C#N)cc3)CCN2c2ccc(OCCO)cc2Cl)cc1] | 462.3 |

TABLE 23-continued
| Ex. # | MOLECULAR STRUCTURE | OBSVD LCMS MS (MH+) |
|---|---|---|
| 96 | 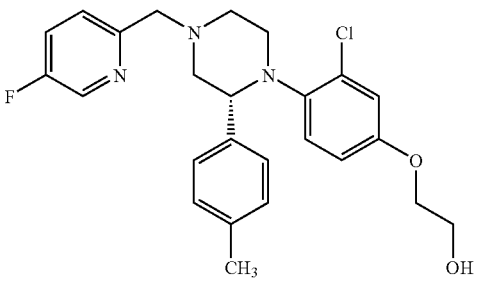 [SMILES: Cc1ccc([C@@H]2CN(Cc3ccc(F)cn3)CCN2c2ccc(OCCO)cc2Cl)cc1] | 456.3 |
| 97 | 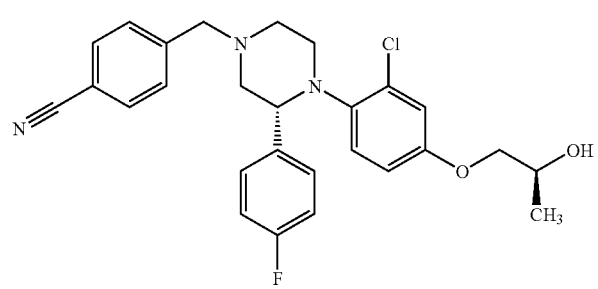 [SMILES: C[C@H](O)COc1ccc(N2CCN(Cc3ccc(C#N)cc3)C[C@H]2c2ccc(F)cc2)c(Cl)c1] | 480.3 |
| 98 | 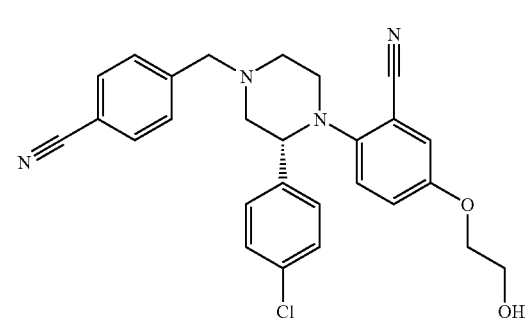 [SMILES: N#Cc1ccc(CN2CCN(c3ccc(OCCO)cc3C#N)[C@H](c3ccc(Cl)cc3)C2)cc1] | 473.3 |
| 99 | 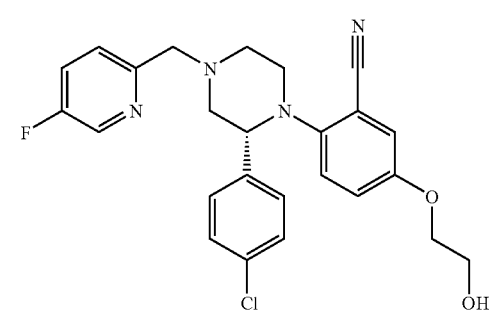 [SMILES: N#Cc1cc(OCCO)ccc1N1CCN(Cc2ccc(F)cn2)C[C@H]1c1ccc(Cl)cc1] | 467.3 |
| 100 | 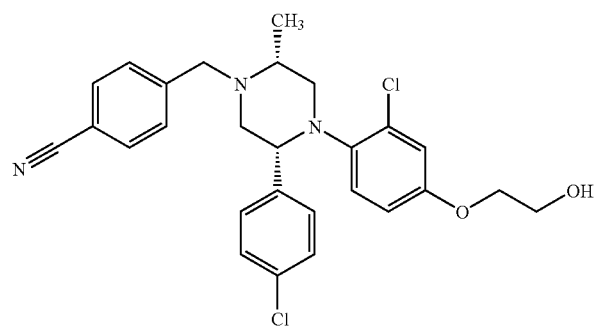 [SMILES: C[C@@H]1CN(c2ccc(OCCO)cc2Cl)[C@H](c2ccc(Cl)cc2)CN1Cc1ccc(C#N)cc1] | 496.3 |

TABLE 23-continued

| Ex. # | MOLECULAR STRUCTURE | OBSVD LCMS MS (MH+) |
|---|---|---|
| 101 | 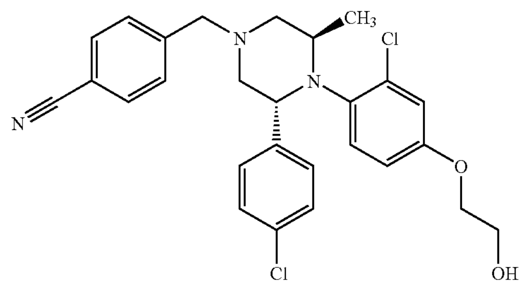 [SMILES: C[C@@H]1CN(Cc2ccc(C#N)cc2)C[C@@H](c2ccc(Cl)cc2)N1c1ccc(OCCO)cc1Cl] | 496.3 |
| 102 | 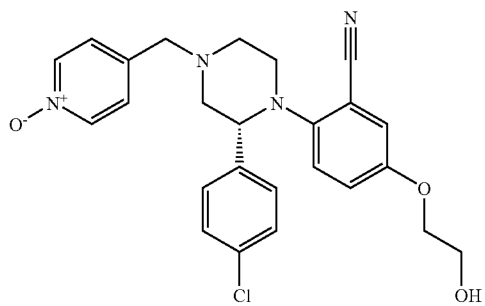 [SMILES: N#Cc1cc(OCCO)ccc1N1CCN(Cc2cc[n+]([O-])cc2)C[C@H]1c1ccc(Cl)cc1] | 465.3 |
| 103 | 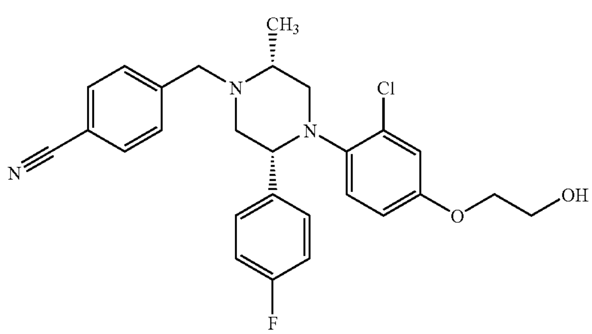 [SMILES: C[C@@H]1CN(c2ccc(OCCO)cc2Cl)[C@H](c2ccc(F)cc2)CN1Cc1ccc(C#N)cc1] | 480.3 |
| 104 | 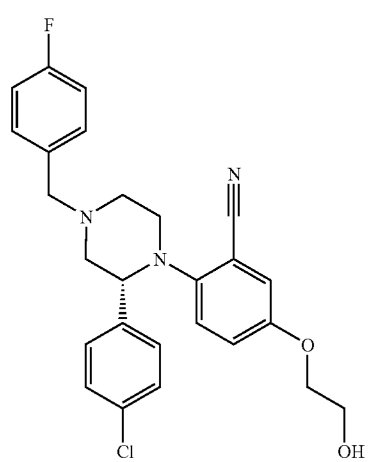 [SMILES: N#Cc1cc(OCCO)ccc1N1CCN(Cc2ccc(F)cc2)C[C@H]1c1ccc(Cl)cc1] | 466.3 |

TABLE 23-continued

| Ex. # | MOLECULAR STRUCTURE | OBSVD LCMS MS (MH+) |
|---|---|---|
| 105 | 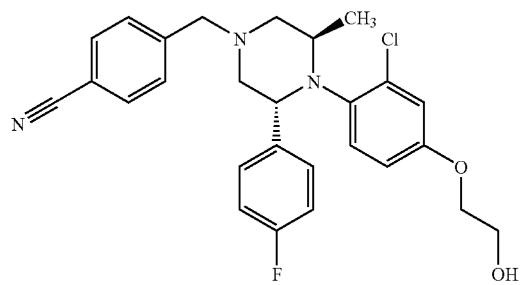 [SMILES: C[C@@H]1CN(Cc2ccc(C#N)cc2)C[C@@H](c2ccc(F)cc2)N1c1ccc(OCCO)cc1Cl] | 480.3 |
| 106 | 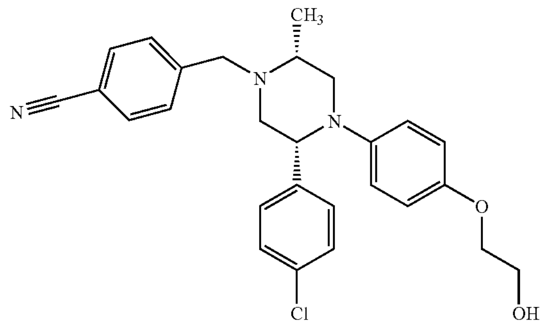 [SMILES: C[C@@H]1CN(c2ccc(OCCO)cc2)[C@H](c2ccc(Cl)cc2)CN1Cc1ccc(C#N)cc1] | 462.3 |
| 107 | 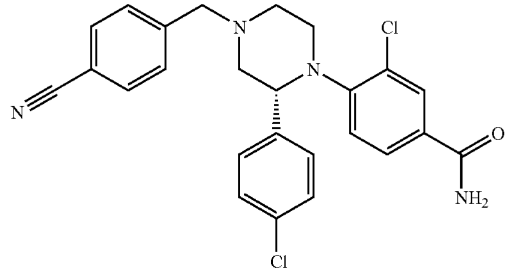 [SMILES: N#Cc1ccc(CN2CCN(c3ccc(C(N)=O)cc3Cl)[C@H](c3ccc(Cl)cc3)C2)cc1] | 465.3 |
| 108 | 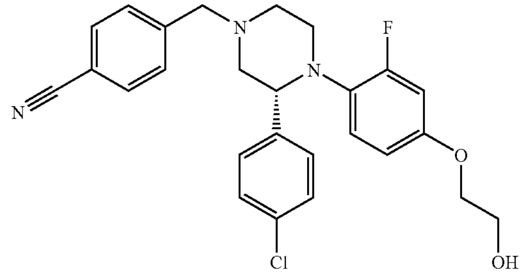 [SMILES: N#Cc1ccc(CN2CCN(c3ccc(OCCO)cc3F)[C@H](c3ccc(Cl)cc3)C2)cc1] | 466.3 |
| 108a | 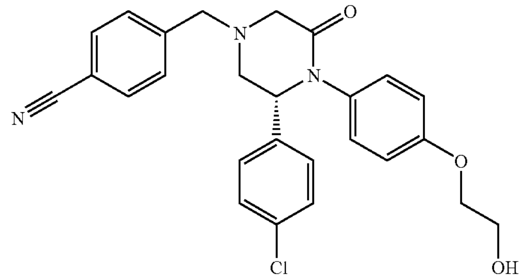 [SMILES: N#Cc1ccc(CN2CC(=O)N(c3ccc(OCCO)cc3)[C@H](c3ccc(Cl)cc3)C2)cc1] | 462.3 |

TABLE 23-continued

| Ex. # | MOLECULAR STRUCTURE | OBSVD LCMS MS (MH+) |
|---|---|---|
| 109 | 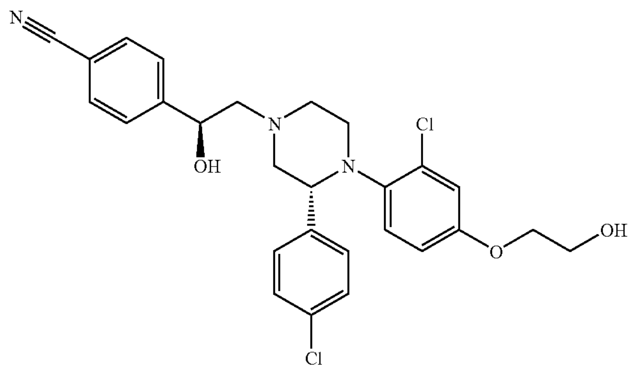 [SMILES: N#Cc1ccc([C@H](O)CN2CCN(c3ccc(OCCO)cc3Cl)[C@H](c3ccc(Cl)cc3)C2)cc1] | 512.3 |
| 110 | 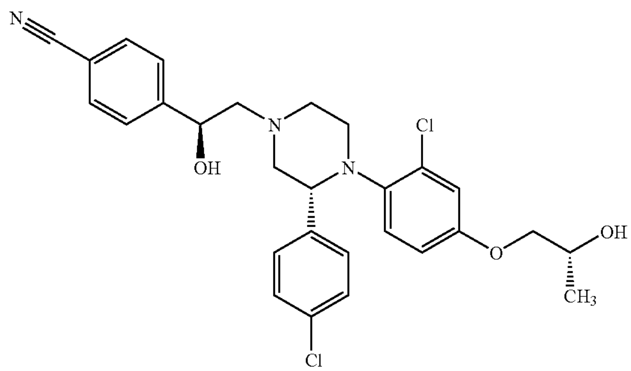 [SMILES: C[C@@H](O)COc1ccc(N2CCN(C[C@@H](O)c3ccc(C#N)cc3)C[C@H]2c2ccc(Cl)cc2)c(Cl)c1] | 526.3 |
| 111 | 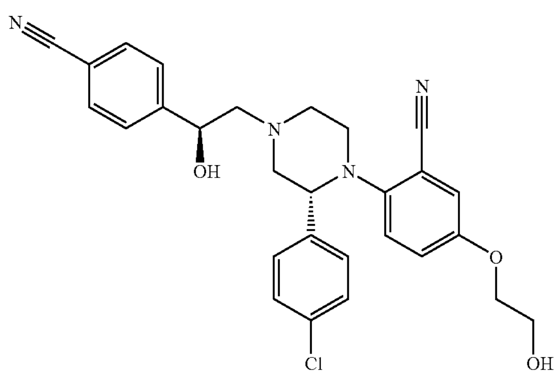 | 503.3 |
| 112 | 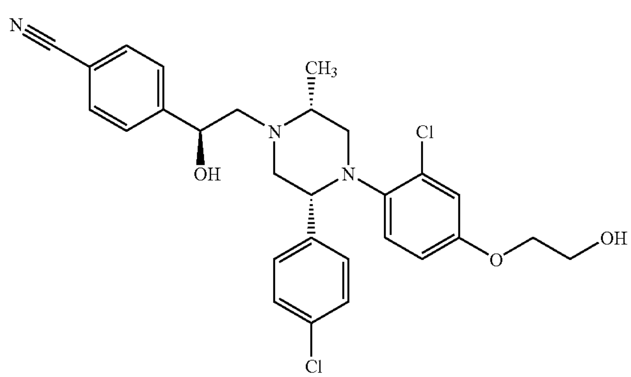 [SMILES: C[C@@H]1CN(c2ccc(OCCO)cc2Cl)[C@H](c2ccc(Cl)cc2)CN1C[C@@H](O)c1ccc(C#N)cc1] | 526.3 |

TABLE 23-continued

| Ex. # | MOLECULAR STRUCTURE | OBSVD LCMS MS (MH+) |
|---|---|---|
| 113 | 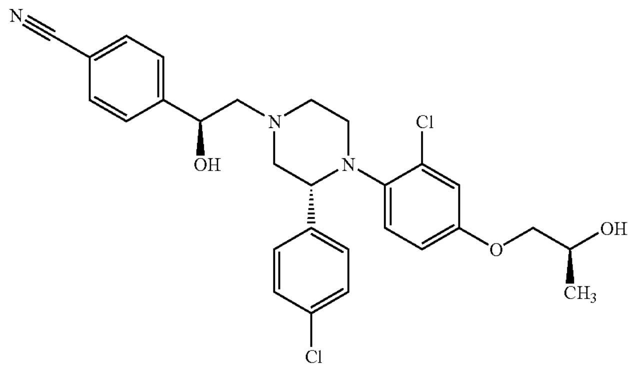 [SMILES: C[C@H](O)COc1ccc(N2CCN(C[C@@H](O)c3ccc(C#N)cc3)C[C@H]2c2ccc(Cl)cc2)c(Cl)c1] | 526.3 |
| 114 | 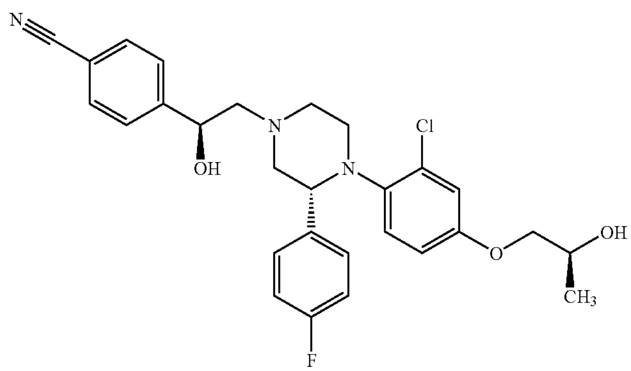 | 510.3 |
| 115 | 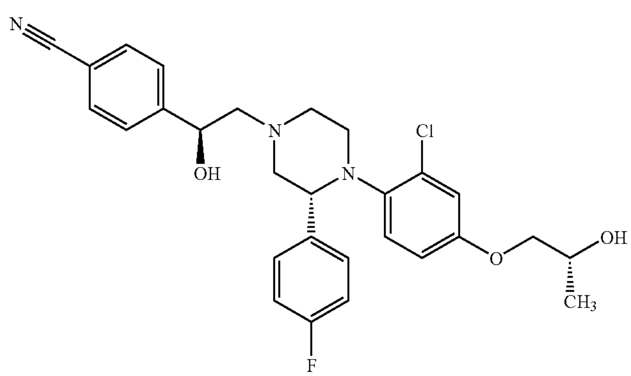 | 510.3 |
| 116 | 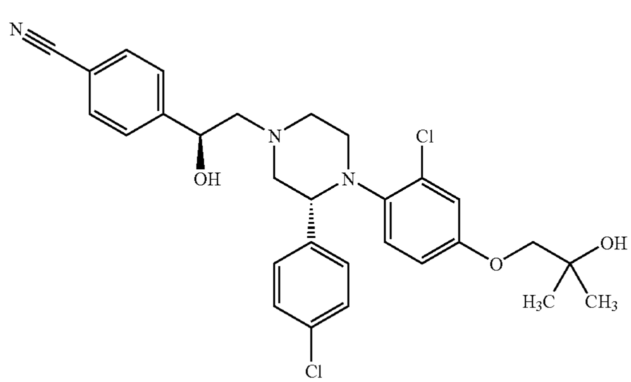 [SMILES: CC(C)(O)COc1ccc(N2CCN(C[C@@H](O)c3ccc(C#N)cc3)C[C@H]2c2ccc(Cl)cc2)c(Cl)c1] | 540.3 |

TABLE 23-continued

| Ex. # | MOLECULAR STRUCTURE | OBSVD LCMS MS (MH+) |
|---|---|---|
| 117 | 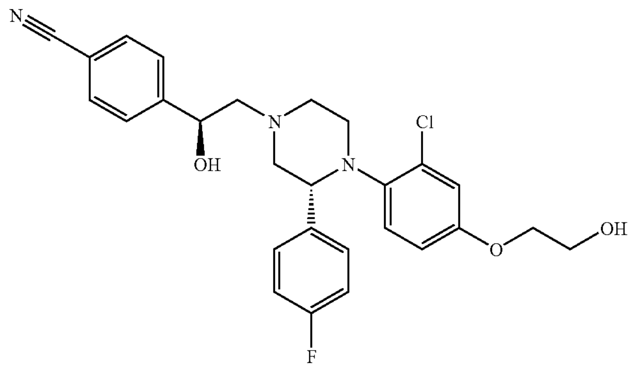 | 496.3 |
| 118 | 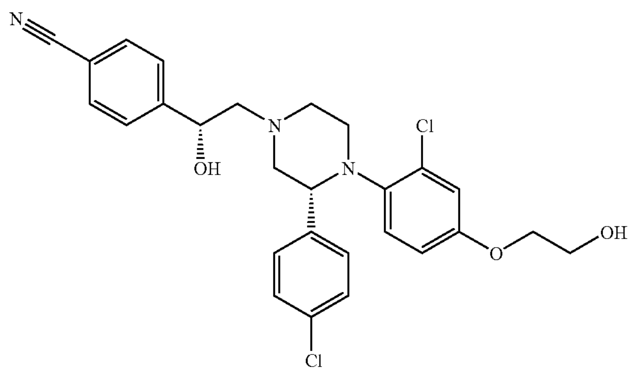 [SMILES: N#Cc1ccc([C@@H](O)CN2CCN(c3ccc(OCCO)cc3Cl)[C@H](c3ccc(Cl)cc3)C2)cc1] | 512.3 |
| 119 | 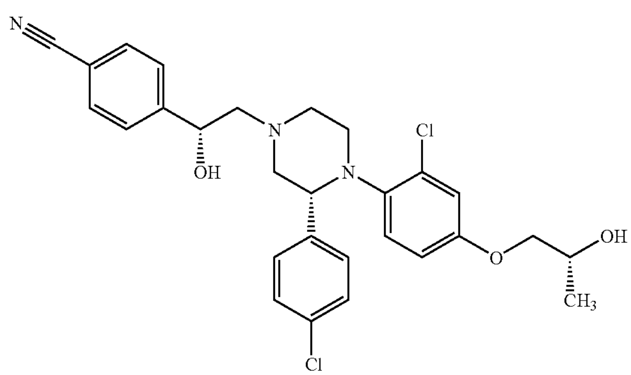 [SMILES: C[C@@H](O)COc1ccc(N2CCN(C[C@H](O)c3ccc(C#N)cc3)C[C@H]2c2ccc(F)cc2)c(Cl)c1] | 526.3 |
| 120 | 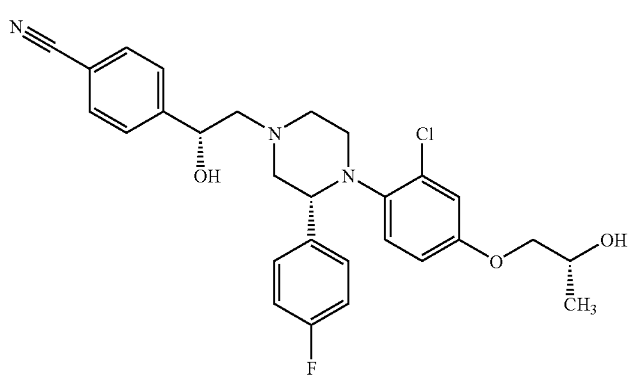 | 510.3 |

TABLE 23-continued

| Ex. # | MOLECULAR STRUCTURE | OBSVD LCMS MS (MH+) |
|---|---|---|
| 121 | 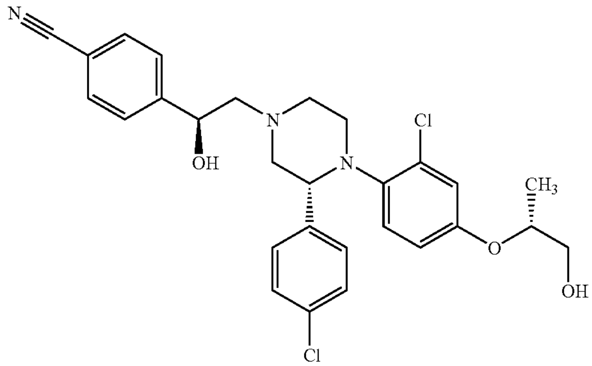 [SMILES: C[C@H](CO)Oc1ccc(N2CCN(C[C@@H](O)c3ccc(C#N)cc3)C[C@H]2c2ccc(Cl)cc2)c(Cl)c1] | 526.3 |
| 122 | 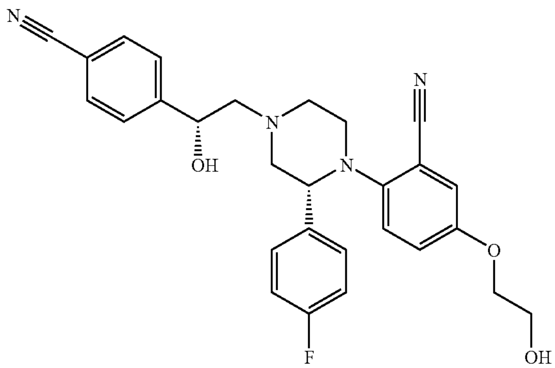 [SMILES: N#Cc1ccc([C@@H](O)CN2CCN(c3ccc(OCCO)cc3C#N)[C@H](c3ccc(F)cc3)C2)cc1] | 487.3 |
| 123 | 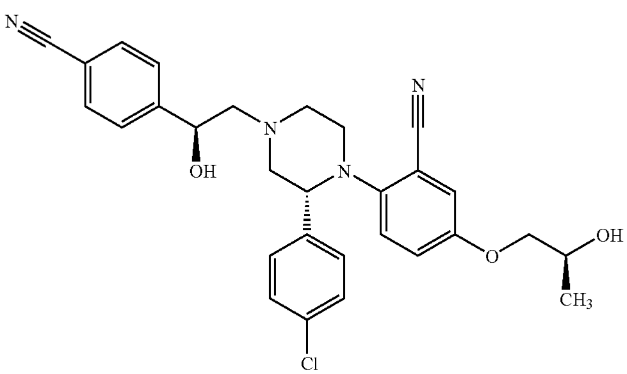 [SMILES: C[C@H](O)COc1ccc(N2CCN(C[C@@H](O)c3ccc(C#N)cc3)C[C@H]2c2ccc(Cl)cc2)c(C#N)c1] | 517.3 |
| 124 | 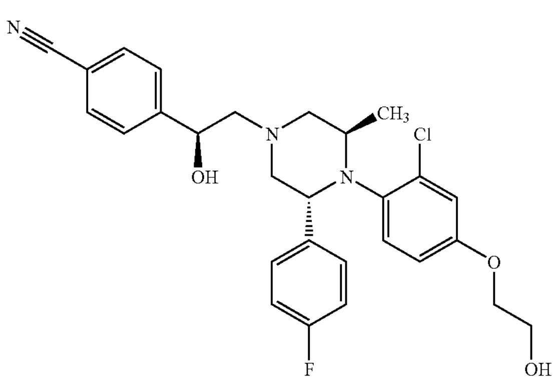 [SMILES: C[C@@H]1CN(C[C@@H](O)c2ccc(C#N)cc2)C[C@@H](c2ccc(F)cc2)N1c1ccc(OCCO)cc1Cl] | 510.3 |

| Ex. # | MOLECULAR STRUCTURE | OBSVD LCMS MS (MH+) |
|---|---|---|
| 125 | 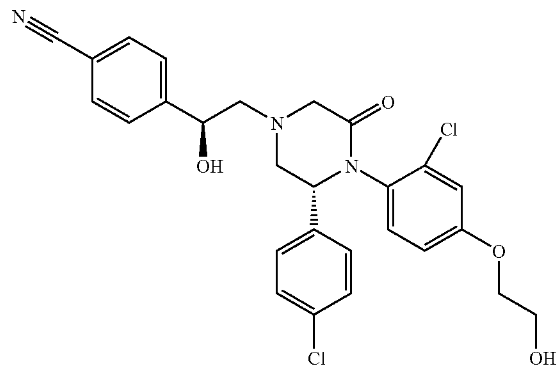 [SMILES: N#Cc1ccc([C@H](O)CN2CC(=O)N(c3ccc(OCCO)cc3Cl)[C@H](c3ccc(Cl)cc3)C2)cc1] | 526.3 |
| 126 | 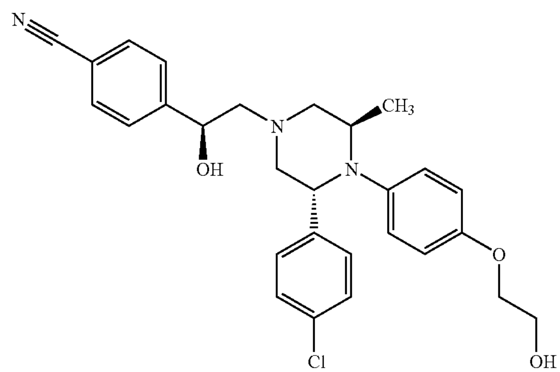 [SMILES: C[C@@H]1CN(C[C@@H](O)c2ccc(C#N)cc2)C[C@@H](c2ccc(Cl)cc2)N1c1ccc(OCCO)cc1] | 492.3 |
| 127 | 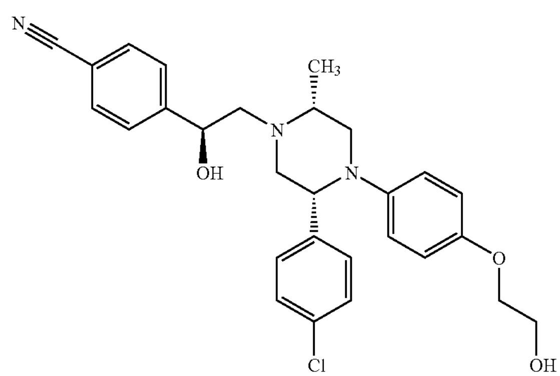 [SMILES: C[C@@H]1CN(c2ccc(OCCO)cc2)[C@H](c2ccc(Cl)cc2)CN1C[C@@H](O)c1ccc(C#N)cc1] | 492.3 |
| 128 | 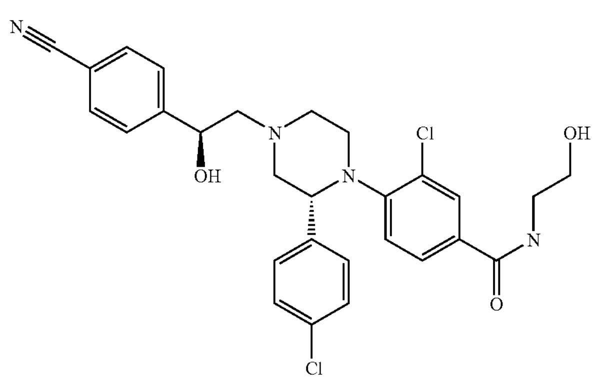 [SMILES: N#Cc1ccc([C@H](O)CN2CCN(c3ccc(C(=O)NCCO)cc3Cl)[C@H](c3ccc(Cl)cc3)C2)cc1] | 539.3 |

TABLE 23-continued

| Ex. # | MOLECULAR STRUCTURE | OBSVD LCMS MS (MH+) |
|---|---|---|
| 129 | 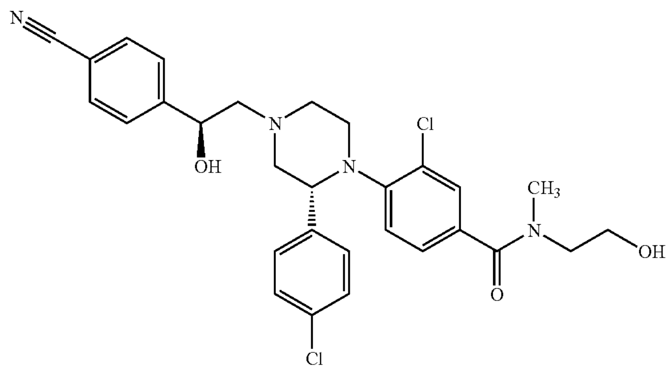 [SMILES: CN(CCO)C(=O)c1ccc(N2CCN(C[C@@H](O)c3ccc(C#N)cc3)C[C@H]2c2ccc(Cl)cc2)c(Cl)c1] | 553.3 |
| 130 | 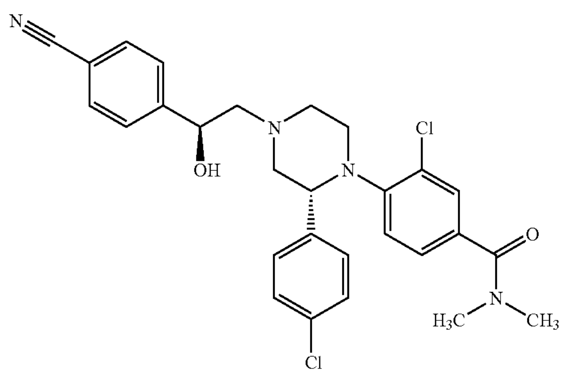 [SMILES: CN(C)C(=O)c1ccc(N2CCN(C[C@@H](O)c3ccc(C#N)cc3)C[C@H]2c2ccc(Cl)cc2)c(Cl)c1] | 523.3 |
| 131a | 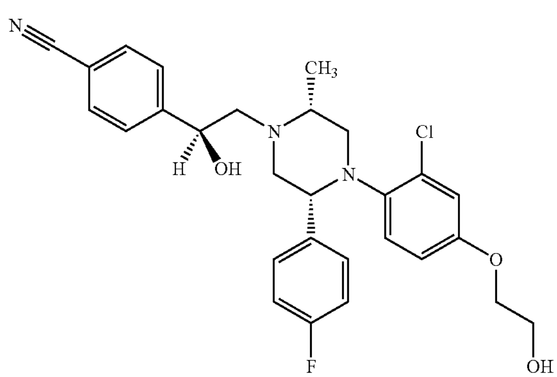 [SMILES: C[C@@H]1CN(c2ccc(OCCO)cc2Cl)[C@H](c2ccc(F)cc2)CN1C[C@@H](O)c1ccc(C#N)cc1] | 510.3 |
| 131 | 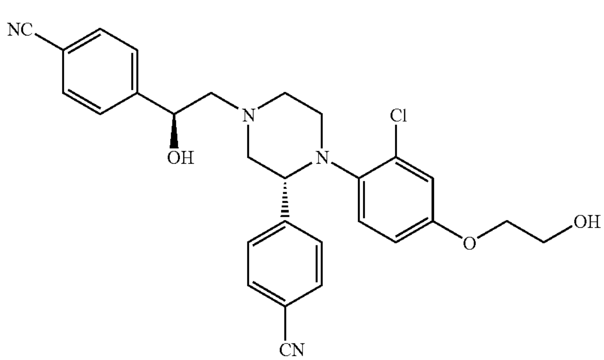 | 503.3 |

TABLE 23-continued

| Ex. # | MOLECULAR STRUCTURE | OBSVD LCMS MS (MH+) |
|---|---|---|
| 131b | 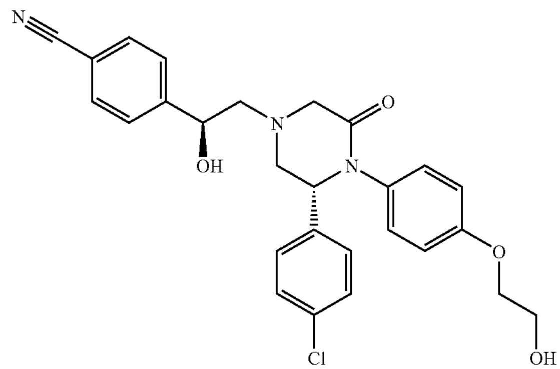 [SMILES: N#Cc1ccc([C@H](O)CN2CC(=O)N(c3ccc(OCCO)cc3)[C@H](c3ccc(Cl)cc3)C2)cc1] | 492.3 |
| 131c | 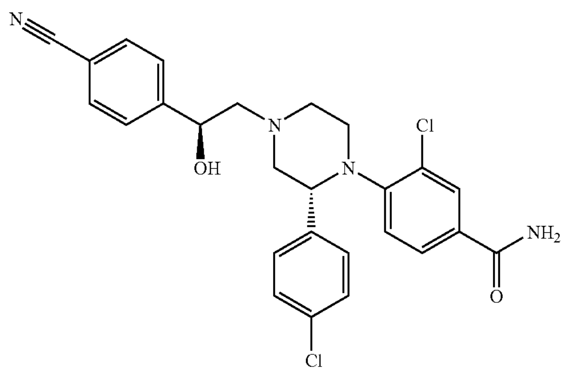 [SMILES: N#Cc1ccc([C@H](O)CN2CCN(c3ccc(C(N)=O)cc3Cl)[C@H](c3ccc(Cl)cc3)C2)cc1] | 495.3 |
| 132 | 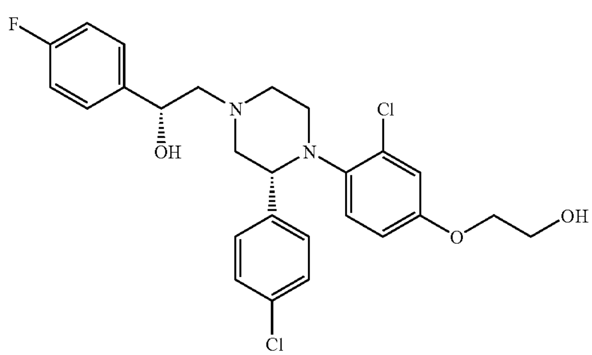 | 505.3 |
| 133 | 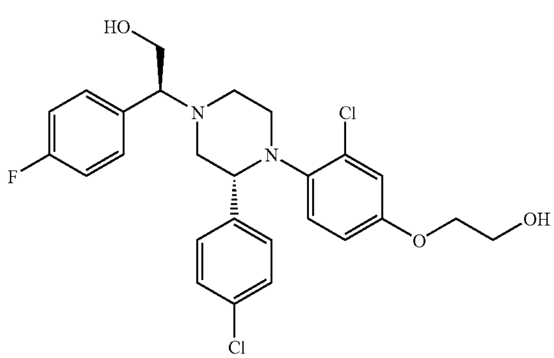 [SMILES: OCCOc1ccc(N2CCN([C@H](CO)c3ccc(F)cc3)C[C@H]2c2ccc(Cl)cc2)c(Cl)c1] | 505.3 |

TABLE 23-continued

| Ex. # | MOLECULAR STRUCTURE | OBSVD LCMS MS (MH+) |
|---|---|---|
| 134 | 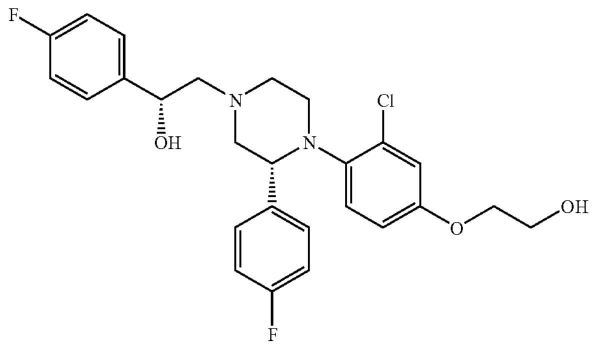 [SMILES: OCCOc1ccc(N2CCN(C[C@H](O)c3ccc(F)cc3)C[C@H]2c2ccc(F)cc2)c(Cl)c1] | 489.3 |
| 135 | 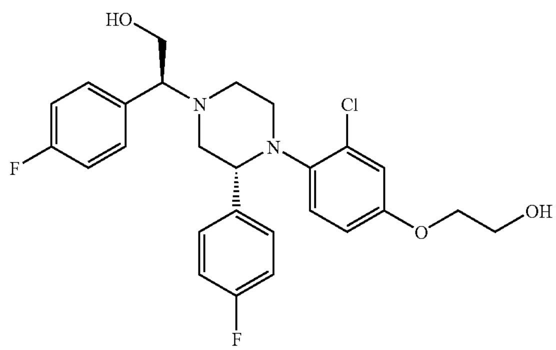 [SMILES: OCCOc1ccc(N2CCN([C@H](CO)c3ccc(F)cc3)C[C@H]2c2ccc(F)cc2)c(Cl)c1] | 489.3 |
| 136 | 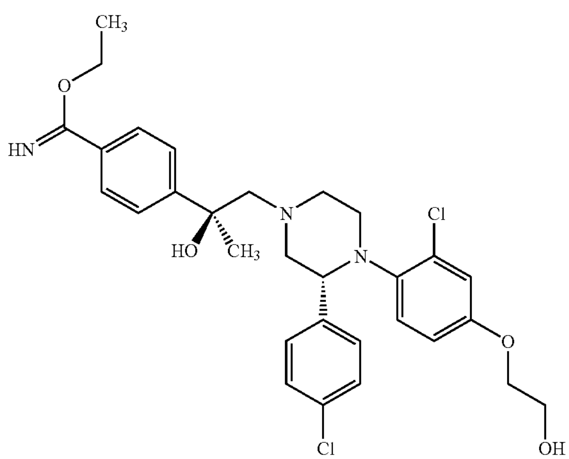 [SMILES: CCOC(=N)c1ccc([C@](C)(O)CN2CCN(c3ccc(OCCO)cc3Cl)[C@H](c3ccc(Cl)cc3)C2)cc1] | 568.3 |
| 137 | 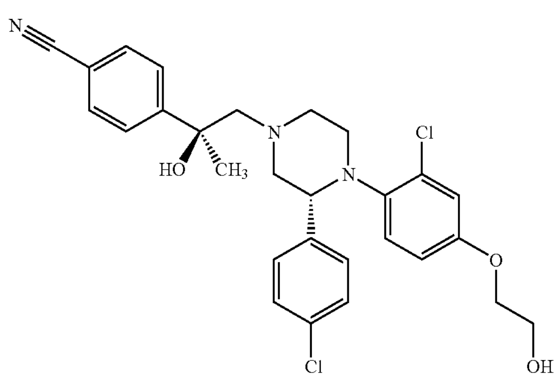 [SMILES: C[C@@](O)(CN1CCN(c2ccc(OCCO)cc2Cl)[C@H](c2ccc(Cl)cc2)C1)c1ccc(C#N)cc1] | 526.3 |

TABLE 23-continued

| Ex. # | MOLECULAR STRUCTURE | OBSVD LCMS MS (MH+) |
|---|---|---|
| 138 | 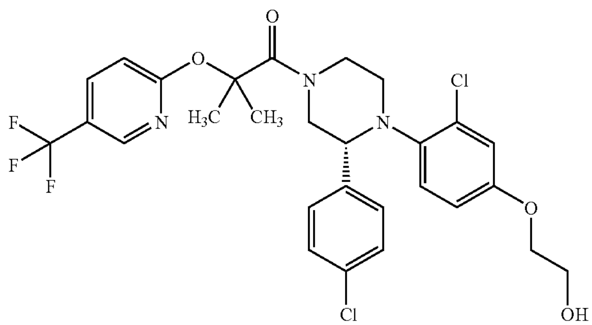 [SMILES: CC(C)(Oc1ccc(C(F)(F)F)cn1)C(=O)N1CCN(c2ccc(OCCO)cc2Cl)[C@H](c2ccc(Cl)cc2)C1] | 590.3 |
| 139 | 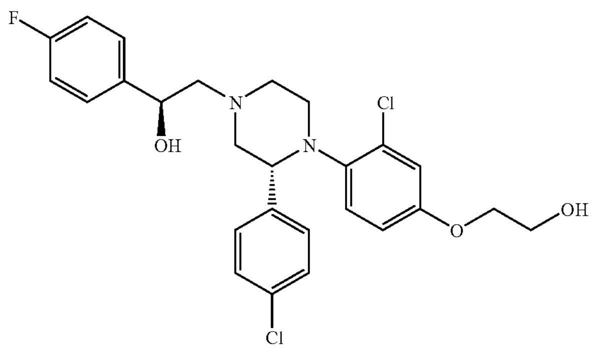 [SMILES: OCCOc1ccc(N2CCN(C[C@@H](O)c3ccc(F)cc3)C[C@H]2c2ccc(Cl)cc2)c(Cl)c1] | 505.3 |
| 140 | 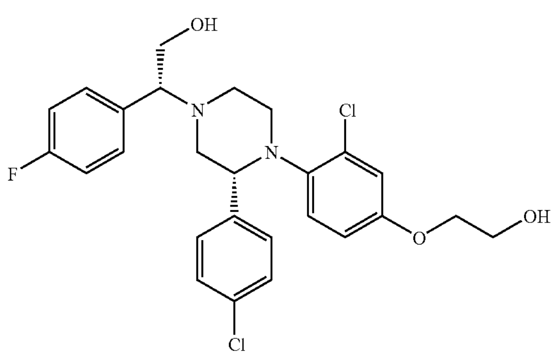 [SMILES: OCCOc1ccc(N2CCN([C@@H](CO)c3ccc(F)cc3)C[C@H]2c2ccc(Cl)cc2)c(Cl)c1] | 505.3 |
| 141 | 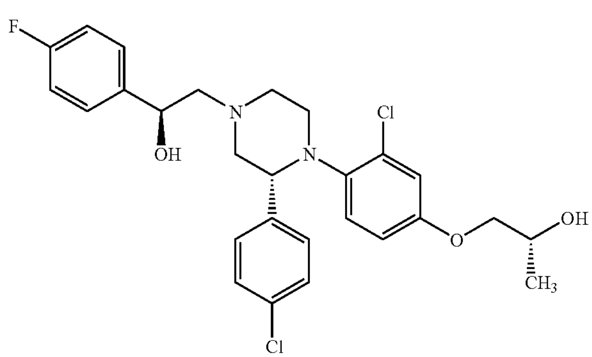 [SMILES: C[C@@H](O)COc1ccc(N2CCN(C[C@@H](O)c3ccc(F)cc3)C[C@H]2c2ccc(Cl)cc2)c(Cl)c1] | 519.3 |

| Ex. # | MOLECULAR STRUCTURE | OBSVD LCMS MS (MH+) |
|---|---|---|
| 142 | 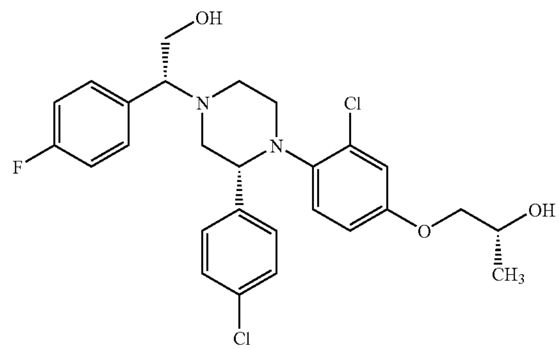 [SMILES: C[C@@H](O)COc1ccc(N2CCN([C@@H](CO)c3ccc(F)cc3)C[C@H]2c2ccc(Cl)cc2)c(Cl)c1] | 519.3 |
| 143 | 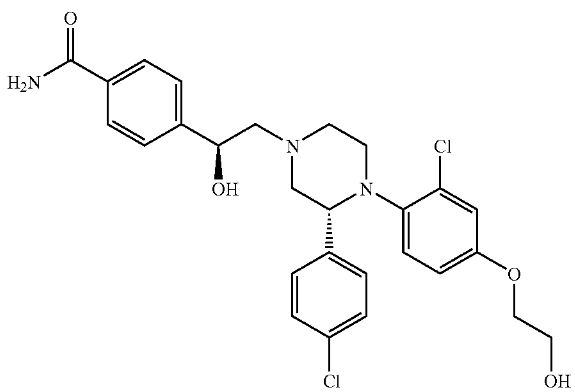 [SMILES: NC(=O)c1ccc([C@H](O)CN2CCN(c3ccc(OCCO)cc3Cl)[C@H](c3ccc(Cl)cc3)C2)cc1] | 530.3 |
| 144 | 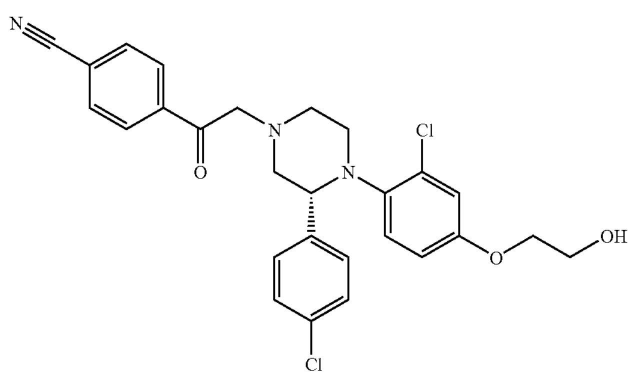 [SMILES: N#Cc1ccc(C(=O)CN2CCN(c3ccc(OCCO)cc3Cl)[C@H](c3ccc(Cl)cc3)C2)cc1] | 510.3 |
| 145 | 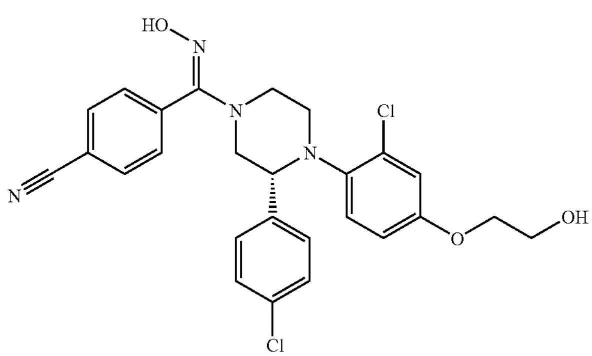 [SMILES: N#Cc1ccc(/C(=N\O)N2CCN(c3ccc(OCCO)cc3Cl)[C@H](c3ccc(Cl)cc3)C2)cc1] | 511.3 |

TABLE 23-continued

| Ex. # | MOLECULAR STRUCTURE | OBSVD LCMS MS (MH+) |
|---|---|---|
| 146 | 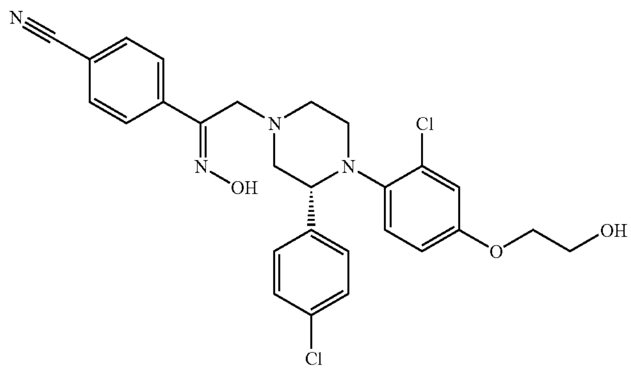 [SMILES: N#Cc1ccc(/C(CN2CCN(c3ccc(OCCO)cc3Cl)[C@H](c3ccc(Cl)cc3)C2)=N/O)cc1] | 525.3 |
| 147 | 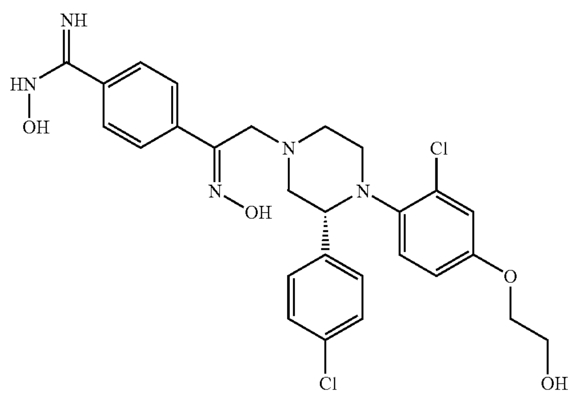 [SMILES: N=C(NO)c1ccc(/C(CN2CCN(c3ccc(OCCO)cc3Cl)[C@H](c3ccc(Cl)cc3)C2)=N/O)cc1] | 558.3 |
| 148 | 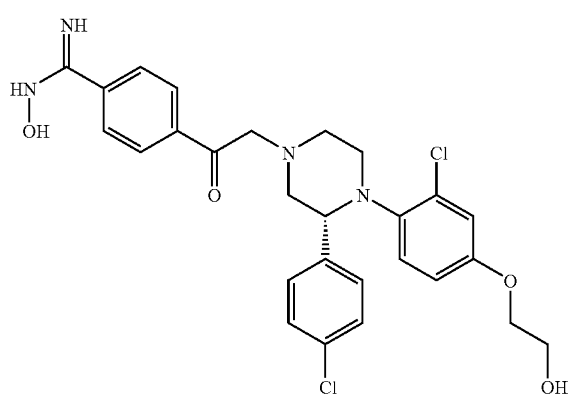 [SMILES: N=C(NO)c1ccc(C(=O)CN2CCN(c3ccc(OCCO)cc3Cl)[C@H](c3ccc(Cl)cc3)C2)cc1] | 543.3 |
| 149 | 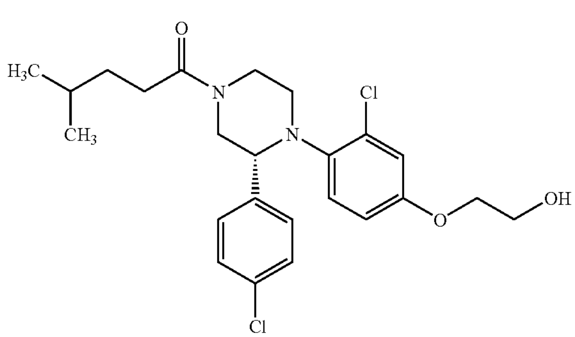 [SMILES: CC(C)CCC(=O)N1CCN(c2ccc(OCCO)cc2Cl)[C@H](c2ccc(Cl)cc2)C1] | 465.3 |

TABLE 23-continued
| Ex. # | MOLECULAR STRUCTURE | OBSVD LCMS MS (MH+) |
|---|---|---|
| 150 | 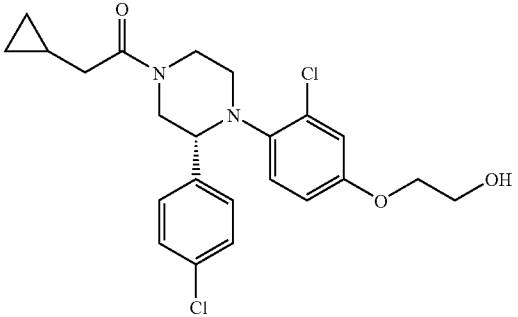 [SMILES: O=C(CC1CC1)N1CCN(c2ccc(OCCO)cc2Cl)[C@H](c2ccc(Cl)cc2)C1] | 449.3 |
| 151 | 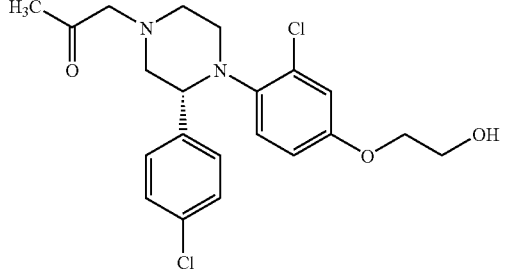 [SMILES: CC(=O)CN1CCN(c2ccc(OCCO)cc2Cl)[C@H](c2ccc(Cl)cc2)C1] | 423.2 |
| 152 | 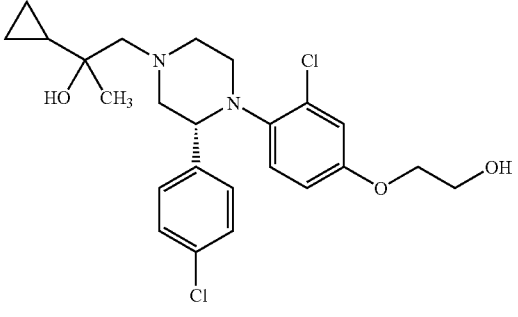 [SMILES: CC(O)(CN1CCN(c2ccc(OCCO)cc2Cl)[C@H](c2ccc(Cl)cc2)C1)C1CC1] | 465.3 |
| 153 | 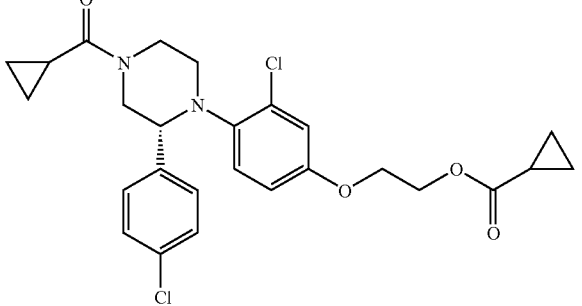 | 503.3 |

TABLE 23-continued

| Ex. # | MOLECULAR STRUCTURE | OBSVD LCMS MS (MH+) |
|---|---|---|
| 154 | 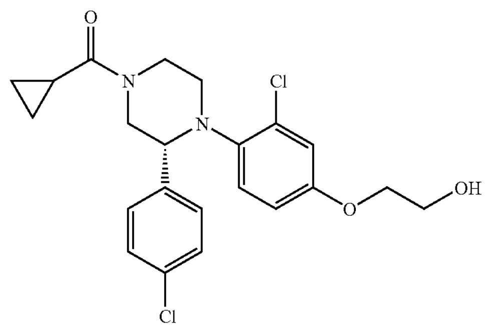 [SMILES: O=C(C1CC1)N1CCN(c2ccc(OCCO)cc2Cl)[C@H](c2ccc(Cl)cc2)C1] | 435.2 |
| 155 | 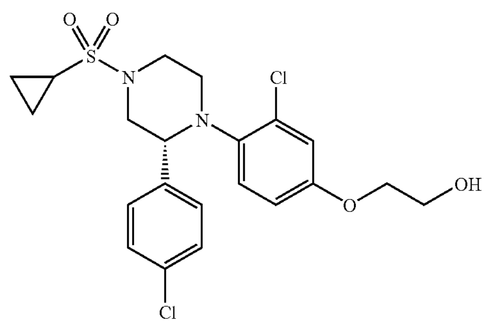 [SMILES: O=S(=O)(C1CC1)N1CCN(c2ccc(OCCO)cc2Cl)[C@H](c2ccc(Cl)cc2)C1] | 471.3 |
| 156 | 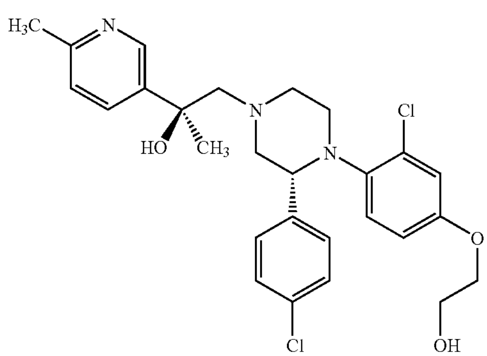 [SMILES: Cc1ccc([C@](C)(O)CN2CCN(c3ccc(OCCO)cc3Cl)[C@H](c3ccc(Cl)cc3)C2)cn1] | 516.3 |
| 157 | 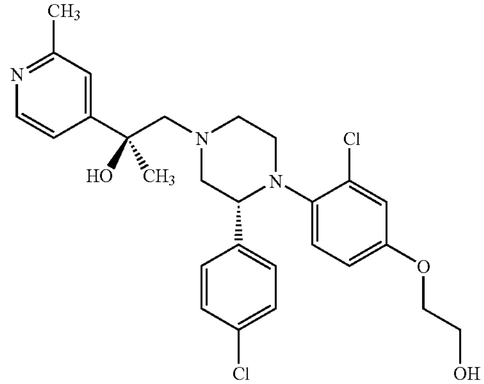 [SMILES: Cc1cc([C@](C)(O)CN2CCN(c3ccc(OCCO)cc3Cl)[C@H](c3ccc(Cl)cc3)C2)ccn1] | 531.3 |

TABLE 23-continued

| Ex. # | MOLECULAR STRUCTURE | OBSVD LCMS MS (MH+) |
|---|---|---|
| 158 | 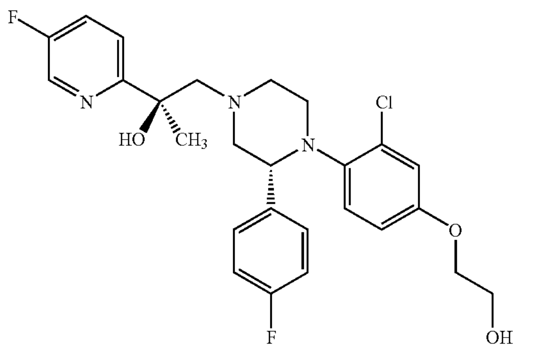 [SMILES: C[C@@](O)(CN1CCN(c2ccc(OCCO)cc2Cl)[C@H](c2ccc(F)cc2)C1)c1ccc(F)cn1] | 504.3 |
| 159 | 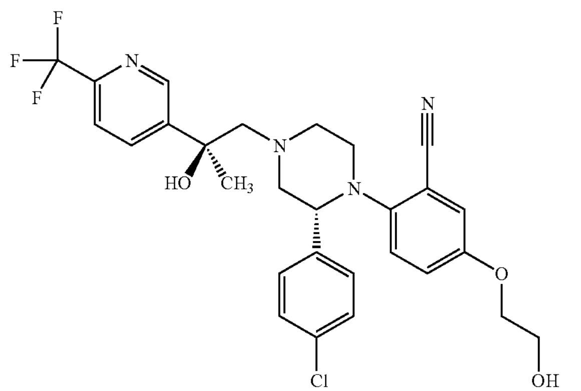 [SMILES: C[C@@](O)(CN1CCN(c2ccc(OCCO)cc2C#N)[C@H](c2ccc(Cl)cc2)C1)c1ccc(C(F)(F)F)nc1] | 561.3 |
| 160 | 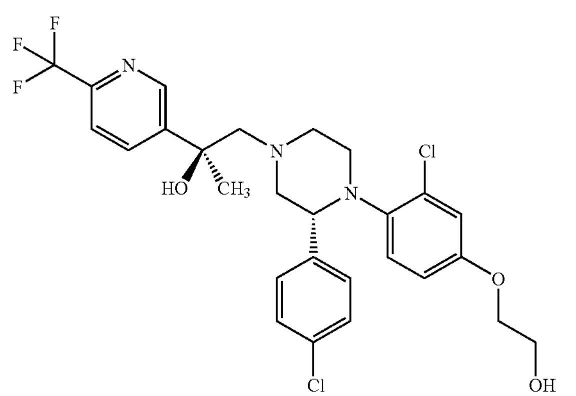 [SMILES: C[C@@](O)(CN1CCN(c2ccc(OCCO)cc2Cl)[C@H](c2ccc(Cl)cc2)C1)c1ccc(C(F)(F)F)nc1] | 570.3 |
| 161 | 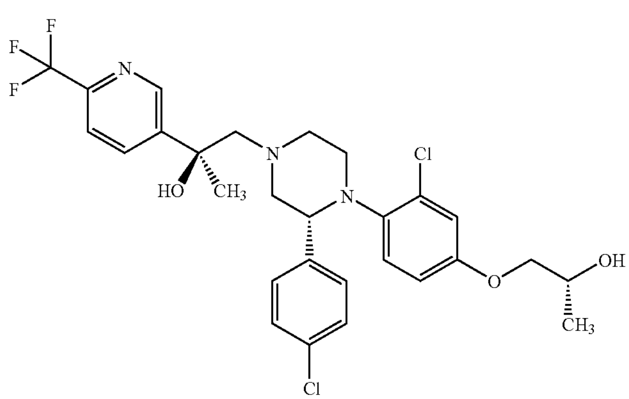 [SMILES: C[C@@H](O)COc1ccc(N2CCN(C[C@@](C)(O)c3ccc(C(F)(F)F)nc3)C[C@H]2c2ccc(Cl)cc2)c(Cl)c1] | 584.3 |

TABLE 23-continued

| Ex. # | MOLECULAR STRUCTURE | OBSVD LCMS MS (MH+) |
|---|---|---|
| 162 | 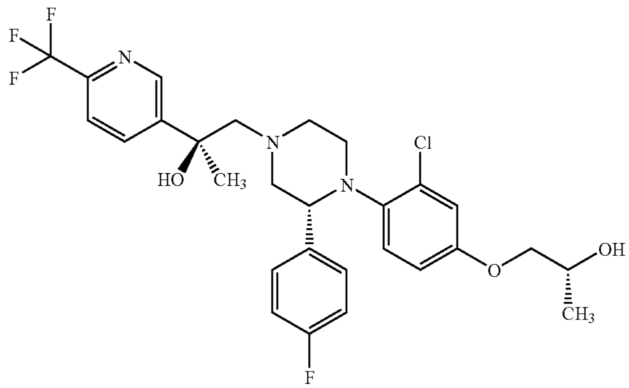 [SMILES: C[C@@H](O)COc1ccc(N2CCN(C[C@@](C)(O)c3ccc(C(F)(F)F)nc3)C[C@H]2c2ccc(F)cc2)c(Cl)c1] | 568.3 |
| 163 | 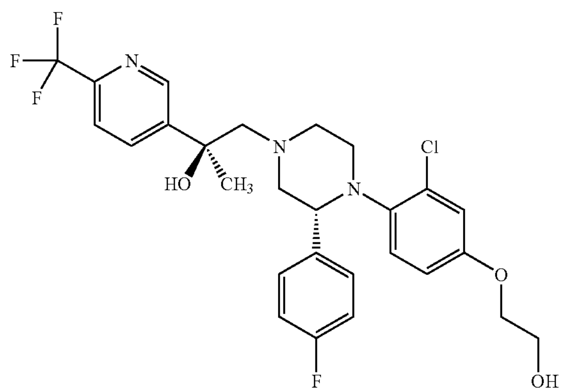 [SMILES: C[C@@](O)(CN1CCN(c2ccc(OCCO)cc2Cl)[C@H](c2ccc(F)cc2)C1)c1ccc(C(F)(F)F)nc1] | 554.3 |
| 164 | 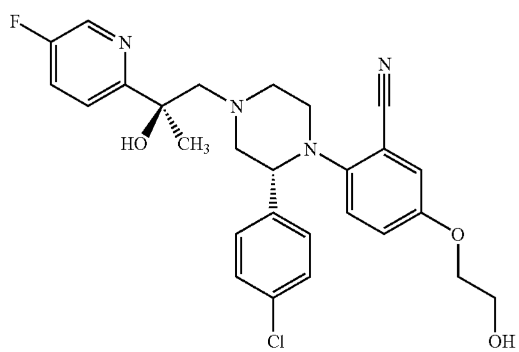 | 511.3 |
| 165 | 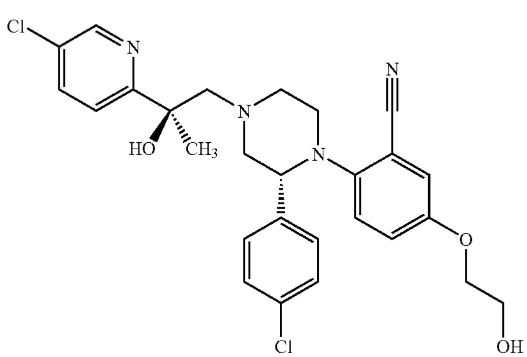 [SMILES: C[C@@](O)(CN1CCN(c2ccc(OCCO)cc2C#N)[C@H](c2ccc(Cl)cc2)C1)c1ccc(Cl)cn1] | 527.3 |

TABLE 23-continued

| Ex. # | MOLECULAR STRUCTURE | OBSVD LCMS MS (MH+) |
|---|---|---|
| 166 | 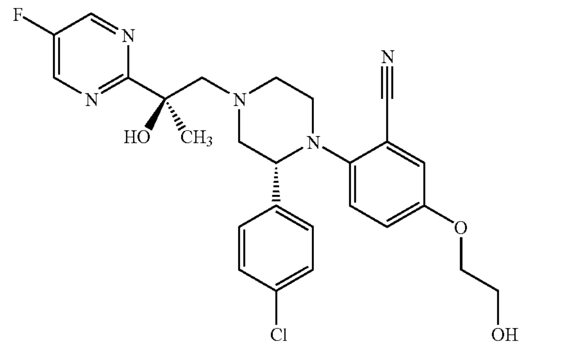 [SMILES: C[C@@](O)(CN1CCN(c2ccc(OCCO)cc2C#N)[C@H](c2ccc(Cl)cc2)C1)c1ncc(F)cn1] | 512.3 |
| 167 | 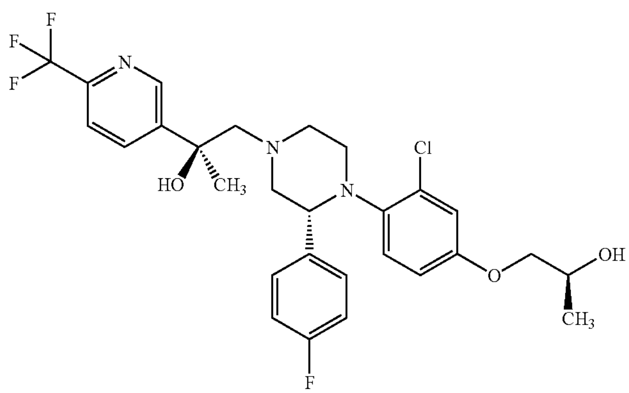 [SMILES: C[C@H](O)COc1ccc(N2CCN(C[C@@](C)(O)c3ccc(C(F)(F)F)nc3)C[C@H]2c2ccc(F)cc2)c(Cl)c1] | 568.3 |
| 168 | 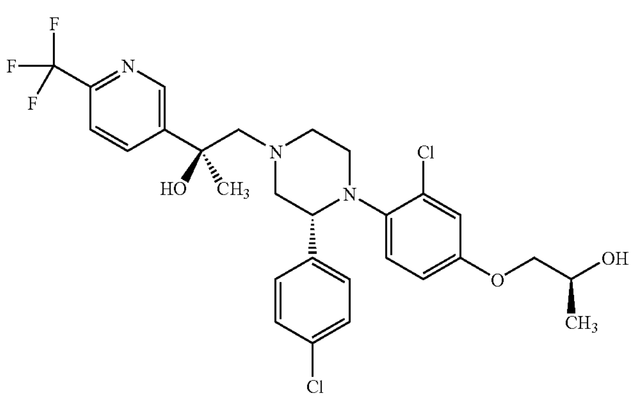 [SMILES: C[C@H](O)COc1ccc(N2CCN(C[C@@](C)(O)c3ccc(C(F)(F)F)nc3)C[C@H]2c2ccc(Cl)cc2)c(Cl)c1] | 584.7 |
| 169 | 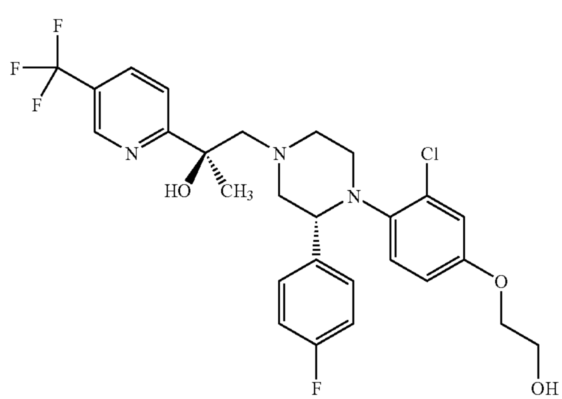 [SMILES: C[C@@](O)(CN1CCN(c2ccc(OCCO)cc2Cl)[C@H](c2ccc(F)cc2)C1)c1ccc(C(F)(F)F)cn1] | 554.3 |

TABLE 23-continued

| Ex. # | MOLECULAR STRUCTURE | OBSVD LCMS MS (MH+) |
|---|---|---|
| 170 | 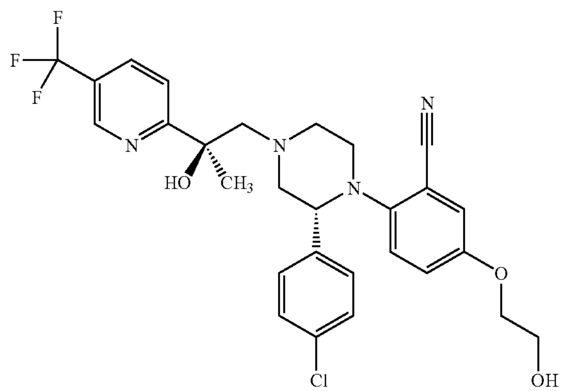 [SMILES: C[C@@](O)(CN1CCN(c2ccc(OCCO)cc2C#N)[C@H](c2ccc(Cl)cc2)C1)c1ccc(C(F)(F)F)cn1] | 561.3 |
| 171 | 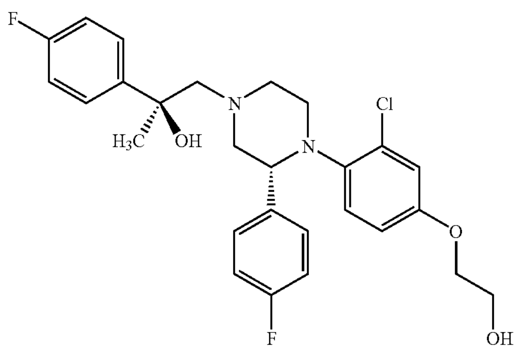 [SMILES: C[C@@](O)(CN1CCN(c2ccc(OCCO)cc2Cl)[C@H](c2ccc(F)cc2)C1)c1ccc(F)cc1] | 503.3 |
| 172 | 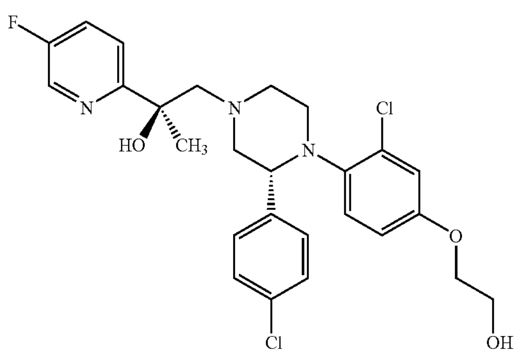 | 520.3 |
| 173 | 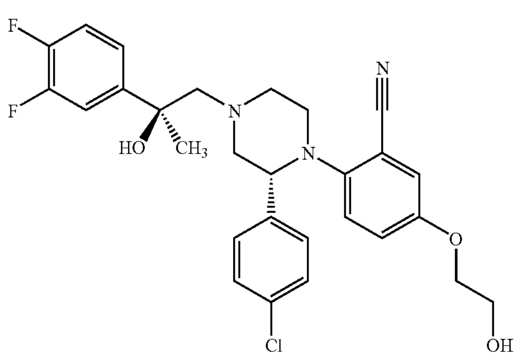 [SMILES: C[C@@](O)(CN1CCN(c2ccc(OCCO)cc2C#N)[C@H](c2ccc(Cl)cc2)C1)c1ccc(F)c(F)c1] | 528.3 |

TABLE 23-continued

| Ex. # | MOLECULAR STRUCTURE | OBSVD LCMS MS (MH+) |
|---|---|---|
| 174 | 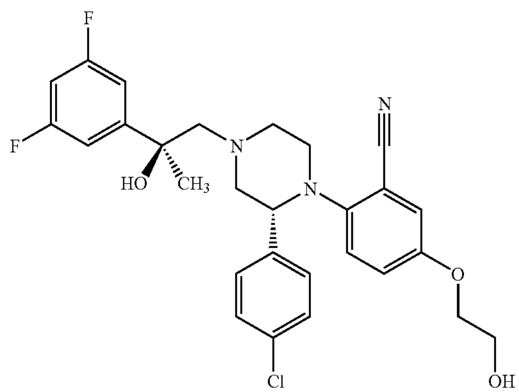 [SMILES: C[C@@](O)(CN1CCN(c2ccc(OCCO)cc2C#N)[C@H](c2ccc(Cl)cc2)C1)c1cc(F)cc(F)c1] | 528.3 |
| 175 | 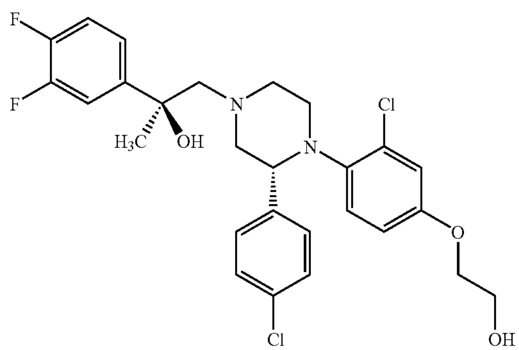 | 537.3 |
| 176 | 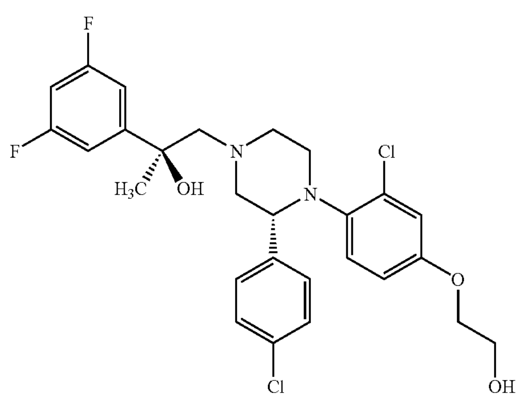 [SMILES: C[C@@](O)(CN1CCN(c2ccc(OCCO)cc2Cl)[C@H](c2ccc(Cl)cc2)C1)c1cc(F)cc(F)c1] | 537.3 |
| 177 | 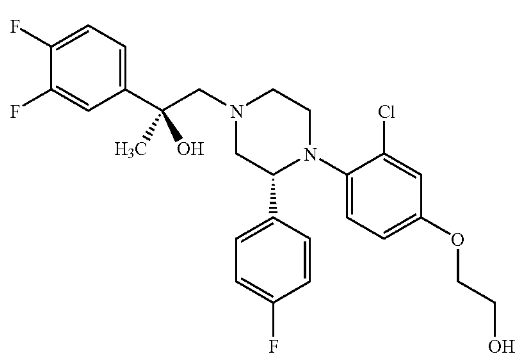 [SMILES: C[C@@](O)(CN1CCN(c2ccc(OCCO)cc2Cl)[C@H](c2ccc(F)cc2)C1)c1ccc(F)c(F)c1] | 521.3 |

TABLE 23-continued

| Ex. # | MOLECULAR STRUCTURE | OBSVD LCMS MS (MH+) |
|---|---|---|
| 178 | 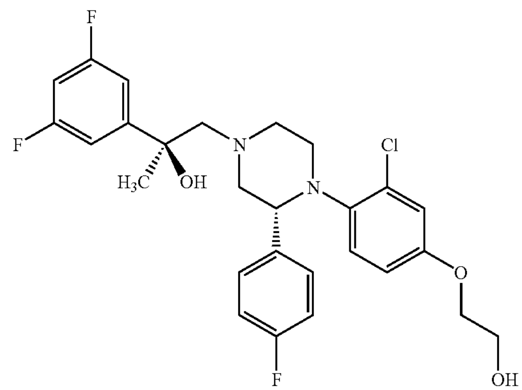 [SMILES: C[C@@](O)(CN1CCN(c2ccc(OCCO)cc2Cl)[C@H](c2ccc(F)cc2)C1)c1cc(F)cc(F)c1] | 521.3 |
| 179 | 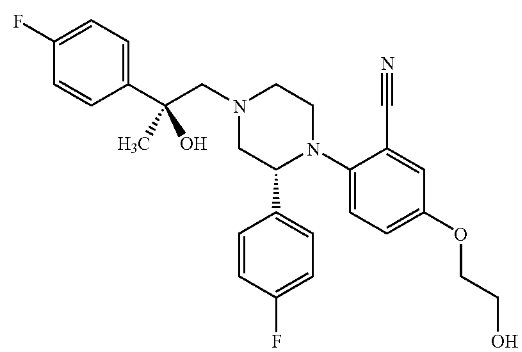 [SMILES: C[C@@](O)(CN1CCN(c2ccc(OCCO)cc2C#N)[C@H](c2ccc(F)cc2)C1)c1ccc(F)cc1] | 494.3 |
| 180 | 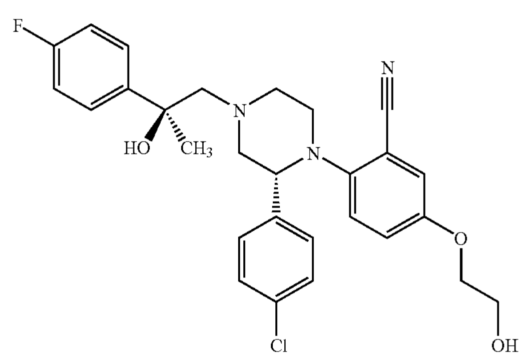 [SMILES: C[C@@](O)(CN1CCN(c2ccc(OCCO)cc2C#N)[C@H](c2ccc(Cl)cc2)C1)c1ccc(F)cc1] | 510.3 |
| 181 | 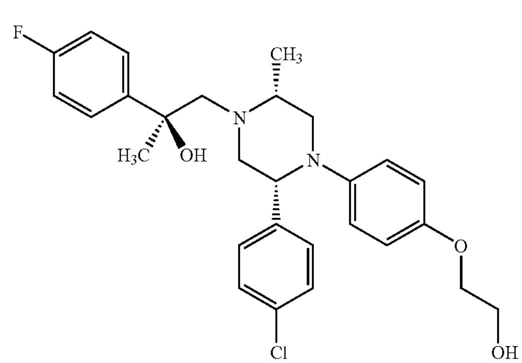 [SMILES: C[C@@H]1CN(c2ccc(OCCO)cc2)[C@H](c2ccc(Cl)cc2)CN1C[C@@](C)(O)c1ccc(F)cc1] | 499.3 |

TABLE 23-continued

| Ex. # | MOLECULAR STRUCTURE | OBSVD LCMS MS (MH+) |
|---|---|---|
| 182 | 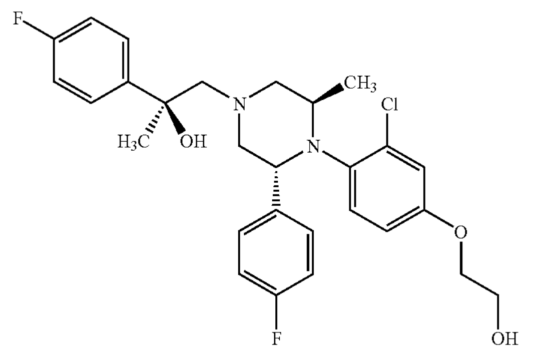 [SMILES: C[C@@H]1CN(C[C@@](C)(O)c2ccc(F)cc2)C[C@@H](c2ccc(F)cc2)N1c1ccc(OCCO)cc1Cl] | 517.3 |
| 183 | 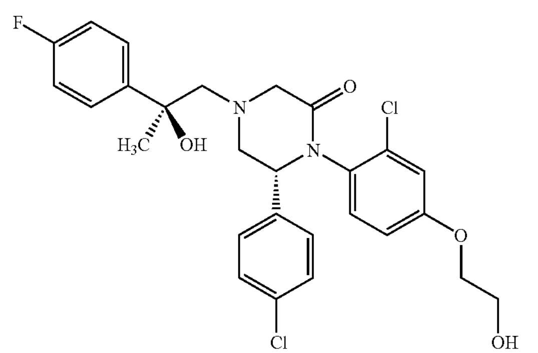 [SMILES: C[C@@](O)(CN1CC(=O)N(c2ccc(OCCO)cc2Cl)[C@H](c2ccc(Cl)cc2)C1)c1ccc(F)cc1] | 533.3 |
| 184 | 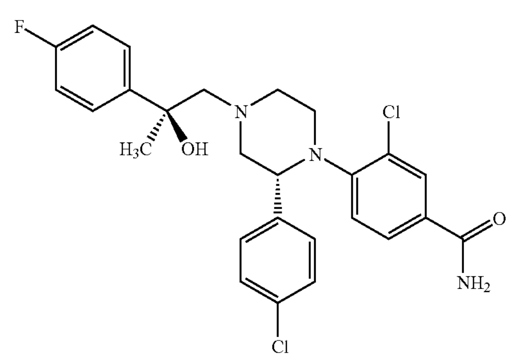 [SMILES: C[C@@](O)(CN1CCN(c2ccc(C(N)=O)cc2Cl)[C@H](c2ccc(Cl)cc2)C1)c1ccc(F)cc1] | 502.3 |
| 185 | 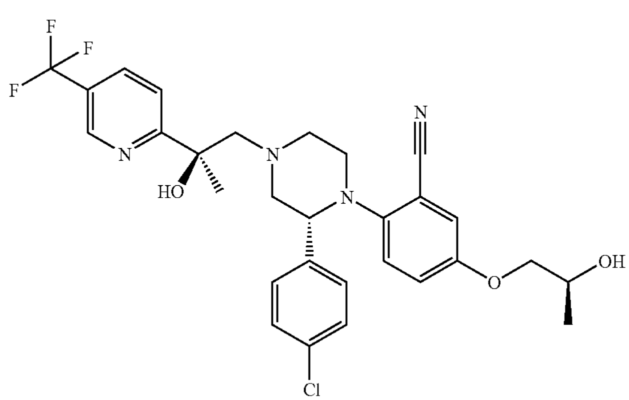 [SMILES: C[C@H](O)COc1ccc(N2CCN(C[C@@](C)(O)c3ccc(C(F)(F)F)cn3)C[C@H]2c2ccc(Cl)cc2)c(C#N)c1] | 575.3 |

TABLE 23-continued

| Ex. # | MOLECULAR STRUCTURE | OBSVD LCMS MS (MH+) |
|---|---|---|
| 186 | 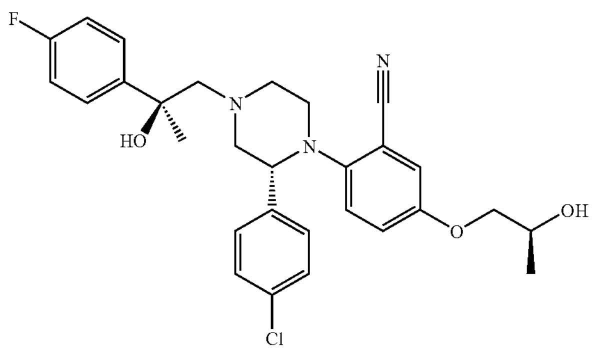 [SMILES: C[C@H](O)COc1ccc(N2CCN(C[C@@](C)(O)c3ccc(F)cc3)C[C@H]2c2ccc(Cl)cc2)c(C#N)c1] | 524.3 |
| 187 | 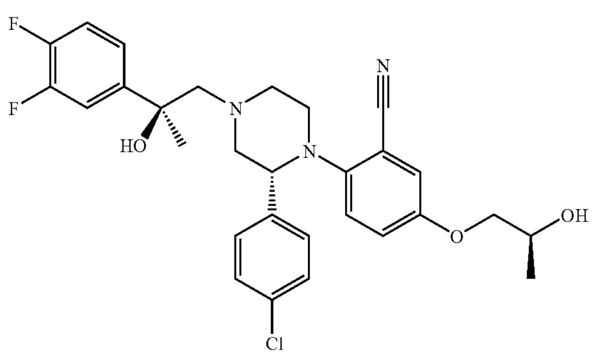 [SMILES: C[C@H](O)COc1ccc(N2CCN(C[C@@](C)(O)c3ccc(F)c(F)c3)C[C@H]2c2ccc(Cl)cc2)c(C#N)c1] | 542.3 |
| 188 | 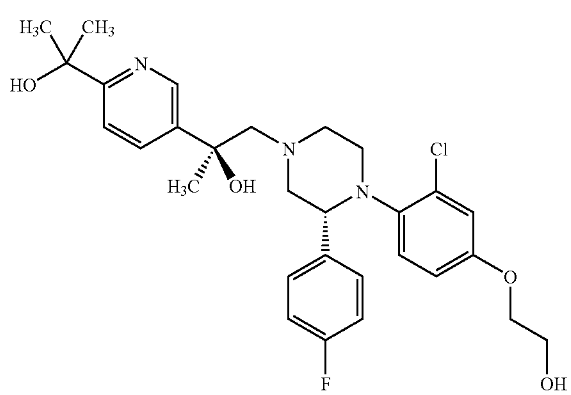 [SMILES: CC(C)(O)c1ccc([C@](C)(O)CN2CCN(c3ccc(OCCO)cc3Cl)[C@H](c3ccc(F)cc3)C2)cn1] | 544.3 |
| 189 | 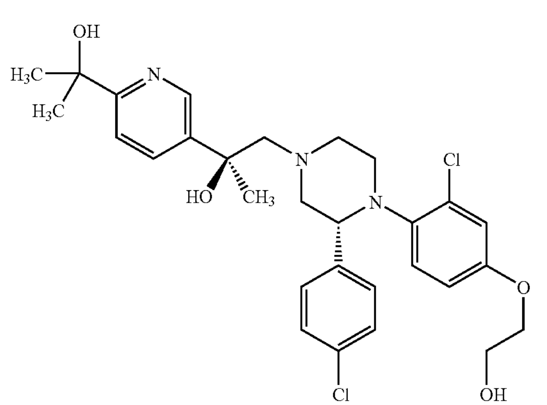 [SMILES: CC(C)(O)c1ccc([C@](C)(O)CN2CCN(c3ccc(OCCO)cc3Cl)[C@H](c3ccc(Cl)cc3)C2)cn1] | 560.3 |

TABLE 23-continued

| Ex. # | MOLECULAR STRUCTURE | OBSVD LCMS MS (MH+) |
|---|---|---|
| 190 | 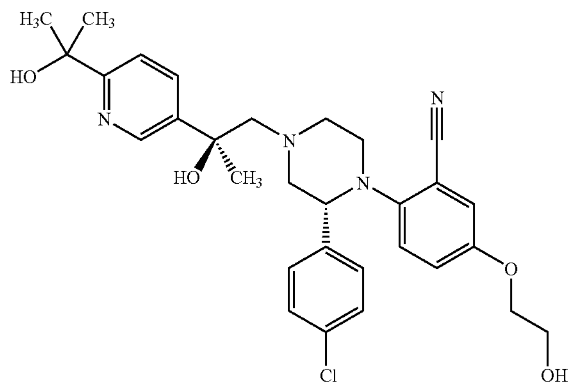 [SMILES: CC(C)(O)c1ccc([C@](C)(O)CN2CCN(c3ccc(OCCO)cc3C#N)[C@H](c3ccc(Cl)cc3)C2)cn1] | 551.3 |
| 191 | 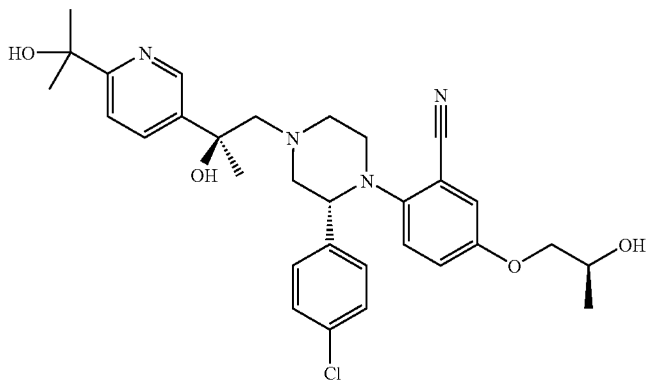 [SMILES: C[C@H](O)COc1ccc(N2CCN(C[C@@](C)(O)c3ccc(C(C)(C)O)nc3)C[C@H]2c2ccc(Cl)cc2)c(C#N)c1] | 565.3 |
| 192 | 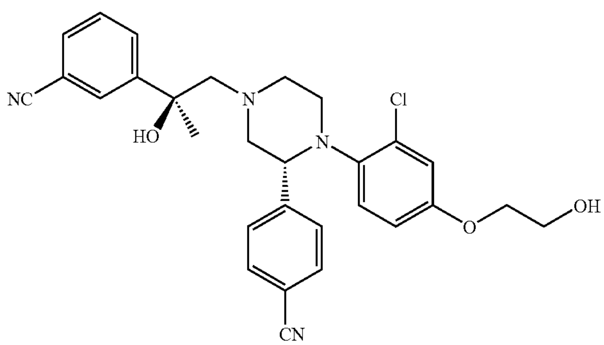 | 517.3 |
| 193 | 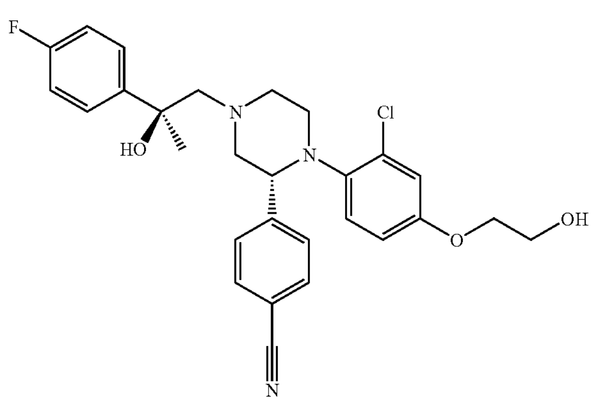 [SMILES: C[C@@](O)(CN1CCN(c2ccc(OCCO)cc2Cl)[C@H](c2ccc(C#N)cc2)C1)c1ccc(F)cc1] | 510.3 |

TABLE 23-continued

| Ex. # | MOLECULAR STRUCTURE | OBSVD LCMS MS (MH+) |
|---|---|---|
| 194 | 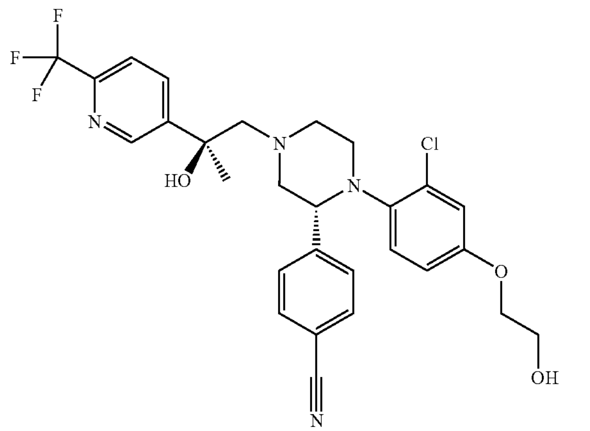 [SMILES: C[C@@](O)(CN1CCN(c2ccc(OCCO)cc2Cl)[C@H](c2ccc(C#N)cc2)C1)c1ccc(C(F)(F)F)nc1] | 561.3 |
| 195 | 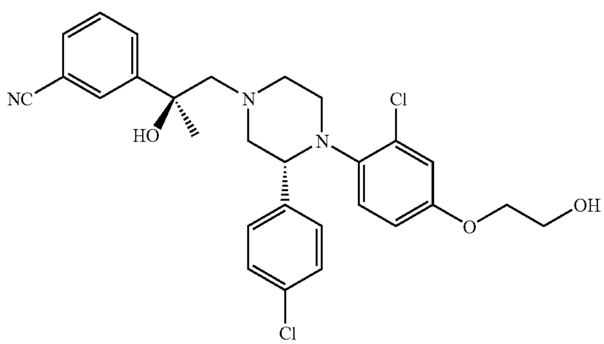 | 526.3 |
| 196 | 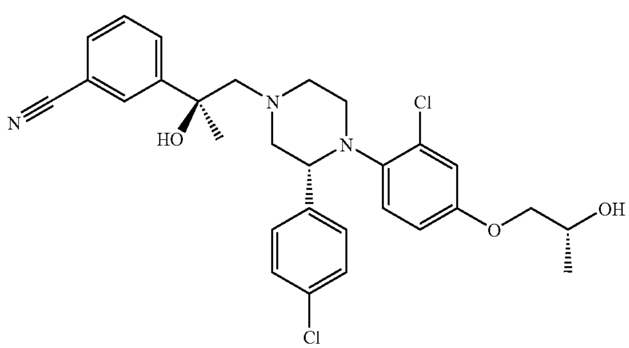 [SMILES: C[C@@H](O)COc1ccc(N2CCN(C[C@@](C)(O)c3cccc(C#N)c3)C[C@H]2c2ccc(Cl)cc2)c(Cl)c1] | 540.3 |
| 197 | 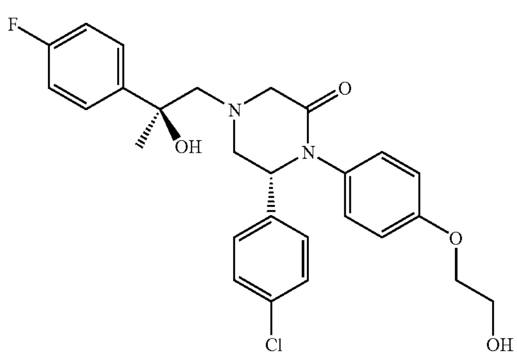 | 499.3 |

TABLE 23-continued

| Ex. # | MOLECULAR STRUCTURE | OBSVD LCMS MS (MH+) |
|---|---|---|
| 198 | 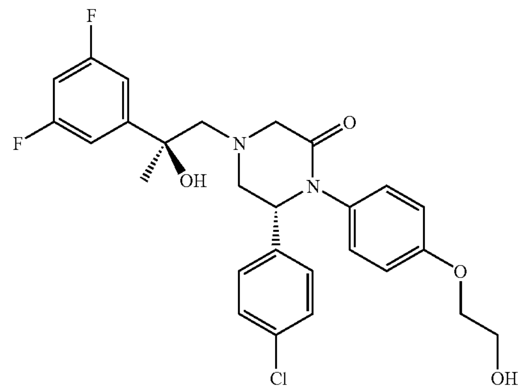 [SMILES: C[C@@](O)(CN1CC(=O)N(c2ccc(OCCO)cc2)[C@H](c2ccc(Cl)cc2)C1)c1cc(F)cc(F)c1] | 517.3 |
| 199 | 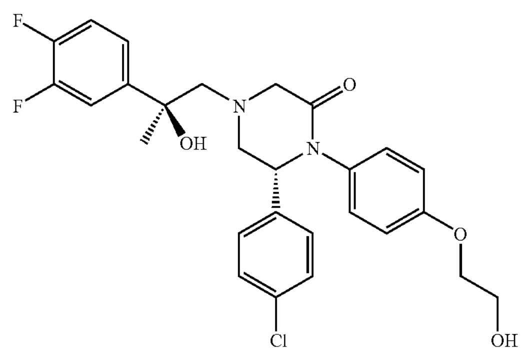 [SMILES: C[C@@](O)(CN1CC(=O)N(c2ccc(OCCO)cc2)[C@H](c2ccc(Cl)cc2)C1)c1ccc(F)c(F)c1] | 517.3 |
| 200 | 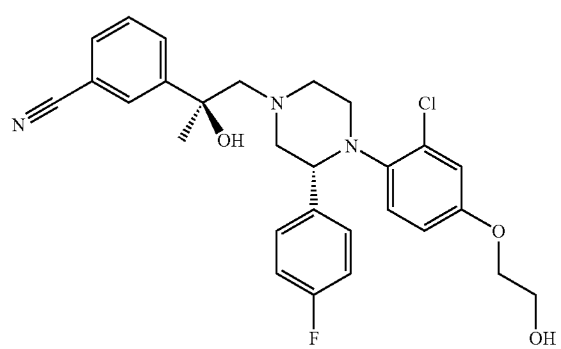 [SMILES: C[C@@](O)(CN1CCN(c2ccc(OCCO)cc2Cl)[C@H](c2ccc(F)cc2)C1)c1cccc(C#N)c1] | 510.3 |
| 200a | 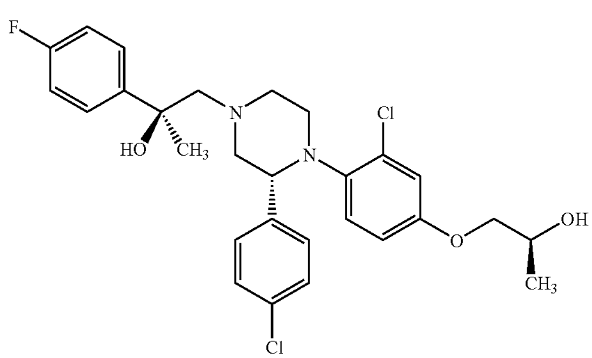 [SMILES: C[C@H](O)COc1ccc(N2CCN(C[C@@](C)(O)c3ccc(F)cc3)C[C@H]2c2ccc(Cl)cc2)c(Cl)c1] | 533.3 |

TABLE 23-continued

| Ex. # | MOLECULAR STRUCTURE | OBSVD LCMS MS (MH+) |
|---|---|---|
| 200b | 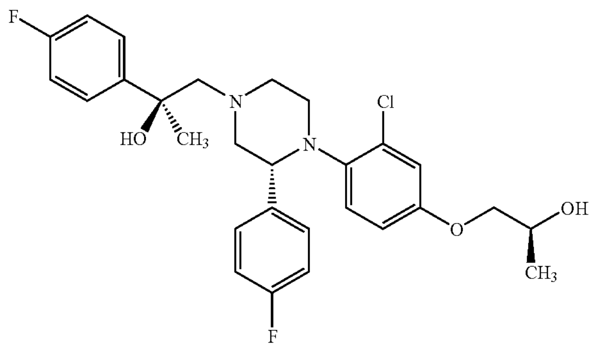 [SMILES: C[C@H](O)COc1ccc(N2CCN(C[C@@](C)(O)c3ccc(F)cc3)C[C@H]2c2ccc(F)cc2)c(Cl)c1] | 517.3 |
| 200c | 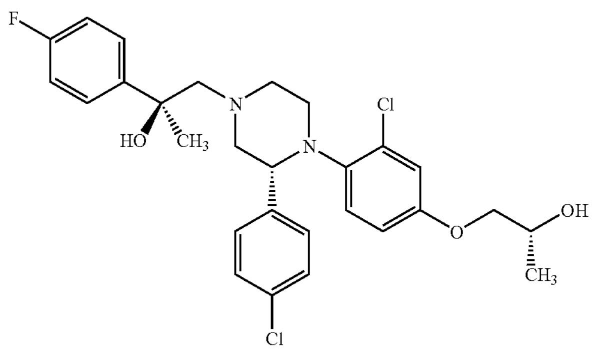 [SMILES: C[C@@H](O)COc1ccc(N2CCN(C[C@@](C)(O)c3ccc(F)cc3)C[C@H]2c2ccc(Cl)cc2)c(Cl)c1] | 533.3 |
| 200d | 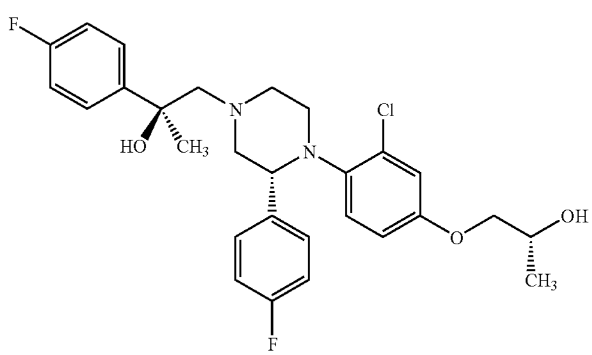 [SMILES: C[C@@H](O)COc1ccc(N2CCN(C[C@@](C)(O)c3ccc(F)cc3)C[C@H]2c2ccc(F)cc2)c(Cl)c1] | 517.3 |
| 200e | 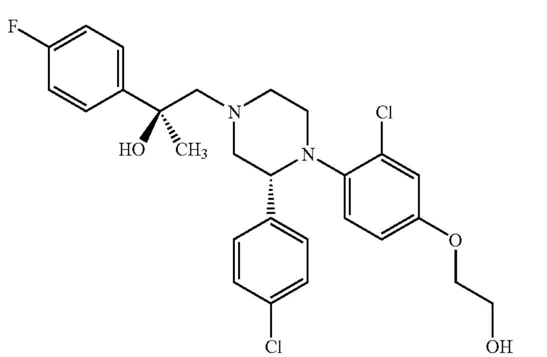 [SMILES: C[C@@](O)(CN1CCN(c2ccc(OCCO)cc2Cl)[C@H](c2ccc(Cl)cc2)C1)c1ccc(F)cc1] | 519.3 |

TABLE 23-continued
| Ex. # | MOLECULAR STRUCTURE | OBSVD LCMS MS (MH+) |
|---|---|---|
| 200F | 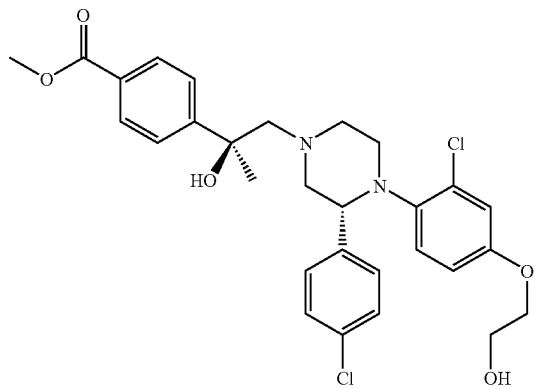 [SMILES: COC(=O)c1ccc([C@](C)(O)CN2CCN(c3ccc(OCCO)cc3Cl)[C@H](c3ccc(Cl)cc3)C2)cc1] | 559.3 |
| 200g | 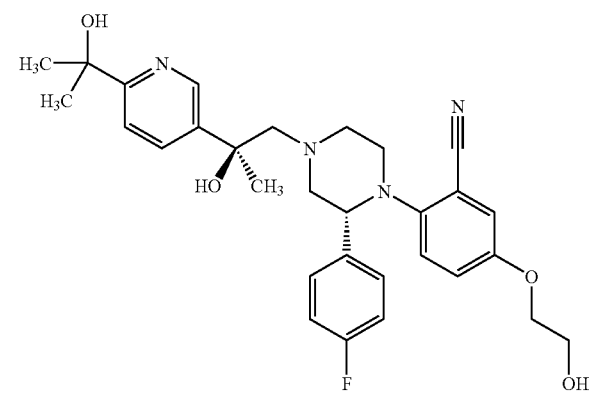 [SMILES: CC(C)(O)c1ccc([C@](C)(O)CN2CCN(c3ccc(OCCO)cc3C#N)[C@H](c3ccc(F)cc3)C2)cn1] | 535.3 |
| 200h | 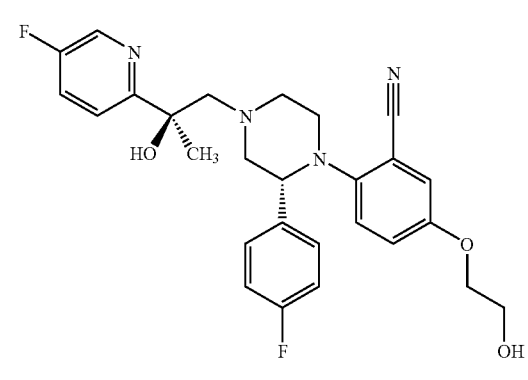 [SMILES: C[C@@](O)(CN1CCN(c2ccc(OCCO)cc2C#N)[C@H](c2ccc(F)cc2)C1)c1ccc(F)cn1] | 495.3 |
| 200i | 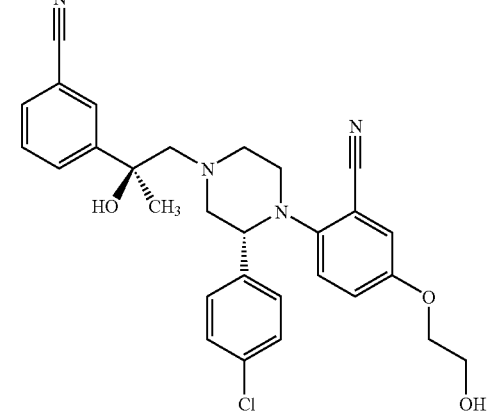 | 517.3 |

TABLE 23-continued
| Ex. # | MOLECULAR STRUCTURE | OBSVD LCMS MS (MH+) |
|---|---|---|
| 200j | 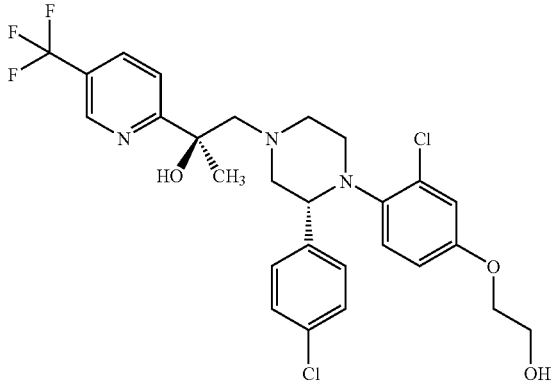 [SMILES: C[C@@](O)(CN1CCN(c2ccc(OCCO)cc2Cl)[C@H](c2ccc(Cl)cc2)C1)c1ccc(C(F)(F)F)cn1] | 531.3 |
| 200k | 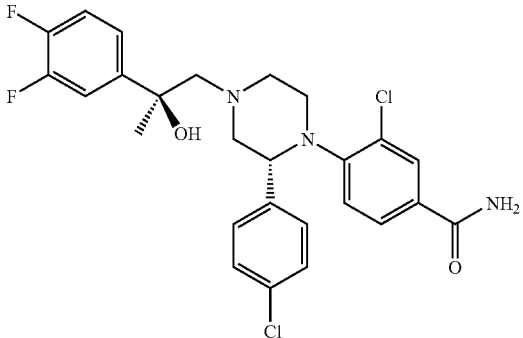 [SMILES: C[C@@](O)(CN1CCN(c2ccc(C(N)=O)cc2Cl)[C@H](c2ccc(Cl)cc2)C1)c1ccc(F)c(F)c1] | 520.3 |
| 200l | 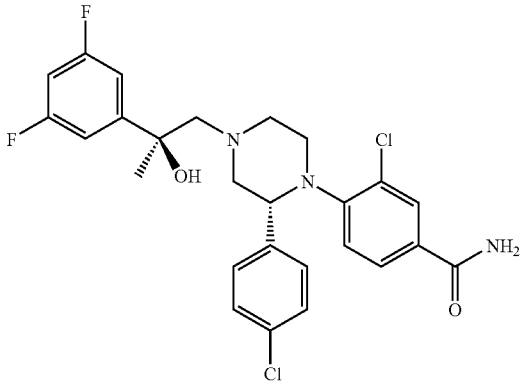 [SMILES: C[C@@](O)(CN1CCN(c2ccc(C(N)=O)cc2Cl)[C@H](c2ccc(Cl)cc2)C1)c1cc(F)cc(F)c1] | 520.3 |
| 200m | 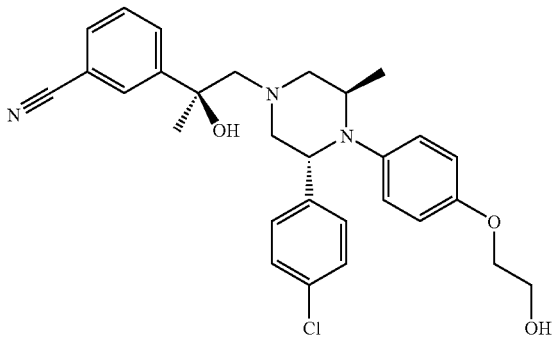 [SMILES: C[C@@H]1CN(C[C@@](C)(O)c2cccc(C#N)c2)C[C@@H](c2ccc(Cl)cc2)N1c1ccc(OCCO)cc1] | 506.3 |

TABLE 23-continued

| Ex. # | MOLECULAR STRUCTURE | OBSVD LCMS MS (MH+) |
|---|---|---|
| 200n | 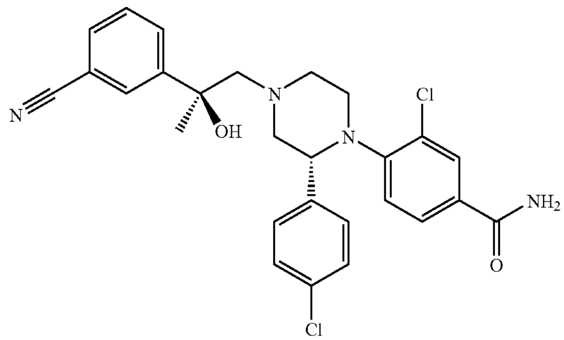 [SMILES: C[C@@](O)(CN1CCN(c2ccc(C(N)=O)cc2Cl)[C@H](c2ccc(Cl)cc2)C1)c1cccc(C#N)c1] | 509.3 |
| 200o | 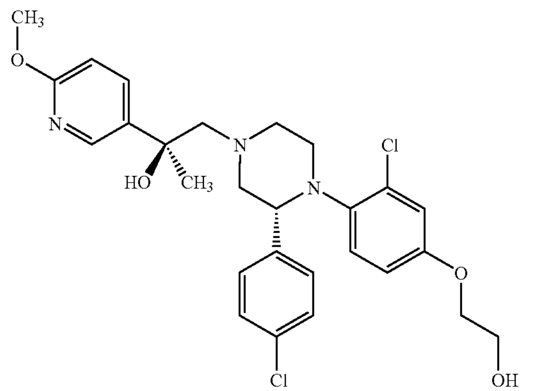 [SMILES: COc1ccc([C@](C)(O)CN2CCN(c3ccc(OCCO)cc3Cl)[C@H](c3ccc(Cl)cc3)C2)cn1] | 532.3 |
| 200p | 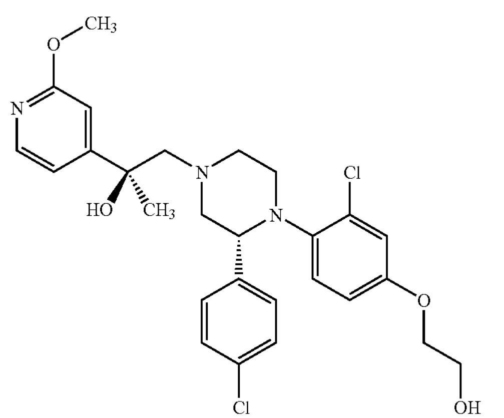 [SMILES: COc1cc([C@](C)(O)CN2CCN(c3ccc(OCCO)cc3Cl)[C@H](c3ccc(Cl)cc3)C2)ccn1] | 532.3 |
| 200q | 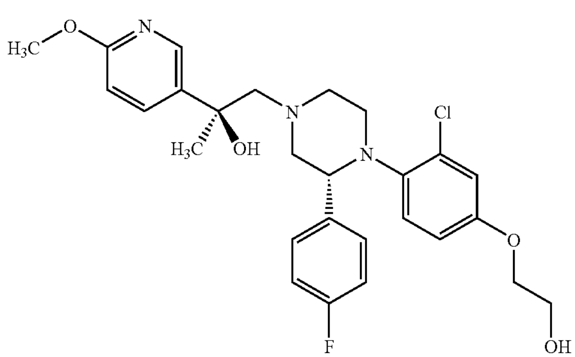 [SMILES: COc1ccc([C@](C)(O)CN2CCN(c3ccc(OCCO)cc3Cl)[C@H](c3ccc(F)cc3)C2)cn1] | 516.3 |

TABLE 23-continued

| Ex. # | MOLECULAR STRUCTURE | OBSVD LCMS MS (MH+) |
|---|---|---|
| 200r | 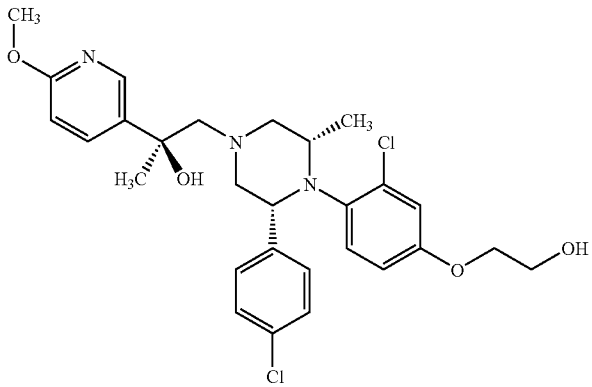 [SMILES: COc1ccc([C@](C)(O)CN2C[C@H](C)N(c3ccc(OCCO)cc3Cl)[C@H](c3ccc(Cl)cc3)C2)cn1] | 546.3 |
| 200s | 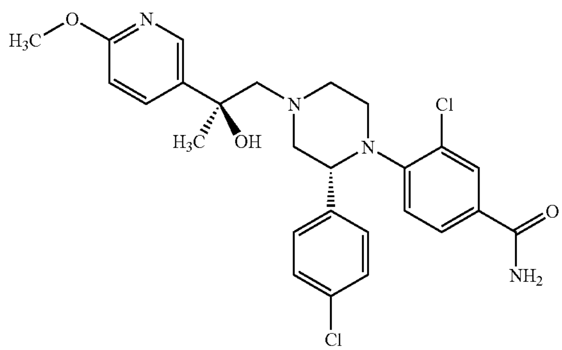 [SMILES: COc1ccc([C@](C)(O)CN2CCN(c3ccc(C(N)=O)cc3Cl)[C@H](c3ccc(Cl)cc3)C2)cn1] | 515.3 |
| 201 | 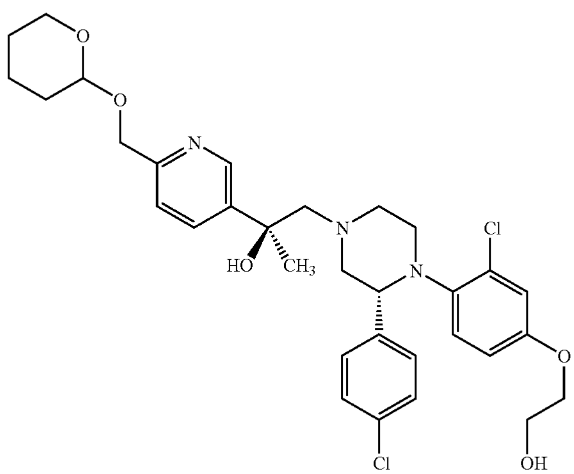 | 616.3 |
| 202 | 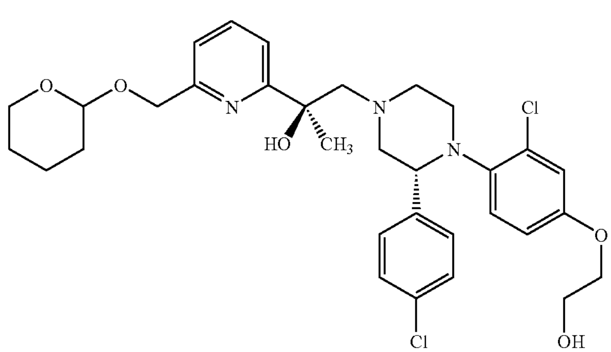 [SMILES: C[C@@](O)(CN1CCN(c2ccc(OCCO)cc2Cl)[C@H](c2ccc(Cl)cc2)C1)c1cccc(COC2CCCCO2)n1] | 616.3 |

TABLE 23-continued

| Ex. # | MOLECULAR STRUCTURE | OBSVD LCMS MS (MH+) |
|---|---|---|
| 203a | 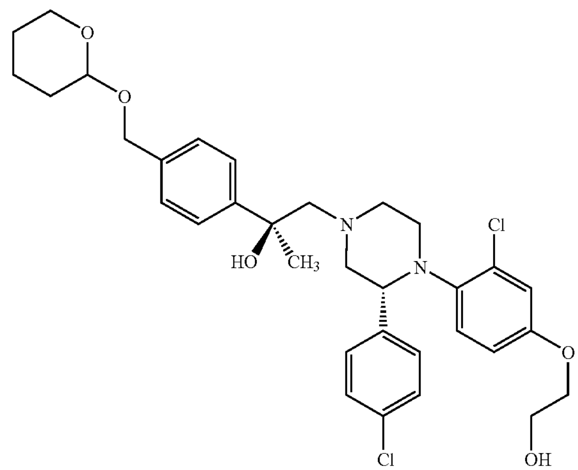 [SMILES: C[C@@](O)(CN1CCN(c2ccc(OCCO)cc2Cl)[C@H](c2ccc(Cl)cc2)C1)c1ccc(COC2CCCCO2)cc1] | 615.3 |
| 203 | 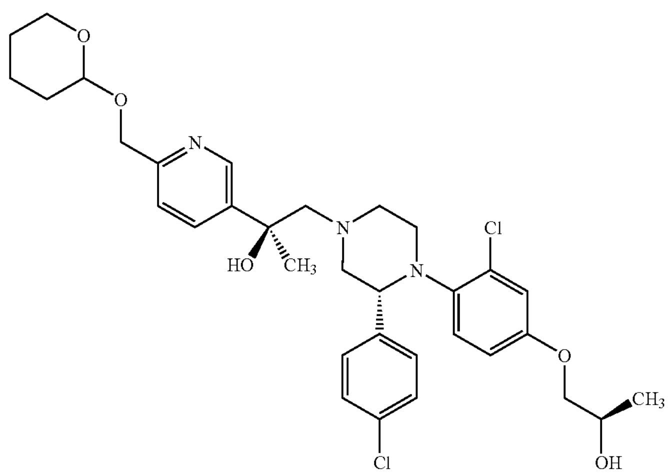 [SMILES: C[C@@H](O)COc1ccc(N2CCN(C[C@@](C)(O)c3ccc(COC4CCCCO4)nc3)C[C@H]2c2ccc(Cl)cc2)c(Cl)c1] | 630.3 |
| 204 | 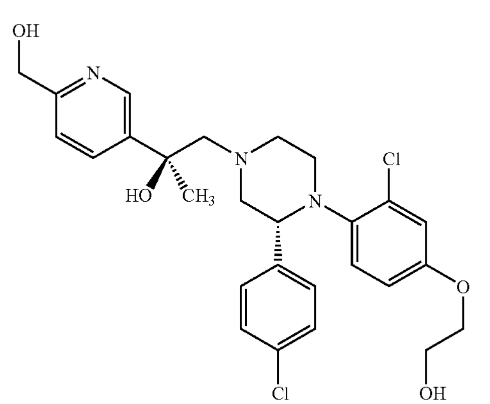 [SMILES: C[C@@](O)(CN1CCN(c2ccc(OCCO)cc2Cl)[C@H](c2ccc(Cl)cc2)C1)c1ccc(CO)nc1] | 532.3 |

TABLE 23-continued
| Ex. # | MOLECULAR STRUCTURE | OBSVD LCMS MS (MH+) |
|---|---|---|
| 205 | 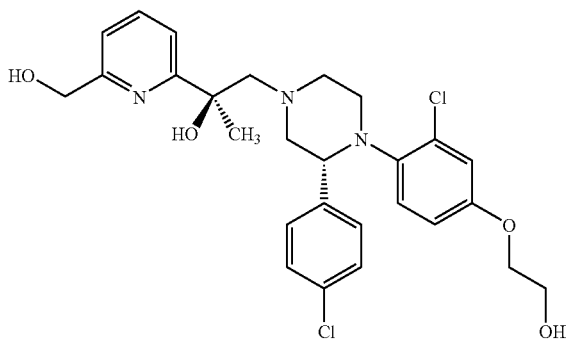 [SMILES: C[C@@](O)(CN1CCN(c2ccc(OCCO)cc2Cl)[C@H](c2ccc(Cl)cc2)C1)c1cccc(CO)n1] | 532.3 |
| 206a | 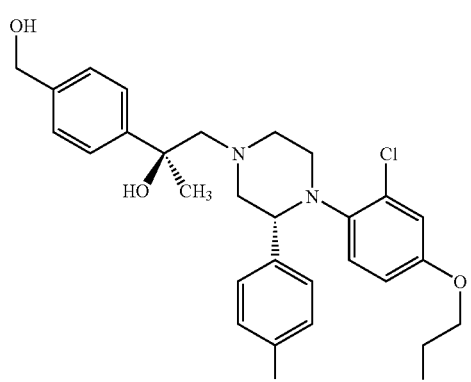 | 531.3 |
| 206 | 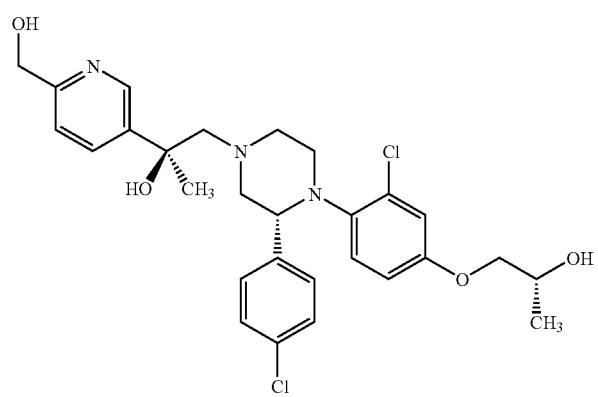 | 546.3 |
| 207 | 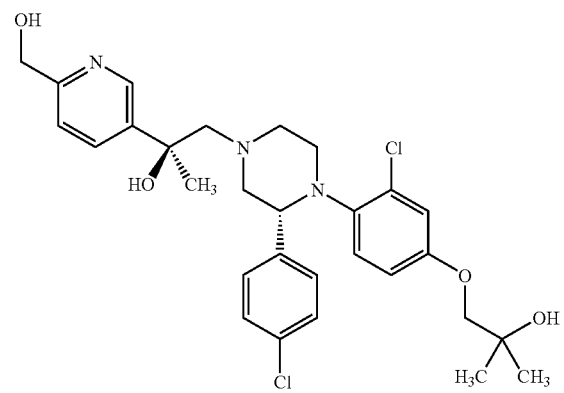 [SMILES: CC(C)(O)COc1ccc(N2CCN(C[C@@](C)(O)c3ccc(CO)nc3)C[C@H]2c2ccc(Cl)cc2)c(Cl)c1] | 560.3 |

TABLE 23-continued

| Ex. # | MOLECULAR STRUCTURE | OBSVD LCMS MS (MH+) |
|---|---|---|
| 208 | 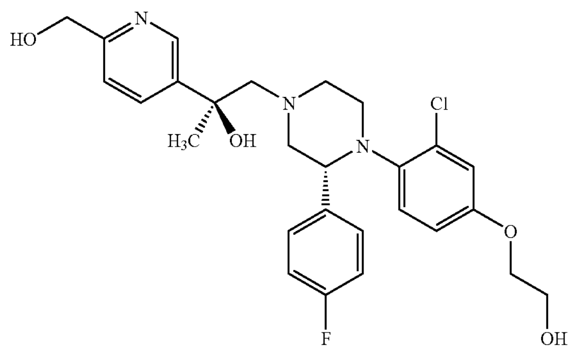 [SMILES: C[C@@](O)(CN1CCN(c2ccc(OCCO)cc2Cl)[C@H](c2ccc(F)cc2)C1)c1ccc(CO)nc1] | 516.3 |
| 209 | 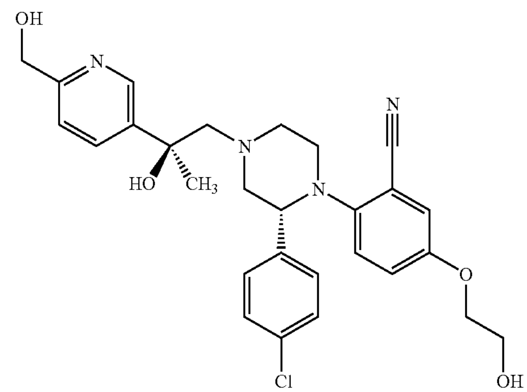 [SMILES: C[C@@](O)(CN1CCN(c2ccc(OCCO)cc2C#N)[C@H](c2ccc(Cl)cc2)C1)c1ccc(CO)nc1] | 523.3 |
| 210 | 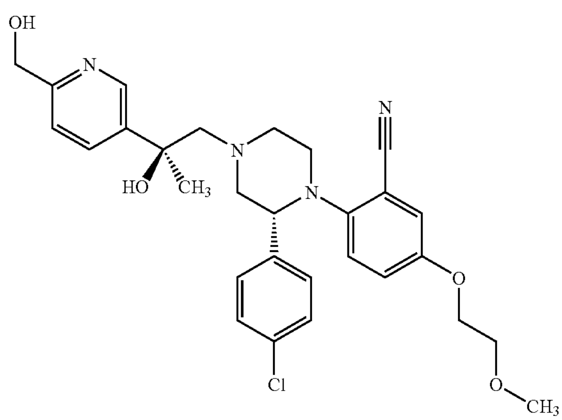 [SMILES: COCCOc1ccc(N2CCN(C[C@@](C)(O)c3ccc(CO)nc3)C[C@H]2c2ccc(Cl)cc2)c(C#N)c1] | 537.3 |
| 211 | 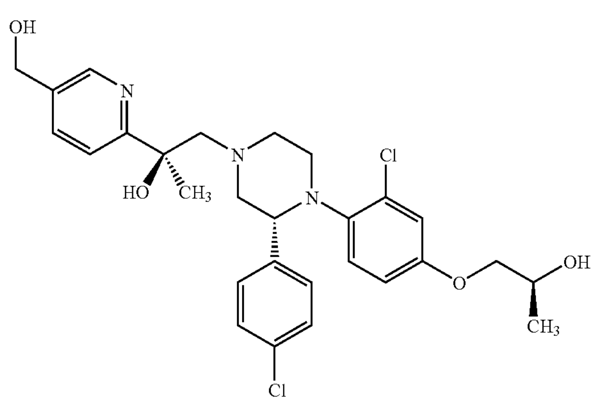 [SMILES: C[C@H](O)COc1ccc(N2CCN(C[C@@](C)(O)c3ccc(CO)cn3)C[C@H]2c2ccc(Cl)cc2)c(Cl)c1] | 546.3 |

TABLE 23-continued

| Ex. # | MOLECULAR STRUCTURE | OBSVD LCMS MS (MH+) |
|---|---|---|
| 212 | 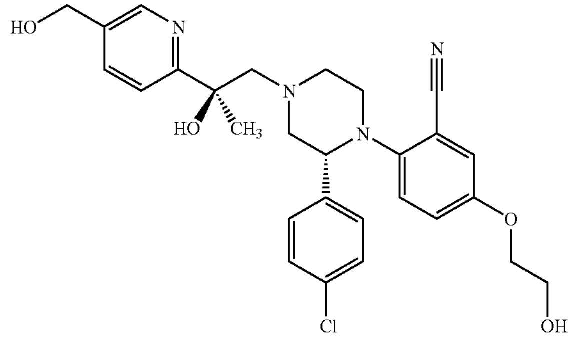 [SMILES: C[C@@](O)(CN1CCN(c2ccc(OCCO)cc2C#N)[C@H](c2ccc(Cl)cc2)C1)c1ccc(CO)cn1] | 523.3 |
| 213 | 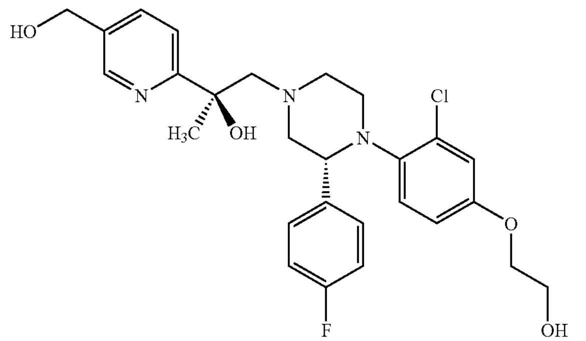 [SMILES: C[C@@](O)(CN1CCN(c2ccc(OCCO)cc2Cl)[C@H](c2ccc(F)cc2)C1)c1ccc(CO)cn1] | 516.3 |
| 214 | 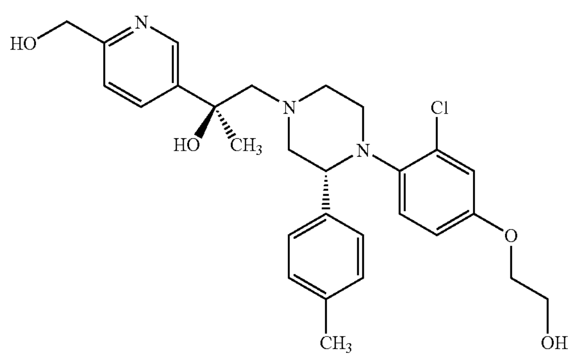 [SMILES: Cc1ccc([C@@H]2CN(C[C@@](C)(O)c3ccc(CO)nc3)CCN2c2ccc(OCCO)cc2Cl)cc1] | 512.3 |
| 215 | 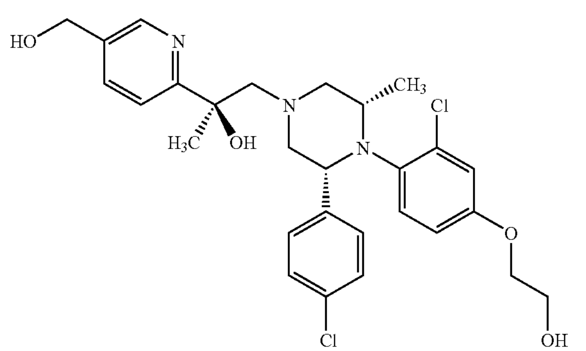 [SMILES: C[C@H]1CN(C[C@@](C)(O)c2ccc(CO)cn2)C[C@@H](c2ccc(Cl)cc2)N1c1ccc(OCCO)cc1Cl] | 546.3 |

TABLE 23-continued

| Ex. # | MOLECULAR STRUCTURE | OBSVD LCMS MS (MH+) |
|---|---|---|
| 216 | 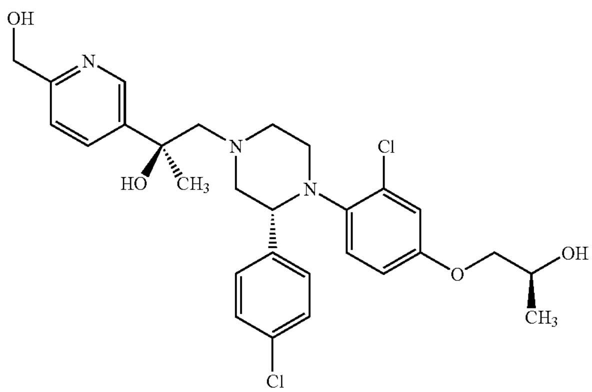 | 546.3 |
| 217 | 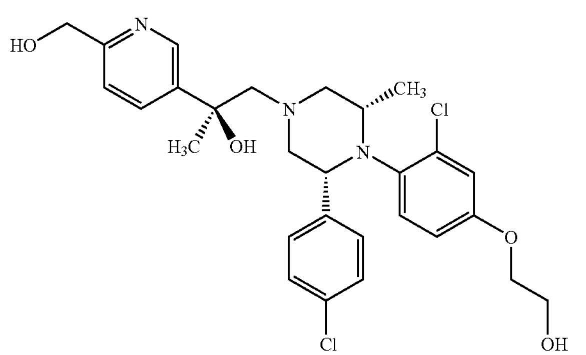 [SMILES: C[C@H]1CN(C[C@@](C)(O)c2ccc(CO)nc2)C[C@@H](c2ccc(Cl)cc2)N1c1ccc(OCCO)cc1Cl] | 546.3 |
| 218 | 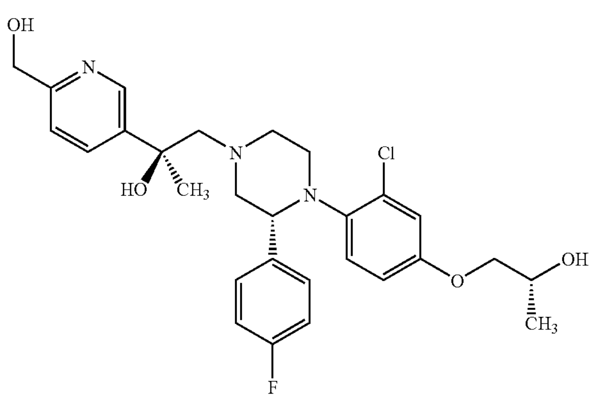 [SMILES: C[C@@H](O)COc1ccc(N2CCN(C[C@@](C)(O)c3ccc(CO)nc3)C[C@H]2c2ccc(F)cc2)c(Cl)c1] | 530.3 |
| 219 | 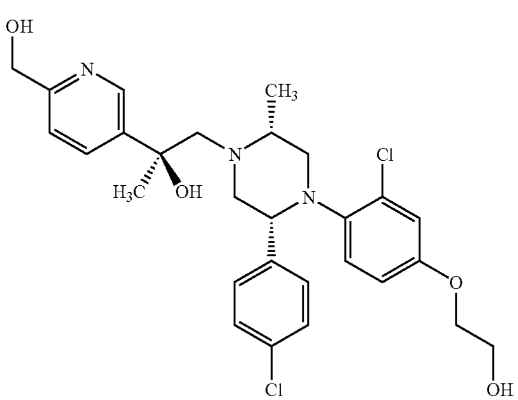 [SMILES: C[C@@H]1CN(c2ccc(OCCO)cc2Cl)[C@H](c2ccc(Cl)cc2)CN1C[C@@](C)(O)c1ccc(CO)nc1] | 546.3 |

TABLE 23-continued

| Ex. # | MOLECULAR STRUCTURE | OBSVD LCMS MS (MH+) |
|---|---|---|
| 220 | 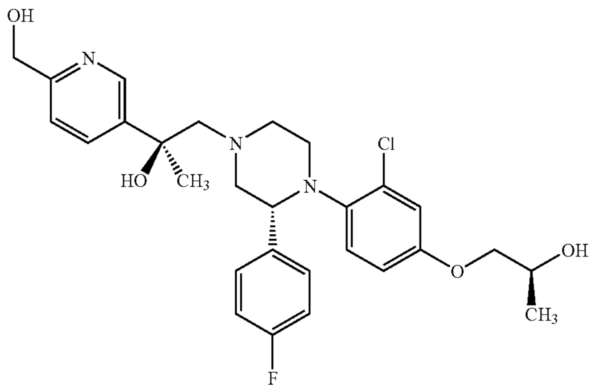 [SMILES: C[C@H](O)COc1ccc(N2CCN(C[C@@](C)(O)c3ccc(CO)nc3)C[C@H]2c2ccc(F)cc2)c(Cl)c1] | 530.3 |
| 221 | 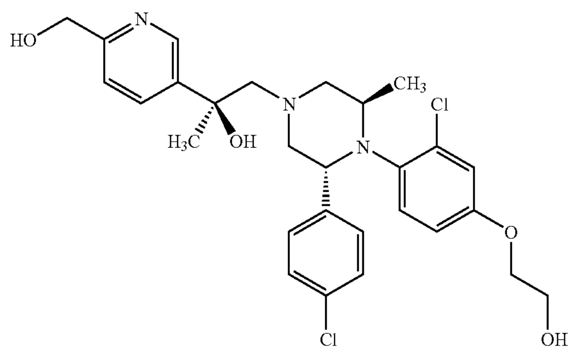 | 546.3 |
| 222 | 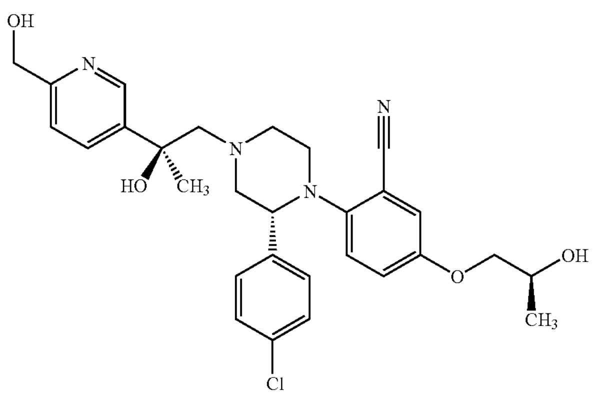 [SMILES: C[C@H](O)COc1ccc(N2CCN(C[C@@](C)(O)c3ccc(CO)nc3)C[C@H]2c2ccc(Cl)cc2)c(C#N)c1] | 537.3 |
| 223 | 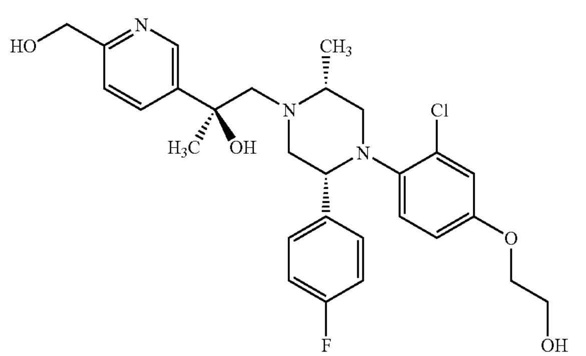 [SMILES: C[C@@H]1CN(c2ccc(OCCO)cc2Cl)[C@H](c2ccc(F)cc2)CN1C[C@@](C)(O)c1ccc(CO)nc1] | 530.3 |

TABLE 23-continued

| Ex. # | MOLECULAR STRUCTURE | OBSVD LCMS MS (MH+) |
|---|---|---|
| 224 | 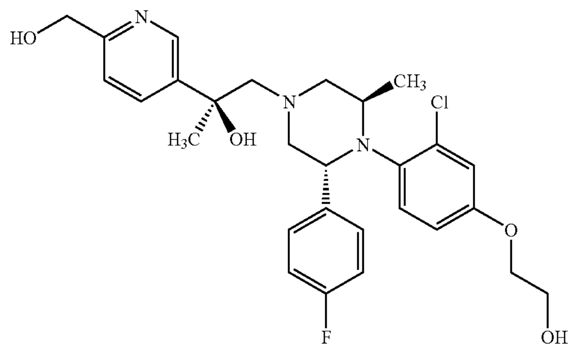 [SMILES: C[C@@H]1CN(C[C@@](C)(O)c2ccc(CO)nc2)C[C@@H](c2ccc(F)cc2)N1c1ccc(OCCO)cc1Cl] | 530.5 |
| 225 | 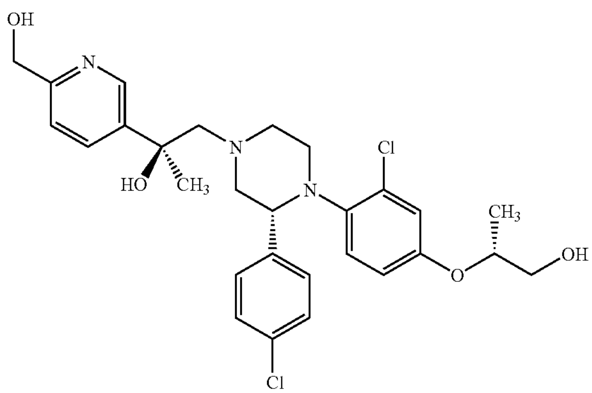 [SMILES: C[C@H](CO)Oc1ccc(N2CCN(C[C@@](C)(O)c3ccc(CO)nc3)C[C@H]2c2ccc(Cl)cc2)c(Cl)c1] | 546.3 |
| 226 | 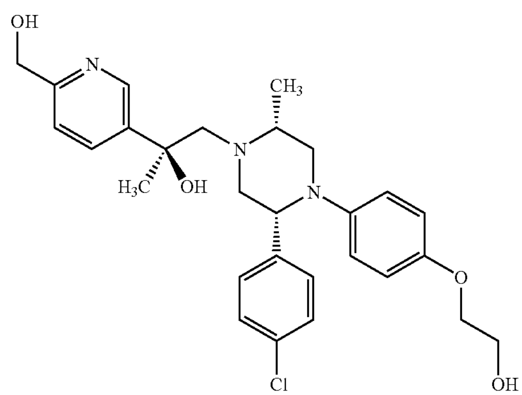 [SMILES: C[C@@H]1CN(c2ccc(OCCO)cc2)[C@H](c2ccc(Cl)cc2)CN1C[C@@](C)(O)c1ccc(CO)nc1] | 512.3 |
| 227 | 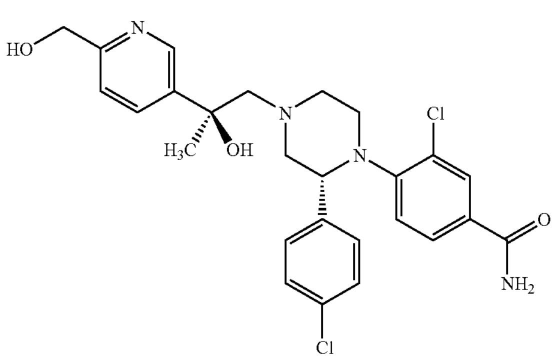 [SMILES: C[C@@](O)(CN1CCN(c2ccc(C(N)=O)cc2Cl)[C@H](c2ccc(Cl)cc2)C1)c1ccc(CO)nc1] | 515.3 |

TABLE 23-continued

| Ex. # | MOLECULAR STRUCTURE | OBSVD LCMS MS (MH+) |
|---|---|---|
| 228 | 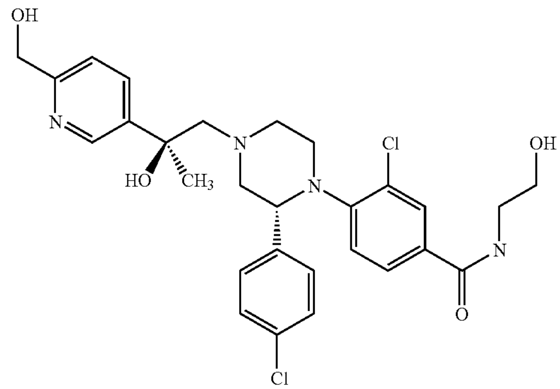 [SMILES: C[C@@](O)(CN1CCN(c2ccc(C(=O)NCCO)cc2Cl)[C@H](c2ccc(Cl)cc2)C1)c1ccc(CO)nc1] | 559.3 |
| 229 | 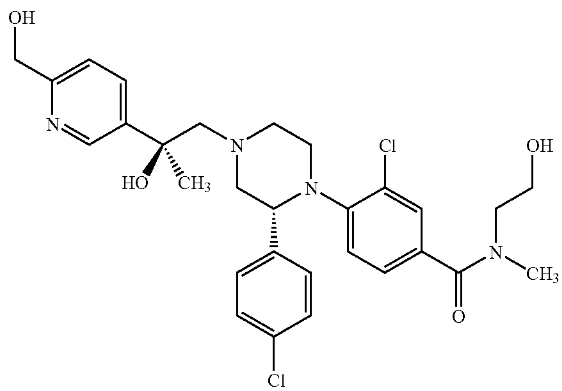 [SMILES: CN(CCO)C(=O)c1ccc(N2CCN(C[C@@](C)(O)c3ccc(CO)nc3)C[C@H]2c2ccc(Cl)cc2)c(Cl)c1] | 573.3 |
| 230 | 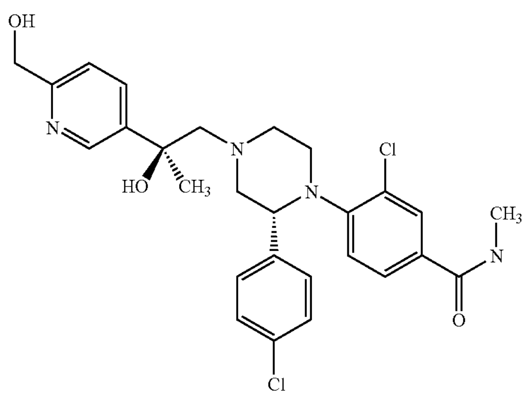 [SMILES: CNC(=O)c1ccc(N2CCN(C[C@@](C)(O)c3ccc(CO)nc3)C[C@H]2c2ccc(Cl)cc2)c(Cl)c1] | 529.3 |
| 231 | 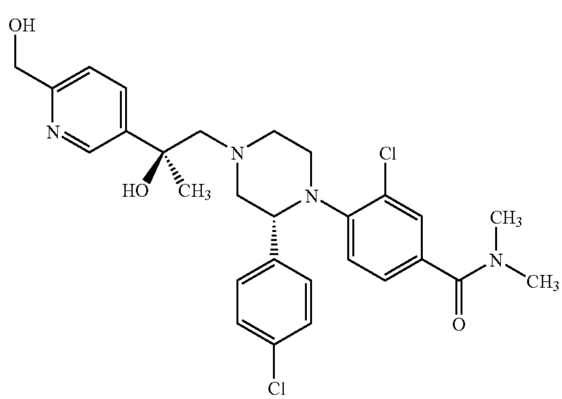 [SMILES: CN(C)C(=O)c1ccc(N2CCN(C[C@@](C)(O)c3ccc(CO)nc3)C[C@H]2c2ccc(Cl)cc2)c(Cl)c1] | 543.3 |

TABLE 23-continued
| Ex. # | MOLECULAR STRUCTURE | OBSVD LCMS MS (MH+) |
|---|---|---|
| 232 | 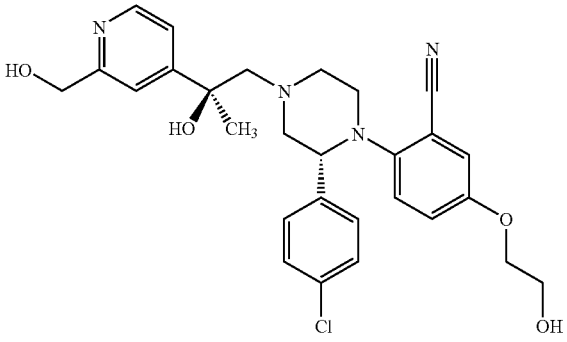 [SMILES: C[C@@](O)(CN1CCN(c2ccc(OCCO)cc2C#N)[C@H](c2ccc(Cl)cc2)C1)c1ccnc(CO)c1] | 523.3 |
| 233 | 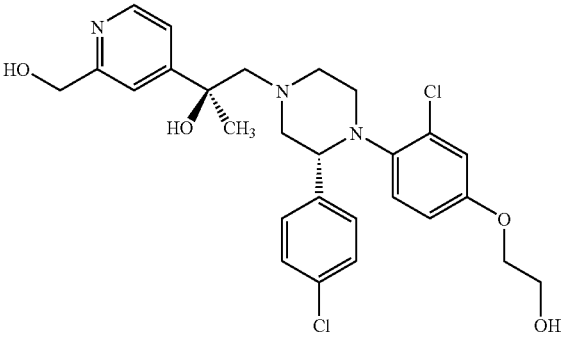 [SMILES: C[C@@](O)(CN1CCN(c2ccc(OCCO)cc2Cl)[C@H](c2ccc(Cl)cc2)C1)c1ccnc(CO)c1] | 532.3 |
| 234 | 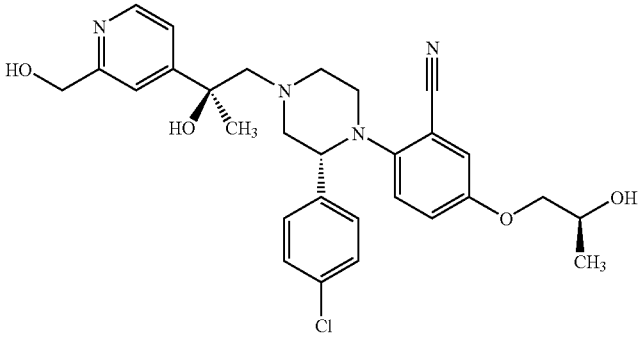 [SMILES: C[C@H](O)COc1ccc(N2CCN(C[C@@](C)(O)c3ccnc(CO)c3)C[C@H]2c2ccc(Cl)cc2)c(C#N)c1] | 537.3 |
| 235a | 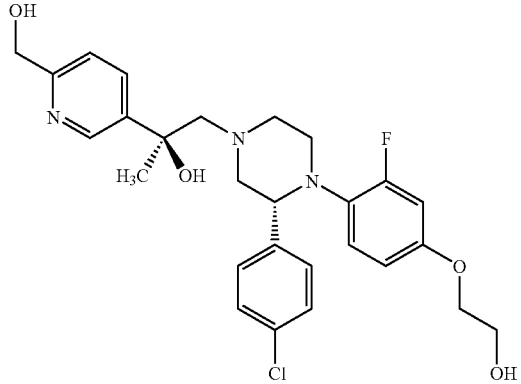 [SMILES: C[C@@](O)(CN1CCN(c2ccc(OCCO)cc2F)[C@H](c2ccc(Cl)cc2)C1)c1ccc(CO)nc1] | 516.3 |

TABLE 23-continued

| Ex. # | MOLECULAR STRUCTURE | OBSVD LCMS MS (MH+) |
|---|---|---|
| 235b | 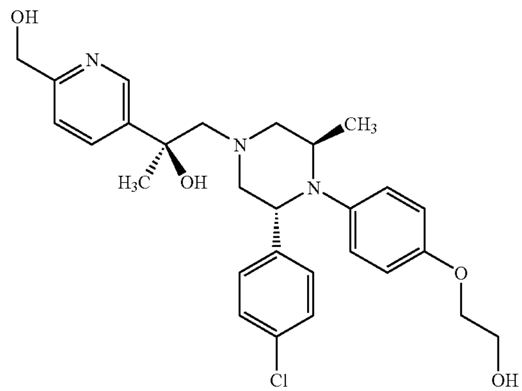 [SMILES: C[C@@H]1CN(C[C@@](C)(O)c2ccc(CO)nc2)C[C@@H](c2ccc(Cl)cc2)N1c1ccc(OCCO)cc1] | 512.3 |
| 235 | 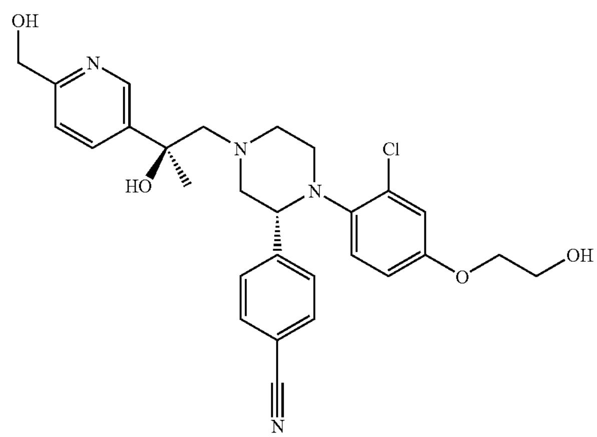 [SMILES: C[C@@](O)(CN1CCN(c2ccc(OCCO)cc2Cl)[C@H](c2ccc(C#N)cc2)C1)c1ccc(CO)nc1] | 523.3 |
| 235c | 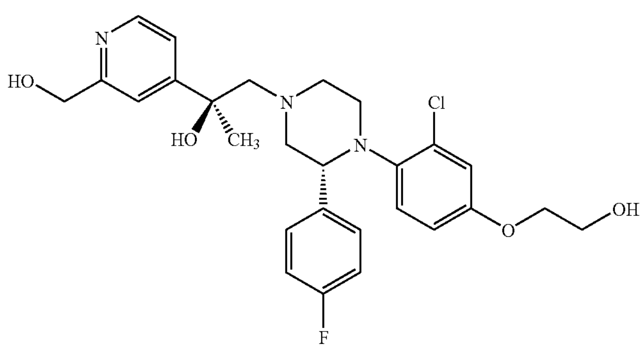 [SMILES: C[C@@](O)(CN1CCN(c2ccc(OCCO)cc2Cl)[C@H](c2ccc(F)cc2)C1)c1ccnc(CO)c1] | 516.3 |
| 235d | 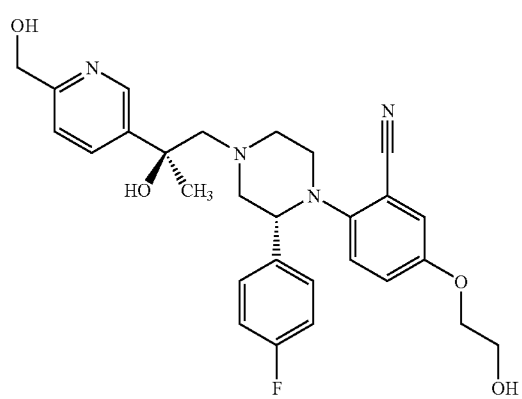 | 507.3 |

TABLE 23-continued

| Ex. # | MOLECULAR STRUCTURE | OBSVD LCMS MS (MH+) |
|---|---|---|
| 236 | 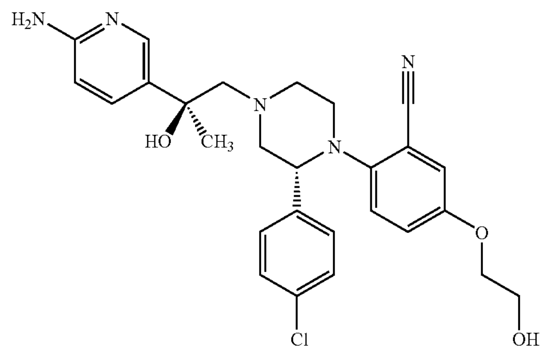 [SMILES: C[C@@](O)(CN1CCN(c2ccc(OCCO)cc2C#N)[C@H](c2ccc(Cl)cc2)C1)c1ccc(N)nc1] | 508.3 |
| 237 | 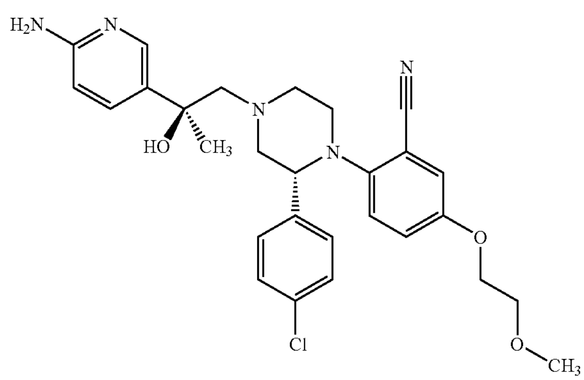 [SMILES: COCCOc1ccc(N2CCN(C[C@@](C)(O)c3ccc(N)nc3)C[C@H]2c2ccc(Cl)cc2)c(C#N)c1] | 522.3 |
| 238 | 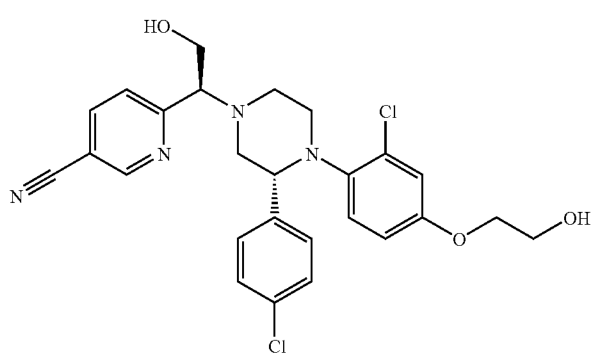 [SMILES: N#Cc1ccc([C@@H](CO)N2CCN(c3ccc(OCCO)cc3Cl)[C@H](c3ccc(Cl)cc3)C2)nc1] | 513.3 |
| 239 | 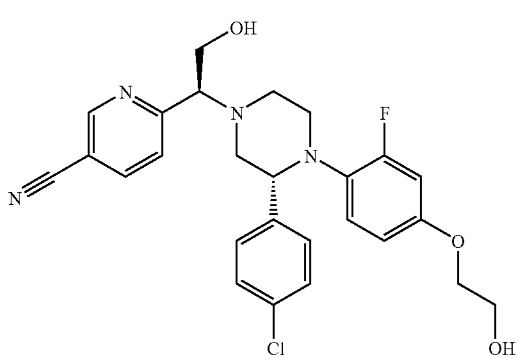 | 497.3 |

TABLE 23-continued

| Ex. # | MOLECULAR STRUCTURE | OBSVD LCMS MS (MH+) |
|---|---|---|
| 240 | 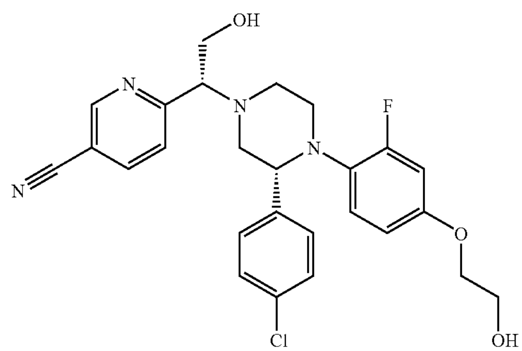 [SMILES: N#Cc1ccc([C@H](CO)N2CCN(c3ccc(OCCO)cc3F)[C@H](c3ccc(Cl)cc3)C2)nc1] | 497.3 |
| 241 | 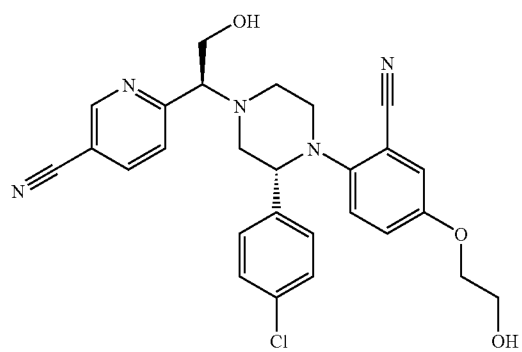 [SMILES: N#Cc1ccc([C@@H](CO)N2CCN(c3ccc(OCCO)cc3C#N)[C@H](c3ccc(Cl)cc3)C2)nc1] | 504.3 |
| 242 | 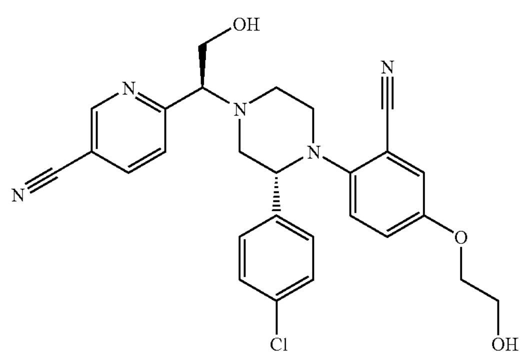 [SMILES: N#Cc1ccc([C@@H](CO)N2CCN(c3ccc(OCCO)cc3C#N)[C@H](c3ccc(Cl)cc3)C2)nc1] | 504.3 |
| 243 | 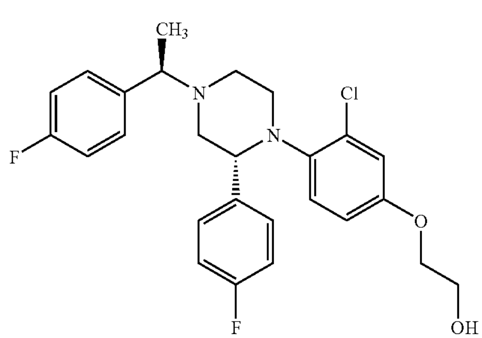 [SMILES: C[C@H](c1ccc(F)cc1)N1CCN(c2ccc(OCCO)cc2Cl)[C@H](c2ccc(F)cc2)C1] | 473.3 |

TABLE 23-continued

| Ex. # | MOLECULAR STRUCTURE | OBSVD LCMS MS (MH+) |
|---|---|---|
| 244 | 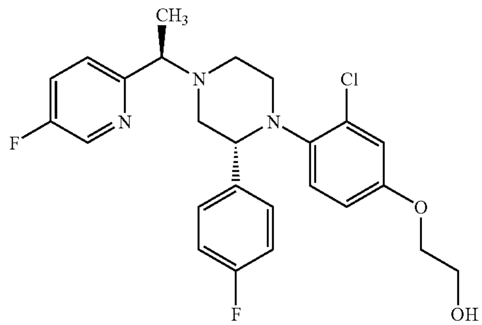 | 474.3 |
| 245 | 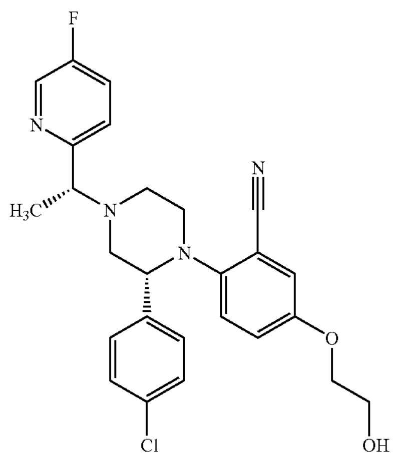 [SMILES: C[C@H](c1ccc(F)cn1)N1CCN(c2ccc(OCCO)cc2C#N)[C@H](c2ccc(Cl)cc2)C1] | 481.3 |
| 246 | 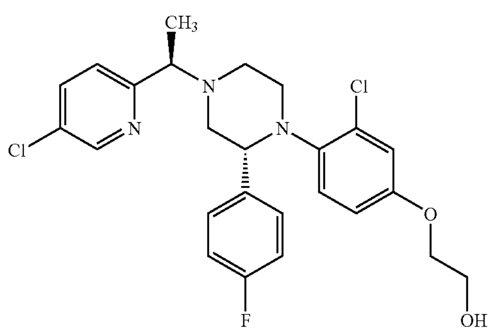 [SMILES: C[C@H](c1ccc(Cl)cn1)N1CCN(c2ccc(OCCO)cc2Cl)[C@H](c2ccc(F)cc2)C1] | 490.3 |
| 247 | 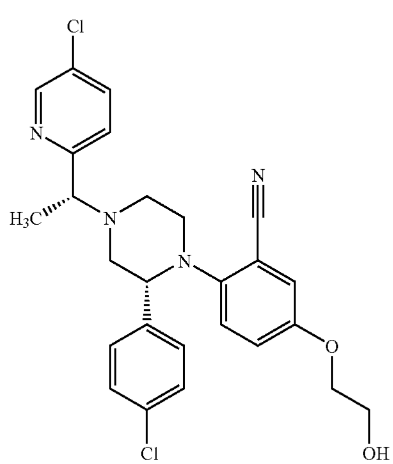 | 497.3 |

TABLE 23-continued
| Ex. # | MOLECULAR STRUCTURE | OBSVD LCMS MS (MH+) |
|---|---|---|
| 248 | 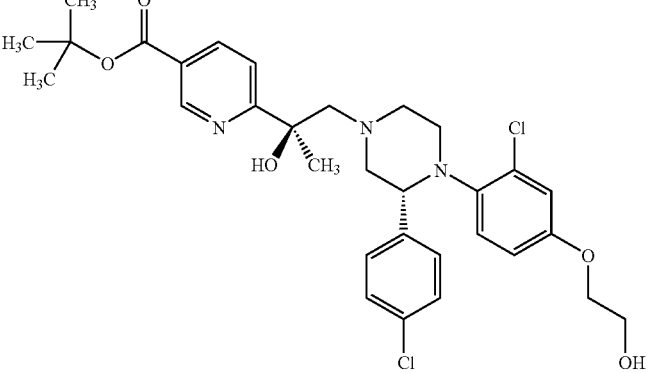 | 602.3 |
| 249 | 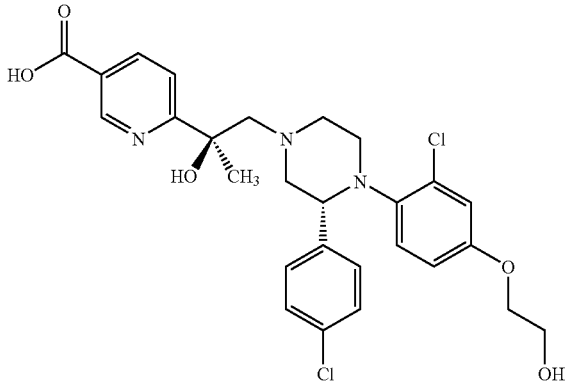 [SMILES: C[C@@](O)(CN1CCN(c2ccc(OCCO)cc2Cl)[C@H](c2ccc(Cl)cc2)C1)c1ccc(C(=O)O)cn1] | 548.3 |
| 250 | 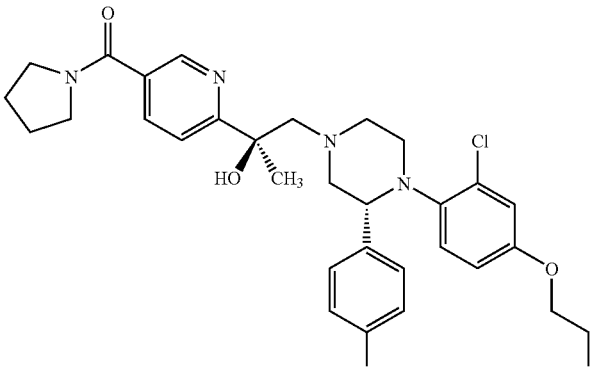 | 601.3 |
| 251 | 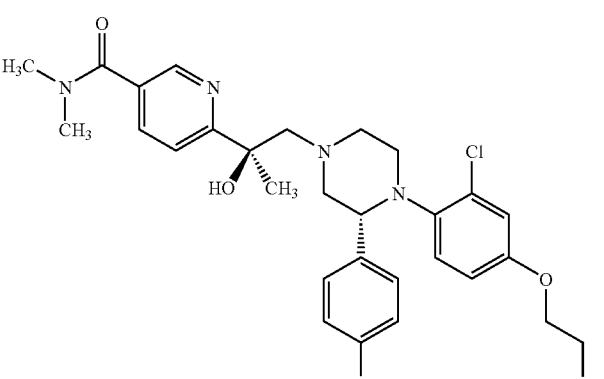 | 573.3 |

TABLE 23-continued

| Ex. # | MOLECULAR STRUCTURE | OBSVD LCMS MS (MH+) |
|---|---|---|
| 252 | 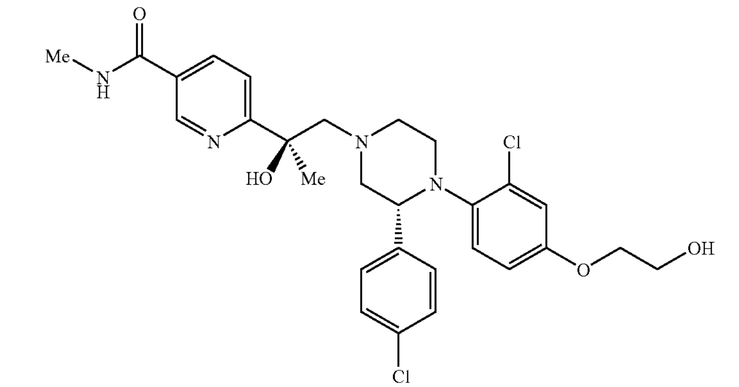 [SMILES: CNC(=O)c1ccc([C@](C)(O)CN2CCN(c3ccc(OCCO)cc3Cl)[C@H](c3ccc(Cl)cc3)C2)nc1] | 559.3 |
| 253 | 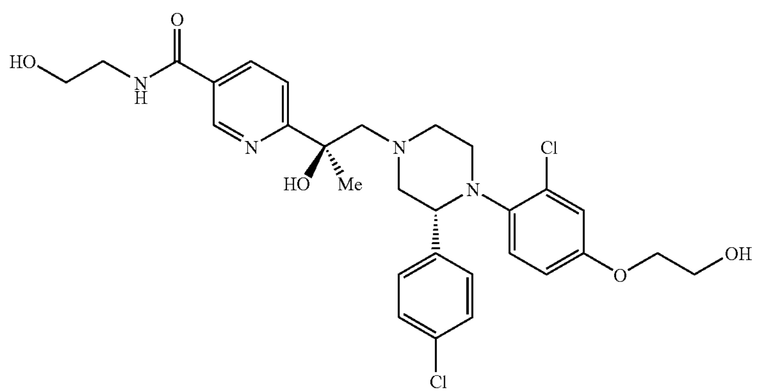 [SMILES: C[C@@](O)(CN1CCN(c2ccc(OCCO)cc2Cl)[C@H](c2ccc(Cl)cc2)C1)c1ccc(C(=O)NCCO)cn1] | 589.3 |
| 254 | 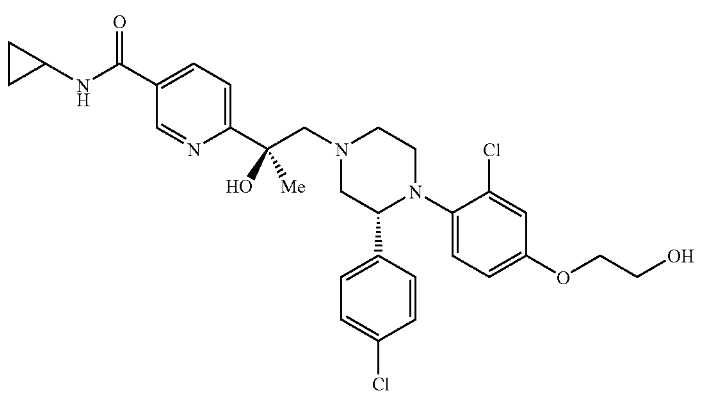 [SMILES: C[C@@](O)(CN1CCN(c2ccc(OCCO)cc2Cl)[C@H](c2ccc(Cl)cc2)C1)c1ccc(C(=O)NC2CC2)cn1] | 585.3 |
| 256 | 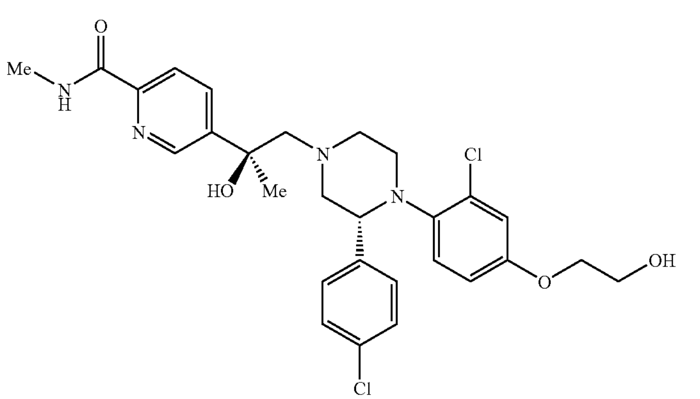 | 559.3 |

TABLE 23-continued

| Ex. # | MOLECULAR STRUCTURE | OBSVD LCMS MS (MH+) |
|---|---|---|
| 257 | 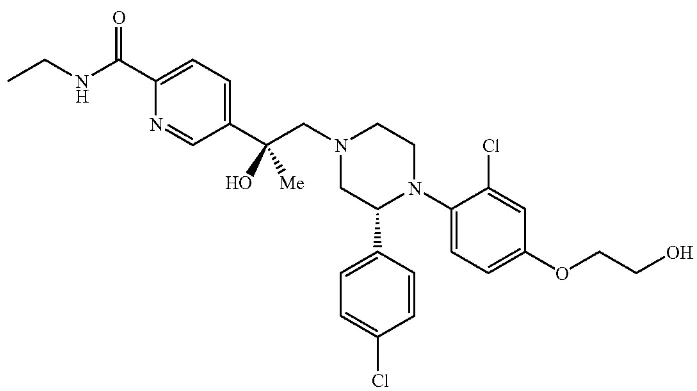 [SMILES: CCNC(=O)c1ccc([C@](C)(O)CN2CCN(c3ccc(OCCO)cc3Cl)[C@H](c3ccc(Cl)cc3)C2)cn1] | 573.3 |
| 258 | 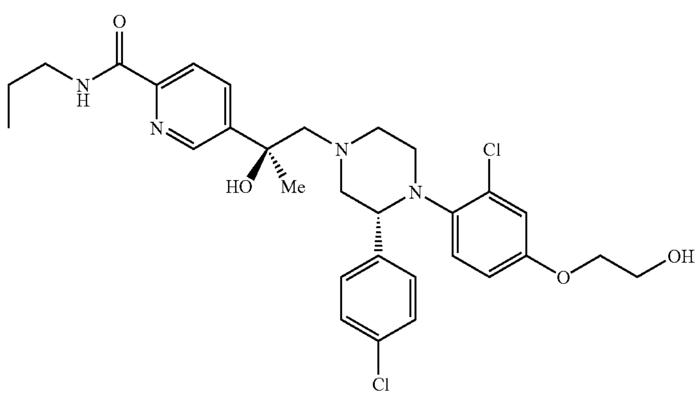 [SMILES: CCCNC(=O)c1ccc([C@](C)(O)CN2CCN(c3ccc(OCCO)cc3Cl)[C@H](c3ccc(Cl)cc3)C2)cn1] | 570.3 |
| 259 | 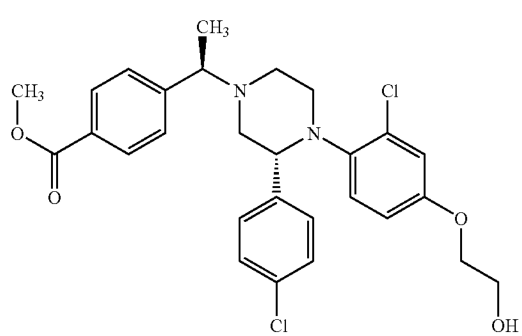 [SMILES: COC(=O)c1ccc([C@@H](C)N2CCN(c3ccc(OCCO)cc3Cl)[C@H](c3ccc(Cl)cc3)C2)cc1] | 529.3 |
| 260 | 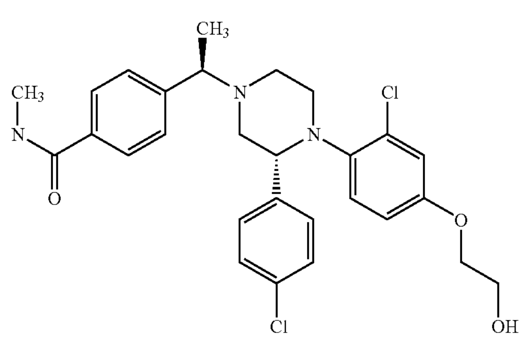 | 528.3 |

TABLE 23-continued

| Ex. # | MOLECULAR STRUCTURE | OBSVD LCMS MS (MH+) |
|---|---|---|
| 261 | 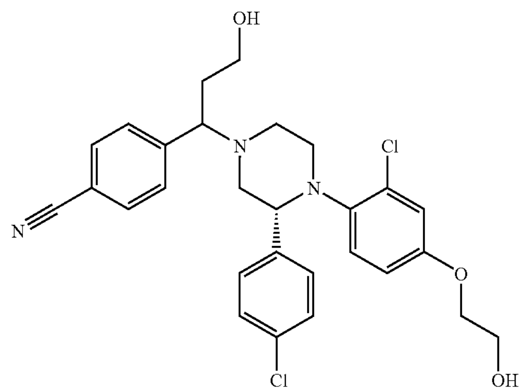 [SMILES: N#Cc1ccc(C(CCO)N2CCN(c3ccc(OCCO)cc3Cl)[C@H](c3ccc(Cl)cc3)C2)cc1] | 526.3 |
| 262 | 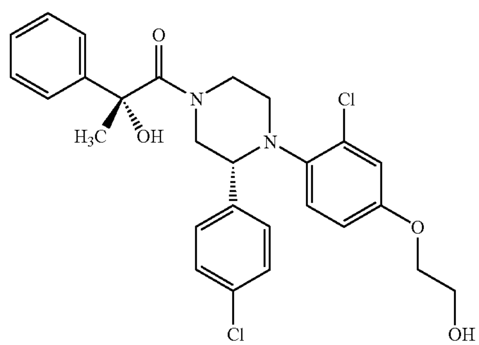 [SMILES: C[C@](O)(C(=O)N1CCN(c2ccc(OCCO)cc2Cl)[C@H](c2ccc(Cl)cc2)C1)c1ccccc1] | 515.3 |
| 263 | 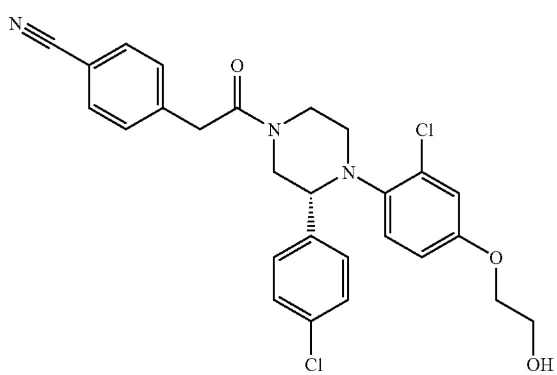 [SMILES: N#Cc1ccc(CC(=O)N2CCN(c3ccc(OCCO)cc3Cl)[C@H](c3ccc(Cl)cc3)C2)cc1] | 510.3 |
| 264 | 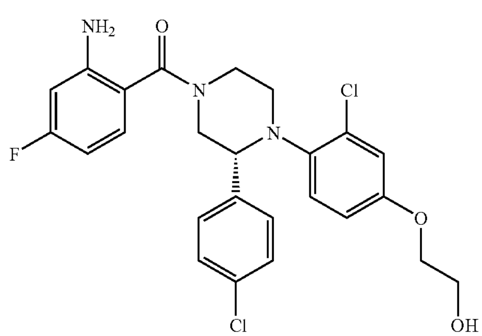 [SMILES: Nc1cc(F)ccc1C(=O)N1CCN(c2ccc(OCCO)cc2Cl)[C@H](c2ccc(Cl)cc2)C1] | 504.3 |

TABLE 23-continued

| Ex. # | MOLECULAR STRUCTURE | OBSVD LCMS MS (MH+) |
|---|---|---|
| 265 | 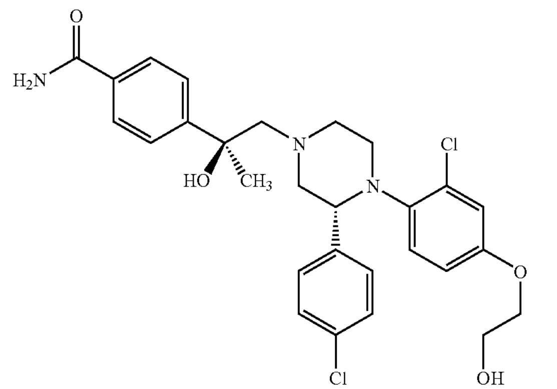 [SMILES: C[C@@](O)(CN1CCN(c2ccc(OCCO)cc2Cl)[C@H](c2ccc(Cl)cc2)C1)c1ccc(C(N)=O)cc1] | 544.3 |
| 266 | 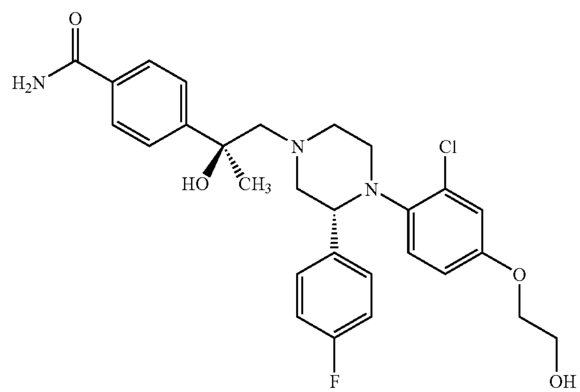 [SMILES: C[C@@](O)(CN1CCN(c2ccc(OCCO)cc2Cl)[C@H](c2ccc(F)cc2)C1)c1ccc(C(N)=O)cc1] | 528.3 |
| 267 | 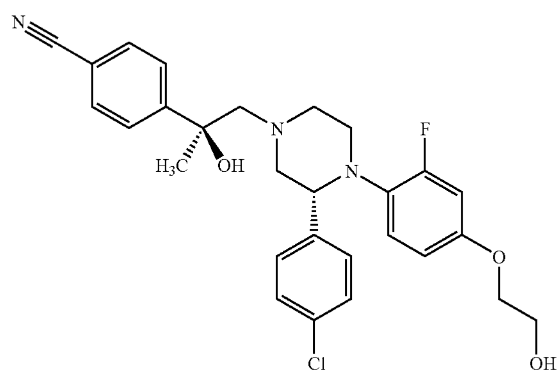 | 510.3 |
| 268 | 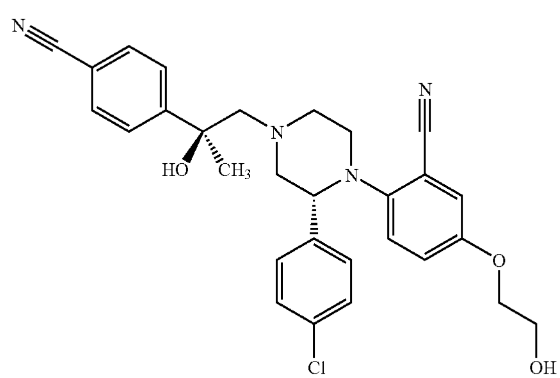 [SMILES: C[C@@](O)(CN1CCN(c2ccc(OCCO)cc2C#N)[C@H](c2ccc(Cl)cc2)C1)c1ccc(C#N)cc1] | 517.3 |

TABLE 23-continued

| Ex. # | MOLECULAR STRUCTURE | OBSVD LCMS MS (MH+) |
|---|---|---|
| 269 | 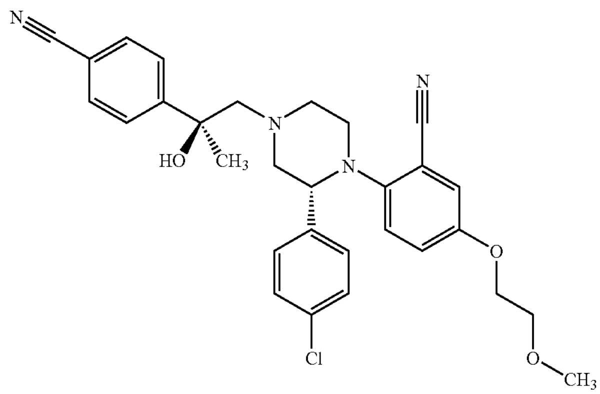 [SMILES: COCCOc1ccc(N2CCN(C[C@@](C)(O)c3ccc(C#N)cc3)C[C@H]2c2ccc(Cl)cc2)c(C#N)c1] | 531.3 |
| 270 | 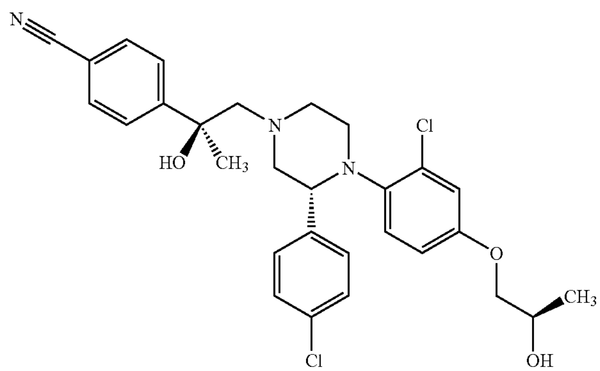 [SMILES: C[C@@H](O)COc1ccc(N2CCN(C[C@@](C)(O)c3ccc(C#N)cc3)C[C@H]2c2ccc(Cl)cc2)c(Cl)c1] | 540.3 |
| 271 | 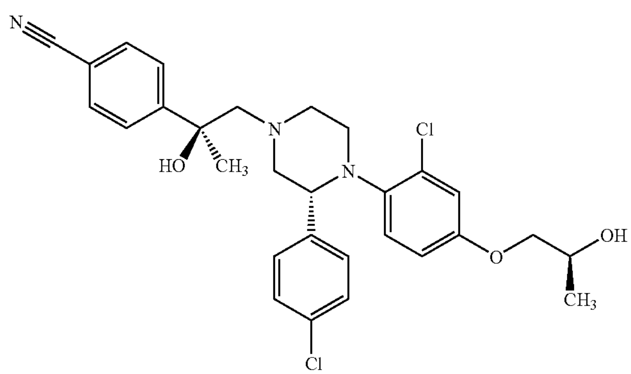 | 540.3 |
| 272 | 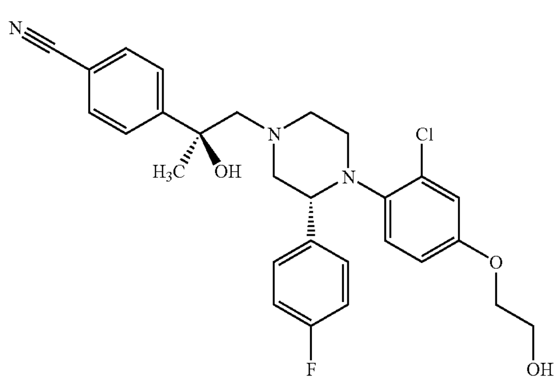 [SMILES: C[C@@](O)(CN1CCN(c2ccc(OCCO)cc2Cl)[C@H](c2ccc(F)cc2)C1)c1ccc(C#N)cc1] | 510.3 |

TABLE 23-continued

| Ex. # | MOLECULAR STRUCTURE | OBSVD LCMS MS (MH+) |
|---|---|---|
| 273 | 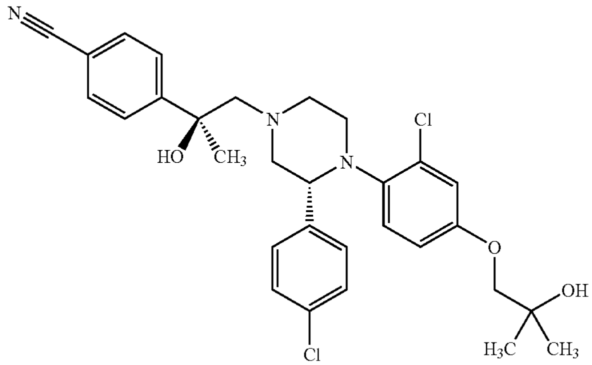 [SMILES: CC(C)(O)COc1ccc(N2CCN(C[C@@](C)(O)c3ccc(C#N)cc3)C[C@H]2c2ccc(Cl)cc2)c(Cl)c1] | 554.3 |
| 274 | 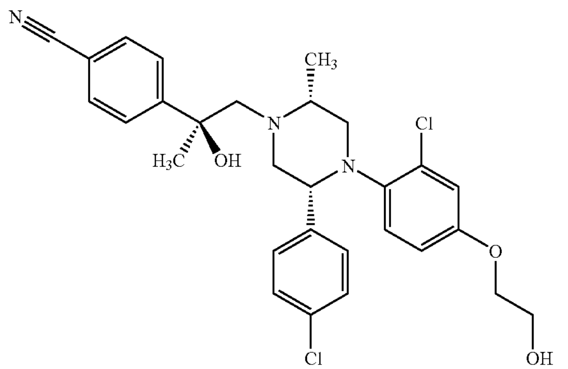 | 540.3 |
| 275 | 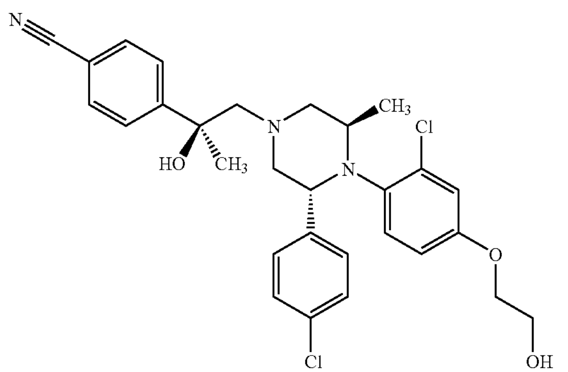 [SMILES: C[C@@H]1CN(C[C@@](C)(O)c2ccc(C#N)cc2)C[C@@H](c2ccc(Cl)cc2)N1c1ccc(OCCO)cc1Cl] | 542.3 |
| 276 | 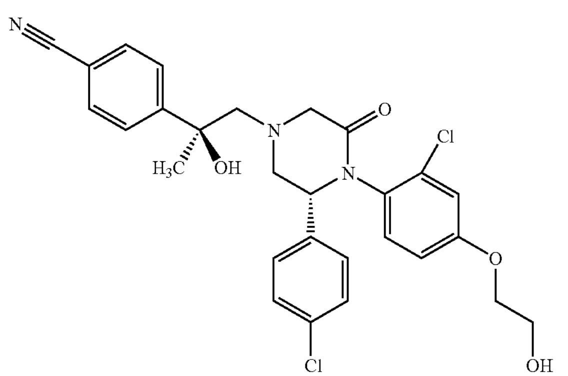 [SMILES: C[C@@](O)(CN1CC(=O)N(c2ccc(OCCO)cc2Cl)[C@H](c2ccc(Cl)cc2)C1)c1ccc(C#N)cc1] | 540.3 |

TABLE 23-continued

| Ex. # | MOLECULAR STRUCTURE | OBSVD LCMS MS (MH+) |
|---|---|---|
| 277 | 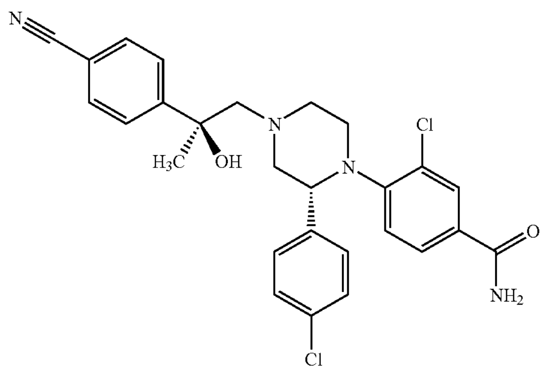 [SMILES: C[C@@](O)(CN1CCN(c2ccc(C(N)=O)cc2Cl)[C@H](c2ccc(Cl)cc2)C1)c1ccc(C#N)cc1] | 509.3 |
| 278 | 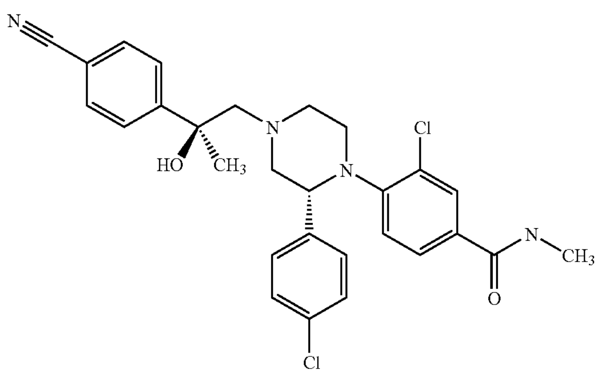 [SMILES: CNC(=O)c1ccc(N2CCN(C[C@@](C)(O)c3ccc(C#N)cc3)C[C@H]2c2ccc(Cl)cc2)c(Cl)c1] | 523.3 |
| 279 | 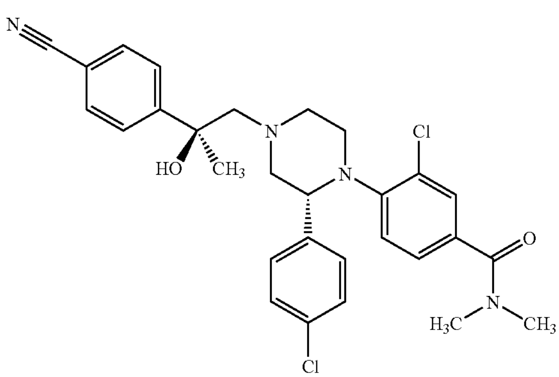 [SMILES: CN(C)C(=O)c1ccc(N2CCN(C[C@@](C)(O)c3ccc(C#N)cc3)C[C@H]2c2ccc(Cl)cc2)c(Cl)c1] | 537.3 |
| 280 | 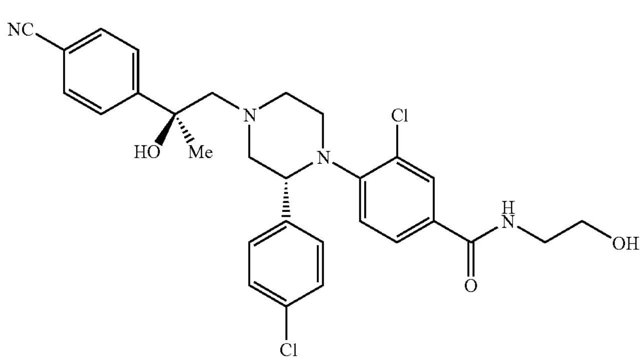 | 553.3 |

TABLE 23-continued

| Ex. # | MOLECULAR STRUCTURE | OBSVD LCMS MS (MH+) |
|---|---|---|
| 281 | 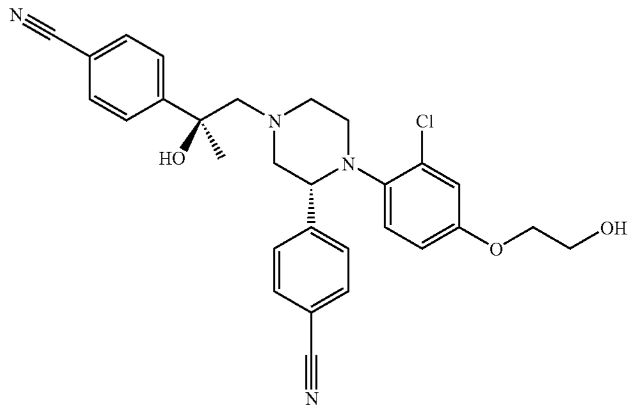 [SMILES: C[C@@](O)(CN1CCN(c2ccc(OCCO)cc2Cl)[C@H](c2ccc(C#N)cc2)C1)c1ccc(C#N)cc1] | 517.3 |
| 282 | 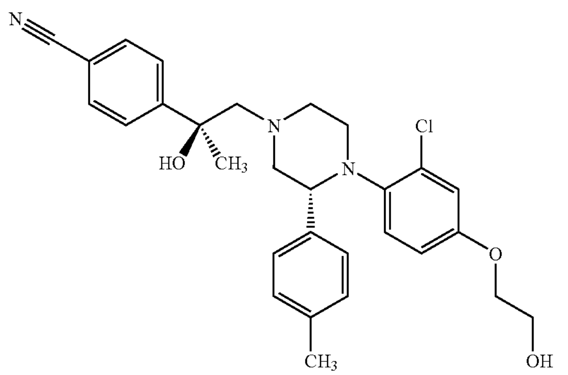 [SMILES: Cc1ccc([C@@H]2CN(C[C@@](C)(O)c3ccc(C#N)cc3)CCN2c2ccc(OCCO)cc2Cl)cc1] | 506.3 |
| 283 | 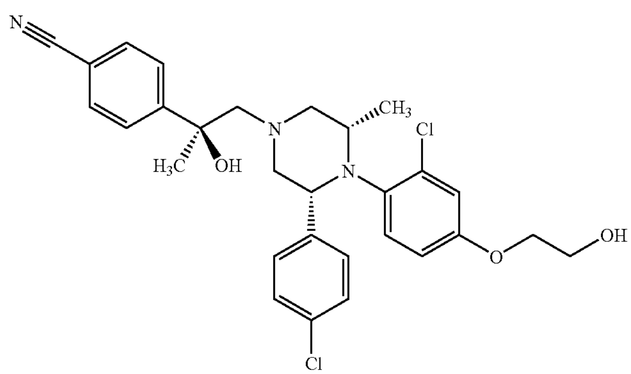 [SMILES: C[C@H]1CN(C[C@@](C)(O)c2ccc(C#N)cc2)C[C@@H](c2ccc(Cl)cc2)N1c1ccc(OCCO)cc1Cl] | 540.3 |
| 284 | 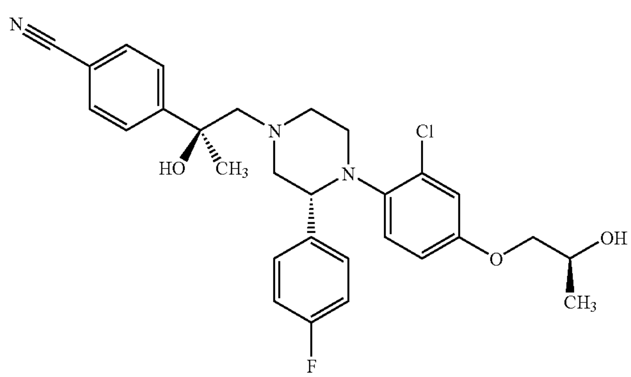 [SMILES: C[C@H](O)COc1ccc(N2CCN(C[C@@](C)(O)c3ccc(C#N)cc3)C[C@H]2c2ccc(F)cc2)c(Cl)c1] | 524.3 |

TABLE 23-continued

| Ex. # | MOLECULAR STRUCTURE | OBSVD LCMS MS (MH+) |
|---|---|---|
| 285 | 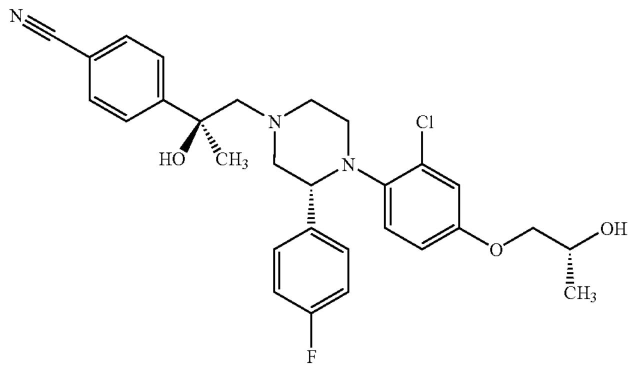 [SMILES: C[C@@H](O)COc1ccc(N2CCN(C[C@@](C)(O)c3ccc(C#N)cc3)C[C@H]2c2ccc(F)cc2)c(Cl)c1] | 524.3 |
| 286 | 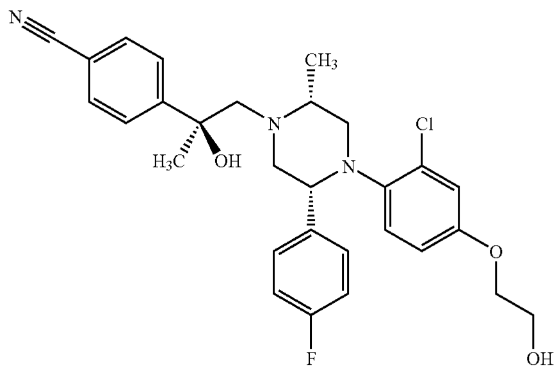 [SMILES: C[C@@H]1CN(c2ccc(OCCO)cc2Cl)[C@H](c2ccc(F)cc2)CN1C[C@@](C)(O)c1ccc(C#N)cc1] | 524.3 |
| 287 | 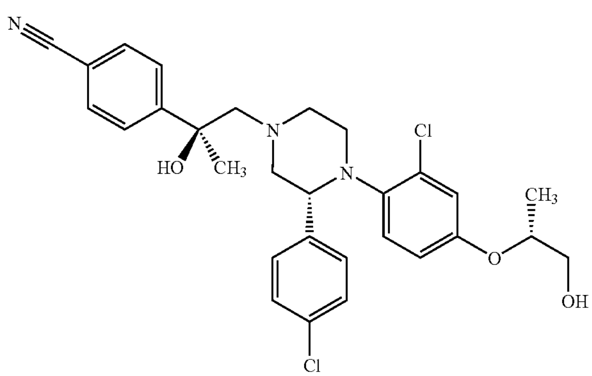 [SMILES: C[C@H](CO)Oc1ccc(N2CCN(C[C@@](C)(O)c3ccc(C#N)cc3)C[C@H]2c2ccc(Cl)cc2)c(Cl)c1] | 540.3 |
| 288 | 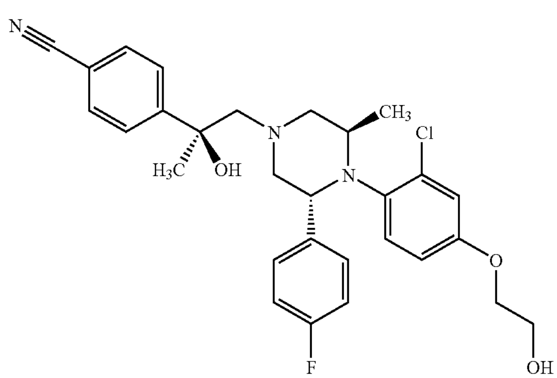 | 524.3 |

TABLE 23-continued

| Ex. # | MOLECULAR STRUCTURE | OBSVD LCMS MS (MH+) |
|---|---|---|
| 289 | 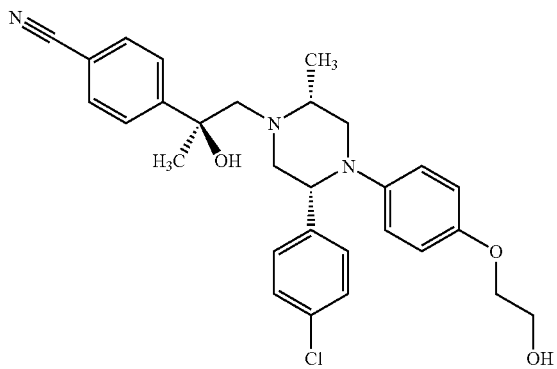 [SMILES: C[C@@H]1CN(c2ccc(OCCO)cc2)[C@H](c2ccc(Cl)cc2)CN1C[C@@](C)(O)c1ccc(C#N)cc1] | 506.3 |
| 290 | 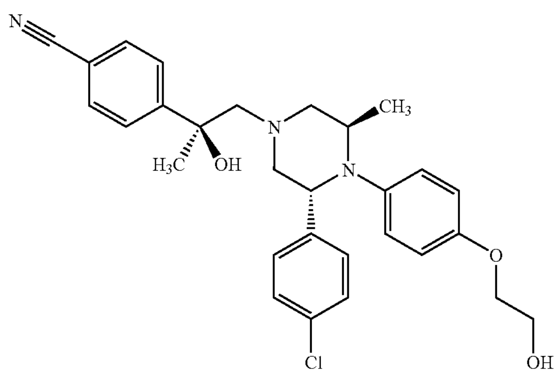 [SMILES: C[C@@H]1CN(C[C@@](C)(O)c2ccc(C#N)cc2)C[C@@H](c2ccc(Cl)cc2)N1c1ccc(OCCO)cc1] | 506.3 |
| 290a | 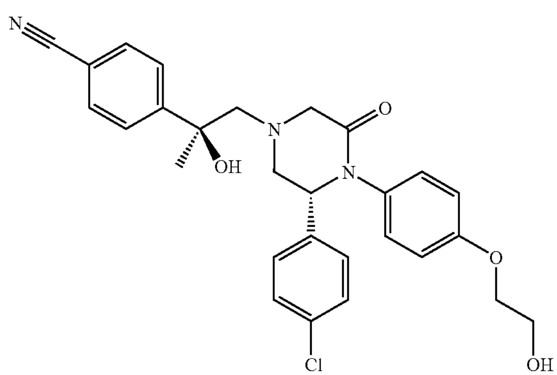 [SMILES: C[C@@](O)(CN1CC(=O)N(c2ccc(OCCO)cc2)[C@H](c2ccc(Cl)cc2)C1)c1ccc(C#N)cc1] | 506.3 |
| 291 | 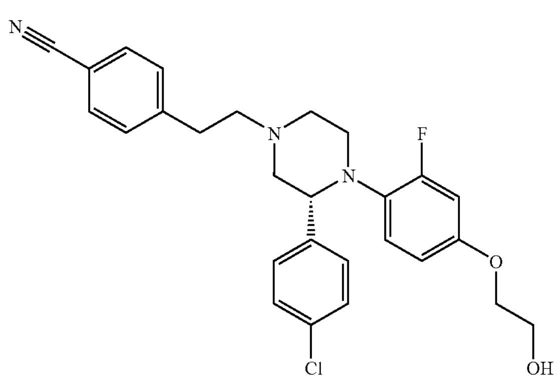 [SMILES: N#Cc1ccc(CCN2CCN(c3ccc(OCCO)cc3Cl)[C@H](c3ccc(F)cc3)C2)cc1] | 480.3 |

TABLE 23-continued
| Ex. # | MOLECULAR STRUCTURE | OBSVD LCMS MS (MH+) |
|---|---|---|
| 292 | 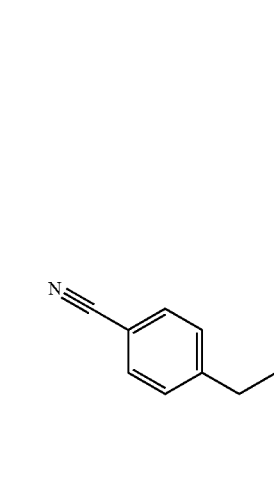 | 476.3 |
| 293 | 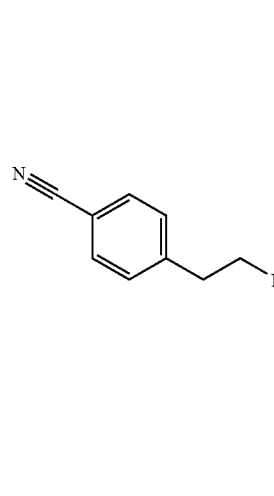 | 487.3 |
| 294 | 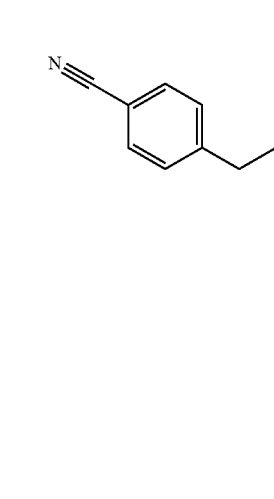 | 496.3 |
| 295 | 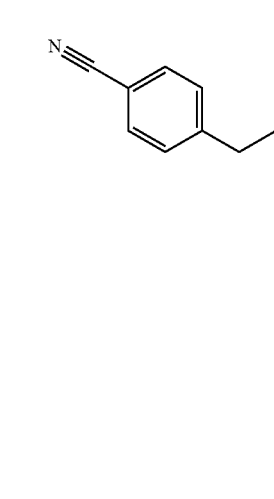 | 480.3 |

TABLE 23-continued

| Ex. # | MOLECULAR STRUCTURE | OBSVD LCMS MS (MH+) |
|---|---|---|
| 296 | 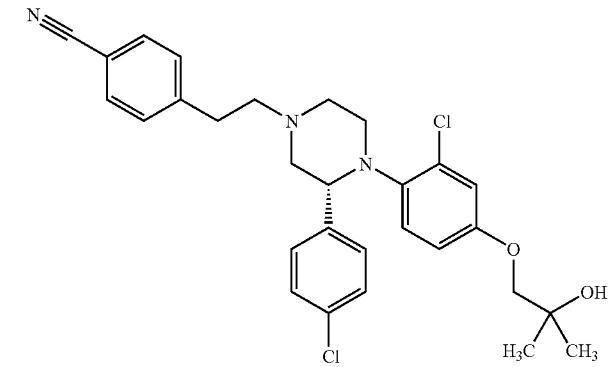 [SMILES: CC(C)(O)COc1ccc(N2CCN(CCc3ccc(C#N)cc3)C[C@H]2c2ccc(Cl)cc2)c(Cl)c1] | 524.3 |
| 297 | 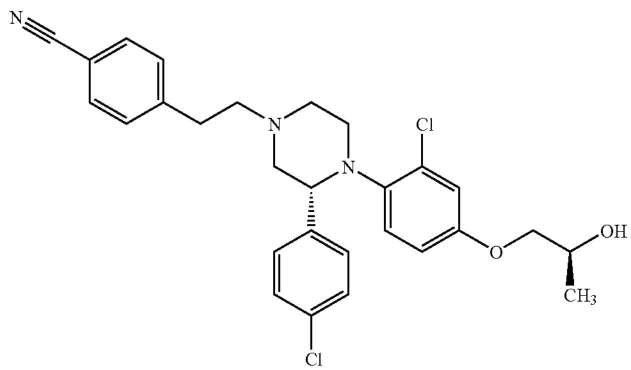 | 510.3 |
| 298 | 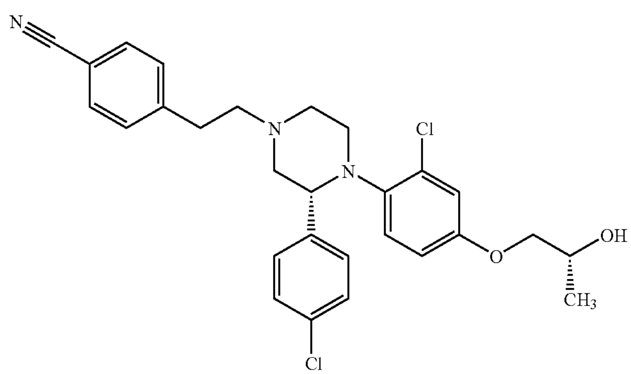 [SMILES: C[C@@H](O)COc1ccc(N2CCN(CCc3ccc(C#N)cc3)C[C@H]2c2ccc(Cl)cc2)c(Cl)c1] | 510.3 |
| 299 | 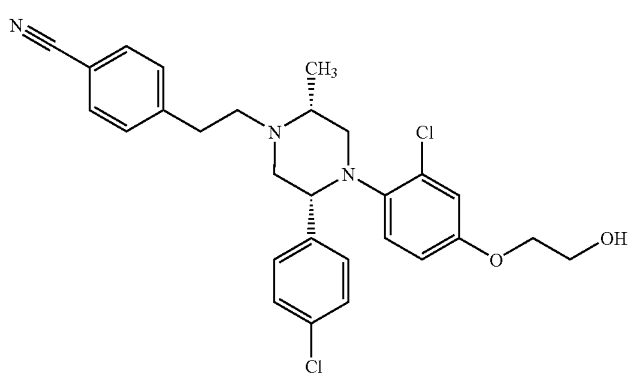 [SMILES: C[C@@H]1CN(c2ccc(OCCO)cc2Cl)[C@H](c2ccc(Cl)cc2)CN1CCc1ccc(C#N)cc1] | 510.3 |

TABLE 23-continued

| Ex. # | MOLECULAR STRUCTURE | OBSVD LCMS MS (MH+) |
|---|---|---|
| 300 | 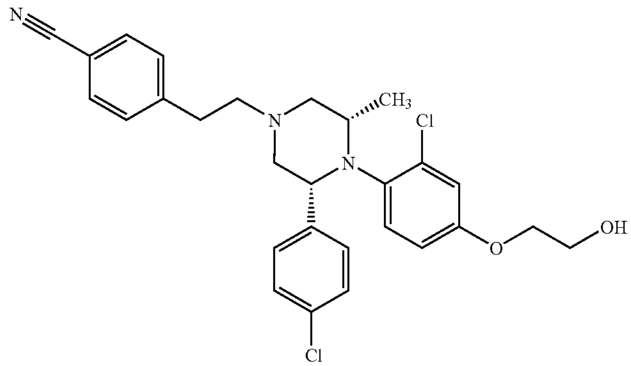 [SMILES: C[C@H]1CN(CCc2ccc(C#N)cc2)C[C@@H](c2ccc(Cl)cc2)N1c1ccc(OCCO)cc1Cl] | 510.3 |
| 301 | 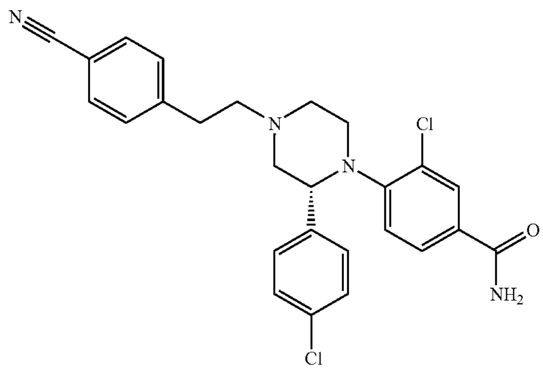 [SMILES: N#Cc1ccc(CCN2CCN(c3ccc(C(N)=O)cc3Cl)[C@H](c3ccc(Cl)cc3)C2)cc1] | 479.3 |
| 302 | 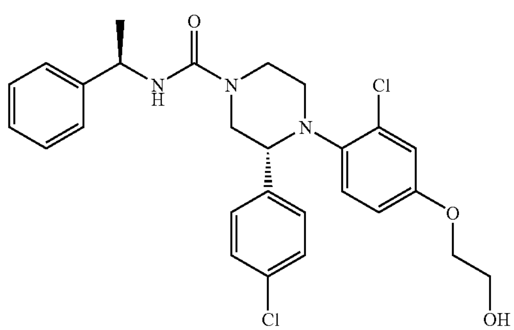 [SMILES: C[C@@H](NC(=O)N1CCN(c2ccc(OCCO)cc2Cl)[C@H](c2ccc(Cl)cc2)C1)c1ccccc1] | 514.3 |
| 303 | 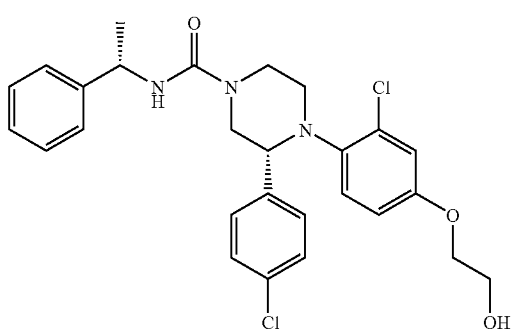 [SMILES: C[C@H](NC(=O)N1CCN(c2ccc(OCCO)cc2Cl)[C@H](c2ccc(Cl)cc2)C1)c1ccccc1] | 514.3 |

TABLE 23-continued

| Ex. # | MOLECULAR STRUCTURE | OBSVD LCMS MS (MH+) |
|---|---|---|
| 304 | 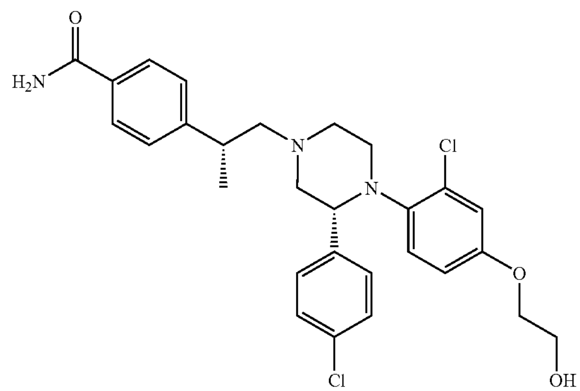 [SMILES: C[C@@H](CN1CCN(c2ccc(OCCO)cc2Cl)[C@H](c2ccc(Cl)cc2)C1)c1ccc(C(N)=O)cc1] | 528.3 |
| 305 | 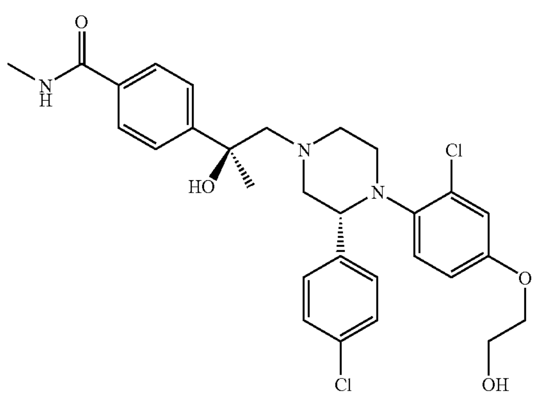 [SMILES: CNC(=O)c1ccc([C@](C)(O)CN2CCN(c3ccc(OCCO)cc3Cl)[C@H](c3ccc(Cl)cc3)C2)cc1] | 558.3 |
| 306 | 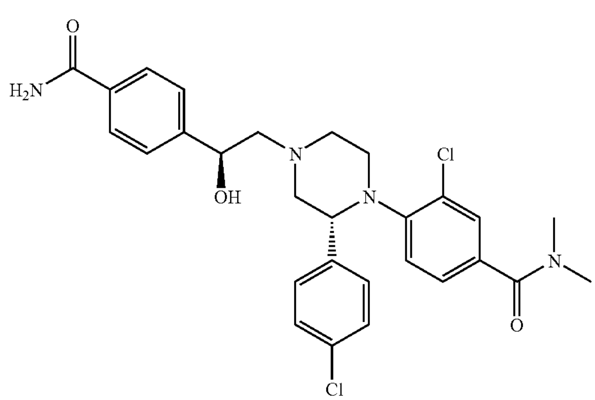 [SMILES: CN(C)C(=O)c1ccc(N2CCN(C[C@@H](O)c3ccc(C(N)=O)cc3)C[C@H]2c2ccc(Cl)cc2)c(Cl)c1] | 541.3 |

TABLE 23-continued

| Ex. # | MOLECULAR STRUCTURE | OBSVD LCMS MS (MH+) |
|---|---|---|
| 307 | 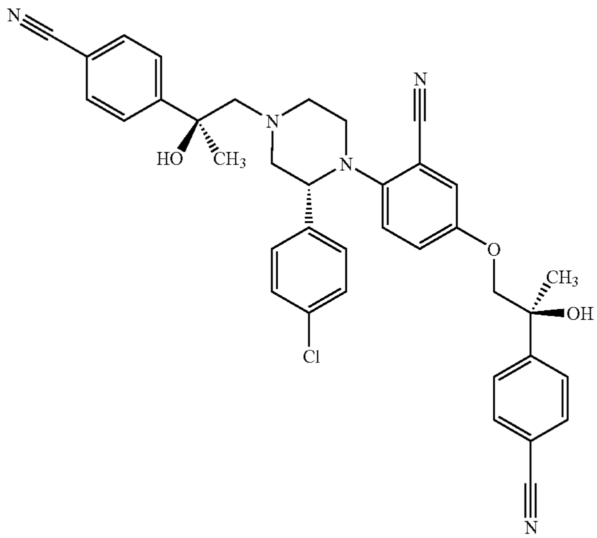 [SMILES: C[C@@](O)(COc1ccc(N2CCN(C[C@@](C)(O)c3ccc(C#N)cc3)C[C@H]2c2ccc(Cl)cc2)c(C#N)c1)c1ccc(C#N)cc1] | 632.3 |
| 308 | 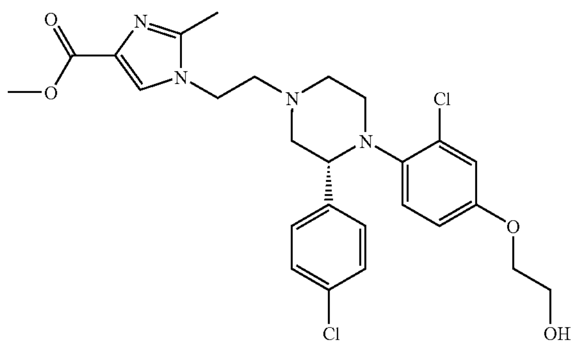 [SMILES: COC(=O)c1cn(CCN2CCN(c3ccc(OCCO)cc3Cl)[C@H](c3ccc(Cl)cc3)C2)c(C)n1] | 533.3 |
| 309 | 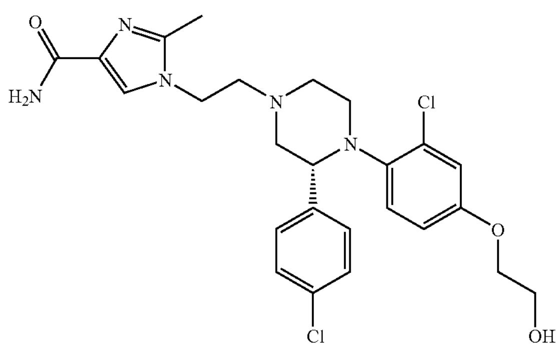 [SMILES: Cc1nc(C(N)=O)cn1CCN1CCN(c2ccc(OCCO)cc2Cl)[C@H](c2ccc(Cl)cc2)C1] | 518.3 |
| 310 | 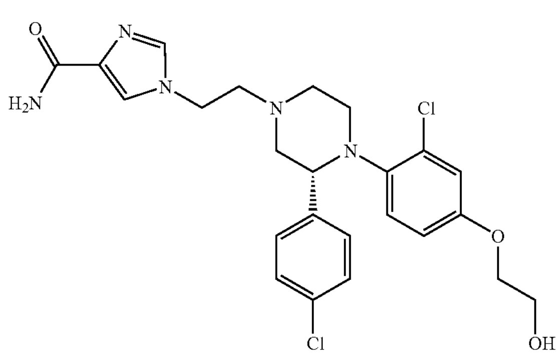 [SMILES: NC(=O)c1cn(CCN2CCN(c3ccc(OCCO)cc3Cl)[C@H](c3ccc(Cl)cc3)C2)cn1] | 504.3 |

TABLE 23-continued

| Ex. # | MOLECULAR STRUCTURE | OBSVD LCMS MS (MH+) |
|---|---|---|
| 311 | | 527.3 |
| 311 | | 527.3 |
| 313 | 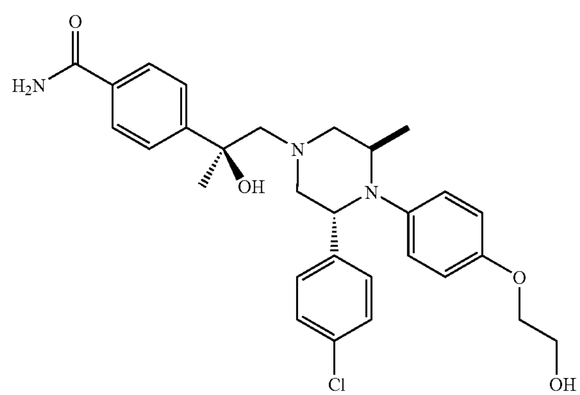 [SMILES: C[C@@H]1CN(C[C@@](C)(O)c2ccc(C(N)=O)cc2)C[C@@H](c2ccc(Cl)cc2)N1c1ccc(OCCO)cc1] | 524.3 |
| 314 | 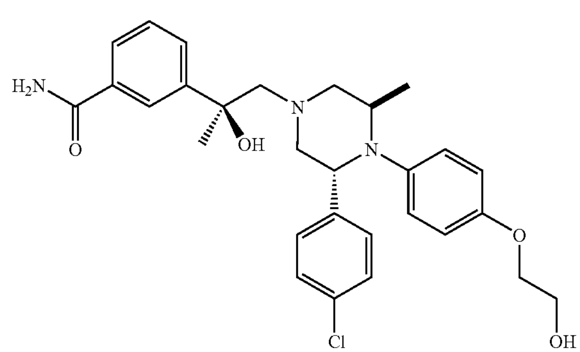 [SMILES: C[C@@H]1CN(C[C@@](C)(O)c2cccc(C(N)=O)c2)C[C@@H](c2ccc(Cl)cc2)N1c1ccc(OCCO)cc1] | 524.3 |

| Ex. # | MOLECULAR STRUCTURE | OBSVD LCMS MS (MH+) |
|---|---|---|
| 315 | 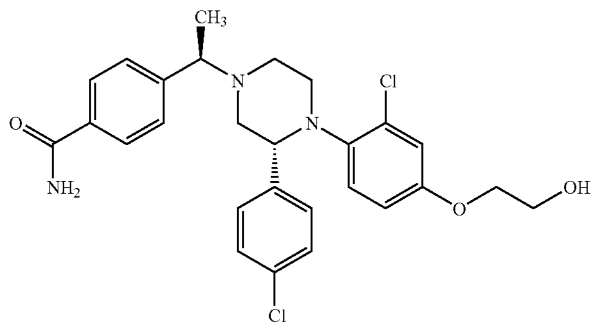 [SMILES: C[C@H](c1ccc(C(N)=O)cc1)N1CCN(c2ccc(OCCO)cc2Cl)[C@H](c2ccc(Cl)cc2)C1] | 514.3 |
| 41c | 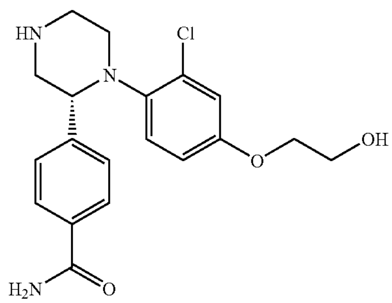 [SMILES: NC(=O)c1ccc([C@@H]2CNCCN2c2ccc(OCCO)cc2Cl)cc1] | 376 |
| 290c | 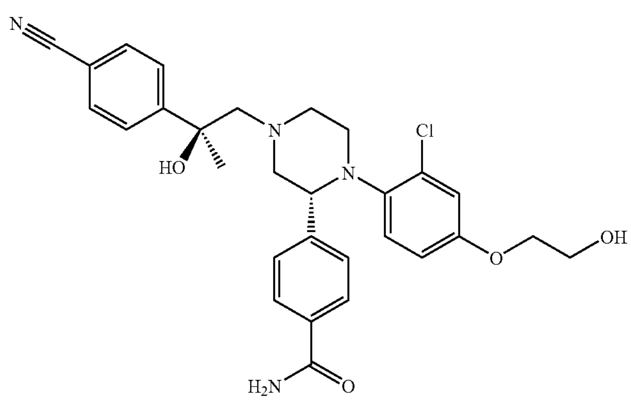 [SMILES: C[C@@](O)(CN1CCN(c2ccc(OCCO)cc2Cl)[C@H](c2ccc(C(N)=O)cc2)C1)c1ccc(C#N)cc1] | 535.3 |
| 80e | 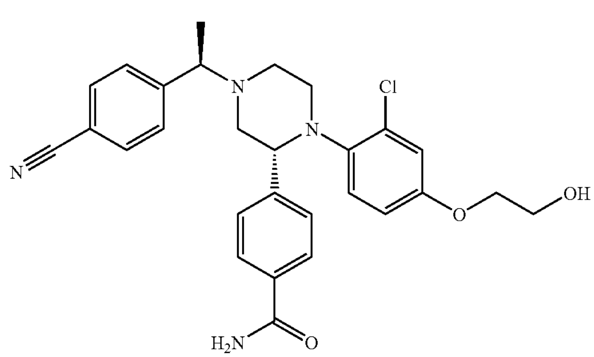 [SMILES: C[C@H](c1ccc(C#N)cc1)N1CCN(c2ccc(OCCO)cc2Cl)[C@H](c2ccc(C(N)=O)cc2)C1] | 505.3 |

TABLE 23-continued
| Ex. # | MOLECULAR STRUCTURE | OBSVD LCMS MS (MH+) |
|---|---|---|
| 131d | 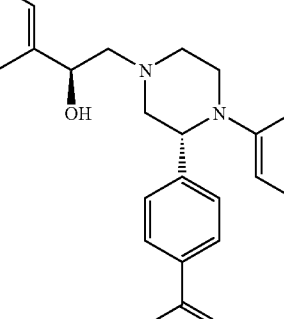 | 521.3 |
| 41d | 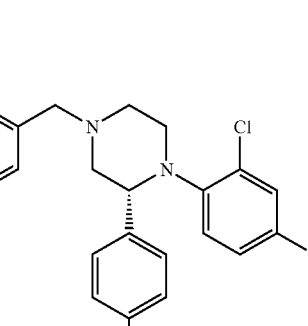 | 452.2 |
| 41h | 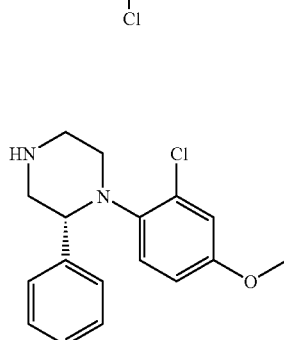 | 362.2 |
| 57c | 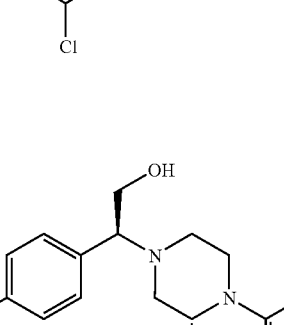 | 509.3 |

TABLE 23-continued

| Ex. # | MOLECULAR STRUCTURE | OBSVD LCMS MS (MH+) |
|---|---|---|
| 131g | 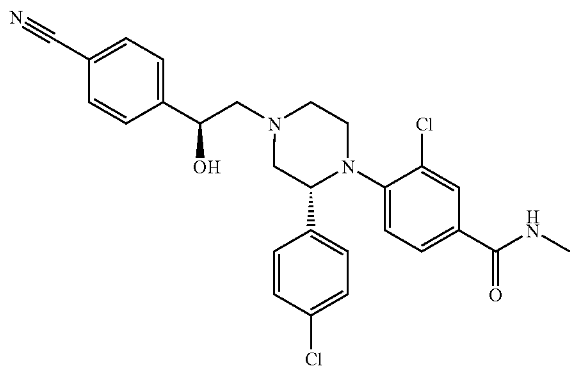 [SMILES: CNC(=O)c1ccc(N2CCN(C[C@@H](O)c3ccc(C#N)cc3)C[C@H]2c2ccc(Cl)cc2)c(Cl)c1] | 509.3 |
| 131e | 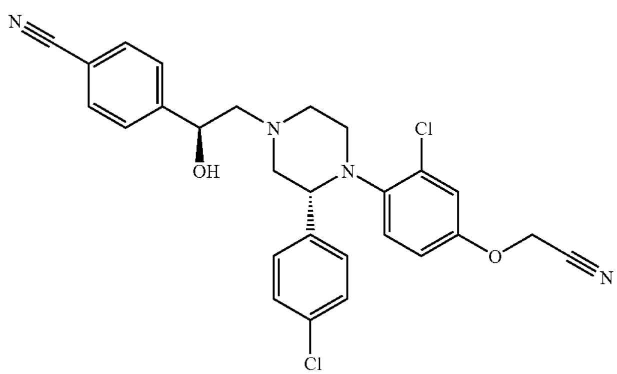 [SMILES: N#CCOc1ccc(N2CCN(C[C@@H](O)c3ccc(C#N)cc3)C[C@H]2c2ccc(Cl)cc2)c(Cl)c1] | 507.3 |
| 290d | 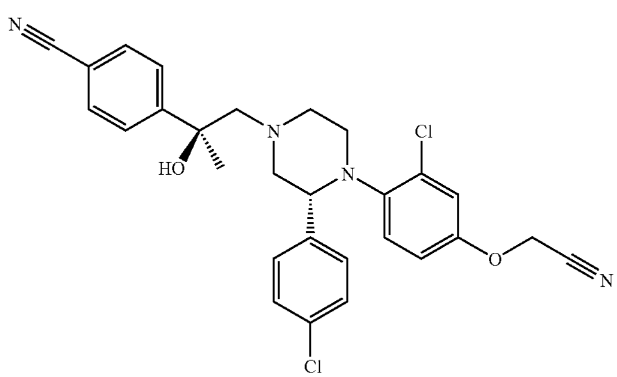 [SMILES: C[C@@](O)(CN1CCN(c2ccc(OCC#N)cc2Cl)[C@H](c2ccc(Cl)cc2)C1)c1ccc(C#N)cc1] | 521.3 |
| 200ab | 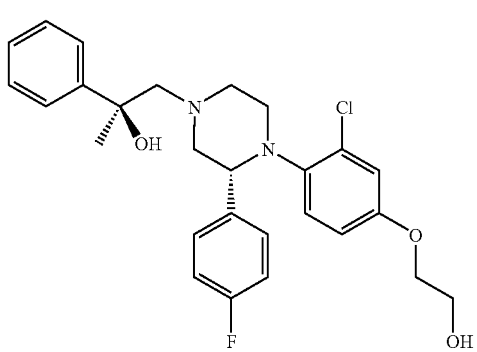 | 485.3 |

TABLE 23-continued

| Ex. # | MOLECULAR STRUCTURE | OBSVD LCMS MS (MH+) |
|---|---|---|
| 200ac | 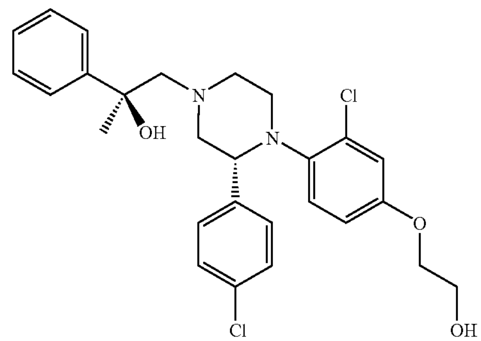 [SMILES: C[C@@](O)(CN1CCN(c2ccc(OCCO)cc2Cl)[C@H](c2ccc(Cl)cc2)C1)c1ccccc1] | 501.3 |
| 200ad | 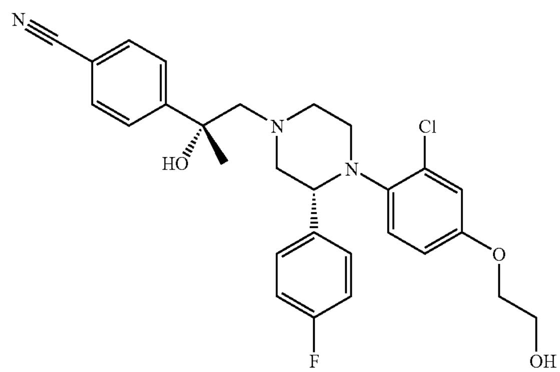 [SMILES: C[C@](O)(CN1CCN(c2ccc(OCCO)cc2Cl)[C@H](c2ccc(F)cc2)C1)c1ccc(C#N)cc1] | 510.3 |
| 200ae | 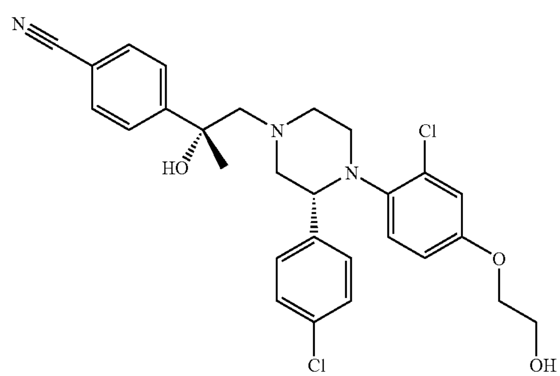 | 526.3 |
| 316 | 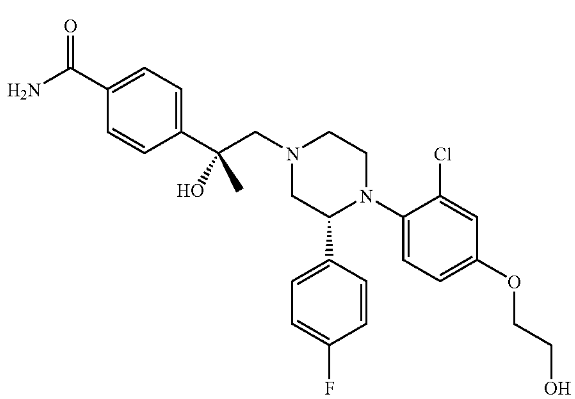 [SMILES: C[C@](O)(CN1CCN(c2ccc(OCCO)cc2Cl)[C@H](c2ccc(F)cc2)C1)c1ccc(C(N)=O)cc1] | 528.3 |

TABLE 23-continued

| Ex. # | MOLECULAR STRUCTURE | OBSVD LCMS MS (MH+) |
|---|---|---|
| 317 | 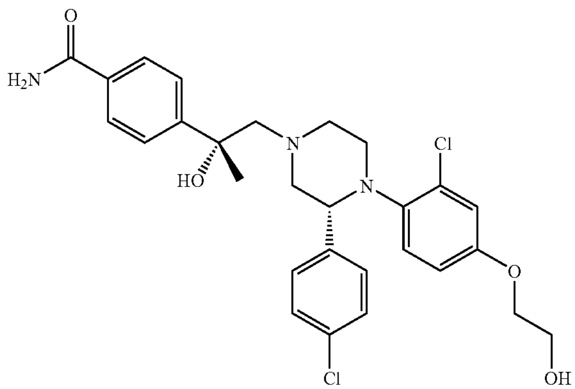 | 544.3 |
| 41e | 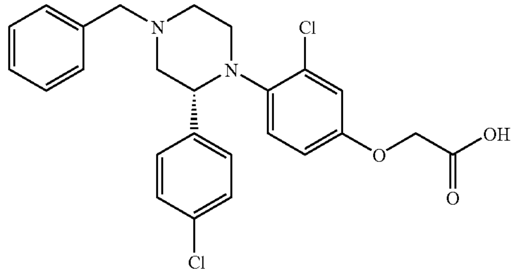 [SMILES: O=C(O)COc1ccc(N2CCN(Cc3ccccc3)C[C@H]2c2ccc(Cl)cc2)c(Cl)c1] | 471.3 |
| 41f | 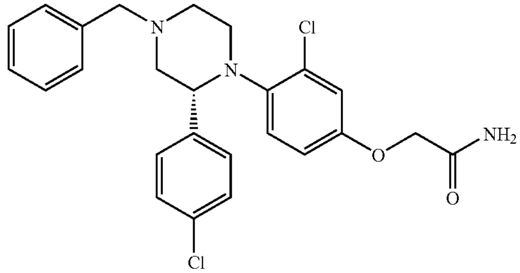 [SMILES: NC(=O)COc1ccc(N2CCN(Cc3ccccc3)C[C@H]2c2ccc(Cl)cc2)c(Cl)c1] | 470.3 |
| 41g | 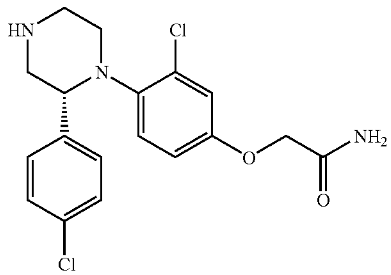 [SMILES: NC(=O)COc1ccc(N2CCNC[C@H]2c2ccc(Cl)cc2)c(Cl)c1] | 380.2 |

TABLE 23-continued

| Ex. # | MOLECULAR STRUCTURE | OBSVD LCMS MS (MH+) |
|---|---|---|
| 290e | 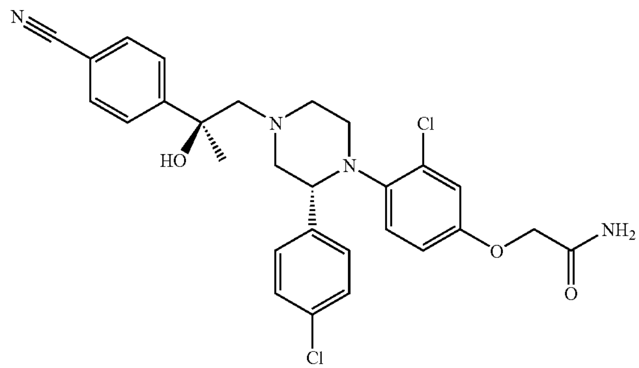 [SMILES: C[C@@](O)(CN1CCN(c2ccc(OCC(N)=O)cc2Cl)[C@H](c2ccc(Cl)cc2)C1)c1ccc(C#N)cc1] | 539.3 |
| 80f | 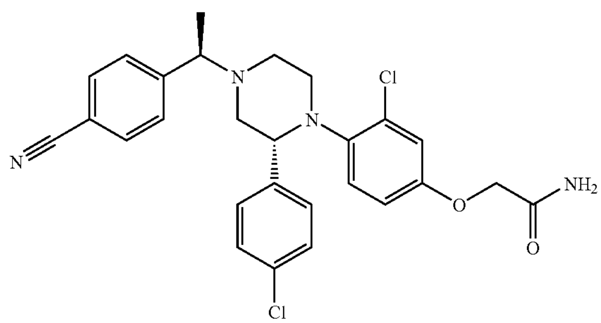 [SMILES: C[C@H](c1ccc(C#N)cc1)N1CCN(c2ccc(OCC(N)=O)cc2Cl)[C@H](c2ccc(Cl)cc2)C1] | 509.3 |
| 131f | 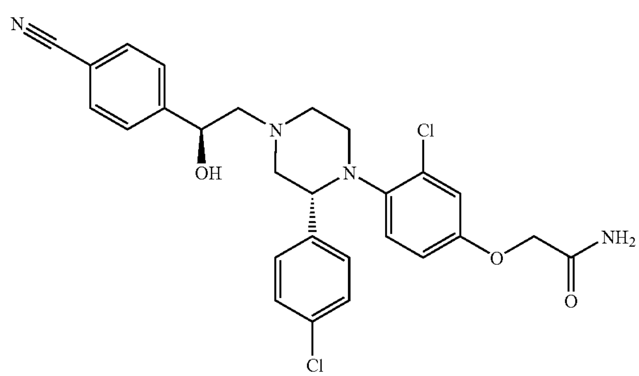 [SMILES: N#Cc1ccc([C@H](O)CN2CCN(c3ccc(OCC(N)=O)cc3Cl)[C@H](c3ccc(Cl)cc3)C2)cc1] | 527.3 |
| 264a | 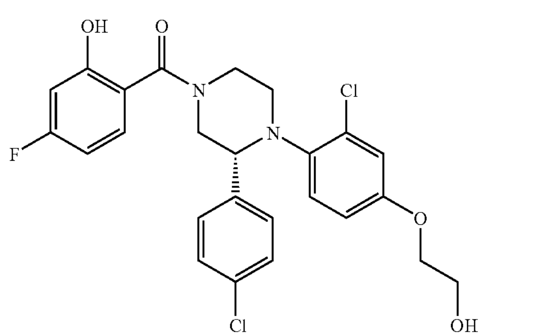 [SMILES: O=C(c1ccc(F)cc1O)N1CCN(c2ccc(OCCO)cc2Cl)[C@H](c2ccc(Cl)cc2)C1] | 505.3 |

TABLE 23-continued

| Ex. # | MOLECULAR STRUCTURE | OBSVD LCMS MS (MH+) |
|---|---|---|
| 200af | 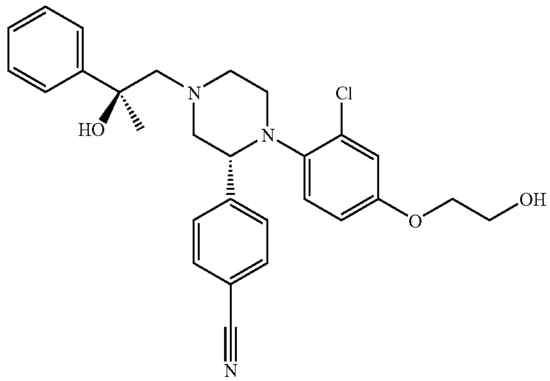 [SMILES: C[C@@](O)(CN1CCN(c2ccc(OCCO)cc2Cl)[C@H](c2ccc(C#N)cc2)C1)c1ccccc1] | 492.3 |
| 200ag | 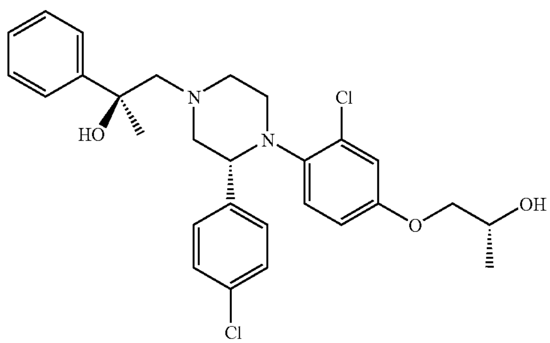 [SMILES: C[C@@H](O)COc1ccc(N2CCN(C[C@@](C)(O)c3ccccc3)C[C@H]2c2ccc(Cl)cc2)c(Cl)c1] | 515.3 |
| 200ah | 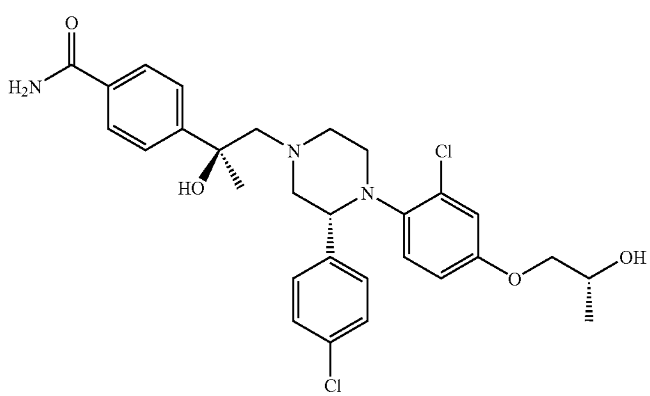 [SMILES: C[C@@H](O)COc1ccc(N2CCN(C[C@@](C)(O)c3ccc(C(N)=O)cc3)C[C@H]2c2ccc(Cl)cc2)c(Cl)c1] | 558.3 |
| 23b | 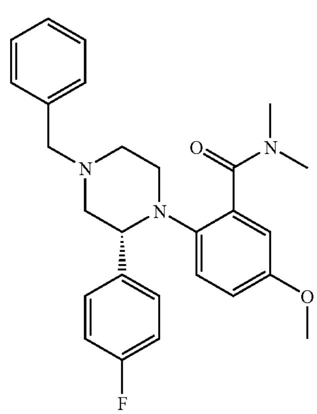 [SMILES: COc1ccc(N2CCN(Cc3ccccc3)C[C@H]2c2ccc(F)cc2)c(C(=O)N(C)C)c1] | 448.2 |

TABLE 23-continued

| Ex. # | MOLECULAR STRUCTURE | OBSVD LCMS MS (MH+) |
|---|---|---|
| 200t | 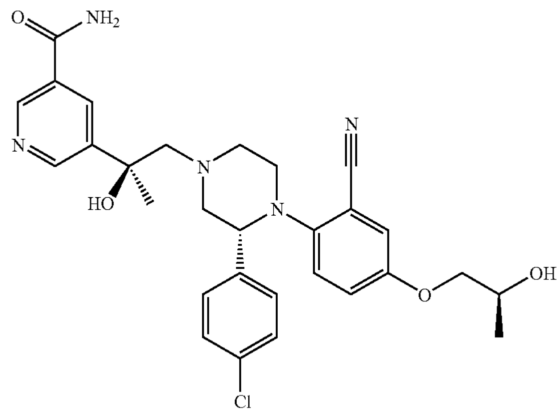 [SMILES: C[C@H](O)COc1ccc(N2CCN(C[C@@](C)(O)c3cncc(C(N)=O)c3)C[C@H]2c2ccc(Cl)cc2)c(C#N)c1] | 550.3 |
| 200u | 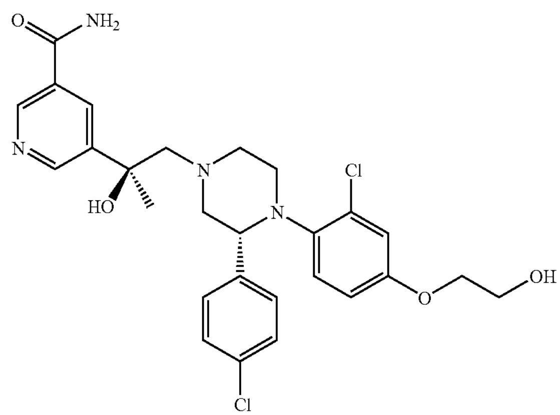 [SMILES: C[C@@](O)(CN1CCN(c2ccc(OCCO)cc2Cl)[C@H](c2ccc(Cl)cc2)C1)c1cncc(C(N)=O)c1] | 545.3 |
| 200ai | 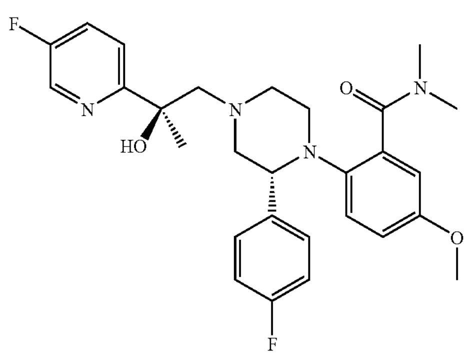 [SMILES: COc1ccc(N2CCN(C[C@@](C)(O)c3ccc(F)cn3)C[C@H]2c2ccc(F)cc2)c(C(=O)N(C)C)c1] | 511.3 |
| 200w | 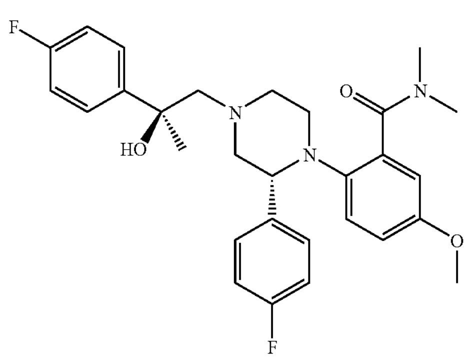 | 510.3 |

TABLE 23-continued

| Ex. # | MOLECULAR STRUCTURE | OBSVD LCMS MS (MH+) |
|---|---|---|
| 200x | 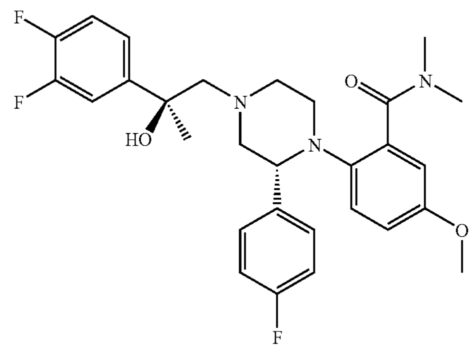 [SMILES: COc1ccc(N2CCN(C[C@@](C)(O)c3ccc(F)c(F)c3)C[C@H]2c2ccc(F)cc2)c(C(=O)N(C)C)c1] | 528.3 |
| 200aa | 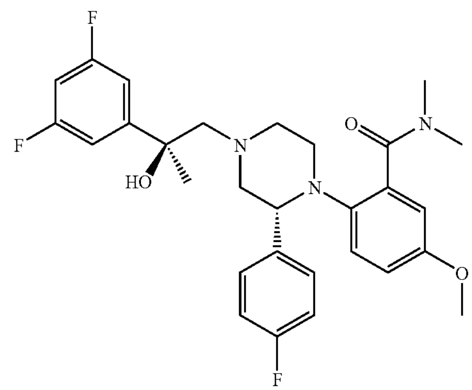 [SMILES: COc1ccc(N2CCN(C[C@@](C)(O)c3cc(F)cc(F)c3)C[C@H]2c2ccc(F)cc2)c(C(=O)N(C)C)c1] | 528.3 |
| 290b | 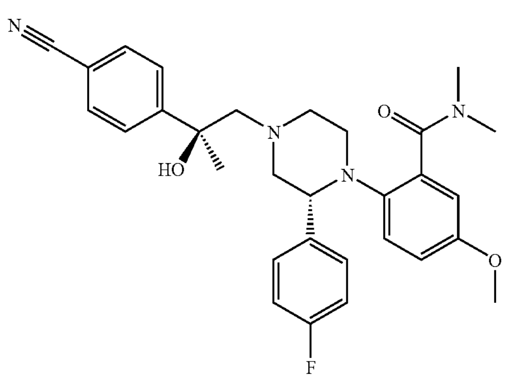 [SMILES: COc1ccc(N2CCN(C[C@@](C)(O)c3ccc(C#N)cc3)C[C@H]2c2ccc(F)cc2)c(C(=O)N(C)C)c1] | 517.3 |
| 200y | 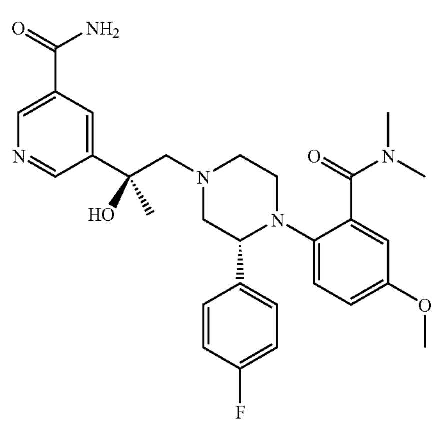 [SMILES: COc1ccc(N2CCN(C[C@@](C)(O)c3cncc(C(N)=O)c3)C[C@H]2c2ccc(F)cc2)c(C(=O)N(C)C)c1] | 536.3 |

TABLE 23-continued

| Ex. # | MOLECULAR STRUCTURE | OBSVD LCMS MS (MH+) |
|---|---|---|
| 200z | 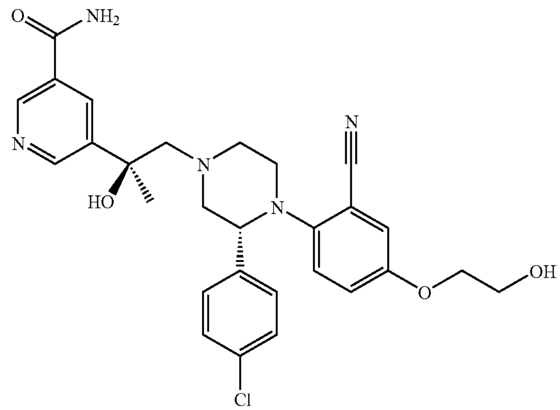 [SMILES: C[C@@](O)(CN1CCN(c2ccc(OCCO)cc2C#N)[C@H](c2ccc(Cl)cc2)C1)c1cncc(C(N)=O)c1] | 536.3 |
| 235e | 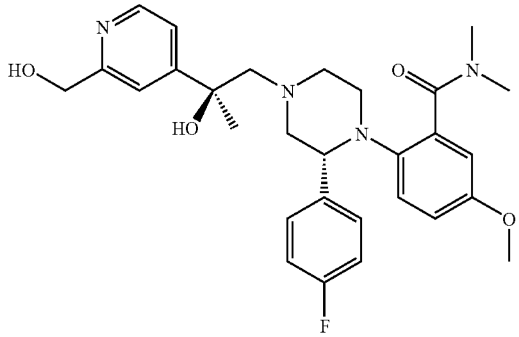 [SMILES: COc1ccc(N2CCN(C[C@@](C)(O)c3ccnc(CO)c3)C[C@H]2c2ccc(F)cc2)c(C(=O)N(C)C)c1] | 523.3 |
| 235f | 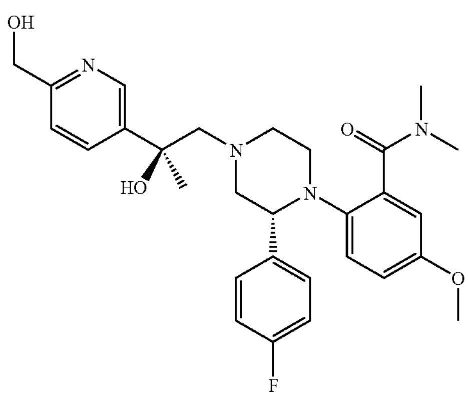 [SMILES: COc1ccc(N2CCN(C[C@@](C)(O)c3ccc(CO)nc3)C[C@H]2c2ccc(F)cc2)c(C(=O)N(C)C)c1] | 523.3 |

We claim:

1. A compound of Formula (I):

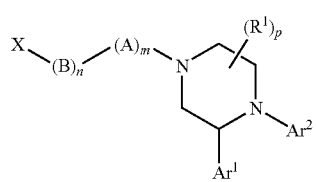

or a pharmaceutically acceptable salt thereof, wherein:

$Ar^1$ and $Ar^2$ are independently aryl or heteroaryl, wherein $Ar^1$ is substituted with one or more groups independently selected from $Y^1$ or $Y^3$, and $Ar^2$ is substituted with one or more groups independently selected from $Y^1$ or $Y^3$, with the proviso that when $Ar^2$ is pyridine or pyrimidine, a nitrogen of said pyridine or pyrimidine is not in the para position relative to the point of attachment to the piperazine ring;

with the proviso that at least one of $Ar^1$ or $Ar^2$ is substituted with at least one group independently selected from $Y^3$;

n and m are independently 0 or 1;

A is selected from the group consisting of —C(O)—, —S(O)$_2$—, —C(=N—OR$^2$)—, and —(C(R$^2$)$_2$)$_q$— wherein q is 1, 2, or 3;

B is selected from the group consisting of —N(R$^2$)—, —C(O)—, and —(C(R$^3$)$_2$)$_r$— wherein r is 1, 2 or 3, with the proviso that when B is —C(O)—, then A is —C(O)— or —(C(R²)₂)_q—;

X is pyridine, which is unsubstituted or optionally substituted with one or more groups independently selected from —C(=NH)—O-alkyl, —C(=N-alkyl)-O-alkyl, —C(O)OH, -alkylene-O-heterocycloalkyl, Y¹ and Y³;

each R¹ is independently selected from the group consisting of alkyl, haloalkyl, -alkylene-N(R⁵)₂, -alkylene-OR², alkylene-N₃, -alkylene-CN, and alkylene-O—S(O)₂-alkyl; or two R¹ groups attached to the same ring carbon atom form a carbonyl group;

p is 0, 1, 2, 3, or 4;

each R² is independently H, alkyl, aryl, heteroaryl, cycloalkyl, or heterocycloalkyl, wherein said aryl, heteroaryl, cycloalkyl, and heterocycloalkyl, of R² is unsubstituted or substituted with one or more groups independently selected from Y¹ and Y³;

each R³ is independently selected from the group consisting of H, alkyl, —OR², -alkylene-O-alkyl, -alkylene-OH, unsubstituted aryl, and aryl substituted with one or more groups independently selected from Y¹ and Y³;

each R⁴ is independently selected from the group consisting of H, alkyl, aryl, —C(O)—O-alkyl, —C(O)-alkyl, —C(O)-aryl, —C(O)-heteroaryl, —C(O)-heterocycloalkyl, —S(O)₂alkyl, —S(O)₂aryl, —S(O)₂heteroaryl, and —S(O)₂heterocycloalkyl;

wherein each said aryl, each aryl portion of said —C(O)-aryl, each aryl portion of said —S(O)₂aryl, and each heteroaryl portion of said —C(O)-heteroaryl and said —S(O)₂heteroaryl of R⁴ is unsubstituted or substituted with one or more groups independently selected from Y¹ and Y³;

each R⁵ is independently selected from the group consisting of H, alkyl, aryl, —S(O)₂-alkyl, —S(O)₂-cycloalkyl, —S(O)₂-aryl, —C(O)—N(R²)₂, —C(O)-alkyl, and -alkylene-OH, wherein each said aryl and each said aryl portion of said —S(O)₂-aryl of R⁵ are unsubstituted or substituted with one or more groups independently selected from Z;

each Y¹ is independently selected from the group consisting of alkyl, cycloalkyl, heterocycloalkyl, heterocycloalkenyl, halo, haloalkyl, aryl, -alkylene-aryl, heteroaryl, —O-alkyl, —O-aryl, —O-heteroaryl, —O-cycloalkyl, —O-heterocycloalkyl, —S-alkyl, —S-aryl, —S-heteroaryl, —S- cycloalkyl, —S-heterocycloalkyl, —S(O)₂-alkyl, —S(O)₂-aryl, —S(O)₂-heteroaryl, —S(O)₂-cycloalkyl, —S(O)₂-heterocycloalkyl, -alkylene-CN, —CN, —C(O)-alkyl, —C(O)-aryl, —C(O)-haloalkyl, —C(O)-heteroaryl, —C(O)-cycloalkyl, —C(O)-heterocycloalkyl, —C(O)O-alkyl, —C(O)O-aryl, —C(O)O-haloalkyl, —C(O)O-heteroaryl, —C(O)O-cycloalkyl, —C(O)O-heterocycloalkyl, —N(R²)C(O) -alkyl, —N(R²)C(O)—N(R²)₂, —OH, —O-haloalkyl, —O-alkylene-C(O)OH, —S-haloalkyl, -alkylene-OH, -alkylene-C(O)—O-alkyl, —O-alkylene-aryl, and —N(R⁵)₂, wherein each aryl, each heteroaryl, each aryl portion of said O-aryl, each aryl portion of said —S-aryl, each aryl portion of said —S(O)₂-aryl, each aryl portion of said —C(O)-aryl, each aryl portion of said —C(O)O-aryl, each aryl portion of said benzyl, and each aryl portion of said —O-alkylene-aryl of Y¹, and each heteroaryl portion of said —O-heteroaryl, each heteroaryl portion of said —S-heteroaryl, each heteroaryl portion of said —S(O)₂-heteroaryl, each heteroaryl portion of said —C(O)-heteroaryl, each heteroaryl portion of said —C(O)O-heteroaryl, each heteroaryl portion of said —O-alkylene-heteroaryl of Y¹ are unsubstituted or substituted with one or more groups independently selected from Z; or two groups Y¹ form a —O—CH₂—O— group;

each Y³ is independently selected from —C(O)N(R⁶)₂, —S(O)₂N(R⁶)₂, —O—Q-L₁—R⁷, —O—Q-CN, —O—Q-C(O)N(R⁶)₂, —O—Q-S(O)₂N(R⁶)₂, —O—Q-OC(O)N(R⁶)₂, and —O—Q-N(R⁶)C(O)N(R⁶)₂, with the proviso that when A is —C(O)—, then Ar² is substituted with at least one Y¹ or Y³ group independently selected from cycloalkyl, benzyl, aryl, —O-haloalkyl, —O-aryl, —O-cycloalkyl, —S-aryl, —S-haloalkyl, —S--cycloalkyl, —S(O)₂-alkyl, —S(O)₂-cycloalkyl, —S(O)₂-aryl, -alkylene-CN, —C(O)-aryl, —C(O)-haloalkyl, —C(O)-cycloalkyl, —C(O)O-aryl, —C(O)O-haloalkyl, —C(O)O-heteroaryl, —C(O)O-cycloalkyl, —C(O)O-heterocycloalkyl, -alkylene-C(O)—O-alkyl, and —O-alkylene-aryl, wherein each benzyl and each aryl portion of said Y¹ or Y³, and each aryl portion and each heteroaryl portion of said —O-aryl, said —S-aryl, said —S(O)₂-aryl, said —C(O)-aryl, said —C(O)O-aryl, —C(O)O-heteroaryl, —C(O)O-heterocycloalkyl, and —O-alkylene-aryl of said Y¹ or Y³ group is unsubstituted or substituted with one or more groups independently selected from Z;

each -Q- is a divalent radical independently selected from -alkylene-, -alkenylene-, -alkynylene-, -cycloalkylene-, -heterocycloalkylene-, -alkylene-cycloalkylene-, -cycloalkylene-alkylene-, -cycloalkylene-alkylene-cycloalkylenewherein the alkylene, alkenylene, alkynylene, cycloalkylene, and heterocycloalkylene portion of said Q is optionally substituted with one to three groups independently selected from

and Z, wherein t is 0, 1, 2, or 3;

each L₁ is independently selected from the group consisting of —O—, —S—, —S(O)—, —S(O)₂—, —OS(O)₂—, —C(O)—, and —OC(O)—;

each R⁶ is independently selected from the group consisting of H, alkyl, haloalkyl, alkoxy, cycloalkyl, heterocycloalkyl, unsubstituted aryl, aryl substituted with one or more groups independently selected from Y¹, unsubstituted heteroaryl, heteroaryl substituted with one or more groups independently selected from Y¹, -alkylene-OH, -alkylene-O-alkyl, -alkylene-O-aryl, -alkylene-OC(O)-alkyl, -alkylene-OC(O)-aryl, -alkylene-OC(O)-heteroaryl, and alkylene-N(R⁴)₂, or two R⁶ groups, together with the nitrogen to which they are attached, form a heterocycloalkenyl, or a benzo-fused heterocycloalkyl group;

each R⁷ is independently selected from the group consisting of H, alkyl, —N(R⁶)₂, cycloalkyl, heterocycloalkyl, aryl, substituted aryl, heteroaryl, and substituted heteroaryl, wherein said substituents are independently selected from Z and —C(O)N(R⁶)₂; and each Z is independently selected from the group consisting of alkyl, halo, haloalkyl, —OH, —O-alkyl, and —CN.

2. The compound of claim 1, or a pharmaceutically acceptable salt thereof, wherein:

$Ar^1$ and $Ar^2$ are independently $(C_6-C_{10})$aryl or $(C_2-C_{10})$heteroaryl, $Ar^1$ is substituted with one or more groups independently selected from $Y^1$ or $Y^3$, and $Ar^2$ is substituted with one or more groups independently selected from $Y^1$ or $Y^3$, with the proviso that when $Ar^2$ is pyridine or pyrimidine, a nitrogen of said pyridine or pyrimidine is not in the para position relative to the point of attachment to the piperazine ring;

with the proviso that at least one of $Ar^1$ or $Ar^2$ is substituted with at least one group independently selected from $Y^3$;

n and m are independently 0 or 1;

A is selected from the group consisting of —C(O)—, —S(O)$_2$—, —C(=N—OR$^2$)—, and —(C(R$^2$)$_2$)$_q$— wherein q is 1, 2, or 3;

B is selected from the group consisting of —N(R$^2$)—, —C(O)—, and —(C(R$^3$)$_2$)$_r$— wherein r is 1, 2 or 3, with the proviso that when B is —C(O)—, then A is —C(O)— or —(C(R$^2$)$_2$)$_q$—;

with the further proviso that when A is —C(O)—, then $Ar^2$ is substituted with one or more groups independently selected from $Y^3$;

X is pyridine which is unsubstituted or substituted with one or more groups independently selected from —C(=NH)—O—(C$_1$-C$_6$)alkyl, —C(=N—(C$_1$-C$_6$)alkyl)-O—(C$_1$-C$_6$)alkyl, —C(O)OH, —(C$_1$-C$_6$)alkylene-O—(C$_2$-C$_{10}$)heterocycloalkyl, $Y^1$ and $Y^3$;

each $R^1$ is independently selected from the group consisting of (C$_1$-C$_6$)alkyl, (C$_1$-C$_6$)haloalkyl, —(C$_1$-C$_6$)alkylene-N(R$^5$)$_2$, —(C$_1$-C$_6$)alkylene-OR$^2$, —(C$_1$-C$_6$)alkylene-N$_3$, —(C$_1$-C$_6$)alkylene-CN, and (C$_1$-C$_6$)alkylene-O—S(O)$_2$—(C$_1$-C$_6$)alkyl; or two $R^1$ groups attached to the same ring carbon atom form a carbonyl group;

p is 0, 1, 2, 3, or 4;

each $R^2$ is independently H, (C$_1$-C$_6$)alkyl, (C$_6$-C$_{10}$)aryl, or (C$_2$-C$_{10}$)heteroaryl, (C$_3$-C$_{10}$)cycloalkyl, or (C$_2$-C$_{10}$)heterocycloalkyl, wherein said (C$_6$-C$_{10}$)aryl of $R^2$ is unsubstituted or substituted with one or more groups independently selected from $Y^1$ and $Y^3$;

each $R^3$ is independently selected from the group consisting of H, (C$_1$-C$_6$)alkyl, —OR$^2$, —(C$_1$-C$_6$)alkylene-O—(C$_1$-C$_6$)alkyl, —(C$_1$-C$_6$)alkylene-OH, unsubstituted (C$_6$-C$_{10}$)aryl, and (C$_6$-C$_{10}$)aryl substituted with one or more groups independently selected from $Y^1$ and $Y^3$;

each $R^4$ is independently selected from the group consisting of H, (C$_1$-C$_6$)alkyl, (C$_6$-C$_{10}$)aryl, —C(O)—O—(C$_1$-C$_6$)alkyl, —C(O)—(C$_1$-C$_6$)alkyl, —C(O)—(C$_6$-C$_{10}$)aryl, —C(O)—(C$_2$-C$_{10}$)heterocycloalkyl, —C(O)—(C$_3$-C$_{10}$)heterocycloalkyl, —S(O)$_2$(C$_1$-C$_6$)alkyl, —S(O)$_2$(C$_6$-C$_{10}$)aryl, —S(O)$_2$(C$_2$-C$_{10}$)heteroaryl, and —S(O)$_2$(C$_3$-C$_{10}$)heterocycloalkyl;

wherein each said (C$_6$-C$_{10}$)aryl, each aryl portion of said C(O)—(C$_6$-C$_{10}$)aryl, each aryl portion of said —S(O)$_2$(C$_6$-C$_{10}$)aryl, and each heteroaryl portion of said —C(O)—(C$_2$-C$_{10}$)heteroaryl and said —S(O)$_2$(C$_2$-C$_{10}$)heterocycloalkyl of $R^4$ is unsubstituted or substituted with one or more groups independently selected from $Y^1$ and $Y^3$;

each $R^5$ is independently selected from the group consisting of H, (C$_1$-C$_6$)alkyl, (C$_6$-C$_{10}$)aryl, —S(O)$_2$—(C$_1$-C$_6$)alkyl, —S(O)$_2$—(C$_3$-C$_{10}$)cycloalkyl, —S(O)$_2$—(C$_6$-C$_{10}$)aryl, —C(O)—N(R$^2$)$_2$, —C(O)—(C$_1$-C$_6$)alkyl, and —(C$_1$-C$_6$)alkylene-OH, wherein each said (C$_6$-C$_{10}$)aryl and each said (C$_6$-C$_{10}$)aryl portion of said —S(O)$_2$—(C$_6$-C$_{10}$)aryl of $R^5$ are unsubstituted or substituted with one or more groups independently selected from Z;

each $Y^1$ is independently selected from the group consisting of (C$_1$-C$_6$)alkyl, (C$_3$-C$_{10}$)cycloalkyl, (C$_2$-C$_{10}$)heterocycloalkyl, (C$_2$-C$_{10}$)heterocycloalkenyl, halo, (C$_1$-C$_6$)haloalkyl, benzyl, (C$_6$-C$_{10}$)aryl, (C$_2$-C$_{10}$)heteroaryl, —O—(C$_6$-C$_{10}$)aryl, —O—(C$_2$-C$_{10}$)heteroaryl, —O—(C$_3$-C$_{10}$)cycloalkyl, —O—(C$_2$-C$_{10}$)heterocycloalkyl, —S—(C$_1$-C$_6$)alkyl, —S—(C$_2$-C$_{10}$)heteroaryl, —S—(C$_3$-C$_{10}$)cycloalkyl, —S—(C$_2$-C$_{10}$)heterocycloalkyl, —S(O)$_2$—(C$_1$-C$_6$)alkyl, —S(O)$_2$—(C$_6$-C$_{10}$)aryl, —S(O)$_2$—(C$_2$-C$_{10}$)heteroaryl, —S(O)$_2$—(C$_3$-C$_{10}$)cycloalkyl, —S(O)$_2$—(C$_2$-C$_{10}$)heterocycloalkyl, —(C$_1$-C$_6$)alkylene-CN, —CN, —C(O)—(C$_1$-C$_6$)alkyl, —C(O)—(C$_6$-C$_{10}$)aryl, —C(O)—(C$_1$-C$_6$)haloalkyl, —C(O)—(C$_2$-C$_{10}$)heteroaryl, —C(O)—(C$_3$-C$_{10}$)cycloalkyl, —C(O)—(C$_2$-C$_{10}$)heterocycloalkyl, —C(O)O—(C$_1$-C$_6$)alkyl, —C(O)O—(C$_6$-C$_{10}$)aryl, —C(O)O—(C$_1$-C$_6$)haloalkyl, —C(O)O—(C$_2$-C$_{10}$)heteroaryl, —C(O)O—(C$_3$-C$_{10}$)cycloalkyl, —C(O)O—(C$_2$-C$_{10}$)heterocycloalkyl, —N(R$^2$)C(O)—(C$_1$-C$_6$)alkyl, —N(R$^2$)C(O)—N(R$^2$)$_2$, —OH, —O—(C$_1$-C$_6$)alkyl, —O—(C$_1$-C$_6$)haloalkyl, —O—(C$_1$-C$_6$)alkylene-C(O)OH, —S—(C$_1$-C$_6$)haloalkyl, —(C$_1$-C$_6$)alkylene-OH, —(C$_1$-C$_6$)alkylene-C(O)—O—(C$_1$-C$_6$)alkyl, —O—(C$_1$-C$_6$)alkylene-(C$_6$-C$_{10}$)aryl, and —N(R$^5$)$_2$, wherein each (C$_6$-C$_{10}$)aryl, each (C$_2$-C$_{10}$)heteroaryl, each aryl portion of said —O—(C$_6$-C$_{10}$)aryl, each aryl portion of said —S—(C$_6$-C$_{10}$)aryl, each aryl portion of said —S(O)$_2$—(C$_6$-C$_{10}$)aryl, each aryl portion of said —C(O)—(C$_6$-C$_{10}$)aryl, each aryl portion of said —C(O)O—(C$_6$-C$_{10}$)aryl, each aryl portion of said benzyl, and each aryl portion of said -O-(C$_1$-C$_6$)alkylene-aryl of $Y^1$, and each heteroaryl portion of said —O—(C$_2$-C$_{10}$)heteroaryl, each heteroaryl portion of said —S—(C$_2$-C$_{10}$)heteroaryl, each heteroaryl portion of said —S(O)$_2$—(C$_2$-C$_{10}$)heteroaryl, each heteroaryl portion of said —C(O)—(C$_2$-C$_{10}$)heteroaryl, each heteroaryl portion of said —C(O)O—(C$_2$-C$_{10}$)heteroaryl, each heteroaryl portion of said —O—(C$_1$-C$_6$)alkylene-(C$_2$-C$_{10}$)heteroaryl of $Y^1$ are unsubstituted or substituted with one or more groups independently selected from Z; or two groups $Y^1$ form a —O—CH$_{2-O-}$ group;

each $Y^3$ is independently selected from —C(O)N(R$^6$)$_2$, —S(O)$_2$N(R$^6$)$_2$, —O-Q-L$_1$-R$^7$, —O-Q-CN, —O-Q-C(O)N(R$^6$)$_2$, —O-Q-S(O)$_2$N(R$^6$)$_2$, —O-Q-OC(O)N(R$^6$)$_2$, and —O-Q-N(R$^6$)C(O)N(R$^6$)$_2$, with the proviso that when A is —C(O)—, then $Ar^2$ is substituted with at least one $Y^1$ or $Y^3$ group independently selected from (C$_3$-C$_{10}$)cycloalkyl, benzyl, (C$_6$-C$_{10}$)aryl, —O—(C$_1$-C$_6$)haloalkyl, —O—(C$_6$-C$_{10}$)aryl, —O—(C$_3$-C$_{10}$)cycloalkyl, —S—(C$_6$-C$_{10}$)aryl, —S—(C$_1$-C$_6$)haloalkyl, —S—(C$_3$-C$_{10}$)cycloalkyl, —S(O)$_2$—(C$_1$-C$_6$)alkyl, —S(O)$_2$—(C$_3$-C$_{10}$)cycloalkyl, —S(O)$_2$—(C$_6$-C$_{10}$)aryl, —(C$_1$-C$_6$)alkylene-CN, —C(O)—(C$_6$-C$_{10}$)aryl, —C(O)—(C$_1$-C$_6$)haloalkyl, —C(O)—(C$_3$-C$_{10}$)cycloalkyl, —C(O)O—(C$_6$-C$_{10}$)aryl, C(O)O—(C$_1$-C$_6$)haloalkyl, —C(O)O—(C$_2$-C$_{10}$)heteroaryl, —C(O)O—(C$_3$-C$_{10}$)cycloalkyl, —C(O)O—(C$_2$-C$_{10}$)heterocycloalkyl, —(C$_1$-C$_6$)alkylene-C(O)—O—(C$_1$-C$_6$)alkyl, and —O—$(C_1$-$C_6)$alkylene-$(C_6$-$C_{10})$aryl, wherein each benzyl and each $(C_6$-$C_{10})$aryl portion of said $Y^1$ or $Y^3$ group, and each aryl portion and each heteroaryl portion of said —O—$(C_6$-$C_{10})$aryl, said —S-$(C_6$-$C_{10})$aryl, said —S(O)$_2$—$(C_6$-$C_{10})$aryl, said —C(O)—$(C_6$-$C_{10})$aryl, said —C(O)O—$(C_6$-$C_{10})$aryl, —C(O)O—$(C_2$-$C_{10})$heteroaryl, —C(O)O—$(C_2$-$C_{10})$heterocycloalkyl, and —O—$(C_1$-$C_6)$alkylene -$(C_6$-$C_{10})$aryl of said $Y^1$ or $Y^3$ group is unsubstituted or substituted with one or more groups independently selected from Z;

each -Q- is a divalent radical independently selected from —$(C_1$-$C_6)$alkylene-, —$(C_2$-$C_6)$alkenylene-, —$(C_2$-$C_6)$alkynylene-, —$(C_3$-$C_{10})$cycloalkylene-, —$(C_2$-$C_{10})$heterocycloalkylene-, —$(C_1$-$C_6)$alkylene-$(C_3$-$C_{10})$cycloalkylene-, —$(C_3$-$C_{10})$cycloalkylene-$(C_1$-$C_6)$alkylene-, —$(C_3$-$C_{10})$cycloalkylene-$(C_1$-$C_6)$alkylene-$(C_3$-$C_{10})$cycloalkylene-wherein the alkylene, alkenylene, alkynylene, cycloalkylene, and heterocycloalkylene portion of said Q is optionally substituted with one to three groups independently selected from

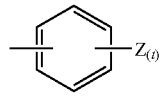

and Z, wherein t is 0, 1, 2, or 3;

each $L_1$ is independently selected from the group consisting of —O—, —S—, —S(O)—, —S(O)$_2$—, —OS(O)$_2$—, —C(O)—, and —OC(O)—;

each $R^6$ is independently selected from the group consisting of H, $(C_1$-$C_6)$alkyl, $(C_1$-$C_6)$haloalkyl, $(C_1$-$C_6)$alkoxy, $(C_3$-$C_{10})$cycloalkyl, $(C_3$-$C_{10})$heterocycloalkyl, unsubstituted $(C_6$-$C_{10})$aryl, $(C_6$-$C_{10})$aryl substituted with one or more groups independently selected from $Y^1$, unsubstituted $(C_2$-$C_{10})$heteroaryl, $(C_2$-$C_{10})$heteroaryl substituted with one or more groups independently selected from $Y^1$, —$(C_1$-$C_6)$alkylene-OH, —$(C_1$-$C_6)$alkylene-O—$(C_1$-$C_6)$alkyl, -$(C_1$-$C_6)$alkylene-O-$(C_6$-$C_{10})$aryl, —$(C_1$-$C_6)$alkylene-OC(O)—$(C_1$-$C_6)$alkyl, —$(C_1$-$C_6)$alkylene-OC(O)—$(C_6$-$C_{10})$aryl, —$(C_1$-$C_6)$alkylene-OC(O)—$(C_2$-$C_{10})$heteroaryl, and $(C_1$-$C_6)$alkylene-N$(R^4)_2$, or two $R^6$ groups, together with the nitrogen to which they are attached, form a $(C_2$-$C_{10})$heterocycloalkenyl, or a benzo-fused $(C_2$-$C_{10})$heterocycloalkyl group;

each $R^7$ is independently selected from the group consisting of H, $(C_1$-$C_6)$alkyl, —N$(R^6)_2$, $(C_3$-$C_{10})$cycloalkyl, $(C_2$-$C_{10})$heterocycloalkyl, $(C_6$-$C_{10})$aryl, substituted $(C_6$-$C_{10})$aryl, $(C_2$-$C_{10})$heteroaryl, and substituted $(C_2$-$C_{10})$heteroaryl, wherein said substituents are independently selected from Z and —C(O)N$(R^6)_2$; and each Z is independently selected from the group consisting of $(C_1$-$C_6)$alkyl, halo, $(C_1$-$C_6)$haloalkyl, —OH, —O—$(C_1$-$C_6)$alkyl, and —CN.

3. The compound of claim 1, or a pharmaceutically acceptable salt thereof, wherein:
at least one group $Y^3$ is —C(O)N$(R^6)_2$.

4. The compound of claim 3, or a pharmaceutically acceptable salt thereof, wherein:
each $R^6$ is independently selected from H, alkyl, and -alkylene-OH.

5. The compound of claim 1, or a pharmaceutically acceptable salt thereof, wherein:
at least one group $Y^3$ is —O-Q-$L_1$-$R^7$.

6. The compound of claim 5, or a pharmaceutically acceptable salt thereof, wherein:
-Q- is unsubstituted -alkylene-.

7. The compound of claim 5, or a pharmaceutically acceptable salt thereof, wherein:
-Q- is -alkylene- substituted with from one to three groups independently selected from

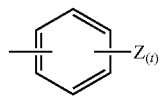

and Z, wherein t is 0, 1, 2, or 3.

8. The compound of claim 7, or a pharmaceutically acceptable salt thereof, wherein:
-Q- is -alkylene- substituted with methyl and

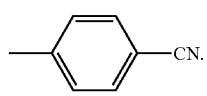

9. The compound of claim 5, or a pharmaceutically acceptable salt thereof, wherein:
-Q- is -alkylene- substituted with one to three groups Z, wherein each Z is independently selected from -alkyl.

10. The compound of claim 5, or a pharmaceutically acceptable salt thereof, wherein:
$L_1$ is —O—.

11. The compound of claim 5, or a pharmaceutically acceptable salt thereof, wherein:
$L_1$ is —OC(O)—.

12. The compound of claim 5, or a pharmaceutically acceptable salt thereof, wherein:
wherein $R^7$ is selected from H, alkyl, —N$(R^6)_2$, cycloalkyl, and heterocycloalkyl.

13. The compound of claim 12, or a pharmaceutically acceptable salt thereof, wherein:
$R^7$ is tetrahydropyran.

14. The compound of claim 1, or a pharmaceutically acceptable salt thereof, wherein:
at least one group $Y^3$ is

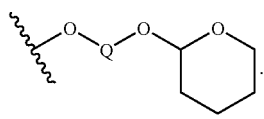

15. The compound of claim 14, or a pharmaceutically acceptable salt thereof, wherein:
Q is unsubstituted -alkylene.

16. The compound of claim 14, or a pharmaceutically acceptable salt thereof, wherein:
Q is -alkylene- substituted with from one to three groups independently selected from

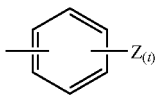

and Z, wherein t is 0, 1, 2, or 3.

17. The compound of claim 1, or a pharmaceutically acceptable salt thereof, wherein:
$Ar^1$ and $Ar^2$ are aryl.

18. The compound of claim 1, or a pharmaceutically acceptable salt thereof, wherein:
$Ar^1$ is phenyl.

19. The compound of claim 1, or a pharmaceutically acceptable salt thereof, wherein:
$Ar^2$ is phenyl.

20. The compound of claim 1, or a pharmaceutically acceptable salt thereof, wherein:
$A^1$ and $Ar^2$ are phenyl.

21. The compound of claim 17, or a pharmaceutically acceptable salt thereof, wherein:
$Ar^2$ is phenyl substituted with one $Y^3$ group and one $Y^1$ group.

22. The compound of claim 21, or a pharmaceutically acceptable salt thereof, wherein:
$Ar^2$ is phenyl substituted with one $Y^3$ group in the 4-position and one $Y^1$ group in the 2-position, relative to the point of attachment to the piperazine ring.

23. The compound according to claim 17, or a pharmaceutically acceptable salt thereof, wherein:
$Ar^1$ is phenyl substituted with one or more groups independently selected from $Y^1$ and $Y^3$.

24. The compound according to claim 17, or a pharmaceutically acceptable salt thereof, wherein:
$Ar^1$ is phenyl substituted with one $Y^1$ group at the 4-position, relative to the point of attachment to the piperazine ring.

25. The compound according to claim 1, or a pharmaceutically acceptable salt thereof, wherein:
$Ar^1$ is aryl and $Ar^2$ is heteroaryl.

26. The compound according to claim 25, or a pharmaceutically acceptable salt thereof, wherein:
$Ar^1$ is phenyl and $Ar^2$ is pyridyl.

27. The compound according to claim 1, or a pharmaceutically acceptable salt thereof, wherein:
$Ar^1$ is heteroaryl and $Ar^2$ is aryl.

28. The compound according to claim 27, or a pharmaceutically acceptable salt thereof, wherein:
$Ar^1$ is pyridyl and $Ar^2$ is phenyl.

29. The compound according to claim 1, or a pharmaceutically acceptable salt thereof, wherein:
$Ar^1$ and $Ar^2$ are heteroaryl.

30. The compound according to claim 29, or a pharmaceutically acceptable salt thereof, wherein:
$Ar^1$ is pyridyl.

31. The compound according to claim 29, or a pharmaceutically acceptable salt thereof, wherein:
$Ar^2$ is pyridyl.

32. The compound according to claim 29, or a pharmaceutically acceptable salt thereof, wherein:
$Ar^1$ and $Ar^2$ are pyridyl.

33. The compound according to claim 1, or a pharmaceutically acceptable salt thereof, wherein:
$Ar^2$ is pyridyl substituted with one $Y^3$ group and one $Y^1$ group.

34. The compound according to claim 33, or a pharmaceutically acceptable salt thereof, wherein:
$Ar^2$ is pyridyl substituted with one $Y^3$ group in the 4-position and one $Y^1$ group in the 2-position, relative to the point of attachment to the piperazine ring.

35. The compound according to claim 1, or a pharmaceutically acceptable salt thereof, wherein:
$Ar^1$ is pyridyl substituted with one or more groups independently selected from $Y^1$ and $Y^3$.

36. The compound according to claim 1, or a pharmaceutically acceptable salt thereof, wherein:
$Ar^1$ is pyridyl substituted with one $Y^1$ group at the 4-position, relative to the point of attachment to the piperazine ring.

37. The compound according to claim 36, or a pharmaceutically acceptable salt thereof, wherein:
$Ar^2$ is:

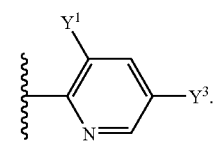

38. The compound according to claim 1, or a pharmaceutically acceptable salt thereof, wherein:
m=0 and n=0.

39. The compound according to claim 1, or a pharmaceutically acceptable salt thereof, wherein:
m=0, n=1, and B is $—(C(R^3)_2)_r—$.

40. The compound according to claim 39, or a pharmaceutically acceptable salt thereof, wherein:
r=1.

41. The compound according to claim 39, or a pharmaceutically acceptable salt thereof, wherein:
each $R^3$ is independently selected from H and -alkylene-OH.

42. The compound according to claim 39, or a pharmaceutically acceptable salt thereof, wherein:
each $R^3$ is independently selected from H and $—(CH_2)—OH$.

43. The compound according to claim 39, or a pharmaceutically acceptable salt thereof, wherein:
each $R^3$ is independently selected from H and $—(CH_2)_2—OH$.

44. The compound according to claim 39, or a pharmaceutically acceptable salt thereof, wherein:
each $R^3$ is independently selected from H and $—(CH_2)_3—OH$.

45. The compound according to claim 39, or a pharmaceutically acceptable salt thereof, wherein:
each $R^3$ is independently selected from H and -alkyl.

46. The compound according to claim 45, or a pharmaceutically acceptable salt thereof, wherein:
each $R^3$ is independently selected from H and methyl.

47. The compound according to claim 45, or a pharmaceutically acceptable salt thereof, wherein:
each $R^3$ is independently selected from H and ethyl.

48. The compound according to claim 1, or a pharmaceutically acceptable salt thereof, wherein:
m=1, n=0, and A is $—(C(R^2)_2)_q—$.

49. The compound according to claim 48, or a pharmaceutically acceptable salt thereof, wherein:
each $R^2$ is independently H or alkyl.

50. The compound according to claim 48, or a pharmaceutically acceptable salt thereof, wherein:
q is 1 and each $R^2$ is H.

51. The compound according to claim 48, or a pharmaceutically acceptable salt thereof, wherein:
q is 2 and each $R^2$ is independently selected from H and alkyl.

52. The compound according to claim 1, or a pharmaceutically acceptable salt thereof, wherein:
m=1, n=0, and A is —C(O)—.

53. The compound according to claim 1, or a pharmaceutically acceptable salt thereof, wherein:
m=1, n=0, and A is —S(O)$_2$—.

54. The compound according to claim 1, or a pharmaceutically acceptable salt thereof, wherein:
m=1, n=1, and A is —(C($R^2$)$_2$)$_q$— and B is —(C($R^3$)$_2$)$_r$—.

55. The compound according to claim 54, or a pharmaceutically acceptable salt thereof, wherein:
each $R^2$ is H.

56. The compound according to claim 54, or a pharmaceutically acceptable salt thereof, wherein:
r=1.

57. The compound according to claim 54, or a pharmaceutically acceptable salt thereof, wherein:
q=1.

58. The compound according to claim 54, or a pharmaceutically acceptable salt thereof, wherein:
each $R^3$ is independently selected from alkyl and —O$R^2$, wherein each $R^2$ is independently H or alkyl.

59. The compound according to claim 54, or a pharmaceutically acceptable salt thereof, wherein:
m=1, n=1, and A is —CH$_2$—, and B is —C(CH$_3$)(OH)—.

60. The compound according to claim 54, or a pharmaceutically acceptable salt thereof, wherein:
m=1, n=1, and A is —CH$_2$—, and B is —CH(OH)—.

61. The compound according to claim 1, or a pharmaceutically acceptable salt thereof, wherein:
m=1, n=1, A is —C(=N—O$R^2$)—.

62. The compound according to claim 61, or a pharmaceutically acceptable salt thereof, wherein:
$R^2$ is H.

63. The compound according to claim 1, or a pharmaceutically acceptable salt thereof, wherein:
m=1, n=1, A is —(C($R^2$)$_2$)$_q$— and B is —C(O)—.

64. The compound according to claim 63, or a pharmaceutically acceptable salt thereof, wherein:
q is 1.

65. The compound according to claim 64 or a pharmaceutically acceptable salt thereof, wherein:
$R^2$ is H.

66. The compound according to claim 1, or a pharmaceutically acceptable salt thereof, wherein:
m=1, n=1, A is —C(O)—, and B is —(C($R^3$)$_2$)$_r$—.

67. The compound according to claim 66, or a pharmaceutically acceptable salt thereof, wherein:
each $R^3$ is independently selected from H, —OH and -alkyl.

68. The compound according to claim 66, or a pharmaceutically acceptable salt thereof, wherein:
r is 1.

69. The compound according to claim 68, or a pharmaceutically acceptable salt thereof, wherein:
each $R^3$ is independently selected from H and alkyl.

70. The compound according to claim 68, or a pharmaceutically acceptable salt thereof, wherein:
B is selected from —C(OH)(CH$_3$)—, —C(OH)(CH$_2$CH$_3$)—, and —C(OH)H—.

71. The compound according to claim 68, or a pharmaceutically acceptable salt thereof, wherein:
B is —CH$_2$—.

72. The compound according to claim 1, or a pharmaceutically acceptable salt thereof, wherein:
m=1, n=1, A is —C(O)—, and B is —N($R^6$)—.

73. The compound according to claim 72, or a pharmaceutically acceptable salt thereof, wherein:
$R^6$ is H.

74. The compound according to claim 1, or a pharmaceutically acceptable salt thereof, wherein:
X is unsubstituted.

75. The compound according to claim 1, or a pharmaceutically acceptable salt thereof, wherein:
X is substituted with one or more groups independently selected from —C(=NH)—O-alkyl, —C(=N-alkyl)—O-alkyl, —C(O)OH, -alkylene-O-heterocycloalkyl, $Y^1$ and $Y^3$.

76. The compound according to claim 1, or a pharmaceutically acceptable salt thereof, wherein:
p=0.

77. The compound according to claim 1, or a pharmaceutically acceptable salt thereof, wherein:
p=1, and $R^1$ is alkyl.

78. The compound according to claim 77, or a pharmaceutically acceptable salt thereof, wherein:
$R^1$ is methyl.

79. The compound according to claim 1, or a pharmaceutically acceptable salt thereof, wherein:
p=2.

80. The compound according to claim 1, or a pharmaceutically acceptable salt thereof, wherein:
two groups $R^1$ are taken together to form a carbonyl group.

81. The compound according to claim 1, or a pharmaceutically acceptable salt thereof, having the following Formula (IA):

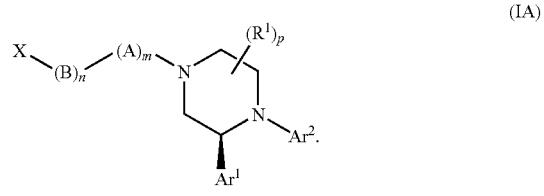

82. The compound according to claim 1, or a pharmaceutically acceptable salt thereof, having the following Formula (IB):

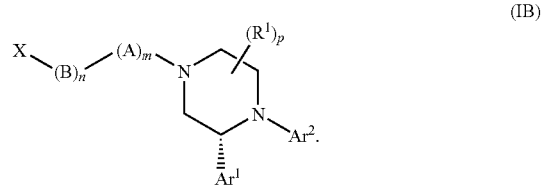

83. The compound according to claim 1, or a pharmaceutically acceptable salt thereof, having the following Formula (IC):

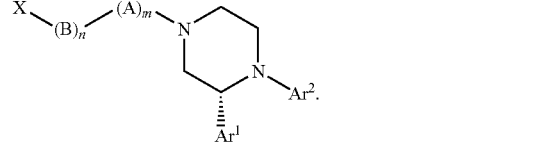

84. A compound, or a pharmaceutically acceptable salt thereof, selected from:
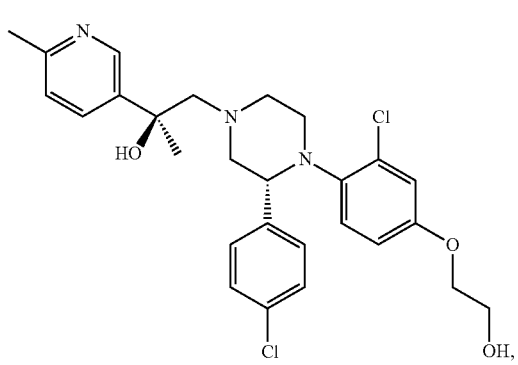
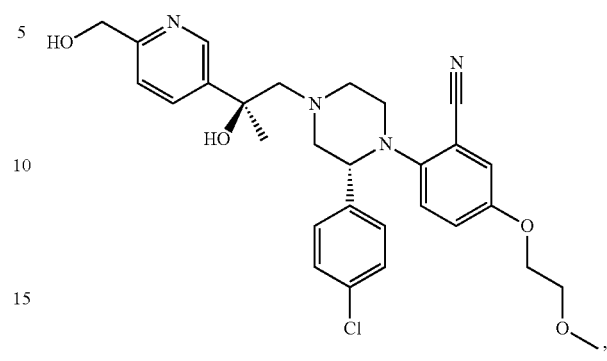
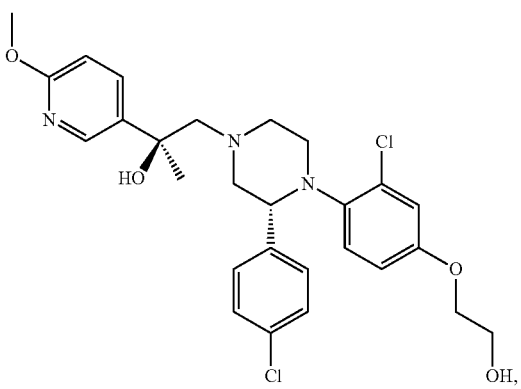
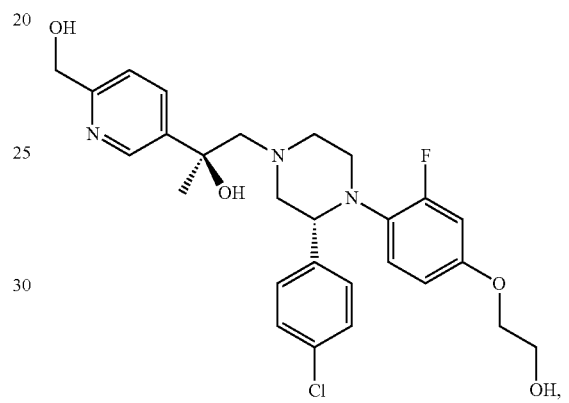
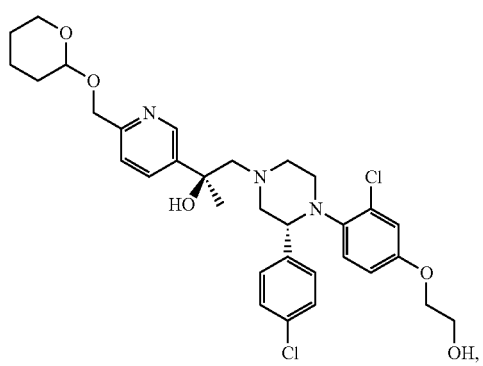
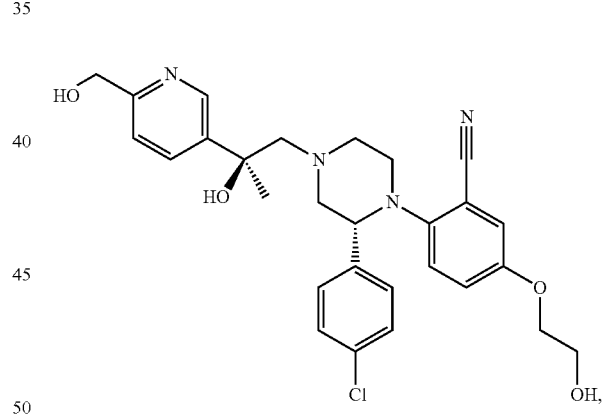
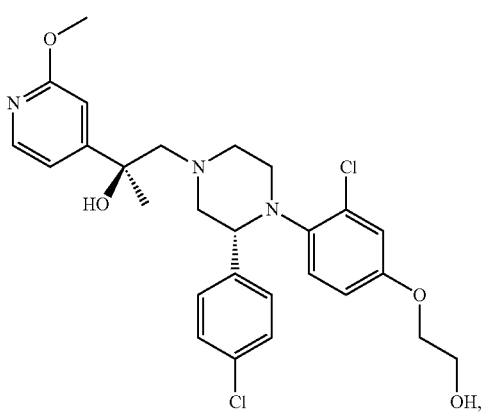
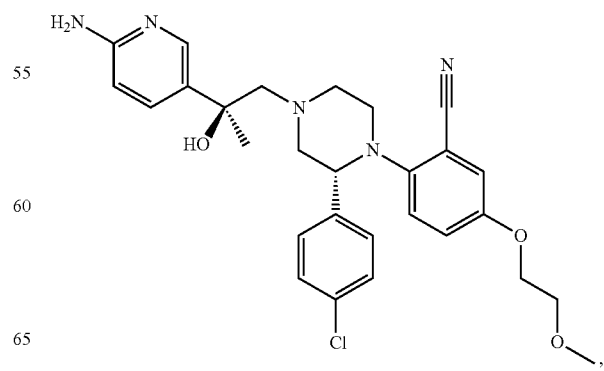

693
-continued
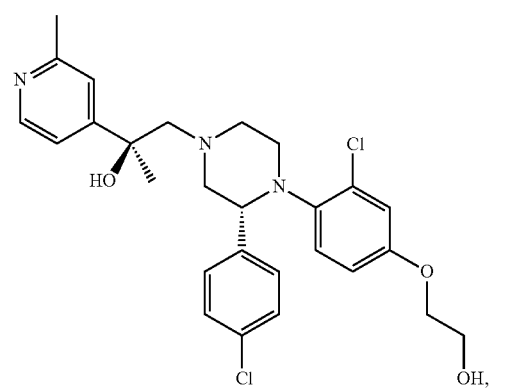
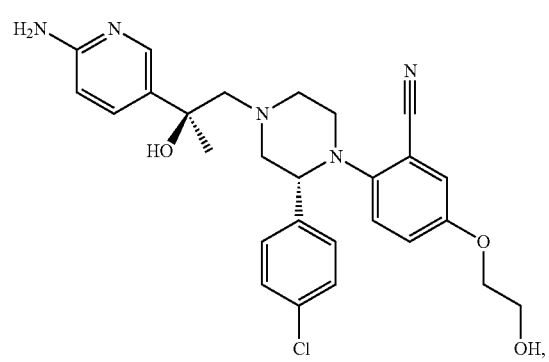
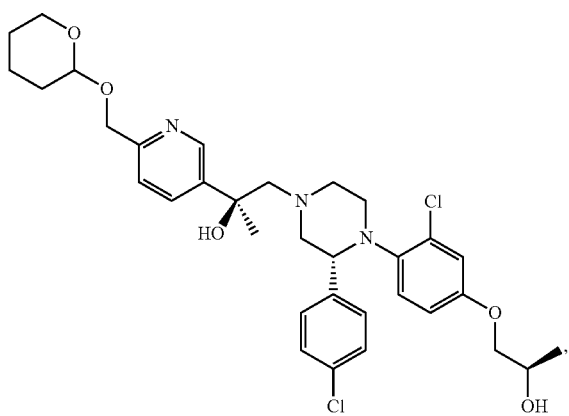
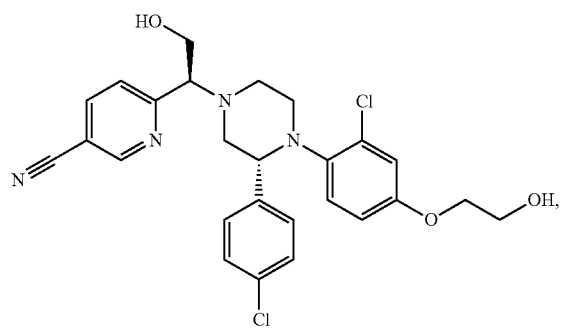
694
-continued
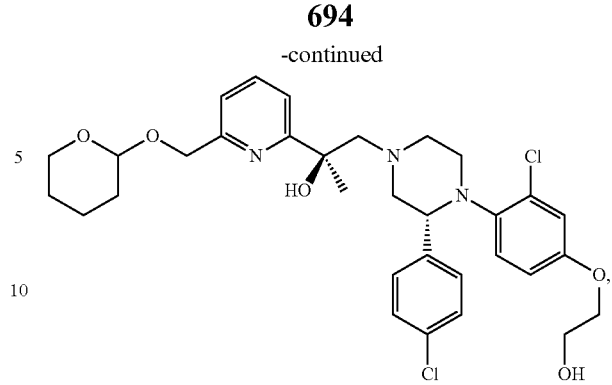
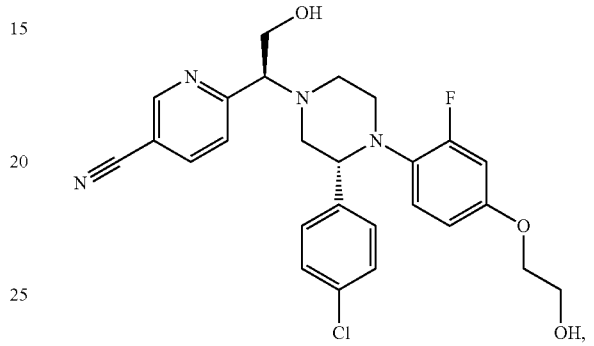
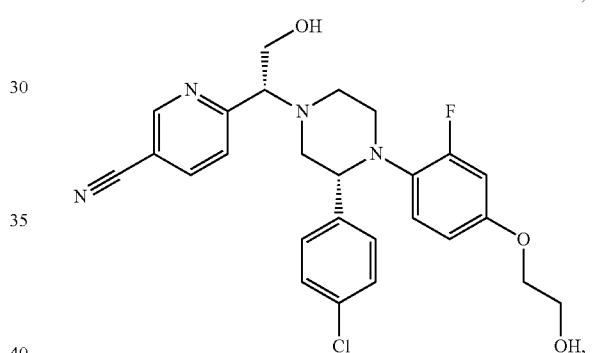
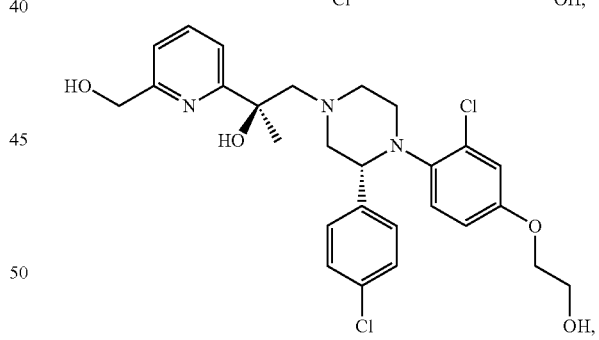
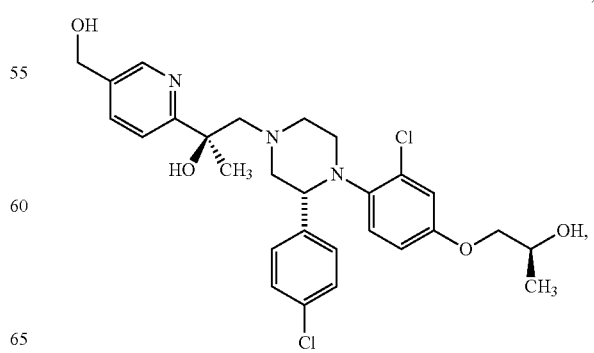

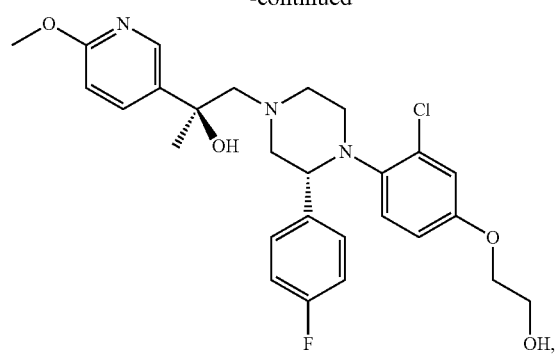
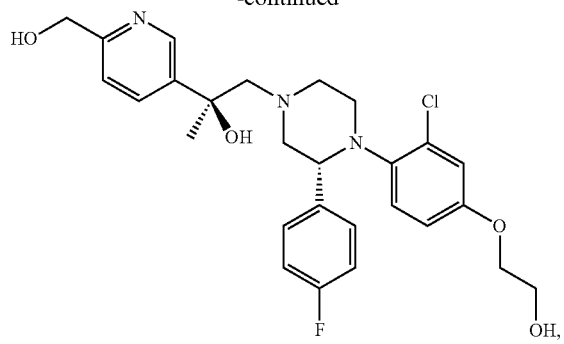
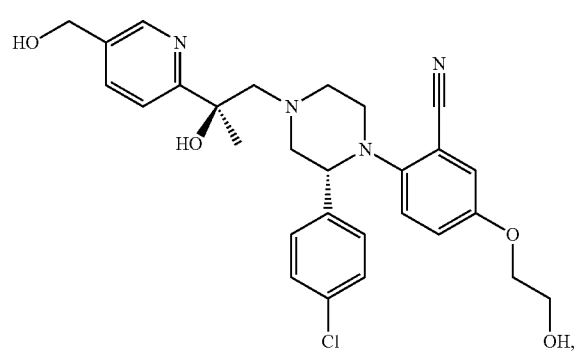
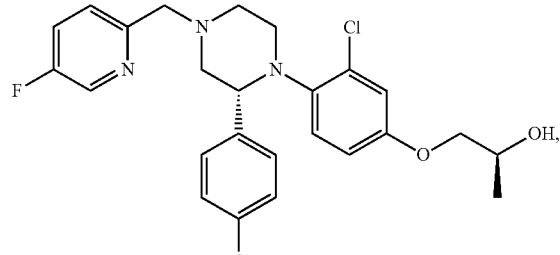
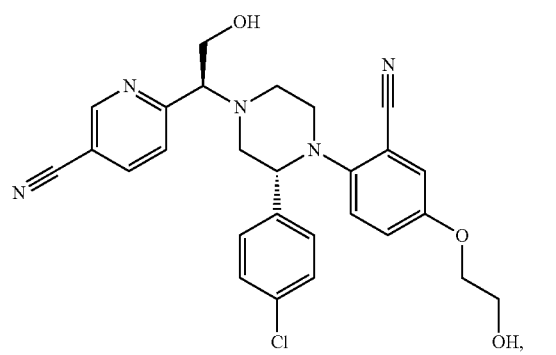
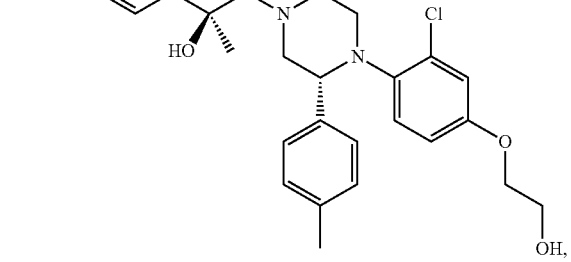
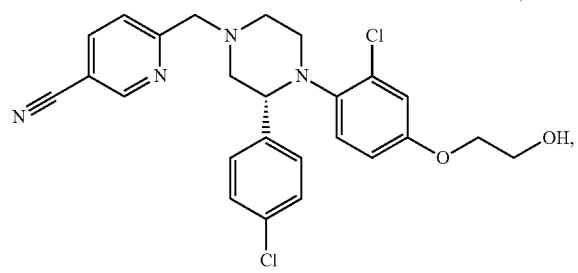
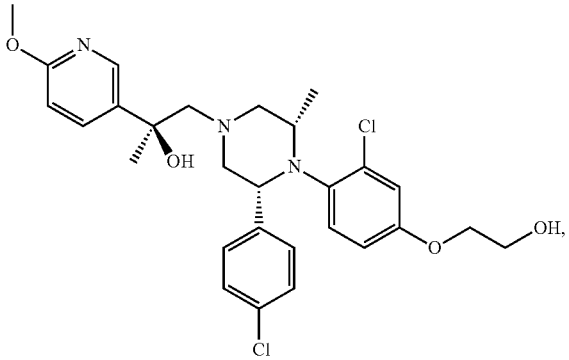
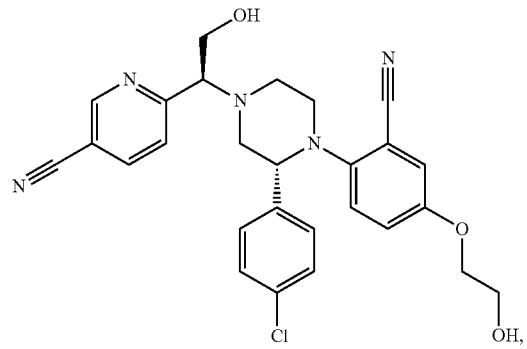

697
-continued
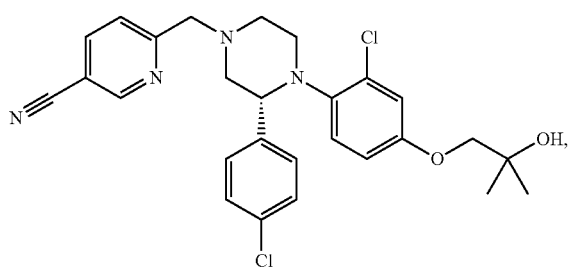
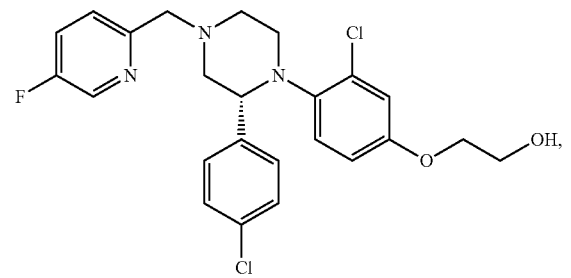
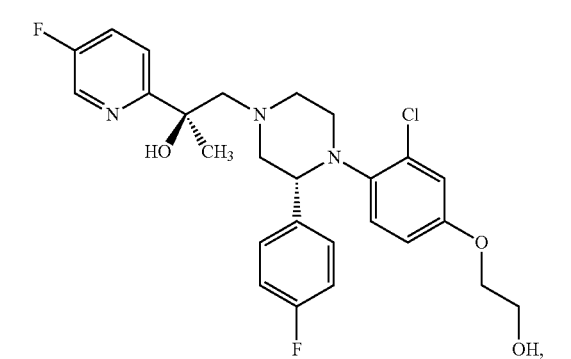
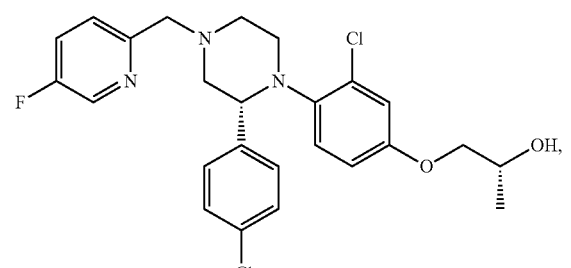
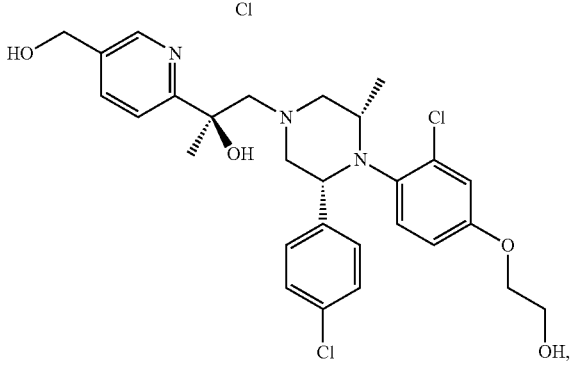
698
-continued
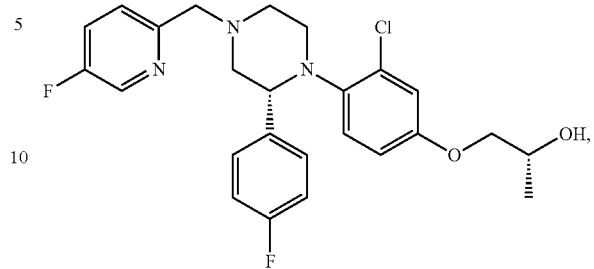
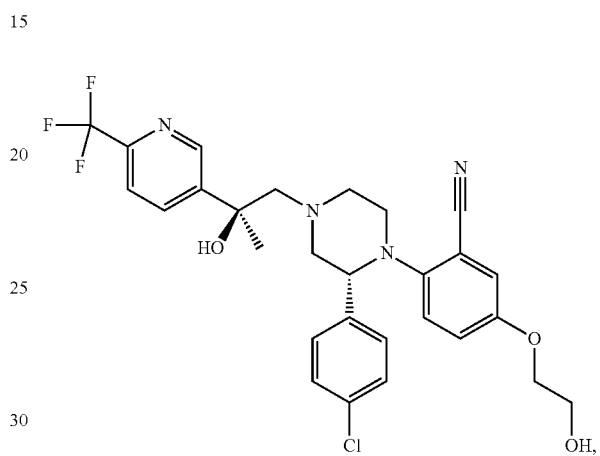
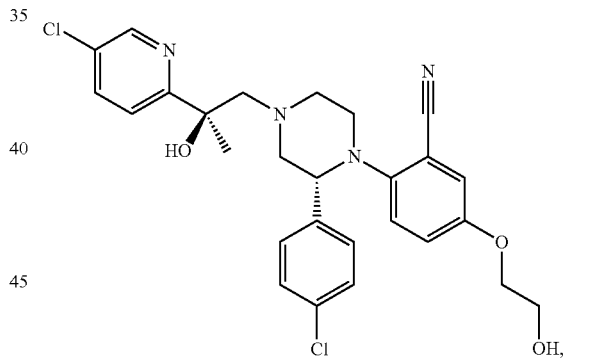
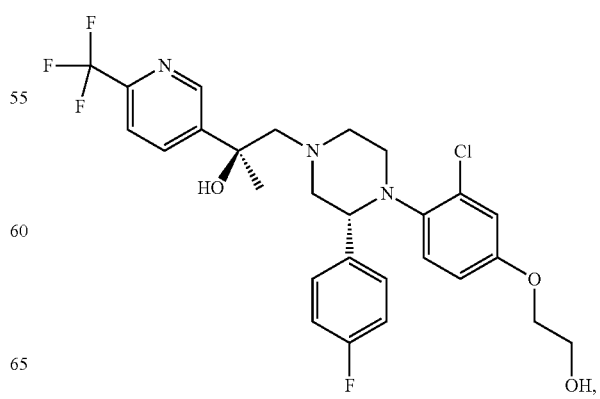

699
-continued
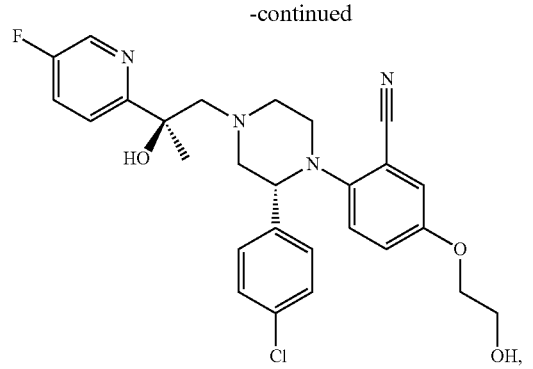
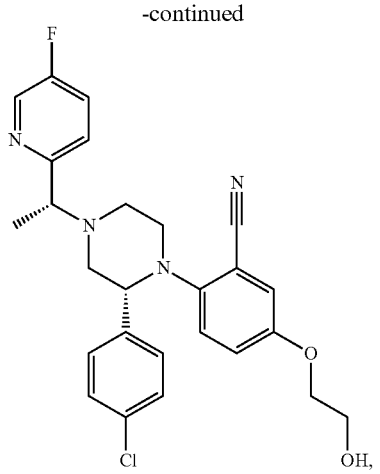
700
-continued
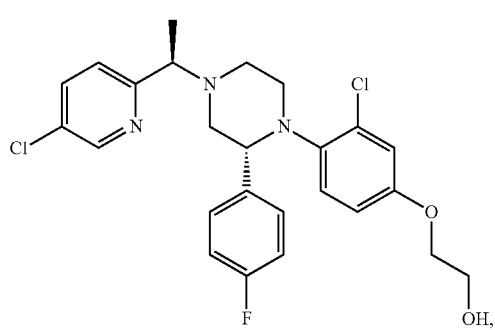
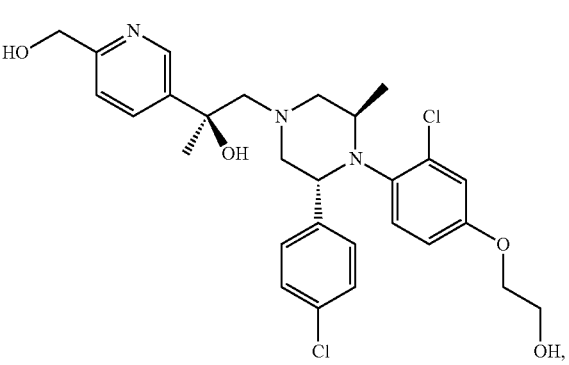
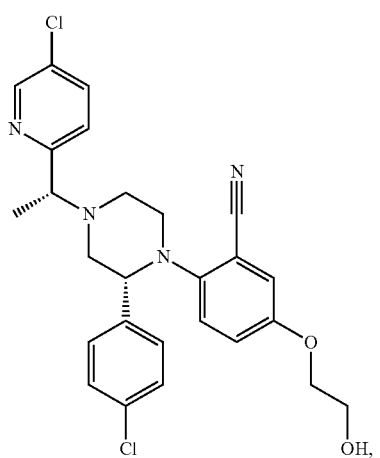

701
-continued
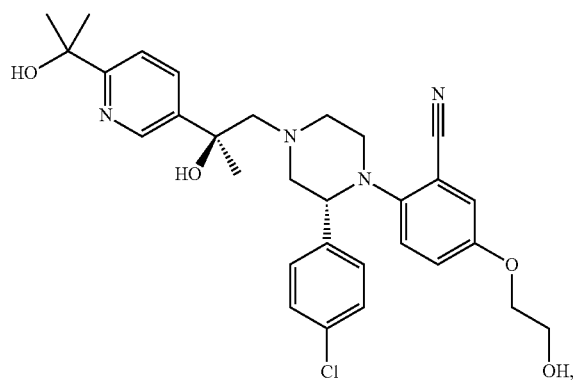
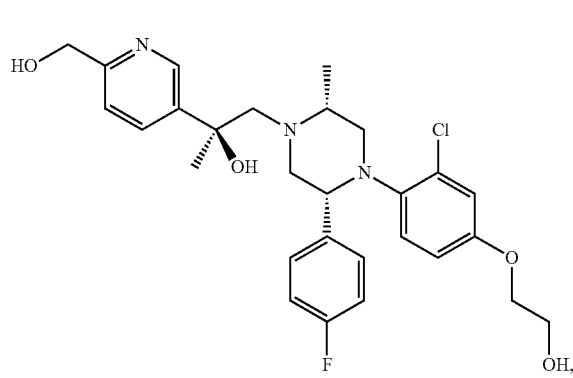
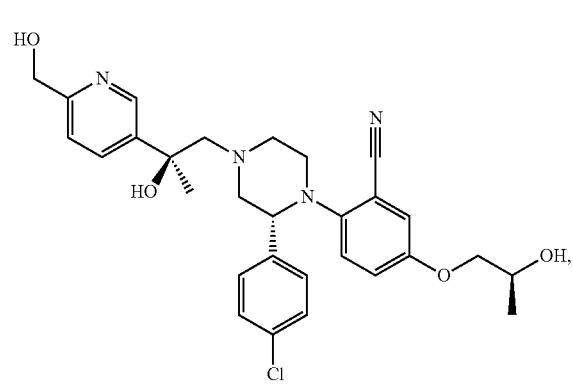
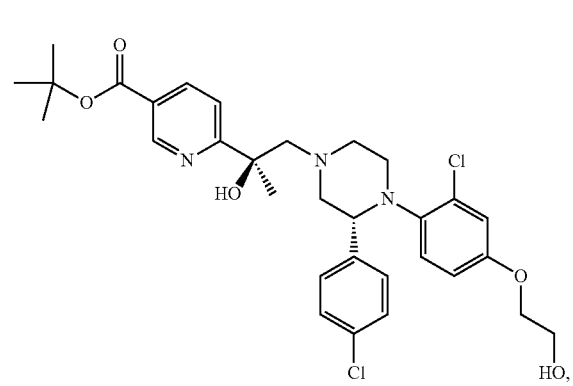
702
-continued
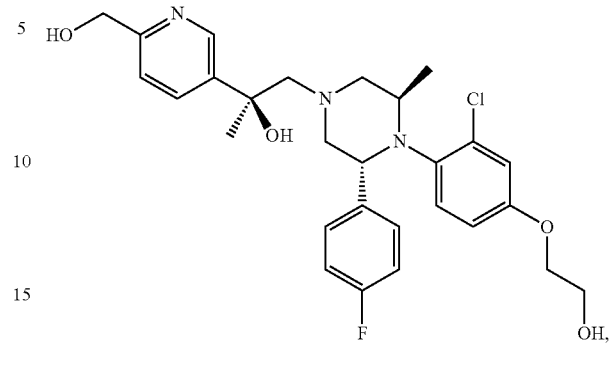
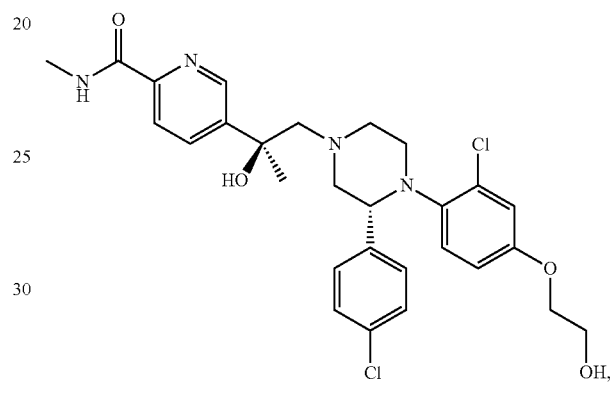
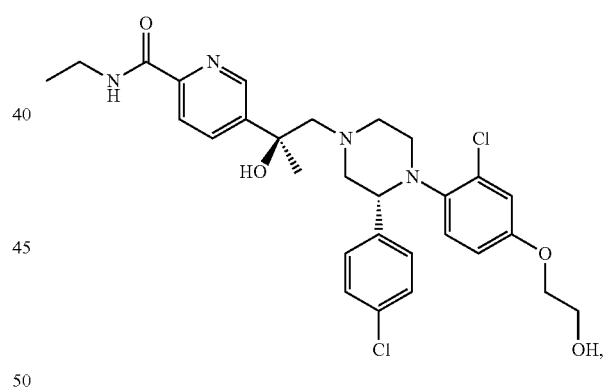
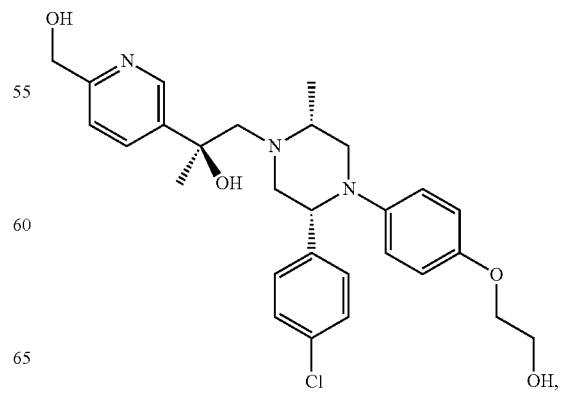

703
-continued
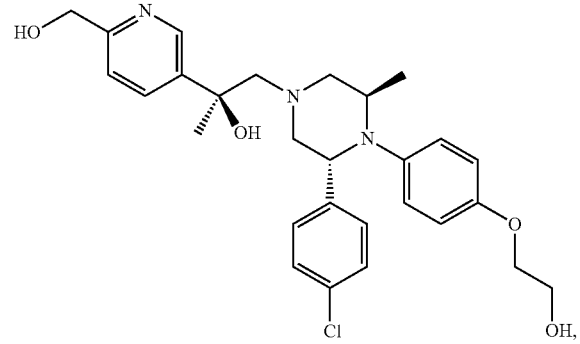
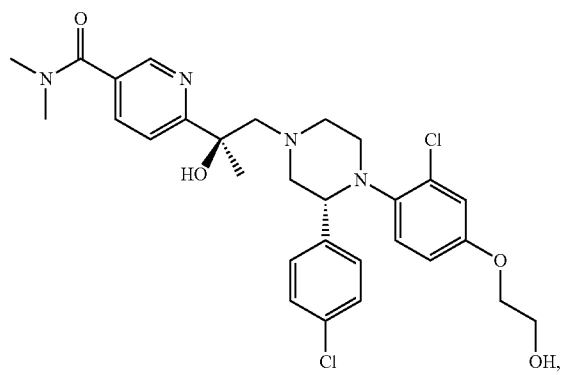
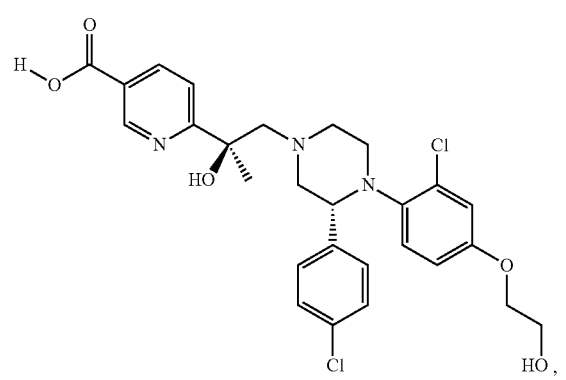
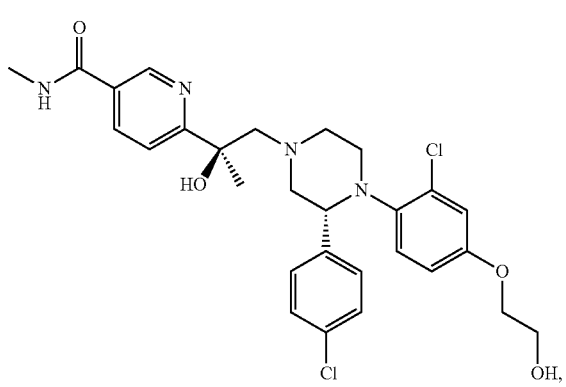
704
-continued
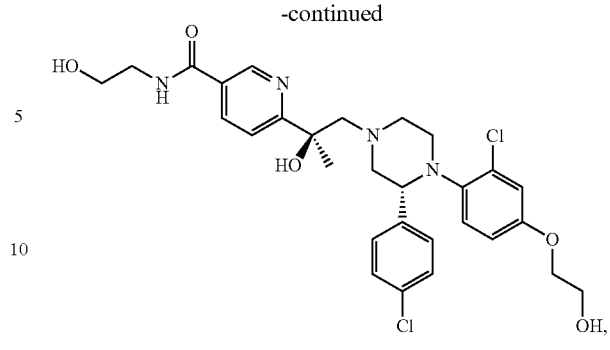
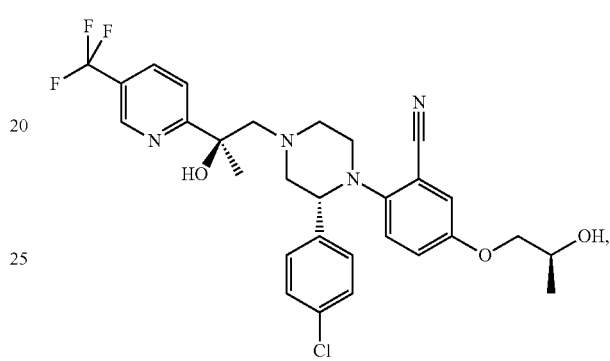
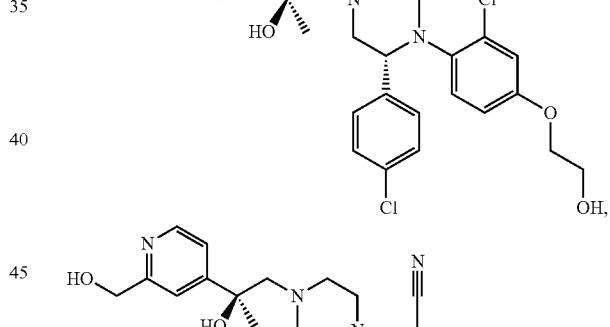
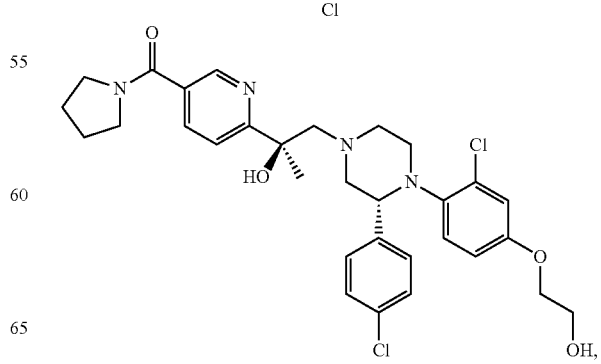

705
-continued
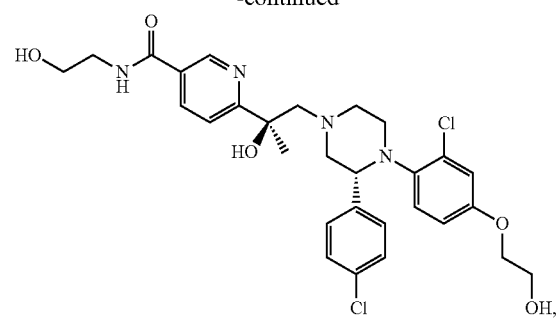
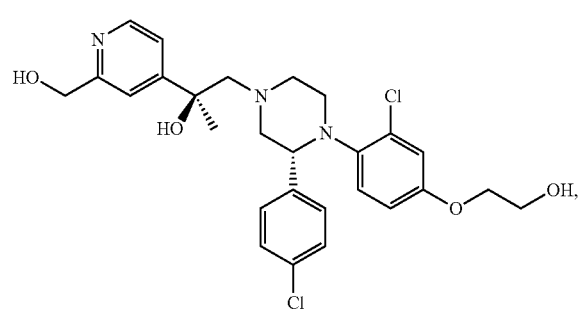
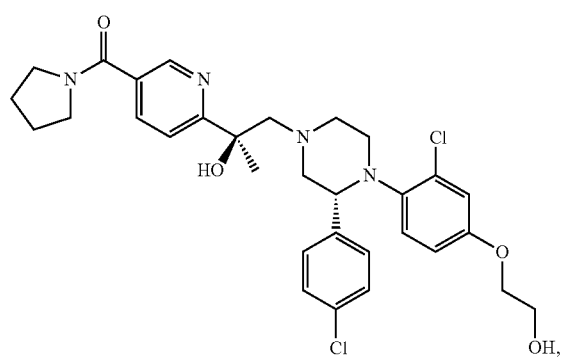
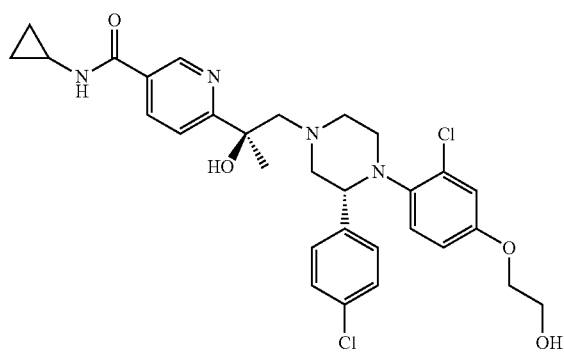
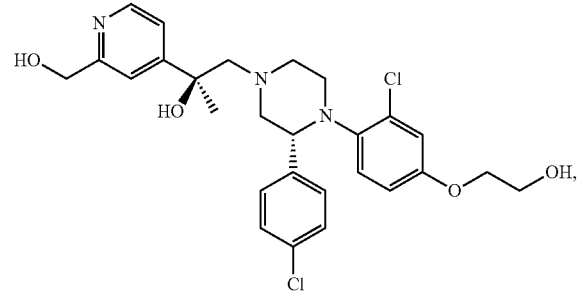
706
-continued
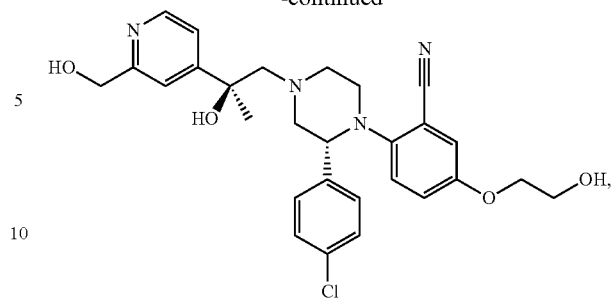
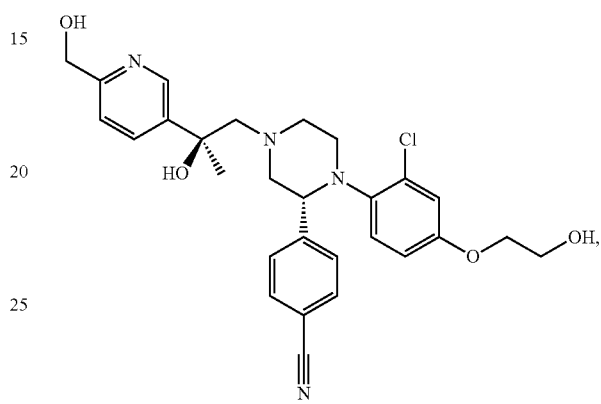
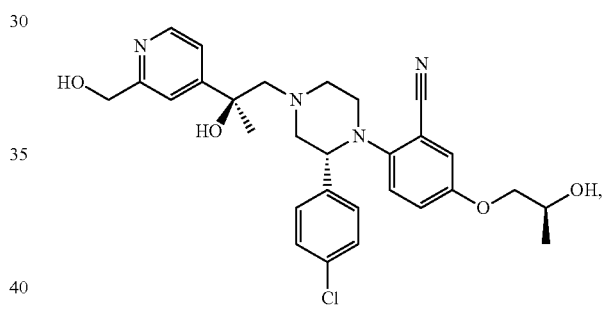
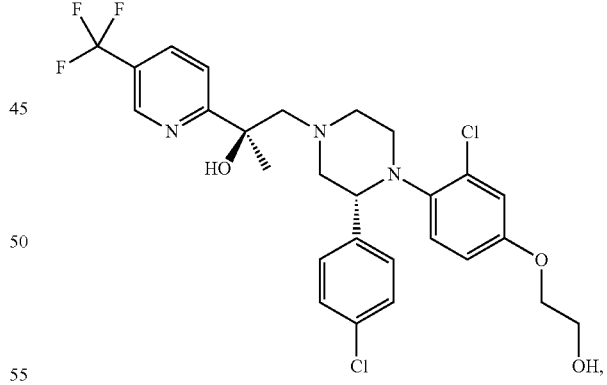
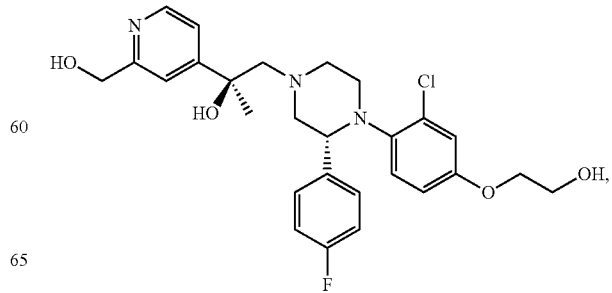

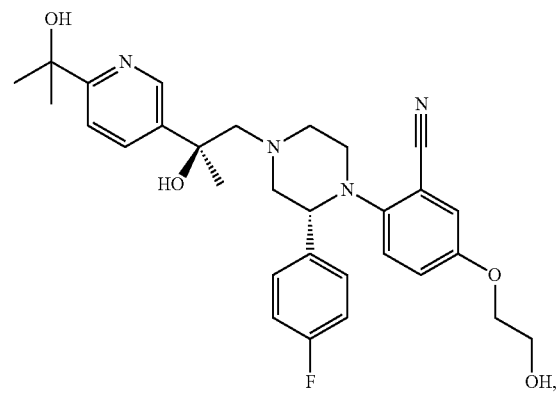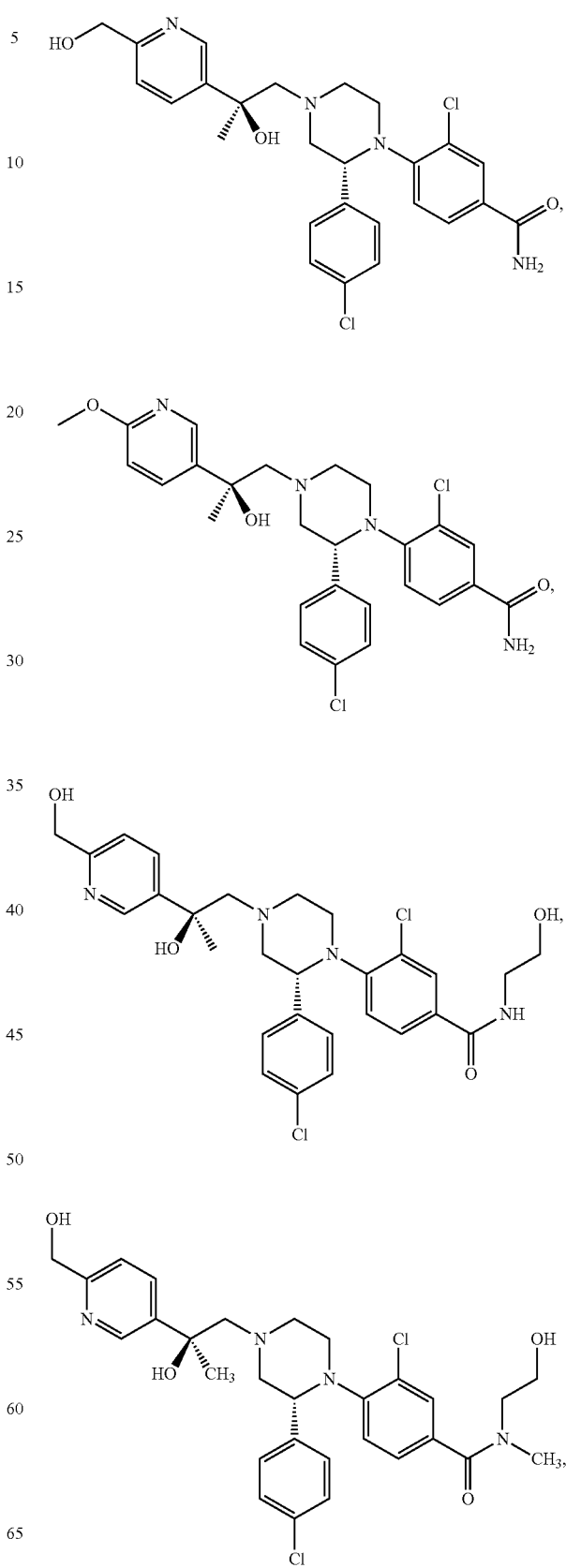

709
-continued
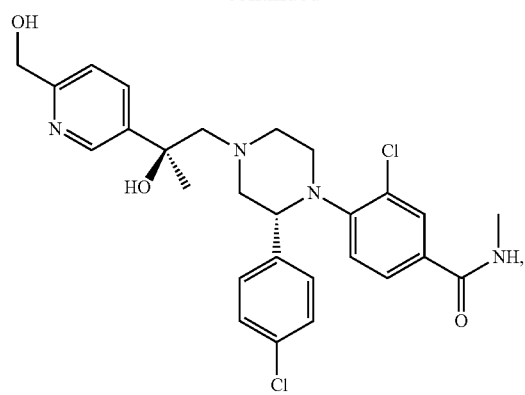
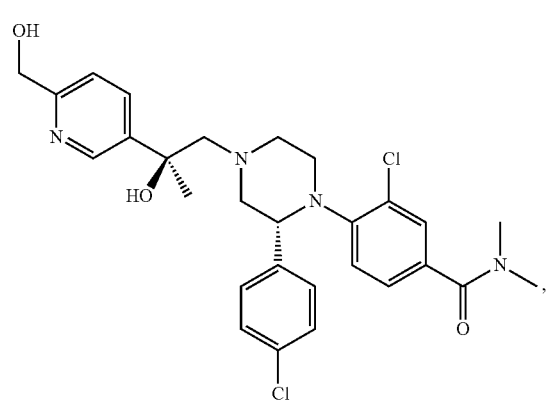
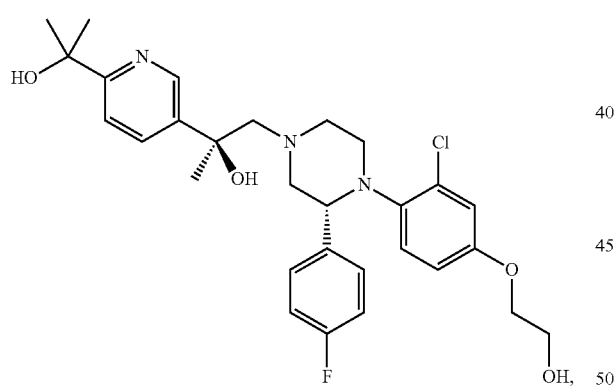
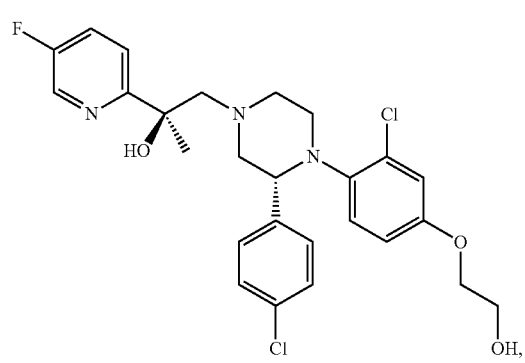
710
-continued
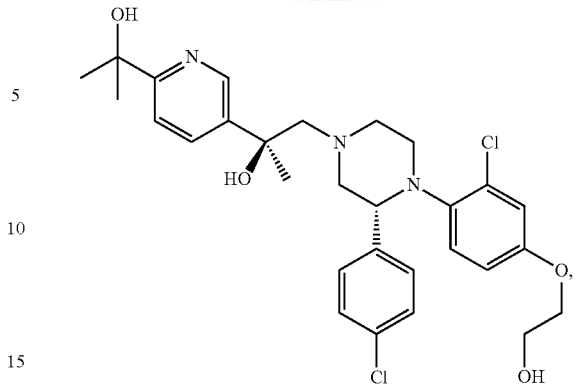
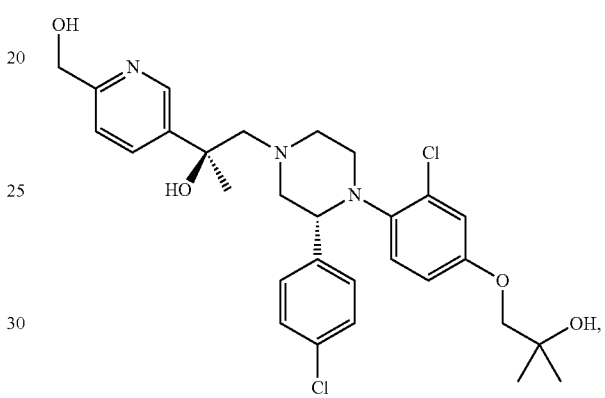
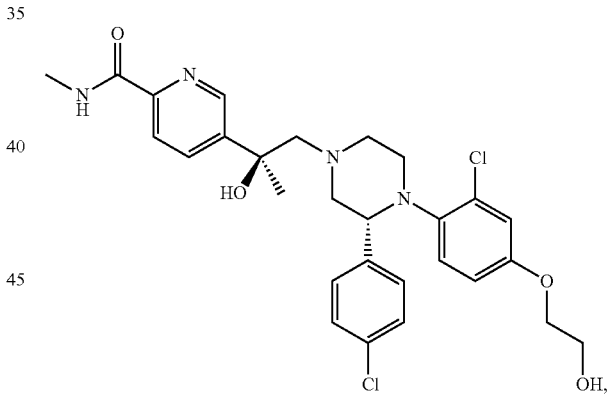
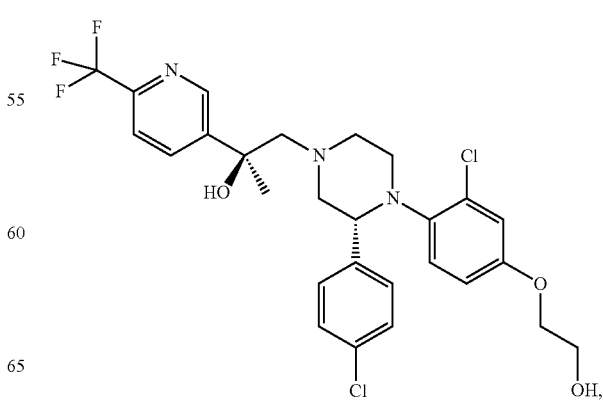

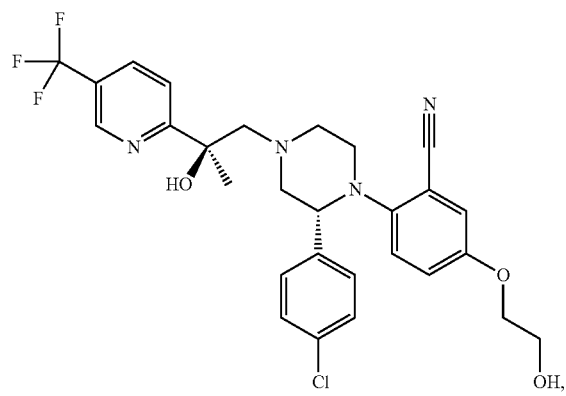
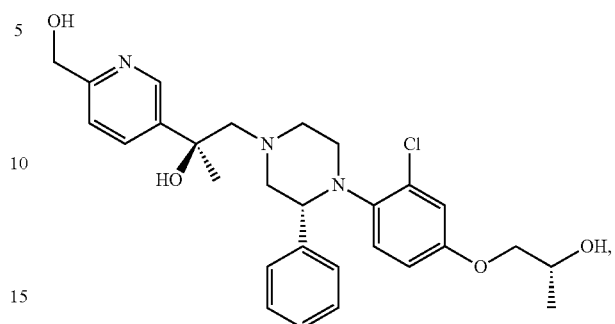
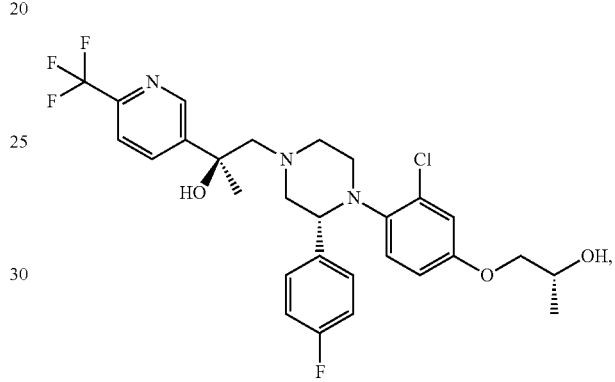
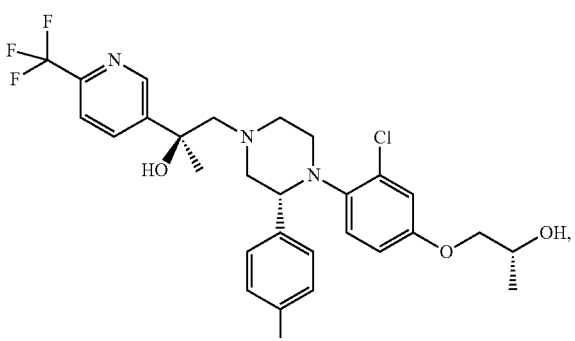
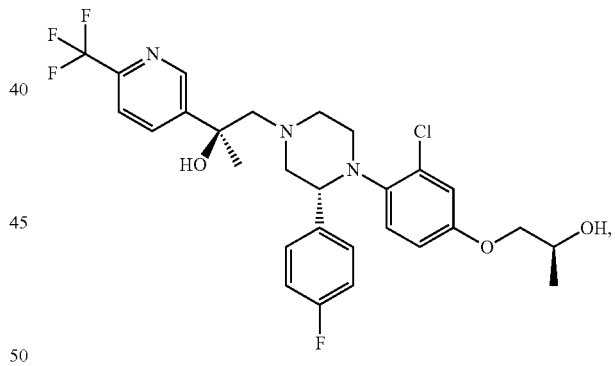
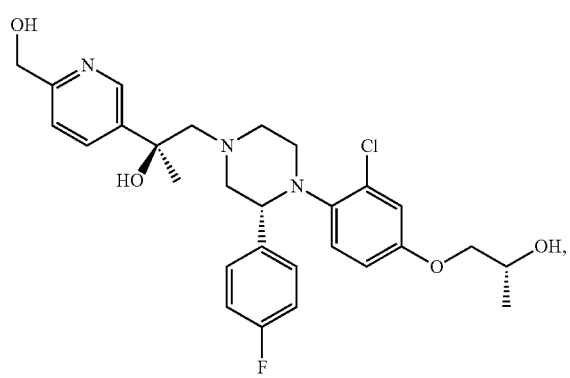
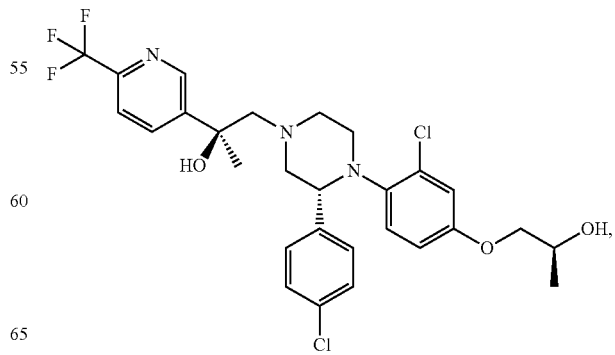

713
-continued
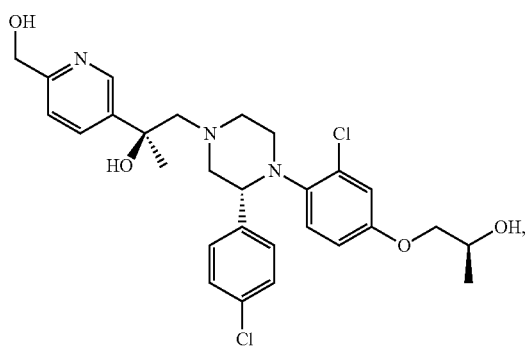
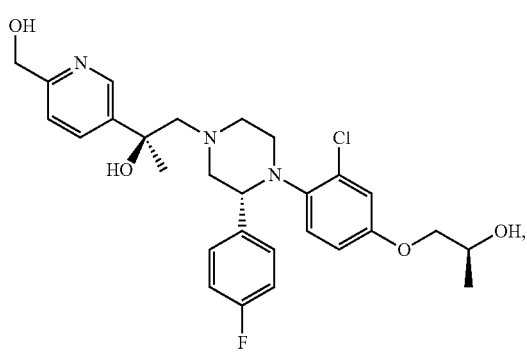
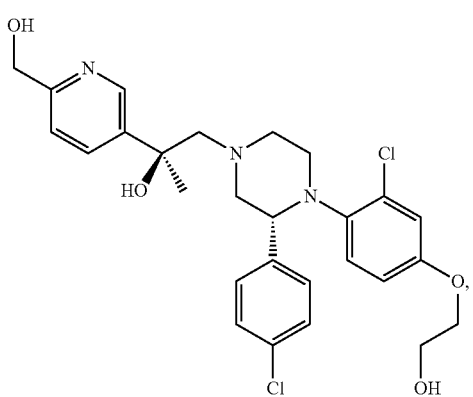
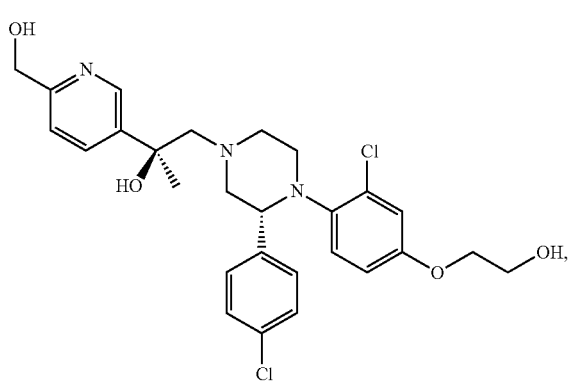
714
-continued
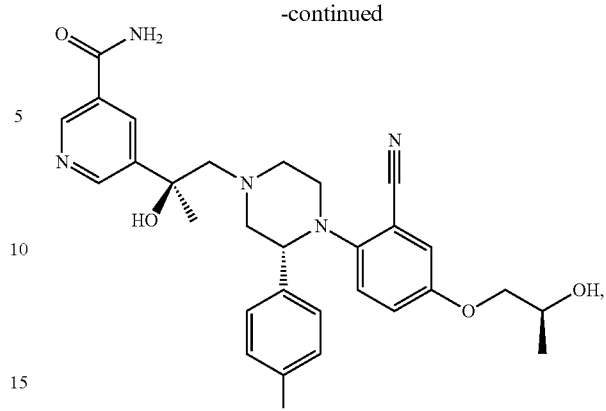
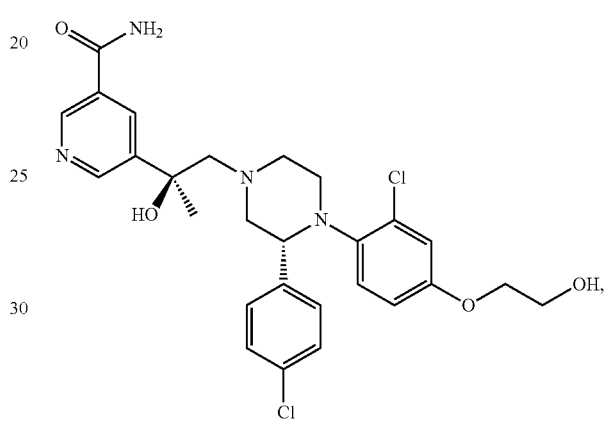
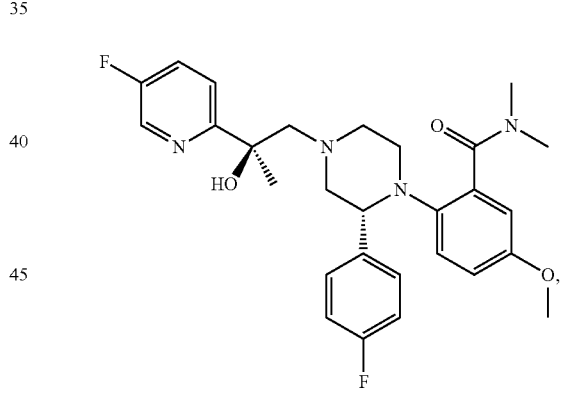
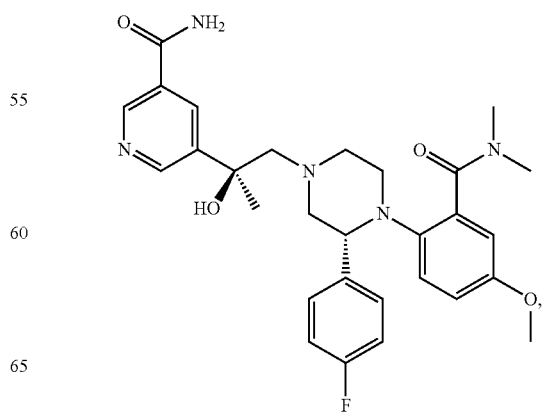

-continued

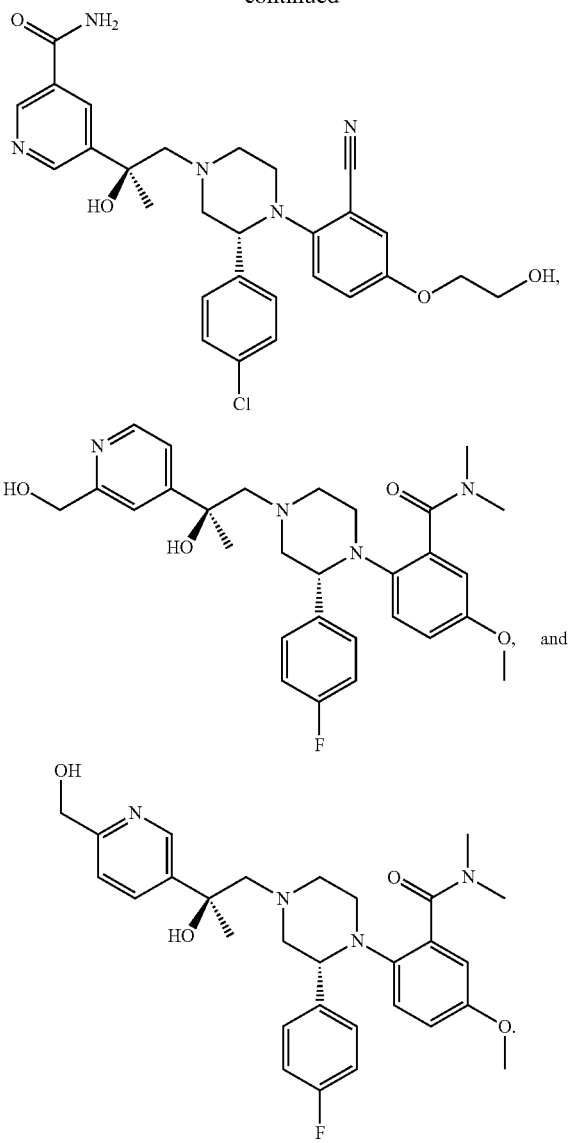

and

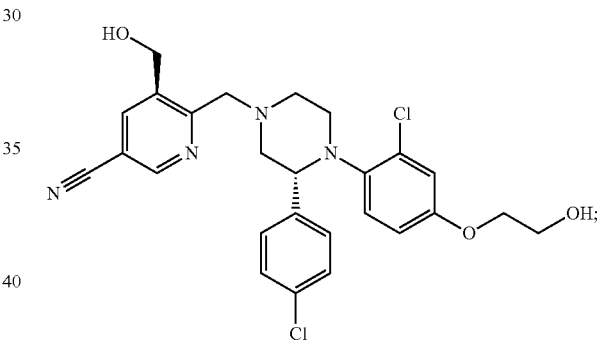

or a pharmaceutically acceptable salt thereof.

85. A composition comprising: at least one compound according to claim 1, or a pharmaceutically acceptable salt thereof; and at least one pharmaceutically acceptable carrier.

86. A composition comprising: at least one compound of claim 1, or a pharmaceutically acceptable salt thereof; and at least one additional active agent other than a compound of claim 1.

87. A composition of claim 86, wherein said at least one additional active agent is selected from a centrally acting agent and a peripheral acting agent.

88. A composition of claim 86, wherein said at least one additional active agent is selected from a histamine-3 receptor antagonist and a NPY5 antagonist.

89. A composition of claim 86, wherein said at least one additional active agent is selected from a microsomal triglyceride transfer protein (MTP) inhibitor.

90. A composition comprising: at least one compound of claim 1, or a pharmaceutically acceptable salt thereof; and at least one cholesterol lowering compound.

91. The composition of claim 90, wherein said at least one cholesterol lowering compound is at least one sterol absorption inhibitor or at least one 5α-stanol absorption inhibitor.

92. The composition of claim 90, wherein said at least one cholesterol lowering compound is at least one substituted azetidinone compound or substituted β-lactam compound or a pharmaceutically acceptable salt thereof.

93. The composition of claim 90, wherein said at least one cholesterol lowering compound is ezetimibe.

94. A compound of the following formula

* * * * *